United States Patent
Sánchez et al.

(10) Patent No.: US 8,163,793 B2
(45) Date of Patent: Apr. 24, 2012

(54) PROLINE DERIVATIVES

(75) Inventors: Rubén Alvarez Sánchez, Rosenau (FR); David Banner, Basel (CH); Simona M. Ceccarelli, Basel (CH); Uwe Grether, Efringen-Kirchen (DE); Wolfgang Haap, Loerrach (DE); Peter Hartman, Loerrach (DE); Guido Hartmann, Loerrach (DE); Hans Hilpert, Muenchenstein (CH); Holger Kuehne, Loerrach (DE); Harald Mauser, Schliengen (DE); Jean-Marc Plancher, Hagenthal-le-Bas (FR)

(73) Assignee: Hoffman-La Roche Inc., Nutley, NJ (US)

( * ) Notice: Subject to any disclaimer, the term of this patent is extended or adjusted under 35 U.S.C. 154(b) by 186 days.

(21) Appl. No.: 12/761,427

(22) Filed: Apr. 16, 2010

(65) Prior Publication Data
US 2010/0267722 A1 Oct. 21, 2010

(30) Foreign Application Priority Data
Apr. 20, 2009 (EP) .................................. 09158212

(51) Int. Cl.
| | |
|---|---|
| C07D 417/14 | (2006.01) |
| C07D 417/10 | (2006.01) |
| C07D 417/04 | (2006.01) |
| C07D 413/14 | (2006.01) |
| C07D 413/10 | (2006.01) |
| C07D 413/04 | (2006.01) |
| C07D 409/14 | (2006.01) |
| C07D 409/10 | (2006.01) |
| C07D 409/04 | (2006.01) |
| C07D 405/14 | (2006.01) |
| C07D 405/10 | (2006.01) |
| C07D 405/04 | (2006.01) |
| C07D 401/14 | (2006.01) |
| C07D 401/10 | (2006.01) |
| C07D 401/04 | (2006.01) |
| C07D 403/14 | (2006.01) |
| C07D 403/10 | (2006.01) |
| C07D 403/04 | (2006.01) |
| C07D 403/06 | (2006.01) |
| C07D 401/06 | (2006.01) |
| C07D 405/06 | (2006.01) |
| C07D 409/06 | (2006.01) |
| C07D 413/06 | (2006.01) |
| C07D 417/06 | (2006.01) |
| C07D 207/16 | (2006.01) |
| A61K 31/541 | (2006.01) |
| A61K 31/5377 | (2006.01) |
| A61K 31/501 | (2006.01) |
| A61K 31/497 | (2006.01) |
| A61K 31/496 | (2006.01) |
| A61K 31/454 | (2006.01) |
| A61K 31/4439 | (2006.01) |
| A61K 31/427 | (2006.01) |
| A61K 31/422 | (2006.01) |
| A61K 31/4178 | (2006.01) |
| A61K 31/4155 | (2006.01) |
| A61K 31/4025 | (2006.01) |

(52) U.S. Cl. ........ 514/423; 514/406; 514/397; 514/326; 514/254.01; 514/343; 514/394; 514/252.05; 514/422; 514/376; 514/235.5; 514/413; 514/269; 514/370; 548/537; 548/364.1; 548/314.7; 548/361.1; 548/519; 548/518; 548/229; 548/512; 548/193; 546/208; 546/278.4; 544/372; 544/238; 544/141; 544/327

(58) Field of Classification Search .................. 514/423, 514/406, 397, 326, 254.01, 343, 394, 252.05, 514/422, 376, 235.5, 413, 269, 370; 548/537, 548/364.1, 314.7, 361.1, 519, 518, 229, 512, 548/193; 546/208, 278.4; 544/372, 238, 544/141, 327
See application file for complete search history.

(56) References Cited

FOREIGN PATENT DOCUMENTS
| | | |
|---|---|---|
| WO | 98/01133 | 1/1998 |
| WO | 00/55126 | 9/2000 |
| WO | 01/47886 | 7/2001 |
| WO | 02/069901 | 9/2002 |
| WO | 03/075836 | 9/2003 |
| WO | 2006/113942 | 10/2006 |
| WO | 2007/137080 | 11/2007 |

OTHER PUBLICATIONS

Bondebjerg, J. et al, Bioorg. Med Chem Lett. 16 (2006) 3614-3617 XP002589243.
Loeser, R. et al, J. Med. Chem. 48:24 (2005) 7688-7707 XP002589244.

(Continued)

*Primary Examiner* — Joseph Kosack
*Assistant Examiner* — Matthew Coughlin
(74) *Attorney, Agent, or Firm* — George W. Johnston; Patricia S. Rocha-Tramaloni; Gene J. Yao

(57) ABSTRACT

The invention relates to a compound of formula (I)

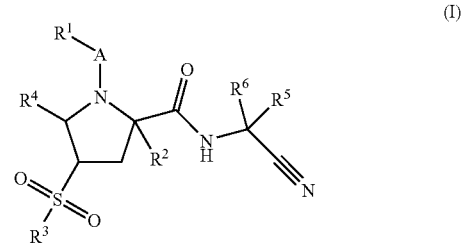

wherein A, $R^1$-$R^6$ are as defined in the description and in the claims. The compound of formula (I) can be used as a medicament.

33 Claims, No Drawings

OTHER PUBLICATIONS

Guay, D et al, Bioorg. Med. Chem. Lett. 19 (2009) 5392-5396 XP002589245.
Aikawa, et al., Circulation, vol. 119(13) pp. 1785-1794 (2009).
Bromme, D., Curr. Protoc. Protein Sci. Chapter 21, Unit 21, p. 2 (2001).
Burns-Kurtis et al., Cardiovascular Research vol. 62(3) pp. 610-620 (2004).
Cheng et al., American J. Pathol. vol. 164(1) pp. 243-251 (2004).
De Nooijer et al., Arterioscler. Thromb. Vasular Biol. vol. 29(2) pp. 188-194 (2009).
Driessen et al., J. Cell Biol vol. 147(4) pp. 776-790, (1999).
Funkelstein et al., J. Biol. Chem vol. 283 (51) pp. 35652-35659 (2008).
Hsing et al., Immunol. Rev. vol. 207 pp. 229-241 (2005).
Kitamoto et al., Circulation vol. 115(15) pp. 2065-2075 (2007).
Liu et al., Artherosclerosis vol. 186(2) pp. 411-419 (2006).
Roberts. R. Drug News Perspect. vol. 18(10) pp. 605-614 (2005).
Rodgers et al., Arterioscler. Thromb Vasc. Biol vol. 26(4) pp. 851-856 (2006).
Rudnesky et al, Ernst Scheisng Res. Found. Workshop vol. 56, pp. 81-95 (2006).
Sever et al., J. Clin. Invest. vol. 117(8) pp. 2095-2104 (2007).
Shi et al., Circ. Res. vol. 92(5) pp. 493-500 (2003).
Sukhova et al., J. Clin. Invest vol. 102(3) pp. 576-583 (1998).
Sukhova et al., J. Clin. Invest vol. 111(6) pp. 897-906 (2003).
Wang et al., J. Biol. Chem. vol. 281(9) pp. 6020-6029 (2006).
Williams et al., Pulm. Pharmacol. Ther vol. 22(1) pp. 27-32 (2009).
Burden et al., Clin. Cancer Res. vol. 15(19). pp. 6042-6051 (2009).
Laimas et al. Organic Letters vol. No. 9, pp. 1795-1798 (2006).

PROLINE DERIVATIVES

PRIORITY TO RELATED APPLICATION(S)

This application claims the benefit of European Patent Application No. 09158212.2, filed Apr. 20, 2009, which is hereby incorporated by reference in its entirety.

FIELD OF THE INVENTION

The present invention relates to compounds that are preferential inhibitors of the cysteine protease cathepsin, in particular of the cysteine protease cathepsin S or L.

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme 2001; Roberts 2005).

Cathepsin S is prominently expressed in antigen presenting cells like macrophages and dendritic cells and smooth muscle cells. (Hsing and Rudensky 2005; Rudensky and Beers 2006). While Cathepsin S is only weakly expressed in normal arterial tissue, strong upregulation is seen in atherosclerotic arteries (Liu et al. 2006; Sukhova et al. 1998).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fibre breakdown and chronic arterial inflammation is reported. In APO E deficient mice a significant reduction of acute plaque rupture events was reported. When chronic renal disease is introduced into CatS/In APO-E deficient mice a strong reduction of accelerated calcification is seen on top of the anti atherosclerotic activity in arteries and heart valves (Aikawa et al. 2009; de Nooijer et al. 2009; Rodgers et al. 2006; Sukhova et al. 2003). This suggests a potential inhibitor of Cathepsin S would stabilise atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly; Cathepsin S is involved in the degradation of extracellular matrix that stabilises the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells, resulting in reduced contribution of Tcells to the chronic inflammation of the atherosclerotic tissue. Elevated inflammation results in further oxidative and proteolytic tissue damage and subsequently plaque destabilisation (Cheng et al. 2004; Driessen et al. 1999; Rudensky and Beers 2006).

The anti-inflammatory and anti-elastinolytic properties of a Cat S inhibitor make it also a prominent target for chronic obstructive pulmonary disease (Williams et al. 2009). Furthermore due to its extracellular functions in matrix degradation, inhibition of cathepsin S will impact neointima formation and angiogenesis (Burns-Kurtis et al. 2004; Cheng et al. 2004; Shi et al. 2003; Wang et al. 2006). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15(19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

Cathepsin L shows a broader expression profile than cathepsin S and there are also data which suggest a role of cathepsin L in atherosclerosis, e.g. LDLrec & Cat L deficient mice show a reduced atherosclerotic phenotype (Kitamoto et al. 2007). In addition, Cat L was suggested to be involved in metabolic syndrome as it controls adipogenesis and peripheral glucose tolerance. In renal disease Cathepsin L is described to regulate podocyte function by proteolytically processing dynamin and thereby proteinuria (Sever et al. 2007).

Tissue remodelling, extracellular matrix degradation, the generation of active neuropeptides and roles in antigen presentation in thymic epithelial cells are cellular activities described for Cathepsin L (Funkelstein et al. 2008; Rudensky and Beers 2006).

SUMMARY OF THE INVENTION

The present invention relates to compounds of formula (I)

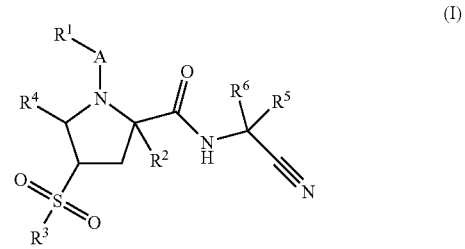

wherein
$R^1$ is selected from the group consisting of: hydrogen, alkyl, haloalkyl, alkoxy, alkoxyalkyl, cycloalkyl, cycloalkylalkyl, alkylcycloalkyl, haloalkylcycloalkyl, phenylcycloalkyl, halocycloalkyl, phenylhaloalkyl, halophenylcycloalkyl, alkoxycarbonylaminocycloalkyl, cyanoalkylcycloalkyl, halophenylalkyl, pyridinylcycloalkyl, aminocycloalkylalkyl, aminocarbonylphenylcycloalkyl, haloalkyloxyphenylcycloalkyl, alkylpyrazolylphenylcycloalkyl, bis(halophenyl)alkyl, phenylcycloalkyl, alkylphenylcycloalkyl, haloalkylphenylcycloalykl, halophenyldioxolane, naphtylcycloalkyl, halopyridinylcycloalkyl, benzo[1,3]dioxolyl, naphtyldioxolane, halo-1H-indazolyl, halophenylhyrdoxyalkyl, (halophenyl)(alkoxycarbonylamino)alkyl, alkylthiazolylcycloalkyl, halopyrimidinylalkyl, (halophenyl)(amino)alkyl, (halophenyl)(haloalkylamino)alkyl, haloalkylpyrazolylalkyl, (halophenyl)(alkoxycarbonylpiperidinyl), (halophenyl)(morpholinyl)alkyl, halophenylhaloalkyl, alkylphenylcycloalkyl, hydroxyalkylcycloalkyl, (halophenyl)(alkenylamino)alkyl, alkoxyhalophenylcycloalkyl, halonaphtylcycloalkyl, halophenyloxycycloalkyl, phenyltetrahydropyranyl and $R^{11}$;
A is absent or selected from the group consisting of: —CH$_2$—, —CH$_2$CH$_2$—, carbonyl, —C(O)O—, and —SO$_2$—;
$R^2$ is selected from the group consisting of: hydrogen, alkyl, haloalkyl, cycloalkyl, phenyl, phenylalkyl and phenylsulfonylalkyl; or A, $R^1$ and $R^2$ together form —$CH_2CH_2$—, —$CH_2CF_2CH_2$—, —$CH_2CH_2CH_2$—, —$CH_2CH_2CH_2CH_2$—; —$CH_2CH_2OCH_2$— or —$CH_2CH_2CH(CN)$—;

$R^3$ is selected from the group consisting of: alkyl, hydroxyalkyl, cycloalkyl, phenyl, phenylalkyl and substituted phenyl, wherein said substituted phenyl is phenyl substituted with one to three substituents independently selected from the group consisting of: alkyl, haloalkyl, hydroxyalkyl, alkoxy, haloalkyloxy, halogen, pyrazolyl, alkylopyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, haloalkylpiperidinyl, piperidinylalkoxy, oxetanyloxy, alkylpyrazolyl, halopyridinyl, alkylpyridinyl, cycloalkyl, cycloalkylalkyl, halophenyl, alkylcarbonylaminocycloalkylalkyl, haloalkylpiperazinyl, alkylamino, alkoxyalkylpiperazinyl, cycloalkylpiperazinyl, hexahydropyrrolo[1,2-a]pyrazinyl, 5,6-dihydro-8H-[1,2,4]triazolo[4,3-a]pyrazin-7-yl, alkylimidazolyl, azetidinyl, cycloalkylpiperazinyl, alkylimidazolyl, alkoxyalkoxy, imidazo[4,5-c]pyridinyl, alkylpiperazinyl, hexahydro-pyrrolo[1,2-a]pyrazinyl, haloazetidinyl, pyrimindinyl and alkenyloxy;

$R^4$ is selected from the group consisting of: hydrogen, alkyl, haloalkyl, alkoxy, alkoxyalkyl, cycloalkyl, cycloalkyloxy, phenyl, alkylphenyl, halophenyl, phenyloxy and halophenyloxy;

$R^5$ and $R^6$ are each independently selected from the group consisting of: hydrogen, alkyl, cycloalkyl, alkyloxy, hydroxyalkyl, haloalkyl, haloalkyloxy, phenyl and phenylalkyloxy;

or $R^5$ and $R^6$, together with the carbon atom to which they are attached, form cycloalkyl, pyrrolidinyl or piperidinyl; and $R^{11}$ is selected from the group consisting of: phenyl, substituted phenyl, tetrahydropyranyl, pyridinyl, alkylpyridinyl, haloalkylpyridinyl, oxetanyl, alkyloxetanyl, pyrrolidinyl, alkylpyrrolidinyl, pyrimidinyl, haloalkylpyrimidinyl, alkylpiperidinyl, naphtyl, biphenyl, haloalkyl-[1,3,4]thiadiazolyl, alkoxycarbonylpiperidinyl, halo-[1,2,4]thiadiazolyl, pyrazolyl and substituted pyrazolyl, wherein substituted phenyl and substituted pyrazolyl are phenyl and pyrazolyl each substituted with one to three substituents independently selected from the group consisting of: alkyl, halogen, haloalkyl, alkoxy, alkoxycarbonyl, halophenyl, halopyridinyl, oxodihydropyridinyl, nitro, thiazolyl, haloalkylphenyl, alkylphenyl, phenyl, alkylpyridinyl, tetrahydropyranyl, pyridazinyl, cycloalkyl, phenylalkyl, oxazolyl, alkoxyphenyl, quinolinyl, alkylcarbonylaminophenyl, haloalkoxy, alkylsulfonyl, phenylalkoxycarbonylpiperidinyl, piperidinyl, thiopyranyl, dioxothiopyranyl, morpholinylalkyl and alkylimidazolyl;

or a pharmaceutically acceptable salt thereof.

The compounds of the invention are preferential inhibitors of the cysteine protease Cathepsin (Cat), in particular Cathepsin S or Cathepsin L, and are therefore useful to treat metabolic diseases like diabetes, atherosclerosis, abdominal aortic aneurysm, peripheral arterial disease, cancer, reduction of cardiovascular events in chronic kidney disease and diabetic nephropathy. In addition, immune mediated diseases like rheumatoid arthritis, multiple sclerosis, sjorgen syndrome, lupus erythematosus, neuropathic pain, diabetes type I, asthma and allergy and skin related immune disease are suitable diseases to be treated with a cathepsin S inhibitor.

Further objects of the present invention are the use of the aforementioned compounds as therapeutically active substances, a process for the manufacture of the said compounds, intermediates, pharmaceutical compositions, medicaments containing the said compounds, their pharmaceutically acceptable salts, the use of the said compounds and salts for the prophylaxis and/or therapy of illnesses, especially in the treatment or prophylaxis of diabetes, atherosclerosis, abdominal aortic aneurysm, peripheral arterial disease, cancer, reduction of cardiovascular events in chronic kidney disease and diabetic nephropathy, and the use of the said compounds and salts for the production of medicaments for the treatment or prophylaxis of diabetes, atherosclerosis, abdominal aortic aneurysm, peripheral arterial disease, cancer, reduction of cardiovascular events in chronic kidney disease and diabetic nephropathy.

DETAILED DESCRIPTION OF THE INVENTION

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl, ethyl, propyl, isopropyl, isobutyl and tert.-butyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, cyclobutyl, cyclopentyl, cyclohexyl, cycloheptyl, and cyclooctyl. Preferred cycloalkyl are cyclopropyl, cyclobutyl, cyclopentyl and cyclohexyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy, ethoxy, propoxy, isopropoxy and tert.butoxy.

The term "cycloalkyloxy", alone or in combination, signifies a group of the formula cycloalkyl-O— in which the term "cycloalkyl" has the previously given significance, such as cyclobutyloxy, cyclopentyloxy or cyclohexyloxy.

The term "phenyloxy", alone or in combination, signifies a phenyl-O— group.

The term "oxy", alone or in combination, signifies the —O— group.

The term "halogen" or "halo", alone or in combination, signifies fluorine, chlorine, bromine or iodine and preferably fluorine, chlorine or bromine.

The terms "haloalkyl", "halocycloalkyl" and "haloalkoxy", alone or in combination, denote an alkyl group, a cycloalkyl group and an alkoxy group substituted with at least one halogen, preferably substituted with one to five halogens. Fluoroalkyl is a subgroup of haloalkyl. Preferred haloalkyl are difluoromethyl, trifluoromethyl, trifluoroethyl, trifluoropropyl, pentafluoroethyl and pentafluoropropyl. Fluorocycloalkyl is a subgroup of halocycloalkyl. A preferred fluorocycloalkyl is difluorocyclopropyl. Preferred haloalkyl are difluoromethyl, trifluoromethyl, trifluoroethyl, trifluoropropyl, pentafluoroethyl and pentafluoropropyl.

The term "carbonyl", alone or in combination, signifies the —C(O)— group.

The term "carboxy", alone or in combination, signifies the —COOH group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula (I) can also be present in the form of zwitterions. Particularly preferred pharmaceutically acceptable salts of compounds of formula (I) are the hydrochlorides, formiates, sulfates, phosphates and mesylates, in particular the hydrochlorides and formiates.

The present invention relates in part to a compound of formula (I)

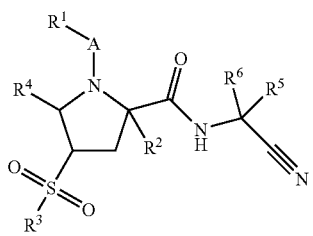

wherein $R^1$ is selected from the group consisting of: hydrogen, alkyl, haloalkyl, alkoxy, alkoxyalkyl, cycloalkyl, cycloalkylalkyl, alkylcycloalkyl, haloalkylcycloalkyl, phenylcycloalkyl, halocycloalkyl, phenylhaloalkyl, halophenylcycloalkyl, alkoxycarbonylaminocycloalkyl, cyanoalkylcycloalkyl, halophenylalkyl, pyridinylcycloalkyl, aminocycloalkylalkyl, aminocarbonylphenylcycloalkyl, haloalkyloxyphenylcycloalkyl, alkylpyrazolylphenylcycloalkyl, bis(halophenyl)alkyl, phenylcycloalkyl, alkylphenylcycloalkyl, haloalkylphenylcycloalykl, halophenyldioxolane, naphtylcycloalkyl, halopyridinylcycloalkyl, benzo[1,3]dioxolyl, naphtyldioxolane, halo-1H-indazolyl, halophenylhyrdoxyalkyl, (halophenyl)(alkoxycarbonylamino)alkyl, alkylthiazolylcycloalkyl, halopyrimidinylalkyl, (halophenyl)(amino) alkyl, (halophenyl)(haloalkylamino)alkyl, haloalkylpyrazolylalkyl, (halophenyl)(alkoxycarbonylpiperidinyl), (halophenyl)(morpholinyl)alkyl, halophenylhaloalkyl, alkylphenylcycloalkyl, hydroxyalkylcycloalkyl, (halophenyl)(alkenylamino)alkyl, alkoxyhalophenylcycloalkyl, halonaphtylcycloalkyl, halophenyloxycycloalkyl, phenyltetrahydropyranyl and $R^{11}$;

A is absent or selected from the group consisting of: —CH$_2$—, —CH$_2$CH$_2$—, carbonyl, —C(O)O—, and —SO$_2$—;

$R^2$ is selected from the group consisting of: hydrogen, alkyl, haloalkyl, cycloalkyl, phenyl, phenylalkyl and phenylsulfonylalkyl;

or A, $R^1$ and $R^2$ together form —CH$_2$CH$_2$—, —CH$_2$CF$_2$CH$_2$—, —CH$_2$CH$_2$CH$_2$—, —CH$_2$CH$_2$CH$_2$CH$_2$—; —CH$_2$CH$_2$OCH$_2$— or —CH$_2$CH$_2$CH(CN)—;

$R^3$ is selected from the group consisting of: alkyl, hydroxyalkyl, cycloalkyl, phenyl, phenylalkyl and substituted phenyl, wherein said substituted phenyl is phenyl substituted with one to three substituents independently selected from the group consisting of: alkyl, haloalkyl, hydroxyalkyl, alkoxy, haloalkyloxy, halogen, pyrazolyl, alkylopyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxomorpholinyl, oxo-pyridinyl, 2-oxo-2H-pyrazinyl, difluoropiperidinyl, haloalkylpiperidinyl, piperidinylalkoxy, oxetanyloxy, alkylpyrazolyl, halopyridinyl, alkylpyridinyl, cycloalkyl, cycloalkylalkyl, halophenyl, alkylcarbonylaminocycloalkylalkyl, haloalkylpiperazinyl, alkylamino, alkoxyalkylpiperazinyl, cycloalkylpiperazinyl, hexahydropyrrolo[1,2-a]pyrazinyl, 5,6-dihydro-8H-[1,2,4]triazolo[4,3-a]pyrazin-7-yl, alkylimidazolyl, azetidinyl, cycloalkylpiperazinyl, alkylimidazolyl, alkoxyalkoxy, imidazo[4,5-c]pyridinyl, alkylpiperazinyl, hexahydro-pyrrolo[1,2-a]pyrazinyl, haloazetidinyl, pyrimindinyl and alkenyloxy;

$R^4$ is selected from the group consisting of: hydrogen, alkyl, haloalkyl, alkoxy, alkoxyalkyl, cycloalkyl, cycloalkyloxy, phenyl, alkylphenyl, halophenyl, phenyloxy and halophenyloxy;

$R^5$ and $R^6$ are each independently selected from the group consisting of: hydrogen, alkyl, cycloalkyl, alkyloxy, hydroxyalkyl, haloalkyl, haloalkyloxy, phenyl and phenylalkyloxy;

or $R^5$ and $R^6$, together with the carbon atom to which they are attached, form cycloalkyl, pyrrolidinyl or piperidinyl; and $R^{11}$ is selected from the group consisting of: phenyl, substituted phenyl, tetrahydropyranyl, pyridinyl, alkylpyridinyl, haloalkylpyridinyl, oxetanyl, alkyloxetanyl, pyrrolidinyl, alkylpyrrolidinyl, pyrimidinyl, haloalkylpyrimidinyl, alkylpiperidinyl, naphtyl, biphenyl, haloalkyl-[1,3,4]thiadiazolyl, alkoxycarbonylpiperidinyl, halo-[1,2,4]thiadiazolyl, pyrazolyl and substituted pyrazolyl, wherein substituted phenyl and substituted pyrazolyl are phenyl and pyrazolyl each substituted with one to three substituents independently selected from the group consisting of: alkyl, halogen, haloalkyl, alkoxy, alkoxycarbonyl, halophenyl, halopyridinyl, oxodihydropyridinyl, nitro, thiazolyl, haloalkylphenyl, alkylphenyl, phenyl, alkylpyridinyl, tetrahydropyranyl, pyridazinyl, cycloalkyl, phenylalkyl, oxazolyl, alkoxyphenyl, quinolinyl, alkylcarbonylaminophenyl, haloalkoxy, alkylsulfonyl, phenylalkoxycarbonylpiperidinyl, piperidinyl, thiopyranyl, dioxothiopyranyl, morpholinylalkyl and alkylimidazolyl;

or a pharmaceutically acceptable salt thereof.

One embodiment of the invention is a compounds of formula (I) wherein:

$R^1$ is selected from the group consisting of: hydrogen, alkyl, haloalkyl, alkoxy, alkoxyalkyl, cycloalkyl, cycloalkylalkyl, alkylcycloalkyl, haloalkylcycloalkyl, phenylcycloalkyl, halocycloalkyl, phenylhaloalkyl and $R^{11}$;

A is absent or selected from the group consisting of: —$CH_2$—, —$CH_2CH_2$—, carbonyl, —C(O)O—, and —$SO_2$—;

$R^2$ is selected from the group consisting of: hydrogen, alkyl, haloalkyl, cycloalkyl, phenyl and phenylalkyl;

or A, $R^1$ and $R^2$ together form —$CH_2CH_2$—, —$CH_2CF_2CH_2$—, —$CH_2CH_2CH_2$—, —$CH_2CH_2CH_2CH_2$— or —$CH_2CH_2OCH_2$—;

$R^3$ is selected from the group consisting of: alkyl, hydroxyalkyl, cycloalkyl, phenyl, phenylalkyl or substituted phenyl, wherein said substituted phenyl is phenyl substituted with one to three substituents independently selected from the group consisting of: alkyl, haloalkyl, hydroxyalkyl, haloalkyloxy, halogen, pyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, haloalkylpiperidinyl, piperidinylalkoxy and oxetanyloxy;

$R^4$ is selected from the group consisting of: hydrogen, alkyl, haloalkyl, alkoxy, alkoxyalkyl, cycloalkyl, cycloalkyloxy, phenyl, halophenyl, phenyloxy and halophenyloxy;

$R^5$ and $R^6$ are each independently selected from the group consisting of: hydrogen, alkyl, cycloalkyl, alkyloxy, hydroxyalkyl, haloalkyl, haloalkyloxy, phenyl and phenylalkyloxy;

or $R^5$ and $R^6$, together with the carbon atom to which they are attached, form cycloalkyl, pyrrolidinyl or piperidinyl; and $R^{11}$ is selected from the group consisting of: phenyl, substituted phenyl, tetrahydropyranyl, pyridinyl, alkylpyridinyl, haloalkylpyridinyl, oxetanyl, pyrrolidinyl, alkylpyrrolidinyl, pyrimidinyl, haloalkylpyrimidinyl, alkylpiperidinyl, pyrazolyl and substituted pyrazolyl, wherein said substituted phenyl and substituted pyrazolyl are respectively phenyl and pyrazolyl substituted with one to three substituents independently selected from the group consisting of: alkyl, halogen, haloalkyl, alkoxy, alkoxycarbonyl, halophenyl, halopyridinyl, oxodihydropyridinyl and nitro; or a pharmaceutically acceptable salt thereof.

In another embodiment of the present invention, $R^1$ is selected from the group consisting of: hydrogen, alkyl, haloalkyl, alkoxy, alkoxyalkyl, cycloalkyl, cycloalkylalkyl, alkylcycloalkyl, haloalkylcycloalkyl, phenylcycloalkyl, halocycloalkyl, phenylhaloalkyl and $R^{11}$.

In a further embodiment of the invention, $R^1$ is selected from the group consisting of: hydrogen, alkyl, fluoroalkyl, phenylfluoroalkyl, alkoxy, alkoxymethyl, alkylcyclopropyl, difluorocyclopropyl, trifluoromethylcyclopropyl, phenylcyclopropyl, chlorophenylcyclopropyl, cyclobutyl, cyclohexyl, trifluoromethylcyclohexyl, trifluoromethylcyclobutyl and cyclopentyloxy.

Furthermore, in another embodiment, $R^1$ is selected from the group consisting of: hydrogen, methyl, ethyl, propyl, butyl, difluoromethyl, trifluoromethyl, trifluoroethyl, pentafluoroethyl, trifluoropropyl, phenyltrifluoroethyl, methoxy, propyloxy, butyloxy, methoxymethyl, methylcyclopropyl, difluorocyclopropyl, trifluoromethylcyclopropyl, phenylcyclopropyl, chlorophenylcyclopropyl, cyclobutyl, cyclohexyl, trifluoromethylcyclohexyl, trifluoromethylcyclobutyl and cyclopentyloxy.

In a further embodiment of the invention, $R^1$ is selected from the group consisting of: tert-butyl, trifluoromethylcyclopropyl, methylcyclopropyl and chlorophenylcyclopropyl.

A compound of formula (I) wherein $R^1$ is selected from the group consisting of: alkyl, haloalkylcycloalkyl, alkylcycloalkyl and halophenylcycloalkyl is also another embodiment of the invention.

A compound of formula (I) wherein $R^1$ is selected from the group consisting of: alkyl, fluoroalkylcyclopropyl, alkylcyclopropyl and chlorophenylcyclopropyl is a further embodiment of the invention.

Moreover, in a particular embodiment of the invention, A is absent or selected from the group consisting of: —$CH_2$—, —$CH_2CH_2$—, and carbonyl.

In a further embodiment of the invention, A is carbonyl.

A compound of formula (I) wherein $R^2$ is hydrogen or alkyl is another embodiment of the invention.

A compound of formula (I) wherein $R^2$ is hydrogen is a particular embodiment of the invention.

In a particular embodiment of the invention, $R^2$ is butyl, in particular i-butyl.

Further, in another embodiment of the invention, A, $R^1$ and $R^2$ together form —$CH_2CH_2$—, —$CH_2CF_2CH_2$—, —$CH_2CH_2CH_2$—, —$CH_2CH_2CH_2CH_2$— or —$CH_2CH_2OCH_2$—. In this case, a compound of formula (I) wherein A, $R^1$ and $R^2$ together form —$CH_2CF_2CH_2$— is a particular embodiment of the invention.

In another embodiment of the invention, $R^3$ is selected from the group consisting of: alkyl, hydroxyalkyl, cycloalkyl, phenyl and substituted phenyl, wherein said substituted phenyl is phenyl substituted with one to three substituents independently selected from the group consisting of: alkyl, haloalkyl, haloalkoxy, hydroxyalkyl, halogen, pyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, trifluoromethylpiperidinyl, piperidinylmethoxy and oxetanyloxy.

Furthermore, in another embodiment, $R^3$ is selected from the group consisting of: alkyl, hydroxyalkyl, cycloalkyl, phenyl and substituted phenyl, wherein said substituted phenyl is phenyl substituted with one to three substituents independently selected from the group consisting of: methyl, trifluoromethyl, trifluoroethyloxy, trifluoromethoxy, hydroxymethyl, fluoro, bromo, chloro, pyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, trifluoromethylpiperidinyl, piperidinylmethoxy and oxetanyloxy.

A compound of formula (I) wherein $R^3$ is phenyl substituted with one or two substituents independently selected from the group consisting of: chloro, trifluoromethyl, trifluoromethoxy, trifluoroethyloxy and pyrazolyl is a particular embodiment of the invention.

Moreover, a compound of formula (I) wherein $R^3$ is selected from the group consisting of: dichlorophenyl, (chloro)(pyrazolyl)phenyl, (chloro)(trifluoroethoxy)phenyl, (chloro)(trifluoropropoxy)phenyl, trifluoromethylphenyl, (trifluoroethoxy) (trifluoromethyl)phenyl and chlorophenyl is another particular embodiment of the invention.

A compound of formula (I) wherein $R^3$ is phenyl substituted with one or two substituents independently selected from the group consisting of: halogen, haloalkyl, haloalkoxy and pyrazolyl is also an embodiment of the invention.

In a particular embodiment of the invention, $R^4$ is hydrogen.

In another embodiment of the invention, R⁵ is selected from the group consisting of: hydrogen, alkyl, cycloalkyl and phenyl.

In a further embodiment of the invention, R⁵ is selected from the group consisting of: hydrogen, methyl, cyclopropyl and phenyl.

In a still further embodiment of the invention, R⁶ is hydrogen.

In an embodiment of the invention, R⁵ and R⁶, together with the carbon atom to which they are attached, form cycloalkyl.

Furthermore, a compound of formula (I) wherein R⁵ and R⁶, together with the carbon atom to which they are attached, form cyclopropyl, cyclobutyl, or cyclohexyl is a particular embodiment of the invention.

A compound of formula (I) wherein R⁵ and R⁶, together with the carbon atom to which they are attached, form cyclopropyl is another embodiment of the invention.

In a particular embodiment of the invention, R¹¹ is selected from the group consisting of: phenyl, substituted phenyl, tetrahydropyranyl, pyridinyl, alkylpyridinyl, alkylpyridinyl, oxetanyl, pyrrolidinyl, alkylpyrrolidinyl, pyrimidinyl, haloalkylpyrimidinyl, alkylpiperidinyl, pyrazolyl and substituted pyrazolyl, wherein said substituted phenyl and substituted pyrazolyl are respectively phenyl and pyrazolyl each substituted with one to three substituents independently selected from the group consisting of: alkyl, halogen, alkoxy, alkoxycarbonyl, haloalkoxy, haloalkyl, halophenyl, halopyridinyl, oxodihydropyridinyl and nitro.

In another particular embodiment of the invention, R¹¹ is selected from the group consisting of: phenyl, substituted phenyl, tetrahydropyranyl, pyridinyl, methylpyridinyl, trifluoromethylpyridinyl, oxetanyl, pyrrolidinyl, methylpyrrolidinyl, pyrimidinyl, trifluoromethylpyrimidinyl, methylpiperidinyl, pyrazolyl and substituted pyrazolyl, wherein said substituted phenyl and substituted pyrazolyl are respectively phenyl and pyrazolyl each substituted with one to three substituents independently selected from the group consisting of: methyl, fluoro, methoxy, methoxycarbonyl, trifluoromethoxy, trifluoromethyl, chlorophenyl, fluorophenyl, chloropyridinyl, oxodihydropyridinyl and nitro.

In a further embodiment of the invention, R¹¹ is selected from the group consisting of: phenyl, fluorophenyl, chlorophenyl, methoxyphenyl, methoxycarbonylphenyl, trifluoromethylphenyl, nitrophenyl, tetrahydropyranyl, pyridinyl, methylpyridinyl, trifluoromethylpyridinyl, oxetanyl, pyrrolidinyl, methylpyrrolidinyl, pyrimidinyl, trifluoromethylpyrimidinyl, methylpiperidinyl, pyrazolyl, methyl-phenyl-pyrazolyl, chloropyridinyl-methyl-pyrazolyl, chlorophenyl-methyl-pyrazolyl, fluorophenyl-methyl-pyrazolyl and oxodihydropyridinyl-methyl-pyrazolyl.

The following compounds of formula (I) are particular embodiments of the invention:

(2S,4R)-4-Benzenesulfonyl-1-benzoyl-pyrrolidine-2-carboxylic acid cyanomethyl-amide;
(2S,4R)-4-Benzenesulfonyl-1-benzyl-pyrrolidine-2-carboxylic acid cyanomethyl-amide;
(2S,4R)-4-Benzenesulfonyl-1-cyclohexylmethyl-pyrrolidine-2-carboxylic acid cyanomethyl-amide;
(2S,4R)-4-Benzenesulfonyl-1-(2,2,2-trifluoro-1-phenyl-ethyl)-pyrrolidine-2-carboxylic acid cyanomethyl-amide;
(2S,4R)-4-Benzenesulfonyl-1-cyclohexanecarbonyl-pyrrolidine-2-carboxylic acid cyanomethyl-amide;
(2S,4R)-1-Benzoyl-4-(2-chloro-benzenesulfonyl)-pyrrolidine-2-carboxylic acid cyanomethyl-amide;
(2S,4R)-4-Benzenesulfonyl-1-benzoyl-pyrrolidine-2-carboxylic acid (1-cyano-cyclopropyl)-amide;
(2S,4R)-4-Benzenesulfonyl-1-(tetrahydro-pyran-4-carbonyl)-pyrrolidine-2-carboxylic acid (1-cyano-cyclopropyl)-amide;
(2S,4R)-4-(2-Chloro-benzenesulfonyl)-1-(2,2,2-trifluoro-1-phenyl-ethyl)-pyrrolidine-2-carboxylic acid cyanomethyl-amide;
(2S,4R)-4-(2-Chloro-benzenesulfonyl)-1-(4-fluoro-benzoyl)-pyrrolidine-2-carboxylic acid (1-cyano-cyclopropyl)-amide;
(2S,4R)-4-(2-Trifluoromethyl-benzenesulfonyl)-pyrrolidine-2-carboxylic acid (1-cyano-cyclopropyl)-amide;
(2S,4R)-1-Cyclohexanecarbonyl-4-(2-trifluoromethyl-benzenesulfonyl)-pyrrolidine-2-carboxylic acid (1-cyano-cyclopropyl)-amide;
(2S,4R)-1-(4-Fluoro-benzoyl)-4-(2-trifluoromethyl-benzenesulfonyl)-pyrrolidine-2-carboxylic acid (1-cyano-cyclopropyl)-amide;
(2S,4R)-4-(2-Trifluoromethyl-benzenesulfonyl)-1-(4-trifluoromethyl-cyclohexanecarbonyl)-pyrrolidine-2-carboxylic acid (1-cyano-cyclopropyl)-amide;
(2S,4R)-4-(2-Chloro-benzenesulfonyl)-pyrrolidine-2-carboxylic acid (1-cyano-cyclopropyl)-amide hydrochloride;
(2S,4R)-1-(2,2,3,3,3-Pentafluoro-propyl)-4-(2-trifluoromethyl-benzenesulfonyl)-pyrrolidine-2-carboxylic acid (1-cyano-cyclopropyl)-amide;
(2S,4R)-1-Benzoyl-4-(2-chloro-benzenesulfonyl)-pyrrolidine-2-carboxylic acid (1-cyano-cyclopropyl)-amide;
(2S,4R)-4-(2-Chloro-benzenesulfonyl)-1-cyclohexanecarbonyl-pyrrolidine-2-carboxylic acid (1-cyano-cyclopropyl)-amide;
(2S,4R)-4-(2-Chloro-benzenesulfonyl)-2-(1-cyano-cyclopropylcarbamoyl)-pyrrolidine-1-carboxylic acid ethyl ester;
(2S,4R)-4-(2-Chloro-benzenesulfonyl)-2-(1-cyano-cyclopropylcarbamoyl)-pyrrolidine-1-carboxylic acid cyclopentyl ester;
(2S,4R)-4-(2-Chloro-benzenesulfonyl)-2-(1-cyano-cyclopropylcarbamoyl)-pyrrolidine-1-carboxylic acid 4-fluorophenyl ester;
(2S,4R)-4-(2-Chloro-benzenesulfonyl)-1-pyridin-4-ylmethyl-pyrrolidine-2-carboxylic acid (1-cyano-cyclopropyl)-amide;
(2S,4R)-4-(2-Chloro-benzenesulfonyl)-1-ethyl-pyrrolidine-2-carboxylic acid (1-cyano-cyclopropyl)-amide;
(2S,4R)-4-(2-Chloro-benzenesulfonyl)-1-phenethyl-pyrrolidine-2-carboxylic acid (1-cyano-cyclopropyl)-amide;
(2S,4R)-4-(2-Chloro-benzenesulfonyl)-1-cyclobutyl-pyrrolidine-2-carboxylic acid (1-cyano-cyclopropyl)-amide;
(2S,4R)-4-(2-Chloro-benzenesulfonyl)-1-cyclohexyl-pyrrolidine-2-carboxylic acid (1-cyano-cyclopropyl)-amide;
(2S,4R)-4-(2-Chloro-benzenesulfonyl)-1-methyl-pyrrolidine-2-carboxylic acid (1-cyano-cyclopropyl)-methyl-amide;
(2S,4R)-4-(2-Chloro-benzenesulfonyl)-1-(2,2,2-trifluoro-ethyl)-pyrrolidine-2-carboxylic acid (1-cyano-cyclopropyl)-amide;
(2S,4R)-4-(2-Chloro-benzenesulfonyl)-1-(2,2-difluoro-ethyl)-pyrrolidine-2-carboxylic acid (1-cyano-cyclopropyl)-amide;
(2S,4R)-4-(2-Chloro-benzenesulfonyl)-1-(4-fluoro-benzoyl)-pyrrolidine-2-carboxylic acid cyanomethyl-amide;
(2S,4R)-4-(2-Chloro-benzenesulfonyl)-1-cyclohexanecarbonyl-pyrrolidine-2-carboxylic acid cyanomethyl-amide;
(2S,4R)-4-(2-Chloro-benzenesulfonyl)-1-propionyl-pyrrolidine-2-carboxylic acid cyanomethyl-amide;

(2S,4R)-4-(2-Chloro-benzenesulfonyl)-1-(2-methoxy-acetyl)-pyrrolidine-2-carboxylic acid cyanomethyl-amide;
(2S,4R)-4-(2-Chloro-benzenesulfonyl)-1-oxetan-3-yl-pyrrolidine-2-carboxylic acid cyanomethyl-amide;
(2S,4R)-4-(2-Chloro-benzenesulfonyl)-1-(tetrahydro-pyran-4-yl)-pyrrolidine-2-carboxylic acid cyanomethyl-amide;
(2S,4R)-1-Benzoyl-4-(2-trifluoromethyl-benzenesulfonyl)-pyrrolidine-2-carboxylic acid cyanomethyl-amide;
(2S,4R)-1-(4-Fluoro-benzoyl)-4-(2-trifluoromethyl-benzenesulfonyl)-pyrrolidine-2-carboxylic acid cyanomethyl-amide;
(2S,4R)-1-(4-Methyl-benzoyl)-4-(2-trifluoromethyl-benzenesulfonyl)-pyrrolidine-2-carboxylic acid cyanomethyl-amide;
(2S,4R)-1-Cyclohexanecarbonyl-4-(2-trifluoromethyl-benzenesulfonyl)-pyrrolidine-2-carboxylic acid cyanomethyl-amide;
(2S,4R)-1-(Tetrahydro-pyran-4-carbonyl)-4-(2-trifluoromethyl-benzenesulfonyl)-pyrrolidine-2-carboxylic acid cyanomethyl-amide;
(2S,4R)-1-(Pyridine-4-carbonyl)-4-(2-trifluoromethyl-benzenesulfonyl)-pyrrolidine-2-carboxylic acid cyanomethyl-amide;
(2S,4R)-1-(1-Methyl-piperidine-4-carbonyl)-4-(2-trifluoromethyl-benzenesulfonyl)-pyrrolidine-2-carboxylic acid cyanomethyl-amide;
(2S,4R)-2-(Cyanomethyl-carbamoyl)-4-(2-trifluoromethyl-benzenesulfonyl)-pyrrolidine-1-carboxylic acid cyclopentyl ester;
(2S,4R)-4-(2-Chloro-benzenesulfonyl)-1-(2,2,3,3,3-pentafluoro-propyl)-pyrrolidine-2-carboxylic acid (1-cyano-cyclopropyl)-amide;
(2S,4R)-4-(2-Chloro-benzenesulfonyl)-1-(3,3,3-trifluoro-2-methyl-propyl)-pyrrolidine-2-carboxylic acid (1-cyano-cyclopropyl)-amide;
(2S,4R)-4-(2-Chloro-benzenesulfonyl)-1-(3,3,3-trifluoro-propyl)-pyrrolidine-2-carboxylic acid (1-cyano-cyclopropyl)-amide;
6-Benzenesulfonyl-2,2-difluoro-tetrahydro-pyrrolizine-7a-carboxylic acid cyanomethyl-amide;
1-Benzenesulfonyl-6,6-difluoro-tetrahydro-pyrrolizine-7a-carboxylic acid cyanomethyl-amide;
1-Benzenesulfonyl-6,6-difluoro-tetrahydro-pyrrolizine-7a-carboxylic acid cyanomethyl-amide;
(2S,4R)-1-Acetyl-4-(2-chloro-benzenesulfonyl)-pyrrolidine-2-carboxylic acid (1-cyano-cyclopropyl)-amide;
(2S,4R)-4-(2-Chloro-benzenesulfonyl)-2-(1-cyano-cyclopropylcarbamoyl)-pyrrolidine-1-carboxylic acid methyl ester;
(2S,4R)-4-(2-Chloro-benzenesulfonyl)-2-(1-cyano-cyclopropylcarbamoyl)-pyrrolidine-1-carboxylic acid isopropyl ester;
(2S,4R)-4-(2-Chloro-benzenesulfonyl)-1-(2,2,2-trifluoro-acetyl)-pyrrolidine-2-carboxylic acid (1-cyano-cyclopropyl)-amide;
(2S,4R)-2-(1-Cyano-cyclopropylcarbamoyl)-4-(2,4-dimethyl-benzenesulfonyl)-pyrrolidine-1-carboxylic acid tert-butyl ester;
(2S,4R)-4-(2,4-Dimethyl-benzenesulfonyl)-pyrrolidine-2-carboxylic acid (1-cyano-cyclopropyl)-amide;
(2S,4R)-4-(2-Chloro-benzenesulfonyl)-2-[(cyano-phenyl-methyl)-carbamoyl]-pyrrolidine-1-carboxylic acid tert-butyl ester;
(2S,4R)-4-(2-Chloro-benzenesulfonyl)-2-[(cyano-methyl-phenyl-methyl)-carbamoyl]-pyrrolidine-1-carboxylic acid tert-butyl ester;
(2S,4R)-1-Benzyl-4-(2-trifluoromethyl-benzenesulfonyl)-pyrrolidine-2-carboxylic acid (1-cyano-cyclopropyl)-amide;
(2S,4R)-1-Pyridin-4-ylmethyl-4-(2-trifluoromethyl-benzenesulfonyl)-pyrrolidine-2-carboxylic acid (1-cyano-cyclopropyl)-amide;
(2S,4R)-4-(4-Chloro-2-methyl-benzenesulfonyl)-2-(1-cyano-cyclopropylcarbamoyl)-pyrrolidine-1-carboxylic acid tert-butyl ester;
(2S,4R)-4-(4-Chloro-2-methyl-benzenesulfonyl)-pyrrolidine-2-carboxylic acid (1-cyano-cyclopropyl)-amide;
(2S,4R)-4-(2-Chloro-benzenesulfonyl)-pyrrolidine-2-carboxylic acid (cyano-phenyl-methyl)-amide;
(2S,4R)-4-(2-Chloro-benzenesulfonyl)-pyrrolidine-2-carboxylic acid (cyano-methyl-phenyl-methyl)-amide;
(2S,4R)-1-Acetyl-4-(2-trifluoromethyl-benzenesulfonyl)-pyrrolidine-2-carboxylic acid (1-cyano-cyclopropyl)-amide;
(2S,4R)-1-(2,2,2-Trifluoro-acetyl)-4-(2-trifluoromethyl-benzenesulfonyl)-pyrrolidine-2-carboxylic acid (1-cyano-cyclopropyl)-amide;
(2S,4R)-4-(2-Chloro-benzenesulfonyl)-1-methyl-pyrrolidine-2-carboxylic acid (1-cyano-cyclopropyl)-amide;
(2S,4R)-4-(2-Chloro-benzenesulfonyl)-2-[(cyano-dimethyl-methyl)-carbamoyl]-pyrrolidine-1-carboxylic acid tert-butyl ester;
(2S,4R)-4-(2-Chloro-benzenesulfonyl)-2-(1-cyano-cyclobutylcarbamoyl)-pyrrolidine-1-carboxylic acid tert-butyl ester;
(2S,4R)-4-(2-Chloro-benzenesulfonyl)-2-(1-cyano-cyclohexylcarbamoyl)-pyrrolidine-1-carboxylic acid tert-butyl ester;
(2S,4R)-4-(2-Chloro-benzenesulfonyl)-pyrrolidine-2-carboxylic acid (1-cyano-cyclohexyl)-amide;
(2S,4R)-4-(2-Chloro-benzenesulfonyl)-pyrrolidine-2-carboxylic acid (cyano-dimethyl-methyl)-amide;
(2S,4R)-4-(2-Chloro-benzenesulfonyl)-pyrrolidine-2-carboxylic acid (1-cyano-cyclobutyl)-amide;
(2S,4R)-2-(1-Cyano-cyclopropylcarbamoyl)-4-(2,3-dichloro-benzenesulfonyl)-pyrrolidine-1-carboxylic acid tert-butyl ester;
(2S,4R)-4-(2,3-Dichloro-benzenesulfonyl)-pyrrolidine-2-carboxylic acid (1-cyano-cyclopropyl)-amide;
(R)-4-(2-Chloro-benzenesulfonyl)-1-((S)-1-methyl-pyrrolidine-2-carbonyl)-pyrrolidine-2-carboxylic acid (1-cyano-cyclopropyl)-amide;
(2S,4R)-1-Propionyl-4-(2-trifluoromethyl-benzenesulfonyl)-pyrrolidine-2-carboxylic acid (1-cyano-cyclopropyl)-amide;
(2S,4R)-4-(2-Chloro-benzenesulfonyl)-1-(1-methyl-piperidine-4-carbonyl)-pyrrolidine-2-carboxylic acid (1-cyano-cyclopropyl)-amide;
(2S,4R)-1-(2-Methoxy-ethyl)-4-(2-trifluoromethyl-benzenesulfonyl)-pyrrolidine-2-carboxylic acid (1-cyano-cyclopropyl)-amide;
(2S,4R)-4-(2-Ethyl-benzenesulfonyl)-pyrrolidine-2-carboxylic acid (1-cyano-cyclopropyl)-amide;
(2S,4R)-2-(1-Cyano-cyclopropylcarbamoyl)-4-(2,4-dichloro-benzenesulfonyl)-pyrrolidine-1-carboxylic acid tert-butyl ester;
(2S,4R)-4-(2,4-Dichloro-benzenesulfonyl)-pyrrolidine-2-carboxylic acid (1-cyano-cyclopropyl)-amide;
(2S,4R)-2-(1-Cyano-cyclopropylcarbamoyl)-4-(2,6-dichloro-benzenesulfonyl)-pyrrolidine-1-carboxylic acid tert-butyl ester;
(2S,4R)-4-(2,6-Dichloro-benzenesulfonyl)-pyrrolidine-2-carboxylic acid (1-cyano-cyclopropyl)-amide;

(2S,4R)-2-(1-Cyano-cyclopropylcarbamoyl)-4-(2-hydroxymethyl-benzenesulfonyl)-pyrrolidine-1-carboxylic acid tert-butyl ester;
(2S,4R)-4-(2-Hydroxymethyl-benzenesulfonyl)-pyrrolidine-2-carboxylic acid (1-cyano-cyclopropyl)-amide;
4-[(2S,4R)-2-(1-Cyano-cyclopropylcarbamoyl)-4-(2-trifluoromethyl-benzenesulfonyl)-pyrrolidine-1-carbonyl]-benzoic acid methyl ester;
(2S,4R)-1-Phenyl-4-(2-trifluoromethyl-benzenesulfonyl)-pyrrolidine-2-carboxylic acid (1-cyano-cyclopropyl)-amide;
(2S,4R)-2-(1-Cyano-cyclopropylcarbamoyl)-4-(2-trifluoromethoxy-benzenesulfonyl)-pyrrolidine-1-carboxylic acid tert-butyl ester;
(2S,4R)-2-(1-Cyano-cyclopropylcarbamoyl)-4-(2,4-difluoro-benzenesulfonyl)-pyrrolidine-1-carboxylic acid tert-butyl ester;
(2S,4R)-2-(1-Cyano-cyclopropylcarbamoyl)-4-(4-imidazol-1-yl-benzenesulfonyl)-pyrrolidine-1-carboxylic acid tert-butyl ester;
(2S,4R)-4-(2-Trifluoromethoxy-benzenesulfonyl)-pyrrolidine-2-carboxylic acid (1-cyano-cyclopropyl)-amide;
(2S,4R)-4-(2,4-Difluoro-benzenesulfonyl)-pyrrolidine-2-carboxylic acid (1-cyano-cyclopropyl)-amide;
(2S,4R)-2-[(Cyano-cyclopropyl-methyl)-carbamoyl]-4-(2-trifluoromethyl-benzenesulfonyl)-pyrrolidine-1-carboxylic acid tert-butyl ester;
(2S,4R)-4-(4-Imidazol-1-yl-benzenesulfonyl)-pyrrolidine-2-carboxylic acid (1-cyano-cyclopropyl)-amide;
(2S,4R)-4-(4-Bromo-2-trifluoromethyl-benzenesulfonyl)-2-(1-cyano-cyclopropylcarbamoyl)-pyrrolidine-1-carboxylic acid tert-butyl ester;
(2S,4R)-4-(4-Bromo-2-trifluoromethyl-benzenesulfonyl)-pyrrolidine-2-carboxylic acid (1-cyano-cyclopropyl)-amide;
(2S,4R)-4-(2-Chloro-benzenesulfonyl)-1-formyl-pyrrolidine-2-carboxylic acid (1-cyano-cyclopropyl)-amide;
(2S,4R)-4-(2-Chloro-4-pyrazol-1-yl-benzenesulfonyl)-2-(1-cyano-cyclopropylcarbamoyl)-pyrrolidine-1-carboxylic acid tert-butyl ester;
(2S,4R)-4-(2-Chloro-4-piperidin-1-yl-benzenesulfonyl)-2-(1-cyano-cyclopropylcarbamoyl)-pyrrolidine-1-carboxylic acid tert-butyl ester;
(2S,4R)-4-[2-Chloro-4-(2,2,2-trifluoro-1-methyl-ethoxy)-benzenesulfonyl]-2-(1-cyano-cyclopropylcarbamoyl)-pyrrolidine-1-carboxylic acid tert-butyl ester;
(2R,4S,5R)-5-(4-Fluoro-phenyl)-2-isobutyl-4-methanesulfonyl-pyrrolidine-2-carboxylic acid (1-cyano-cyclopropyl)-amide;
(2S,4R)-4-(2-Chloro-4-fluoro-benzenesulfonyl)-2-(1-cyano-cyclopropylcarbamoyl)-pyrrolidine-1-carboxylic acid tert-butyl ester;
(2R,4S,5R)-2-(1-Cyano-cyclopropylcarbamoyl)-5-(4-fluoro-phenyl)-2-isobutyl-4-methanesulfonyl-pyrrolidine-1-carboxylic acid tert-butyl ester;
(2R,4S,5R)-4-Benzenesulfonyl-5-(4-fluoro-phenyl)-2-isobutyl-pyrrolidine-2-carboxylic acid (1-cyano-cyclopropyl)-amide;
(2S,4R)-1-Formyl-4-(2-trifluoromethyl-benzenesulfonyl)-pyrrolidine-2-carboxylic acid (1-cyano-cyclopropyl)-amide;
(2S,4R)-4-(4-Pyrazol-1-yl-2-trifluoromethyl-benzenesulfonyl)-pyrrolidine-2-carboxylic acid (1-cyano-cyclopropyl)-amide;
(2S,4R)-4-(4-Imidazol-1-yl-2-trifluoromethyl-benzenesulfonyl)-pyrrolidine-2-carboxylic acid (1-cyano-cyclopropyl)-amide;
(2S,4R)-2-(1-Cyano-cyclopropylcarbamoyl)-4-(2-methyl-propane-1-sulfonyl)-pyrrolidine-1-carboxylic acid tert-butyl ester;
(2S,4R)-4-(2-Methyl-propane-1-sulfonyl)-pyrrolidine-2-carboxylic acid (1-cyano-cyclopropyl)-amide;
(2S,4R)-4-(4-Benzoimidazol-1-yl-2-trifluoromethyl-benzenesulfonyl)-2-(1-cyano-cyclopropylcarbamoyl)-pyrrolidine-1-carboxylic acid tert-butyl ester;
(2S,4R)-2-(1-Cyano-cyclopropylcarbamoyl)-4-[4-(3-methyl-6-oxo-6H-pyridazin-1-yl)-2-trifluoromethyl-benzenesulfonyl]-pyrrolidine-1-carboxylic acid tert-butyl ester;
(2S,4R)-2-(1-Cyano-cyclopropylcarbamoyl)-4-[4-(4-methyl-piperazin-1-yl)-2-trifluoromethyl-benzenesulfonyl]-pyrrolidine-1-carboxylic acid tert-butyl ester;
(2S,4R)-4-(2-Chloro-4-piperidin-1-yl-benzenesulfonyl)-pyrrolidine-2-carboxylic acid (1-cyano-cyclopropyl)-amide;
(2S,4R)-4-(2-Chloro-4-pyrazol-1-yl-benzenesulfonyl)-pyrrolidine-2-carboxylic acid (1-cyano-cyclopropyl)-amide;
(2S,4R)-4-[2-Chloro-4-(2,2,2-trifluoro-1-methyl-ethoxy)-benzenesulfonyl]-pyrrolidine-2-carboxylic acid (1-cyano-cyclopropyl)-amide;
(2S,4R)-4-[2-Chloro-4-(3,3-difluoro-pyrrolidin-1-yl)-benzenesulfonyl]-2-(1-cyano-cyclopropylcarbamoyl)-pyrrolidine-1-carboxylic acid tert-butyl ester;
(2S,4R)-1-Acetyl-4-(2-chloro-4-pyrazol-1-yl-benzenesulfonyl)-pyrrolidine-2-carboxylic acid (1-cyano-cyclopropyl)-amide;
(2S,4R)-1-Acetyl-4-[2-chloro-4-(2,2,2-trifluoro-1-methyl-ethoxy)-benzenesulfonyl]-pyrrolidine-2-carboxylic acid (1-cyano-cyclopropyl)-amide;
(2S,4R)-1-Acetyl-4-(2-chloro-4-piperidin-1-yl-benzenesulfonyl)-pyrrolidine-2-carboxylic acid (1-cyano-cyclopropyl)-amide;
(2S,4R)-1-Acetyl-4-(2-chloro-4-fluoro-benzenesulfonyl)-pyrrolidine-2-carboxylic acid (1-cyano-cyclopropyl)-amide;
(2S,4R)-4-(2-Chloro-4-piperidin-1-yl-benzenesulfonyl)-1-(1-trifluoromethyl-cyclopropanecarbonyl)-pyrrolidine-2-carboxylic acid (1-cyano-cyclopropyl)-amide;
(2S,4R)-4-[4-(4-Methyl-piperazin-1-yl)-2-trifluoromethyl-benzenesulfonyl]-pyrrolidine-2-carboxylic acid (1-cyano-cyclopropyl)-amide;
(2S,4R)-4-(4-Benzoimidazol-1-yl-2-trifluoromethyl-benzenesulfonyl)-pyrrolidine-2-carboxylic acid (1-cyano-cyclopropyl)-amide;
(2S,4R)-4-[2-Chloro-4-(3,3-difluoro-pyrrolidin-1-yl)-benzenesulfonyl]-pyrrolidine-2-carboxylic acid (1-cyano-cyclopropyl)-amide;
4-[(2S,4R)-2-(Cyanomethyl-carbamoyl)-4-(2-trifluoromethyl-benzenesulfonyl)-pyrrolidine-1-carbonyl]-benzoic acid methyl ester;
(2S,4R)-4-[4-(3-Methyl-6-oxo-6H-pyridazin-1-yl)-2-trifluoromethyl-benzenesulfonyl]-pyrrolidine-2-carboxylic acid (1-cyano-cyclopropyl)-amide;
(2S,4R)-4-[2-Chloro-4-(4-ethyl-piperazin-1-yl)-benzenesulfonyl]-2-(1-cyano-cyclopropylcarbamoyl)-pyrrolidine-1-carboxylic acid tert-butyl ester;
(2S,4R)-4-[2-Chloro-4-(2-piperidin-1-yl-ethoxy)-benzenesulfonyl]-2-(1-cyano-cyclopropylcarbamoyl)-pyrrolidine-1-carboxylic acid tert-butyl ester;
(2S,4R)-4-[2-Chloro-4-(4-ethyl-piperazin-1-yl)-benzenesulfonyl]-pyrrolidine-2-carboxylic acid (1-cyano-cyclopropyl)-amide;
(2S,4R)-4-[4-(2-Methyl-imidazol-1-yl)-2-trifluoromethyl-benzenesulfonyl]-pyrrolidine-2-carboxylic acid (1-cyano-cyclopropyl)-amide;

(2S,4R)-4-[4-(2-Phenyl-imidazol-1-yl)-2-trifluoromethyl-benzenesulfonyl]-pyrrolidine-2-carboxylic acid (1-cyano-cyclopropyl)-amide;

(2S,4R)-4-[4-(2-Oxo-pyrrolidin-1-yl)-2-trifluoromethyl-benzenesulfonyl]-pyrrolidine-2-carboxylic acid (1-cyano-cyclopropyl)-amide;

(2S,4R)-4-[4-(2-oxo-oxazolidin-3-yl)-2-trifluoromethyl-benzenesulfonyl]-pyrrolidine-2-carboxylic acid (1-cyano-cyclopropyl)-amide;

(2S,4R)-4-[4-(3,3-Difluoro-pyrrolidin-1-yl)-2-trifluoromethyl-benzenesulfonyl]-pyrrolidine-2-carboxylic acid (1-cyano-cyclopropyl)-amide;

(2S,4R)-4-(4-Morpholin-4-yl-2-trifluoromethyl-benzenesulfonyl)-pyrrolidine-2-carboxylic acid (1-cyano-cyclopropyl)-amide;

(2S,4R)-4-[4-(3-oxo-morpholin-4-yl)-2-trifluoromethyl-benzenesulfonyl]-pyrrolidine-2-carboxylic acid (1-cyano-cyclopropyl)-amide;

(2S,4R)-4-[4-(2-Oxo-2H-pyridin-1-yl)-2-trifluoromethyl-benzenesulfonyl]-pyrrolidine-2-carboxylic acid (1-cyano-cyclopropyl)-amide;

(2S,4R)-4-[4-(2-Oxo-2H-pyrazin-1-yl)-2-trifluoromethyl-benzenesulfonyl]-pyrrolidine-2-carboxylic acid (1-cyano-cyclopropyl)-amide;

(2S,4R)-4-[2-Chloro-4-(4-ethyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(4-ethyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(4-ethyl-piperazin-1-yl)-benzenesulfonyl]-1-formyl-pyrrolidine-2-carboxylic acid (1-cyano-cyclopropyl)-amide;

(2S,4R)-1-Acetyl-4-(4-imidazol-1-yl-2-trifluoromethyl-benzenesulfonyl)-pyrrolidine-2-carboxylic acid (1-cyano-cyclopropyl)-amide;

(2S,4R)-1-Acetyl-4-(4-pyrazol-1-yl-2-trifluoromethyl-benzenesulfonyl)-pyrrolidine-2-carboxylic acid (1-cyano-cyclopropyl)-amide;

(2S,4R)-4-(2-Chloro-4-fluoro-benzenesulfonyl)-pyrrolidine-2-carboxylic acid (1-cyano-cyclopropyl)-amide;

(2S,4R)-4-(2-Chloro-4-fluoro-benzenesulfonyl)-1-(1-trifluoromethyl-cyclopropanecarbonyl)-pyrrolidine-2-carboxylic acid (1-cyano-cyclopropyl)-amide;

(2S,4R)-4-(2-Chloro-4-piperidin-1-yl-benzenesulfonyl)-1-formyl-pyrrolidine-2-carboxylic acid (1-cyano-cyclopropyl)-amide;

(2S,4R)-4-(2-Chloro-4-pyrazol-1-yl-benzenesulfonyl)-1-(1-trifluoromethyl-cyclopropanecarbonyl)-pyrrolidine-2-carboxylic acid (1-cyano-cyclopropyl)-amide;

(2S,4R)-4-(2-Chloro-4-pyrazol-1-yl-benzenesulfonyl)-1-formyl-pyrrolidine-2-carboxylic acid (1-cyano-cyclopropyl)-amide;

(2S,4R)-4-[2-Chloro-4-(2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-1-methyl-ethoxy)-benzenesulfonyl]-1-formyl-pyrrolidine-2-carboxylic acid (1-cyano-cyclopropyl)-amide (2S,4R)-1-Phenyl-4-(2-trifluoromethyl-benzenesulfonyl)-pyrrolidine-2-carboxylic acid cyanomethyl-amide;

(2S,4R)-4-[2-Chloro-4-(4,4-difluoro-piperidin-1-yl)-benzenesulfonyl]-2-(1-cyano-cyclopropylcarbamoyl)-pyrrolidine-1-carboxylic acid tert-butyl ester;

(2S,4R)-4-[2-Chloro-4-(4-trifluoromethyl-piperidin-1-yl)-benzenesulfonyl]-2-(1-cyano-cyclopropylcarbamoyl)-pyrrolidine-1-carboxylic acid tert-butyl ester;

(2S,4R)-4-[2-Chloro-4-(4-trifluoromethyl-piperidin-1-yl)-benzenesulfonyl]-pyrrolidine-2-carboxylic acid (1-cyano-cyclopropyl)-amide;

(2S,4R)-4-[2-Chloro-4-(4,4-difluoro-piperidin-1-yl)-benzenesulfonyl]-pyrrolidine-2-carboxylic acid (1-cyano-cyclopropyl)-amide;

(2S,4R)-4-[2-Chloro-4-(4-trifluoromethyl-piperidin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(4,4-difluoro-piperidin-1-yl)-benzenesulfonyl]-1-(1-trifluoromethyl-cyclopropanecarbonyl)-pyrrolidine-2-carboxylic acid (1-cyano-cyclopropyl)-amide;

(2S,4S)-2-(1-Cyano-cyclopropylcarbamoyl)-4-(2-trifluoromethyl-benzenesulfonyl)-pyrrolidine-1-carboxylic acid tert-butyl ester;

(2S,4S)-4-(2-Trifluoromethyl-benzenesulfonyl)-pyrrolidine-2-carboxylic acid (1-cyano-cyclopropyl)-amide;

(2S,4R)-1-(4-Methoxy-phenyl)-4-(2-trifluoromethyl-benzenesulfonyl)-pyrrolidine-2-carboxylic acid (1-cyano-cyclopropyl)-amide;

(2S,4R)-4-(2-Chloro-4-morpholin-4-yl-benzenesulfonyl)-1-(1-trifluoromethyl-cyclopropanecarbonyl)-pyrrolidine-2-carboxylic acid (1-cyano-cyclopropyl)-amide;

(2R,4R)-4-(2-Chloro-4-morpholin-4-yl-benzenesulfonyl)-1-(1-trifluoromethyl-cyclopropanecarbonyl)-pyrrolidine-2-carboxylic acid (1-cyano-cyclopropyl)-amide;

(2S,4R)-4-(2-Chloro-4-piperazin-1-yl-benzenesulfonyl)-1-(1-trifluoromethyl-cyclopropanecarbonyl)-pyrrolidine-2-carboxylic acid (1-cyano-cyclopropyl)-amide;

(2S,4R)-1-(2-Nitro-phenyl)-4-(2-trifluoromethyl-benzenesulfonyl)-pyrrolidine-2-carboxylic acid cyanomethyl-amide;

(2R,4R)-4-(2-Chloro-4-pyrazol-1-yl-benzenesulfonyl)-1-(1-trifluoromethyl-cyclopropanecarbonyl)-pyrrolidine-2-carboxylic acid (1-cyano-cyclopropyl)-amide;

(2S,4R)-1-(2-Nitro-phenyl)-4-(2-trifluoromethyl-benzenesulfonyl)-pyrrolidine-2-carboxylic acid (1-cyano-cyclopropyl)-amide;

(2S,4R)-4-(2,4-Dichloro-benzenesulfonyl)-1-(2-nitro-phenyl)-pyrrolidine-2-carboxylic acid (1-cyano-cyclopropyl)-amide;

(2S,4R)-4-(2,4-Dichloro-benzenesulfonyl)-1-(1-trifluoromethyl-cyclopropanecarbonyl)-pyrrolidine-2-carboxylic acid (1-cyano-cyclopropyl)-amide;

(2S,4R)-4-(2,4-Dichloro-benzenesulfonyl)-1-(1-trifluoromethyl-cyclobutanecarbonyl)-pyrrolidine-2-carboxylic acid (1-cyano-cyclopropyl)-amide;

(2S,4R)-4-(2,4-Dichloro-benzenesulfonyl)-1-(2,2-difluoro-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-2-(1-cyano-cyclopropylcarbamoyl)-pyrrolidine-1-carboxylic acid tert-butyl ester;

(2S,4R)-4-[2-Chloro-4-(2,2,2-trifluoro-ethoxy)-benzenesulfonyl]-1-(1-trifluoromethyl-cyclopropanecarbonyl)-pyrrolidine-2-carboxylic acid (1-cyano-cyclopropyl)-amide;

(R)-4-[2-Chloro-4-(2,2,2-trifluoro-ethoxy)-benzenesulfonyl]-pyrrolidine-2-carboxylic acid (1-cyano-cyclopropyl)-amide;

(2S,4R)-4-[2-Chloro-4-(oxetan-3-yloxy)-benzenesulfonyl]-2-(1-cyano-cyclopropylcarbamoyl)-pyrrolidine-1-carboxylic acid tert-butyl ester;
(2S,4R)-4-[2-Chloro-4-(2,2,2-trifluoro-ethoxy)-benzenesulfonyl]-1-(1-methyl-cyclopropanecarbonyl)-pyrrolidine-2-carboxylic acid (1-cyano-cyclopropyl)-amide;
(2S,4R)-4-[2-Chloro-4-(2,2,2-trifluoro-ethoxy)-benzenesulfonyl]-1-(2,2-dimethyl-propionyl)-pyrrolidine-2-carboxylic acid (1-cyano-cyclopropyl)-amide;
(2S,4R)-4-[2-Chloro-4-(2,2,2-trifluoro-ethoxy)-benzenesulfonyl]-1-(2-trifluoromethyl-benzoyl)-pyrrolidine-2-carboxylic acid (1-cyano-cyclopropyl)-amide;
(2S,4R)-1-[1-(4-Chloro-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;
(2S,4R)-4-[2-Chloro-4-(2,2,2-trifluoro-ethoxy)-benzenesulfonyl]-1-isobutyryl-pyrrolidine-2-carboxylic acid (1-cyano-cyclopropyl)-amide;
(2S,4R)-4-[2-Chloro-4-(2,2,2-trifluoro-ethoxy)-benzenesulfonyl]-1-(3-methyl-butyryl)-pyrrolidine-2-carboxylic acid (1-cyano-cyclopropyl)-amide;
(2S,4R)-4-[2-Chloro-4-(oxetan-3-yloxy)-benzenesulfonyl]-pyrrolidine-2-carboxylic acid (1-cyano-cyclopropyl)-amide;
(R)-4-[2-Chloro-4-(2,2,2-trifluoro-ethoxy)-benzenesulfonyl]-1-formyl-pyrrolidine-2-carboxylic acid (1-cyano-cyclopropyl)-amide;
(2S,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide;
(2R,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide;
(2S,4R)-4-(2-Trifluoromethyl-benzenesulfonyl)-1-(2-trifluoromethyl-pyrimidin-4-yl)-pyrrolidine-2-carboxylic acid (1-cyano-cyclopropyl)-amide;
(2S,4R)-4-(2-Trifluoromethyl-benzenesulfonyl)-1-(3-trifluoromethyl-pyridin-2-yl)-pyrrolidine-2-carboxylic acid (1-cyano-cyclopropyl)-amide;
(2R,4R)-4-(2-Trifluoromethyl-benzenesulfonyl)-1-(3-trifluoromethyl-pyridin-2-yl)-pyrrolidine-2-carboxylic acid (1-cyano-cyclopropyl)-amide;
(2S,4R)-4-(2,4-Dichloro-benzenesulfonyl)-1-(3-trifluoromethyl-pyridin-2-yl)-pyrrolidine-2-carboxylic acid (1-cyano-cyclopropyl)-amide;
(2R,4R)-4-(2,4-Dichloro-benzenesulfonyl)-1-(3-trifluoromethyl-pyridin-2-yl)-pyrrolidine-2-carboxylic acid (1-cyano-cyclopropyl)-amide;
(2R,4R)-4-[2-Chloro-4-(4-ethyl-piperazin-1-yl)-benzenesulfonyl]-1-(3-trifluoromethyl-pyridin-2-yl)-pyrrolidine-2-carboxylic acid (1-cyano-cyclopropyl)-amide;
(2S,4R)-4-[2-Chloro-4-(4-ethyl-piperazin-1-yl)-benzenesulfonyl]-1-(3-trifluoromethyl-pyridin-2-yl)-pyrrolidine-2-carboxylic acid (1-cyano-cyclopropyl)-amide;
(2S,4R)-1-(5-Methyl-2-phenyl-2H-pyrazol-3-yl)-4-(2-trifluoromethyl-benzenesulfonyl)-pyrrolidine-2-carboxylic acid (1-cyano-cyclopropyl)-amide;
(2S,4R)-1-[2-(2-Chloro-pyridin-4-yl)-5-methyl-2H-pyrazol-3-yl]-4-(2-trifluoromethyl-benzenesulfonyl)-pyrrolidine-2-carboxylic acid (1-cyano-cyclopropyl)-amide;
(2S,4R)-1-[2-(4-Chloro-phenyl)-5-methyl-2H-pyrazol-3-yl]-4-(2-trifluoromethyl-benzenesulfonyl)-pyrrolidine-2-carboxylic acid (1-cyano-cyclopropyl)-amide;
(2S,4R)-1-[2-(4-Fluoro-phenyl)-5-methyl-2H-pyrazol-3-yl]-4-(2-trifluoromethyl-benzenesulfonyl)-pyrrolidine-2-carboxylic acid (1-cyano-cyclopropyl)-amide;
(2S,4R)-1-[5-Methyl-2-(2-oxo-1,2-dihydro-pyridin-4-yl)-2H-pyrazol-3-yl]-4-(2-trifluoromethyl-benzenesulfonyl)-pyrrolidine-2-carboxylic acid (1-cyano-cyclopropyl)-amide;
(2S,4R)-4-[2-Chloro-4-((S)-2,2,2-trifluoro-1-methyl-ethoxy)-benzenesulfonyl]-1-cyclopropanecarbonyl-pyrrolidine-2-carboxylic acid (1-cyano-cyclopropyl)-amide;
(2R,4R)-4-[2-Chloro-4-((S)-2,2,2-trifluoro-1-methyl-ethoxy)-benzenesulfonyl]-1-cyclopropanecarbonyl-pyrrolidine-2-carboxylic acid (1-cyano-cyclopropyl)-amide;
(2S,4R)-4-[2-Chloro-4-((S)-2,2,2-trifluoro-1-methyl-ethoxy)-benzenesulfonyl]-1-(1-methyl-cyclopropanecarbonyl)-pyrrolidine-2-carboxylic acid (1-cyano-cyclopropyl)-amide;
(2R,4R)-4-[2-Chloro-4-((S)-2,2,2-trifluoro-1-methyl-ethoxy)-benzenesulfonyl]-1-(1-methyl-cyclopropanecarbonyl)-pyrrolidine-2-carboxylic acid (1-cyano-cyclopropyl)-amide;
(2S,4R)-4-[2-Chloro-4-(oxetan-3-yloxy)-benzenesulfonyl]-1-(1-trifluoromethyl-cyclopropanecarbonyl)-pyrrolidine-2-carboxylic acid (1-cyano-cyclopropyl)-amide;
(2S,4R)-1-[1-(4-Chloro-phenyl)-cyclopropanecarbonyl]-4-(2-trifluoromethyl-benzenesulfonyl)-pyrrolidine-2-carboxylic acid (1-cyano-cyclopropyl)-amide;
(2S,4R)-4-[2-Chloro-4-((S)-2,2,2-trifluoro-1-methyl-ethoxy)-benzenesulfonyl]-1-(2,2-dimethyl-propionyl)-pyrrolidine-2-carboxylic acid (1-cyano-cyclopropyl)-amide;
(2R,4R)-4-[2-Chloro-4-((S)-2,2,2-trifluoro-1-methyl-ethoxy)-benzenesulfonyl]-1-(2,2-dimethyl-propionyl)-pyrrolidine-2-carboxylic acid (1-cyano-cyclopropyl)-amide;
(2S,4R)-4-(2-Trifluoromethyl-benzenesulfonyl)-1-(1-trifluoromethyl-cyclopropanecarbonyl)-pyrrolidine-2-carboxylic acid (1-cyano-cyclopropyl)-amide;
(2S,4R)-4-(2-Trifluoromethyl-benzenesulfonyl)-1-(3,3,3-trifluoro-propionyl)-pyrrolidine-2-carboxylic acid (1-cyano-cyclopropyl)-amide;
(2S,4R)-1-(1-Methyl-cyclopropanecarbonyl)-4-(2-trifluoromethyl-benzenesulfonyl)-pyrrolidine-2-carboxylic acid (1-cyano-cyclopropyl)-amide;
(2S,4R)-2-(1-Cyano-cyclopropylcarbamoyl)-4-[4-(2,2,2-trifluoro-ethoxy)-2-trifluoromethyl-benzenesulfonyl]-pyrrolidine-1-carboxylic acid tert-butyl ester;
(2S,4R)-4-(4-Fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide;
(2S,4R)-1-(2,2-Dimethyl-propionyl)-4-(4-fluoro-2-trifluoromethyl-benzenesulfonyl)-pyrrolidine-2-carboxylic acid (1-cyano-cyclopropyl)-amide;
(2S,4R)-1-(1-Methyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide;
(2S,4R)-1-(2,2-Dimethyl-propionyl)-4-[4-(2,2,2-trifluoro-ethoxy)-2-trifluoromethyl-benzenesulfonyl]-pyrrolidine-2-carboxylic acid (1-cyano-cyclopropyl)-amide;
(2S,4R)-4-(2-Chloro-benzenesulfonyl)-1-(1-trifluoromethyl-cyclopropanecarbonyl)-pyrrolidine-2-carboxylic acid (1-cyano-cyclopropyl)-amide;
(2S,4R)-4-(2-Chloro-benzenesulfonyl)-1-(1-methyl-cyclopropanecarbonyl)-pyrrolidine-2-carboxylic acid (1-cyano-cyclopropyl)-amide;

(2S,4R)-4-(2-Chloro-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-(1-phenyl-cyclopropanecarbonyl)-pyrrolidine-2-carboxylic acid (1-cyano-cyclopropyl)-amide;

(2S,4R)-4-(2-Chloro-benzenesulfonyl)-1-(2,2-dimethyl-propionyl)-pyrrolidine-2-carboxylic acid (1-cyano-cyclopropyl)-amide;

(2S,4R)-4-(2-Chloro-benzenesulfonyl)-1-isobutyryl-pyrrolidine-2-carboxylic acid (1-cyano-cyclopropyl)-amide;

(2S,4R)-4-(2-Chloro-benzenesulfonyl)-1-(3,3,3-trifluoro-propionyl)-pyrrolidine-2-carboxylic acid (1-cyano-cyclopropyl)-amide;

(2S,4R)-4-(2-Chloro-benzenesulfonyl)-1-(3-methyl-butyryl)-pyrrolidine-2-carboxylic acid (1-cyano-cyclopropyl)-amide;

(2S,4R)-4-[4-Chloro-2-(2,2,2-trifluoro-ethoxy)-benzenesulfonyl]-2-(1-cyano-cyclopropylcarbamoyl)-pyrrolidine-1-carboxylic acid tert-butyl ester;

(2S,4R)-4-(2,4-Dichloro-benzenesulfonyl)-1-(1-methyl-cyclopropanecarbonyl)-pyrrolidine-2-carboxylic acid (1-cyano-cyclopropyl)-amide;

(2S,4R)-1-[1-(4-Chloro-phenyl)-cyclopropanecarbonyl]-4-(2,4-dichloro-benzenesulfonyl)-pyrrolidine-2-carboxylic acid (1-cyano-cyclopropyl)-amide;

(2S,4R)-4-(2,4-Dichloro-benzenesulfonyl)-1-(1-phenyl-cyclopropanecarbonyl)-pyrrolidine-2-carboxylic acid (1-cyano-cyclopropyl)-amide;

(2S,4R)-4-(2,4-Dichloro-benzenesulfonyl)-1-(2,2-dimethyl-propionyl)-pyrrolidine-2-carboxylic acid (1-cyano-cyclopropyl)-amide;

(2S,4R)-4-(2,4-Dichloro-benzenesulfonyl)-1-isobutyryl-pyrrolidine-2-carboxylic acid (1-cyano-cyclopropyl)-amide;

(2S,4R)-4-(2,4-Dichloro-benzenesulfonyl)-1-(3,3,3-trifluoro-propionyl)-pyrrolidine-2-carboxylic acid (1-cyano-cyclopropyl)-amide; and (2S,4R)-4-(2,4-Dichloro-benzenesulfonyl)-1-(3-methyl-butyryl)-pyrrolidine-2-carboxylic acid (1-cyano-cyclopropyl)-amide.

The following compounds of formula (I) are further particular embodiments of the invention:

(2S,4R)-4-(2-Chloro-4-pyrazol-1-yl-benzenesulfonyl)-1-(1-trifluoromethyl-cyclopropanecarbonyl)-pyrrolidine-2-carboxylic acid (1-cyano-cyclopropyl)-amide;

(2S,4R)-4-(2,4-Dichloro-benzenesulfonyl)-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-methyl-cyclopropanecarbonyl)-pyrrolidine-2-carboxylic acid (1-cyano-cyclopropyl)-amide;

(2S,4R)-1-[1-(4-Chloro-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(1-methyl-cyclopropanecarbonyl)-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(2,2-dimethyl-propionyl)-pyrrolidine-2-carboxylic acid (1-cyano-cyclopropyl)-amide;

(2S,4R)-4-(2-Trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-1-(1-Methyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-1-(2,2-Dimethyl-propionyl)-4-[4-(2,2,2-trifluoro-ethoxy)-2-trifluoromethyl-benzenesulfonyl]-pyrrolidine-2-carboxylic acid (1-cyano-cyclopropyl)-amide; and (2S,4R)-4-(2-Chloro-benzenesulfonyl)-1-[1-(4-chloro-phenyl)-cyclopropanecarbonyl]-pyrrolidine-2-carboxylic acid (1-cyano-cyclopropyl)-amide.

The following compounds of formula (I) are further embodiments of the present invention:

(2S,4R)-4-[2-Chloro-4-((S)-2,2,2-trifluoro-1-methyl-ethoxy)-benzenesulfonyl]-2-(1-cyano-cyclopropylcarbamoyl)-pyrrolidine-1-carboxylic acid tert-butyl ester;

(2S,4R)-4-[2-Chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[5-Methyl-2-(2-oxo-1,2-dihydro-pyridin-4-yl)-2H-pyrazol-3-yl]-4-(2-trifluoromethyl-benzenesulfonyl)-pyrrolidine-2-carboxylic acid (1-cyano-cyclopropyl)-amide;

(2S,4R)-1-[5-Methyl-2-(4-trifluoromethyl-phenyl)-2H-pyrazol-3-yl]-4-(2-trifluoromethyl-benzenesulfonyl)-pyrrolidine-2-carboxylic acid (1-cyano-cyclopropyl)-amide;

(2S,4R)-1-[2-(3-Chloro-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-1-(5-Methyl-2-thiazol-2-yl-2H-pyrazol-3-yl)-4-(2-trifluoromethyl-benzenesulfonyl)-pyrrolidine-2-carboxylic acid (1-cyano-cyclopropyl)-amide;

(2S,4R)-1-[1-(4-Chloro-phenyl)-cyclopropanecarbonyl]-4-(2,4-difluoro-benzenesulfonyl)-pyrrolidine-2-carboxylic acid (1-cyano-cyclopropyl)-amide;

(2S,4R)-1-[1-(4-Chloro-phenyl)-cyclopropanecarbonyl]-4-(2-methyl-propane-1-sulfonyl)-pyrrolidine-2-carboxylic acid (1-cyano-cyclopropyl)-amide;

(2S,4R)-4-[4-(2,2,2-Trifluoro-ethoxy)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(1-Methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[1-(3,4-dichloro-phenyl)-cyclopropanecarbonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-phenyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2,2-difluoro-cyclopropanecarbonyl)-pyrrolidine-2-carboxylic acid (1-cyano-cyclopropyl)-amide;

{1-[(2S,4R)-4-[2-Chloro-4-(2,2,2-trifluoro-ethoxy)-benzenesulfonyl]-2-(1-cyano-cyclopropylcarbamoyl)-pyrrolidine-1-carbonyl]-cyclopropyl}-carbamic acid tert-butyl ester;

(2S,4R)-4-[2-Chloro-4-(2,2,2-trifluoro-ethoxy)-benzenesulfonyl]-1-(1-cyano-cyclopropanecarbonyl)-pyrrolidine-2-carboxylic acid (1-cyano-cyclopropyl)-amide;

(2S,4R)-1-[2-(4-Chloro-phenyl)-acetyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[4-(2-Chloro-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2-phenyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2-phenyl-cyclopropanecarbonyl)-pyrrolidine-2-carboxylic acid (1-cyano-cyclopropyl)-amide;

(2S,4R)-4-[4-(2-Methyl-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-1-(1-Methyl-cyclopropanecarbonyl)-4-[4-(1-methyl-1H-pyrazol-4-yl)-2-trifluoromethyl-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-pyridin-4-yl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2,2-difluoro-2-phenyl-acetyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-2-(1-cyano-cyclopropylcarbamoyl)-pyrrolidine-1-carboxylic acid 4-chloro-phenyl ester;

(2S,4R)-4-(2-Chloro-benzenesulfonyl)-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-4-(2-Chloro-benzenesulfonyl)-1-[2-(2-chloro-pyridin-4-yl)-5-methyl-2H-pyrazol-3-yl]-pyrrolidine-2-carboxylic acid (1-cyano-cyclopropyl)-amide;

(2S,4R)-1-(1,5-Dimethyl-1H-pyrazol-3-yl)-4-(2-trifluoromethyl-benzenesulfonyl)-pyrrolidine-2-carboxylic acid (1-cyano-cyclopropyl)-amide;

(2S,4R)-4-(4-Cyclopropyl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-1-(1-Methyl-cyclopropanecarbonyl)-4-[4-(2-methyl-pyridin-4-yl)-2-trifluoromethyl-benzenesulfonyl]-pyrrolidine-2-carboxylic acid (1-cyano-cyclopropyl)-amide;

(2S,4R)-4-[4-(2-Chloro-pyridin-4-yl)-2-trifluoromethyl-benzenesulfonyl]-1-(1-methyl-cyclopropanecarbonyl)-pyrrolidine-2-carboxylic acid (1-cyano-cyclopropyl)-amide;

(2S,4R)-4-(2',4'-Difluoro-3-trifluoromethyl-biphenyl-4-sulfonyl)-1-(1-methyl-cyclopropanecarbonyl)-pyrrolidine-2-carboxylic acid (1-cyano-cyclopropyl)-amide;

(2S,4R)-4-[4-(4-Methyl-piperazin-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-Benzenesulfonyl-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-4-Benzenesulfonyl-1-[2-(2-chloro-pyridin-4-yl)-5-methyl-2H-pyrazol-3-yl]-pyrrolidine-2-carboxylic acid (1-cyano-cyclopropyl)-amide;

(2S,4R)-4-(2',4'-Difluoro-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide;

(4-{2-[(2S,4R)-4-[2-Chloro-4-(2,2,2-trifluoro-ethoxy)-benzenesulfonyl]-2-(1-cyano-cyclopropylcarbamoyl)-pyrrolidin-1-yl]-2-oxo-ethyl}-cyclohexyl)-carbamic acid tert-butyl ester;

(2S,4R)-1-[2-(4-Amino-cyclohexyl)-acetyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2-(2-Chloro-pyridin-4-yl)-5-methyl-2H-pyrazol-3-yl]-4-(4-fluoro-2-trifluoromethyl-benzenesulfonyl)-pyrrolidine-2-carboxylic acid (1-cyano-cyclopropyl)-amide;

(2S,4R)-4-(4-Fluoro-2-trifluoromethyl-benzenesulfonyl)-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-1-(2-Isopropyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-[5-Methyl-2-(2,2,2-trifluoro-ethyl)-2H-pyrazol-3-yl]-4-(2-trifluoromethyl-benzenesulfonyl)-pyrrolidine-2-carboxylic acid (1-cyano-cyclopropyl)-amide;

(2S,4R)-4-(4-Bromo-2-trifluoromethyl-benzenesulfonyl)-1-(1-methyl-cyclopropanecarbonyl)-pyrrolidine-2-carboxylic acid (1-cyano-cyclopropyl)-amide;

(2S,4R)-4-(4-Cyclopropyl-2-trifluoromethyl-benzenesulfonyl)-1-(1-methyl-cyclopropanecarbonyl)-pyrrolidine-2-carboxylic acid (1-cyano-cyclopropyl)-amide;

(2S,4R)-1-(1-Methyl-cyclopropanecarbonyl)-4-[4-(4-methyl-piperazin-1-yl)-2-trifluoromethyl-benzenesulfonyl]-pyrrolidine-2-carboxylic acid (1-cyano-cyclopropyl)-amide;

(2S,4R)-1-[1-(4-Bromo-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2-(4-Acetylamino-cyclohexyl)-acetyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2,2-Bis-(4-chloro-phenyl)-acetyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-(5-Methyl-2-m-tolyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-[1-(4-Carbamoyl-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[1-(4-Chloro-phenyl)-cyclobutanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2-(4-Chloro-phenyl)-2-methyl-propionyl]-4-[2-chloro-4-(2,2,2-trifluoro-ethoxy)-benzenesulfonyl]-pyrrolidine-2-carboxylic acid (1-cyano-cyclopropyl)-amide;

(2R,4S)-4-[2-Chloro-4-(2,2,2-trifluoro-ethoxy)-benzenesulfonyl]-1-(1-trifluoromethyl-cyclopropanecarbonyl)-pyrrolidine-2-carboxylic acid (1-cyano-cyclopropyl)-amide;

(2S,4R)-4-(2-Chloro-benzenesulfonyl)-1-[1-(4-trifluoromethoxy-phenyl)-cyclopropanecarbonyl]-pyrrolidine-2-carboxylic acid (1-cyano-cyclopropyl)-amide;

(2S,4R)-4-(2-Chloro-benzenesulfonyl)-1-[2-(4-chloro-phenyl)-2-methyl-propionyl]-pyrrolidine-2-carboxylic acid (1-cyano-cyclopropyl)-amide;

(2S,4R)-4-(2-Chloro-benzenesulfonyl)-1-[1-(4-chloro-phenyl)-cyclobutanecarbonyl]-pyrrolidine-2-carboxylic acid (1-cyano-cyclopropyl)-amide;

(2S,4R)-4-(2-Chloro-benzenesulfonyl)-1-[1-(3,4-dichloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-(1-pyridin-4-yl-cyclopropanecarbonyl)-pyrrolidine-2-carboxylic acid (1-cyano-cyclopropyl)-amide;

(2S,4R)-1-(5-Methyl-1H-pyrazol-3-yl)-4-(2-trifluoromethyl-benzenesulfonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(4-phenyl-tetrahydro-pyran-4-carbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-{1-[4-(1-methyl-1H-pyrazol-4-yl)-phenyl]-cyclopropanecarbonyl}-pyrrolidine-2-carboxylic acid (1-cyano-cyclopropyl)-amide;

(2S,4R)-1-[5-Methyl-2-(2-methyl-pyridin-4-yl)-2H-pyrazol-3-yl]-4-(2-trifluoromethyl-benzenesulfonyl)-pyrrolidine-2-carboxylic acid (1-cyano-cyclopropyl)-amide;

(2S,4R)-4-[2-Chloro-4-(4-methyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-[4-(2,2,2-trifluoro-ethyl)-piperazin-1-yl]-benzenesulfonyl]-1-(1-trifluoromethyl-cyclopropanecarbonyl)-pyrrolidine-2-carboxylic acid (1-cyano-cyclopropyl)-amide;

(2S,4R)-4-(2-Chloro-4-dimethylamino-benzenesulfonyl)-1-(1-trifluoromethyl-cyclopropanecarbonyl)-pyrrolidine-2-carboxylic acid (1-cyano-cyclopropyl)-amide;

(2S,4R)-4-[2-Chloro-4-(4-isopropyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(3-methyl-oxetane-3-carbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[1-(4-fluoro-phenyl)-cyclopropanecarbonyl]-pyrrolidine-2-carboxylic acid (1-cyano-cyclopropyl)-amide;

(2S,4R)-4-[4-(4-tert-Butyl-piperazin-1-yl)-2-chloro-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-[4-(2-methoxy-ethyl)-piperazin-1-yl]-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(4-cyclopropyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-4-((S)-2-Chloro-4-hexahydro-pyrrolo[1,2-a]pyrazin-2-yl-benzenesulfonyl)-1-(1-trifluoromethyl-cyclopropanecarbonyl)-pyrrolidine-2-carboxylic acid (1-cyano-cyclopropyl)-amide;

(2S,4R)-1-(2,5-Dimethyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-[2-Chloro-4-(5,6-dihydro-8H-[1,2,4]triazolo[4,3-a]pyrazin-7-yl)-benzenesulfonyl]-1-(1-trifluoromethyl-cyclopropanecarbonyl)-pyrrolidine-2-carboxylic acid (1-cyano-cyclopropyl)-amide;

(2S,4R)-1-[1-(4-Chloro-phenyl)-cyclopentanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-phenyl-cyclohexanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-p-tolyl-cyclopropanecarbonyl)-pyrrolidine-2-carboxylic acid (1-cyano-cyclopropyl)-amide (R)-4-[2-Chloro-4-(4-methyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-1-[5-Methyl-2-(4-trifluoromethyl-phenyl)-2H-pyrazol-3-yl]-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-1-[5-Methyl-2-(tetrahydro-pyran-4-yl)-2H-pyrazol-3-yl]-4-(2-trifluoromethyl-benzenesulfonyl)-pyrrolidine-2-carboxylic acid (1-cyano-cyclopropyl)-amide;

(2S,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide;

(2R,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[1-(4-trifluoromethyl-phenyl)-cyclopropanecarbonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[1-(3-trifluoromethyl-phenyl)-cyclopropanecarbonyl]-pyrrolidine-2-carboxylic acid (1-cyano-cyclopropyl)-amide;

(2S,4R)-4-(2-Chloro-4-fluoro-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-(naphthalene-2-sulfonyl)-pyrrolidine-2-carboxylic acid (1-cyano-cyclopropyl)-amide;

(2S,4R)-1-[1-(4-Chloro-phenyl)-cyclohexanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-(2-Chloro-benzenesulfonyl)-1-(4-chloro-benzenesulfonyl)-pyrrolidine-2-carboxylic acid (1-cyano-cyclopropyl)-amide;

(2S,4R)-1-(Biphenyl-4-sulfonyl)-4-(2-chloro-benzenesulfonyl)-pyrrolidine-2-carboxylic acid (1-cyano-cyclopropyl)-amide;

(2S,4R)-1-(5-Methyl-2-pyridazin-3-yl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Cyclohexyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Benzyl-5-methyl-2H-pyrazol-3-yl)-4-(2-trifluoromethyl-benzenesulfonyl)-pyrrolidine-2-carboxylic acid (1-cyano-cyclopropyl)-amide;

(2R,4R)-1-(2-Cyclohexyl-5-methyl-2H-pyrazol-3-yl)-4-(2-trifluoromethyl-benzenesulfonyl)-pyrrolidine-2-carboxylic acid (1-cyano-cyclopropyl)-amide;

(2R,4R)-1-(2-Benzyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Cyclobutyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-(2-Chloro-benzenesulfonyl)-1-(4-oxazol-5-yl-benzenesulfonyl)-pyrrolidine-2-carboxylic acid (1-cyano-cyclopropyl)-amide;

(2S,4R)-4-[2-Chloro-4-(4-methyl-piperazin-1-yl)-benzenesulfonyl]-1-[1-(4-chloro-phenyl)-cyclopropanecarbonyl]-pyrrolidine-2-carboxylic acid (1-cyano-cyclopropyl)-amide;

(2S,4R)-4-(2-Chloro-4-imidazol-1-yl-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-[2-Chloro-4-(2-methyl-imidazol-1-yl)-benzenesulfonyl]-1-[1-(4-chloro-phenyl)-cyclopropanecarbonyl]-pyrrolidine-2-carboxylic acid (1-cyano-cyclopropyl)-amide;

(2S,4R)-1-[1-(4-Chloro-phenyl)-cyclopropanecarbonyl]-4-(2-chloro-4-pyrazol-1-yl-benzenesulfonyl)-pyrrolidine-2-carboxylic acid (1-cyano-cyclopropyl)-amide;

(2S,4R)-4-(4-Azetidin-1-yl-2-chloro-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-[4-(4-tert-Butyl-piperazin-1-yl)-2-chloro-benzenesulfonyl]-1-[1-(4-chloro-phenyl)-cyclopropanecarbonyl]-pyrrolidine-2-carboxylic acid (1-cyano-cyclopropyl)-amide;

(2S,4R)-4-[2-Chloro-4-(4-cyclopropyl-piperazin-1-yl)-benzenesulfonyl]-1-[1-(4-chloro-phenyl)-cyclopropanecarbonyl]-pyrrolidine-2-carboxylic acid (1-cyano-cyclopropyl)-amide;

(2S,4R)-1-[1-(3-Chloro-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[1-(3-Bromo-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2-(3-Methoxy-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2R,4R)-1-[2-(3-Methoxy-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-4-(2-Trifluoromethyl-benzenesulfonyl)-1-(5-trifluoromethyl-[1,3,4]thiadiazol-2-yl)-pyrrolidine-2-carboxylic acid (1-cyano-cyclopropyl)-amide;

(2S,4R)-4-[2-Chloro-4-(2-isopropyl-imidazol-1-yl)-benzenesulfonyl]-1-[1-(4-chloro-phenyl)-cyclopropanecarbonyl]-pyrrolidine-2-carboxylic acid (1-cyano-cyclopropyl)-amide;

(2S,4R)-1-(5-Methyl-2-phenethyl-2H-pyrazol-3-yl)-4-(2-trifluoromethyl-benzenesulfonyl)-pyrrolidine-2-carboxylic acid (1-cyano-cyclopropyl)-amide;

(2R,4R)-1-(5-Methyl-2-phenethyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-tert-Butyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Isobutyl-5-methyl-2H-pyrazol-3-yl)-4-(2-trifluoromethyl-benzenesulfonyl)-pyrrolidine-2-carboxylic acid (1-cyano-cyclopropyl)-amide;

(2R,4R)-1-(2-Isobutyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-[2-Chloro-4-(2-methoxy-ethoxy)-benzenesulfonyl]-1-[1-(4-chloro-phenyl)-cyclopropanecarbonyl]-pyrrolidine-2-carboxylic acid (1-cyano-cyclopropyl)-amide;

1-Biphenyl-2-yl-4-(2-trifluoromethyl-benzenesulfonyl)-pyrrolidine-2-carboxylic acid (1-cyano-cyclopropyl)-amide;

(2S,4R)-4-(4-Fluoro-2-trifluoromethyl-benzenesulfonyl)-1-(1-methyl-cyclopropanecarbonyl)-pyrrolidine-2-carboxylic acid (1-cyano-cyclopropyl)-amide;

1-Naphthalen-1-yl-4-(2-trifluoromethyl-benzenesulfonyl)-pyrrolidine-2-carboxylic acid (1-cyano-cyclopropyl)-amide;

(2S,4R)-1-[2-(4-Bromo-phenyl)-[1,3]dioxolane-2-carbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-naphthalen-1-yl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-naphthalen-2-yl-cyclopropanecarbonyl)-pyrrolidine-2-carboxylic acid (1-cyano-cyclopropyl)-amide;

(2S,4R)-4-(2-Chloro-4-imidazo[4,5-c]pyridin-1-yl-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-(2-Chloro-4-imidazo[4,5-c]pyridin-5-yl-benzenesulfonyl)-1-[1-(4-chloro-phenyl)-cyclopropanecarbonyl]-pyrrolidine-2-carboxylic acid (1-cyano-cyclopropyl)-amide;

(2S,4R)-1-[2-(2,6-Dimethyl-pyridin-4-yl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-1-(5-Methyl-2-quinolin-4-yl-2H-pyrazol-3-yl)-4-(2-trifluoromethyl-benzenesulfonyl)-pyrrolidine-2-carboxylic acid (1-cyano-cyclopropyl)-amide;

(2S,4R)-4-(2-Chloro-benzenesulfonyl)-1-(2-cyclobutyl-5-methyl-2H-pyrazol-3-yl)-pyrrolidine-2-carboxylic acid (1-cyano-cyclopropyl)-amide;

4-(2-Triuoromethyl-benzenesulfonyl)-1-(3-trifluoromethyl-phenyl)-pyrrolidine-2-carboxylic acid (1-cyano-cyclopropyl)-amide;

1-(2-tert-Butyl-phenyl)-4-(2-trifluoromethyl-benzenesulfonyl)-pyrrolidine-2-carboxylic acid (1-cyano-cyclopropyl)-amide;

(2S,4R)-1-[2-(3-Acetylamino-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2R,4R)-1-[2-(3-Acetylamino-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

1-(3-Cyano-phenyl)-4-(2-trifluoromethyl-benzenesulfonyl)-pyrrolidine-2-carboxylic acid (1-cyano-cyclopropyl)-amide;

(2S,4R)-4-(2-Chloro-benzenesulfonyl)-1-(5-methyl-2-phenethyl-2H-pyrazol-3-yl)-pyrrolidine-2-carboxylic acid (1-cyano-cyclopropyl)-amide;

(2S,4R)-1-[1-(4-Chloro-phenyl)-cyclobutanecarbonyl]-4-(2-trifluoromethyl-benzenesulfonyl)-pyrrolidine-2-carboxylic acid (1-cyano-cyclopropyl)-amide;

(2S,4R)-1-[1-(6-Chloro-pyridin-3-yl)-cyclopropanecarbonyl]-4-(2-trifluoromethyl-benzenesulfonyl)-pyrrolidine-2-carboxylic acid (1-cyano-cyclopropyl)-amide;

1-(Tetrahydro-pyran-4-yl)-4-(2-trifluoromethyl-benzenesulfonyl)-pyrrolidine-2-carboxylic acid (1-cyano-cyclopropyl)-amide;

(2S,4R)-1-[5-Cyclopropyl-2-(4-trifluoromethyl-phenyl)-2H-pyrazol-3-yl]-4-(2-trifluoromethyl-benzenesulfonyl)-pyrrolidine-2-carboxylic acid (1-cyano-cyclopropyl)-amide;

4-[2-(1-Cyano-cyclopropylcarbamoyl)-4-(2-trifluoromethyl-benzenesulfonyl)-pyrrolidin-1-yl]-piperidine-1-carboxylic acid tert-butyl ester;

(2S,4R)-1-[1-(4-Chloro-phenyl)-cyclopropylmethyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[4-(2,2,2-Trifluoro-ethoxy)-2-trifluoromethyl-benzenesulfonyl]-1-(5-trifluoromethyl-[1,3,4]thiadiazol-2-yl)-pyrrolidine-2-carboxylic acid (1-cyano-cyclopropyl)-amide;

1-(3-Trifluoromethoxy-phenyl)-4-(2-trifluoromethyl-benzenesulfonyl)-pyrrolidine-2-carboxylic acid (1-cyano-cyclopropyl)-amide;

(2S,4R)-4-(2-Chloro-4-fluoro-benzenesulfonyl)-1-[1-(6-chloro-pyridin-3-yl)-cyclopropanecarbonyl]-pyrrolidine-2-carboxylic acid (1-cyano-cyclopropyl)-amide;

(2S,4R)-4-[2-Chloro-4-(4-methyl-piperazin-1-yl)-benzenesulfonyl]-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-[2-Chloro-4-(4-isopropyl-piperazin-1-yl)-benzenesulfonyl]-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-[4-(4-tert-Butyl-piperazin-1-yl)-2-chloro-benzenesulfonyl]-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-[2-Chloro-4-[4-(2-methoxy-ethyl)-piperazin-1-yl]-benzenesulfonyl]-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-((S)-2-Chloro-4-hexahydro-pyrrolo[1,2-a]pyrazin-2-yl-benzenesulfonyl)-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-[2-Chloro-4-(4-cyclopropyl-piperazin-1-yl)-benzenesulfonyl]-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-(2-Chloro-4-methoxy-benzenesulfonyl)-1-(2-cyclobutyl-5-methyl-2H-pyrazol-3-yl)-pyrrolidine-2-carboxylic acid (1-cyano-cyclopropyl)-amide;

(2S,4R)-1-(2-Benzyl-5-methyl-2H-pyrazol-3-yl)-4-(2-chloro-4-methoxy-benzenesulfonyl)-pyrrolidine-2-carboxylic acid (1-cyano-cyclopropyl)-amide;

(R)-1-[1-(6-Chloro-pyridin-3-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(R)-4-[2-Chloro-4-(2-methoxy-ethoxy)-benzenesulfonyl]-1-[1-(6-chloro-pyridin-3-yl)-cyclopropanecarbonyl]-pyrrolidine-2-carboxylic acid (1-cyano-cyclopropyl)-amide;

(2S,4R)-1-(2-Benzyl-5-methyl-2H-pyrazol-3-yl)-4-(2-chloro-benzenesulfonyl)-pyrrolidine-2-carboxylic acid (1-cyano-cyclopropyl)-amide;

(2S,4R)-4-(2-Chloro-4-pyrazol-1-yl-benzenesulfonyl)-1-[1-(6-chloro-pyridin-3-yl)-cyclopropanecarbonyl]-pyrrolidine-2-carboxylic acid (1-cyano-cyclopropyl)-amide;

(2S,4R)-1-[1-(6-Chloro-pyridin-3-yl)-cyclopropanecarbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-4-(2-Chloro-4-imidazol-1-yl-benzenesulfonyl)-1-[1-(6-chloro-pyridin-3-yl)-cyclopropanecarbonyl]-pyrrolidine-2-carboxylic acid (1-cyano-cyclopropyl)-amide;

(6R,7aS)-6-(2-Chloro-4-fluoro-benzenesulfonyl)-1-cyano-tetrahydro-pyrrolizine-7a-carboxylic acid (1-cyano-cyclopropyl)-amide;

(2S,4R)-1-(1-Benzo[1,3]dioxol-5-yl-cyclopropanecarbonyl)-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-(2-Chloro-4-fluoro-benzenesulfonyl)-1-(2-cyclobutyl-5-methyl-2H-pyrazol-3-yl)-pyrrolidine-2-carboxylic acid (1-cyano-cyclopropyl)-amide;

(2S,4R)-1-(5-tert-Butyl-2-methyl-2H-pyrazole-3-carbonyl)-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-(2-Chloro-4-methoxy-benzenesulfonyl)-2-(1-cyano-cyclopropylcarbamoyl)-pyrrolidine-1-carboxylic acid tert-butyl ester;

(2S,4R)-1-(2-Cyclobutyl-5-methyl-2H-pyrazol-3-yl)-4-(4-fluoro-2-trifluoromethyl-benzenesulfonyl)-pyrrolidine-2-carboxylic acid (1-cyano-cyclopropyl)-amide;

(2S,4R)-1-(2-Cyclobutyl-5-methyl-2H-pyrazol-3-yl)-4-[4-(4-methyl-piperazin-1-yl)-2-trifluoromethyl-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2-naphthalen-1-yl-[1,3]dioxolane-2-carbonyl)-pyrrolidine-2-carboxylic acid (1-cyano-cyclopropyl)-amide;

(2S,4R)-1-(2-Cyclobutyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide;

(2R,4R)-1-(2-Cyclobutyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-1-[1-Methyl-5-(tetrahydro-pyran-4-yl)-1H-pyrazol-3-yl]-4-(2-trifluoromethyl-benzenesulfonyl)-pyrrolidine-2-carboxylic acid (1-cyano-cyclopropyl)-amide;

(2S,4R)-1-(3-Chloro-4-fluoro-phenyl)-4-(2-trifluoromethyl-benzenesulfonyl)-pyrrolidine-2-carboxylic acid (1-cyano-cyclopropyl)-amide;

(2R,4S)-1-(3-Chloro-4-fluoro-phenyl)-4-(2-trifluoromethyl-benzenesulfonyl)-pyrrolidine-2-carboxylic acid (1-cyano-cyclopropyl)-amide;

(2S,4R)-4-(4-Fluoro-2-trifluoromethyl-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-1-[2-Cyclobutyl-5-(tetrahydro-pyran-4-yl)-2H-pyrazol-3-yl]-4-(2-trifluoromethyl-benzenesulfonyl)-pyrrolidine-2-carboxylic acid (1-cyano-cyclopropyl)-amide;

(2S,4R)-1-(2-Cyclobutyl-5-cyclopropyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-(2-Chloro-benzenesulfonyl)-1-(5-trifluoromethyl-[1,3,4]thiadiazol-2-yl)-pyrrolidine-2-carboxylic acid (1-cyano-cyclopropyl)-amide;

(2S,4R)-1-(5-Cyclopropyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-[2-Chloro-4-(4-methyl-piperazin-1-yl)-benzenesulfonyl]-1-(2-cyclobutyl-5-methyl-2H-pyrazol-3-yl)-pyrrolidine-2-carboxylic acid (1-cyano-cyclopropyl)-amide;

(2S,4R)-1-(3-Methanesulfonyl-phenyl)-4-(2-trifluoromethyl-benzenesulfonyl)-pyrrolidine-2-carboxylic acid (1-cyano-cyclopropyl)-amide;

(2S,4R)-4-[4-(3,3-Difluoro-azetidin-1-yl)-2-trifluoromethyl-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-4-[4-(4-Methyl-piperazin-1-yl)-2-trifluoromethyl-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-1-(3-Chloro-[1,2,4]thiadiazol-5-yl)-4-(2-trifluoromethyl-benzenesulfonyl)-pyrrolidine-2-carboxylic acid (1-cyano-cyclopropyl)-amide;

4-{5-[(2S,4R)-2-(1-Cyano-cyclopropylcarbamoyl)-4-(2-trifluoromethyl-benzenesulfonyl)-pyrrolidin-1-yl]-3-methyl-pyrazol-1-yl}-piperidine-1-carboxylic acid benzyl ester;

(2S,4R)-1-(5-Methyl-2-piperidin-4-yl-2H-pyrazol-3-yl)-4-(2-trifluoromethyl-benzenesulfonyl)-pyrrolidine-2-carboxylic acid (1-cyano-cyclopropyl)-amide;

(2S,4R)-1-Pyrimidin-2-yl-4-(2-trifluoromethyl-benzenesulfonyl)-pyrrolidine-2-carboxylic acid (1-cyano-cyclopropyl)-amide;

(2S,4R)-1-[1-(4-Chloro-phenyl)-cyclopropanecarbonyl]-4-methanesulfonyl-pyrrolidine-2-carboxylic acid (1-cyano-cyclopropyl)-amide;

(2S,4R)-4-(2-Chloro-benzenesulfonyl)-1-(6-chloro-1H-indazole-3-carbonyl)-pyrrolidine-2-carboxylic acid (1-cyano-cyclopropyl)-amide;

(2S,4R)-4-(2-Chloro-benzenesulfonyl)-1-[(R)-2-(4-chloro-phenyl)-2-hydroxy-acetyl]-pyrrolidine-2-carboxylic acid (1-cyano-cyclopropyl)-amide;

[(R)-2-[(2S,4R)-4-(2-Chloro-benzenesulfonyl)-2-(1-cyano-cyclopropylcarbamoyl)-pyrrolidin-1-yl]-1-(4-chloro-phenyl)-2-oxo-ethyl]-carbamic acid tert-butyl ester;

(2S,4R)-4-(2-Chloro-benzenesulfonyl)-1-[1-(4-methyl-thiazol-2-yl)-cyclopropanecarbonyl]-pyrrolidine-2-carboxylic acid (1-cyano-cyclopropyl)-amide;

(2S,4R)-4-(2-Chloro-benzenesulfonyl)-1-[2-(5-chloro-pyrimidin-2-yl)-acetyl]-pyrrolidine-2-carboxylic acid (1-cyano-cyclopropyl)-amide;

(2S,4R)-1-(2-Cyclobutyl-5-methyl-2H-pyrazol-3-yl)-4-[4-(3,3-difluoro-azetidin-1-yl)-2-trifluoromethyl-benzenesulfonyl]-pyrrolidine-2-carboxylic acid (1-cyano-cyclopropyl)-amide;

(2S,4R)-1-(2-Cyclobutyl-5-methyl-2H-pyrazol-3-yl)-4-(4-pyrazol-1-yl-2-trifluoromethyl-benzenesulfonyl)-pyrrolidine-2-carboxylic acid (1-cyano-cyclopropyl)-amide;

(2S,4R)-1-[(R)-2-Amino-2-(4-chloro-phenyl)-acetyl]-4-(2-chloro-benzenesulfonyl)-pyrrolidine-2-carboxylic acid (1-cyano-cyclopropyl)-amide;

(2S,4R)-4-(2-Chloro-benzenesulfonyl)-1-[2-(4-chloro-benzyl)-5-methyl-2H-pyrazol-3-yl]-pyrrolidine-2-carboxylic acid (1-cyano-cyclopropyl)-amide;

(2S,4R)-1-(2-Cyclobutyl-5-methyl-2H-pyrazol-3-yl)-4-(4-pyrimidin-4-yl-2-trifluoromethyl-benzenesulfonyl)-pyrrolidine-2-carboxylic acid (1-cyano-cyclopropyl)-amide;

(2S,4R)—N-(1-cyanocyclopropyl)-1-(1-cyclobutyl-3-methyl-1H-pyrazol-5-yl)-4-(4-(1-methyl-1H-pyrazol-5-yl)-2-(trifluoromethyl)phenylsulfonyl)pyrrolidine-2-carboxamide;

(R)-4-(2-Chloro-benzenesulfonyl)-1-[2-(4-chloro-phenyl)-2-(2,2,2-trifluoro-ethylamino)-acetyl]-pyrrolidine-2-carboxylic acid (1-cyano-cyclopropyl)-amide;

(2S,4R)-4-(2-Chloro-benzenesulfonyl)-1-[2-(3-trifluoromethyl-pyrazol-1-yl)-acetyl]-pyrrolidine-2-carboxylic acid (1-cyano-cyclopropyl)-amide;

(2S,4R)-4-Cyclopropylmethanesulfonyl-1-(1-trifluoromethyl-cyclopropane carbonyl)-pyrrolidine-2-carboxylic acid (1-cyano-cyclopropyl)-amide;

(2S,4R)-1-[1-(4-Chloro-phenyl)-cyclopropanecarbonyl]-4-cyclopropylmethanesulfonyl-pyrrolidine-2-carboxylic acid (1-cyano-cyclopropyl)-amide;

(2S,4R)-4-(2-chlorophenylsulfonyl)-N-(1-cyanocyclopropyl)-1-(1-(4-fluorophenyl)cyclopropanecarbonyl)pyrrolidine-2-carboxamide;

(2S,4R)-1-(1-(4-bromophenyl)cyclopropanecarbonyl)-4-(2-chlorophenylsulfonyl)-N-(1-cyanocyclopropyl)pyrrolidine-2-carboxamide;

(2S,4R)-4-(2-chlorophenylsulfonyl)-N-(1-cyanocyclopropyl)-1-(1-(4-(trifluoromethyl)phenyl)cyclopropanecarbonyl)pyrrolidine-2-carboxamide;

(2S,4R)-1-(1-(3-chlorophenyl)cyclopropanecarbonyl)-4-(2-chlorophenylsulfonyl)-N-(1-cyanocyclopropyl)pyrrolidine-2-carboxamide;

(2S,4R)-4-(2-chlorophenylsulfonyl)-N-(1-cyanocyclopropyl)-1-(1-(3-(trifluoromethyl)phenyl)cyclopropanecarbonyl)pyrrolidine-2-carboxamide;

(2S,4R)-1-(2-(4-chlorophenyl)propanoyl)-4-(2-chlorophenylsulfonyl)-N-(1-cyanocyclopropyl)pyrrolidine-2-carboxamide;

(2S,4R)-1-(2-(4-chlorophenyl)propanoyl)-4-(2-chlorophenylsulfonyl)-N-(1-cyanocyclopropyl)pyrrolidine-2-carboxamide;

(2S,4R)-1-(2-(4-chlorophenyl)-3-methylbutanoyl)-4-(2-chlorophenylsulfonyl)-N-(1-cyanocyclopropyl)pyrrolidine-2-carboxamide;

tert-butyl 4-(4-chlorophenyl)-4-((2S,4R)-4-(2-chlorophenylsulfonyl)-2-(1-cyanocyclopropylcarbamoyl)pyrrolidine-1-carbonyl)piperidine-1-carboxylate;

(2S,4R)-4-(2-Chloro-benzenesulfonyl)-1-[2-(4-chloro-phenyl)-2-morpholin-4-yl-acetyl]-pyrrolidine-2-carboxylic acid (1-cyano-cyclopropyl)-amide;

(2S,4R)-4-(2-Chloro-benzenesulfonyl)-1-[2-(4-chloro-phenyl)-2-morpholin-4-yl-acetyl]-pyrrolidine-2-carboxylic acid (1-cyano-cyclopropyl)-amide;

(2S,4R)-4-(2-Chloro-benzenesulfonyl)-1-[2-(4-chloro-phenyl)-2-morpholin-4-yl-acetyl]-pyrrolidine-2-carboxylic acid (1-cyano-cyclopropyl)-amide;

(2S,4R)-4-(2-Chloro-benzenesulfonyl)-1-[2-(3,4-dichloro-phenyl)-2,2-difluoro-acetyl]-pyrrolidine-2-carboxylic acid (1-cyano-cyclopropyl)-amide;

(2S,4R)-4-(2-chlorophenylsulfonyl)-N-(1-cyanocyclopropyl)-1-(1-p-tolylcyclopropanecarbonyl)pyrrolidine-2-carboxamide;

(2S,4R)-1-(1-(4-chloro-2-fluorophenyl)cyclopropanecarbonyl)-4-(2-chlorophenylsulfonyl)-N-(1-cyanocyclopropyl) pyrrolidine-2-carboxamide;

(2S,4R)-4-Methanesulfonyl-1-(1-trifluoromethyl-cyclopropanecarbonyl)-pyrrolidine-2-carboxylic acid (1-cyano-cyclopropyl)-amide;

(2S,4R,5S)-5-(4-tert-butylphenyl)-N-(1-cyanocyclopropyl)-4-(phenylsulfonyl)-2-(2-(phenylsulfonyl)ethyl)pyrrolidine-2-carboxamide;

(2S,4R)-4-(2-Chloro-benzenesulfonyl)-1-[2-(4-chloro-phenyl)-2,2-difluoro-acetyl]-pyrrolidine-2-carboxylic acid (1-cyano-cyclopropyl)-amide;

(2S,4R)-4-(2-Chloro-benzenesulfonyl)-1-[1-(2,4-dichloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-[2-(4-chloro-3-fluoro-phenyl)-acetyl]-pyrrolidine-2-carboxylic acid (1-cyano-cyclopropyl)-amide;

(2S,4R)-1-(2-Benzyl-5-methyl-2H-pyrazol-3-yl)-4-cyclopropylmethanesulfonyl-pyrrolidine-2-carboxylic acid (1-cyano-cyclopropyl)-amide;

(2S,4R)-4-(2-Chloro-benzenesulfonyl)-1-[1-(4-chloro-3-fluoro-phenyl)-cyclopropanecarbonyl]-pyrrolidine-2-carboxylic acid (1-cyano-cyclopropyl)-amide;

4-Benzenesulfonyl-5-(4-tert-butyl-phenyl)-pyrrolidine-2-carboxylic acid (1-cyano-cyclopropyl)-amide;

(2S,4R)-4-Methanesulfonyl-1-(5-methyl-2-phenethyl-2H-pyrazol-3-yl)-pyrrolidine-2-carboxylic acid (1-cyano-cyclopropyl)-amide;

(2S,4R)-1-(2-Benzyl-5-methyl-2H-pyrazol-3-yl)-4-methanesulfonyl-pyrrolidine-2-carboxylic acid (1-cyano-cyclopropyl)-amide;

(2S,4R)-4-(2-Allyloxy-benzenesulfonyl)-2-(1-cyano-cyclopropylcarbamoyl)-pyrrolidine-1-carboxylic acid tert-butyl ester;

(2S,4R)-1-(1-Hydroxymethyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-4-(2-Chloro-benzenesulfonyl)-1-(1-hydroxymethyl-cyclopropanecarbonyl)-pyrrolidine-2-carboxylic acid (1-cyano-cyclopropyl)-amide;

(2S,4R)-4-(2-Allyloxy-benzenesulfonyl)-pyrrolidine-2-carboxylic acid (1-cyano-cyclopropyl)-amide;

(2S,4R)-4-Cyclopropylmethanesulfonyl-1-(1-methyl-cyclopropanecarbonyl)-pyrrolidine-2-carboxylic acid (1-cyano-cyclopropyl)-amide;

(2S,4R)-1-[(R)-2-Allylamino-2-(4-chloro-phenyl)-acetyl]-4-(2-allyloxy-benzenesulfonyl)-pyrrolidine-2-carboxylic acid (1-cyano-cyclopropyl)-amide;

(2S,4R)-4-(2-chloro-4-(3,3-difluoroazetidin-1-yl)phenylsulfonyl)-N-(1-cyanocyclopropyl)-1-(1-cyclobutyl-3-methyl-1H-pyrazol-5-yl)pyrrolidine-2-carboxamide;

(2S,4R)-1-(1-(4-chlorophenyl)cyclopropanecarbonyl)-N-(1-cyanocyclopropyl)-4-(phenylsulfonyl)pyrrolidine-2-carboxamide;

(2S,4R)-4-(benzylsulfonyl)-1-(1-(4-chlorophenyl)cyclopropanecarbonyl)-N-(1-cyanocyclopropyl)pyrrolidine-2-carboxamide;

(2S,4R)-4-(2-Chloro-benzenesulfonyl)-1-[1-(4-iodo-phenyl)-cyclopropanecarbonyl]-pyrrolidine-2-carboxylic acid (1-cyano-cyclopropyl)-amide;

(2S,4R)-4-(2-Chloro-benzenesulfonyl)-1-[1-(2,4-dichloro-5-methoxy-phenyl)-cyclopropanecarbonyl]-pyrrolidine-2-carboxylic acid (1-cyano-cyclopropyl)-amide;

(2S,4R)-4-(2-Chloro-benzenesulfonyl)-1-[1-(2,4-dichloro-5-fluoro-phenyl)-cyclopropanecarbonyl]-pyrrolidine-2-carboxylic acid (1-cyano-cyclopropyl)-amide;

(2S,4R)-4-Methanesulfonyl-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-1-[2-(2-Chloro-pyridin-4-yl)-5-methyl-2H-pyrazol-3-yl]-4-methanesulfonyl-pyrrolidine-2-carboxylic acid (1-cyano-cyclopropyl)-amide;

(2S,4R)-4-(2-chloro-4-(3,3-difluoroazetidin-1-yl)phenylsulfonyl)-N-(1-cyanocyclopropyl)-1-(3-methyl-1-(tetrahydro-2H-pyran-4-yl)-1H-pyrazol-5-yl)pyrrolidine-2-carboxamide;

(2S,4R)-4-(2-chlorophenylsulfonyl)-N-(1-cyanocyclopropyl)-1-(3-methyl-1-(tetrahydro-2H-thiopyran-4-yl)-1H-pyrazol-5-yl)pyrrolidine-2-carboxamide;

(2S,4R)-4-Methanesulfonyl-1-[5-methyl-2-(2,2,2-trifluoro-ethyl)-2H-pyrazol-3-yl]-pyrrolidine-2-carboxylic acid (1-cyano-cyclopropyl)-amide;

(2S,4R)-4-Cyclopropylmethanesulfonyl-1-[5-methyl-2-(2,2,2-trifluoro-ethyl)-2H-pyrazol-3-yl]-pyrrolidine-2-carboxylic acid (1-cyano-cyclopropyl)-amide;

(2S,4R)-1-[2-(2-Chloro-pyridin-4-yl)-5-methyl-2H-pyrazol-3-yl]-4-cyclopropylmethanesulfonyl-pyrrolidine-2-carboxylic acid (1-cyano-cyclopropyl)-amide;

(2S,4R)-4-Cyclopropylmethanesulfonyl-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-4-Cyclopropylmethanesulfonyl-1-(5-methyl-2-phenethyl-2H-pyrazol-3-yl)-pyrrolidine-2-carboxylic acid (1-cyano-cyclopropyl)-amide;

(2S,4R)-1-(2-Cyclobutyl-5-methyl-2H-pyrazol-3-yl)-4-methanesulfonyl-pyrrolidine-2-carboxylic acid (1-cyano-cyclopropyl)-amide;

(2S,4R)-1-[1-(4-Bromo-naphthalen-1-yl)-cyclopropanecarbonyl]-4-(2-chloro-benzenesulfonyl)-pyrrolidine-2-carboxylic acid (1-cyano-cyclopropyl)-amide;

(2S,4R)-4-(2-Chloro-benzenesulfonyl)-1-[1-(4-chloro-phenoxy)-cyclopropanecarbonyl]-pyrrolidine-2-carboxylic acid (1-cyano-cyclopropyl)-amide;

(2S,4R)-1-[1-(4-Chloro-phenyl)-cyclopropanecarbonyl]-4-(diphenyl-methanesulfonyl)-pyrrolidine-2-carboxylic acid (1-cyano-cyclopropyl)-amide;

(2S,4R)-4-(4-Bromo-phenylmethanesulfonyl)-1-[1-(4-chloro-phenyl)-cyclopropanecarbonyl]-pyrrolidine-2-carboxylic acid (1-cyano-cyclopropyl)-amide;

(2S,4R)-4-[4-(4-tert-Butyl-piperazin-1-yl)-phenylmethanesulfonyl]-1-[1-(4-chloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-(2-cyclohexyl-5-methyl-2H-pyrazol-3-yl)-pyrrolidine-2-carboxylic acid (1-cyano-cyclopropyl)-amide;

(2S,4R)-4-(2-Chloro-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide;

(4R)-4-[(2-chlorophenyl)sulfonyl]-N-(1-cyanocyclopropyl)-1-[1-(1,1-dioxidotetrahydro-2H-thiopyran-4-yl)-3-methyl-1H-pyrazol-5-yl]-L-prolinamide;

(2S,4R)-4-[2-Chloro-4-(3,3-difluoro-azetidin-1-yl)-benzenesulfonyl]-1-(2-cyclobutyl-5-methyl-2H-pyrazol-3-yl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2-cyclobutyl-5-methyl-2H-pyrazol-3-yl)-pyrrolidine-2-carboxylic acid (1-cyano-cyclopropyl)-amide;

(2S,4R)-4-[4-(4-tert-Butyl-piperazin-1-yl)-2-chloro-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-4-[2-Chloro-4-(3,3-difluoro-azetidin-1-yl)-benzenesulfonyl]-1-(5-methyl-2-phenethyl-2H-pyrazol-3-yl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(5-methyl-2-phenethyl-2H-pyrazol-3-yl)-pyrrolidine-2-carboxylic acid (1-cyano-cyclopropyl)-amide;

(2S,4R)-4-[4-(4-tert-Butyl-piperazin-1-yl)-2-chloro-benzenesulfonyl]-1-(5-methyl-2-phenethyl-2H-pyrazol-3-yl)-pyrrolidine-2-carboxylic acid (1-cyano-cyclopropyl)-amide;

(2S,4R)-4-(2-Chloro-benzenesulfonyl)-1-(3-chloro-[1,2,4]thiadiazol-5-yl)-pyrrolidine-2-carboxylic acid (1-cyano-cyclopropyl)-amide;

(2S,4R)-4-(2-Chloro-benzenesulfonyl)-1-[5-methyl-2-(3-phenyl-propyl)-2H-pyrazol-3-yl]-pyrrolidine-2-carboxylic acid (1-cyano-cyclopropyl)-amide; and (2S,4R)-4-(2-Chloro-benzenesulfonyl)-1-[5-methyl-2-(2-morpholin-4-yl-ethyl)-2H-pyrazol-3-yl]-pyrrolidine-2-carboxylic acid (1-cyano-cyclopropyl)-amide.

The compounds of the present invention can be prepared, for example, by the general synthetic procedures described below.

Orthogonally protected cis-4-hydroxy proline derivatives such as (2S,4S)-4-hydroxy-pyrrolidine-1,2-dicarboxylic acid 1-tert.-butyl ester is reacted with an appropriate aminoacetonitrile derivative in presence of one of the various amide coupling reagents such as BOP—Cl, TBTU, BOP, PyBop, HATU, EDCI/HOBT, DIC/HOBT; DCC/HOBT, etc. to yield corresponding amide. The amide is reacted with a sulfonyl chloride such as Mes-Cl, Nos-Cl, Tos-Cl or triflic anhydride to yield compound A. Reaction of A with thiols, in the presence of an appropriate base such as NaH, LiHMDS, DIPEA, TEA, etc yields compounds of type B. Oxidation of the obtained thioether is accomplished by an appropriate oxidizing agent such as $H_2O_2$, Oxone, MCPBA, etc. to yield compounds C. The protecting group is removed, in the case of Boc as protecting group with TFA, HCl or formic acid in an appropriate solvent such as THF, dioxane, $CH_2Cl_2$, etc. to yield the final compound D.

Scheme 2

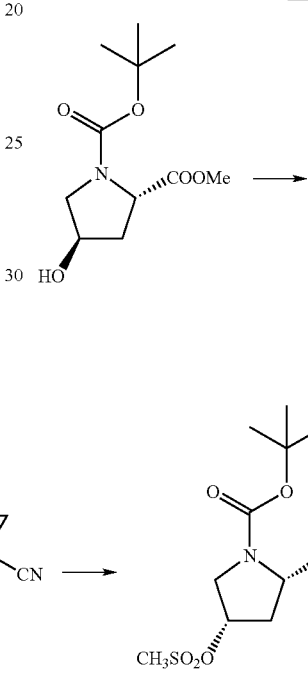

Scheme 1

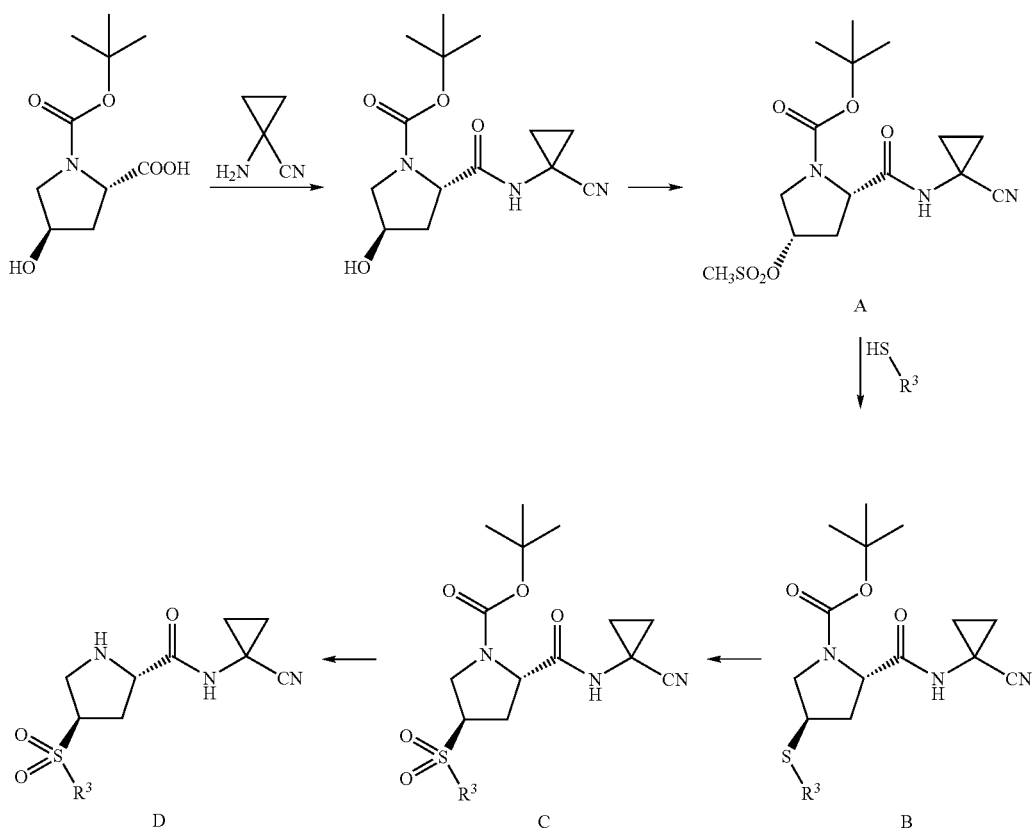

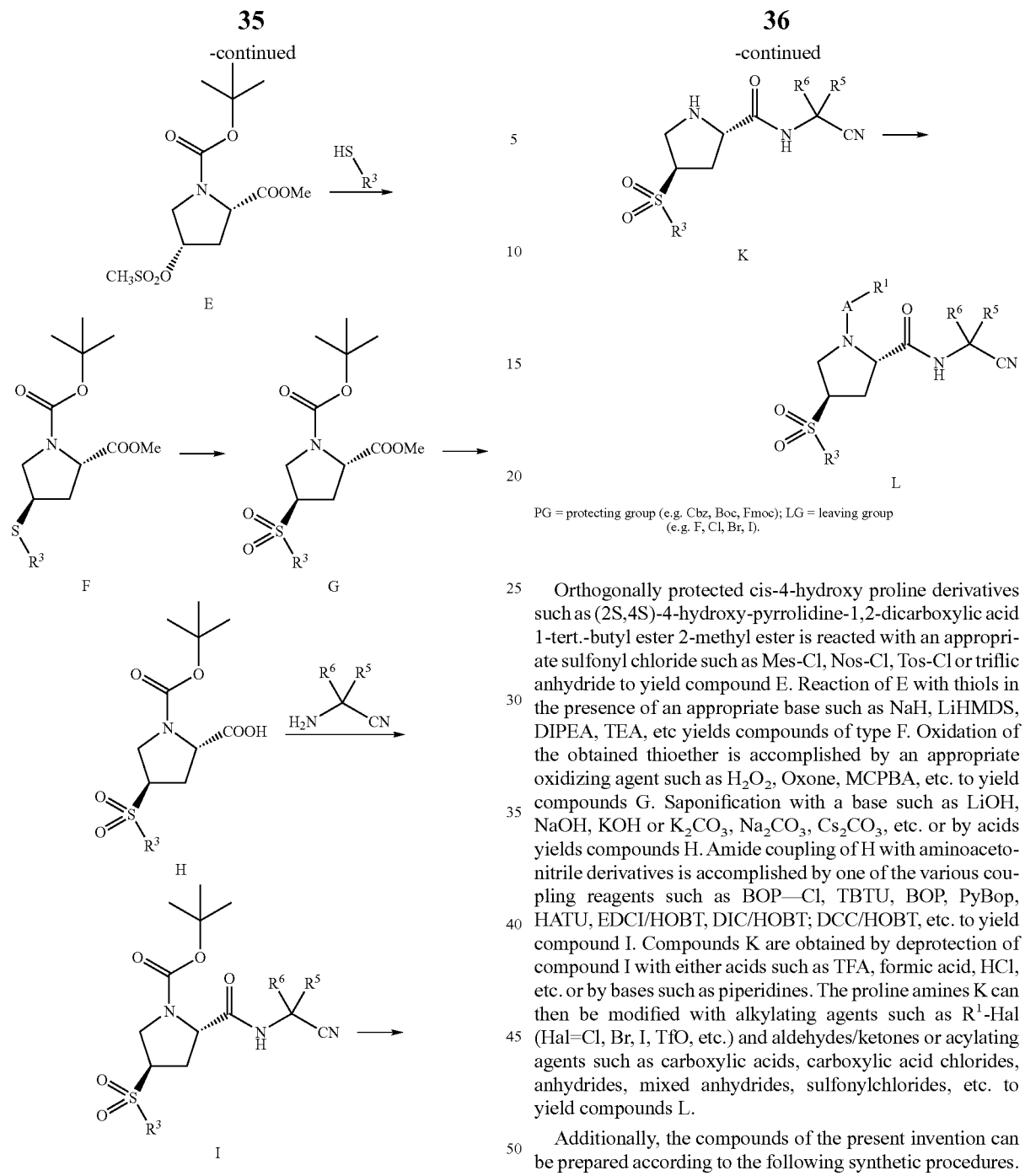

PG = protecting group (e.g. Cbz, Boc, Fmoc); LG = leaving group (e.g. F, Cl, Br, I).

Orthogonally protected cis-4-hydroxy proline derivatives such as (2S,4S)-4-hydroxy-pyrrolidine-1,2-dicarboxylic acid 1-tert.-butyl ester 2-methyl ester is reacted with an appropriate sulfonyl chloride such as Mes-Cl, Nos-Cl, Tos-Cl or triflic anhydride to yield compound E. Reaction of E with thiols in the presence of an appropriate base such as NaH, LiHMDS, DIPEA, TEA, etc yields compounds of type F. Oxidation of the obtained thioether is accomplished by an appropriate oxidizing agent such as $H_2O_2$, Oxone, MCPBA, etc. to yield compounds G. Saponification with a base such as LiOH, NaOH, KOH or $K_2CO_3$, $Na_2CO_3$, $Cs_2CO_3$, etc. or by acids yields compounds H. Amide coupling of H with aminoacetonitrile derivatives is accomplished by one of the various coupling reagents such as BOP—Cl, TBTU, BOP, PyBop, HATU, EDCI/HOBT, DIC/HOBT; DCC/HOBT, etc. to yield compound I. Compounds K are obtained by deprotection of compound I with either acids such as TFA, formic acid, HCl, etc. or by bases such as piperidines. The proline amines K can then be modified with alkylating agents such as $R^1$-Hal (Hal=Cl, Br, I, TfO, etc.) and aldehydes/ketones or acylating agents such as carboxylic acids, carboxylic acid chlorides, anhydrides, mixed anhydrides, sulfonylchlorides, etc. to yield compounds L.

Additionally, the compounds of the present invention can be prepared according to the following synthetic procedures.

Scheme 3

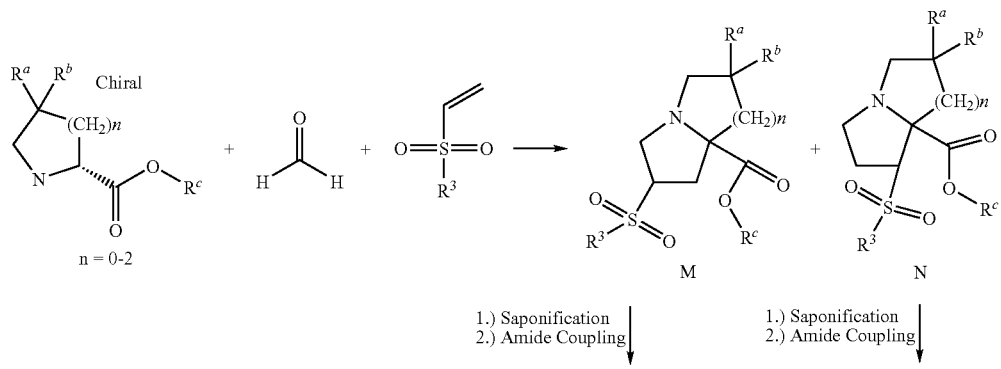

-continued

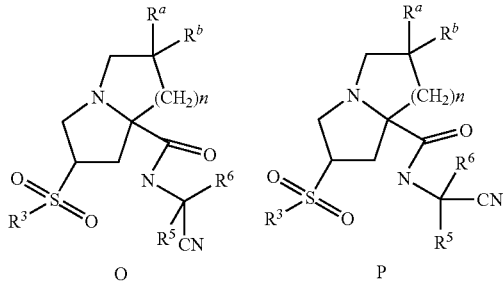

$R^a$ and $R^b$ are independently selected from hydrogen and fluorine. $R^c$ is alkyl or benzyl, preferably methyl, ethyl or benzyl.

An optionally substituted carboxy-protected cyclic amino acid derivative, such as L-proline methyl ester, L-proline benzyl ester, L-proline ethyl ester, 4,4-difluoro-L-proline methyl ester, 4,4-difluoro-L-proline ethyl ester, 4,4-difluoro-L-proline benzyl ester, and corresponding homo proline derivatives, is condensed with formaldehyde in presence of an appropriate vinylsulfone. The obtained pyrrolizine regioisomeres M and N are saponified with a base such as LiOH, NaOH, KOH or $K_2CO_3$, $Na_2CO_3$, $Cs_2CO_3$, etc. or by acids yields or by catalytic hydrogenation to yield the corresponding acids which are reacted with aminoacetonitrile derivatives under amide coupling conditions in the presence of one of the various coupling reagents such as BOP—Cl, TBTU, BOP, PyBop, HATU, EDCI/HOBT, DIC/HOBT; DCC/HOBT, etc. to yield compounds O and P.

-continued

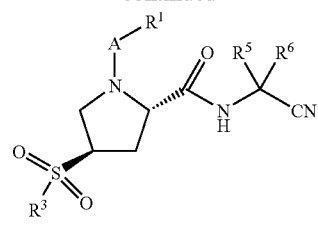

R is methyl, ethyl, isopropyl or tert. butyl.

Compounds of type 1, prepared by methods described above or analogous methods, can be converted to N-aryl derivatives of type 2 (where $R^1=R^{11}$) by methods well known in the art, for example by copper or palladium promoted N-arylation using aryl boronic acids or aryl boronic esters as aryl source and various types of palladium or copper salts with or without ligands, eventually in the presence of additives like bases or oxygen. Alternatively, compounds of type 2 where $R^1=R^{11}$ can be prepared by aromatic nucleophilic substitution with suitable aryl donors. Such reactions are run at room temperature or with heating, eventually in the presence of a base. Saponification with a base such as LiOH, NaOH, KOH or $K_2CO_3$, $Na_2CO_3$, $Cs_2CO_3$, etc. or by acids yields compounds 3. Amide coupling of 3 with aminoacetonitrile derivatives is accomplished by one of the various coupling reagents such as BOP—Cl, TBTU, BOP, PyBop, HATU, EDCI/HOBT, DIC/HOBT; DCC/HOBT, etc. or by formation of a mixed anhydride with alkyl-chloroformiates like ethyl chloroformiate or i-butyl chloroformiate followed by reaction with an aminoacetonitrile, to yield compounds 4.

Scheme 4

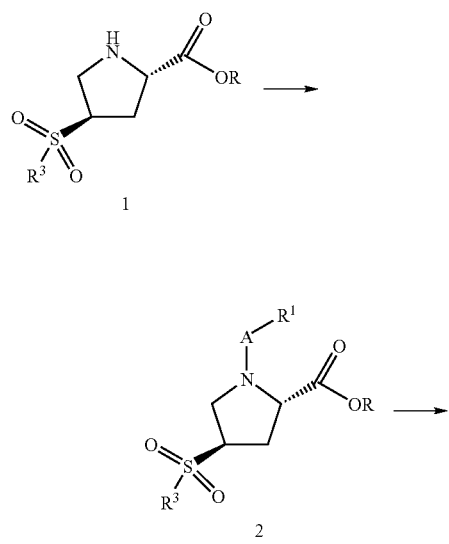

Scheme 5

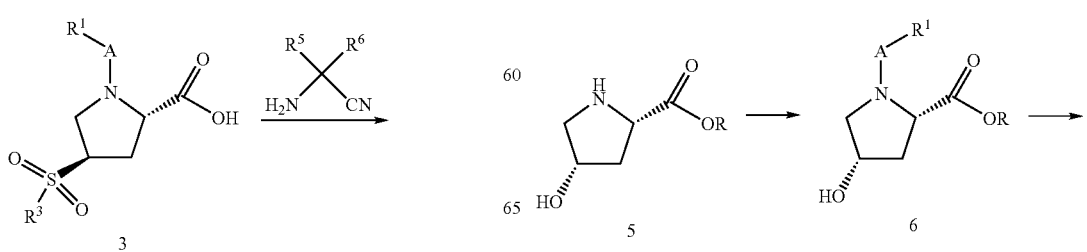

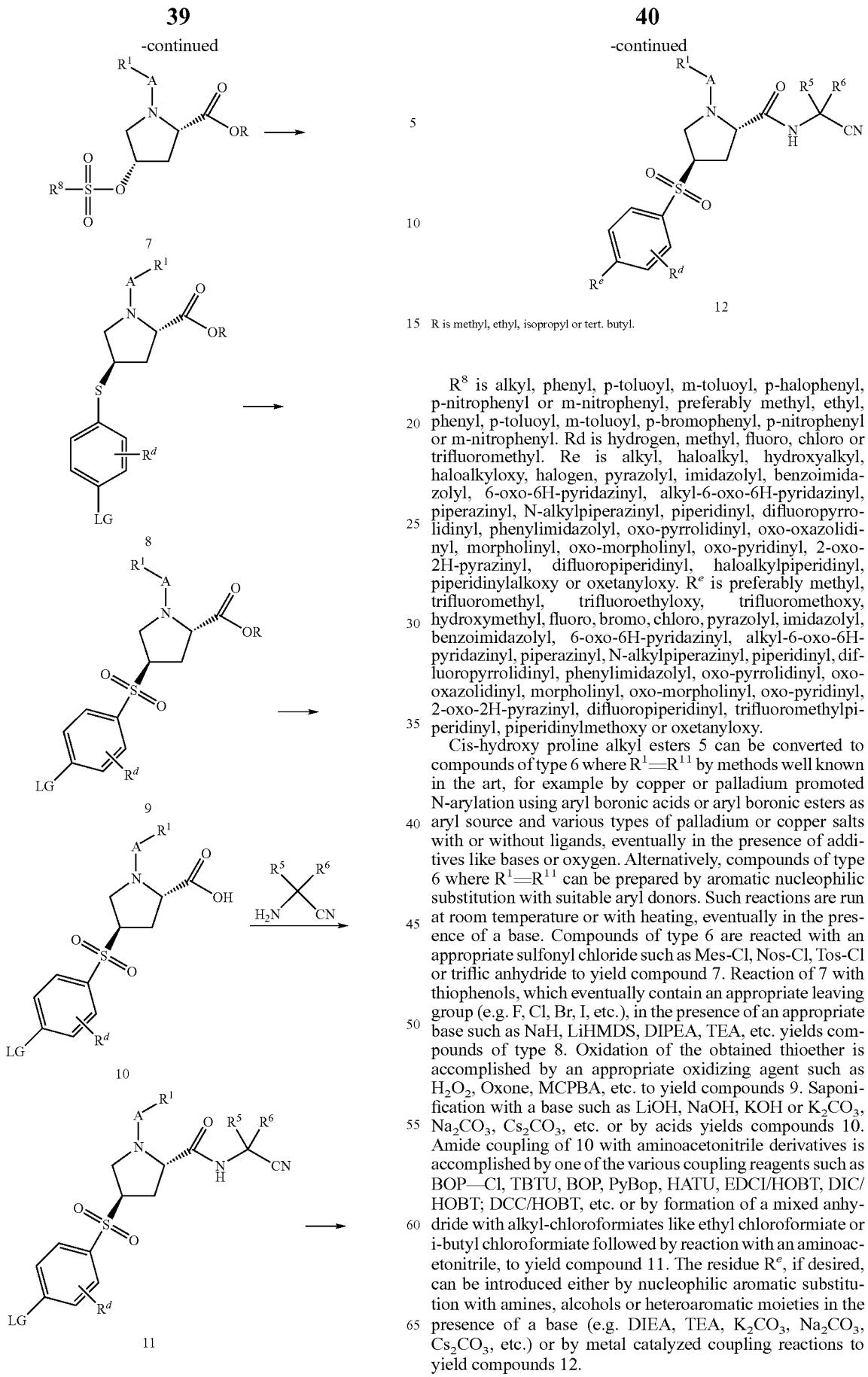

R is methyl, ethyl, isopropyl or tert. butyl.

R[8] is alkyl, phenyl, p-toluoyl, m-toluoyl, p-halophenyl, p-nitrophenyl or m-nitrophenyl, preferably methyl, ethyl, phenyl, p-toluoyl, m-toluoyl, p-bromophenyl, p-nitrophenyl or m-nitrophenyl. $R^d$ is hydrogen, methyl, fluoro, chloro or trifluoromethyl. $R^e$ is alkyl, haloalkyl, hydroxyalkyl, haloalkyloxy, halogen, pyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, haloalkylpiperidinyl, piperidinylalkoxy or oxetanyloxy. $R^e$ is preferably methyl, trifluoromethyl, trifluoroethyloxy, trifluoromethoxy, hydroxymethyl, fluoro, bromo, chloro, pyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, trifluoromethylpiperidinyl, piperidinylmethoxy or oxetanyloxy.

Cis-hydroxy proline alkyl esters 5 can be converted to compounds of type 6 where $R^1=R^{11}$ by methods well known in the art, for example by copper or palladium promoted N-arylation using aryl boronic acids or aryl boronic esters as aryl source and various types of palladium or copper salts with or without ligands, eventually in the presence of additives like bases or oxygen. Alternatively, compounds of type 6 where $R^1=R^{11}$ can be prepared by aromatic nucleophilic substitution with suitable aryl donors. Such reactions are run at room temperature or with heating, eventually in the presence of a base. Compounds of type 6 are reacted with an appropriate sulfonyl chloride such as Mes-Cl, Nos-Cl, Tos-Cl or triflic anhydride to yield compound 7. Reaction of 7 with thiophenols, which eventually contain an appropriate leaving group (e.g. F, Cl, Br, I, etc.), in the presence of an appropriate base such as NaH, LiHMDS, DIPEA, TEA, etc. yields compounds of type 8. Oxidation of the obtained thioether is accomplished by an appropriate oxidizing agent such as $H_2O_2$, Oxone, MCPBA, etc. to yield compounds 9. Saponification with a base such as LiOH, NaOH, KOH or $K_2CO_3$, $Na_2CO_3$, $Cs_2CO_3$, etc. or by acids yields compounds 10. Amide coupling of 10 with aminoacetonitrile derivatives is accomplished by one of the various coupling reagents such as BOP—Cl, TBTU, BOP, PyBop, HATU, EDCI/HOBT, DIC/HOBT; DCC/HOBT, etc. or by formation of a mixed anhydride with alkyl-chloroformiates like ethyl chloroformiate or i-butyl chloroformiate followed by reaction with an aminoacetonitrile, to yield compound 11. The residue $R^e$, if desired, can be introduced either by nucleophilic aromatic substitution with amines, alcohols or heteroaromatic moieties in the presence of a base (e.g. DIEA, TEA, $K_2CO_3$, $Na_2CO_3$, $Cs_2CO_3$, etc.) or by metal catalyzed coupling reactions to yield compounds 12.

Scheme 6

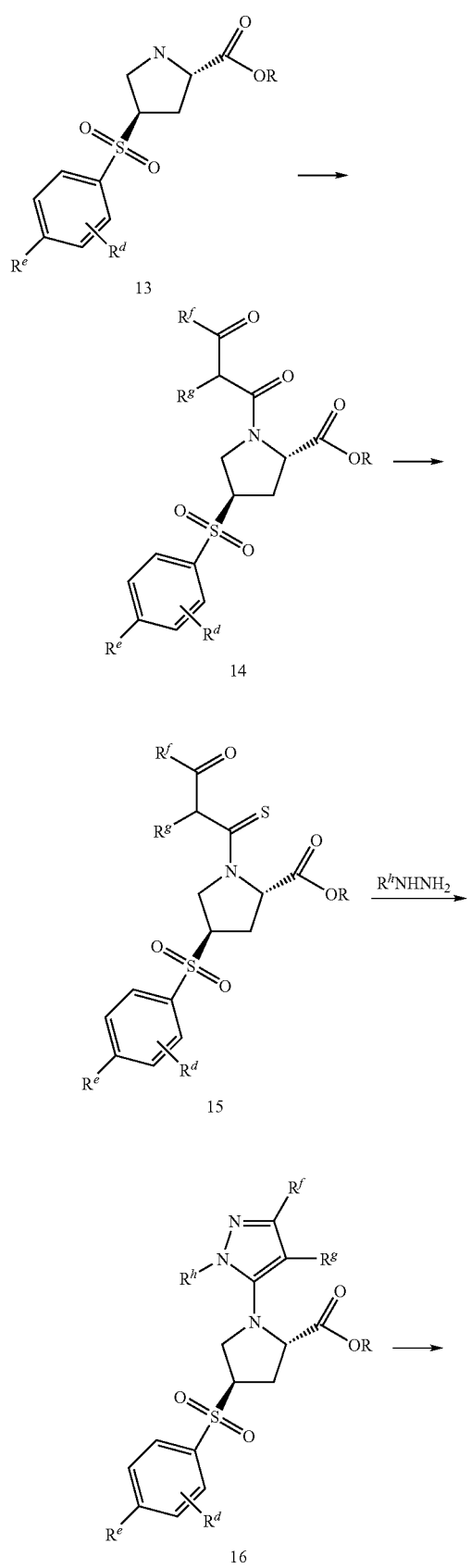

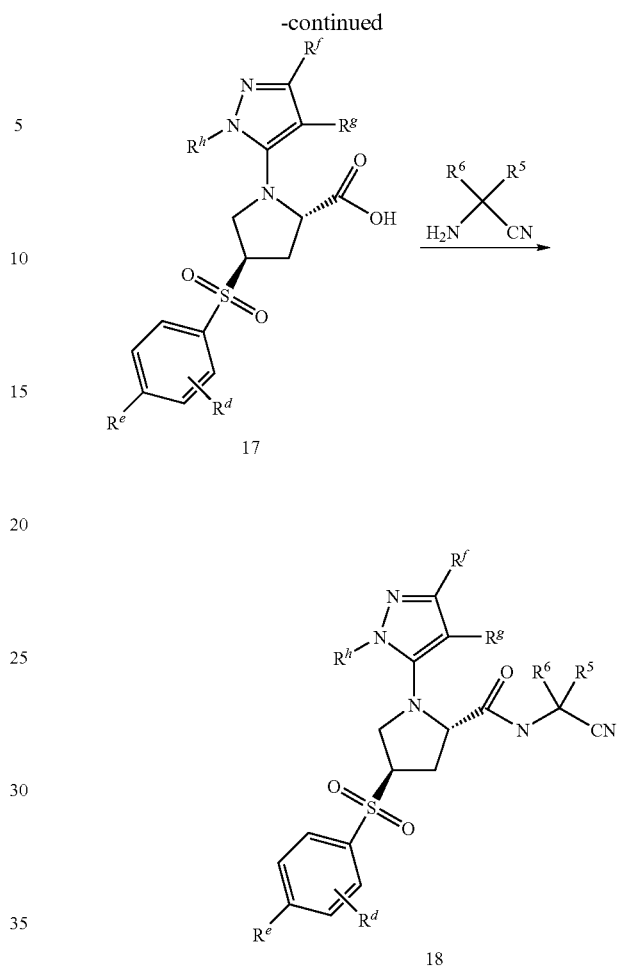

R, R$^d$ and R$^e$ are as defined above.

R$^f$, R$^g$ and R$^h$ are independently selected from alkyl, halogen, haloalkyl, alkoxy, alkoxycarbonyl, halophenyl, halopyridinyl, oxodihydropyridinyl and nitro, preferably independently selected from methyl, fluoro, methoxy, methoxycarbonyl, trifluoromethoxy, trifluoromethyl, chlorophenyl, fluorophenyl, chloropyridinyl, oxodihydropyridinyl and nitro.

Compounds of type 13, prepared by methods described above or analogous methods, can be converted to the β-keto amides of type 14 by reaction with an appropriate β-keto ester, typically a tert-butyl β-keto ester under thermic exchange conditions, according to methods known in the art. Conversion to the corresponding thioamide 15 can be easily obtained for example with Lawesson's reagent. Cyclization to pyrazoles 16 is obtained by treatment with a hydrazine under thermic conditions. Optionally, conversion of β-keto amides 14 to pyrazoles 16 can also be performed in a one-pot reaction. Saponification with a base such as LiOH, NaOH, KOH or K$_2$CO$_3$, Na$_2$CO$_3$, Cs$_2$CO$_3$, etc. or by acids yields compounds 17. Amide coupling of 17 with aminoacetonitrile derivatives is accomplished by one of the various coupling reagents such as BOP—Cl, TBTU, BOP, PyBop, HATU, EDCI/HOBT, DIC/HOBT; DCC/HOBT, etc. or by formation of a mixed anhydride with alkyl-chloroformiates like ethyl chloroformiate or i-butyl chloroformiate followed by reaction with an aminoacetonitrile, to yield compounds 18.

Scheme 7

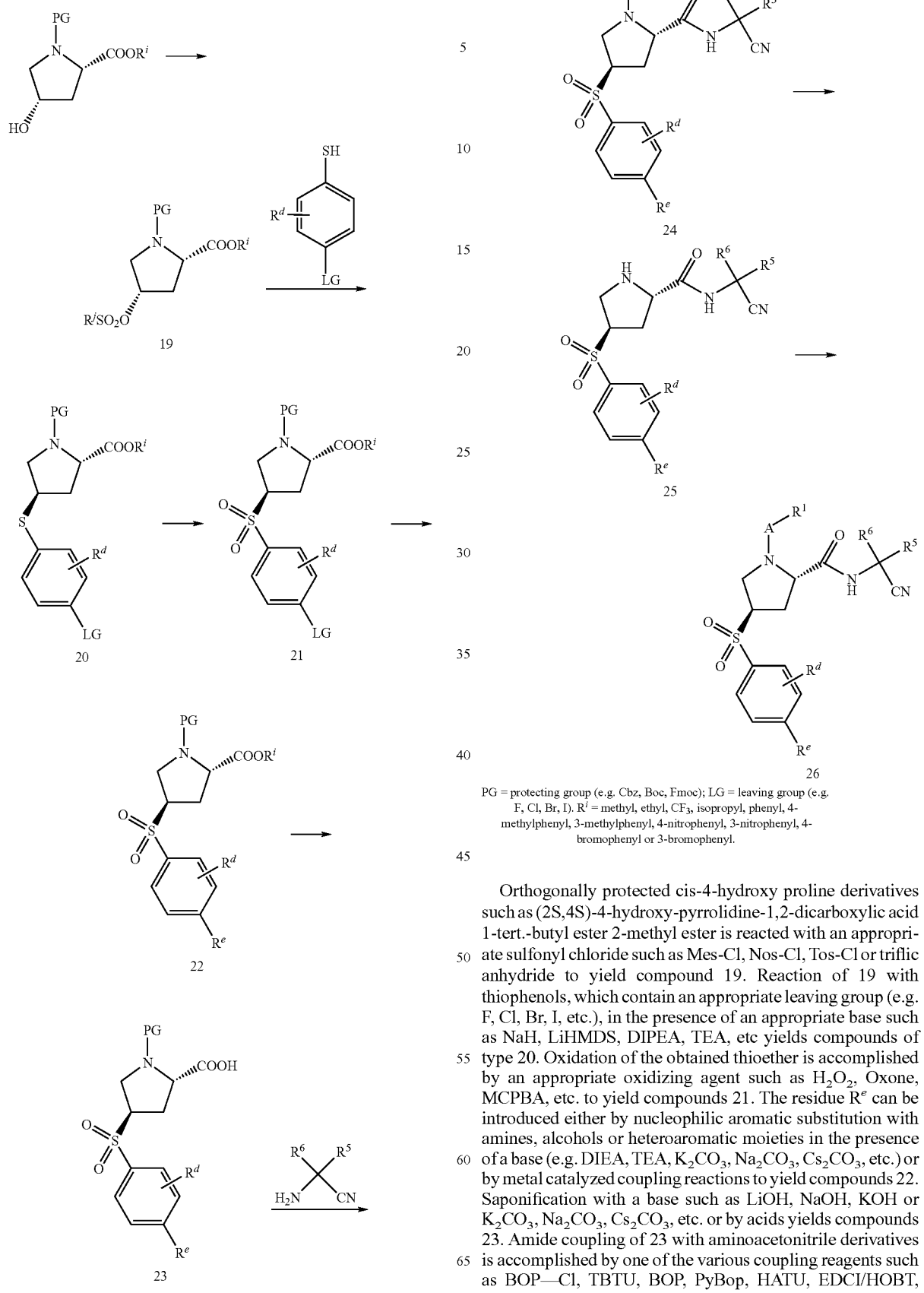

PG = protecting group (e.g. Cbz, Boc, Fmoc); LG = leaving group (e.g. F, Cl, Br, I). $R^i$ = methyl, ethyl, $CF_3$, isopropyl, phenyl, 4-methylphenyl, 3-methylphenyl, 4-nitrophenyl, 3-nitrophenyl, 4-bromophenyl or 3-bromophenyl.

Orthogonally protected cis-4-hydroxy proline derivatives such as (2S,4S)-4-hydroxy-pyrrolidine-1,2-dicarboxylic acid 1-tert.-butyl ester 2-methyl ester is reacted with an appropriate sulfonyl chloride such as Mes-Cl, Nos-Cl, Tos-Cl or triflic anhydride to yield compound 19. Reaction of 19 with thiophenols, which contain an appropriate leaving group (e.g. F, Cl, Br, I, etc.), in the presence of an appropriate base such as NaH, LiHMDS, DIPEA, TEA, etc yields compounds of type 20. Oxidation of the obtained thioether is accomplished by an appropriate oxidizing agent such as $H_2O_2$, Oxone, MCPBA, etc. to yield compounds 21. The residue $R^e$ can be introduced either by nucleophilic aromatic substitution with amines, alcohols or heteroaromatic moieties in the presence of a base (e.g. DIEA, TEA, $K_2CO_3$, $Na_2CO_3$, $Cs_2CO_3$, etc.) or by metal catalyzed coupling reactions to yield compounds 22. Saponification with a base such as LiOH, NaOH, KOH or $K_2CO_3$, $Na_2CO_3$, $Cs_2CO_3$, etc. or by acids yields compounds 23. Amide coupling of 23 with aminoacetonitrile derivatives is accomplished by one of the various coupling reagents such as BOP—Cl, TBTU, BOP, PyBop, HATU, EDCI/HOBT, DIC/HOBT; DCC/HOBT, etc. to yield compound 24. Compounds 25 are obtained by deprotection of compound 24 with either acids such as TFA, formic acid, HCl, etc. or by bases such as piperidines. The proline amines 25 can then be modified with alkylating agents such as $R^1$-Hal (Hal=Cl, Br, I, TfO, etc.) and aldehydes/ketones or acylating agents such as carboxylic acids, carboxylic acid chlorides, anhydrides, mixed anhydrides, sulfonylchlorides, etc. to yield compounds 26.

Alternatively the compounds can be prepared by the reaction sequence of scheme 8 using similar reaction conditions as described above. In this sequence $R^e$ is introduced in the final step from 33 to 34.

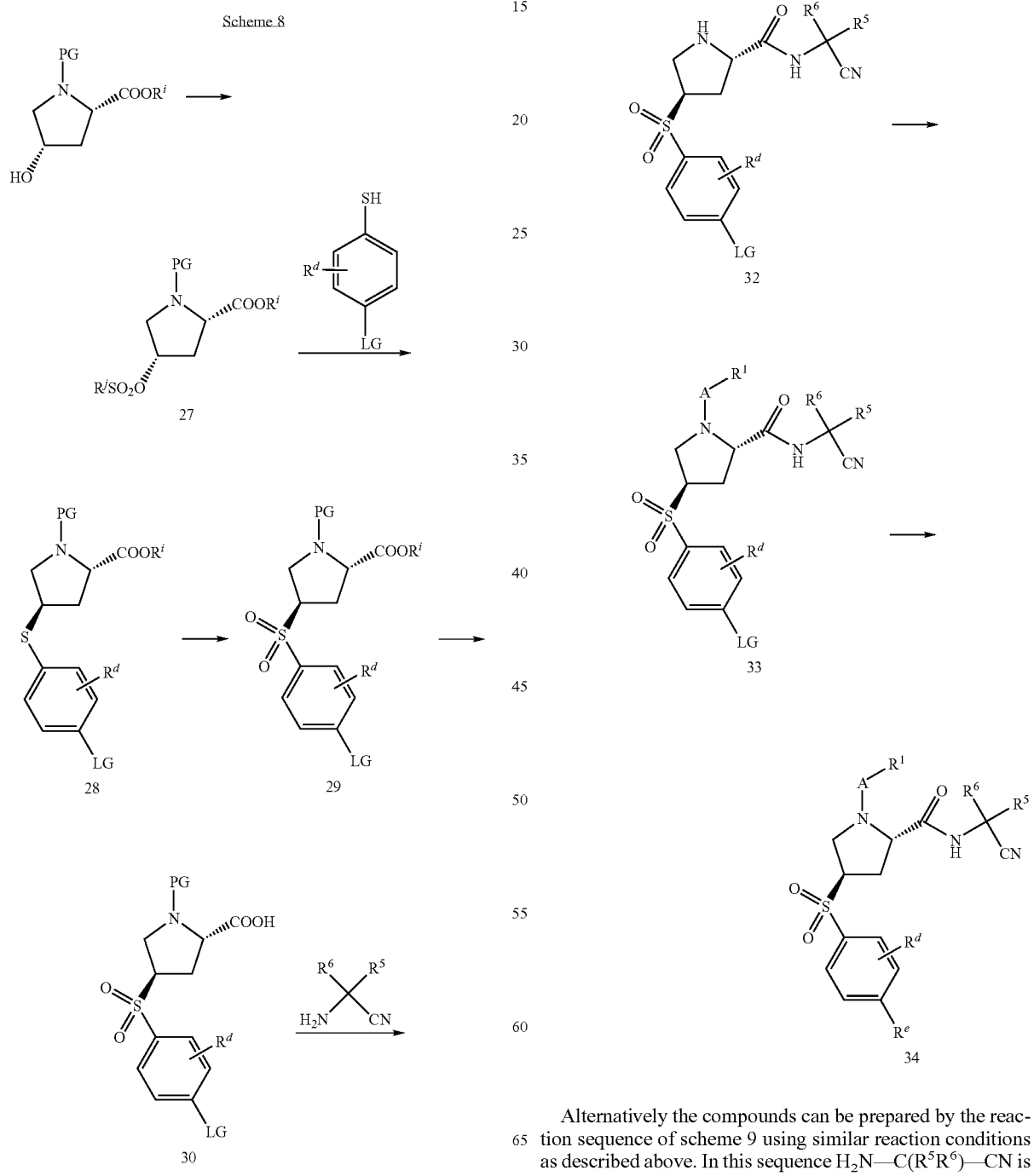

Alternatively the compounds can be prepared by the reaction sequence of scheme 9 using similar reaction conditions as described above. In this sequence $H_2N-C(R^5R^6)-CN$ is introduced in the final step from 41 to 42.

Scheme 9
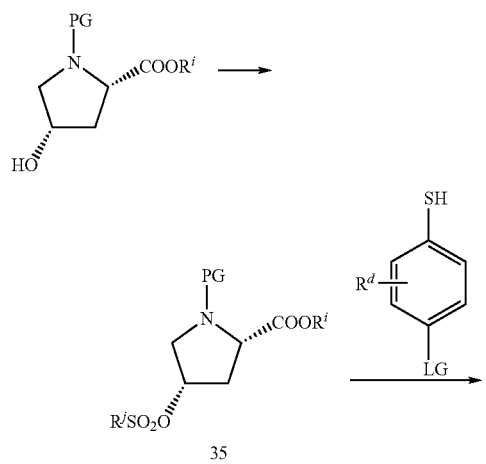
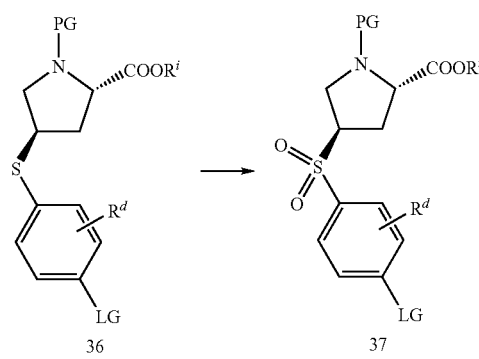
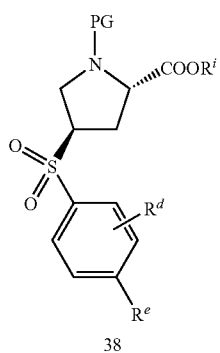
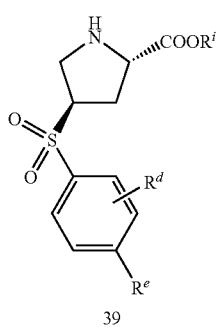
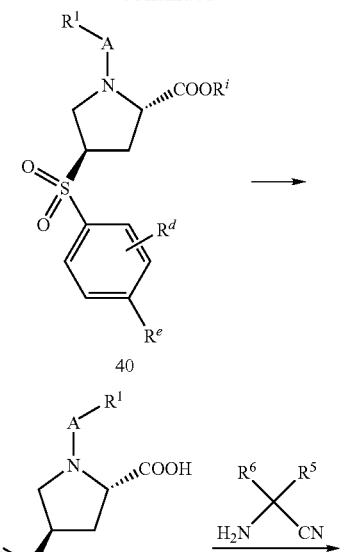
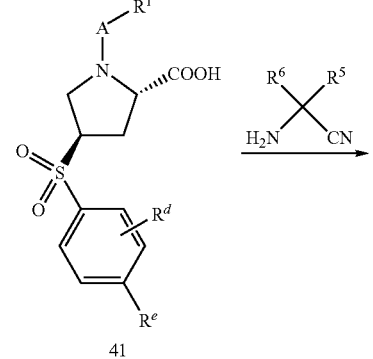
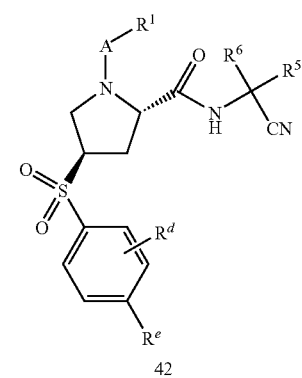
Scheme 10
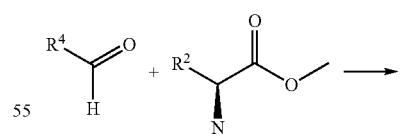
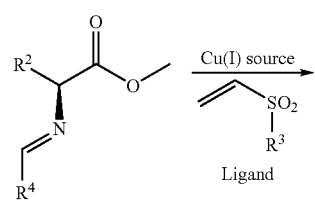

-continued

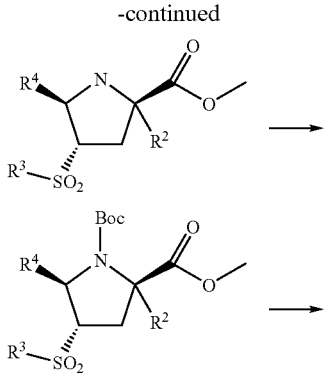

imine in the presence a dehydrating agent such as Na$_2$SO$_4$, CaCl$_2$, MgCl$_2$, mol sieve etc. In the presence of a Cu(I) source such as CuClO$_4$, CuOAc or a Ag(I) source, a substituted vinylsulfone and a chiral ligand such as Binap, Chiraphos, Norphos, Josiphos, Mandyphos, Taniaphos etc. the 1,3-dipolar cycloaddition reaction occurs. Subsequent protection with an appropriate protecting group such as Boc, Fmoc, Cbz, etc. and saponifiaction with LiOH, NaOH, etc. yields the corresponding N-protected amino acid. Reaction of the amino acid with cyclopropyl amino acetonitrile in the presence of a suitable amide coupling reagent such as CDI, EDCI, DIC, DCC, HATU, TBTU, BOP, PyBop and subsequent deprotection yields the final compounds.

Scheme 11

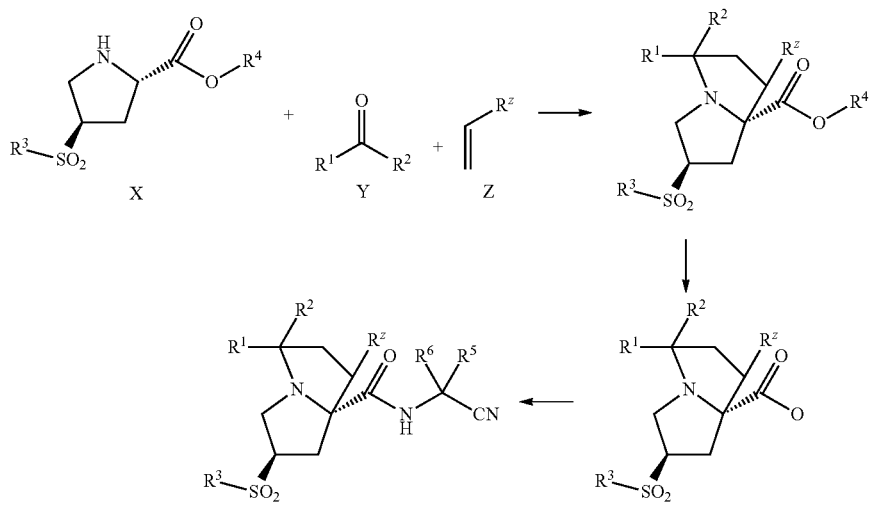

In scheme 11, R$^1$ and R$^2$ are independently selected from hydrogen and alkyl. R$^4$ is alkyl or benzyl, preferably methyl, ethyl or benzyl. R$^5$ and R$^6$ are as defined above. Rz is CN, COOR, C(O)ONHR or SO$_2$R(R=alkyl, alkylaryl, aryl, hetaryl).

An arylsulfonyl substituted carboxy-protected cyclic amino acid derivative X is condensed under acid catalysis (TFA, MesOS, trifluoromethane sulfonic acid, HCl, HBr, H$_2$SO$_4$, H$_3$PO$_4$ etc.) with formaldehyde or aldehydes or ketones Y in presence of an appropriate activated vinyl derivative Z. The obtained pyrrolizine derivative is saponified with a base such as LiOH, NaOH, KOH or K$_2$CO$_3$, Na$_2$CO$_3$, Cs$_2$CO$_3$, etc. or by acids or by catalytic hydrogenation to yield the corresponding acids which are reacted with aminoacetonitrile derivatives under amide coupling conditions in the presence of one of the various coupling reagents such as BOP—Cl, TBTU, BOP, PyBop, HATU, EDCI/HOBT, DIC/HOBT, DCC/HOBT, etc. to yield the final compound. If compound Z contains a functional group which is not stable or is reactive under the reaction conditions of one or more reaction steps, appropriate protecting groups (PG) (as described e.g. in "Protective Groups in Organic Chemistry" by T. W. Greene and P. G. M. Wutts, 2nd Ed., 1991, Wiley N.Y.) can be introduced before the critical step applying methods well known in the art. Such protecting groups can be removed at a later stage of the synthesis using standard methods described in the literature.

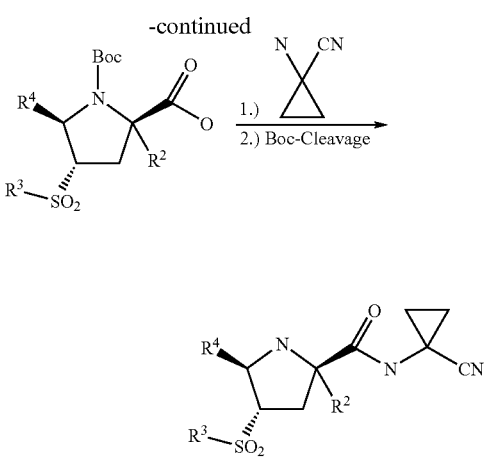

The tetrasubstituted pyrrolidine derivatives were prepared in analogy to the procedures described in J. C. Carretero et al., Org. Lett., Vol. 8, No. 9, 2006, 1795-1798. A suitable amino acid is condensed with an aldehyde to yield the corresponding

Scheme 12

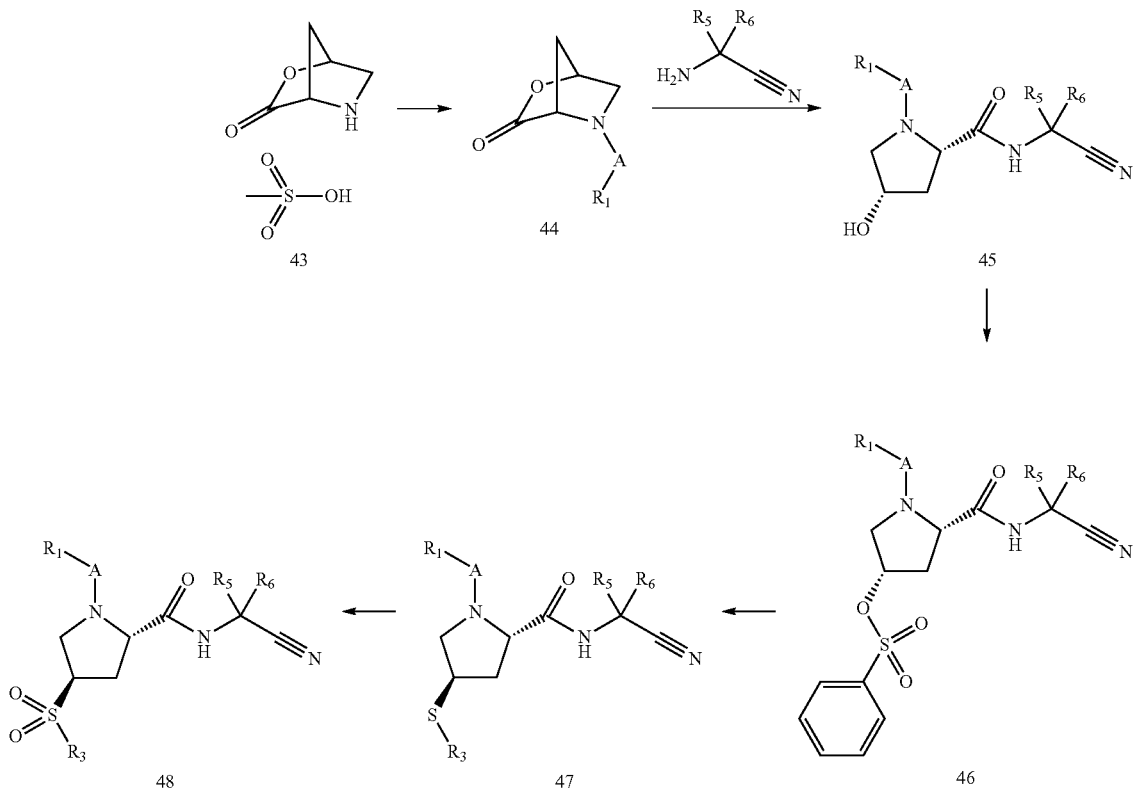

Scheme 12 describes a modification of the synthesis described above. It is taking advantage of the known (1S,4S)-2-oxa-5-azabicyclo[2.2.1]heptan-3-one, methanesulfonate salt 43 (CAS #: 769167-53-5) to set the relative and absolute configuration. After introduction of the N-substituent, amino acetonitrile is then coupled to form hydroxylamide 45 using for example sodium 2-ethylhexanoate in water. The free alcohol in 45 is activated using, for example, chlorophenylsulfonate. The sulfonate is displaced in an $SN_2$ reaction to introduce the thioether. This thioether 47 is then oxidized to the sulfone 48 using, for example oxone.

The invention also relates to a process for the preparation of a compound of formula (I) comprising one of the following steps:

(a) the reaction of a compound of formula (Ia)

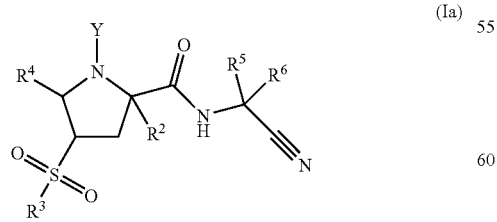

(Ia)

in the presence of an amine deprotecting agent;

(b) the reaction of a compound of formula (Ib)

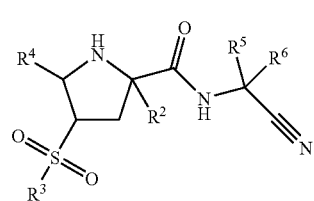

(Ib)

in the presence of $R^1$—A—X; or (c) the reaction of a compound of formula (Ic)

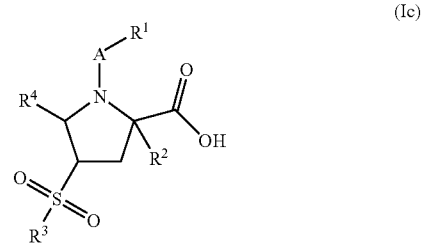

(Ic)

in the presence of $H_2N$—$CR^5R^6$—CN;

wherein A, $R^1$ to $R^6$ are as defined above and wherein Y is an amine protecting group. Examples of amine deprotecting agent are TFA, HCl, $MeSO_3H$, HBr/AcOH, HCOOH, TBAF, hexafluoroisopropanol, piperidine and $Pd(PPh_3)_4/Bu_3SnH$.

Examples of suitable amine protecting group are Z (benzyloxycarbonyl), Boc (tert. butyloxycarbonyl), Fmoc (9-fluorenyloxycarbonyl), Teoc (trimethylsilylethyloxycarbonyl), Trt (trityl), Moz (4-methoxyphenylmethyloxycarbonyl) and Alloc (allyloxycarbonyl).

Step (a) is preferably carried out in a solvent selected from dichloromethane, dioxane, acetonitrile, toluene, DMF, DMA, NMP, THF or acetic acid. The temperature of step (a) is preferably between −10° C. and +100° C.

Step (b) is preferably carried out in a solvent selected from dichloromethane, dioxane, acetonitrile, toluene, DMF, DMA, NMP and THF. The temperature of step (b) is preferably between −10° C. and +100° C.

Step (c) is preferably carried out in a solvent selected from dichloromethane, dioxane, acetonitrile, toluene, DMF, DMA, NMP and THF. The temperature of step (c) is preferably between −10° C. and +100° C. and more preferably between −10° C. and +50° C.

The invention also relates to a compound of formula (I) for use as therapeutically active substance.

Further, a pharmaceutical composition comprising a compound of formula (I) and a therapeutically inert carrier is also an object of the invention.

The invention further relates to the use of a compound of formula (I) for the preparation of medicaments for the treatment or prophylaxis of diabetes, atherosclerosis, abdominal aortic aneurysm, peripheral arterial disease or diabetic nephropathy.

The compounds of formula (I) can be used in the treatment of cancer or in the reduction of cardiovascular events or disease in patients with chronic kidney disease.

A compound of formula (I), when manufactured according to a process according to the invention, is also an object of the invention.

Furthermore, the invention also relates to a method for the treatment or prophylaxis of diabetes, atherosclerosis, abdominal aortic aneurysm, peripheral arterial disease or diabetic nephropathy, which method comprises administering an effective amount of a compound of formula (I).

The invention will now be illustrated by the following examples which have no limiting character.

EXAMPLES

Abbreviations

ACN: Acetonitrile;
BOP: Benzotriazolyl-N-oxy-tris(dimethylamino)-phosphonium hexafluorophosphate;
BOP—Cl: Bis-(2-oxo-3-oxazolidinyl)-phosphinic acid chloride;
CDI: 1,1'-Carbonyldiimidazole;
DIEA: Diisopropyl ethyl amine;
DMA: N,N-Dimethylacetamide;
DMF: N,N-Dimethylformamide;
EDCI: N-(3-Dimethylaminopropyl)-N'-ethyl-carbodiimide hydrochloride;
HATU: O-(7-azabenzotriazol-1-yl)-1,1,3,3-tetramethyluronium hexafluorophosphate;
HOBT: 1-Hydroxybenzotriazole;
iPrOAc: Isopropyl acetate
LiHMDS: Lithium bis(trimethylsilyl)amide;
MCPBA: 3-Chloroperbenzoic acid;
Mes-Cl: Mesyl chloride;
$Na_2SO_4$: Sodium sulfate
NMP═N-Methylpyrrolidinone;
Nos-Cl: 3-Nitrobenzenesulfonyl chloride;
PyBOP: Benzotriazol-1-yl-oxytripyrrolidinephosphonium hexafluorophosphate;

quant.: Quantitative;
TEA: Triethylamine;
TBAF: Tetrabutylammonium fluoride;
TBTU: O-(Benzotriazol-1-yl)-N,N,N',N'-tetramethyluronium terafluoroborate;
THF: Tetrahydrofurane;
TFA: Trifluoroacetic acid; and
Tos-Cl: Toluene-4-sulfonyl chloride.

A. Synthesis of intermediate (2S,4S)-2-(1-cyano-cyclopropylcarbamoyl)-4-methanesulfonyloxy-pyrrolidine-1-carboxylic acid t-butyl ester A A1. A mixture of (2S,4R)-4-hydroxypyrrolidine-2-carboxylic acid t-butyl ester (2.2 mmole) and 1-amino-cyclopropanecarbonitrile hydrochloride (2.2 mmole) in acetonitrile (5 ml) was subsequently treated with diisopropylethyl amine (10.8 mmole), 1-hydroxybenzotriazole hydrate (2.2 mmole) and 1-(3-dimethylaminopropyl)-3-ethylcarbodiimide hydrochloride (EDC, 2.4 mmole) and stirring was continued at 22° C. for 4 h. The mixture was partitioned between ethyl acetate and aqueous sodium carbonate (1 N), the organic was dried and evaporated. The residue was chromatographed on silica using ethyl acetate/methanol (95:5) to give the (2S,4R)-2-(1-cyano-cyclopropylcarbamoyl)-4-hydroxy-pyrrolidine-1-carboxylic acid t-butyl ester (390 mg) as a white solid. MS: 196.2 $[M+H-Boc]^+$.

A2. To a solution of methanesulfonic acid (1.6 mmole) in THF (3 ml) was added triethylamine (1.6 mmole) and triphenylphosphine (1.7 mmole) and the mixture was stirred at 22° C. for 30 min. The mixture was added to a solution of (2S, 4R)-2-(1-cyano-cyclopropyl-carbamoyl)-4-hydroxy-pyrrolidine-1-carboxylic acid t-butyl ester (1.3 mmole) in THF (10 ml) followed by addition of diisopropyl azodicarboxylate (1.7 mmole) and stirring was continued at reflux temperature for 3 days. The reaction mixture was partitioned between ethyl acetate and aqueous $KHSO_4$, the organic layer was dried, evaporated and the residue chromatographed on silica using cyclohexane/ethyl acetate (1:2) to give the title compound (273 mg) containing minor quantities of triphenylphosphine oxide as a white solid. MS: 372.3 $[M-H]^-$.

B. Synthesis of the Intermediate Thioethers B

General Procedure

To a solution of the thiols (0.41 mmole) in THF (4 ml) was added NaH (55% in oil, 0.41 mmole) at 22° C. and stirring was continued until gas evolution ceased. To the mixture was added a solution of (2S,4S)-2-(1-cyano-cyclopropylcarbamoyl)-4-methanesulfonyloxy-pyrrolidine-1-carboxylic acid t-butyl ester (0.28 mmole, obtained from experiment A2) in THF (4 ml) and stirring was continued at 50° C. until completion of the reaction. The mixture was partitioned between ethyl acetate and water, the organic layer was dried, evaporated and the residue chromatographed on silica using mixtures of cyclohexane and ethyl acetate to give the thioethers B.

B1. The reaction of the mesylate from experiment A2 with 2-ethylbenzenethiol yielded (2S,4R)-2-(1-cyano-cyclopropylcarbamoyl)-4-(2-ethyl-phenylsulfanyl)-pyrrolidine-1-carboxylic acid t-butyl ester as a colorless oil. MS: 414.4 $[M-H]^-$.

B2. The reaction of the mesylate from experiment A2 with 2-mercaptobenzyl alcohol yielded (2S,4R)-2-(1-cyano-cyclopropylcarbamoyl)-4-(2-hydroxymethyl-phenylsulfanyl)-pyrrolidine-1-carboxylic acid t-butyl ester as a colorless oil. MS: 416.5 [M–H]⁻.

B3. The reaction of the mesylate from experiment A2 with 2-trifluoromethoxy-benzenethiol yielded (2S,4R)-2-(1-cyano-cyclopropylcarbamoyl)-4-(2-trifluoromethoxy-phenylsulfanyl)-pyrrolidine-1-carboxylic acid t-butyl ester as a colorless foam. MS: 470.3 [M–H]⁻.

B4. The reaction of the mesylate from experiment A2 with 4-imidazol-1-yl-benzenethiol (prepared according to patent application FR 2267101, 1975) yielded (2S,4R)-2-(1-cyano-cyclopropylcarbamoyl)-4-(4-imidazol-1-yl-phenylsulfanyl)-pyrrolidine-1-carboxylic acid t-butyl ester as a colorless foam. MS: 454.2 [M+H]⁺.

B5. The reaction of the mesylate from experiment A2 with 2,4-dichlorothiophenol yielded ((2S,4R)-2-(1-cyano-cyclopropylcarbamoyl)-4-(2,4-dichloro-phenylsulfanyl)-pyrrolidine-1-carboxylic acid t-butyl ester as a colorless oil. MS: 454.3 [M–H]⁻.

B6. The reaction of the mesylate from experiment A2 with 2,6-dichlorothiophenol yielded (2S,4R)-2-(1-cyano-cyclopropylcarbamoyl)-4-(2,6-dichloro-phenylsulfanyl)-pyrrolidine-1-carboxylic acid t-butyl ester as a white solid. MS: 454.4 [M–H]⁻.

B7. The reaction of the mesylate from experiment A2 with 2,4-difluorothiophenol yielded (2S,4R)-2-(1-cyano-cyclopropylcarbamoyl)-4-(2,4-difluoro-phenylsulfanyl)-pyrrolidine-1-carboxylic acid t-butyl ester as a colorless foam. MS: 422.2 [M–H]⁻.

B8. To as solution of 4-bromo-2-trifluoromethyl-benzenesulfonyl chloride (4.85 g) in dioxane (29 ml) was added at 22° C. water (6.5 ml) and tris-(2-carboxyethyl)phosphine hydrochloride (17.3 g) and the mixture was heated to reflux temperature for 6 h. The cooled mixture was partitioned between water and dichloromethane, the organic layer was washed with water, dried and evaporated give pure 4-bromo-2-trifluoromethyl-benzenethiol (3.85 g) as a colorless liquid. MS: 257.2 and 255.1 [M–H]⁻.

The reaction of the mesylate from experiment A2 with 4-bromo-2-trifluoromethyl-benzenethiol yielded (2S,4R)-4-(4-bromo-2-trifluoromethyl-phenylsulfanyl)-2-(1-cyano-cyclopropylcarbamoyl)-pyrrolidine-1-carboxylic acid t-butyl ester as a colorless foam. MS: 436.2 and 434.2 [M+H-Boc]⁺.

C. Synthesis of the Sulfones C

General Procedure

To a solution of the thioethers B (0.1 mmole) in dichloromethane (1 ml) was added a solution of m-chloroperbenzoic acid (70%, 0.4 mmole) in dichloromethane (2 ml) and stirring was continued at 22° C. until completion of the reaction. The mixture was vigorously shaken with aqueous NaHSO₃, the organic layer was washed with aqueous Na₂CO₃ and water, the organic layer was dried, evaporated and the residue chromatographed on silica using mixtures of cyclohexane and ethyl acetate to give the sulfones C.

C1. The oxidation of the thioether from experiment B1 yielded (2S,4R)-2-(1-cyano-cyclopropylcarbamoyl)-4-(2-ethyl-benzenesulfonyl)-pyrrolidine-1-carboxylic acid t-butyl ester as a colorless oil. MS: 348.2 [M+H-Boc]⁺.

Example 1

(2S,4R)-2-(1-Cyano-cyclopropylcarbamoyl)-4-(2-hydroxymethyl-benzenesulfonyl)-pyrrolidine-1-carboxylic acid tert-butyl ester

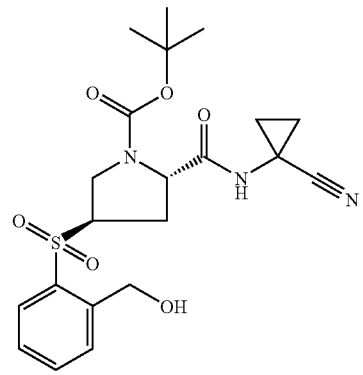

C2. The oxidation of the thioether from experiment B2 yielded (2S,4R)-2-(1-cyano-cyclopropylcarbamoyl)-4-(2-hydroxymethyl-benzenesulfonyl)-pyrrolidine-1-carboxylic acid t-butyl ester as a colorless foam. MS: 448.4 [M–H]⁻.

Example 2

(2S,4R)-2-(1-Cyano-cyclopropylcarbamoyl)-4-(2-trifluoromethoxy-benzenesulfonyl)-pyrrolidine-1-carboxylic acid tert-butyl ester

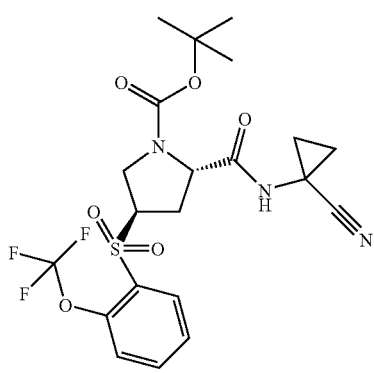

C3. The oxidation of the thioether from experiment B3 yielded (2S,4R)-2-(1-cyano-cyclopropylcarbamoyl)-4-(2- trifluoromethoxy-benzenesulfonyl)-pyrrolidine-1-carboxylic acid t-butyl ester as a colorless foam. MS: 502.4 [M–H]⁻.

Example 3

(2S,4R)-2-(1-Cyano-cyclopropylcarbamoyl)-4-(4-imidazol-1-yl-benzenesulfonyl)-pyrrolidine-1-carboxylic acid tert-butyl ester

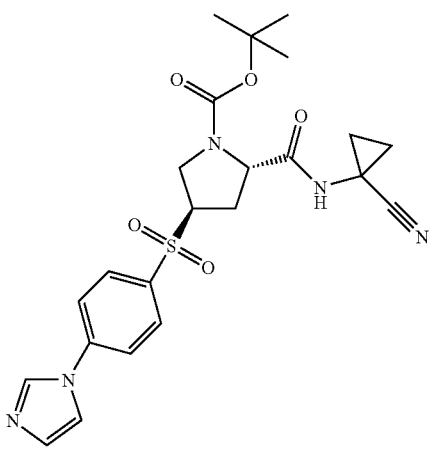

C4. The oxidation of the thioether from experiment B4 yielded (2S,4R)-2-(1-cyano-cyclopropylcarbamoyl)-4-(4-imidazol-1-yl-benzenesulfonyl)-pyrrolidine-1-carboxylic acid t-butyl ester as a white solid. MS: 484.3 [M–H]⁻.

Example 4

(2S,4R)-2-(1-Cyano-cyclopropylcarbamoyl)-4-(2,4-dichloro-benzenesulfonyl)-pyrrolidine-1-carboxylic acid-tert-butyl ester

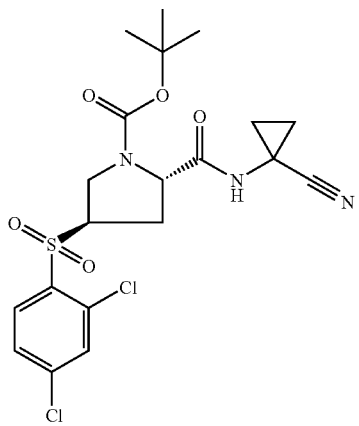

C5. The oxidation of the thioether from experiment B5 yielded (2S,4R)-2-(1-cyano-cyclopropylcarbamoyl)-4-(2,4-dichloro-benzenesulfonyl)-pyrrolidine-1-carboxylic acid t-butyl ester as a white solid. MS: 486.5 [M–H]⁻.

Example 5

(2S,4R)-2-(1-Cyano-cyclopropylcarbamoyl)-4-(2,6-dichloro-benzenesulfonyl)-pyrrolidine-1-carboxylic acid tert-butyl ester

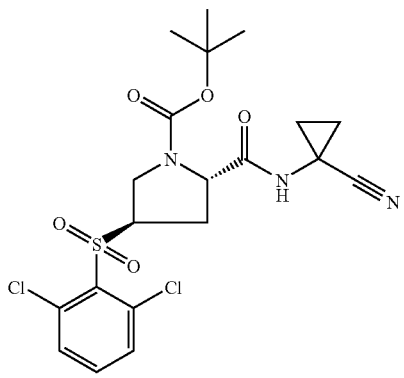

C6. The oxidation of the thioether from experiment B6 yielded (2S,4R)-2-(1-cyano-cyclopropylcarbamoyl)-4-(2,6-dichloro-benzenesulfonyl)-pyrrolidine-1-carboxylic acid t-butyl ester as a colorless oil. MS: 486.5 [M–H]⁻.

Example 6

(2S,4R)-2-(1-Cyano-cyclopropylcarbamoyl)-4-(2,4-difluoro-benzenesulfonyl)-pyrrolidine-1-carboxylic acid tert-butyl ester

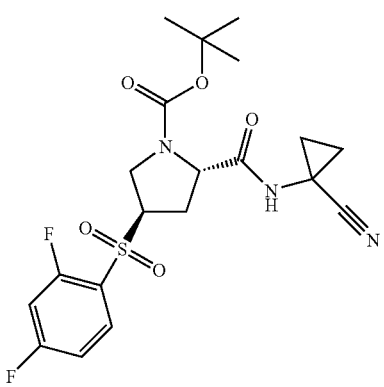

C7. The oxidation of the thioether from experiment B7 yielded (2S,4R)-2-(1-cyano-cyclopropylcarbamoyl)-4-(2,4-difluoro-benzenesulfonyl)-pyrrolidine-1-carboxylic acid t-butyl ester as a colorless oil. MS: 454.4 [M–H]⁻.

Example 7

(2S,4R)-4-(4-Bromo-2-trifluoromethyl-benzene-sulfonyl)-2-(1-cyano-cyclopropylcarbamoyl)-pyrrolidine-1-carboxylic acid tert-butyl ester

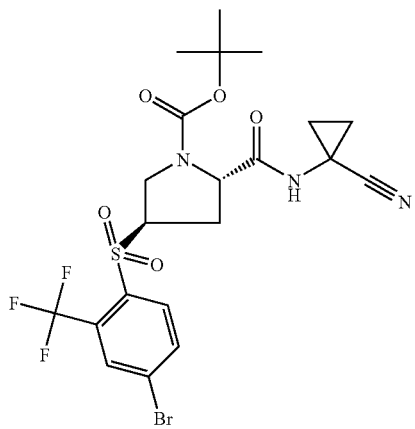

C8. The oxidation of the thioether from experiment B8 yielded (2S,4R)-4-(4-bromo-2-trifluoromethyl-benzenesulfonyl)-2-(1-cyano-cyclopropylcarbamoyl)-pyrrolidine-1-carboxylic acid t-butyl ester as a white solid. MS: 566.2 and 564.2 [M−H]$^−$.

C9. A mixture of the bromide (0.18 mmole) from experiment C8, 1H-pyrazole (0.20 mmole), $K_2CO_3$ (30 mg) and CuI (7 mg) in N,N-dimethylformamide (1 ml) was subjected to microwave irradiation at 140° C. until completion of the reaction. The mixture was partitioned between water and ethyl acetate, the organic layer was dried and evaporated. The residue was purified by preparative HPLC on a RP-18 column using a gradient of a mixture of acetonitrile and water to give (2S,4R)-2-(1-cyano-cyclopropylcarbamoyl)-4-(4-pyrazol-1-yl-2-trifluoromethyl-benzenesulfonyl)-pyrrolidine-1-carboxylic acid t-butyl ester as a pale yellow solid. MS: 552.2 [M−H]$^−$.

C10. The reaction of the bromide from experiment C8 and 1H-imidazole carried out according to experiment C9 gave (2S,4R)-2-(1-cyano-cyclopropylcarbamoyl)-4-(4-imidazol-1-yl-2-trifluoromethyl-benzenesulfonyl)-pyrrolidine-1-carboxylic acid t-butyl ester as a yellow oil. MS: 554.3 [M+H]$^+$.

Example 8

(2S,4R)-2-(1-Cyano-cyclopropylcarbamoyl)-4-[4-(4-methyl-piperazin-1-yl)-2-trifluoromethyl-benzene-sulfonyl]-pyrrolidine-1-carboxylic acid tert-butyl ester

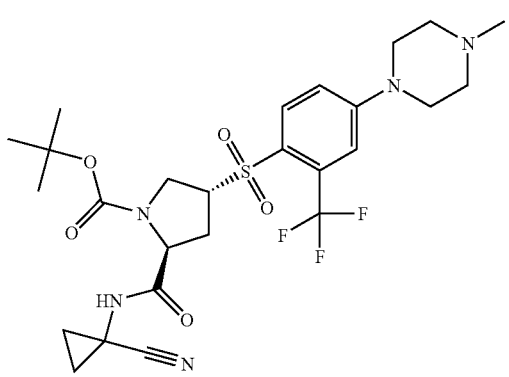

C11. The reaction of the bromide from experiment C8 and 1-methyl-piperazine carried out according to experiment C9 gave (2S,4R)-2-(1-cyano-cyclopropylcarbamoyl)-4-[4-(4-methyl-piperazin-1-yl)-2-trifluoromethyl-benzenesulfonyl]-pyrrolidine-1-carboxylic acid t-butyl ester as a white powder. MS: 586.2 [M+H]$^+$.

Example 9

(2S,4R)-4-(4-Benzoimidazol-1-yl-2-trifluoromethyl-benzenesulfonyl)-2-(1-cyano-cyclopropylcarbamoyl)-pyrrolidine-1-carboxylic acid tert-butyl ester

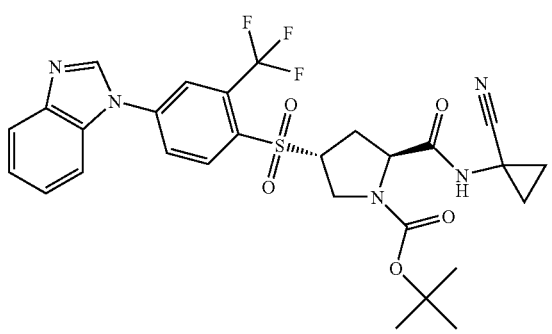

C12. The reaction of the bromide from experiment C8 and 1H-benzoimidazole carried out according to experiment C9 gave (2S,4R)-4-(4-benzoimidazol-1-yl-2-trifluoromethyl-benzenesulfonyl)-2-(1-cyano-cyclopropylcarbamoyl)-pyrrolidine-1-carboxylic acid t-butyl ester as a yellow solid. MS: 604.3 [M+H]$^+$.

Example 10

(2S,4R)-2-(1-Cyano-cyclopropylcarbamoyl)-4-[4-(3-methyl-6-oxo-6H-pyridazin-1-yl)-2-trifluoromethyl-benzenesulfonyl]-pyrrolidine-1-carboxylic acid tert-butyl ester

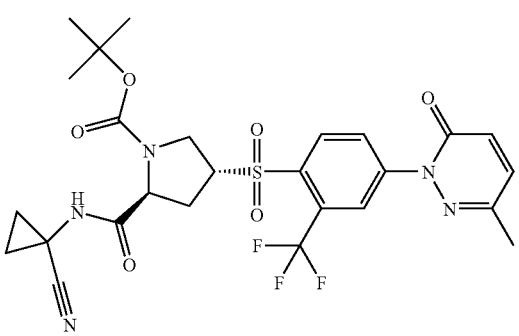

C13. The reaction of the bromide from experiment C8 and 6-methyl-2H-pyridazin-3-one carried out according to experiment C9 gave (2S,4R)-2-(1-cyano-cyclopropylcarbamoyl)-4-[4-(3-methyl-6-oxo-6H-pyridazin-1-yl)-2-trifluoromethyl-benzenesulfonyl]-pyrrolidine-1-carboxylic acid t-butyl ester as a white powder. MS: 596.2 [M+H]$^+$.

C14. The reaction of the bromide from experiment C8 and 2-methyl-1H-imidazole carried out according to experiment C9 gave (2S,4R)-2-(1-cyano-cyclopropylcarbamoyl)-4-[4-(2-methyl-imidazol-1-yl)-2-trifluoromethyl-benzenesulfonyl]-pyrrolidine-1-carboxylic acid t-butyl ester as pale yellow oil. MS: 568.3 [M+H]⁺.

C15. The reaction of the bromide from experiment C8 and 2-phenyl-1H-imidazole carried out according to experiment C9 gave (2S,4R)-2-(1-cyano-cyclopropylcarbamoyl)-4-[4-(2-phenyl-imidazol-1-yl)-2-trifluoromethyl-benzenesulfonyl]-pyrrolidine-1-carboxylic acid t-butyl ester as pale yellow oil. MS: 630.3 [M+H]⁺.

C16. The reaction of the bromide from experiment C8 and pyrrolidin-2-one carried out according to experiment C9 gave (2S,4R)-2-(1-cyano-cyclopropylcarbamoyl)-4-[4-(2-oxo-pyrrolidin-1-yl)-2-trifluoromethyl-benzenesulfonyl]-pyrrolidine-1-carboxylic acid t-butyl ester as a colorless oil. MS: 471.3 [M+H-Boc]⁺.

C17. The reaction of the bromide from experiment C8 and oxazolidin-2-one carried out according to experiment C9 gave (2S,4R)-2-(1-cyano-cyclopropylcarbamoyl)-4-[4-(2-oxo-oxazolidin-3-yl)-2-trifluoromethyl-benzenesulfonyl]-pyrrolidine-1-carboxylic acid t-butyl ester as pale yellow oil. MS: 571.5 [M−H]⁻.

C18. The reaction of the bromide from experiment C8 and 3,3-difluoro-pyrrolidine carried out according to experiment C9 gave (2S,4R)-2-(1-cyano-cyclopropylcarbamoyl)-4-[4-(3,3-difluoro-pyrrolidin-1-yl)-2-trifluoromethyl-benzenesulfonyl]-pyrrolidine-1-carboxylic acid t-butyl ester as pale yellow oil. MS: 493.2 [M+H-Boc]⁻.

C19. The reaction of the bromide from experiment C8 and morpholine carried out according to experiment C9 gave (2S,4R)-2-(1-cyano-cyclopropylcarbamoyl)-4-(4-morpholin-4-yl-2-trifluoromethyl-benzenesulfonyl)-pyrrolidine-1-carboxylic acid t-butyl ester as pale red oil. MS: 473.1 [M+H-Boc]⁻.

C20. The reaction of the bromide from experiment C8 and morpholin-3-one carried out according to experiment C9 gave (2S,4R)-2-(1-cyano-cyclopropylcarbamoyl)-4-[4-(3-oxo-morpholin-4-yl)-2-trifluoromethyl-benzenesulfonyl]-pyrrolidine-1-carboxylic acid t-butyl ester as pale yellow oil. MS: 487.3 [M+H-Boc]⁺.

C21. The reaction of the bromide from experiment C8 and 1H-pyridin-2-one carried out according to experiment C9 gave (2S,4R)-2-(1-cyano-cyclopropylcarbamoyl)-4-[4-(2-oxo-2H-pyridin-1-yl)-2-trifluoromethyl-benzenesulfonyl]-pyrrolidine-1-carboxylic acid t-butyl ester as colorless oil. MS: 481.2 [M+H-Boc]⁺.

C22. The reaction of the bromide from experiment C8 and 1H-pyrazin-2-one carried out according to experiment C9 gave (2S,4R)-2-(1-cyano-cyclopropylcarbamoyl)-4-[4-(2-oxo-2H-pyrazin-1-yl)-2-trifluoromethyl-benzenesulfonyl]-pyrrolidine-1-carboxylic acid t-butyl ester as yellow oil. MS: 482.1 [M+H-Boc]⁺.

D. Synthesis of the Prolines D

General Procedure

To a solution of the sulfones C (0.1 mmole) in 1,4-dioxane (2 ml) was added a solution of 4M HCl in 1,4-dioxane (0.8 mmole) and stirring was continued at 22° C. until completion of the reaction. The mixture was diluted with diethyl ether (8 ml), the suspension was filtered and the residue dried to give the prolines D.

Example 11

(2S,4R)-4-(2-Ethyl-benzenesulfonyl)-pyrrolidine-2-carboxylic acid (1-cyano-cyclopropyl)-amide Hydrochloride

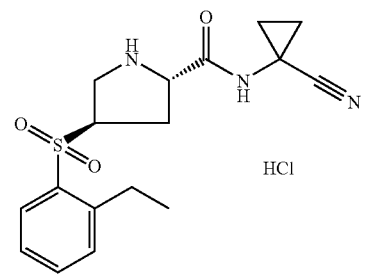

D1. The deprotection of the sulfone from experiment C1 yielded (2S,4R)-4-(2-ethyl-benzenesulfonyl)-pyrrolidine-2-carboxylic acid (1-cyano-cyclopropyl)-amide hydrochloride as a white solid. MS: 346.3 [M−H]⁻.

Example 12

(2S,4R)-4-(2-Hydroxymethyl-benzenesulfonyl)-pyrrolidine-2-carboxylic acid (1-cyano-cyclopropyl)-amide Hydrochloride

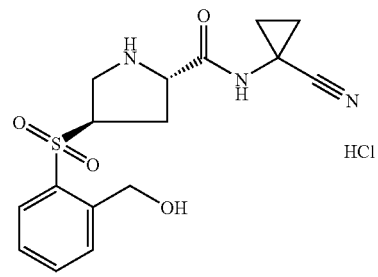

D2. The deprotection of the sulfone from experiment C2 yielded (2S,4R)-4-(2-hydroxymethyl-benzenesulfonyl)-pyrrolidine-2-carboxylic acid (1-cyano-cyclopropyl)-amide hydrochloride as a white solid. MS: 348.3 [M−H]⁻.

Example 13

(2S,4R)-4-(2-Trifluoromethoxy-benzenesulfonyl)-pyrrolidine-2-carboxylic acid (1-cyano-cyclopropyl)-amide Hydrochloride

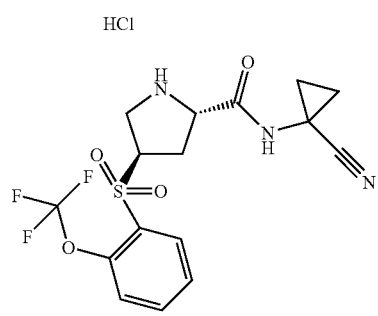

D3. The deprotection of the sulfone from experiment C3 yielded (2S,4R)-4-(2-trifluoromethoxy-benzenesulfonyl)-pyrrolidine-2-carboxylic acid (1-cyano-cyclopropyl)-amide hydrochloride as a white solid. MS: 404.3 [M+H]⁻.

Example 14

(2S,4R)-4-(4-Imidazol-1-yl-benzenesulfonyl)-pyrrolidine-2-carboxylic acid (1-cyano-cyclopropyl)-amide Hydrochloride

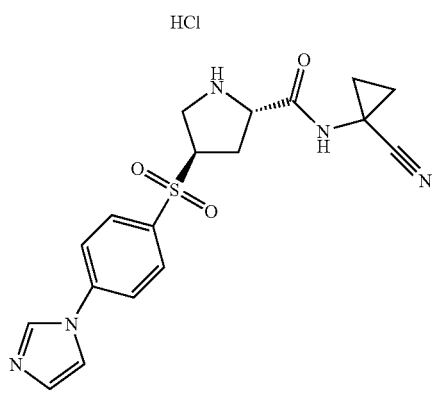

D4. The deprotection of the sulfone from experiment C4 yielded (2S,4R)-4-(4-imidazol-1-yl-benzenesulfonyl)-pyrrolidine-2-carboxylic acid (1-cyano-cyclopropyl)-amide hydrochloride as a pale yellow solid. MS: 386.1 [M+H]⁺.

Example 15

(2S,4R)-4-(2,4-Dichloro-benzenesulfonyl)-pyrrolidine-2-carboxylic acid (1-cyano-cyclopropyl)-amide Hydrochloride

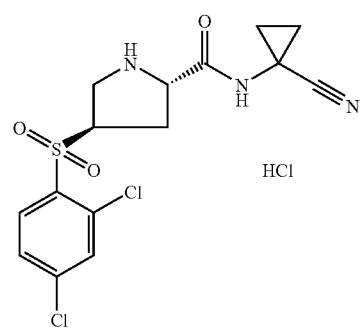

D5. The deprotection of the sulfone from experiment C5 yielded (2S,4R)-4-(2,4-dichloro-benzenesulfonyl)-pyrrolidine-2-carboxylic acid (1-cyano-cyclopropyl)-amide hydrochloride as a white solid. MS: 388.1 [M+H]⁺.

Example 16

(2S,4R)-4-(2,6-Dichloro-benzenesulfonyl)-pyrrolidine-2-carboxylic acid (1-cyano-cyclopropyl)-amide Hydrochloride

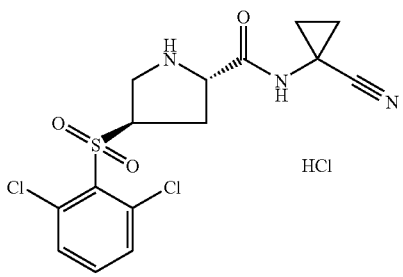

D6. The deprotection of the sulfone from experiment C6 yielded (2S,4R)-4-(2,6-dichloro-benzenesulfonyl)-pyrrolidine-2-carboxylic acid (1-cyano-cyclopropyl)-amide hydrochloride as a white solid. MS: 388.1 [M+H]⁺.

Example 17

(2S,4R)-4-(2,4-Difluoro-benzenesulfonyl)-pyrrolidine-2-carboxylic acid (1-cyano-cyclopropyl)-amide Hydrochloride

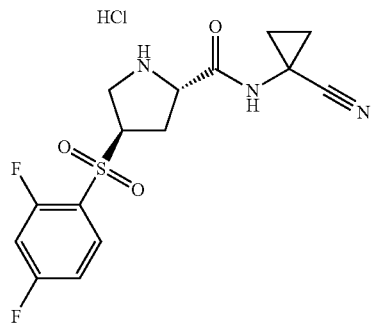

D7. The deprotection of the sulfone from experiment C7 yielded (2S,4R)-4-(2,4-difluoro-benzenesulfonyl)-pyrrolidine-2-carboxylic acid (1-cyano-cyclopropyl)-amide hydrochloride as a white solid. MS: 356.1 [M+H]⁺.

Example 18

(2S,4R)-4-(4-Bromo-2-trifluoromethyl-benzenesulfonyl)-pyrrolidine-2-carboxylic acid (1-cyano-cyclopropyl)-amide hydrochloride

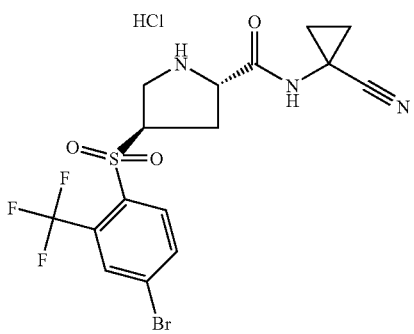

D8. The deprotection of the sulfone from experiment C8 yielded (2S,4R)-4-(4-bromo-2-trifluoromethyl-benzenesulfonyl)-pyrrolidine-2-carboxylic acid (1-cyano-cyclopropyl)-amide hydrochloride as a white solid. MS: 468.0 and 466.1 [M+H]$^+$.

Example 19

(2S,4R)-4-(4-Pyrazol-1-yl-2-trifluoromethyl-benzenesulfonyl)-pyrrolidine-2-carboxylic acid (1-cyano-cyclopropyl)-amide hydrochloride

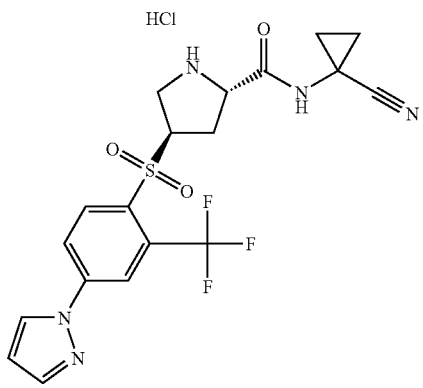

D9. The deprotection of the sulfone from experiment C9 yielded (2S,4R)-4-(4-pyrazol-1-yl-2-trifluoromethyl-benzenesulfonyl)-pyrrolidine-2-carboxylic acid (1-cyano-cyclopropyl)-amide as a pale yellow foam. MS: 454.2 [M+H]$^+$.

Example 20

(2S,4R)-4-(4-Imidazol-1-yl-2-trifluoromethyl-benzenesulfonyl)-pyrrolidine-2-carboxylic acid (1-cyano-cyclopropyl)-amide hydrochloride

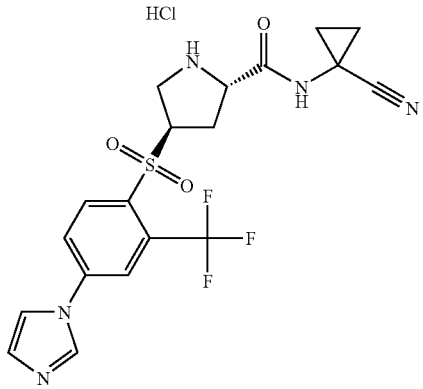

D10. The deprotection of the sulfone from experiment C10 yielded (2S,4R)-4-(4-imidazol-1-yl-2-trifluoromethyl-benzenesulfonyl)-pyrrolidine-2-carboxylic acid (1-cyano-cyclopropyl)-amide hydrochloride as a pale yellow solid. MS: 454.2 [M+H]$^+$.

Example 21

(2S,4R)-4-[4-(4-Methyl-piperazin-1-yl)-2-trifluoromethyl-benzenesulfonyl]-pyrrolidine-2-carboxylic acid (1-cyano-cyclopropyl)-amide hydrochloride

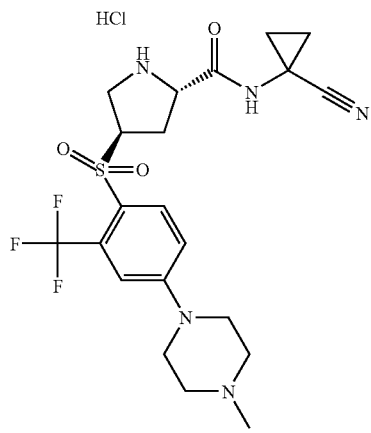

D11. The deprotection of the sulfone from experiment C11 yielded (2S,4R)-4-[4-(4-methyl-piperazin-1-yl)-2-trifluoromethyl-benzenesulfonyl]-pyrrolidine-2-carboxylic acid (1-cyano-cyclopropyl)-amide hydrochloride as a white solid. MS: 486.3 [M+H]$^+$.

Example 22

(2S,4R)-4-(4-Benzoimidazol-1-yl-2-trifluoromethyl-benzenesulfonyl)-pyrrolidine-2-carboxylic Acid (1-cyano-cyclopropyl)-amide hydrochloride

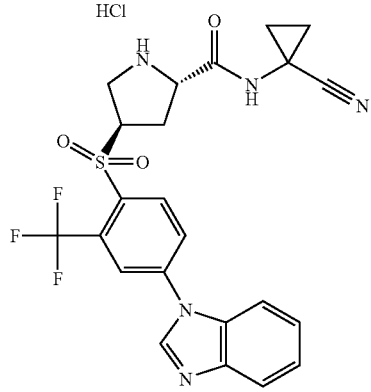

D12. The deprotection of the sulfone from experiment C12 yielded (2S,4R)-4-(4-benzoimidazol-1-yl-2-trifluoromethylbenzenesulfonyl)-pyrrolidine-2-carboxylic acid (1-cyano-cyclopropyl)-amide hydrochloride as a white solid. MS: 504.1 [M+H]+.

Example 23

(2S,4R)-4-[4-(3-Methyl-6-oxo-6H-pyridazin-1-yl)-2-trifluoromethyl-benzenesulfonyl]-pyrrolidine-2-carboxylic acid (1-cyano-cyclopropyl)-amide hydrochloride

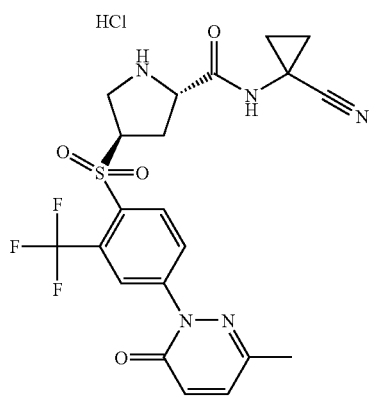

D13. The deprotection of the sulfone from experiment C13 yielded (2S,4R)-4-[4-(3-methyl-6-oxo-6H-pyridazin-1-yl)-2-trifluoromethyl-benzenesulfonyl]-pyrrolidine-2-carboxylic acid (1-cyano-cyclopropyl)-amide hydrochloride as a white solid. MS: 496.3 [M+H]+.

Example 24

(2S,4R)-4-[4-(2-Methyl-imidazol-1-yl)-2-trifluoromethyl-benzenesulfonyl]-pyrrolidine-2-carboxylic acid (1-cyano-cyclopropyl)-amide hydrochloride

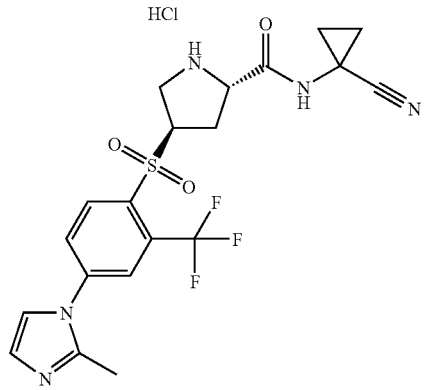

D14. The deprotection of the sulfone from experiment C14 yielded (2S,4R)-4-[4-(2-methyl-imidazol-1-yl)-2-trifluoromethyl-benzenesulfonyl]-pyrrolidine-2-carboxylic acid (1-cyano-cyclopropyl)-amide hydrochloride as a pale yellow solid. MS: 468.2 [M+H]+.

Example 25

(2S,4R)-4-[4-(2-Phenyl-imidazol-1-yl)-2-trifluoromethyl-benzenesulfonyl]-pyrrolidine-2-carboxylic acid (1-cyano-cyclopropyl)-amide hydrochloride

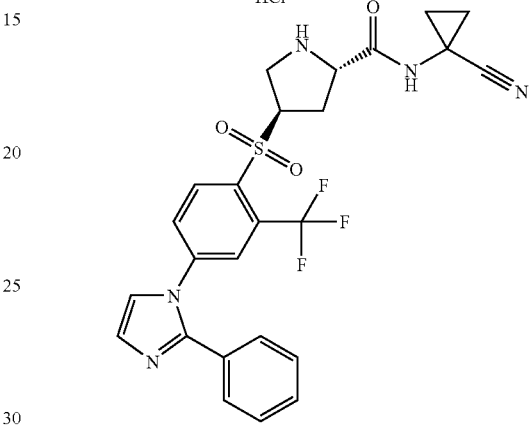

D15. The deprotection of the sulfone from experiment C15 yielded (2S,4R)-4-[4-(2-phenyl-imidazol-1-yl)-2-trifluoromethyl-benzenesulfonyl]-pyrrolidine-2-carboxylic acid (1-cyano-cyclopropyl)-amide hydrochloride as a pale yellow solid. MS: 530.1 [M+H]+.

Example 26

(2S,4R)-4-[4-(2-Oxo-pyrrolidin-1-yl)-2-trifluoromethyl-benzenesulfonyl]-pyrrolidine-2-carboxylic acid (1-cyano-cyclopropyl)-amide hydrochloride

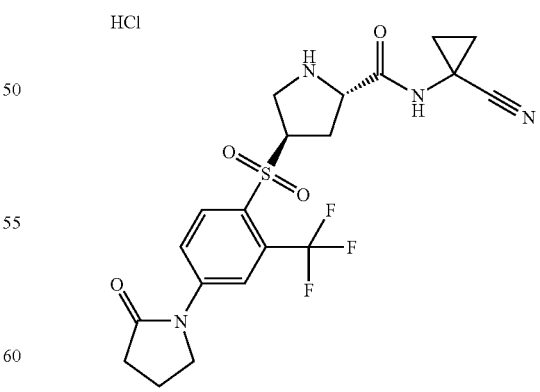

D16. The deprotection of the sulfone from experiment C16 yielded (2S,4R)-4-[4-(2-oxo-pyrrolidin-1-yl)-2-trifluoromethyl-benzenesulfonyl]-pyrrolidine-2-carboxylic acid (1-cyano-cyclopropyl)-amide hydrochloride as a yellow oil. MS: 471.3 [M+H]⁺.

Example 27

(2S,4R)-4-[4-(2-oxo-oxazolidin-3-yl)-2-trifluoromethyl-benzenesulfonyl]-pyrrolidine-2-carboxylic acid (1-cyano-cyclopropyl)-amide hydrochloride

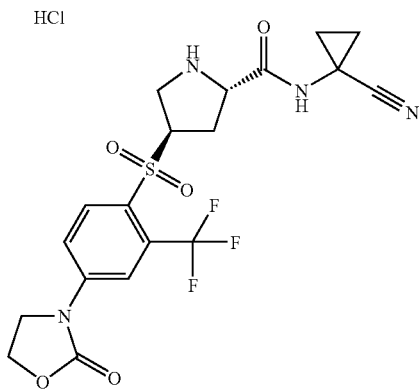

D17. The deprotection of the sulfone from experiment C17 yielded (2S,4R)-4-[4-(2-oxo-oxazolidin-3-yl)-2-trifluoromethyl-benzenesulfonyl]-pyrrolidine-2-carboxylic acid (1-cyano-cyclopropyl)-amide hydrochloride as a yellow oil. MS: 473.1 [M+H]⁺.

Example 28

(2S,4R)-4-[4-(3,3-Difluoro-pyrrolidin-1-yl)-2-trifluoromethyl-benzenesulfonyl]-pyrrolidine-2-carboxylic acid (1-cyano-cyclopropyl)-amide hydrochloride

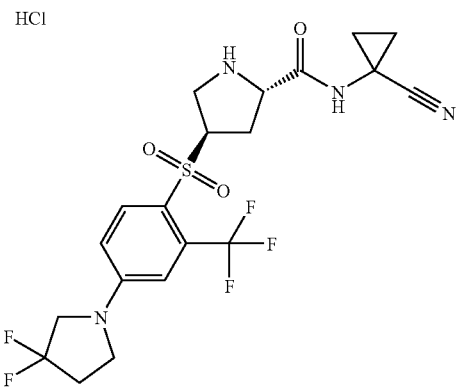

D18. The deprotection of the sulfone from experiment C18 yielded (2S,4R)-4-[4-(3,3-difluoro-pyrrolidin-1-yl)-2-trifluoromethyl-benzenesulfonyl]-pyrrolidine-2-carboxylic acid (1-cyano-cyclopropyl)-amide hydrochloride as a yellow oil. MS: 493.2 [M+H]⁺.

Example 29

(2S,4R)-4-(4-Morpholin-4-yl-2-trifluoromethyl-benzenesulfonyl)-pyrrolidine-2-carboxylic acid (1-cyano-cyclopropyl)-amide hydrochloride

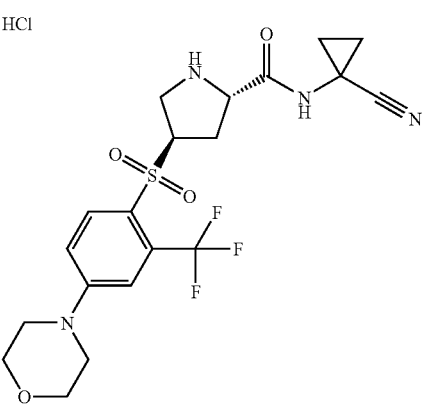

D19. The deprotection of the sulfone from experiment C19 yielded (2S,4R)-4-(4-morpholin-4-yl-2-trifluoromethyl-benzenesulfonyl)-pyrrolidine-2-carboxylic acid (1-cyano-cyclopropyl)-amide hydrochloride as a pale brown solid. MS: 473.2 [M+H]⁺.

Example 30

(2S,4R)-4-[4-(3-Oxo-morpholin-4-yl)-2-trifluoromethyl-benzenesulfonyl]-pyrrolidine-2-carboxylic acid (1-cyano-cyclopropyl)-amide hydrochloride

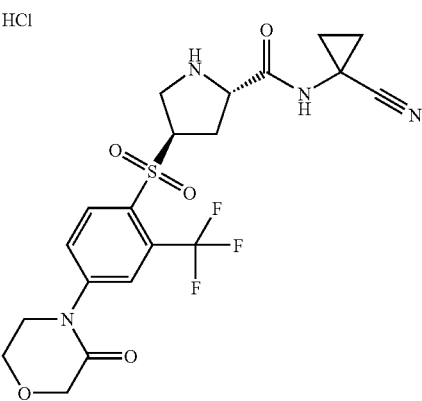

D20. The deprotection of the sulfone from experiment C20 yielded (2S,4R)-4-[4-(3-oxo-morpholin-4-yl)-2-trifluoromethyl-benzenesulfonyl]-pyrrolidine-2-carboxylic acid (1-cyano-cyclopropyl)-amide hydrochloride as a yellow solid. MS: 487.3 [M+H]$^+$.

Example 31

(2S,4R)-4-[4-(2-Oxo-2H-pyridin-1-yl)-2-trifluoromethyl-benzenesulfonyl]-pyrrolidine-2-carboxylic acid (1-cyano-cyclopropyl)-amide hydrochloride

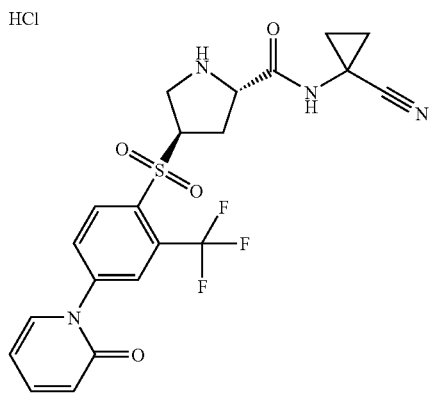

D21. The deprotection of the sulfone from experiment C21 yielded (2S,4R)-4-[4-(2-oxo-2H-pyridin-1-yl)-2-trifluoromethyl-benzenesulfonyl]-pyrrolidine-2-carboxylic acid (1-cyano-cyclopropyl)-amide hydrochloride as a yellow solid. MS: 481.2 [M+H]$^+$.

Example 32

(2S,4R)-4-[4-(2-Oxo-2H-pyrazin-1-yl)-2-trifluoromethyl-benzenesulfonyl]-pyrrolidine-2-carboxylic acid (1-cyano-cyclopropyl)-amide hydrochloride

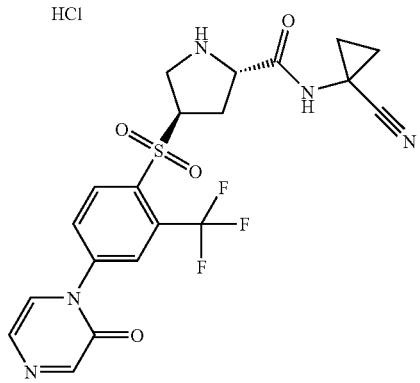

D22. The deprotection of the sulfone from experiment C22 yielded (2S,4R)-4-[4-(2-oxo-2H-pyrazin-1-yl)-2-trifluoromethyl-benzenesulfonyl]-pyrrolidine-2-carboxylic acid (1-cyano-cyclopropyl)-amide hydrochloride as a yellow oil. MS: 482.1 [M+H]$^+$.

Synthesis of the intermediate (2S,4S)-4-methanesulfonyloxy-pyrrolidine-1,2-dicarboxylic acid 1-t-butyl ester 2-methyl ester E The title compound was obtained from (2S,4R)-4-hydroxy-pyrrolidine-1,2-dicarboxylic acid 1-t-butyl ester 2-methyl ester using the procedure A2. MS: 324.4 [M+H]$^+$.

F. Synthesis of the Intermediate Thioethers F

General Procedure

The thioethers F were prepared from (2S,4S)-4-methanesulfonyloxy-pyrrolidine-1,2-dicarboxylic acid 1-t-butyl ester 2-methyl ester from experiment E and the thiols using general procedure B.

F1. The reaction of the mesylate with benzenethiol yielded (2S,4R)-4-phenylsulfanyl-pyrrolidine-1,2-dicarboxylic acid 1-t-butyl ester 2-methyl ester as a pale yellow oil. MS: 338.4 [M+H]$^+$.

F2. The reaction of the mesylate with 2-chloro-benzenethiol yielded (2S,4R)-4-(2-chloro-phenylsulfanyl)-pyrrolidine-1,2-dicarboxylic acid 1-t-butyl ester 2-methyl ester as a white solid. MS: 372.1 [M+H]$^+$.

F3. The reaction of the mesylate with 2-trifluoromethyl-benzenethiol yielded (2S,4R)-4-(2-trifluoromethyl-phenylsulfanyl)-pyrrolidine-1,2-dicarboxylic acid 1-t-butyl ester 2-methyl ester as a colorless oil. MS: 406.2 [M+H]$^+$.

F4. The reaction of the mesylate with 2,4-dimethyl-benzenethiol yielded (2S,4R)-4-(2,4-dimethyl-phenylsulfanyl)-pyrrolidine-1,2-dicarboxylic acid 1-t-butyl ester 2-methyl ester as a colorless oil. MS: 366.2 [M+H]$^+$.

F5. The reaction of the mesylate with 4-chloro-2-methyl-benzenethiol yielded (2S,4R)-4-(4-chloro-2-methyl-phenylsulfanyl)-pyrrolidine-1,2-dicarboxylic acid 1-t-butyl ester 2-methyl ester as a colorless oil. MS: 386.2 [M+H]$^+$.

F6. The reaction of the mesylate with 2,3-dichloro-benzenethiol yielded (2S,4R)-4-(2,3-dichloro-phenylsulfanyl)-pyrrolidine-1,2-dicarboxylic acid 1-t-butyl ester 2-methyl ester as a pale yellow oil. MS: 306.1 [M+H-Boc]$^+$.

G. Synthesis of the Intermediate Sulfone Esters G

The sulfone esters G were prepared from thiothers F using general procedure C.

G1. The oxidation of the thioether from experiment F1 yielded (2S,4R)-4-benzenesulfonyl-pyrrolidine-1,2-dicarboxylic acid 1-t-butyl ester 2-methyl ester as a colorless oil. MS: 370.1 [M+H]$^+$.

G2. The oxidation of the thioether from experiment F2 yielded (2S,4R)-4-(2-chloro-benzenesulfonyl)-pyrrolidine-1,2-dicarboxylic acid 1-t-butyl ester 2-methyl ester as a colorless oil. MS: 404.5 [M+H]$^+$.

G3. The oxidation of the thioether from experiment F3 yielded (2S,4R)-4-(2-trifluoromethyl-benzenesulfonyl)-pyrrolidine-1,2-dicarboxylic acid 1-t-butyl ester 2-methyl ester as a colorless oil. MS: 438.1 [M+H]$^+$.

G4. The oxidation of the thioether from experiment F4 yielded (2S,4R)-4-(2,4-dimethyl-benzenesulfonyl)-pyrrolidine-1,2-dicarboxylic acid 1-t-butyl ester 2-methyl ester as a colorless oil. MS: 298.3 [M+H-Boc]$^+$.

G5. The oxidation of the thioether from experiment F5 yielded (2S,4R)-4-(4-chloro-2-methyl-benzenesulfonyl)-pyrrolidine-1,2-dicarboxylic acid 1-t-butyl ester 2-methyl ester as a colorless oil. MS: 318.1 [M+H-Boc]$^+$.

G6. The oxidation of the thioether from experiment F6 yielded (2S,4R)-4-(2,3-dichloro-benzenesulfonyl)-pyrrolidine-1,2-dicarboxylic acid 1-t-butyl ester 2-methyl ester as a colorless oil. MS: 338.1 [M+H-Boc]$^+$.

H. Synthesis of the Intermediate Acids H

General Procedure

To a solution of the sulfone esters G (1.35 mmole) in THF (10 ml) was added a solution of LiOH (3.0 mmole) in water (3 ml) and methanol (3 ml) and stirring was continued at 22° C. until completion of the reaction. The mixture was evaporated and the residue partitioned between ethyl acetate and hydrochloric acid (0.1 N). The organic layer was dried, evaporated and the residue was triturated with ether or pentane to give the acids H.

H1. The hydrolysis of the sulfone ester from experiment G1 yielded (2S,4R)-4-benzenesulfonyl-pyrrolidine-1,2-dicarboxylic acid 1-t-butyl ester as an amorphous white solid. MS: 354.4 [M−H]⁻.

H2. The hydrolysis of the sulfone ester from experiment G2 yielded (2S,4R)-4-(2-chloro-benzenesulfonyl)-pyrrolidine-1,2-dicarboxylic acid 1-t-butyl ester as a colorless foam. MS: 289.9 [M+H-Boc]⁺.

H3. The hydrolysis of the sulfone ester from experiment G3 yielded (2S,4R)-4-(2-trifluoromethyl-benzenesulfonyl)-pyrrolidine-1,2-dicarboxylic acid 1-t-butyl ester as a white solid. MS: 422.3 [M−H]⁻.

H4. The hydrolysis of the sulfone ester from experiment G4 yielded (2S,4R)-4-(2,4-dimethyl-benzenesulfonyl)-pyrrolidine-1,2-dicarboxylic acid 1-t-butyl ester as a white solid. MS: 382.4 [M−H]⁻.

H5. The hydrolysis of the sulfone ester from experiment G5 yielded (2S,4R)-4-(4-chloro-2-methyl-benzenesulfonyl)-pyrrolidine-1,2-dicarboxylic acid 1-t-butyl ester as a white solid. MS: 402.4 [M−H]⁻.

H6. The hydrolysis of the sulfone ester from experiment G6 yielded (2S,4R)-4-(2,3-dichloro-benzenesulfonyl)-pyrrolidine-1,2-dicarboxylic acid 1-t-butyl ester as a white solid. MS: 424.2 [M−H]⁻.

I. Synthesis of the Nitriles I

General Procedure

To a solution of the acids H (10 mmole) and 4-methylmorpholine (30 mmole) in THF (50 ml) was added at −15° C. isobutyl chloroformate (12 mmole) and stirring was continued until the intermediate mixed anhydride was formed. The mixture was treated at the same temperature with a solution of the aminonitrile hydrochloride (12 mmole) in dimethylformamide (17 ml) and stirring was continued until completion of the reaction. The mixture was partitioned between ethyl acetate and aqueous NH₄Cl, the organic layer was washed with aqueous NaHCO₃, dried, evaporated and the residue was chromatographed on silica using mixtures of ethyl acetate and n-heptane to give the nitriles I.

I1. The coupling of the acid from experiment H2 and amino-acetonitrile hydrochloride yielded (2S,4R)-4-(2-chloro-benzenesulfonyl)-2-(cyanomethyl-carbamoyl)-pyrrolidine-1-carboxylic acid t-butyl ester as an amorphous white solid. MS: 426.2 [M−H]⁻.

I2. The coupling of the acid from experiment H3 and amino-acetonitrile hydrochloride yielded (2S,4R)-2-(cyanomethyl-carbamoyl)-4-(2-trifluoromethyl-benzenesulfonyl)-pyrrolidine-1-carboxylic acid t-butyl ester as an amorphous white solid. MS: 460.5 [M−H]⁻.

I3. The coupling of the acid from experiment H1 and 1-amino-cyclopropanecarbonitrile hydrochloride yielded (2S,4R)-4-benzenesulfonyl-2-(1-cyano-cyclopropylcarbamoyl)-pyrrolidine-1-carboxylic acid t-butyl ester as an amorphous white solid. MS: 320.1 [M+H-Boc]⁺.

I4. The coupling of the acid from experiment H2 and 1-amino-cyclopropanecarbonitrile hydrochloride yielded (2S,4R)-4-(2-chloro-benzenesulfonyl)-2-(1-cyano-cyclopropylcarbamoyl)-pyrrolidine-1-carboxylic acid t-butyl ester as a colorless foam. MS: 354.1 [M+H-Boc]⁺.

I5. The coupling of the acid from experiment H3 and 1-amino-cyclopropanecarbonitrile hydrochloride yielded (2S,4R)-2-(1-cyano-cyclopropylcarbamoyl)-4-(2-trifluoromethyl-benzenesulfonyl)-pyrrolidine-1-carboxylic acid t-butyl ester as a white solid. MS: 486.5 [M−H]⁻.

Example 33

(2S,4R)-4-(2-Chloro-benzenesulfonyl)-2-[(cyano-dimethyl-methyl)-carbamoyl]-pyrrolidine-1-carboxylic acid tert-butyl ester

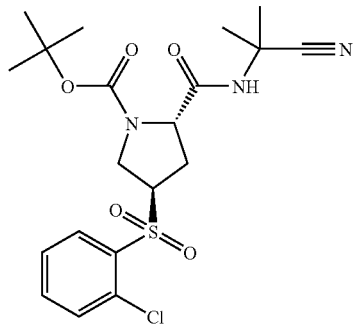

I6. The coupling of the acid from experiment H2 and 2-amino-2-methyl-propionitrile hydrochloride yielded (2S,4R)-4-(2-chloro-benzenesulfonyl)-2-[(cyano-dimethyl-methyl)-carbamoyl]-pyrrolidine-1-carboxylic acid t-butyl ester as a colorless oil. MS: 456.2 [M+H]⁺.

Example 34

(2S,4R)-4-(2-Chloro-benzenesulfonyl)-2-(1-cyano-cyclobutylcarbamoyl)-pyrrolidine-1-carboxylic acid tert-butyl ester

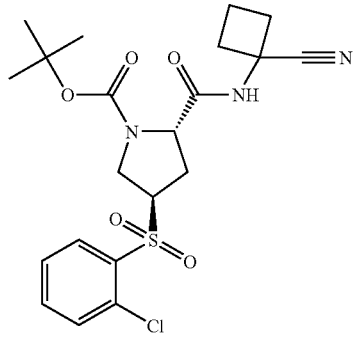

I7. The coupling of the acid from experiment H2 and 1-amino-cyclobutanecarbonitrile hydrochloride yielded (2S,4R)-4-(2-chloro-benzenesulfonyl)-2-(1-cyano-cyclobutyl-carbamoyl)-pyrrolidine-1-carboxylic acid t-butyl ester as a colorless oil. MS: 468.2 [M+H]$^+$.

Example 35

(2S,4R)-4-(2-Chloro-benzenesulfonyl)-2-(1-cyano-cyclohexylcarbamoyl)-pyrrolidine-1-carboxylic acid tert-butyl ester

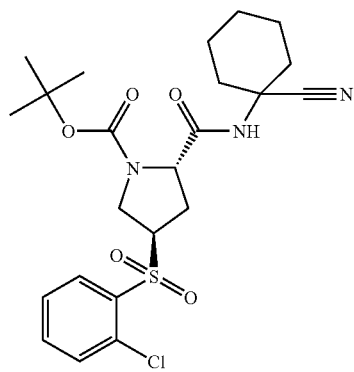

I8. The coupling of the acid from experiment H2 and 1-amino-cyclohexanecarbonitrile hydrochloride yielded (2S,4R)-4-(2-chloro-benzenesulfonyl)-2-(1-cyano-cyclohexyl-carbamoyl)-pyrrolidine-1-carboxylic acid t-butyl ester as a colorless solid. MS: 496.3 [M+H]$^+$.

Example 36

(2S,4R)-4-(2-Chloro-benzenesulfonyl)-2-[(cyano-phenyl-methyl)-carbamoyl]-pyrrolidine-1-carboxylic acid tert-butyl ester

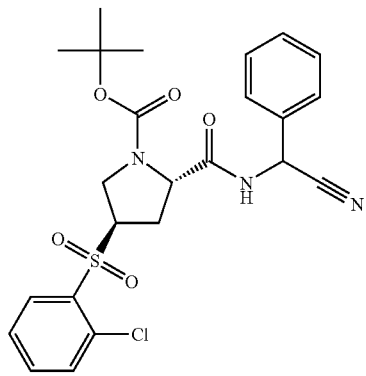

I9. The coupling of the acid from experiment H2 and rac amino-phenyl-acetonitrile hydrochloride yielded (2S,4R)-4-(2-chloro-benzenesulfonyl)-2-[(cyano-phenyl-methyl)-carbamoyl]-pyrrolidine-1-carboxylic acid t-butyl ester as a colorless foam. MS: 504.1 [M+H]$^+$.

Example 37

(2S,4R)-4-(2-Chloro-benzenesulfonyl)-2-[(cyano-methyl-phenyl-methyl)-carbamoyl]-pyrrolidine-1-carboxylic acid tert-butyl ester

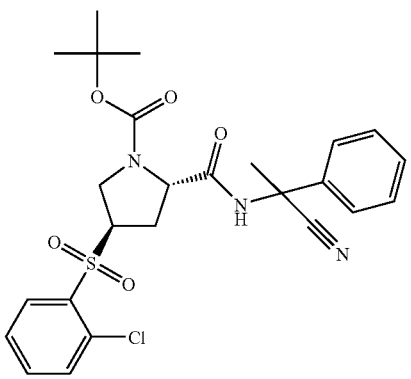

I10. The coupling of the acid from experiment H2 and rac 2-amino-2-phenyl-propionitrile hydrochloride yielded (2S,4R)-4-(2-chloro-benzenesulfonyl)-2-[(cyano-methyl-phenyl-methyl)-carbamoyl]-pyrrolidine-1-carboxylic acid t-butyl ester as a pale yellow solid. MS: 518.2 [M+H]$^+$.

Example 38

(2S,4R)-2-[(Cyano-cyclopropyl-methyl)-carbamoyl]-4-(2-trifluoromethyl-benzenesulfonyl)-pyrrolidine-1-carboxylic acid tert-butyl ester

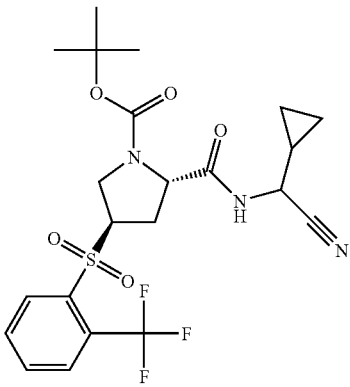

I11. The coupling of the acid from experiment H3 and rac amino-cyclopropyl-acetonitrile hydrochloride (preparation described in T. Gabriel et al., international patent application WO2004106285, 2004) yielded (2S,4R)-2-[(cyano-cyclopropyl-methyl)-carbamoyl]-4-(2-trifluoromethyl-benzenesulfonyl)-pyrrolidine-1-carboxylic acid t-butyl ester as a colorless oil. MS: 402.2 [M+H-Boc]$^+$.

Example 39

(2S,4R)-2-(1-Cyano-cyclopropylcarbamoyl)-4-(2,4-dimethyl-benzenesulfonyl)-pyrrolidine-1-carboxylic acid tert-butyl ester

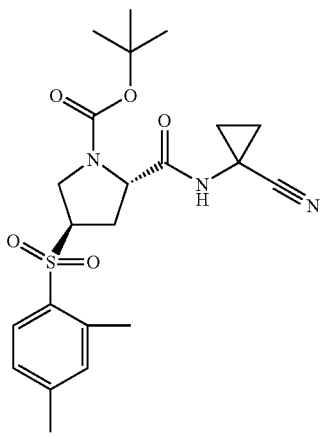

I12. The coupling of the acid from experiment H4 and 1-amino-cyclopropanecarbonitrile hydrochloride yielded (2S,4R)-2-(1-cyano-cyclopropylcarbamoyl)-4-(2,4-dimethyl-benzenesulfonyl)-pyrrolidine-1-carboxylic acid t-butyl ester as a colorless oil. MS: 348.2 [M+H-Boc]$^+$.

Example 40

(2S,4R)-4-(4-Chloro-2-methyl-benzenesulfonyl)-2-(1-cyano-cyclopropylcarbamoyl)-pyrrolidine-1-carboxylic acid tert-butyl ester

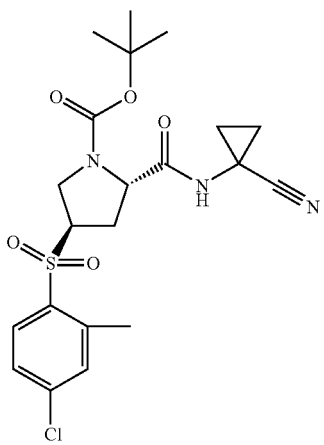

I13. The coupling of the acid from experiment H5 and 1-amino-cyclopropanecarbonitrile hydrochloride yielded (2S,4R)-4-(4-chloro-2-methyl-benzenesulfonyl)-2-(1-cyano-cyclopropylcarbamoyl)-pyrrolidine-1-carboxylic acid t-butyl ester as a white amorphous solid. MS: 368.0 [M+H-Boc]$^+$.

Example 41

(2S,4R)-2-(1-Cyano-cyclopropylcarbamoyl)-4-(2,3-dichloro-benzenesulfonyl)-pyrrolidine-1-carboxylic acid tert-butyl ester

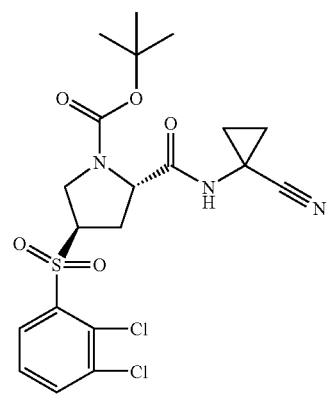

I14. The coupling of the acid from experiment H6 and 1-amino-cyclopropanecarbonitrile hydrochloride yielded (2S,4R)-2-(1-cyano-cyclopropylcarbamoyl)-4-(2,3-dichloro-benzenesulfonyl)-pyrrolidine-1-carboxylic acid t-butyl ester as a white amorphous solid. MS: 388.1 [M+H-Boc]$^+$.

K. Synthesis of the Prolines K

The prolines K were prepared from the nitriles I using general procedure D.

K1. The deprotection of the nitrile from experiment I1 yielded (2S,4R)-4-(2-chloro-benzenesulfonyl)-pyrrolidine-2-carboxylic acid cyanomethyl-amide hydrochloride as a white solid. MS: 328.1 [M+H]$^+$.

K2. The deprotection of the nitrile from experiment I2 yielded (2S,4R)-4-(2-trifluoromethyl-benzenesulfonyl)-pyrrolidine-2-carboxylic acid cyanomethyl-amide hydrochloride as a white solid. MS: 362.2 [M+H]$^+$.

K3. The deprotection of the nitrile from experiment I3 was performed in trifluoroacetic acid at 22° C. to yield (2S,4R)-4-benzenesulfonyl-pyrrolidine-2-carboxylic acid (1-cyano-cyclopropyl)-amide trifluoro-acetate as a colorless oil. MS: 320.0 [M+H]$^+$.

Example 42

(2S,4R)-4-(2-Chloro-benzenesulfonyl)-pyrrolidine-2-carboxylic acid (1-cyano-cyclopropyl)-amide Hydrochloride

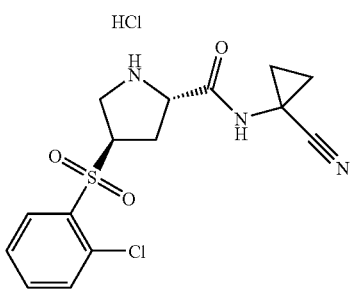

K4. The deprotection of the nitrile from experiment I4 yielded (2S,4R)-4-(2-chloro-benzenesulfonyl)-pyrrolidine-2-carboxylic acid (1-cyano-cyclopropyl)-amide hydrochloride as a colorless solid. MS: 354.1 [M+H]+.

Example 43

(2S,4R)-4-(2-Trifluoromethyl-benzenesulfonyl)-pyrrolidine-2-carboxylic acid (1-cyano-cyclopropyl)-amide

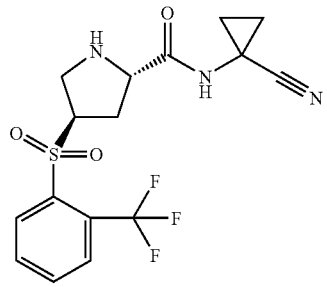

K5. The deprotection of the nitrile from experiment I5 yielded (2S,4R)-4-(2-trifluoromethyl-benzenesulfonyl)-pyrrolidine-2-carboxylic acid (1-cyano-cyclopropyl)-amide hydrochloride as a colorless solid. MS: 388.1 [M+H]+.

Example 44

(2S,4R)-4-(2-Chloro-benzenesulfonyl)-pyrrolidine-2-carboxylic acid (cyano-dimethyl-methyl)-amide Hydrochloride

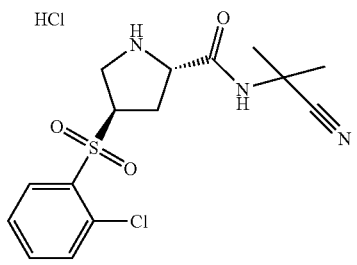

K6. The deprotection of the nitrile from experiment I6 yielded (2S,4R)-4-(2-chloro-benzenesulfonyl)-pyrrolidine-2-carboxylic acid (cyano-dimethyl-methyl)-amide hydrochloride as a white solid. MS: 356.0 [M+H]+.

Example 45

(2S,4R)-4-(2-Chloro-benzenesulfonyl)-pyrrolidine-2-carboxylic acid (1-cyano-cyclobutyl)-amide Hydrochloride

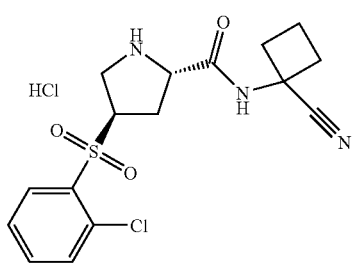

K7. The deprotection of the nitrile from experiment I7 yielded (2S,4R)-4-(2-chloro-benzenesulfonyl)-pyrrolidine-2-carboxylic acid (1-cyano-cyclobutyl)-amide hydrochloride as a white solid. MS: 368.1 [M+H]+.

Example 46

(2S,4R)-4-(2-Chloro-benzenesulfonyl)-pyrrolidine-2-carboxylic acid (1-cyano-cyclohexyl)-amide Hydrochloride

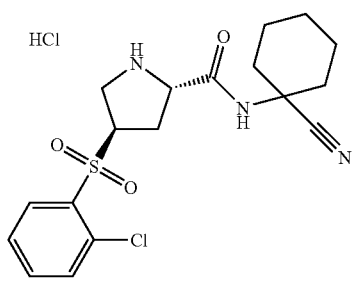

K8. The deprotection of the nitrile from experiment I8 yielded (2S,4R)-4-(2-chloro-benzenesulfonyl)-pyrrolidine-2-carboxylic acid (1-cyano-cyclohexyl)-amide hydrochloride as a white solid. MS: 396.1 [M+H]+.

Example 47

(2S,4R)-2-(1-Cyano-cyclopropylcarbamoyl)-4-(2,6-dichloro-benzenesulfonyl)-pyrrolidine-1-carboxylic acid tert-butyl ester

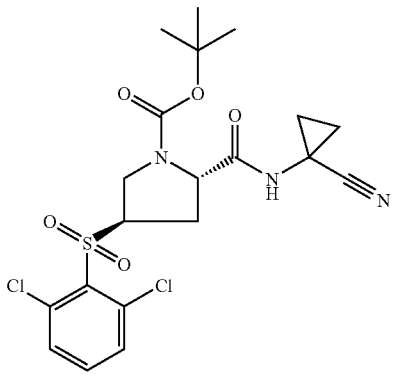

K9. The deprotection of the nitrile from experiment I9 yielded a 1:1 mixture of epimers of (2S,4R)-4-(2-chloro-benzenesulfonyl)-pyrrolidine-2-carboxylic acid (cyano-phenyl-methyl)-amide hydrochloride as a pale yellow solid. MS: 404.2 [M+H]+.

Example 48

(2S,4R)-4-(2-Chloro-benzenesulfonyl)-pyrrolidine-2-carboxylic acid (cyano-methyl-phenyl-methyl)-amide Hydrochloride

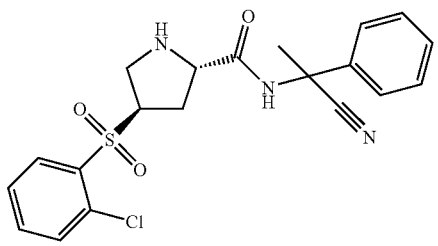

K10. The deprotection of the nitrile from experiment I10 yielded a 1:1 mixture of epimers of (2S,4R)-4-(2-chloro-benzenesulfonyl)-pyrrolidine-2-carboxylic acid (cyano-methyl-phenyl-methyl)-amide hydrochloride as a pale yellow solid. MS: 418.2 [M+H]$^+$.

Example 49

(2S,4R)-4-(2,4-Dimethyl-benzenesulfonyl)-pyrrolidine-2-carboxylic acid (1-cyano-cyclopropyl)-amide Hydrochloride

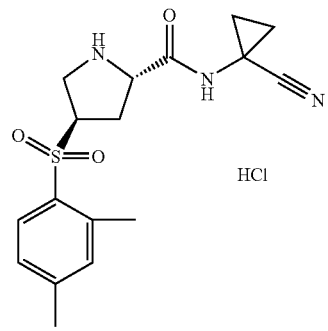

K11. The deprotection of the nitrile from experiment I12 yielded (2S,4R)-4-(2,4-dimethyl-benzenesulfonyl)-pyrrolidine-2-carboxylic acid (1-cyano-cyclopropyl)-amide hydrochloride as a white solid. MS: 348.1 [M+H]$^+$.

Example 50

(2S,4R)-4-(4-Chloro-2-methyl-benzenesulfonyl)-pyrrolidine-2-carboxylic acid (1-cyano-cyclopropyl)-amide Hydrochloride

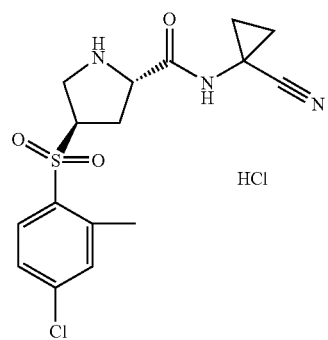

K12. The deprotection of the nitrile from experiment I13 yielded (2S,4R)-4-(4-chloro-2-methyl-benzenesulfonyl)-pyrrolidine-2-carboxylic acid (1-cyano-cyclopropyl)-amide hydrochloride as a white solid. MS: 368.0 [M+H]$^+$.

Example 51

(2S,4R)-4-(2,3-Dichloro-benzenesulfonyl)-pyrrolidine-2-carboxylic acid (1-cyano-cyclopropyl)-amide Hydrochloride

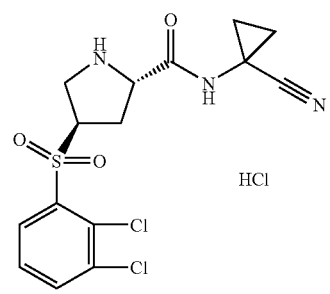

K13. The deprotection of the nitrile from experiment I14 yielded (2S,4R)-4-(2,3-dichloro-benzenesulfonyl)-pyrrolidine-2-carboxylic acid (1-cyano-cyclopropyl)-amide hydrochloride as a white solid. MS: 388.1 [M+H]$^+$.

L. Synthesis of the Prolines L

The prolines L were prepared from the prolines K

Example 52

(2S,4R)-4-Benzenesulfonyl-1-benzoyl-pyrrolidine-2-carboxylic acid cyanomethyl-amide

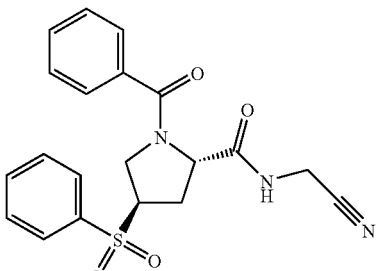

L1. (2S,4R)-4-Benzenesulfonyl-pyrrolidine-2-carboxylic acid cyanomethyl-amide hydrochloride prepared in analogy to experiment K1 was coupled with benzoic acid in analogy to experiment A1 to give (2S,4R)-1-benzoyl-4-(2-chloro-benzenesulfonyl)-pyrrolidine-2-carboxylic acid (1-cyano-cyclopropyl)-amide as a colorless solid. MS: 458.2 [M+H]$^+$.

Example 53

(2S,4R)-4-Benzenesulfonyl-1-cyclohexanecarbonyl-pyrrolidine-2-carboxylic acid cyanomethyl-amide

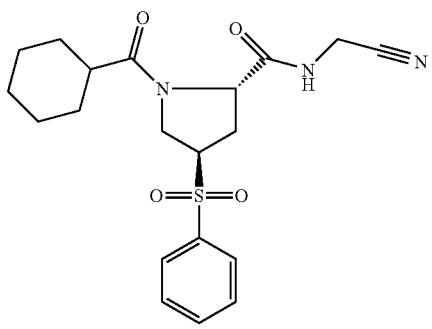

L2. (2S,4R)-4-Benzenesulfonyl-pyrrolidine-2-carboxylic acid cyanomethyl-amide hydrochloride prepared in analogy to experiment K1 was coupled with cyclohexanecarboxylic acid in analogy to experiment A1 to give (2S,4R)-4-benzenesulfonyl-1-cyclohexanecarbonyl-pyrrolidine-2-carboxylic acid cyanomethyl-amide as a white solid. MS: 404.3 [M+H]$^+$.

Example 54

(2S,4R)-4-Benzenesulfonyl-1-benzyl-pyrrolidine-2-carboxylic acid cyanomethyl-amide

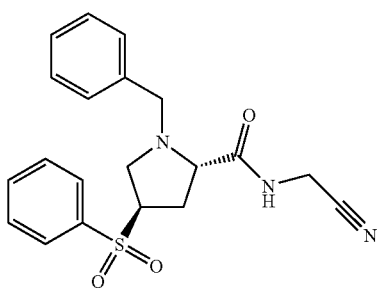

L3. To a suspension of (2S,4R)-4-benzenesulfonyl-pyrrolidine-2-carboxylic acid cyanomethyl-amide hydrochloride (0.13 mmole) prepared in analogy to experiment K1 in THF (1 ml) was added acetic acid (15 ul) followed by the addition of benzaldehyde (0.14 mmole) and stirring was continued at 22° C. for 1 h. Sodium triacetoxyborohydride (0.38 mmole) was added in one portion and stirring was continued at 22° C. for 3 h. The mixture was quenched with aqueous HCL and MeOH and the solution was purified by prep. HPLC (RP-18) using a mixture of acetonitrile and water to give (2S,4R)-4-benzenesulfonyl-1-benzyl-pyrrolidine-2-carboxylic acid cyanomethyl-amide as a colourless oil. MS: 384.1 [M+H]$^+$.

Example 55

(2S,4R)-4-Benzenesulfonyl-1-cyclohexylmethyl-pyrrolidine-2-carboxylic acid cyanomethyl-amide

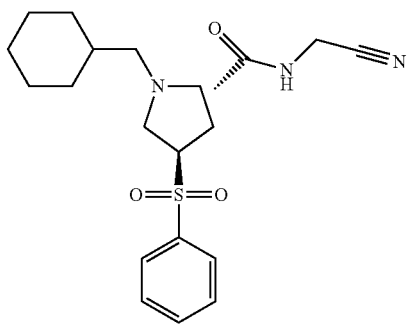

L4. (2S,4R)-4-Benzenesulfonyl-pyrrolidine-2-carboxylic acid cyanomethyl-amide hydrochloride prepared in analogy to experiment K1 was reductively aminated with cyclohexanecarbaldehyde in analogy to experiment L3 to give (2S,4R)-4-benzenesulfonyl-1-cyclohexylmethyl-pyrrolidine-2-carboxylic acid cyanomethyl-amide as a white solid. MS: 390.4 [M+H]$^+$.

Example 56

(2S,4R)-4-Benzenesulfonyl-1-(2,2,2-trifluoro-1-phenyl-ethyl)-pyrrolidine-2-carboxylic acid cyanomethyl-amide

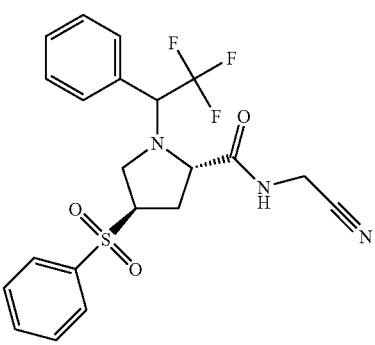

L5. To a solution of 1-phenyl-2,2,2-trifluoroethanol (0.4 mmole) in dichloromethane (1.4 ml) was added at −50° C. diisopropylethyl amine (2.0 mmole) and triflic anhydride (0.42 mmole) and stirring was continued at −50° for 1 h. To the mixture was added at −50° C. a solution of (2S,4R)-4-benzenesulfonyl-pyrrolidine-2-carboxylic acid cyanomethyl-amide hydrochloride (0.4 mmole) prepared in analogy to experiment K1 in dichloromethane (0.4 ml) and stirring was continued at 22° C. for 2 d. The mixture was partitioned between ethyl acetate and water, the organic layer was dried, evaporated and the residue was chromatographed on silica to give (2S,4R)-4-benzenesulfonyl-1-(2,2,2-trifluoro-1-phenyl-ethyl)-pyrrolidine-2-carboxylic acid cyanomethyl-amide as a colorless solid. MS: 452.1 [M+H]+.

Example 57

(2S,4R)-4-(2-Chloro-benzenesulfonyl)-1-(2,2,2-trifluoro-1-phenyl-ethyl)-pyrrolidine-2-carboxylic acid cyanomethyl-amide

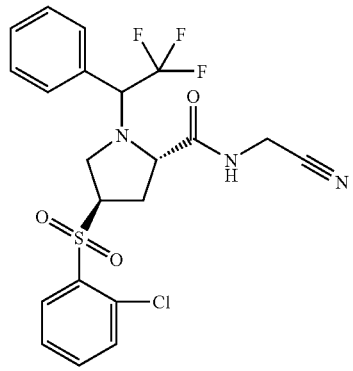

L6. (2S,4R)-4-(2-chloro-benzenesulfonyl)-pyrrolidine-2-carboxylic acid cyanomethyl-amide hydrochloride from experiment K1 was reacted with 1-phenyl-2,2,2-trifluoroethanol as described in experiment L5 to give (2S,4R)-4-(2-chloro-benzenesulfonyl)-1-(2,2,2-trifluoro-1-phenyl-ethyl)-pyrrolidine-2-carboxylic acid cyanomethyl-amide as a white amorphous solid. MS: 486.2 [M+H]+.

Example 58

(2S,4R)-1-Benzoyl-4-(2-chloro-benzenesulfonyl)-pyrrolidine-2-carboxylic acid cyanomethyl-amide

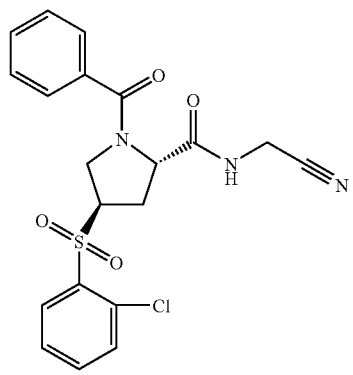

L7. (2S,4R)-4-(2-chloro-benzenesulfonyl)-pyrrolidine-2-carboxylic acid cyanomethyl-amide hydrochloride from experiment K1 was coupled with benzoic acid in analogy to experiment A1 to give (2S,4R)-1-benzoyl-4-(2-chloro-benzenesulfonyl)-pyrrolidine-2-carboxylic acid cyanomethyl-amide as an amorphous solid. MS: 432.2 [M+H]+.

Example 59

(2S,4R)-4-(2-Chloro-benzenesulfonyl)-1-(4-fluoro-benzoyl)-pyrrolidine-2-carboxylic acid cyanomethyl-amide

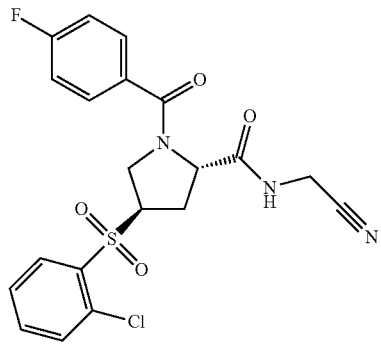

L8. (2S,4R)-4-(2-chloro-benzenesulfonyl)-pyrrolidine-2-carboxylic acid cyanomethyl-amide hydrochloride from experiment K1 was coupled with 4-fluorobenzoic acid in analogy to experiment A1 to give (2S,4R)-4-(2-chloro-benzenesulfonyl)-1-(4-fluoro-benzoyl)-pyrrolidine-2-carboxylic acid cyanomethyl-amide as a colorless oil. MS: 450.1 [M+H]+.

Example 60

(2S,4R)-4-(2-Chloro-benzenesulfonyl)-1-cyclohexanecarbonyl-pyrrolidine-2-carboxylic acid cyanomethyl-amide

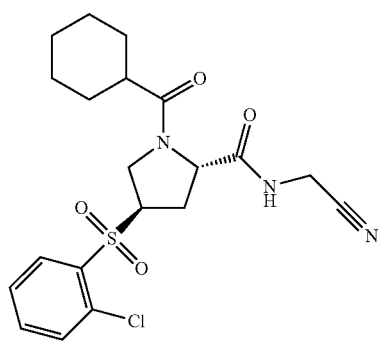

L9. (2S,4R)-4-(2-chloro-benzenesulfonyl)-pyrrolidine-2-carboxylic acid cyanomethyl-amide hydrochloride from experiment K1 was coupled with cyclohexanecarboxylic acid in analogy to experiment A1 to give (2S,4R)-4-(2-chlorobenzenesulfonyl)-1-cyclohexanecarbonyl-pyrrolidine-2-carboxylic acid cyanomethyl-amide as a colorless oil. MS: 438.1 [M+H]$^+$.

Example 61

(2S,4R)-4-(2-Chloro-benzenesulfonyl)-1-propionyl-pyrrolidine-2-carboxylic acid cyanomethyl-amide

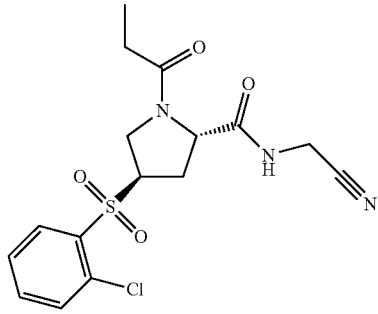

L10. (2S,4R)-4-(2-chloro-benzenesulfonyl)-pyrrolidine-2-carboxylic acid cyanomethyl-amide hydrochloride from experiment K1 was coupled with propionic acid in analogy to experiment A1 to give (2S,4R)-4-(2-chloro-benzenesulfonyl)-1-propionyl-pyrrolidine-2-carboxylic acid cyanomethyl-amide as a colorless oil. MS: 384.1 [M+H]$^+$.

Example 62

(2S,4R)-4-(2-Chloro-benzenesulfonyl)-1-(2-methoxy-acetyl)-pyrrolidine-2-carboxylic acid cyanomethyl-amide

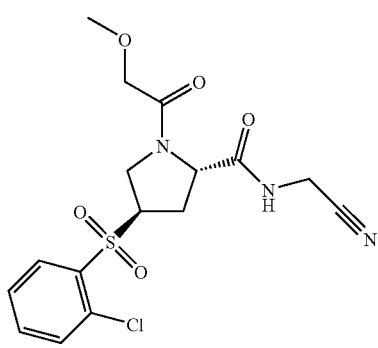

L11. (2S,4R)-4-(2-chloro-benzenesulfonyl)-pyrrolidine-2-carboxylic acid cyanomethyl-amide hydrochloride from experiment K1 was coupled with methoxy-acetic acid in analogy to experiment A1 to give (2S,4R)-4-(2-chloro-benzenesulfonyl)-1-(2-methoxy-acetyl)-pyrrolidine-2-carboxylic acid cyanomethyl-amide as a colorless foam. MS: 400.1 [M+H]$^+$.

Example 63

(2S,4R)-4-(2-Chloro-benzenesulfonyl)-1-oxetan-3-yl-pyrrolidine-2-carboxylic acid cyanomethyl-amide

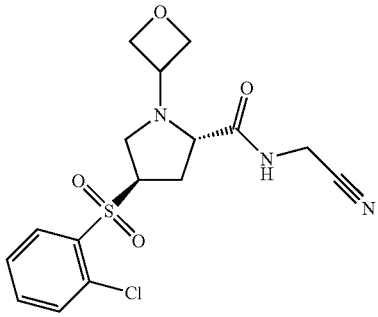

L12. (2S,4R)-4-(2-chloro-benzenesulfonyl)-pyrrolidine-2-carboxylic acid cyanomethyl-amide hydrochloride from experiment K1 was reductively aminated with oxetane-3-one (prepared according to G. Wuitschik et al., Angewandte Chemie, International Edition (2006), 45(46), 7736) in analogy to experiment L3 to give to give (2S,4R)-4-(2-chloro-benzenesulfonyl)-1-oxetan-3-yl-pyrrolidine-2-carboxylic acid cyanomethyl-amide as a colorless foam. MS: 384.1 [M+H]$^+$.

Example 64

(2S,4R)-4-(2-Chloro-benzenesulfonyl)-1-(tetrahydro-pyran-4-yl)-pyrrolidine-2-carboxylic acid cyanomethyl-amide

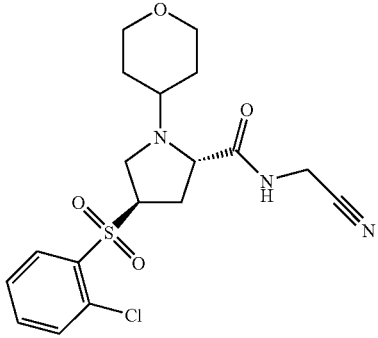

L13. (2S,4R)-4-(2-chloro-benzenesulfonyl)-pyrrolidine-2-carboxylic acid cyanomethyl-amide hydrochloride from experiment K1 was reductively aminated with tetrahydro-4H-pyran-4-one in analogy to experiment L3 to give to give (2S,4R)-4-(2-chloro-benzenesulfonyl)-1-(tetrahydro-pyran-4-yl)-pyrrolidine-2-carboxylic acid cyanomethyl-amide as a colorless oil. MS: 412.1 [M+H]$^+$.

Example 65

(2S,4R)-1-(4-Fluoro-benzoyl)-4-(2-trifluoromethyl-benzenesulfonyl)-pyrrolidine-2-carboxylic acid cyanomethyl-amide

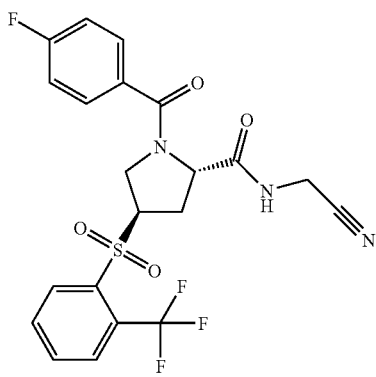

L14. (2S,4R)-4-(2-trifluoromethyl-benzenesulfonyl)-pyrrolidine-2-carboxylic acid cyanomethyl-amide hydrochloride from experiment K2 was coupled with 4-fluoro-benzoic acid in analogy to experiment A1 to give (2S,4R)-1-(4-fluoro-benzoyl)-4-(2-trifluoromethyl-benzenesulfonyl)-pyrrolidine-2-carboxylic acid cyanomethyl-amide as a colorless oil. MS: 484.1 [M+H]$^+$.

Example 66

(2S,4R)-1-(4-Methyl-benzoyl)-4-(2-trifluoromethyl-benzenesulfonyl)-pyrrolidine-2-carboxylic acid cyanomethyl-amide

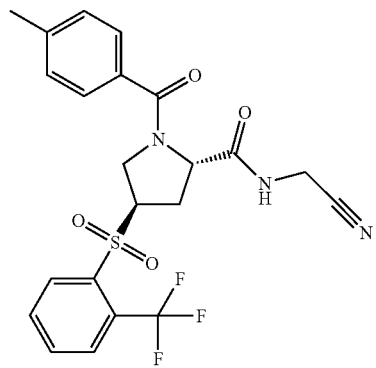

L15. (2S,4R)-4-(2-trifluoromethyl-benzenesulfonyl)-pyrrolidine-2-carboxylic acid cyanomethyl-amide hydrochloride from experiment K2 was coupled with 4-methyl-benzoic acid in analogy to experiment A1 to give (2S,4R)-1-(4-methyl-benzoyl)-4-(2-trifluoromethyl-benzenesulfonyl)-pyrrolidine-2-carboxylic acid cyanomethyl-amide as a colorless oil. MS: 480.1 [M+H]$^+$.

Example 67

(2S,4R)-1-Cyclohexanecarbonyl-4-(2-trifluoromethyl-benzenesulfonyl)-pyrrolidine-2-carboxylic acid cyanomethyl-amide

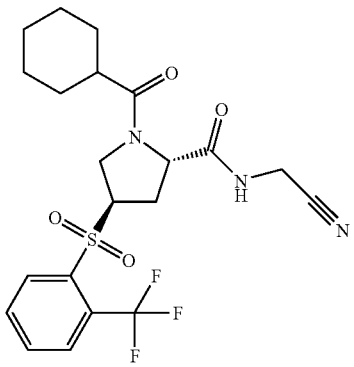

L16. (2S,4R)-4-(2-trifluoromethyl-benzenesulfonyl)-pyrrolidine-2-carboxylic acid cyanomethyl-amide hydrochloride from experiment K2 was coupled with cyclohexanecarboxylic acid in analogy to experiment A1 to give (2S,4R)-1-cyclohexanecarbonyl-4-(2-trifluoromethyl-benzenesulfonyl)-pyrrolidine-2-carboxylic acid cyanomethyl-amide as a colorless oil. MS: 472.2 [M+H]$^+$.

Example 68

(2S,4R)-1-(Tetrahydro-pyran-4-carbonyl)-4-(2-trifluoromethyl-benzenesulfonyl)-pyrrolidine-2-carboxylic acid cyanomethyl-amide

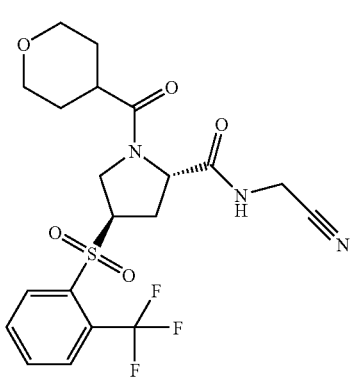

L17. (2S,4R)-4-(2-trifluoromethyl-benzenesulfonyl)-pyrrolidine-2-carboxylic acid cyanomethyl-amide hydrochloride from experiment K2 was coupled with tetrahydro-pyran-4-carboxylic acid in analogy to experiment A1 to give (2S,4R)-1-(tetrahydro-pyran-4-carbonyl)-4-(2-trifluoromethyl-benzenesulfonyl)-pyrrolidine-2-carboxylic acid cyanomethyl-amide as a colorless oil. MS: 474.1 [M+H]$^+$.

Example 69

(2S,4R)-1-(Pyridine-4-carbonyl)-4-(2-trifluoromethyl-benzenesulfonyl)-pyrrolidine-2-carboxylic acid cyanomethyl-amide

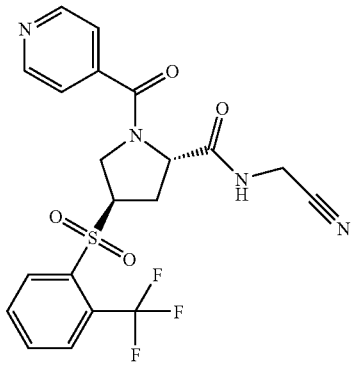

L18. (2S,4R)-4-(2-trifluoromethyl-benzenesulfonyl)-pyrrolidine-2-carboxylic acid cyanomethyl-amide hydrochloride from experiment K2 was coupled with isonicotinic acid in analogy to experiment A1 to give (2S,4R)-1-(pyridine-4-carbonyl)-4-(2-trifluoromethyl-benzenesulfonyl)-pyrrolidine-2-carboxylic acid cyanomethyl-amide as a colorless oil. MS: 467.2 [M+H]$^+$.

Example 70

(2S,4R)-1-(1-Methyl-piperidine-4-carbonyl)-4-(2-trifluoromethyl-benzenesulfonyl)-pyrrolidine-2-carboxylic acid cyanomethyl-amide formiate

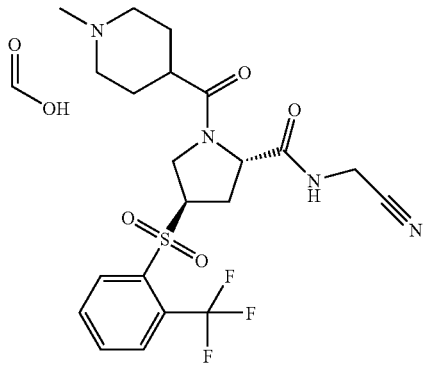

L19. (2S,4R)-4-(2-trifluoromethyl-benzenesulfonyl)-pyrrolidine-2-carboxylic acid cyanomethyl-amide hydrochloride from experiment K2 was coupled with 1-methylpiperidine-4-carboxylic acid in analogy to experiment A1 to give (2S,4R)-1-(1-methyl-piperidine-4-carbonyl)-4-(2-trifluoromethyl-benzenesulfonyl)-pyrrolidine-2-carboxylic acid cyanomethyl-amide; salt with formic acid as a colorless oil. MS: 487.3 [M+H]$^+$.

Example 71

(2S,4R)-1-Benzoyl-4-(2-trifluoromethyl-benzenesulfonyl)-pyrrolidine-2-carboxylic acid cyanomethyl-amide

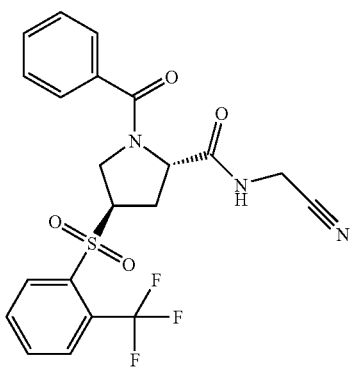

L20. (2S,4R)-4-(2-trifluoromethyl-benzenesulfonyl)-pyrrolidine-2-carboxylic acid cyanomethyl-amide hydrochloride from experiment K2 was coupled with benzoic acid in analogy to experiment A1 to give (2S,4R)-1-benzoyl-4-(2-trifluoromethyl-benzenesulfonyl)-pyrrolidine-2-carboxylic acid cyanomethyl-amide as a colorless oil. MS: 466.2 [M+H]$^+$.

Example 72

(2S,4R)-2-(Cyanomethyl-carbamoyl)-4-(2-trifluoromethyl-benzenesulfonyl)-pyrrolidine-1-carboxylic acid Cyclopentyl Ester

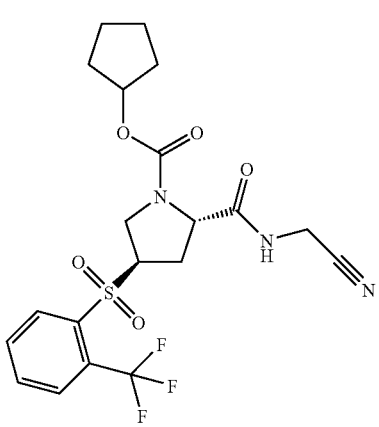

L21. To a suspension of (2S,4R)-4-(2-trifluoromethyl-benzenesulfonyl)-pyrrolidine-2-carboxylic acid cyanomethyl-amide hydrochloride (0.13 mmole) from experiment K2 in acetonitrile (1 ml) was added at 22° C. diisopropyl ethyl amine (0.40 mmole) and cyclopentyl chloroformate (0.15 mmole) and stirring was continued for 2 h. The mixture was quenched with methanol, acidified with acetic acid and subjected to prep. HPLC (RP-18) using a mixture of acetonitrile and water to give (2S,4R)-2-(cyanomethyl-carbamoyl)-4-(2-trifluoromethyl-benzenesulfonyl)-pyrrolidine-1-carboxylic acid cyclopentyl ester as a colorless oil. MS: 474.1 [M+H]⁺.

Example 73

(2S,4R)-4-Benzenesulfonyl-1-benzoyl-pyrrolidine-2-carboxylic acid (1-cyano-cyclopropyl)-amide

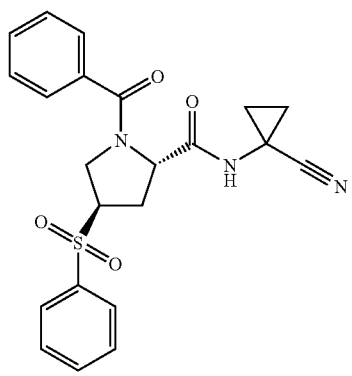

L22. (2S,4R)-4-benzenesulfonyl-pyrrolidine-2-carboxylic acid (1-cyano-cyclopropyl)-amide trifluoro-acetate from experiment K3 was coupled with benzoic acid in analogy to experiment A1 to give (2S,4R)-4-benzenesulfonyl-1-benzoyl-pyrrolidine-2-carboxylic acid (1-cyano-cyclopropyl)-amide as a pale yellow solid. MS: 424.2 [M+H]⁺.

Example 74

(2S,4R)-4-Benzenesulfonyl-1-(tetrahydro-pyran-4-carbonyl)-pyrrolidine-2-carboxylic acid (1-cyano-cyclopropyl)-amide

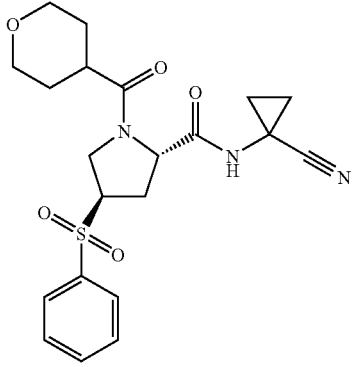

L23. (2S,4R)-4-benzenesulfonyl-pyrrolidine-2-carboxylic acid (1-cyano-cyclopropyl)-amide trifluoro-acetate from experiment K3 was coupled with tetrahydro-pyran-4-carboxylic acid in analogy to experiment A1 to give (2S,4R)-4-benzenesulfonyl-1-(tetrahydro-pyran-4-carbonyl)-pyrrolidine-2-carboxylic acid (1-cyano-cyclopropyl)-amide as a colorless oil. MS: 432.3 [M+H]⁺.

Example 75

(2S,4R)-1-Benzoyl-4-(2-chloro-benzenesulfonyl)-pyrrolidine-2-carboxylic acid (1-cyano-cyclopropyl)-amide

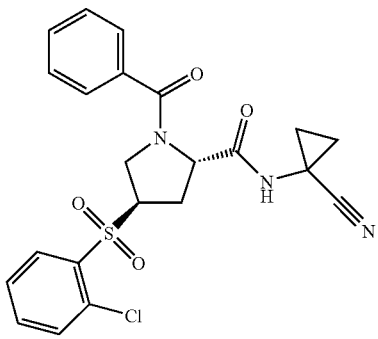

L24. (2S,4R)-4-(2-chloro-benzenesulfonyl)-pyrrolidine-2-carboxylic acid (1-cyano-cyclopropyl)-amide hydrochloride from experiment K4 was coupled with benzoic acid in analogy to experiment A1 to give (2S,4R)-1-benzoyl-4-(2-chloro-benzenesulfonyl)-pyrrolidine-2-carboxylic acid (1-cyano-cyclopropyl)-amide as a colorless solid. MS: 458.2 [M+H]⁺.

Example 76

(2S,4R)-4-(2-Chloro-benzenesulfonyl)-1-(4-fluoro-benzoyl)-pyrrolidine-2-carboxylic acid (1-cyano-cyclopropyl)-amide

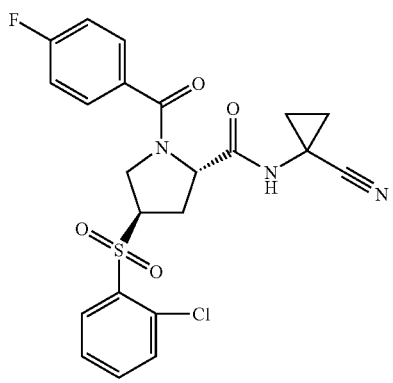

L25. (2S,4R)-4-(2-chloro-benzenesulfonyl)-pyrrolidine-2-carboxylic acid (1-cyano-cyclopropyl)-amide hydrochloride from experiment K4 was coupled with 4-fluoro benzoic acid in analogy to experiment A1 to give (2S,4R)-4-(2-chloro-benzenesulfonyl)-1-(4-fluoro-benzoyl)-pyrrolidine-2-carboxylic acid (1-cyano-cyclopropyl)-amide as an amorphous white solid. MS: 476.0 [M+H]⁺.

Example 77

(2S,4R)-4-(2-Chloro-benzenesulfonyl)-1-cyclohexanecarbonyl-pyrrolidine-2-carboxylic acid (1-cyano-cyclopropyl)-amide

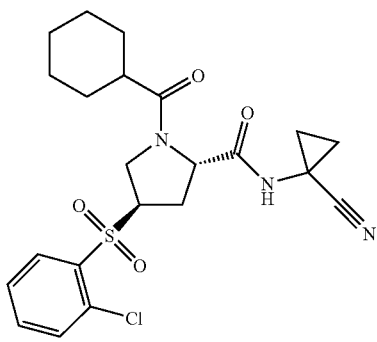

L26. (2S,4R)-4-(2-chloro-benzenesulfonyl)-pyrrolidine-2-carboxylic acid (1-cyano-cyclopropyl)-amide hydrochloride from experiment K4 was coupled with cyclohexanecarboxylic acid in analogy to experiment A1 to give (2S,4R)-4-(2-chloro-benzenesulfonyl)-1-cyclohexanecarbonyl-pyrrolidine-2-carboxylic acid (1-cyano-cyclopropyl)-amide as a colorless oil. MS: 464.1 [M+H]+.

Example 78

(2S,4R)-4-(2-Chloro-benzenesulfonyl)-1-formyl-pyrrolidine-2-carboxylic acid (1-cyano-cyclopropyl)-amide

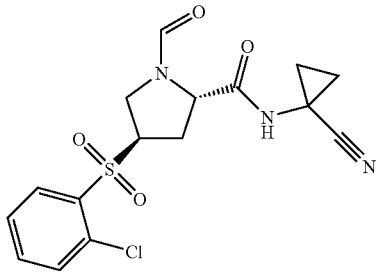

L27. To as solution of (2S,4R)-4-(2-chloro-benzenesulfonyl)-pyrrolidine-2-carboxylic acid (1-cyano-cyclopropyl)-amide hydrochloride (0.12 mmole) from experiment K4 in acetonitrile (1.0 ml) was added at 22° C. N,N-diisopropylethyl amine (0.38 mmole) and p-nitrophenyl formate (0.14 mmole) and stirring was continued for 2 h. The mixture was evaporated, the residue partitioned between ethyl acetate and aqueous sodium carbonate, the organic layer was washed with water, dried and evaporated. The residue was purified by prep. HPLC (RP-18) using a mixture of acetonitrile and water to give (2S,4R)-4-(2-chloro-benzenesulfonyl)-1-formyl-pyrrolidine-2-carboxylic acid (1-cyano-cyclopropyl)-amide as a colorless oil. MS: 482.3 [M+H]+.

Example 79

(2S,4R)-1-Acetyl-4-(2-chloro-benzenesulfonyl)-pyrrolidine-2-carboxylic acid (1-cyano-cyclopropyl)-amide

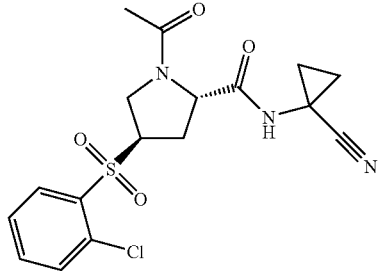

L28. (2S,4R)-4-(2-chloro-benzenesulfonyl)-pyrrolidine-2-carboxylic acid (1-cyano-cyclopropyl)-amide hydrochloride from experiment K4 was coupled with acetic acid in analogy to experiment A1 to give (2S,4R)-1-acetyl-4-(2-chloro-benzenesulfonyl)-pyrrolidine-2-carboxylic acid (1-cyano-cyclopropyl)-amide as a colorless solid. MS: 496.0 [M+H]+.

Example 80

(2S,4R)-4-(2-Chloro-benzenesulfonyl)-1-(2,2,2-trifluoro-acetyl)-pyrrolidine-2-carboxylic acid (1-cyano-cyclopropyl)-amide

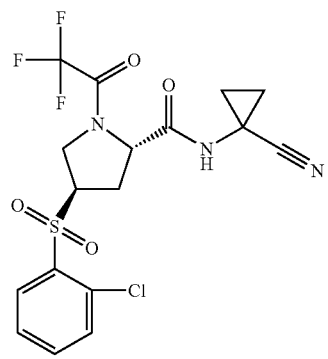

L29. To a mixture of (2S,4R)-4-(2-chloro-benzenesulfonyl)-pyrrolidine-2-carboxylic acid (1-cyano-cyclopropyl)-amide hydrochloride (0.13 mmole) from experiment K4 in acetonitrile (2.0 ml) was added at 22° C. N,N-diisopropylethyl amine (0.77 mmole) and trifluoroacetic anhydride (0.61 mmole) and stirring was continued for 3 h. The mixture was evaporated, the residue partitioned between ethyl acetate and water, the organic layer was dried and evaporated. The residue was purified by chromatography using cyclohexane/ethyl acetate (1:1) to give (2S,4R)-4-(2-chloro-benzenesulfonyl)-1-(2,2,2-trifluoro-acetyl)-pyrrolidine-2-carboxylic acid (1-cyano-cyclopropyl)-amide as a pale yellow oil. MS: 450.1 [M+H]+.

Example 81

(R)-4-(2-Chloro-benzenesulfonyl)-1-((S)-1-methyl-pyrrolidine-2-carbonyl)-pyrrolidine-2-carboxylic acid (1-cyano-cyclopropyl)-amide formiate

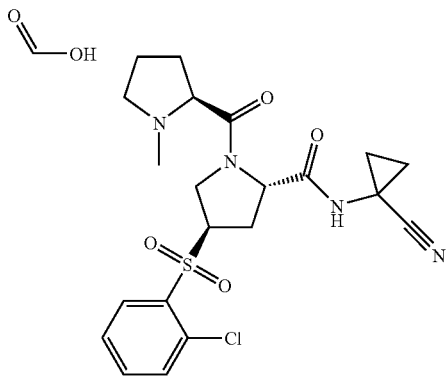

L30. (2S,4R)-4-(2-chloro-benzenesulfonyl)-pyrrolidine-2-carboxylic acid (1-cyano-cyclopropyl)-amide hydrochloride from experiment K4 was coupled with (S)-1-methyl-pyrrolidine carboxylic acid in analogy to experiment A1 to give (R)-4-(2-chloro-benzenesulfonyl)-1-((S)-1-methyl-pyrrolidine-2-carbonyl)-pyrrolidine-2-carboxylic acid (1-cyano-cyclopropyl)-amide; salt with formic acid as a colorless solid. MS: 465.2 [M+H]$^+$.

Example 82

(2S,4R)-4-(2-Chloro-benzenesulfonyl)-1-(1-methyl-piperidine-4-carbonyl)-pyrrolidine-2-carboxylic acid (1-cyano-cyclopropyl)-amide

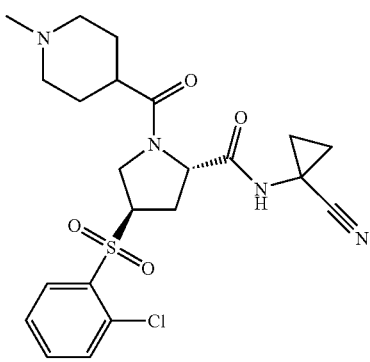

L31. (2S,4R)-4-(2-chloro-benzenesulfonyl)-pyrrolidine-2-carboxylic acid (1-cyano-cyclopropyl)-amide hydrochloride from experiment K4 was coupled with 1-methyl-piperidine-4-carboxylic acid in analogy to experiment A1 to give (2S,4R)-4-(2-chloro-benzenesulfonyl)-1-(1-methyl-piperidine-4-carbonyl)-pyrrolidine-2-carboxylic acid (1-cyano-cyclopropyl)-amide as a white solid. MS: 479.1 [M+H]$^+$.

Example 83

(2S,4R)-4-(2-Chloro-benzenesulfonyl)-1-ethyl-pyrrolidine-2-carboxylic acid (1-cyano-cyclopropyl)-amide

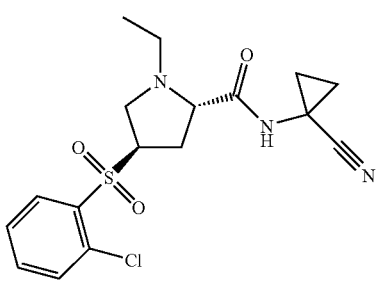

L32. (2S,4R)-4-(2-chloro-benzenesulfonyl)-pyrrolidine-2-carboxylic acid (1-cyano-cyclopropyl)-amide hydrochloride from experiment K4 was reductively aminated with acetaldehyde in analogy to experiment L3 to give (2S,4R)-4-(2-chloro-benzenesulfonyl)-1-ethyl-pyrrolidine-2-carboxylic acid (1-cyano-cyclopropyl)-amide as a colorless oil. MS: 382.3 [M+H]$^+$.

Example 84

(2S,4R)-4-(2-Chloro-benzenesulfonyl)-1-cyclobutyl-pyrrolidine-2-carboxylic acid (1-cyano-cyclopropyl)-amide

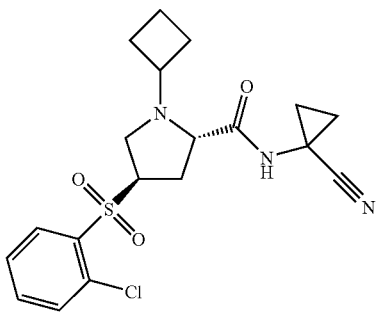

L33. (2S,4R)-4-(2-chloro-benzenesulfonyl)-pyrrolidine-2-carboxylic acid (1-cyano-cyclopropyl)-amide hydrochloride from experiment K4 was reductively aminated with cylobutanone in analogy to experiment L3 to give (2S,4R)-4-(2-chloro-benzenesulfonyl)-1-cyclobutyl-pyrrolidine-2-carboxylic acid (1-cyano-cyclopropyl)-amide as a colorless oil. MS: 408.3 [M+H]$^+$.

Example 85

(2S,4R)-4-(2-Chloro-benzenesulfonyl)-1-cyclohexyl-pyrrolidine-2-carboxylic acid (1-cyano-cyclopropyl)-amide

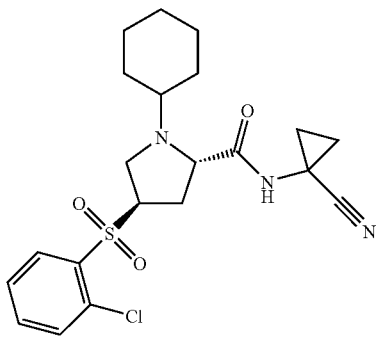

L34. (2S,4R)-4-(2-chloro-benzenesulfonyl)-pyrrolidine-2-carboxylic acid (1-cyano-cyclopropyl)-amide hydrochloride from experiment K4 was reductively aminated with cylohexanone in analogy to experiment L3 to give (2S,4R)-4-(2-chloro-benzenesulfonyl)-1-cyclohexyl-pyrrolidine-2-carboxylic acid (1-cyano-cyclopropyl)-amide as a colorless oil. MS: 436.2 [M+H]$^+$.

Example 86

(2S,4R)-4-(2-Chloro-benzenesulfonyl)-1-pyridin-4-ylmethyl-pyrrolidine-2-carboxylic acid (1-cyano-cyclopropyl)-amide

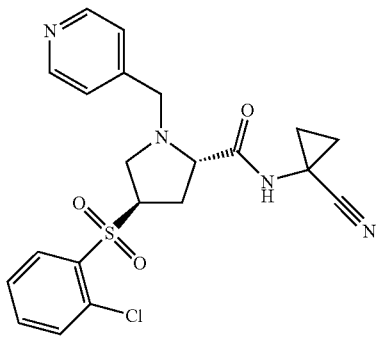

L35. (2S,4R)-4-(2-chloro-benzenesulfonyl)-pyrrolidine-2-carboxylic acid (1-cyano-cyclopropyl)-amide hydrochloride from experiment K4 was reductively aminated with 4-pyridine carboxaldehyde in analogy to experiment L3 to give (2S,4R)-4-(2-Chloro-benzenesulfonyl)-1-pyridin-4-yl-methyl-pyrrolidine-2-carboxylic acid (1-cyano-cyclopropyl)-amide as a colorless oil. MS: 445.3 [M+H]$^+$.

Example 87

(2S,4R)-4-(2-Chloro-benzenesulfonyl)-1-phenethyl-pyrrolidine-2-carboxylic acid (1-cyano-cyclopropyl)-amide

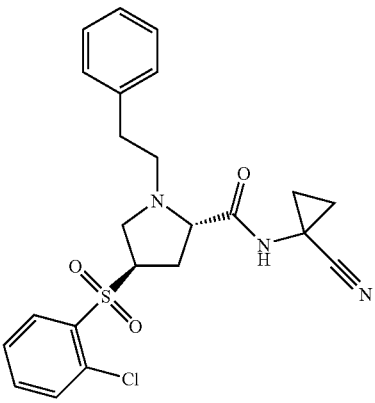

L36. (2S,4R)-4-(2-chloro-benzenesulfonyl)-pyrrolidine-2-carboxylic acid (1-cyano-cyclopropyl)-amide hydrochloride from experiment K4 was reductively aminated with phenyl acetaldehyde in analogy to experiment L3 to give (2S,4R)-4-(2-chloro-benzenesulfonyl)-1-phenethyl-pyrrolidine-2-carboxylic acid (1-cyano-cyclopropyl)-amide as a colorless oil. MS: 458.2 [M+H]$^+$.

Example 88

(2S,4R)-4-(2-Chloro-benzenesulfonyl)-1-(2,2-difluoro-ethyl)-pyrrolidine-2-carboxylic acid (1-cyano-cyclopropyl)-amide

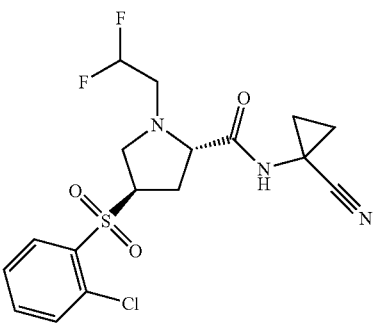

L37. To a suspension of (2S,4R)-4-(2-chloro-benzenesulfonyl)-pyrrolidine-2-carboxylic acid (1-cyano-cyclopropyl)-amide hydrochloride (0.13 mmole) from experiment K4 in THF (2 ml) was added at 22° C. diisopropyl ethyl amine (0.75 mmole) and 2,2-difluoroethyl triflate (0.60 mmole) and stirring was continued at 60° C. for 24 h. The mixture was quenched with methanol, acidified with acetic acid and subjected to prep. HPLC (RP-18) using a mixture of acetonitrile and water to give (2S,4R)-4-(2-chloro-benzenesulfonyl)-1-

(2,2-difluoro-ethyl)-pyrrolidine-2-carboxylic acid (1-cyano-cyclopropyl)-amide as a colorless oil. MS: 418.2 [M+H]+.

Example 89

(2S,4R)-4-(2-Chloro-benzenesulfonyl)-1-(2,2,2-trifluoro-ethyl)-pyrrolidine-2-carboxylic acid (1-cyano-cyclopropyl)-amide

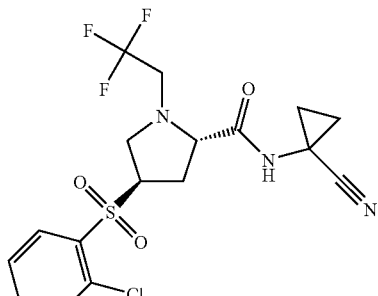

L38. (2S,4R)-4-(2-chloro-benzenesulfonyl)-pyrrolidine-2-carboxylic acid (1-cyano-cyclopropyl)-amide hydrochloride from experiment K4 was alkylated with 2,2,2-trifluoroethyl triflate in analogy to experiment L37 to give (2S,4R)-4-(2-chloro-benzenesulfonyl)-1-(2,2,2-trifluoro-ethyl)-pyrrolidine-2-carboxylic acid (1-cyano-cyclopropyl)-amide as a colorless oil. MS: 436.2 [M+H]+.

Example 90

(2S,4R)-4-(2-Chloro-benzenesulfonyl)-1-(3,3,3-trifluoro-2-methyl-propyl)-pyrrolidine-2-carboxylic acid (1-cyano-cyclopropyl)-amide

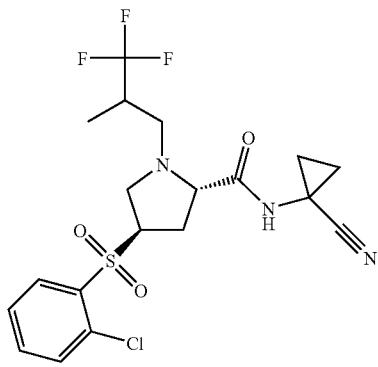

L39. (2S,4R)-4-(2-chloro-benzenesulfonyl)-pyrrolidine-2-carboxylic acid (1-cyano-cyclopropyl)-amide hydrochloride from experiment K4 was reductively alkylated with rac-2-methyl-trifluoropropionaldehyde in analogy to experiment L3 to give (2S,4R)-4-(2-chloro-benzenesulfonyl)-1-(3,3,3-trifluoro-2-methyl-propyl)-pyrrolidine-2-carboxylic acid (1-cyano-cyclopropyl)-amide as a colorless solid. MS: 464.1 [M+H]+.

Example 91

(2S,4R)-4-(2-Chloro-benzenesulfonyl)-1-(3,3,3-trifluoro-propyl)-pyrrolidine-2-carboxylic acid (1-cyano-cyclopropyl)-amide

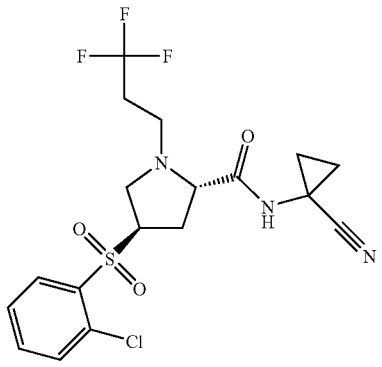

L40. (2S,4R)-4-(2-chloro-benzenesulfonyl)-pyrrolidine-2-carboxylic acid (1-cyano-cyclopropyl)-amide hydrochloride from experiment K4 was reductively alkylated with 3,3,3-trifluoropropionaldehyde in analogy to experiment L3 to give (2S,4R)-4-(2-chloro-benzenesulfonyl)-1-(3,3,3-trifluoro-propyl)-pyrrolidine-2-carboxylic acid (1-cyano-cyclopropyl)-amide as a colorless oil. MS: 450.2 [M+H]+.

Example 92

(2S,4R)-4-(2-Chloro-benzenesulfonyl)-1-(2,2,3,3,3-pentafluoro-propyl)-pyrrolidine-2-carboxylic acid (1-cyano-cyclopropyl)-amide

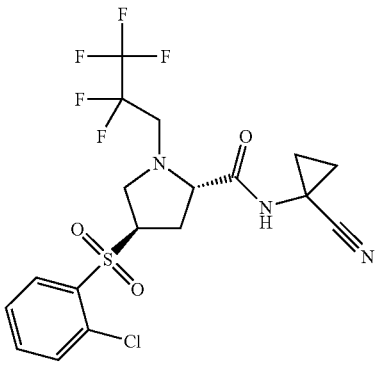

L41. (2S,4R)-4-(2-chloro-benzenesulfonyl)-pyrrolidine-2-carboxylic acid (1-cyano-cyclopropyl)-amide hydrochloride from experiment K4 was alkylated with 2,2,3,3,3-pentafluoropropyl triflate in analogy to experiment L37 to give (2S,4R)-4-(2-chloro-benzenesulfonyl)-1-(2,2,3,3,3-pentafluoro-propyl)-pyrrolidine-2-carboxylic acid (1-cyano-cyclopropyl)-amide as a colorless oil. MS: 486.2 [M+H]+.

Example 93

(2S,4R)-4-(2-Chloro-benzenesulfonyl)-1-methyl-pyrrolidine-2-carboxylic acid (1-cyano-cyclopropyl)-amide

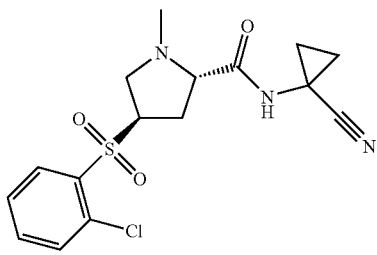

L42. (2S,4R)-4-(2-chloro-benzenesulfonyl)-pyrrolidine-2-carboxylic acid (1-cyano-cyclopropyl)-amide hydrochloride from experiment K4 was reductively alkylated with aqueous formaldehyde in analogy to experiment L3 to give (2S,4R)-4-(2-chloro-benzenesulfonyl)-1-methyl-pyrrolidine-2-carboxylic acid (1-cyano-cyclopropyl)-amide as a colorless oil. MS: 368.0 [M+H]$^+$.

Example 94

(2S,4R)-4-(2-Chloro-benzenesulfonyl)-1-methyl-pyrrolidine-2-carboxylic acid (1-cyano-cyclopropyl)-methyl-amide Formiate

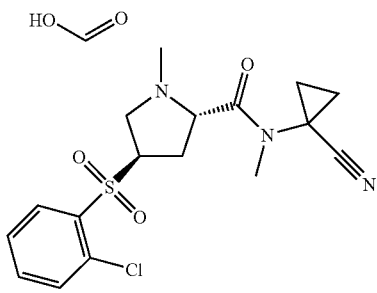

A second fraction contained (2S,4R)-4-(2-chloro-benzenesulfonyl)-1-methyl-pyrrolidine-2-carboxylic acid (1-cyano-cyclopropyl)-methyl-amide as a colorless oil. MS: 382.3 [M+H]$^+$.

Example 95

(2S,4R)-4-(2-Chloro-benzenesulfonyl)-2-(1-cyano-cyclopropylcarbamoyl)-pyrrolidine-1-carboxylic acid methyl ester

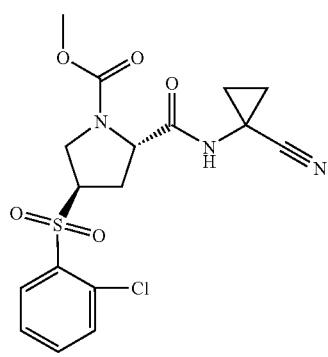

L43. (2S,4R)-4-(2-chloro-benzenesulfonyl)-pyrrolidine-2-carboxylic acid (1-cyano-cyclopropyl)-amide hydrochloride from experiment K4 was acylated with methyl chloroformate in analogy to experiment L21 to give (2S,4R)-4-(2-chloro-benzenesulfonyl)-2-(1-cyano-cyclopropylcarbamoyl)-pyrrolidine-1-carboxylic acid methyl ester as a colorless oil. MS: 412.1 [M+H]$^+$.

Example 96

(2S,4R)-4-(2-Chloro-benzenesulfonyl)-2-(1-cyano-cyclopropylcarbamoyl)-pyrrolidine-1-carboxylic acid ethyl ester

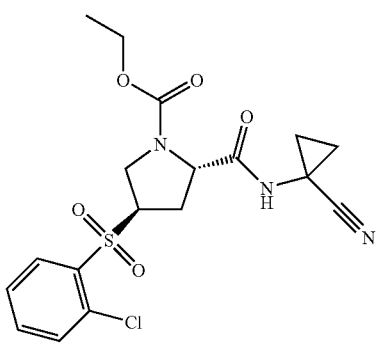

L44. (2S,4R)-4-(2-chloro-benzenesulfonyl)-pyrrolidine-2-carboxylic acid (1-cyano-cyclopropyl)-amide hydrochloride from experiment K4 was acylated with ethyl chloroformate in analogy to experiment L21 to give (2S,4R)-4-(2-chloro-benzenesulfonyl)-2-(1-cyano-cyclopropylcarbamoyl)-pyrrolidine-1-carboxylic acid ethyl ester as a colorless oil. MS: 426.0 [M+H]$^+$.

Example 97

(2S,4R)-4-(2-Chloro-benzenesulfonyl)-2-(1-cyano-cyclopropylcarbamoyl)-pyrrolidine-1-carboxylic acid Isopropyl Ester

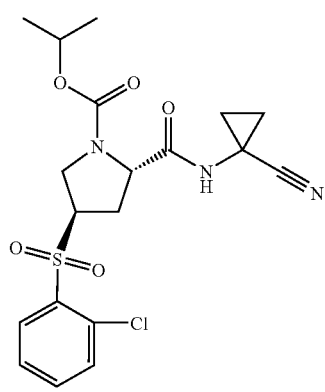

L45. (2S,4R)-4-(2-chloro-benzenesulfonyl)-pyrrolidine-2-carboxylic acid (1-cyano-cyclopropyl)-amide hydrochloride from experiment K4 was acylated with isopropyl chloroformate in analogy to experiment L21 to give (2S,4R)-4-(2-chloro-benzenesulfonyl)-2-(1-cyano-cyclopropyl-carbamoyl)-pyrrolidine-1-carboxylic acid isopropyl ester as a colorless oil. MS: 440.2 [M+H]⁺.

Example 98

(2S,4R)-4-(2-Chloro-benzenesulfonyl)-2-(1-cyano-cyclopropylcarbamoyl)-pyrrolidine-1-carboxylic acid Cyclopentyl Ester

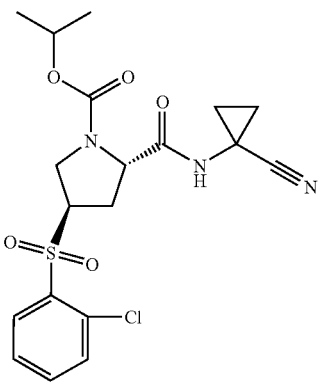

L46. (2S,4R)-4-(2-chloro-benzenesulfonyl)-pyrrolidine-2-carboxylic acid (1-cyano-cyclopropyl)-amide hydrochloride from experiment K4 was acylated with cyclopentyl chloroformate in analogy to experiment L21 to give (2S,4R)-4-(2-chloro-benzenesulfonyl)-2-(1-cyano-cyclopropylcarbamoyl)-pyrrolidine-1-carboxylic acid cyclopentyl ester as a colorless oil. MS: 466.2 [M+H]⁺.

Example 99

(2S,4R)-4-(2-Chloro-benzenesulfonyl)-2-(1-cyano-cyclopropylcarbamoyl)-pyrrolidine-1-carboxylic acid 4-fluoro-phenyl Ester

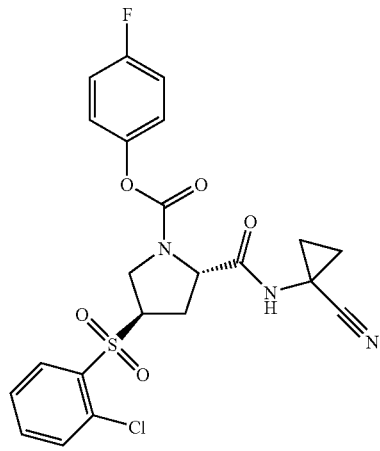

L47. (2S,4R)-4-(2-chloro-benzenesulfonyl)-pyrrolidine-2-carboxylic acid (1-cyano-cyclopropyl)-amide hydrochloride from experiment K4 was acylated with 4-fluorophenyl chloroformate in analogy to experiment L21 to give (2S,4R)-4-(2-chloro-benzenesulfonyl)-2-(1-cyano-cyclopropylcarbamoyl)-pyrrolidine-1-carboxylic acid 4-fluoro-phenyl ester as a colorless oil. MS: 492.1 [M+H]⁺.

Example 100

(2S,4R)-1-Formyl-4-(2-trifluoromethyl-benzenesulfonyl)-pyrrolidine-2-carboxylic acid (1-cyano-cyclopropyl)-amide

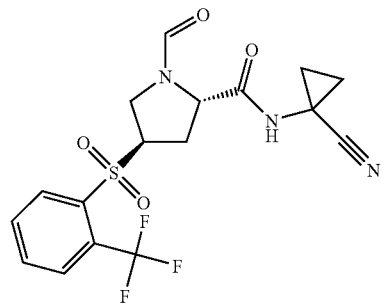

L48. (2S,4R)-4-(2-trifluoromethyl-benzenesulfonyl)-pyrrolidine-2-carboxylic acid (1-cyano-cyclopropyl)-amide hydrochloride from experiment K5 was coupled with p-nitrophenyl formate in analogy to experiment L27 to give (2S,4R)-1-formyl-4-(2-trifluoromethyl-benzenesulfonyl)-pyrrolidine-2-carboxylic acid (1-cyano-cyclopropyl)-amide as a colorless oil. MS: 416.2 [M+H]⁺.

Example 101

(2S,4R)-1-Acetyl-4-(2-trifluoromethyl-benzenesulfonyl)-pyrrolidine-2-carboxylic acid (1-cyano-cyclopropyl)-amide

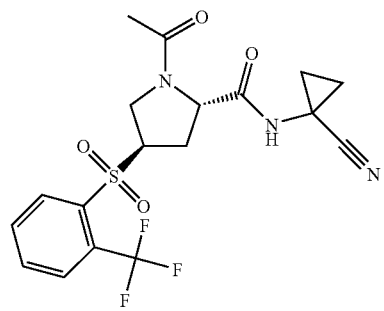

L49. (2S,4R)-4-(2-trifluoromethyl-benzenesulfonyl)-pyrrolidine-2-carboxylic acid (1-cyano-cyclopropyl)-amide hydrochloride from experiment K5 was acylated with acetic anhydride in analogy to experiment L29 to give (2S,4R)-1-

Example 102

(2S,4R)-1-(2,2,2-Trifluoro-acetyl)-4-(2-trifluoromethyl-benzenesulfonyl)-pyrrolidine-2-carboxylic acid (1-cyano-cyclopropyl)-amide

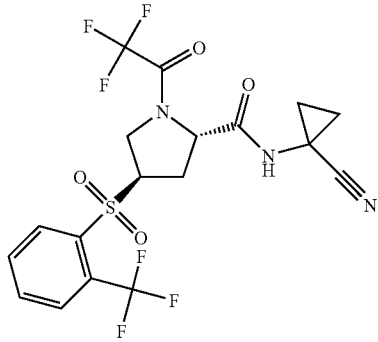

L50. (2S,4R)-4-(2-trifluoromethyl-benzenesulfonyl)-pyrrolidine-2-carboxylic acid (1-cyano-cyclopropyl)-amide hydrochloride from experiment K5 was acylated with trifluoroacetic anhydride in analogy to experiment L29 to give (2S,4R)-1-(2,2,2-trifluoro-acetyl)-4-(2-trifluoromethyl-benzenesulfonyl)-pyrrolidine-2-carboxylic acid (1-cyano-cyclopropyl)-amide as a pale yellow solid. MS: 484.1 [M+H]$^+$.

Example 103

(2S,4R)-1-Propionyl-4-(2-trifluoromethyl-benzenesulfonyl)-pyrrolidine-2-carboxylic acid (1-cyanocyclopropyl)-amide

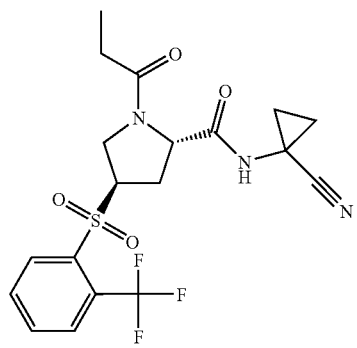

L51. (2S,4R)-4-(2-trifluoromethyl-benzenesulfonyl)-pyrrolidine-2-carboxylic acid (1-cyano-cyclopropyl)-amide hydrochloride from experiment K5 was acylated with propionic anhydride in analogy to experiment L29 to give (2S,4R)-1-propionyl-4-(2-trifluoromethyl-benzenesulfonyl)-pyrrolidine-2-carboxylic acid (1-cyano-cyclopropyl)-amide as a colorless oil. MS: 444.3 [M+H]$^+$.

Example 104

(2S,4R)-1-Cyclohexanecarbonyl-4-(2-trifluoromethyl-benzenesulfonyl)-pyrrolidine-2-carboxylic acid (1-cyano-cyclopropyl)-amide

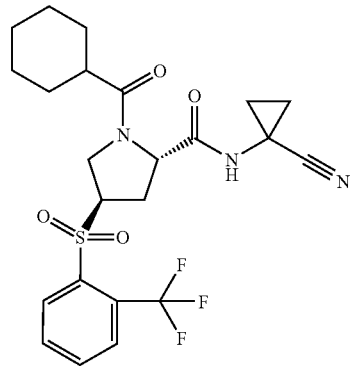

L52. (2S,4R)-4-(2-trifluoromethyl-benzenesulfonyl)-pyrrolidine-2-carboxylic acid (1-cyano-cyclopropyl)-amide hydrochloride from experiment K5 was coupled with cyclohexane carboxylic acid in analogy to experiment A1 to give (2S,4R)-1-cyclohexanecarbonyl-4-(2-trifluoromethyl-benzenesulfonyl)-pyrrolidine-2-carboxylic acid (1-cyano-cyclopropyl)-amide as an amorphous pale yellow solid. MS: 498.3 [M+H]$^+$.

Example 105

(2S,4R)-4-(2-Trifluoromethyl-benzenesulfonyl)-1-(4-trifluoromethyl-cyclohexanecarbonyl)-pyrrolidine-2-carboxylic acid (1-cyano-cyclopropyl)-amide

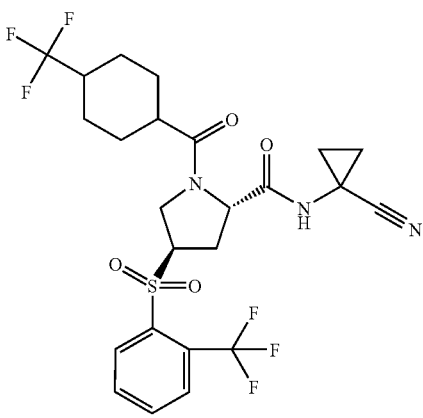

L53. (2S,4R)-4-(2-trifluoromethyl-benzenesulfonyl)-pyrrolidine-2-carboxylic acid (1-cyano-cyclopropyl)-amide hydrochloride from experiment K5 was coupled with 4-(trifluoromethyl)-cyclohexane carboxylic acid in analogy to experiment A1 to give (2S,4R)-4-(2-trifluoromethyl-benzenesulfonyl)-1-(4-trifluoromethyl-cyclohexanecarbonyl)-pyrrolidine-2-carboxylic acid (1-cyano-cyclopropyl)-amide as a pale yellow oil. MS: 566.3 [M+H]$^+$.

Example 106

(2S,4R)-1-(4-Fluoro-benzoyl)-4-(2-trifluoromethyl-benzenesulfonyl)-pyrrolidine-2-carboxylic Acid (1-cyano-cyclopropyl)-amide

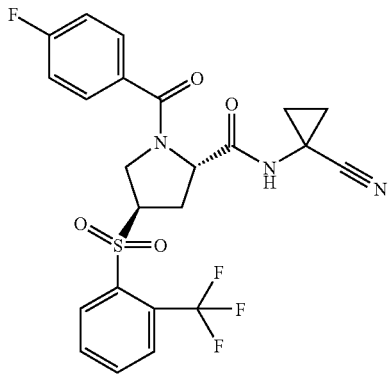

L54. (2S,4R)-4-(2-trifluoromethyl-benzenesulfonyl)-pyrrolidine-2-carboxylic acid (1-cyano-cyclopropyl)-amide hydrochloride from experiment K5 was coupled with 4-fluorobenzoic acid in analogy to experiment A1 to give (2S,4R)-1-(4-fluoro-benzoyl)-4-(2-trifluoromethyl-benzenesulfonyl)-pyrrolidine-2-carboxylic acid (1-cyano-cyclopropyl)-amide as a pale yellow solid. MS: 510.2 [M+H]⁺.

Example 107

(2S,4R)-1-Benzyl-4-(2-trifluoromethyl-benzenesulfonyl)-pyrrolidine-2-carboxylic acid (1-cyano-cyclopropyl)-amide

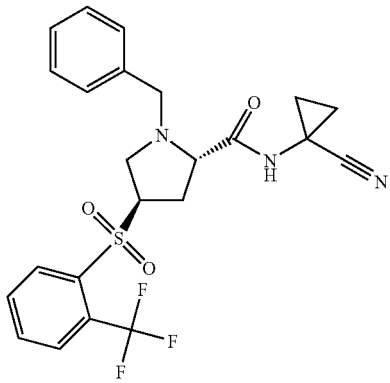

L55. (2S,4R)-4-(2-trifluoromethyl-benzenesulfonyl)-pyrrolidine-2-carboxylic acid (1-cyano-cyclopropyl)-amide hydrochloride from experiment K5 was reductively aminated with benzaldehyde in analogy to experiment L3 to give (2S,4R)-1-benzyl-4-(2-trifluoromethyl-benzenesulfonyl)-pyrrolidine-2-carboxylic acid (1-cyano-cyclopropyl)-amide as a colorless oil. MS: 478.1 [M+H]⁺.

Example 108

(2S,4R)-1-Pyridin-4-ylmethyl-4-(2-trifluoromethyl-benzenesulfonyl)-pyrrolidine-2-carboxylic Acid (1-cyano-cyclopropyl)-amide

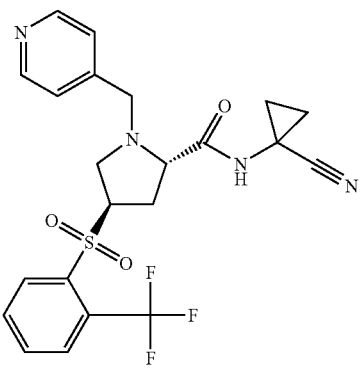

L56. (2S,4R)-4-(2-trifluoromethyl-benzenesulfonyl)-pyrrolidine-2-carboxylic acid (1-cyano-cyclopropyl)-amide hydrochloride from experiment K5 was reductively aminated with pyridine-4-carbaldehyde in analogy to experiment L3 to give (2S,4R)-1-pyridin-4-ylmethyl-4-(2-trifluoromethyl-benzenesulfonyl)-pyrrolidine-2-carboxylic acid (1-cyano-cyclopropyl)-amide as a colorless oil. MS: 479.1 [M+H]⁺.

Example 109

(2S,4R)-1-(2,2,3,3,3-Pentafluoro-propyl)-4-(2-trifluoromethyl-benzenesulfonyl)-pyrrolidine-2-carboxylic acid (1-cyano-cyclopropyl)-amide

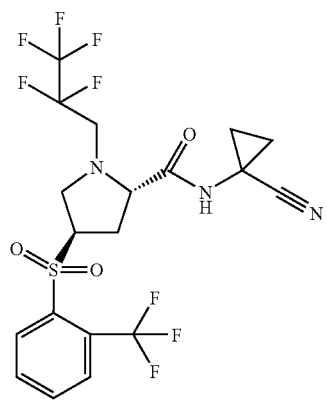

L57. (2S,4R)-4-(2-trifluoromethyl-benzenesulfonyl)-pyrrolidine-2-carboxylic acid (1-cyano-cyclopropyl)-amide hydrochloride from experiment K5 was reductively aminated with 2,2,3,3,3-pentafluoropropyltrifluoromethane sulfonate in analogy to experiment L3 to give (2S,4R)-1-(2,2,3,3,3-pentafluoro-propyl)-4-(2-trifluoromethyl-benzenesulfonyl)-pyrrolidine-2-carboxylic acid (1-cyano-cyclopropyl)-amide as a pale brown oil. MS: 520.1 [M+H]⁺.

Example 110

(2S,4R)-1-(2-Methoxy-ethyl)-4-(2-trifluoromethyl-benzenesulfonyl)-pyrrolidine-2-carboxylic Acid (1-cyano-cyclopropyl)-amide

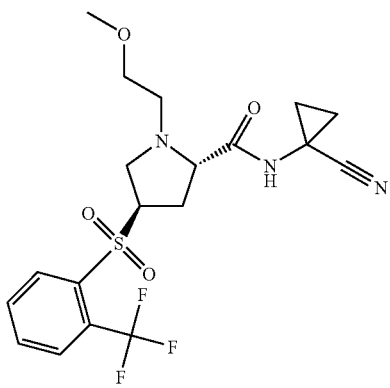

L58. (2S,4R)-4-(2-trifluoromethyl-benzenesulfonyl)-pyrrolidine-2-carboxylic acid (1-cyano-cyclopropyl)-amide hydrochloride from experiment K5 was reductively aminated with methoxy acetaldehyde in analogy to experiment L3 to give (2S,4R)-1-(2-methoxy-ethyl)-4-(2-trifluoromethyl-benzenesulfonyl)-pyrrolidine-2-carboxylic acid (1-cyano-cyclopropyl)-amide as a colorless oil. MS: 446.3 [M+H]$^+$.

Example 111

(2S,4R)-1-Acetyl-4-(4-pyrazol-1-yl-2-trifluoromethyl-benzenesulfonyl)-pyrrolidine-2-carboxylic acid (1-cyano-cyclopropyl)-amide

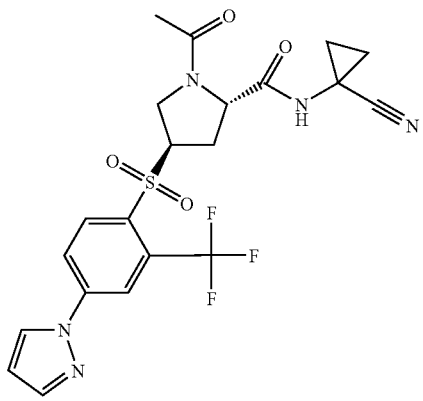

L59. (2S,4R)-4-(4-pyrazol-1-yl-2-trifluoromethyl-benzenesulfonyl)-pyrrolidine-2-carboxylic acid (1-cyano-cyclopropyl)-amide from experiment D9 was acylated with acetic anhydride in analogy to experiment L29 to give (2S,4R)-1-acetyl-4-(4-pyrazol-1-yl-2-trifluoromethyl-benzenesulfonyl)-pyrrolidine-2-carboxylic acid (1-cyano-cyclopropyl)-amide as a colorless solid. MS: 496.3 [M+H]$^+$.

Example 112

(2S,4R)-1-Acetyl-4-(4-imidazol-1-yl-2-trifluoromethyl-benzenesulfonyl)-pyrrolidine-2-carboxylic acid (1-cyano-cyclopropyl)-amide

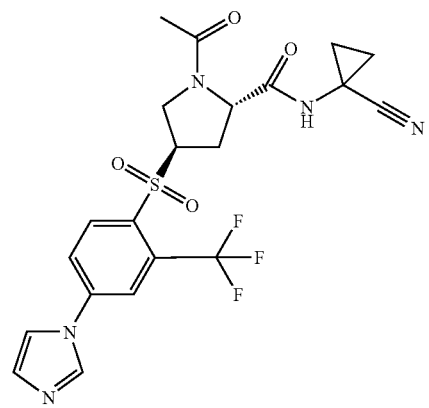

L60. (2S,4R)-4-(4-imidazol-1-yl-2-trifluoromethyl-benzenesulfonyl)-pyrrolidine-2-carboxylic acid (1-cyano-cyclopropyl)-amide hydrochloride from experiment D10 was acylated with acetic anhydride in analogy to experiment L29 to give (2S,4R)-1-acetyl-4-(4-imidazol-1-yl-2-trifluoromethyl-benzenesulfonyl)-pyrrolidine-2-carboxylic acid (1-cyano-cyclopropyl)-amide as a colorless solid. MS: 496.3 [M+H]$^+$.

Example 113

(2S,4R)-2-(1-Cyano-cyclopropylcarbamoyl)-4-(2-methyl-propane-1-sulfonyl)-pyrrolidine-1-carboxylic acid tert-butyl ester

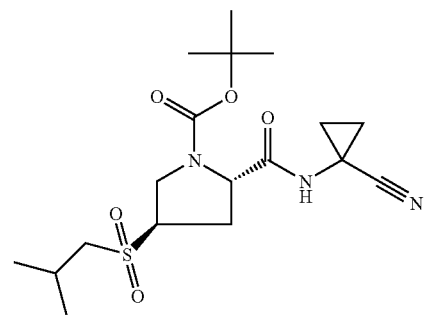

L61. (2S,4S)-2-(1-cyano-cyclopropylcarbamoyl)-4-methanesulfonyloxy-pyrrolidine-1-carboxylic acid t-butyl ester from experiment A2 was reacted with 2-methyl-1-propanethiole according to general procedure B to give (2S,4R)-2-(1-cyano-cyclopropylcarbamoyl)-4-isobutylsulfanyl-pyrrolidine-1-carboxylic acid tert-butyl ester as a white solid. MS: 366.3 [M−H]$^-$. The intermediate thioether was oxidized with m-chloroperbenzoic acid according to general procedure C to give (2S,4R)-2-(1-cyano-cyclopropylcarbamoyl)-

4-(2-methyl-propane-1-sulfonyl)-pyrrolidine-1-carboxylic acid tert-butyl ester as a white foam. MS: 400.2 [M+H]$^+$.

Example 114

(2S,4R)-4-(2-Methyl-propane-1-sulfonyl)-pyrrolidine-2-carboxylic acid (1-cyano-cyclopropyl)-amide Hydrochloride

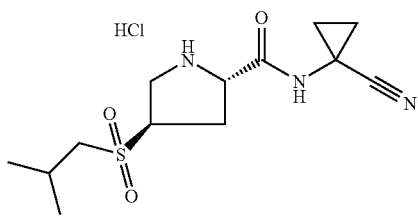

L62. (2S,4R)-2-(1-cyano-cyclopropylcarbamoyl)-4-(2-methyl-propane-1-sulfonyl)-pyrrolidine-1-carboxylic acid tert-butyl ester from experiment L61 was deprotected according to general procedure D to give (2S,4R)-4-(2-methyl-propane-1-sulfonyl)-pyrrolidine-2-carboxylic acid (1-cyano-cyclopropyl)-amide hydrochloride as a pale yellow solid. MS: 300.0 [M+H]$^+$.

Example 115

6-Benzenesulfonyl-2,2-difluoro-tetrahydro-pyrrolizine-7a-carboxylic acid cyanomethyl-amide

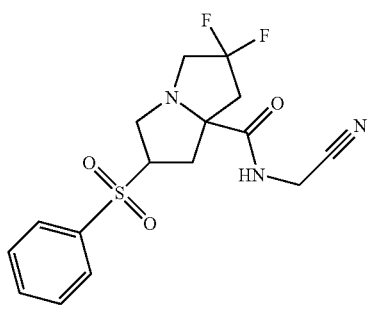

a) Isomeric Mixture of 6-benzenesulfonyl-2,2-difluoro-tetrahydro-pyrrolizine-7a-carboxylic Acid Benzyl Ester (115a1) and 1-benzenesulfonyl-6,6-difluoro-tetrahydro-pyrrolizine-7a-carboxylic acid Benzyl Ester (115a2)

(R)-4,4-Difluoro-pyrrolidine-2-carboxylic acid benzyl ester hydrochloride (500 mg) is suspended in THF (5 mL) and DIEA (1.8 mL) is added. To the resulting solution aqueous formaldehyde solution (36.5% w/w) is added and the solution is stirred for 15 min at 25° C. After that TFA (20.5 mg) is added and a solution of phenylvinylsulfone (303 mg) in THF (5 mL) is added to the reaction mixture. The reaction mixture is stirred for 18 h at 25° C. After that according to LC-MS analysis product is formed (m/z=422.1 [M+H]$^{++}$). For further completion the reaction mixture is heated for 2 h at 60° C. After that the mixture is cooled to 25° C., evaporated to dryness, dissolved in AcOEt and washed with aq. NH$_4$Cl solution, Na$_2$CO$_3$ solution and brine. The organic layer was dried over Na$_2$SO$_4$, filtrated and evaporated to dryness. The resulting oil is purified by flash chromatography using a silica gel column (20 g) and a gradient n-heptane:AcOEt (100:0)->n-heptane:AcOEt (50:50) within 1 hour. Two isomers could be isolated each with approx. 32 mg (4%) as an off-white solid. MS (ESI): m/z=422.1 [M+H]$^+$.

b) 6-Benzenesulfonyl-2,2-difluoro-tetrahydro-pyrrolizine-7a-carboxylic acid cyanomethyl-amide Example 115(a1) (30 mg) is dissolved in THF (2 mL) and aq. NaOH (2N, 107 µL) is added to the solution. The mixture is stirred for 18 h at 25° C. LC-MS analysis indicated complete conversion of the ester to the corresponding acid. After that the solution is evaporated to dryness by using toluene to remove water to completeness. The solid remaining material is suspended in acetonitrile (2 mL) and EDCI (27 mg), HOBT (19 mg) and DIEA (50 L; 2 eq) is added. The mixture is stirred for 1 h at 25° C. Aminoacetonitrile hydrochloride (13 mg) is suspended in ACN (2 mL) and DIEA (50 µL; 2 eq) is added. The resulting solution is added to the activated acid. The reaction mixture is stirred for 3 days at 25° C. The reaction mixture is evaporated to dryness and dissolved in DMSO (1 mL) and purified with prep. HPLC to yield the title compound as a light brown foam (12 mg; 45%). MS (ESI): m/z=370.4 [M+H]$^+$.

Example 116

1-Benzenesulfonyl-6,6-difluoro-tetrahydro-pyrrolizine-7a-carboxylic acid cyanomethyl-amide, diasteromer Δ1

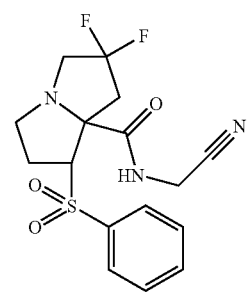

Example 115(a2) (30 mg) is dissolved in THF (2 mL) and aq. NaOH (2N, 107 µL) is added to the solution. The mixture is stirred for 18 h at 25° C. LC-MS analysis indicated complete conversion of the ester to the corresponding acid. After that the solution is evaporated to dryness by using toluene to remove water to completeness. The solid remaining material is suspended in acetonitrile (2 mL) and EDCI (27 mg), HOBT (19 mg) and DIEA (50 µL; 2 eq) is added. The mixture is stirred for 1 h at 25° C. Aminoacetonitrile hydrochloride (13 mg) is suspended in ACN (2 mL) and DIEA (50 µL; 2 eq) is added. The resulting solution is added to the activated acid. The reaction mixture is stirred for 3 days at 25° C. The reaction mixture is evaporated to dryness and dissolved in DMSO (1 mL) and purified with prep. HPLC to yield the title compound as a light yellow foam (12 mg; 45%). MS (ESI): m/z=370.4 [M+H]+.

Example 117

1-Benzenesulfonyl-6,6-difluoro-tetrahydro-pyrrolizine-7a-carboxylic acid cyanomethyl-amide, diastereomer Δ2

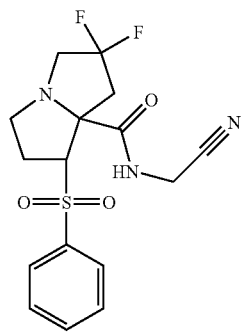

The title compound is obtained as an isomer during the synthesis of example 116 to yield a light yellow foam (4.6 mg; 16%). MS (ESI): m/z=370.4 [M+H]+.

Example 118

4-[(2S,4R)-2-(1-Cyano-cyclopropylcarbamoyl)-4-(2-trifluoromethyl-benzenesulfonyl)-pyrrolidine-1-carbonyl]-benzoic acid methyl ester

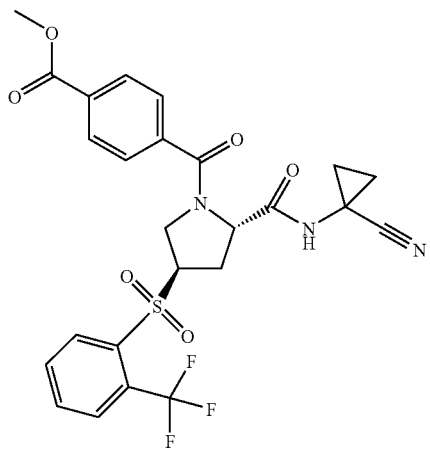

The title compound was prepared in analogy to example 106, using methyl 4-chlorocarbonylbenzoate, triethylamine and dimethylaminopyridine. MS (ESI): m/z=550.2 [M+H]+.

Example 119

(2S,4R)-1-Phenyl-4-(2-trifluoromethyl-benzenesulfonyl)-pyrrolidine-2-carboxylic acid (1-cyano-cyclopropyl)-amide

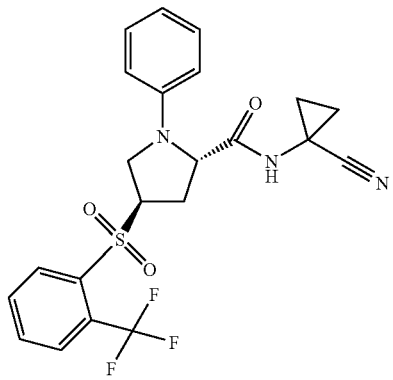

The title compound was obtained in analogy to example 151 (see scheme AB), using 1-aminocyclopropyl cyanic hydrochloride instead of 2-aminoacetonitrile hydrochloride in step c. MS (ESI): m/z=464.1 [M+H]+.

Example 120

(2S,4R)-4-(2-Chloro-4-pyrazol-1-yl-benzenesulfonyl)-2-(1-cyano-cyclopropylcarbamoyl)-pyrrolidine-1-carboxylic acid tert-butyl ester

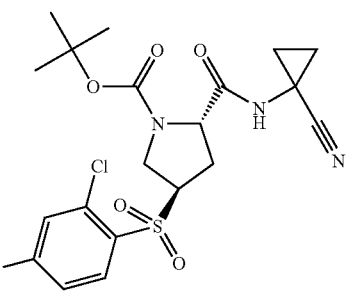

a) (2S,4S)-4-(3-Nitro-benzenesulfonyloxy)-pyrrolidine-1,2-dicarboxylic acid 1-tert.-butyl ester 2-methyl ester N-Boc-cis-4-hydroxy proline methyl ester (1.0 eq, 6.0 g) were dissolved in MeCl₂ (60.0 ml) and 3-nitrobenzenesulfonyl chloride (1.06 eq; 5.747 g) was added. This clear colorless solution was cooled to 0-5° C. and the Et₃N (3.0 eq., 10.19 ml) was carefully added. After 0.5 h a yellowish thin suspension was formed, which was stirred for 18 h at ambient temperature. The mixture turned then into a light brown suspension. LC-MS-analysis revealed that the reaction was complete. The reaction mixture was diluted with additional MeCl$_2$ (100 ml) and extracted in succession with aq. 0.5 N HCl, 10% Na$_2$CO$_3$. The combined org. layers were washed with brine, dried over Na$_2$SO$_4$, filtered and evaporated to dryness to yield a light brown viscous oil (10.8 g; 102%). MS (ESI): m/z=331.2 [M+H-Boc]$^+$ b) (2S,4R)-4-(2-Chloro-4-fluoro-phenylsulfanyl)-pyrrolidine-1,2-dicarboxylic acid 1-tert.-butyl ester 2-methyl ester Example 120a (10.8 g) was dissolved in propionitrile (10.0 ml), 2-chloro-4-fluorothiophenole (4.35 g) and TEA (10.43 ml) were added to the light brown solution. The reaction mixture was stirred at 110° C. for 18 h. LC/MS analysis showed complete conversion. After that the reaction mixture was diluted with AcOEt (250 ml), extracted in succession with aq. 10% Na$_2$CO$_3$-Sln, then the waterlayer was washed 3 times with AcOEt, the combined org layers were washed with sat. NaCl, dried over Na$_2$SO$_4$, filtered and evaporated, subsequently purified over silica with AcOEt:n-Heptan to yield the title compound as a colorless gum (8.8 g; 88%). MS (ESI): m/z=390.1 [M+H]$^+$.

c) (2S,4R)-4-(2-Chloro-4-fluoro-benzenesulfonyl)-pyrrolidine-1,2-dicarboxylic acid 1-tert.-butyl ester 2-methyl ester Example 120b (8.5 g) was dissolved in MeCl$_2$ (50.0 ml) at ambient temperature, after that 3-chloroperbenzoic acid (9.4 g, 2.5 eq) was added to the light yellow solution, which turned into a white suspension after 1 h. The reaction mixture was stirred for 18 h at ambient temperature. The reaction mixture was diluted with MeCl$_2$ (150 ml) and extracted twice with aq. 10% Na$_2$CO$_3$-solution (100 ml), washed with saturated NaCl, dried over Na$_2$SO$_4$, filtered and evaporated to dryness to yield the title compound as colorless gum (9.05 g; 98%). MS (ESI): m/z=322.2 [M+H-Boc]$^+$.

d) (2S,4R)-4-(2-Chloro-4-pyrazol-1-yl-benzene-sulfonyl)-pyrrolidine-1,2-dicarboxylic acid 1-tert.-butyl ester 2-methyl ester Example 120c (0.6 g) was dissolved in DMA (10.0 ml) at ambient temperature. To this solution pyrazole (0.116 g; 1.2 eq.) and Cs$_2$CO$_3$ (0.463 g; 1.2 eq.) were added. The reaction mixture was stirred in a microwave oven at 140° C. for 30 min. After that, the reaction mixture was cooled to room temperature and the reaction mixture was evaporated to dryness under reduced pressure. The remaining solid was suspended in CH$_2$Cl$_2$ (50 ml), extracted in succession with aq. 0.5 N HCl$_3$-solution (30 ml) and brine. The water layer was washed twice with CH$_2$Cl$_2$ (100 ml), combined org layers were washed with brine and dried over Na$_2$SO$_4$, filtered and evaporated to dryness. After that the crude product was purified over silicagel with n-hetpan: AcOEt to yield the title compound as a colorless foam (0.48 g; 72%). MS (ESI): m/z=370.1 [M+H-Boc]$^+$.

e) Lithium-(2S,4R)-1-tert-butoxycarbonyl-4-(2-chloro-4-pyrazol-1-yl-benzenesulfonyl)-pyrrolidine-2-carboxylate To a colorless solution of example 120d (0.480 g) in THF (2.0 ml) was added at ambient temperature under inert atmosphere a solution of Lithium hydroxide (0.051 g; 1.2 eq.) in H2O (3 ml). The solution was stirred at ambient temperature for 18 h. over night. After that additional lithium hydroxide (0.5 eq. +0.2 eq.) was given to the above solution and stirred for 5 h at ambient temperature. The reaction mixture was then evaporated to dryness to yield the title compound as a white solid (0.49 g; 103%). The crude product was used without further purification. MS (ESI): m/z=456.2 [M–H—Li]$^-$.

f) (2S,4R)-4-(2-Chloro-4-pyrazol-1-yl-benzenesulfonyl)-2-(1-cyano-cyclopropylcarbamoyl)-pyrrolidine-1-carboxylic acid tert.-butyl ester Example 120e (480 mg) was suspended in DMF (5 mL). HATU (3.0 eq), DIEA (3.0 eq) and 1-amino-1-cyclopropanole carbonitrile hydrochloride (1.5 eq) were added to the suspension. After addition of HATU a dark yellow suspension was formed. The reaction mixture was stirred for 18 h at ambient temperature. The reaction mixture was evaporated to dryness and subsequently purified over silica gel with n-heptan: AcOEt to yield the title compound as a colorless foam (536 mg; 99%). MS (ESI): m/z=520.3 [M+H]

Example 121

(2S,4R)-4-(2-Chloro-4-piperidin-1-yl-benzenesulfonyl)-2-(1-cyano-cyclopropylcarbamoyl)-pyrrolidine-1-carboxylic acid tert.-butyl ester

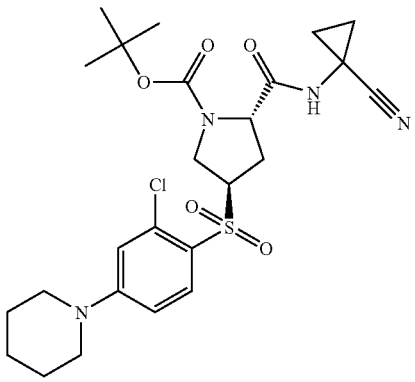

a) (2S,4R)-4-(2-Chloro-4-piperidin-1-yl-benzene-sulfonyl)-pyrrolidine-1,2-dicarboxylic Acid 1-tert.-butyl ester 2-methyl ester Example 120c (500 mg) was dissolved in DMA (10.0 ml) at ambient temperature. To this solution, piperidine (97 mg; 1.2 eq) and Cs$_2$CO$_3$ (371 mg; 1.2 eq) were added. The reaction mixture was stirred in the microwave oven at 140° C. for 30 min. The reaction mixture was cooled to ambient temperature. After that the reaction mixture was evaporated to dryness, dissolved in CH$_2$Cl$_2$ (50 ml), extracted in succession with aq. 0.5 N HCl-solution (30 ml) and brine. The water layer was washed twice with CH$_2$Cl$_2$ (100 ml), the organic layers were washed with brine, the combined organic layer was dried over Na$_2$SO$_4$, filtered and evaporated to dryness. The obtained crude product was purified over silicagel with n-hetpan: AcOEt to yield the title compound as colorless foam (453 mg; 78%). MS (ESI): m/z=487.4 [M+H]$^+$.

b) Lithium-(2S,4R)-1-tert.-butoxycarbonyl-4-(2-chloro-4-piperidin-1-yl-benzenesulfonyl)-pyrrolidine-2-carboxylate Example 121b was prepared from example 99a (450 mg) according to the method described for example 98e to yield the title compound as a white solid (460 mg; 104%). MS (ESI): m/z=402.2 [M−H−Boc-Li]⁻.

c) (2S,4R)-4-(2-Chloro-4-piperidin-1-yl-benzenesulfonyl)-2-(1-cyano-cyclopropylcarbamoyl)-pyrrolidine-1-carboxylic acid tert.-butyl ester Example 121 was prepared form example 121b (460 mg) according to the method described for example 98f to yield the final compound as a colorless foam (510 mg; 98%). MS (ESI): m/z=537.3 [M+H]⁺.

Example 122

(2S,4R)-4-[2-Chloro-4-(2,2,2-trifluoro-1-methyl-ethoxy)-benzenesulfonyl]-2-(1-cyano-cyclopropyl-carbamoyl)-pyrrolidine-1-carboxylic acid tert.-butyl ester

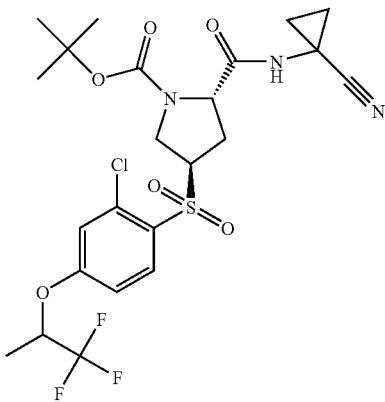

a) (2S,4R)-4-[2-Chloro-4-(2,2,2-trifluoro-1-methyl-ethoxy)-benzenesulfonyl]-pyrrolidine-1,2-dicarboxylic acid 1-tert-butyl ester 2-methyl ester Example 122a was prepared from example 120c (500 mg) in analogy to the methods described for example 121a using 1,1,1-trifluorisopropanol instead of piperidine to yield the title compound as a colorless foam (433 mg; 71%). MS (ESI): m/z=516.4 [M+H]⁺.

b) Lithium-(2S,4R)-1-tert-butoxycarbonyl-4-[2-chloro-4-(2,2,2-trifluoro-1-methyl-ethoxy)-benzenesulfonyl]-pyrrolidine-2-carboxylate Example 122b was prepared from example 100a (430 mg) according to the method described for example 120e to yield the title compound as a white solid (435 mg; 103%). MS (ESI): m/z=402.2 [M−H−Boc-Li].

c) (2S,4R)-4-[2-Chloro-4-(2,2,2-trifluoro-1-methyl-ethoxy)-benzenesulfonyl]-2-(1-cyano-cyclopropyl-carbamoyl)-pyrrolidine-1-carboxylic acid tert.-butyl ester Example 122 was prepared form example 100b (435 mg) according to the method described for example 120f to yield the final compound as a colorless foam (327 mg; 67%). MS (ESI): m/z=566.3 [M+H]⁺.

Example 123

(2R,4S,5R)-5-(4-Fluoro-phenyl)-2-isobutyl-4-methanesulfonyl-pyrrolidine-2-carboxylic acid (1-cyano-cyclopropyl)-amide

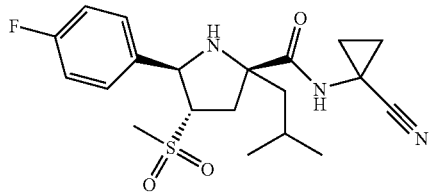

a) (S)-2-{[1-(4-Fluoro-phenyl)-meth-(E)-ylidene]-amino}-4-methyl-pentanoic acid methyl ester L-Leucine methyl ester hydrochloride (3.65 g) was dissolved in methanol (35 mL) and 4-fluoro-benzaldehyde (2.65 mL) and Na₂CO₃ (4.0 g) were added. The mixture was stirred at ambient temperature for 3 days. After that, the mixture was filtrated, evaporated to dryness. The residue was dissolved in TBME. The precipitate was filtrated off. The TBME solution was evaporated to dryness to yield the title compound as a colorless oil (4.66 g; 92%). MS (ESI): m/z=252.3 [M+H]⁺.

b) (2R,4S,5R)-5-(4-Fluoro-phenyl)-2-isobutyl-4-methanesulfonyl-pyrrolidine-2-carboxylic acid methyl ester Taniaphos (CAS 255884-98-1; 61 mg) and copper(I)acetate (10 mg) were dissolved in THF (2 mL) at ambient temperature and stirred for 30 min. A solution of example 101a (390 mg) and TEA (20 µL) in THF (4 mL) was added. The reaction mixture was cooled to 0° C. and methylvinylsulfone (165 mg) dissolved in THF (2 mL) was added. The resulting mixture was stirred at ambient temperature for six days. After that the mixture was filtrated over dicalite and evaporated to dryness. The resulting solid material is purified by flash chromatography (n-heptane: ethyl acetate) to yield the title compound as a light yellow oil (361 mg; 65%). MS (ESI): m/z=358.2 [M+H]⁺.

c) (2R,4S,5R)-5-(4-Fluoro-phenyl)-2-isobutyl-4-methanesulfonyl-pyrrolidine-1,2-dicarboxylic acid 1-tert-butyl ester 2-methyl ester Example 123b (472 mg) was dissolved in acetonitrile (5 mL). Di-tert.-butyl-dicarbonate (365 mg) and K₂CO₃ (432 mg) were added to the solution. The reaction mixture was stirred at ambient temperature for 24 h. After that additional di-tert.-butyl-dicarbonate (1.5 eq) was added and the mixture was again stirred for 24 h at ambient temperature. After overall 68 h reaction time LC-MS analysis revealed complete conversion to the title compound. The reaction mixture was evaporated to dryness and purified by flash chromatography (n-heptane: ethyl acetate). Most of the material degraded again to the starting material which was used without further purification. MS (ESI): m/z=458.2 [M+H]⁺.

d) Lithium (2R,4S,5R)-5-(4-fluoro-phenyl)-2-isobutyl-4-methanesulfonyl-pyrrolidine-2-carboxylate The mixture obtained from example 123c (120 mg) was dissolved in THF/water (4 ml/0.4 ml), after that LiOH hydrate (17 mg; 1.2 eq) was added to the solution. The mixture was stirred for 23 h at ambient temperature. Additional LiOH hydrate (0.2 eq) was added to the mixture. After 3 h additional LiOH hydrate (0.2 eq) was added to the mixture to drive the reaction to completeness. After stirring for 1 h at ambient temperature the mixture was evaporated to dryness to yield a yellow solid (145 mg, 123%) which was used without further purification. MS (ESI): m/z=342.4 [M−H]−.

e) (2R,4S,5R)-5-(4-Fluoro-phenyl)-2-isobutyl-4-methanesulfonyl-pyrrolidine-2-carboxylic acid (1-cyano-cyclopropyl)-amide Example 123d (145 mg) was dissolved in DMF (2 mL). Cyclopropylaminoacetonitrile hydrochloride (150 mg), DIEA (180 μL) and HATU (561 mg) were added subsequently to the mixture. The reaction mixture was stirred for 18 h at ambient temperature. After that the mixture was purified by preparative HPLC to yield the title compound as a light yellow solid (45 mg; 26%). MS (ESI): m/z=408.5 [M+H]+.

Example 124

(2S,4R)-4-(2-Chloro-4-fluoro-benzenesulfonyl)-2-(1-cyano-cyclopropylcarbamoyl)-pyrrolidine-1-carboxylic acid tert.-butyl ester

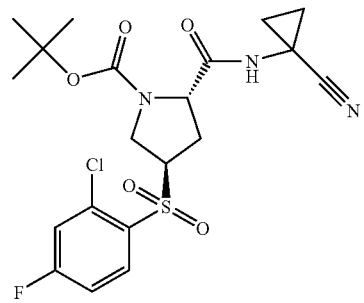

The title compound was prepared from example 120c using the methods described for examples 120e and 120f to yield example 124 as a colorless solid. MS (ESI): m/z=472.3 [M+H]+.

Example 125

(2R,4S,5R)-2-(1-Cyano-cyclopropylcarbamoyl)-5-(4-fluoro-phenyl)-2-isobutyl-4-methanesulfonyl-pyrrolidine-1-carboxylic acid tert.-butyl ester

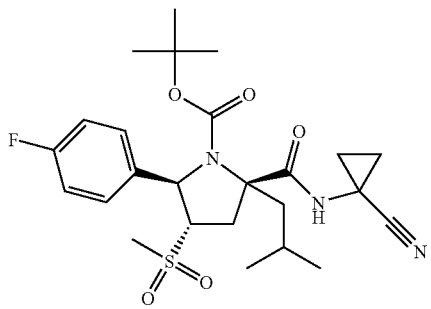

The title compound was obtained as a by-product during the synthesis of example 123. MS (ESI): m/z=508.5 [M+H]+.

Example 126

(2R,4S,5R)-4-Benzenesulfonyl-5-(4-fluoro-phenyl)-2-isobutyl-pyrrolidine-2-carboxylic acid (1-cyano-cyclopropyl)-amide

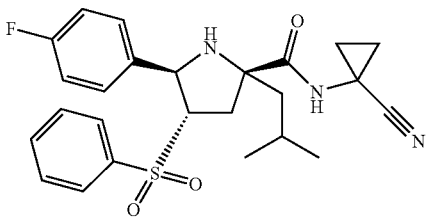

The title compound was prepared in analogy to example 123 using phenylvinyl sulfone instead of methylvinyl sulfone in step 123b to yield the title compound as a viscous yellow oil (36 mg, 24%). MS (ESI): m/z=470.3 [M+H]+.

Example 127

(2S,4R)-4-(2-Chloro-4-piperidin-1-yl-benzenesulfonyl)-pyrrolidine-2-carboxylic acid (1-cyano-cyclopropyl)-amide

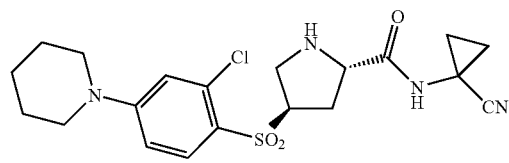

Example 121 (480 mg) was dissolved in formic acid (10 ml) and stirred at room temperature for 3.5 h. The reaction mixture was then evaporated to half of the volume, then diluted with AcOEt (30 ml) and extracted with aq. 10% Na2CO3-solution (40 ml). The water phase was washed with AcOEt (30 ml), the combined organic layers were washed with brine, dried over Na2SO4, filtered and evaporated to dryness to yield the title compound as colorless amorphous material (231 mg; 59%). MS (ESI): m/z=437.3 [M+H]+.

Example 128

(2S,4R)-4-(2-Chloro-4-pyrazol-1-yl-benzenesulfonyl)-pyrrolidine-2-carboxylic acid (1-cyano-cyclopropyl)-amide

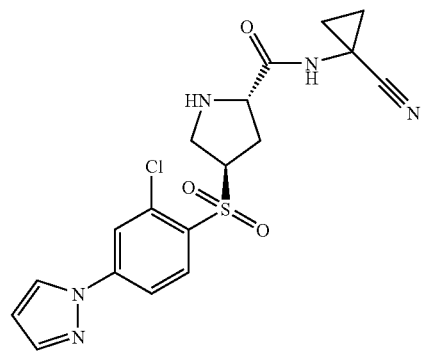

Example 129

(2S,4R)-4-[2-Chloro-4-(2,2,2-trifluoro-1-methyl-ethoxy)-benzenesulfonyl]-pyrrolidine-2-carboxylic acid (1-cyano-cyclopropyl)-amide

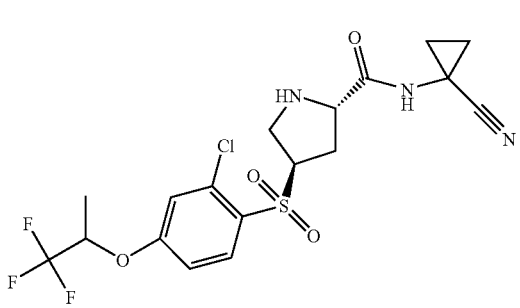

The title compound was prepared according to the methods described for example 127 starting from example 122 (310 mg) to yield an amorphous colorless solid (220 mg; 86%) MS (ESI): m/z=466.2 [M+H]⁺.

Example 130

(2S,4R)-4-[2-Chloro-4-(3,3-difluoro-pyrrolidin-1-yl)-benzenesulfonyl]-2-(1-cyano-cyclopropylcarbamoyl)-pyrrolidine-1-carboxylic acid tert.-butyl ester

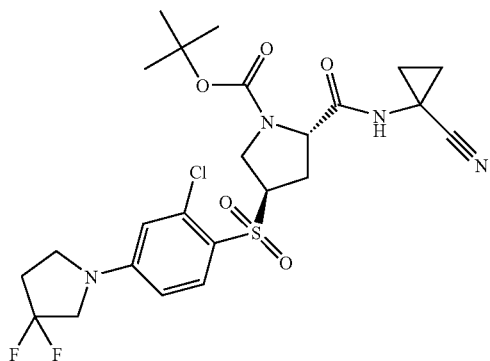

Example 124 (100 mg) was dissolved in 2.0 ml DMA at rt. To this solution 3,3-difluoro-pyrrolidine HCl salt (1.2 eq.; 0.037 g) and Cs₂CO₃ (2.4 eq.; 0.166 g) were added. The reaction mixture was stirred in the microwave oven at 140° C. for 2×30 min (until complete conversion of example 124). The reaction mixture was diluted with CH₂Cl₂ (20 mL) and extracted with water, 0.1 N aqueous HCl solution and brine. The organic layer was evaporated to dryness to yield a concentrated DMA solution. The solution was diluted to 2.5 mL DMA solution and directly purified with preparative HPLC.

MS (ESI): m/z=559.2 [M+H]⁺ Cl-Isotopes; 503.2 [M+H-tBu]⁺ Cl-Isotopes; 459.3 [M+H-Boc]⁺ Cl-Isotopes.

Example 131

(2S,4R)-1-Acetyl-4-(2-chloro-4-pyrazol-1-yl-benzenesulfonyl)-pyrrolidine-2-carboxylic acid (1-cyano-cyclopropyl)-amide formiate

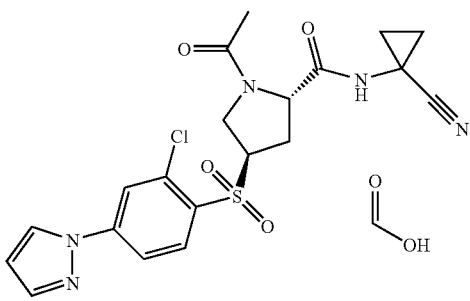

Example 128 (90 mg) were dissolved in CH₂Cl₂ (2 ml), Et₃N (2.0 eq, 43 mg) and acetyl chloride (1.3 eq; 22 mg) were added to the solution and stirred over night at ambient temperature. The solvent was evaporated to dryness, the remaining solid material was dissolved in DMF and purified with prep HPLC to yield the title compound as amorphous colorless solid as formic acid salt (61 mg; 61%). MS (ESI): m/z=462.3 [M+H]⁺.

Example 132

(2S,4R)-1-Acetyl-4-[2-chloro-4-(2,2,2-trifluoro-1-methyl-ethoxy)-benzenesulfonyl]-pyrrolidine-2-carboxylic acid (1-cyano-cyclopropyl)-amide

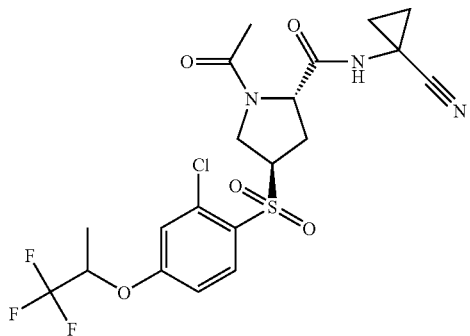

The title compound was prepared in analogy to example 131 using example 129 (90 mg) as starting material to yield 56 mg (57%) of an amorphous colorless solid. MS (ESI): m/z=508.2 [M+H]⁺.

Example 133

(2S,4R)-1-Acetyl-4-(2-chloro-4-piperidin-1-yl-benzenesulfonyl)-pyrrolidine-2-carboxylic acid (1-cyano-cyclopropyl)-amide formiate

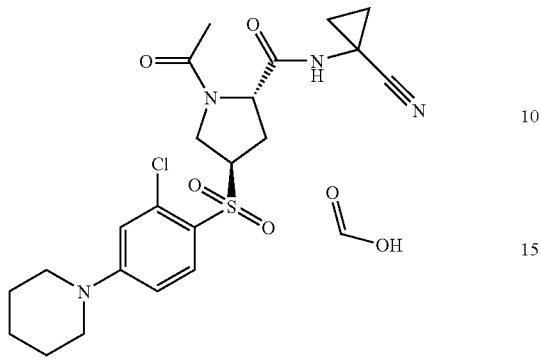

The title compound was prepared in analogy to example 131 using example 127 (100 mg) as starting material to yield 82 mg (75%) of an amorphous colorless solid. MS (ESI): m/z=479.1 [M+H]$^+$.

Example 134

(2S,4R)-1-Acetyl-4-(2-chloro-4-fluoro-benzenesulfonyl)-pyrrolidine-2-carboxylic acid (1-cyano-cyclopropyl)-amide

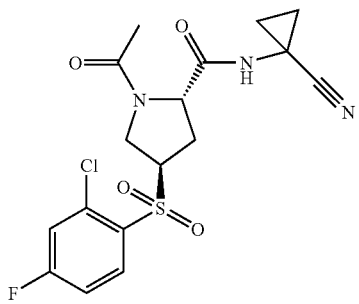

The title compound was prepared in analogy to example 131 using example 144 (30 mg) as starting material to yield 19 mg (57%) of an amorphous colorless solid. MS (ESI): m/z=414.2 [M+H]$^+$.

Example 135

(2S,4R)-4-(2-Chloro-4-piperidin-1-yl-benzenesulfonyl)-1-(1-trifluoromethyl-cyclopropanecarbonyl)-pyrrolidine-2-carboxylic acid (1-cyano-cyclopropyl)-amide

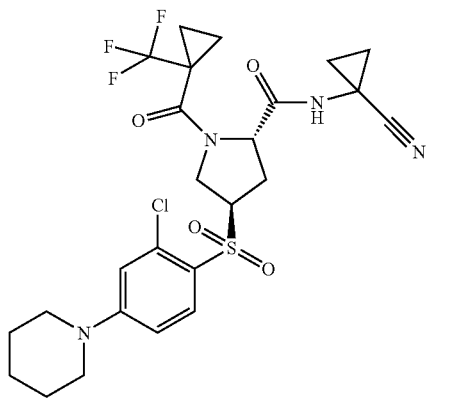

Example 127 (70 mg) was dissolved in DMF (2 ml). To this solution HATU (122 mg), DIEA (41 mg) and 1-(trifluoromethyl)-cyclopropane-1-carboxylic acid (30 mg) were added and stirred for 18 h at ambient temperature. The reaction mixture was purified by prep. HPLC to yield the title compound as an amorphous colorless solid (42 mg; 46%). MS (ESI): m/z=573.3 [M+H]$^+$.

Example 136

(2S,4R)-4-[2-Chloro-4-(3,3-difluoro-pyrrolidin-1-yl)-benzenesulfonyl]-pyrrolidine-2-carboxylic acid (1-cyano-cyclopropyl)-amide formiate

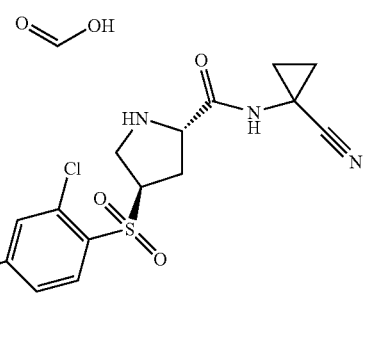

The title compound was prepared in analogy to example 127 using example 130 (18 mg) as starting material to yield 16 mg (96%) of an amorphous colorless solid. MS (ESI): m/z=459.3 [M+H]$^+$.

Example 137

4-[(2S,4R)-2-(Cyanomethyl-carbamoyl)-4-(2-trifluoromethyl-benzenesulfonyl)-pyrrolidine-1-carbonyl]-benzoic acid methyl ester

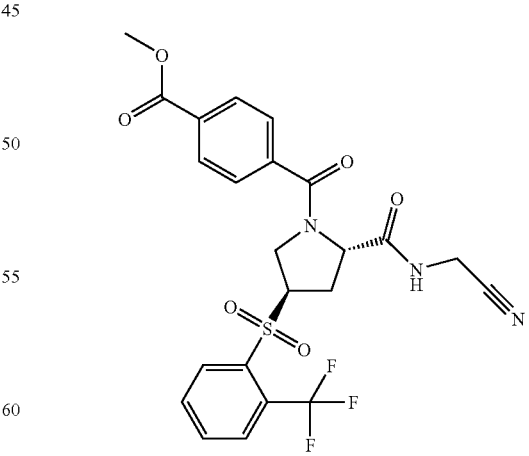

The title compound was prepared in analogy to example 118, using methyl 4-chlorocarbonylbenzoate, triethylamine and dimethylaminopyridine in the last step. MS (ESI): m/z=524.3 [M+H]$^+$.

Example 138

(2S,4R)-4-[2-Chloro-4-(4-ethyl-piperazin-1-yl)-benzenesulfonyl]-2-(1-cyano-cyclopropylcarbamoyl)-pyrrolidine-1-carboxylic acid tert.-butyl ester

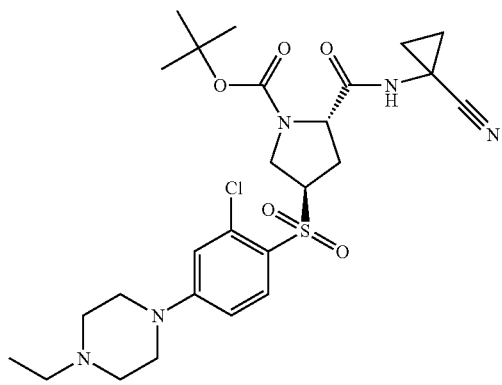

The title compound was prepared in analogy to example 130 using example 124 (100 mg) and N-ethylpiperazine (29 mg) as starting materials to yield 54 mg (45%) of an amorphous colorless solid. MS (ESI): m/z=566.4 [M+H]$^+$.

Example 139

(2S,4R)-4-[2-Chloro-4-(2-piperidin-1-yl-ethoxy)-benzenesulfonyl]-2-(1-cyano-cyclopropylcarbamoyl)-pyrrolidine-1-carboxylic acid tert.-butyl ester

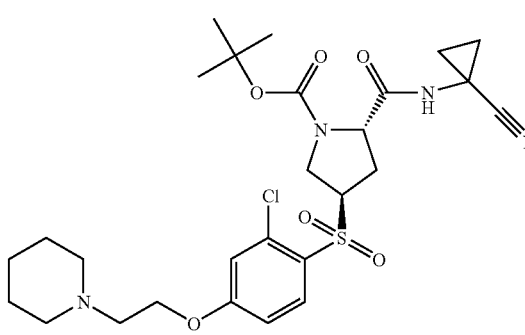

The title compound was prepared in analogy to example 130 using example 124 (100 mg) and 1-(2-hydroxyethyl) piperidine (33 mg) as starting materials to yield 0.5 mg (0.2%) of light brown gum. MS (ESI): m/z=581.4 [M+H]$^+$.

Example 140

(2S,4R)-4-[2-Chloro-4-(4-ethyl-piperazin-1-yl)-benzenesulfonyl]-pyrrolidine-2-carboxylic acid (1-cyano-cyclopropyl)-amide formiate

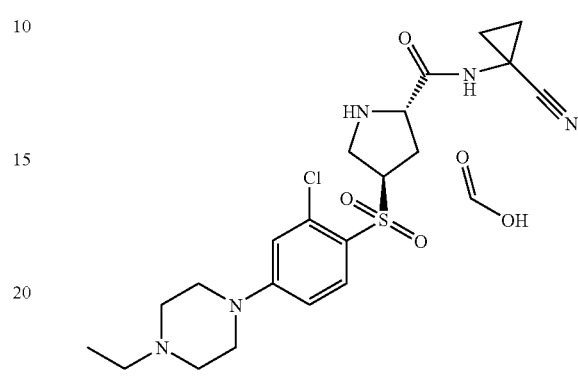

The title compound was prepared in analogy to example 127 using example 138 (52 mg) as starting material to yield 47 mg (99%) of a yellow gum. MS (ESI): m/z=466.2 [M+H]$^+$.

Example 141

(2S,4R)-4-[2-Chloro-4-(4-ethyl-piperazin-1-yl)-benzenesulfonyl]-1-(1-trifluoromethyl-cyclopropanecarbonyl)-pyrrolidine-2-carboxylic acid (1-cyano-cyclopropyl)-amide

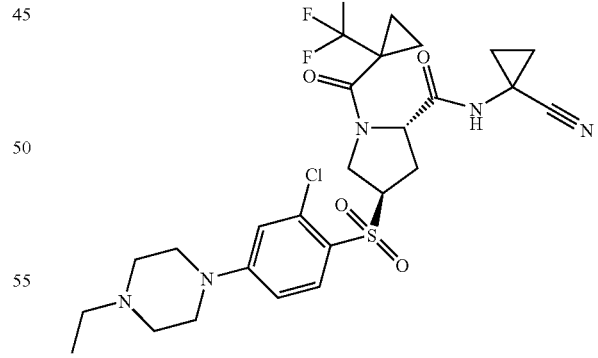

The title compound was prepared in analogy to example 135 using example 140 (37 mg) as starting material to yield 6 mg (13%) of an amorphous light yellow solid. MS (ESI): m/z=602.2 [M+H]$^+$.

Example 142

(2S,4R)-4-[2-Chloro-4-(4-ethyl-piperazin-1-yl)-benzenesulfonyl]-1-(1-trifluoromethyl-cyclopropanecarbonyl)-pyrrolidine-2-carboxylic acid (1-cyano-cyclopropyl)-amide formiate

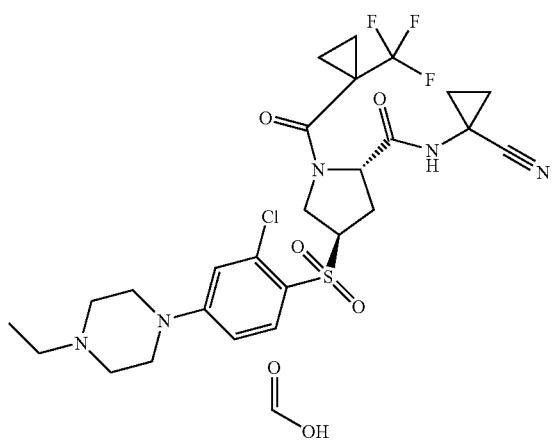

(Alternative Route to Yield Example 141)

Example 145 (200 mg) was dissolved in DMA (4 mL). N-ethylpiperazine (0.06 mL) and Cs$_2$CO$_3$ (0.154 g) were added. The reaction mixture was stirred in the microwave oven at 140° C. for 30 min. The reaction mixture was purified by prep. HPLC to yield the title compound (101 mg, 40%) as an amorphous colorless solid as an formic acid salt. MS (ESI): m/z=602.2 [M+H]$^+$.

Example 143

(2S,4R)-4-[2-Chloro-4-(4-ethyl-piperazin-1-yl)-benzenesulfonyl]-1-formyl-pyrrolidine-2-carboxylic acid (1-cyano-cyclopropyl)-amide

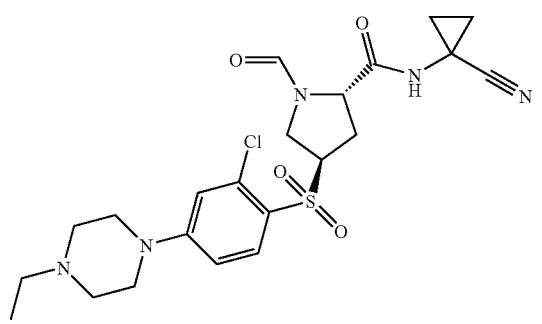

The title compound was obtained as a side-product during the synthesis of example 141 to yield 14 mg (39%) of an amorphous colorless solid. MS (ESI): m/z=494.2 [M+H]$^+$.

Example 144

(2S,4R)-4-(2-Chloro-4-fluoro-benzenesulfonyl)-pyrrolidine-2-carboxylic acid (1-cyano-cyclopropyl)-amide

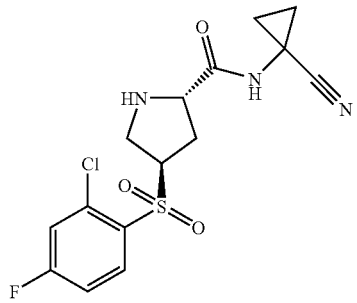

The title compound was prepared in analogy to example 127 using example 124 (500 mg) as starting material to yield 345 mg (88%) of a colorless foam. MS (ESI): m/z=372.2 [M+H]$^+$.

Example 145

(2S,4R)-4-(2-Chloro-4-fluoro-benzenesulfonyl)-1-(1-trifluoromethyl-cyclopropanecarbonyl)-pyrrolidine-2-carboxylic acid (1-cyano-cyclopropyl)-amide

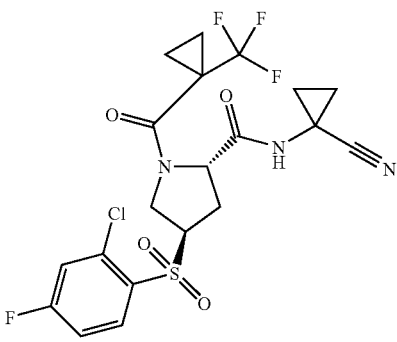

The title compound was prepared in analogy to example 135 using example 144 (340 mg) as starting material to yield 313 mg (67%) of an amorphous light yellow solid. MS (ESI): m/z=508.2 [M+H]$^+$.

Example 146

(2S,4R)-4-(2-Chloro-4-piperidin-1-yl-benzenesulfonyl)-1-formyl-pyrrolidine-2-carboxylic acid (1-cyano-cyclopropyl)-amide formiate

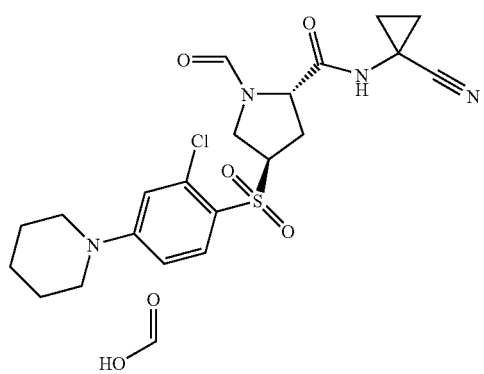

The title compound was obtained as a side-product during the synthesis of example 135 to yield 7 mg (8%) of an amorphous colorless solid. MS (ESI): m/z=465.3 [M+H]⁺.

Example 147

(2S,4R)-4-(2-Chloro-4-pyrazol-1-yl-benzenesulfonyl)-1-(1-trifluoromethyl-cyclopropanecarbonyl)-pyrrolidine-2-carboxylic acid (1-cyano-cyclopropyl)-amide

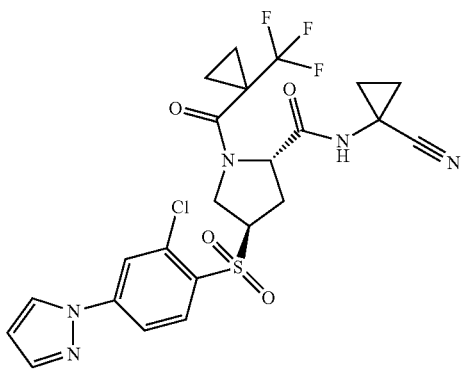

The title compound was prepared in analogy to example 135 using example 128 (128 mg) as starting material to yield 103 mg (61%) of an amorphous colorless solid. MS (ESI): m/z=556.3 [M+H]⁺.

Example 148

(2S,4R)-4-(2-Chloro-4-pyrazol-1-yl-benzenesulfonyl)-1-formyl-pyrrolidine-2-carboxylic acid (1-cyano-cyclopropyl)-amide

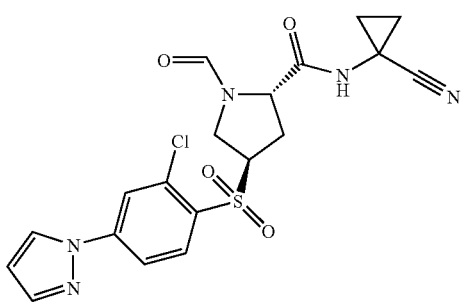

The title compound was obtained as a side-product during the synthesis of example 147 to yield 13 mg (10%) of an amorphous colorless solid. MS (ESI): m/z=448.2 [M+H]⁺.

Example 149

(2S,4R)-4-[2-Chloro-4-(2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide

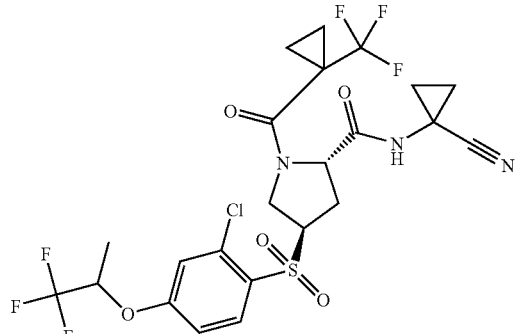

The title compound was prepared in analogy to example 135 using example 129 (110 mg) as starting material to yield 65 mg (46%) of an amorphous colorless solid. MS (ESI): m/z=602.2 [M+H]⁺.

Example 150

(2S,4R)-4-[2-Chloro-4-(2,2,2-trifluoro-1-methyl-ethoxy)-benzenesulfonyl]-1-formyl-pyrrolidine-2-carboxylic acid (1-cyano-cyclopropyl)-amide

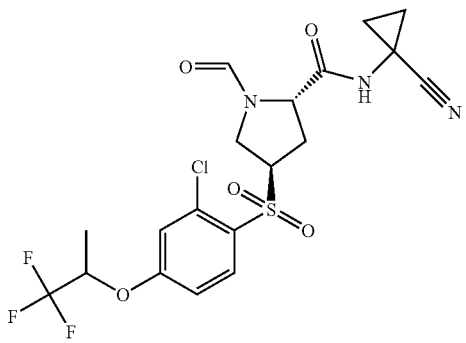

The title compound was obtained as a side-product during the synthesis of example 149 to yield 25 mg (21%) of an amorphous light yellow solid. MS (ESI): m/z=494.2 [M+H]⁺.

Example 151

(2S,4R)-1-Phenyl-4-(2-trifluoromethyl-benzenesulfonyl)-pyrrolidine-2-carboxylic acid cyanomethyl-amide

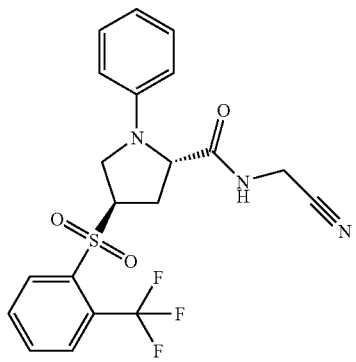

a) (2S,4R)-1-Phenyl-4-(2-trifluoromethyl-benzene-sulfonyl)-pyrrolidine-2-carboxylic acid methyl ester To a solution of (2S,4R)-4-(2-trifluoromethyl-benzenesulfonyl)-pyrrolidine-2-carboxylic acid methyl ester (see example xx) (1.03 g, 1.0 eq) in dry dichloromethane (25 mL) were added freshly powdered molecular sieves (2.88 g). Phenyl boronic acid (0.74 g, 2.0 eq) was added, followed by triethylamine (0.62 g, 2.0 eq) and copper(II)acetate (0.61 g, 1.1 eq). Oxygen gas was bubbled through the reaction mixture for 5 min. The flask was sealed with a rubber septum and left under an atmosphere of oxygen by means of a balloon. After stirring at room temperature for 24 h, the mixture was filtered and the filtrate was treated with water and filtered again. The phases were separated and the organic phase dried over sodium sulfate, filtered and evaporated. Purification by flash chromatography on silica gel with an heptane/ethyl acetate gradient yielded the title compound as a light yellow solid (0.23 g, 18%). MS (ESI): m/z=414.2 [M+H]$^+$.

b) (2S,4R)-1-Phenyl-4-(2-trifluoromethyl-benzene-sulfonyl)-pyrrolidine-2-carboxylic acid 151a (0.14 g, 1.0 eq) was suspended in methanol (3.4 mL) and THF (1.0 mL). LiOH 1N (0.66 mL, 2.0 eq) was added and the reaction was stirred at RT for 2 h. TLC and MS analysis revealed that the reaction was complete. The solvents were evaporated and the resulting residue suspended in water and acidified with aq. 1N HCl to pH 1. The desired acid precipitated and was filtered, washing with water. The title compound was obtained as a white solid (0.12 g, 94%) and used without further purification. MS (ESI): m/z=400.1 [M+H]$^+$.

c) (2S,4R)-1-Phenyl-4-(2-trifluoromethyl-benzene-sulfonyl)-pyrrolidine-2-carboxylic acid cyanomethyl-amide 151b (0.15 g, 1.0 eq) was dissolved in dry DMF (3.0 mL) under argon and treated with diisopropyl ethylamine (0.24 g, 5.0 eq) and HATU (0.17 g, 1.2 eq). The mixture was stirred at RT for 2 h, then treated with 2-aminoacetonitrile hydrochloride (0.05 g, 1.5 eq). The mixture was stirred at RT overnight, then diluted with water and extracted with ethyl acetate. The combined organic phases were washed with water and saturated NaCl, dried over sodium sulfate and evaporated. Purification by flash chromatography on silica gel with an heptane/ethyl acetate gradient yielded the title compound as a white solid (0.03 g, 19%). MS (ESI): m/z=438.2 [M+H]$^+$.

Example 152

(2S,4R)-4-[2-Chloro-4-(4,4-difluoro-piperidin-1-yl)-benzenesulfonyl]-2-(1-cyano-cyclopropylcarbamoyl)-pyrrolidine-1-carboxylic acid tert.-butyl ester

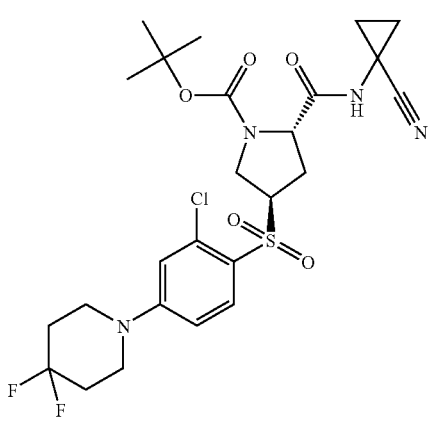

The title compound was prepared in analogy to example 130 using example 124 (400 mg) and 4,4-difluoropiperidine HCl salt (187 mg) as starting material to yield 66 mg (14%) of an amorphous yellow solid. MS (ESI): m/z=573.4 [M+H]$^+$.

Example 153

(2S,4R)-4-[2-Chloro-4-(4-trifluoromethyl-piperidin-1-yl)-benzenesulfonyl]-2-(1-cyano-cyclopropylcarbamoyl)-pyrrolidine-1-carboxylic acid tert.-butyl ester

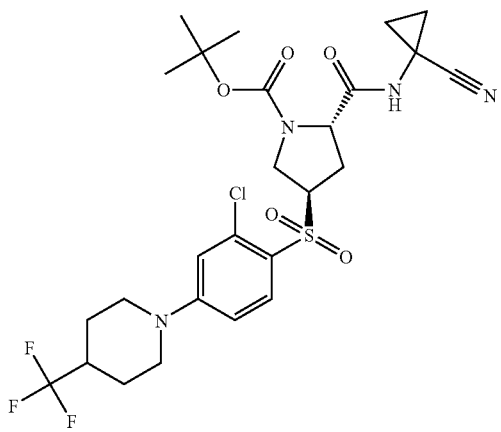

The title compound was prepared in analogy to example 130 using example 124 (400 mg) and 4-trifluoromethylpiperidine HCl salt (225 mg) as starting material to yield 102 mg (20%) of an amorphous yellow solid. MS (ESI): m/z=605.3 [M+H]$^+$.

Example 154

(2S,4R)-4-[2-Chloro-4-(4-trifluoromethyl-piperidin-1-yl)-benzenesulfonyl]-pyrrolidine-2-carboxylic acid (1-cyano-cyclopropyl)-amide

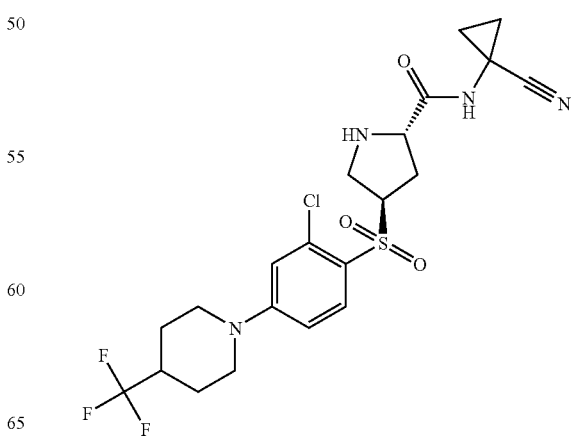

The title compound was prepared in analogy to example 137 using example 153 (95 mg) as starting material to yield 75 mg (95%) of a light yellow solid. MS (ESI): m/z=505.2 [M+H]+.

Example 155

(2S,4R)-4-[2-Chloro-4-(4,4-difluoro-piperidin-1-yl)-benzenesulfonyl]-pyrrolidine-2-carboxylic Acid (1-cyano-cyclopropyl)-amide

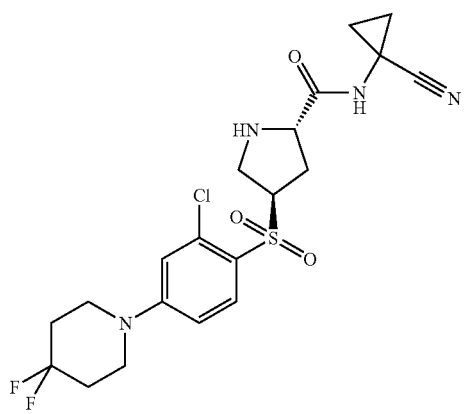

The title compound was prepared in analogy to example 127 using example 152 (62 mg) as starting material to yield 36 mg (70%) of a light yellow solid. MS (ESI): m/z=473.3 [M+H]+.

Example 156

(2S,4R)-4-[2-Chloro-4-(4-trifluoromethyl-piperidin-1-yl)-benzenesulfonyl]-1-(1-trifluoromethyl-cyclopropanecarbonyl)-pyrrolidine-2-carboxylic acid (1-cyano-cyclopropyl)-amide

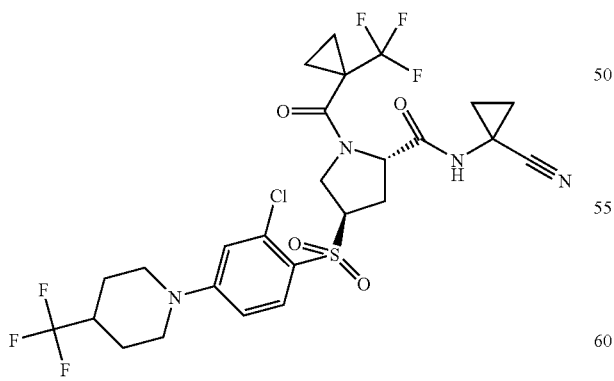

The title compound was prepared in analogy to example 135 using example 154 (70 mg) as starting material to yield 34 mg (38%) of a light yellow solid. MS (ESI): m/z=641.2 [M+H]+.

Example 157

(2S,4R)-4-[2-Chloro-4-(4,4-difluoro-piperidin-1-yl)-benzenesulfonyl]-1-(1-trifluoromethyl-cyclopropanecarbonyl)-pyrrolidine-2-carboxylic acid (1-cyano-cyclopropyl)-amide

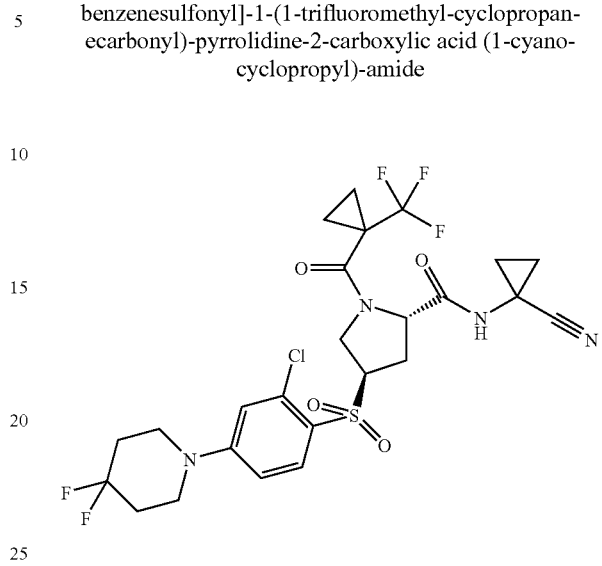

The title compound was prepared in analogy to example 135 using example 155 (35 mg) as starting material to yield 9 mg (20%) of a light yellow solid. MS (ESI): m/z=609.3 [M+H]+.

Example 158

(2S,4S)-2-(1-Cyano-cyclopropylcarbamoyl)-4-(2-trifluoromethyl-benzenesulfonyl)-pyrrolidine-1-carboxylic acid tert.-butyl ester

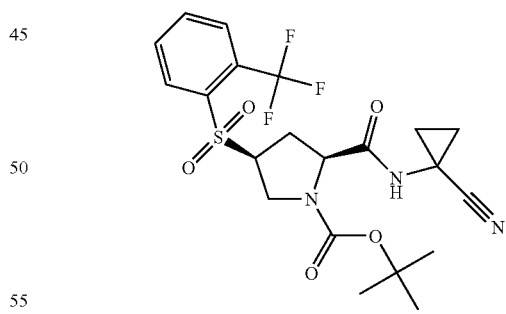

The title compound was prepared in analogy to example 124 using (2S,4R)-4-Hydroxy-pyrrolidine-1,2-dicarboxylic acid 1-tert-butyl ester 2-methyl ester as starting material instead of (2S,4S)-4-hydroxy-pyrrolidine-1,2-dicarboxylic acid 1-tert-butyl ester 2-methyl ester to yield the title compound (130 mg, 31%) as a white solid. MS (ESI): m/z=488.5 [M+H]+.

Example 159

(2S,4S)-4-(2-Trifluoromethyl-benzenesulfonyl)-pyrrolidine-2-carboxylic acid (1-cyano-cyclopropyl)-amide

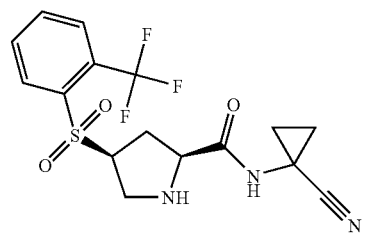

The title compound was prepared in analogy to example 127 using example 158 (120 mg) as starting material to yield 20 mg (21%) of a colorless solid. MS (ESI): m/z=388.2 [M+H]$^+$.

Example 160

(2S,4R)-1-(4-Methoxy-phenyl)-4-(2-trifluoromethyl-benzenesulfonyl)-pyrrolidine-2-carboxylic Acid (1-cyano-cyclopropyl)-amide

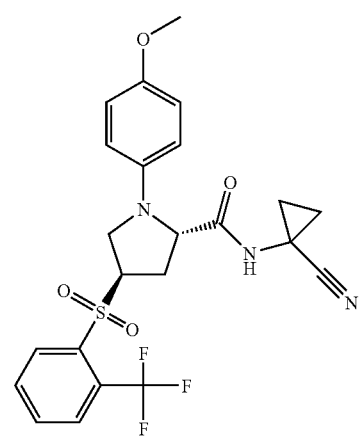

The title compound was obtained in analogy to example 151. 4-Methoxyphenylboronic acid was used in step a instead of phenylboronic acid, and 1-aminocyclopropyl cyanic hydrochloride was used instead of 2-aminoacetonitrile hydrochloride in step c. MS (ESI): m/z=494.2 [M+H]$^+$.

Example 161

(2S,4R)-4-(2-Chloro-4-morpholin-4-yl-benzenesulfonyl)-1-(1-trifluoromethyl-cyclopropanecarbonyl)-pyrrolidine-2-carboxylic acid (1-cyano-cyclopropyl)-amide

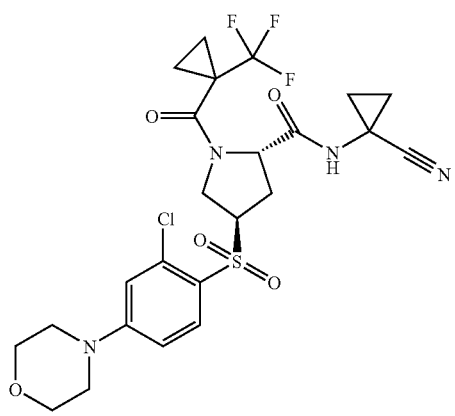

The title compound was prepared in analogy to example 142 using example 145 (250 mg) as starting material to yield 87 mg (31%) of a light yellow solid. MS (ESI): m/z=575.3 [M+H]$^+$.

Example 162

(2R,4R)-4-(2-Chloro-4-morpholin-4-yl-benzenesulfonyl)-1-(1-trifluoromethyl-cyclopropanecarbonyl)-pyrrolidine-2-carboxylic acid (1-cyano-cyclopropyl)-amide

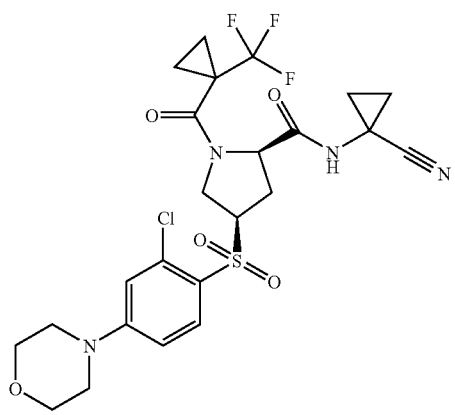

The title compound was obtained as a side-product during the synthesis of example 161 to yield 17 mg (6%) of an amorphous light yellow solid. MS (ESI): m/z=494.2 [M+H]$^+$.

Example 163

(2S,4R)-4-(2-Chloro-4-piperazin-1-yl-benzenesulfonyl)-1-(1-trifluoromethyl-cyclopropanecarbonyl)-pyrrolidine-2-carboxylic acid (1-cyano-cyclopropyl)-amide formiate

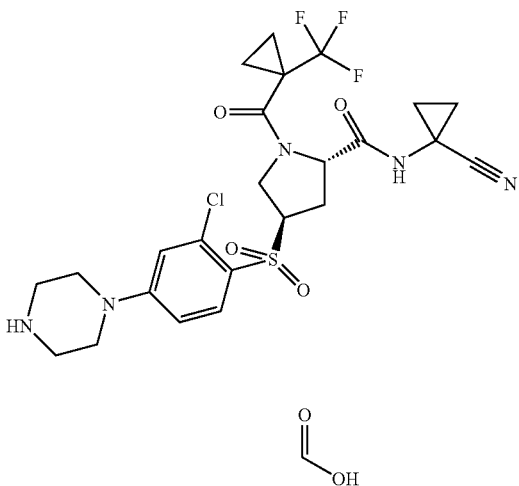

The title compound was prepared in analogy to example 142 using example 145 (250 mg) as starting material to yield 186 mg (66%) of a light yellow oil. MS (ESI): m/z=574.3 [M+H]$^+$.

Example 164

(2S,4R)-1-(2-Nitro-phenyl)-4-(2-trifluoromethyl-benzenesulfonyl)-pyrrolidine-2-carboxylic acid cyanomethyl-amide

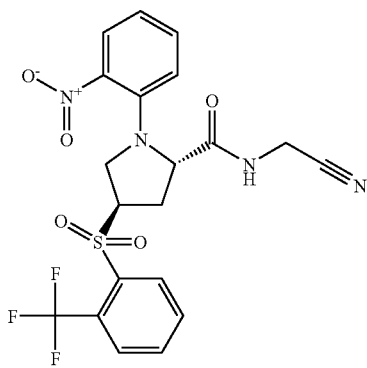

a) (2S,4S)-4-Hydroxy-1-(2-nitro-phenyl)-pyrrolidine-2-carboxylic acid methyl ester A suspension of 2S,4S)-4-hydroxy-pyrrolidine-2-carboxylic acid methyl ester hydrochloride (4.0 g, 1.0 eq) in acetonitrile (55 mL) was treated with TEA (3.8 g, 1.36 eq) and 1-chloro-2-nitrobenzene (4.1 g, 1.05 eq). A solution formed, followed by rapid formation of a white precipitate. The mixture was stirred at 60° C. for 22 h then poured over HCl 1N (60 mL) and extracted several times with ether. The combined organic extracts were dried over sodium sulfate and evaporated. Purification by flash chromatography on silica gel with an heptane/ethyl acetate gradient yielded the title compound as a white solid (5.8 g, 79%).

b) (2S,4S)-4-(3-Nitro-benzenesulfonyloxy)-1-(2-nitro-phenyl)-pyrrolidine-2-carboxylic acid methyl ester 164a (5.8 g, 1.0 eq) was dissolved in dichloromethane (60 mL) and treated with 3-nitrobenzenesulfonylchloride (5.1 g, 1.06 eq). The mixture was cooled to 0° C. and treated with triethylamine (6.6 g, 3.0 eq), which was added dropwise over 20 min. The mixture was stirred at RT overnight, then diluted with dichloromethane (60 mL) and washed with HCl 0.5 N (45 mL), saturated sodium carbonate (60 mL) and brine. The organic phase was dried over sodium sulfate and evaporated to yield the title compound as an orange foam (9.2 g, 94%). The compound was used without further purification. MS (ESI): m/z=452.1 [M+H]$^+$.

c) (2S,4R)-1-(2-Nitro-phenyl)-4-(2-trifluoromethyl-phenylsulfanyl)-pyrrolidine-2-carboxylic acid methyl ester Sodium hydride (55% in mineral oil, 1.3 g, 1.5 eq) was suspended in dry tetrahydrofuran (200 mL) under an argon atmosphere. 2-(Trifluoromethyl)thiophenol (5.6 g, 1.5 eq) was added dropwise over 10 min. The mixture was stirred at RT for 2 h. 164b (9.0 g, 1.0 eq) was dissolved in dry THF (50 mL) and the solution added dropwise to the reaction mixture over 10 min. The reaction mixture was stirred at 50° C. for 2 h, upon which a white suspension appeared. After cooling to RT, the mixture was poured over water (400 mL) and extracted twice with ethyl acetate (2×300 mL). The combined organic phases were washed with brine, dried over sodium sulfate and evaporated. The title compound was obtained as an orange solid (10.2 g, 107%) and was used without further purification. MS (ESI): m/z=427.1 [M+H]$^+$.

d) (2S,4R)-1-(2-Nitro-phenyl)-4-(2-trifluoromethyl-benzenesulfonyl)-pyrrolidine-2-carboxylic acid methyl ester 164c (5.3 g, 1.0 eq) was dissolved in dichloromethane (125 mL) and treated with 3-chloroperbenzoic acid, which was added in portions over 10 min. The mixture was stirred at RT overnight, then treated with 1N sodium carbonate. The phases were separated and the aqueous phase extracted once with dichloromethane. The combined organic phases were washed with brine, dried over sodium sulfate and evaporated. Purification by flash chromatography on silica gel with an heptane/ethyl acetate gradient yielded the title compound as an orange foam (5.3 g, 54%). MS (ESI): m/z=459.2 [M+H]$^+$.

e) (2S,4R)-1-(2-Nitro-phenyl)-4-(2-trifluoromethyl-benzenesulfonyl)-pyrrolidine-2-carboxylic acid 164d (1.0 g, 1.0 eq) was suspended in ethanol (50 mL) and treated with LiOH 1N (4.3 mL, 2.0 eq). The mixture was stirred at RT overnight. After dilution with water and acidification with HCl 1N to pH 1, the acid precipitated and was filtered, washing with water. The title compound was obtained as yellow solid (0.83 g, 86%). MS (ESI): m/z=445.3 [M+H]$^+$.

f) (2S,4R)-1-(2-Nitro-phenyl)-4-(2-trifluoromethyl-benzenesulfonyl)-pyrrolidine-2-carboxylic acid cyanomethyl-amide 164e (0.19 g, 1.0 eq) was dissolved under argon in dry DMF (4.0 mL) and treated with diisopropylethylamine (0.27 g, 5.0 eq) and HATU (0.19 g, 1.2 eq). The mixture was stirred at RT for 1 h, then treated with amino-acetonitrile hydrochloride (0.06 g, 1.5 eq). After stirring at RT overnight, water was added and the mixture was extracted twice with ethyl acetate. The combined organic phases were washed three times with water and once with brine, dried over sodium sulfate and evaporated. Purification by flash chromatography on silica gel with an heptane/ethyl acetate gradient yielded the title compound as yellow solid (0.10 g, 51%). MS (ESI): m/z=483.3 [M+H]+.

Example 165

(2R,4R)-4-(2-Chloro-4-pyrazol-1-yl-benzenesulfonyl)-1-(1-trifluoromethyl-cyclopropanecarbonyl)-pyrrolidine-2-carboxylic acid (1-cyano-cyclopropyl)-amide

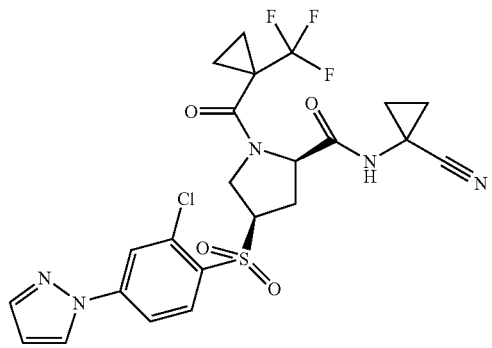

The title compound was obtained as a side-product during the synthesis of example 147 to yield an amorphous light yellow solid. MS (ESI): m/z=556.2 [M+H]+.

Example 166

(2S,4R)-1-(2-Nitro-phenyl)-4-(2-trifluoromethyl-benzenesulfonyl)-pyrrolidine-2-carboxylic Acid (1-cyano-cyclopropyl)-amide

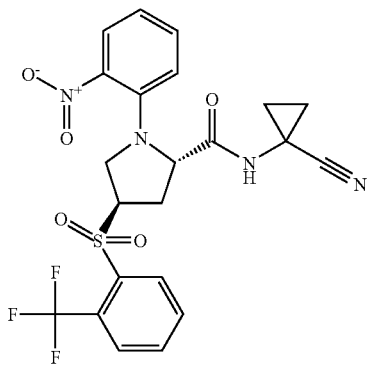

The title compound was obtained in analogy to example 164. The last step was performed as follows:

A solution of 164e (0.20 g, 1.0 eq) in dry THF (6.5 mL) was treated with 4-methylmorpholine (0.14 g, 3.0 eq) and cooled to 0° C. Isobutylchloroformiate (0.074 g, 1.2 eq) was added dropwise during 5 min. The mixture was stirred at 0° C. for 1.5 h, then at RT for 1 h. After cooling back to 0° C., a solution of 1-aminocyclopropyl cyanic hydrochloride (0.064 g, 1.2 eq) in dry DMF (3.0 mL) was added dropwise. The mixture was stirred at RT overnight. After addition of saturated ammonium chloride and water, the mixture was extracted twice with ethyl acetate. The combined organic phases were washed with water and brine, dried over sodium sulfate and evaporated. Purification by flash chromatography on silica gel with an heptane/ethyl acetate/formic acid gradient yielded the title compound as a yellow solid (0.051 g, 22%). MS (ESI): m/z=509.1 [M+H]+

Example 167

(2S,4R)-4-(2,4-Dichloro-benzenesulfonyl)-1-(2-nitro-phenyl)-pyrrolidine-2-carboxylic acid (1-cyano-cyclopropyl)-amide

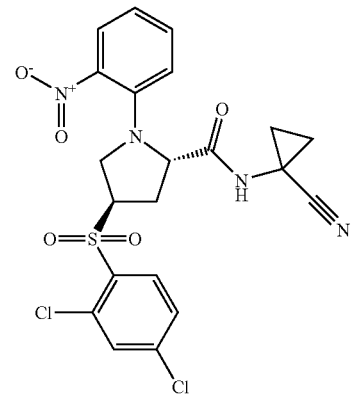

The title compound was obtained in analogy to example 164 and 166, using 2,4-dichlorothiophenol in step 164c. MS (ESI): m/z=509.1 [M+H]+.

Example 168

(2S,4R)-4-(2,4-Dichloro-benzenesulfonyl)-1-(1-trifluoromethyl-cyclopropanecarbonyl)-pyrrolidine-2-carboxylic acid (1-cyano-cyclopropyl)-amide

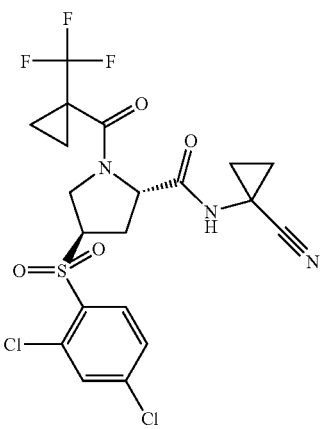

The title compound was prepared in analogy to example 145 using example 15 (250 mg) as starting material to yield 36 mg (11%) of a light yellow solid. MS (ESI): m/z=524.1 [M+H]+.

Example 169

(2S,4R)-4-(2,4-Dichloro-benzenesulfonyl)-1-(1-trifluoromethyl-cyclobutanecarbonyl)-pyrrolidine-2-carboxylic acid (1-cyano-cyclopropyl)-amide

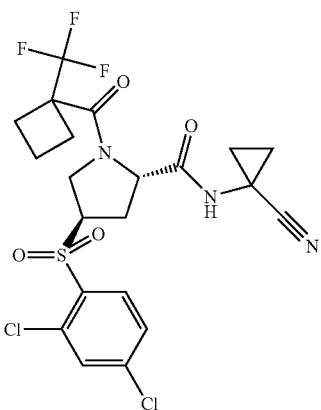

The title compound was prepared in analogy to example 168 using example 15 (250 mg) and 1-(trifluoromethyl)-1-cyclobutanecarboxylic acid (167 mg) as starting material to yield 73 mg (21%) of a light yellow solid. MS (ESI): m/z=538.1 [M+H]$^+$.

Example 170

(2S,4R)-4-(2,4-Dichloro-benzenesulfonyl)-1-(2,2-difluoro-cyclopropanecarbonyl)-pyrrolidine-2-carboxylic acid (1-cyano-cyclopropyl)-amide

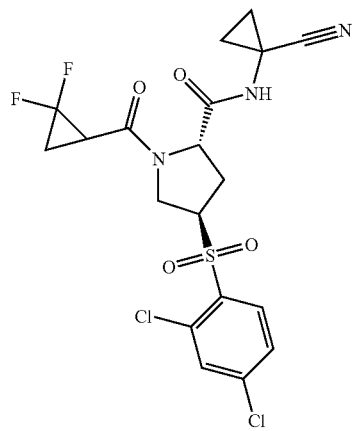

The title compound was prepared in analogy to example 168 using example 15 (250 mg) and 2,2-difluorocyclopropane-1-carbocylic acid (118 mg) as starting material to yield 41 mg (13%) of a light yellow solid. MS (ESI): m/z=492.0 [M+H]$^+$.

Example 171

(2S,4R)-4-[2-Chloro-4-(2,2,2-trifluoro-ethoxy)-benzenesulfonyl]-2-(1-cyano-cyclopropylcarbamoyl)-pyrrolidine-1-carboxylic acid tert.-butyl ester

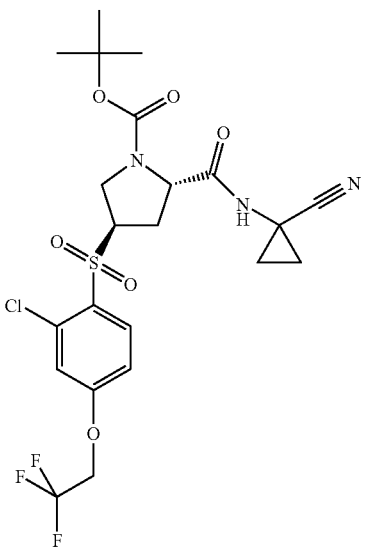

The title compound was prepared in analogy to the reaction sequence of example 122 using 2,2,2-trifluorethanol instead of 1,1,1-trifluoro-propan-2-ol as starting material to yield a white foam. MS (ESI): m/z=552.1 [M+H]$^+$.

Example 172

(2S,4R)-4-[2-Chloro-4-(2,2,2-trifluoro-ethoxy)-benzenesulfonyl]-1-(1-trifluoromethyl-cyclopropanecarbonyl)-pyrrolidine-2-carboxylic acid (1-cyano-cyclopropyl)-amide

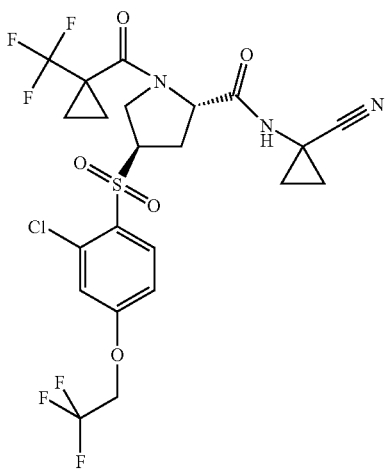

The title compound was prepared in analogy to example 149 using example 173 (56 mg) as starting material to yield 11 mg (15%) of a white solid. MS (ESI): m/z=588.1 [M+H]⁺.

Example 173

(R)-4-[2-Chloro-4-(2,2,2-trifluoro-ethoxy)-benzene-sulfonyl]-pyrrolidine-2-carboxylic acid (1-cyano-cyclopropyl)-amide

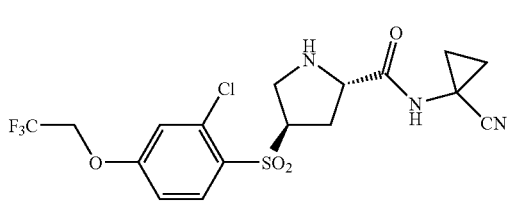

The title compound was prepared in analogy to example 149 using example 171 (86 mg) as starting material to yield 56 mg (79%) of a light yellow solid. MS (ESI): m/z=452.1 [M+H]⁺.

Example 174

(2S,4R)-4-[2-Chloro-4-(oxetan-3-yloxy)-benzene-sulfonyl]-2-(1-cyano-cyclopropylcarbamoyl)-pyrrolidine-1-carboxylic acid tert.-butyl ester

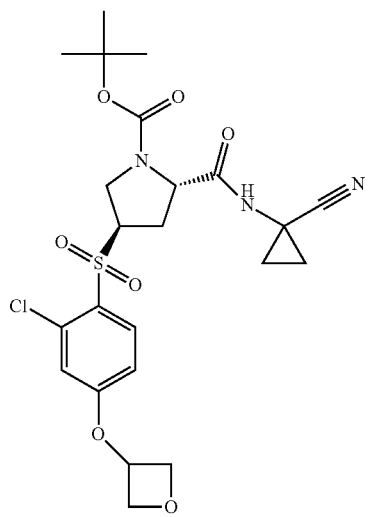

The title compound was prepared in analogy to the reaction sequence of example 122 using 3-hydroxyoxetan instead of 1,1,1-trifluoro-propan-2-ol as starting material to yield an off-white amorphous material. MS (ESI): m/z=526.4 [M+H]⁺.

Example 175

(2S,4R)-4-[2-Chloro-4-(2,2,2-trifluoro-ethoxy)-benzenesulfonyl]-1-(1-methyl-cyclopropanecarbonyl)-pyrrolidine-2-carboxylic acid (1-cyano-cyclopropyl)-amide

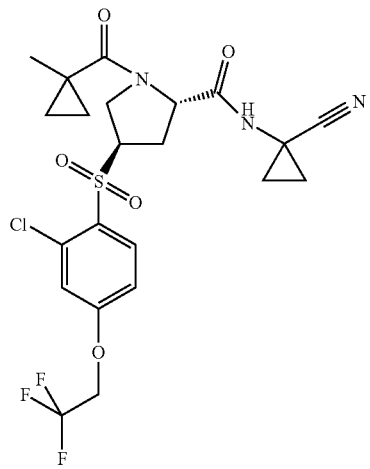

The title compound was prepared in analogy to example 149 using example 173 (100 mg) as starting material to yield 21 mg (18%) of a white solid. MS (ESI): m/z=534.1 [M+H]⁺.

Example 176

(2S,4R)-4-[2-Chloro-4-(2,2,2-trifluoro-ethoxy)-benzenesulfonyl]-1-(2,2-dimethyl-propionyl)-pyrrolidine-2-carboxylic acid (1-cyano-cyclopropyl)-amide

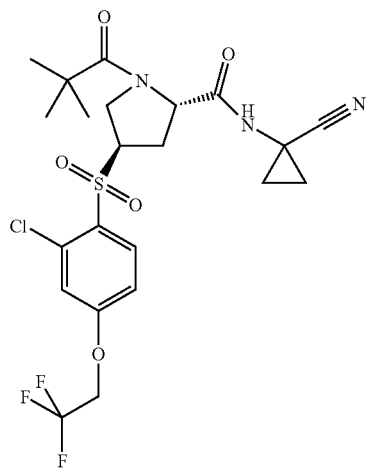

The title compound was prepared in analogy to example 149 using example 173 (100 mg) as starting material to yield 14 mg (12%) of an off-white amorphous material. MS (ESI): m/z=536.1 [M+H]⁺.

Example 177

(2S,4R)-4-[2-Chloro-4-(2,2,2-trifluoro-ethoxy)-benzenesulfonyl]-1-(2-trifluoromethyl-benzoyl)-pyrrolidine-2-carboxylic acid (1-cyano-cyclopropyl)-amide

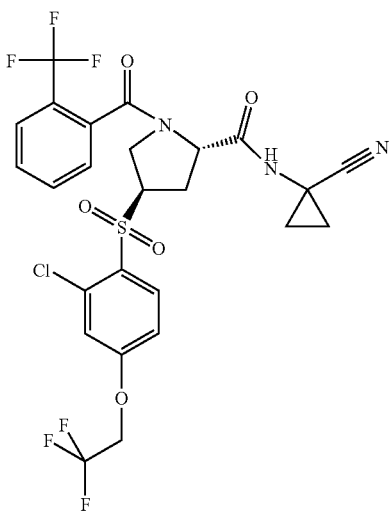

The title compound was prepared in analogy to example 149 using example 173 (100 mg) as starting material to yield 53 mg (38%) of an off-white amorphous material. MS (ESI): m/z=624.2 [M+H]$^+$.

Example 178

(2S,4R)-1-[1-(4-Chloro-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide

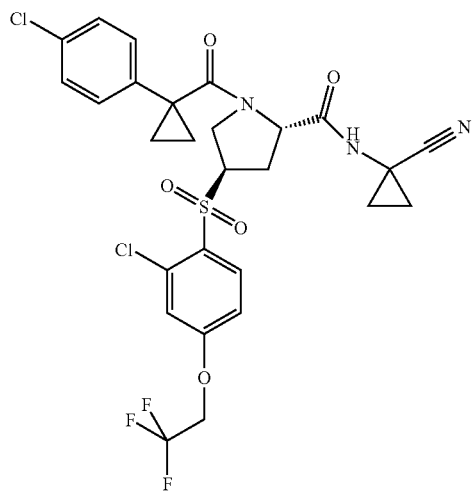

The title compound was prepared in analogy to example 149 using example 173 (100 mg) as starting material to yield 54 mg (39%) of an off-white amorphous material. MS (ESI): m/z=630.1 [M+H]$^+$.

Example 179

(2S,4R)-4-[2-Chloro-4-(2,2,2-trifluoro-ethoxy)-benzenesulfonyl]-1-isobutyryl-pyrrolidine-2-carboxylic acid (1-cyano-cyclopropyl)-amide

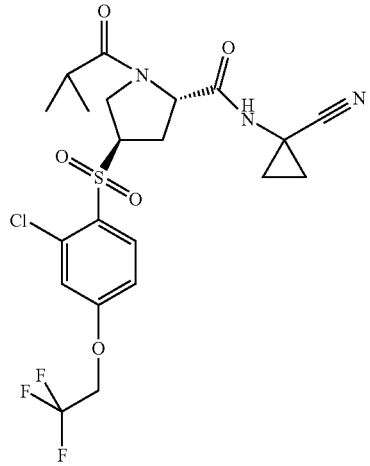

The title compound was prepared in analogy to example 149 using example 173 (100 mg) as starting material to yield 39 mg (34%) of an off-white solid. MS (ESI): m/z=522.2 [M+H]$^+$.

Example 180

(2S,4R)-4-[2-Chloro-4-(2,2,2-trifluoro-ethoxy)-benzenesulfonyl]-1-(3-methyl-butyryl)-pyrrolidine-2-carboxylic acid (1-cyano-cyclopropyl)-amide

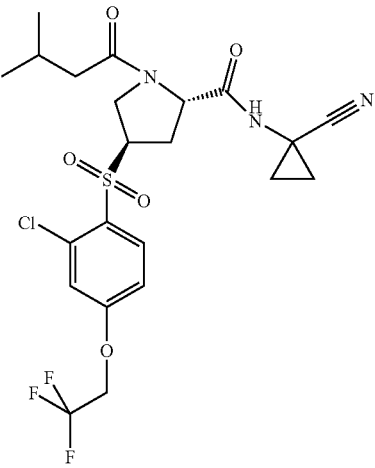

The title compound was prepared in analogy to example 149 using example 173 (100 mg) as starting material to yield 29 mg (24%) of an off-white solid. MS (ESI): m/z=536.1 [M+H]⁺.

Example 181

(2S,4R)-4-[2-Chloro-4-(oxetan-3-yloxy)-benzene-sulfonyl]-pyrrolidine-2-carboxylic acid (1-cyano-cyclopropyl)-amide

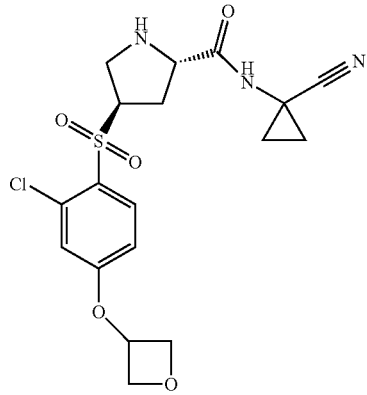

The title compound was prepared in analogy to example 127 using example 174 (261 mg) as starting material to yield 179 mg (85%) of a white solid. MS (ESI): m/z=426.1 [M+H]⁺.

Example 182

(R)-4-[2-Chloro-4-(2,2,2-trifluoro-ethoxy)-benzene-sulfonyl]-1-formyl-pyrrolidine-2-carboxylic Acid (1-cyano-cyclopropyl)-amide

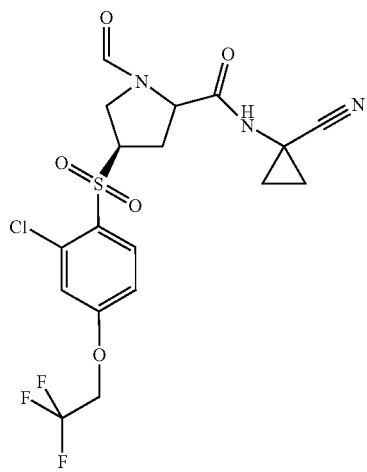

The title compound was obtained as a side-product during the synthesis of example 175 to yield 33 mg (31%) of an off-white solid. MS (ESI): m/z=426.1 [M+H]⁺.

Example 183

(2S,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide

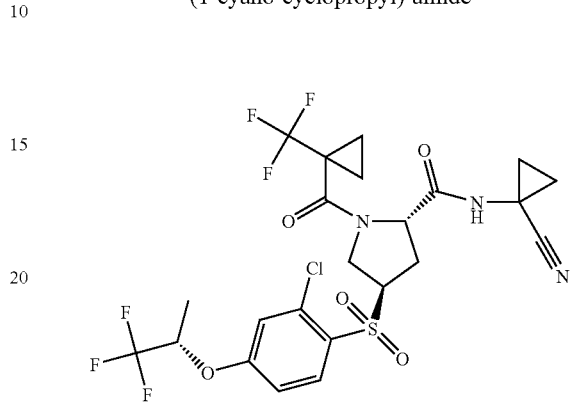

a) (2S,4R)-4-[2-Chloro-4-((S)-2,2,2-trifluoro-1-methyl-ethoxy)-benzenesulfonyl]-pyrrolidine-1,2-dicarboxylic acid 1-tert-butyl ester 2-methyl ester Example 120c (3.0 g) was dissolved in DMA (30 mL) at rt. To this solution (S)-2,2,2-trifluoroisopropanole (1.2 eq.; 0.973 g) and Cs₂CO₃ (1.2 eq.; 2.78 g) were added. The reaction mixture was stirred in a microwave oven at 140° C. for 30 min. After that additional (S)-2,2,2-trifluoroisopropanole (0.4 eq.; 0.324 g) was given to the reaction mixture and stirred again in a microwave oven at 140° C. for 30 min. The reaction mixture was evaporated, the residue was dissolved in CH₂Cl₂ (250 ml), was extracted in succession with aq. 0.5N HCl-solution (100 ml) and brine. The water layer was washed twice with CH₂Cl₂ (150 ml), washed with brine, the combined organic layers were dried over Na₂SO₄, filtered and evaporated. The residue was purified over silicagel with n-hetpan:AcOEt to yield 2.66 g (73%) of 183a as a colorless gum. MS (ESI): m/z=416.1 [M+H-Boc]⁺.

b) (2S,4R)-4-[2-Chloro-4-((S)-2,2,2-trifluoro-1-methyl-ethoxy)-benzenesulfonyl]-pyrrolidine-2-carboxylic acid methyl ester Example 183a (0.5 g) was dissolved in CH₂Cl₂ (5 ml), TFA (10.0 eq.; 0.74 mL) was added to the clear colorless solution. The reaction mixture was stirred over night at ambient temperature. A clear light yellow solution was formed. The reaction mixture was diluted with in CH₂Cl₂ (20 ml), extracted with aqueous 10% Na₂CO₃-solution, the water layer was washed twice with CH₂Cl₂, the combined organic layers were washed with brine, dried over Na₂SO₄, filtered and evaporated to yield 407 mg (100%) of the title compound as a colorless viscous oil. MS (ESI): m/z=416.1 [M+H]⁺.

c) (2S,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid methyl ester Example 183b (400 mg) was dissolved in DMF (4.0 mL). HATU (732 mg), DIEA (249 mg) and 1-(trifluoromethyl)

cyclopropane-1-carboxylic acid (178 mg) were added to the suspension, (after addition of HATU a light yellow suspension was formed). The reaction mixture was stirred over night at ambient temperature. The solvent was evaporated to dryness, the residue was dissolved in CH$_2$Cl$_2$ (25 ml), was extracted in succession with aqueous 0.5N HCl-solution, aqueous 10% Na$_2$CO$_3$-solution and brine. The water layers were washed with totally CH$_2$Cl$_2$ (100 ml), the combined organic layers were dried over Na$_2$SO$_4$, filtered and evaporated. The residue was purified over silica gel chromatography with n-heptan: AcOEt to yield 219 mg (41%) of the title compound as colorless amorphous solid. MS (ESI): m/z=552.1 [M+H]$^+$.

d) Lithium; (2S,4R)-4-[2-chloro-4-((S)-2,2,2-trifluoro-1-methyl-ethoxy)-benzenesulfonyl]-1-(1-trifluoromethyl-cyclopropanecarbonyl)-pyrrolidine-2-carboxylate To a colorless solution of example 183c (0.21 g) in THF (0.8 mL) was added at ambient temperature under inert atmosphere a solution of Lithium hydroxide (1.9 eq.; 17 mg) in water (1.2 mL). The solution was stirred at ambient temperature over night. The solvent was removed under reduced pressure to yield 205 mg (99%) of the title compound as white solid. MS (ESI): m/z=538.1 [M–H-Boc]$^-$.

To prepare (2S,4R)-4-[2-chloro-4-((5)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide, example 183c (200 mg) was dissolved in DMF (2.0 mL). HATU (420 mg), DIEA (143 mg) and 1-amino-1-cyclopropane carbonitrile hydrochloride were added to the solution. The obtained suspension was stirred at ambient temperature for 2 h. After that the solvent was evaporated under reduced pressure to dryness. The residue was dissolved in CH$_2$Cl$_2$ (25 ml), was extracted in succession with aqueous 0.5 NHCl-solution, aqueous 10% Na$_2$CO$_3$-solution and brine. The water layers were washed with totally CH$_2$Cl$_2$ (50 ml), the combined organic layers were dried over Na$_2$SO$_4$, filtered and evaporated. The residue was purified over silica gel chromatography with n-heptan: AcOEt to yield 130 mg (59%) of the title compound as colorless amorphous solid. MS (ESI): m/z=602.1 [M+H]$^+$.

Example 184

(2R,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide

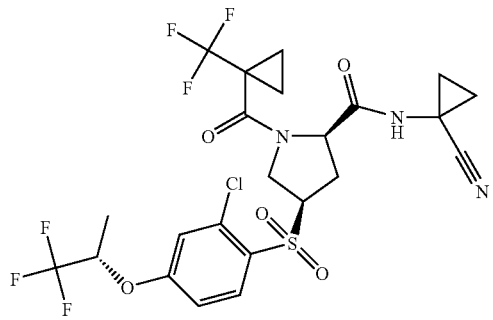

The title compound was obtained as a side-product during the synthesis of example 183 to yield an amorphous colorless solid. MS (ESI): m/z=602.1 [M+H]$^+$.

Example 185

(2S,4R)-4-(2-Trifluoromethyl-benzenesulfonyl)-1-(2-trifluoromethyl-pyrimidin-4-yl)-pyrrolidine-2-carboxylic acid (1-cyano-cyclopropyl)-amide

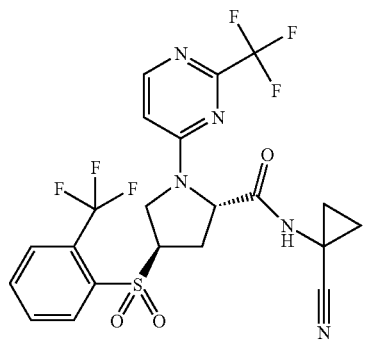

The title compound was prepared in analogy to example 186, using 4-chloro-2-(trifluoromethyl)pyrimidine in step a. MS (ESI): m/z=534.2 [M+H]$^+$.

Example 186 and Example 187

(2S,4R)-4-(2-Trifluoromethyl-benzenesulfonyl)-1-(3-trifluoromethyl-pyridin-2-yl)-pyrrolidine-2-carboxylic acid (1-cyano-cyclopropyl)-amide

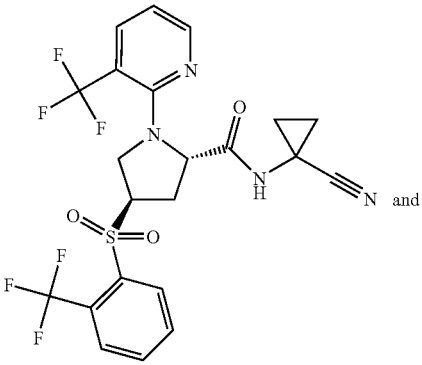

and (2R,4R)-4-(2-Trifluoromethyl-benzenesulfonyl)-1-(3-trifluoromethyl-pyridin-2-yl)-pyrrolidine-2-carboxylic acid (1-cyano-cyclopropyl)-amide

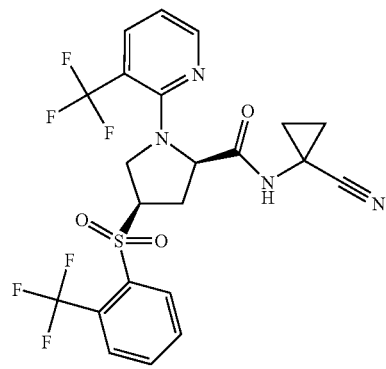

a) (2S,4R)-4-(2-Trifluoromethyl-benzenesulfonyl)-1-(3-trifluoromethyl-pyridin-2-yl)-pyrrolidine-2-carboxylic acid ethyl ester and (2R,4R)-4-(2-Trifluoromethyl-benzenesulfonyl)-1-(3-trifluoromethyl-pyridin-2-yl)-pyrrolidine-2-carboxylic acid ethyl ester A solution of compound 192e (0.20 g, 1.0 eq) in acetonitrile (0.3 mL) was treated with 2-chloro-3-(trifluoromethyl)pyridine (0.72 g, 7.0 eq) and triethylamine (0.14 g, 2.5 eq). The mixture was irradiated in a microwave oven at 190° C. for 1 h then at 200° C. for 30 min. The solvent was evaporated and the residue dissolved in ethyl acetate and washed with water. The organic phase was dried over sodium sulfate and evaporated. Purification by flash chromatography on silica gel with a toluene/ethyl acetate gradient yielded (2S,4R)-4-(2-trifluoromethyl-benzenesulfonyl)-1-(3-trifluoromethyl-pyridin-2-yl)-pyrrolidine-2-carboxylic acid ethyl ester as a light yellow oil (0.048 g, 17%) and (2R,4R)-4-(2-trifluoromethyl-benzenesulfonyl)-1-(3-trifluoromethyl-pyridin-2-yl)-pyrrolidine-2-carboxylic acid ethyl ester as a white solid (0.025 g, 8%). MS (ESI): m/z=497.0 [M+H]$^+$.

b) (2S,4R)-4-(2-Trifluoromethyl-benzenesulfonyl)-1-(3-trifluoromethyl-pyridin-2-yl)-pyrrolidine-2-carboxylic acid (1-cyano-cyclopropyl)-amide and (2R,4R)-4-(2-Trifluoromethyl-benzenesulfonyl)-1-(3-trifluoromethyl-pyridin-2-yl)-pyrrolidine-2-carboxylic acid (1-cyano-cyclopropyl)-amide (2S,4R)-4-(2-Trifluoromethyl-benzenesulfonyl)-1-(3-trifluoromethyl-pyridin-2-yl)-pyrrolidine-2-carboxylic acid ethyl ester (0.043 g, 1.0 eq) was dissolved in ethanol (2.0 mL) and treated with LiOH 1N (0.17 mL, 2.0 eq). The mixture was stirred at RT for 4.5 h. The solvent was evaporated and the residue suspended in water and acidified to pH 1 with HCl 1N. The precipitated acid was filtered and washed with water, to yield a white solid (0.034 g, 84%). The solid was dissolved in dry THF (1.0 mL) and treated with N-methylmorpholine (0.022 g, 3.0 eq). The mixture was cooled to 0° C. and treated with isobutylchloroformate (0.012 g, 1.2 eq). The mixture was stirred at 0° C. for 2 h, upon which a bright red color forms. 1-aminocyclopropyl cyanic hydrochloride (0.010 g, 1.2 eq) was dissolved in dry DMF (1 mL) and this solution was then added dropwise, the ice bath removed and the reaction stirred at RT overnight. The mixture was treated with saturated ammonium chloride and water and extracted twice with ethyl acetate. The combined organic phases were washed with water, dried over sodium sulfate and evaporated. Purification by flash chromatography on silica gel with a toluene/acetonitrile gradient yielded (2S,4R)-4-(2-trifluoromethyl-benzenesulfonyl)-1-(3-trifluoromethyl-pyridin-2-yl)-pyrrolidine-2-carboxylic acid (1-cyano-cyclopropyl)-amide as a light yellow oil (0.005 g, 13%) and (2R,4R)-4-(2-trifluoromethyl-benzenesulfonyl)-1-(3-trifluoromethyl-pyridin-2-yl)-pyrrolidine-2-carboxylic acid (1-cyano-cyclopropyl)-amide as a white solid (0.004 g, 10%). MS (ESI): m/z=533.1 for both compounds [M+H]$^+$.

Example 188 and Example 189

(2S,4R)-4-(2,4-Dichloro-benzenesulfonyl)-1-(3-trifluoromethyl-pyridin-2-yl)-pyrrolidine-2-carboxylic acid (1-cyano-cyclopropyl)-amide

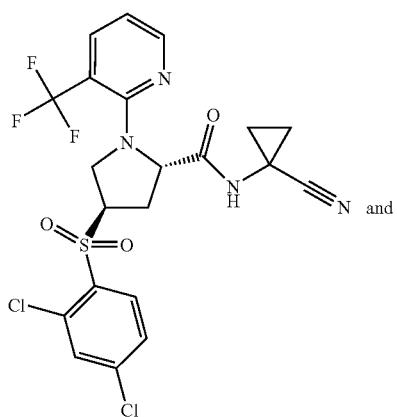

and (2R,4R)-4-(2,4-Dichloro-benzenesulfonyl)-1-(3-trifluoromethyl-pyridin-2-yl)-pyrrolidine-2-carboxylic acid (1-cyano-cyclopropyl)-amide

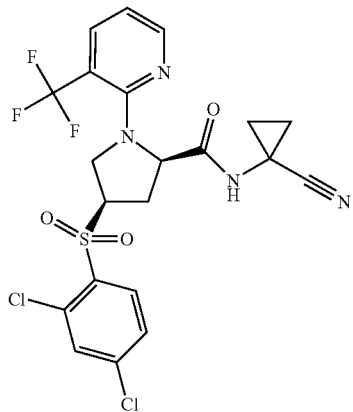

The title compounds were obtained in analogy to example 164 and 166, using 2-chloro-3-trifluoromethyl-pyridine in step 164a and 2,4-dichlorothiophenol in step 164c. The final step was performed as in example 166, and yielded both compounds, which could be separated by two subsequent flash chromatographies on silica gel with dichloromethane/methanol gradient and toluene/acetonitrile gradient. MS (ESI): m/z=533.3 [M+H]$^+$ and 533.1 [M+H]$^+$.

Example 190 and Example 191

(2S,4R)-4-[2-Chloro-4-(4-ethyl-piperazin-1-yl)-benzenesulfonyl]-1-(3-trifluoromethyl-pyridin-2-yl)-pyrrolidine-2-carboxylic acid (1-cyano-cyclopropyl)-amide

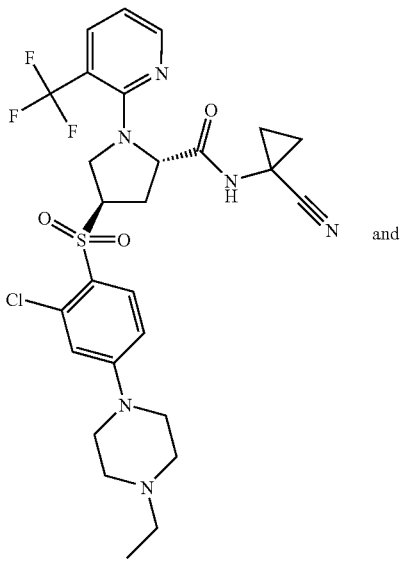

and (2R,4R)-4-[2-Chloro-4-(4-ethyl-piperazin-1-yl)-benzenesulfonyl]-1-(3-trifluoromethyl-pyridin-2-yl)-pyrrolidine-2-carboxylic acid (1-cyano-cyclopropyl)-amide

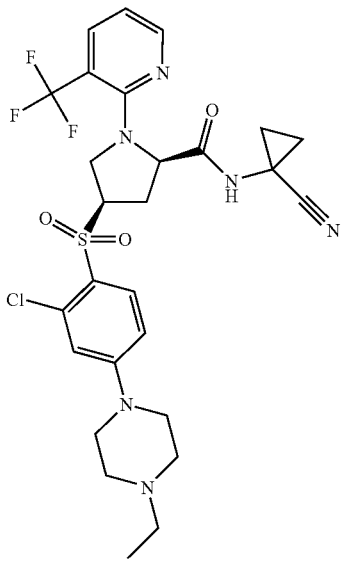

A solution of 4-(2-chloro-4-fluoro-benzenesulfonyl)-1-(3-trifluoromethyl-pyridin-2-yl)-pyrrolidine-2-carboxylic acid (1-cyano-cyclopropyl)-amide (0.084 g, 1.0 eq) in dry DMA (1.5 mL) was treated with N-ethylpiperatine (0.032 g, 1.7 eq) and cesium carbonate (0.09 g, 1.7 eq) and stirred for 3 dd at RT. The mixture was filtered and the filtrate evaporated. Two purifications by flash chromatography on silica gel with dichloromethane/methanol gradient and dichloromethane alone yielded the title compounds as white solids: (2S,4R)-4-[2-chloro-4-(4-ethyl-piperazin-1-yl)-benzenesulfonyl]-1-(3-trifluoromethyl-pyridin-2-yl)-pyrrolidine-2-carboxylic acid (1-cyano-cyclopropyl)-amide (0.003 g, 3%) and (2R,4R)-4-[2-Chloro-4-(4-ethyl-piperazin-1-yl)-benzenesulfonyl]-1-(3-trifluoromethyl-pyridin-2-yl)-pyrrolidine-2-carboxylic acid (1-cyano-cyclopropyl)-amide (0.002 g, 2%). MS (ESI): m/z=611.2 [M+H]$^+$ for both compounds.

4-(2-Chloro-4-fluoro-benzenesulfonyl)-1-(3-trifluoromethyl-pyridin-2-yl)-pyrrolidine-2-carboxylic acid (1-cyano-cyclopropyl)-amide was obtained in analogy to examples 164 and 166, using 2-chloro-4-fluorothiophenol in step 164c.

Example 192

(2S,4R)-1-(5-Methyl-2-phenyl-2H-pyrazol-3-yl)-4-(2-trifluoromethyl-benzenesulfonyl)-pyrrolidine-2-carboxylic acid (1-cyano-cyclopropyl)-amide

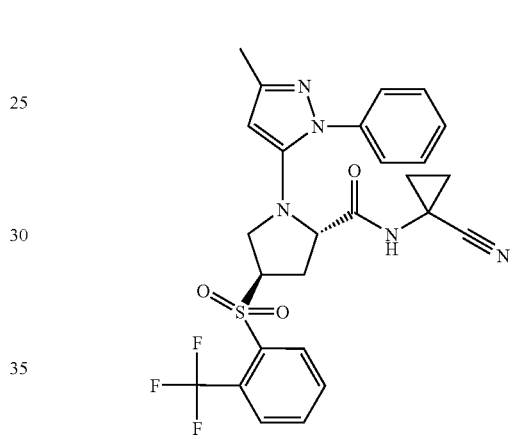

a) (2S,4S)-4-Hydroxy-pyrrolidine-1,2-dicarboxylic acid 1-tert-butyl ester 2-ethyl Ester To a stirred solution of (2S,4S)-4-hydroxy-pyrrolidine-1,2-dicarboxylic acid 1-tert-butyl ester (1.0 eq, 5.0 g) in ethyl acetate (250 mL) was added dicyclohexamine (2.0 eq, 8.62 mL) and the reaction stirred for 5 mins during which time a white precipitate formed. Part of the ethyl acetate was evaporated and the slurry left to stand for 30 mins, then filtered and washed with diethyl ether (30 mL). The filtrate was dried briefly under high vacuum and then resuspended in anhydrous DMF (50 mL). The reaction mixture was then treated with ethyl bromide (4.0 eq, 6.46 mL) and stirred in a sealed flask for 18 hours. TLC and MS revealed that the reaction was complete. The reaction mixture was filtered and washed with ethyl acetate (2×20 mL). The filtrate was then evaporated to dryness, the residue taken up in ethyl acetate (50 mL) and the organic layer washed once with water and once with brine, dried over sodium sulfate, filtered and evaporated to yield a colourless oil (4.87 g; 87%). The crude product was used without further purification. MS (ESI): m/z=204.1 [M+H-Boc]$^+$.

b) (2S,4S)-4-(3-Nitro-benzenesulfonyloxy)-pyrrolidine-1,2-dicarboxylic acid 1-tert-butyl ester 2-ethyl Ester 192a (4.87 g, 1 eq) was dissolved in dichloromethane (50 mL) and treated with 3-nitrobenzenesulfonyl chloride (5.25 g, 1.20 eq). The reaction mixture was then cooled to 0° C. using an ice bath and triethylamine (7.81 mL, 3.0 eq) added dropwise over 10 minutes. A colour change from colourless to bright yellow was apparent. The reaction mixture was then allowed to warm back to RT (still in the ice bath) and stirred overnight. A dark orange solution was formed. TLC and MS analysis revealed that the reaction was complete. The reaction mixture was diluted with additional dichloromethane (50 mL), and extracted in succession with aq 0.5M HCl, and saturated sodium carbonate solution. The combined organic layers were then washed with brine, dried over sodium sulfate, filtered and evaporated to yield a brown gum (8.45 g; 101%). The crude product was used without further purification. MS (ESI): m/z=445.2 [M+H]$^+$.

c) (2S,4R)-4-(2-Trifluoromethyl-phenylsulfanyl)-pyrrolidine-1,2-dicarboxylic acid 1-tert-butyl Ester 2-ethyl Ester NaH (1.24 g, 1.50 eq) was suspended in dry THF (220 mL) under argon. 2-trifluoromethylthiophenol (3.76 mL, 1.50 eq) was added dropwise, under argon over 10 mins, and the reaction stirred at RT for 2 hrs. 192b (8.45 g, 1 eq) was diluted in THF (50 mL) and the solution added under argon over 10 mins to the reaction mixture. The reaction was then stirred at 50° C. for 2 hrs during which time a white suspension appears. TLC and MS analysis revealed the reaction to be complete. At RT, the reaction mixture was poured over water (450 mL), and extracted with ethyl acetate (2×350 mL). The combined organic phases were then washed with brine, dried over sodium sulfate, filtered and evaporated to yield an orange oil (9.11 g; 114%). The crude product was used without further purification. MS (ESI): m/z=419.9 [M+H]$^+$.

d) (2S,4R)-4-(2-Trifluoromethyl-benzenesulfonyl)-pyrrolidine-1,2-dicarboxylic acid 1-tert-butyl Ester 2-ethyl Ester 192c (9.11 g, 1 eq) was dissolved in dichloromethane (65 mL), to which m-chloroperbenzoic acid (13.4 g, 2.5 eq) was added portionwise over 20 mins at RT. The reaction mixture was then stirred at for 17 hrs at RT, during which time a white precipitate forms. The precipitate was filtered and washed with dichloromethane (30 mL). The filtrate was then diluted slightly with dichloromethane (30 mL) and treated with saturated sodium carbonate (50 mL). The aqueous phase was then extracted three times with dichloromethane (3×40 mL), and the combined organic phases dried over sodium sulfate, filtered and evaporated to yield a yellow oil (8.30 g). The crude product was purified over silicagel with n-heptane:ethyl acetate gradient to yield the title compound as a colourless gum (5.14 g; 52%). MS (ESI): m/z=452.1 [M+H]$^+$.

e) (2S,4R)-4-(2-Trifluoromethyl-benzenesulfonyl)-pyrrolidine-2-carboxylic acid ethyl ester 192d (5.14 g, 1 eq) was diluted in dichloromethane (35 mL), to which TFA (10.98 mL, 12.60 eq) was added. The reaction was then stirred at RT for 1.5 hr. The reaction mixture was then evaporated to dryness and the residue taken up in dichloromethane (40 mL) and extracted twice with saturated sodium bicarbonate (30 mL). The combined organic phases were then dried over sodium sulfate, filtered and evaporated to yield a white solid (3.96 g; 99%). The crude product was used without further purification. MS (ESI): m/z=352.2 [M+H]$^+$.

f) (2S,4R)-1-(3-oxo-butyryl)-4-(2-trifluoromethyl-benzenesulfonyl)-pyrrolidine-2-carboxylic Acid Ethyl Ester 192e (3.0 g, 1 eq) was dissolved in toluene (70 mL), to which tert-butyl acetoacetate (1.42 mL, 1 eq) was added with stirring. The reaction mixture was stirred at 100° C. overnight. Reaction progress was monitored via TLC and MS. At completion, the solvent was evaporated to yield a brown oil (4.1 g). The crude product was purified over silicagel with n-heptane:ethyl acetate gradient to yield the title compound as a viscous brown oil (3.1 g, 84%). MS (ESI): m/z=436.1 [M+H]$^+$.

g) (2S,4R)-1-(3-Oxo-thiobutyryl)-4-(2-trifluoromethyl-benzenesulfonyl)-pyrrolidine-2-carboxylic acid ethyl ester 192f (3.1 g, 1 eq) was diluted in toluene (120 mL) under argon, to which Lawesson's reagent (1.45 g, 0.5 eq) was added with stirring. The reaction mixture was then stirred at 75° C. overnight. Reaction progress was monitored via TLC and MS. At completion, the solvent was evaporated to yield a dark red oil (5.0 g). The crude product was purified over silicagel with n-heptane:ethyl acetate gradient to yield the title compound as a brown solid (2.18 g, 67%). MS (ESI): m/z=452.0 [M+H]$^+$.

h) (2S,4R)-1-(5-Methyl-2-phenyl-2H-pyrazol-3-yl)-4-(2-trifluoromethyl-benzenesulfonyl)-pyrrolidine-2-carboxylic acid ethyl ester 192 g (0.290 g, 1 eq) was suspended in toluene (12 mL) under nitrogen, to which phenyl hydrazine (0.08 mL, 1.2 eq) was added and the reaction mixture stirred at 90° C. for 2 hours. TLC and MS analysis revealed that the reaction was complete. The reaction mixture was diluted in toluene (30 mL), and extracted with aq. 0.5N HCl and washed once with brine. The combined organic layers were dried over sodium sulfate, filtered and evaporated to yield a brown oil (0.35 g). The crude product was purified over silicagel with n-heptane:ethyl acetate gradient to yield the title compound as an orange solid (0.17 g, 51%). MS (ESI): m/z=508.2 [M+H]$^+$.

i) (2S,4R)-1-(5-Methyl-2-phenyl-2H-pyrazol-3-yl)-4-(2-trifluoromethyl-benzenesulfonyl)-pyrrolidine-2-carboxylic acid 192 h (0.17 g, 1 eq) was suspended in methanol (20 mL). LiOH 1N (0.66 mL, 2 eq) was added and the reaction was stirred at RT overnight. TLC and MS analysis revealed that the reaction was complete. The methanol was evaporated and the resulting residue dissolved in water (25 mL). The solution was then acidified with aq. 1N HCl. The desired acid did not fully precipitate, therefore the aqueous phase was extracted three times with ethyl acetate (3×30 mL). The combined organic layers were dried over sodium sulfate, filtered and evaporated to yield a colourless oil (0.12 g; 75%). The crude product was used without further purification. MS (ESI): m/z=480.2 [M+H]$^+$.

j) (2S,4R)-1-(5-Methyl-2-phenyl-2H-pyrazol-3-yl)-4-(2-trifluoromethyl-benzenesulfonyl)-pyrrolidine-2-carboxylic acid (1-cyano-cyclopropyl)-amide 192i (0.12 g, 1 eq) was diluted in dry THF (5 mL) under nitrogen, to which 4-methyl morpholine (0.08 mL, 3 eq) was added. Still under nitrogen, the reaction was cooled to −15° C. using a salted ice bath. Isobutyl chloroformate (0.04 mL, 1.2 eq) was then added dropwise over 3 minutes and the reaction stirred at −15° C. for 2 hrs. 1-aminocyclopropyl cyanic hydrochloride (0.035 g, 1.2 eq) was dissolved in dry DMF (2 mL) and this solution was then added dropwise, the ice bath removed and the reaction stirred at RT overnight. The reaction progress was monitored via TLC and MS. At completion, the solvent was evaporated to yield a brown oil (0.200 g). The crude product was purified over silicagel with n-heptane:ethyl acetate gradient to yield the title compound as a colourless solid (0.118 g, 87%). MS (ESI): m/z=544.1 [M+H]⁺.

Example 193

(2S,4R)-1-[2-(2-Chloro-pyridin-4-yl)-5-methyl-2H-pyrazol-3-yl]-4-(2-trifluoromethyl-benzenesulfonyl)-pyrrolidine-2-carboxylic acid (1-cyano-cyclopropyl)-amide

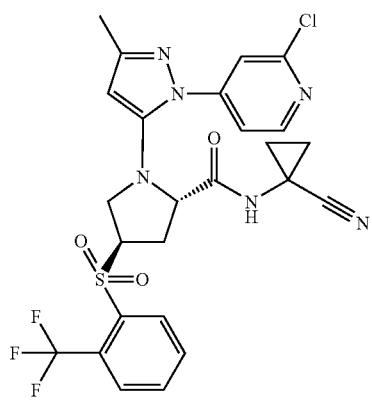

The title compound was prepared in analogy to example 192, by substituting phenyl hydrazine with (2-chloro-pyridin-4-yl)-hydrazine in step h. MS (ESI): m/z=579.1, 581.0 [M+H]⁺.

Example 194

(2S,4R)-1-[2-(4-Chloro-phenyl)-5-methyl-2H-pyrazol-3-yl]-4-(2-trifluoromethyl-benzenesulfonyl)-pyrrolidine-2-carboxylic acid (1-cyano-cyclopropyl)-amide

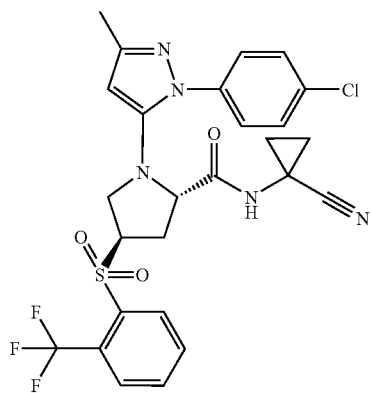

The title compound was prepared in analogy to example 192, by substituting phenyl hydrazine with 4-chloro-phenylhydrazine in step h. MS (ESI): m/z=578.1, 580.0 [M+H]⁺.

Example 195

(2S,4R)-1-[2-(4-Fluoro-phenyl)-5-methyl-2H-pyrazol-3-yl]-4-(2-trifluoromethyl-benzenesulfonyl)-pyrrolidine-2-carboxylic acid (1-cyano-cyclopropyl)-amide

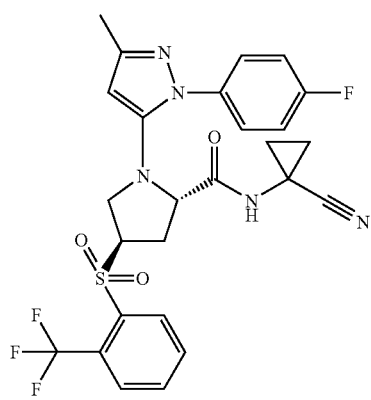

The title compound was prepared in analogy to example 192, by substituting phenyl hydrazine with 4-fluoro-phenylhydrazine in step h. MS (ESI): m/z=562.2 [M+H]⁺.

Example 196

(2S,4R)-1-[5-Methyl-2-(2-oxo-1,2-dihydro-pyridin-4-yl)-2H-pyrazol-3-yl]-4-(2-trifluoromethyl-benzenesulfonyl)-pyrrolidine-2-carboxylic acid (1-cyano-cyclopropyl)-amide

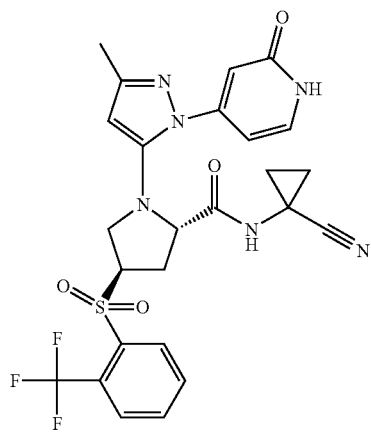

The title compound was prepared in analogy to example 192, by substituting phenyl hydrazine with 4-hydrazino-1H-pyridin-2-one in step h. MS (ESI): m/z=561.2 [M+H]⁺.

Example 197

(2S,4R)-4-[2-Chloro-4-((S)-2,2,2-trifluoro-1-methyl-ethoxy)-benzenesulfonyl]-1-cyclopropanecarbonyl-pyrrolidine-2-carboxylic acid (1-cyano-cyclopropyl)-amide

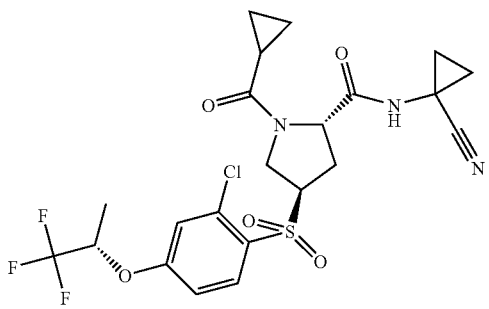

The title compound was prepared from example 183a according to the procedures described for example 149 via the intermediates 197a (Lithium; (2S,4R)-1-tert-butoxycarbonyl-4-[2-chloro-4-((S)-2,2,2-trifluoro-1-methyl-ethoxy)-benzenesulfonyl]-pyrrolidine-2-carboxylate), 197b ((2S,4R)-4-[2-Chloro-4-((S)-2,2,2-trifluoro-1-methyl-ethoxy)-benzenesulfonyl]-2-(1-cyano-cyclopropylcarbamoyl)-pyrrolidine-1-carboxylic acid tert-butyl ester) and 197c ((2S,4R)-4-[2-Chloro-4-((S)-2,2,2-trifluoro-1-methyl-ethoxy)-benzenesulfonyl]-pyrrolidine-2-carboxylic acid (1-cyano-cyclopropyl)-amide; 150 mg) to yield 76 mg (44%) of an amorphous colorless solid. MS (ESI): m/z=534.2 [M+H]⁺.

Example 198

(2R,4R)-4-[2-Chloro-4-((S)-2,2,2-trifluoro-1-methyl-ethoxy)-benzenesulfonyl]-1-cyclopropanecarbonyl-pyrrolidine-2-carboxylic acid (1-cyano-cyclopropyl)-amide

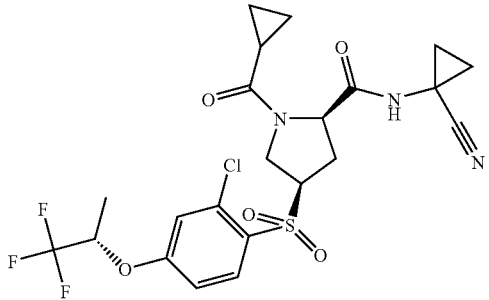

The title compound was obtained as a side-product during the synthesis of example 197 to yield an amorphous colorless solid. MS (ESI): m/z=534.2 [M+H]⁺.

Example 199

(2S,4R)-4-[2-Chloro-4-((S)-2,2,2-trifluoro-1-methyl-ethoxy)-benzenesulfonyl]-1-(1-methyl-cyclopropanecarbonyl)-pyrrolidine-2-carboxylic acid (1-cyano-cyclopropyl)-amide

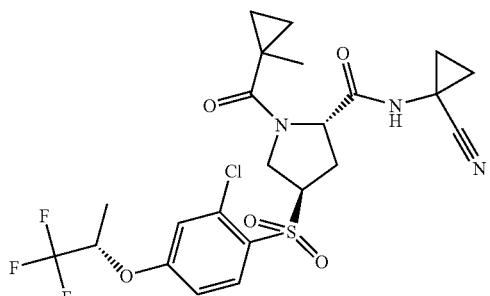

The title compound was prepared in analogy to example 197 using example 197c (150 mg) as starting material to yield 101 mg (57%) of a colorless gum. MS (ESI): m/z=548.2 [M+H]⁺.

Example 200

(2R,4R)-4-[2-Chloro-4-((S)-2,2,2-trifluoro-1-methyl-ethoxy)-benzenesulfonyl]-1-(1-methyl-cyclopropanecarbonyl)-pyrrolidine-2-carboxylic acid (1-cyano-cyclopropyl)-amide

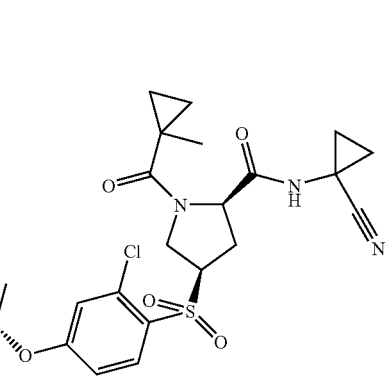

The title compound was obtained as a side-product during the synthesis of example 199 to yield an amorphous colorless solid. MS (ESI): m/z=548.2 [M+H]⁺.

Example 201

(2S,4R)-4-[2-Chloro-4-(oxetan-3-yloxy)-benzene-sulfonyl]-1-(1-trifluoromethyl-cyclopropanecarbo-nyl)-pyrrolidine-2-carboxylic acid (1-cyano-cyclo-propyl)-amide

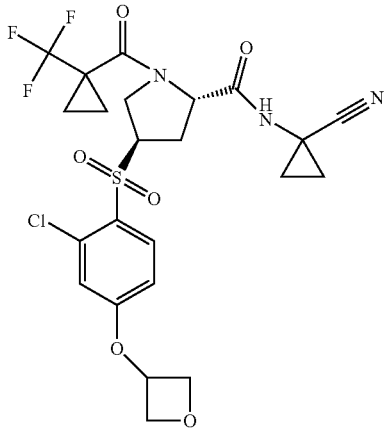

The title compound was prepared in analogy to example 149 using example 181 (90 mg) as starting material to yield 10 mg (8%) of a white solid. MS (ESI): m/z=562.2 [M+H]$^+$.

Example 202

(2S,4R)-1-[1-(4-Chloro-phenyl)-cyclopropanecarbo-nyl]-4-(2-trifluoromethyl-benzenesulfonyl)-pyrroli-dine-2-carboxylic acid (1-cyano-cyclopropyl)-amide

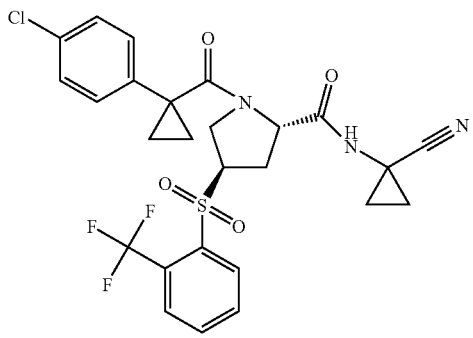

The title compound was prepared in analogy to example 149 using example 43 (160 mg) as starting material to yield 161 mg (75%) of a white solid. MS (ESI): m/z=566.2 [M+H]$^+$.

Example 203

(2S,4R)-4-[2-Chloro-4-((S)-2,2,2-trifluoro-1-methyl-ethoxy)-benzenesulfonyl]-1-(2,2-dimethyl-propio-nyl)-pyrrolidine-2-carboxylic acid (1-cyano-cyclo-propyl)-amide

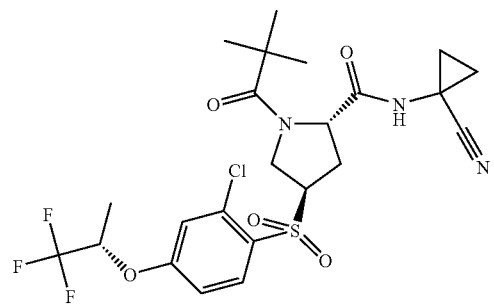

The title compound was prepared in analogy to example 197 using example 197c (150 mg) as starting material to yield 63 mg (36%) of a colorless amorphous solid. MS (ESI): m/z=550.2 [M+H]$^+$.

Example 204

(2R,4R)-4-[2-Chloro-4-((S)-2,2,2-trifluoro-1-me-thyl-ethoxy)-benzenesulfonyl]-1-(2,2-dimethyl-pro-pionyl)-pyrrolidine-2-carboxylic acid (1-cyano-cy-clopropyl)-amide

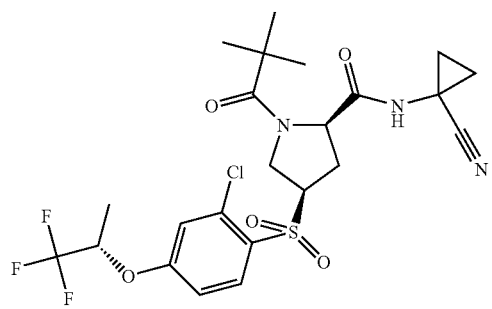

The title compound was obtained as a side-product during the synthesis of example 203 to yield an amorphous colorless solid. MS (ESI): m/z=550.3 [M+H]$^+$.

Example 205

(2S,4R)-4-(2-Trifluoromethyl-benzenesulfonyl)-1-(1-trifluoromethyl-cyclopropanecarbonyl)-pyrroli-dine-2-carboxylic acid (1-cyano-cyclopropyl)-amide

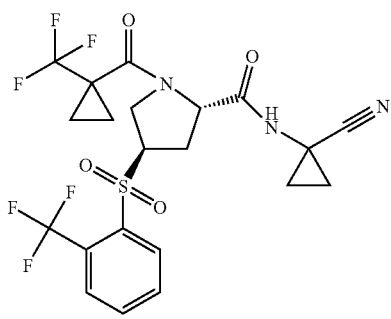

The title compound was prepared in analogy to example 149 using example 43 (80 mg) as starting material to yield 44 mg (45%) of an off-white solid. MS (ESI): m/z=524.1 [M+H]$^+$.

Example 206

(2S,4R)-4-(2-Trifluoromethyl-benzenesulfonyl)-1-(3,3,3-trifluoro-propionyl)-pyrrolidine-2-carboxylic acid (1-cyano-cyclopropyl)-amide

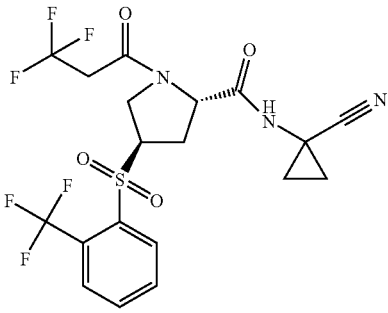

The title compound was prepared in analogy to example 149 using example 43 (80 mg) as starting material to yield 56 mg (60%) of an white solid. MS (ESI): m/z=498.1 [M+H]$^+$.

Example 207

(2S,4R)-1-(1-Methyl-cyclopropanecarbonyl)-4-(2-trifluoromethyl-benzenesulfonyl)-pyrrolidine-2-carboxylic acid (1-cyano-cyclopropyl)-amide

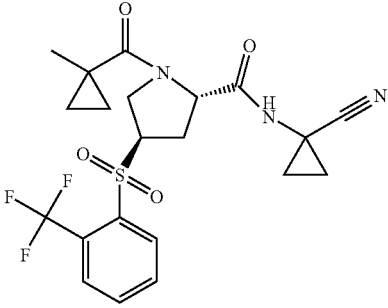

The title compound was prepared in analogy to example 149 using example 43 (80 mg) as starting material to yield 47 mg (53%) of an amorphous solid. MS (ESI): m/z=470.1 [M+H]$^+$.

Example 208

(2S,4R)-2-(1-Cyano-cyclopropylcarbamoyl)-4-[4-(2,2,2-trifluoro-ethoxy)-2-trifluoromethyl-benzenesulfonyl]-pyrrolidine-1-carboxylic acid tert-butyl ester

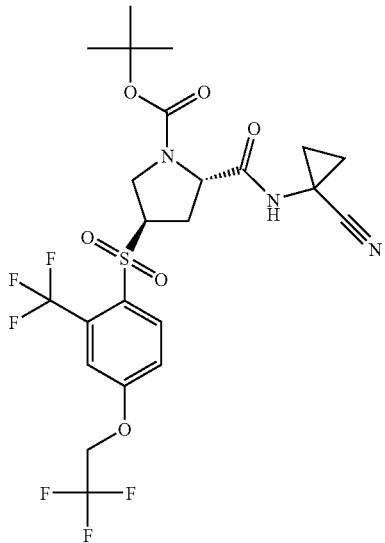

a) 4-Fluoro-2-trifluoromethyl-benzenethiol

4-Fluoro-2-(trifluoromethyl)benzenesulphonyl chloride (2.0 g) was dissolved in dioxane (12 mL) under a N$_2$-atmosphere at ambient temperature. Water (3.0 mL) and tris-(2-carboxylethyl)phosphine hydrochloride (8.73 g) was added afterwards. The reaction mixture is stirred under reflux for 6 h. The reaction mixture is cooled to 25° C. and dissolved with water (30 mL). The product is extracted with CH$_2$Cl$_2$ (100 mL) several times. The combined organic layers are washed with water and dried over Na$_2$SO$_4$. The organic layer is filtrated and evaporated to dryness to yield 1.27 g (85%) of a colorless liquid which is used without further purification. MS (ESI): m/z=194.9 [M−H]$^-$.

b) (2S,4R)-4-(4-Fluoro-2-trifluoromethyl-phenylsulfanyl)-pyrrolidine-1,2-dicarboxylic Acid 1-tert-butyl ester 2-methyl ester The title compound was prepared from example 120a (1.1 g) and example 208a (0.6 g) in analogy to the methods described for example 120b to yield the title compound as a colorless viscous oil (0.93 g; 86%). MS (ESI): m/z=332.2 [M+H]$^+$.

c) (2S,4R)-4-(4-Fluoro-2-trifluoromethyl-benzenesulfonyl)-pyrrolidine-1,2-dicarboxylic Acid 1-tert-butyl ester 2-methyl ester The title compound was prepared from example 208b (0.932 g) in analogy to the methods described for example 120c to yield the title compound as a light yellow viscous oil (0.958 g; 96%). MS (ESI): m/z=456.1 [M+H]$^+$.

d) (2S,4R)-4-[4-(2,2,2-Trifluoro-ethoxy)-2-trifluoromethyl-benzenesulfonyl]-pyrrolidine-1,2-dicarboxylic acid 1-tert-butyl ester 2-methyl ester The title compound was prepared from example 208c (0.5 g) and 2,2,2-trifluoroethanol (0.132 g) in analogy to the methods described for example 122a to yield the title compound as a brown oil (0.587 g; 99%). MS (ESI): m/z=536.1 [M+H]$^+$.

e) (2S,4R)-4-[4-(2,2,2-Trifluoro-ethoxy)-2-trifluoromethyl-benzenesulfonyl]-pyrrolidine-1,2-dicarboxylic acid 1-tert-butyl ester The title compound was prepared from example 208d (0.587 g) in analogy to the methods described for example 122b. To obtained Lithium salt was treated with CH$_2$Cl$_2$ and extracted with aqueous 0.1M HCl solution and brine. The organic layer was dried over Na$_2$SO$_4$. The organic layer was filtrated and evaporated to dryness to yield the title compound as an off-white solid (0.587 g; 100%). MS (ESI): m/z=544.1 [M+Na]$^+$.

(2S,4R)-2-(1-Cyano-cyclopropylcarbamoyl)-4-[4-(2,2,2-trifluoro-ethoxy)-2-trifluoromethyl-benzenesulfonyl]-pyrrolidine-1-carboxylic acid tert-butyl ester The final compound 208 is prepared from example 208e (0.587 g) in analogy to the methods described for example 122 to yield 0.544 g (84%) of an off-white amorphous solid. MS (ESI): m/z=586.1 [M+H]$^+$.

Example 209

(2S,4R)-4-(4-Fluoro-2-trifluoromethyl-benzene-sulfonyl)-1-(1-trifluoromethyl-cyclopropanecarbonyl)-pyrrolidine-2-carboxylic acid (1-cyano-cyclopropyl)-amide

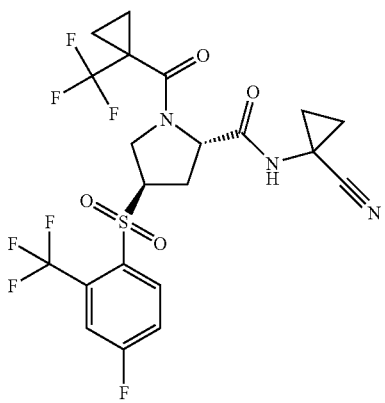

a) (2S,4R)-4-(4-Fluoro-2-trifluoromethyl-benzene-sulfonyl)-pyrrolidine-1,2-dicarboxylic Acid 1-tert-butyl ester The title compound was prepared from example 208c (250 mg) in analogy to the method described for example 208e to yield 236 mg (97%) of a white solid. MS (ESI): m/z=342.0 [M+H-Boc]⁺.

b) (2S,4R)-2-(1-Cyano-cyclopropylcarbamoyl)-4-(4-fluoro-2-trifluoromethyl-benzenesulfonyl)-pyrrolidine-1-carboxylic acid tert-butyl ester The title compound was prepared from example 209a (236 mg) in analogy to the method described for example 208 to yield 373 mg (138%) of a colorless viscous oil. MS (ESI): m/z=504.1 [M+H]⁺.

c) (2S,4R)-4-(4-Fluoro-2-trifluoromethyl-benzene-sulfonyl)-pyrrolidine-2-carboxylic acid (1-cyano-cyclopropyl)-amide Example 209c was prepared from example 209b (373 mg) in analogy to the methods describe for example 197c to yield 318 mg (106%) of an amorphous brown solid. MS (ESI): m/z=404.1 [M+H]⁺.

(2S,4R)-4-(4-Fluoro-2-trifluoromethyl-benzene-sulfonyl)-1-(1-trifluoromethyl-cyclopropanecarbonyl)-pyrrolidine-2-carboxylic acid (1-cyano-cyclopropyl)-amide The final example 209 was prepared from example 209c (106 mg) in analogy to the methods described for example 135 to yield 42 mg (30%) of a white solid. MS (ESI): m/z=542.3 [M+H]⁺.

Example 210

(2S,4R)-1-(2,2-Dimethyl-propionyl)-4-(4-fluoro-2-trifluoromethyl-benzenesulfonyl)-pyrrolidine-2-carboxylic acid (1-cyano-cyclopropyl)-amide

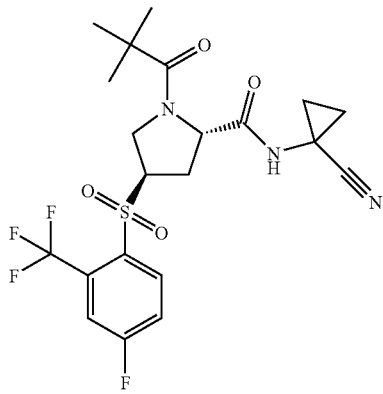

The title compound was prepared from example 209c (106 mg) in analogy to the methods described for example 209 to yield 14 mg (11%) of a colorless solid. MS (ESI): m/z=490.2 [M+H]⁺.

Example 211

(2S,4R)-1-(1-Methyl-cyclopropanecarbonyl)-4-[4-(2,2,2-trifluoro-ethoxy)-2-trifluoromethyl-benzene-sulfonyl]-pyrrolidine-2-carboxylic acid (1-cyano-cyclopropyl)-amide

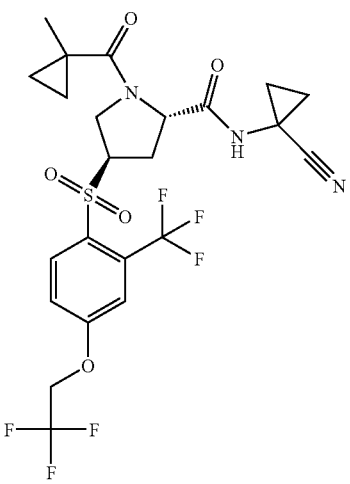

a) (2S,4R)-4-[4-(2,2,2-Trifluoro-ethoxy)-2-trifluoromethyl-benzenesulfonyl]-pyrrolidine-2-carboxylic acid (1-cyano-cyclopropyl)-amide The title compound was prepared from example 208 (389 mg) in analogy to the methods described for example 209c to yield example 211a (258 mg; 80%) as light yellow amorphous material. MS (ESI): m/z=486.2 [M+H]⁺.

(2S,4R)-1-(1-Methyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide The final example 211 was prepared from example 211a (100 mg) in analogy to the methods described for example 210 to yield 85 mg (73%) as a light yellow amorphous material. MS (ESI): m/z=568.3 [M+H]+.

Example 212

(2S,4R)-1-(2,2-Dimethyl-propionyl)-4-[4-(2,2,2-trifluoro-ethoxy)-2-trifluoromethyl-benzenesulfonyl]-pyrrolidine-2-carboxylic acid (1-cyano-cyclopropyl)-amide

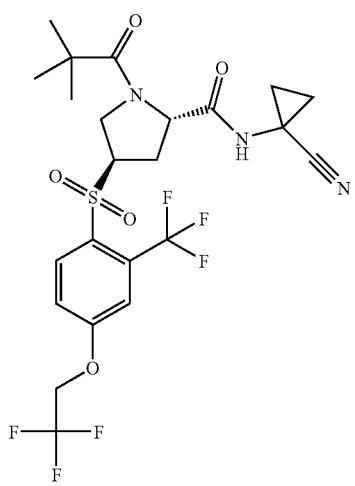

The title compound was prepared from example 211a (100 mg) in analogy to the methods described for example 211 to yield 78 mg (67%) as a light yellow amorphous material. MS (ESI): m/z=570.3 [M+H]+.

Example 213

(2S,4R)-4-(2-Chloro-benzenesulfonyl)-1-(1-trifluoromethyl-cyclopropanecarbonyl)-pyrrolidine-2-carboxylic acid (1-cyano-cyclopropyl)-amide

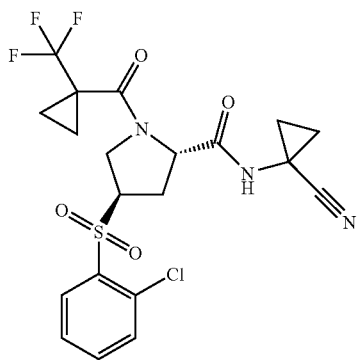

The title compound was prepared in analogy to example 149 using example 42 (100 mg) as starting material to yield 90 mg (72%) of an white solid. MS (ESI): m/z=490.2 [M+H]+.

Example 214

(2S,4R)-4-(2-Chloro-benzenesulfonyl)-1-(1-methyl-cyclopropanecarbonyl)-pyrrolidine-2-carboxylic acid (1-cyano-cyclopropyl)-amide

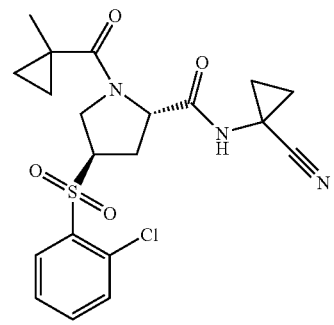

The title compound was prepared in analogy to example 149 using example 42 (100 mg) as starting material to yield 83 mg (75%) of an white solid. MS (ESI): m/z=436.2 [M+H]+.

Example 215

(2S,4R)-4-(2-Chloro-benzenesulfonyl)-1-[1-(4-chloro-phenyl)-cyclopropanecarbonyl]-pyrrolidine-2-carboxylic acid (1-cyano-cyclopropyl)-amide

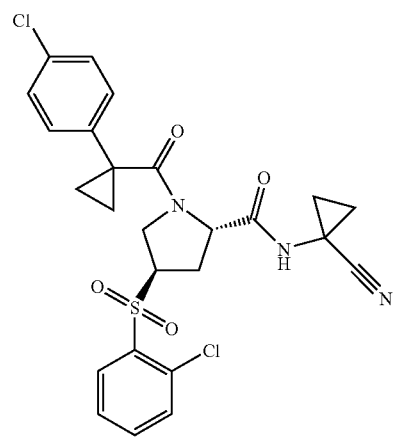

The title compound was prepared in analogy to example 149 using example 42 (100 mg) as starting material to yield 113 mg (83%) of an white solid. MS (ESI): m/z=532.1 [M+H]+.

Example 216

(2S,4R)-4-(2-Chloro-benzenesulfonyl)-1-(1-phenyl-cyclopropanecarbonyl)-pyrrolidine-2-carboxylic acid (1-cyano-cyclopropyl)-amide

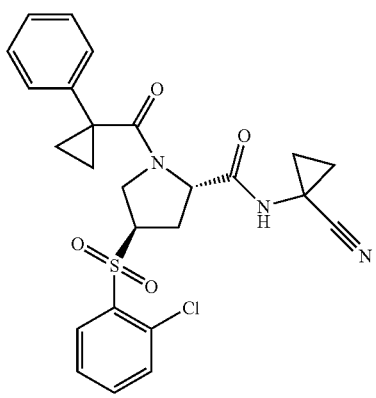

The title compound was prepared in analogy to example 149 using example 42 (100 mg) as starting material to yield 97 mg (76%) of an white solid. MS (ESI): m/z=498.2 [M+H]$^+$.

Example 217

(2S,4R)-4-(2-Chloro-benzenesulfonyl)-1-(2,2-dimethyl-propionyl)-pyrrolidine-2-carboxylic Acid (1-cyano-cyclopropyl)-amide

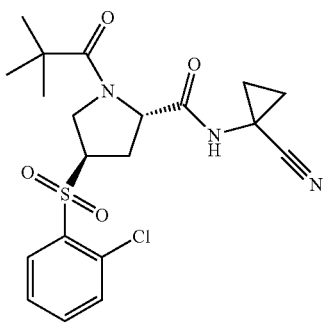

The title compound was prepared in analogy to example 149 using example 42 (100 mg) as starting material to yield 72 mg (64%) of an amorphous solid. MS (ESI): m/z=438.2 [M+H]$^+$.

Example 218

(2S,4R)-4-(2-Chloro-benzenesulfonyl)-1-isobutyryl-pyrrolidine-2-carboxylic acid (1-cyano-cyclopropyl)-amide

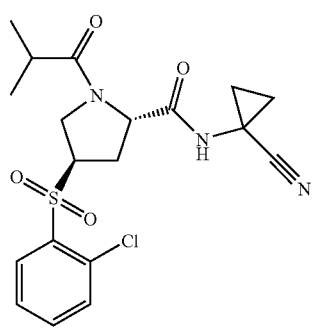

The title compound was prepared in analogy to example 149 using example 42 (100 mg) as starting material to yield 86 mg (79%) of a white solid. MS (ESI): m/z=424.2 [M+H]$^+$.

Example 219

(2S,4R)-4-(2-Chloro-benzenesulfonyl)-1-(3,3,3-trifluoro-propionyl)-pyrrolidine-2-carboxylic Acid (1-cyano-cyclopropyl)-amide

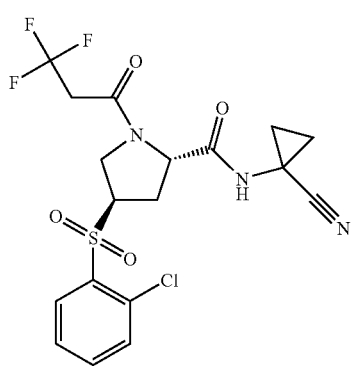

The title compound was prepared in analogy to example 149 using example 42 (100 mg) as starting material to yield 89 mg (75%) of an amorphous light yellow solid. MS (ESI): m/z=464.1 [M+H]$^+$.

Example 220

(2S,4R)-4-(2-Chloro-benzenesulfonyl)-1-(3-methyl-butyryl)-pyrrolidine-2-carboxylic acid (1-cyano-cyclopropyl)-amide

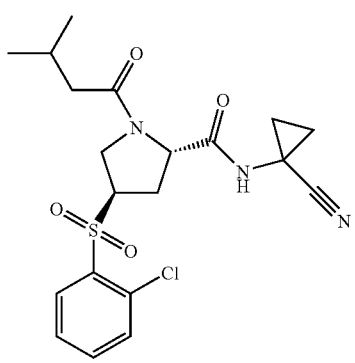

The title compound was prepared in analogy to example 149 using example 42 (100 mg) as starting material to yield 83 mg (74%) of an amorphous light yellow solid. MS (ESI): m/z=438.2 [M+H]$^+$.

Example 221

(2S,4R)-4-[4-Chloro-2-(2,2,2-trifluoro-ethoxy)-benzenesulfonyl]-2-(1-cyano-cyclopropylcarbamoyl)-pyrrolidine-1-carboxylic acid tert-butyl ester

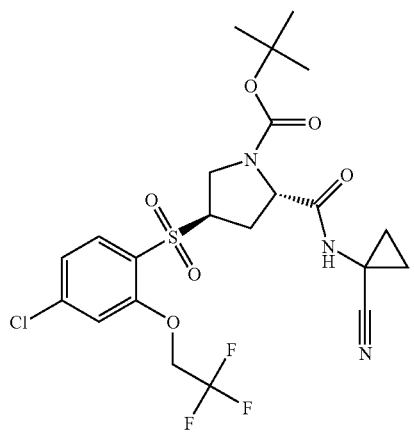

The title compound was isolated as a by-product during the synthesis of example 171 when starting from (2S,4R)-4-(2,4-dichloro-benzenesulfonyl)-pyrrolidine-1,2-dicarboxylic acid 1-tert-butyl ester 2-methyl ester instead of (2S,4R)-4-(2-chloro-4-fluoro-benzenesulfonyl)-pyrrolidine-1,2-dicarboxylic acid 1-tert-butyl ester 2-methyl ester to yield 341 mg (25%) of colorless foam. MS (ESI): m/z=552.2 [M+H]+.

Example 222

(2S,4R)-4-(2,4-Dichloro-benzenesulfonyl)-1-(1-methyl-cyclopropanecarbonyl)-pyrrolidine-2-carboxylic acid (1-cyano-cyclopropyl)-amide

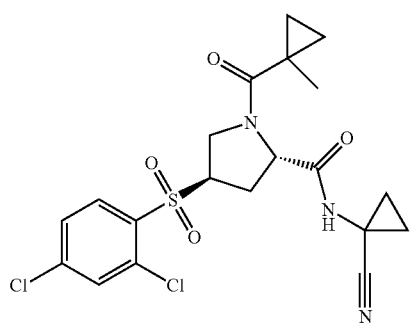

The title compound was prepared in analogy to example 149 using example 15 as a free base (150 mg) as starting material to yield 117 mg (64%) of colorless solid. MS (ESI): m/z=470.1 [M+H]+.

Example 223

(2S,4R)-1-[1-(4-Chloro-phenyl)-cyclopropanecarbonyl]-4-(2,4-dichloro-benzenesulfonyl)-pyrrolidine-2-carboxylic acid (1-cyano-cyclopropyl)-amide

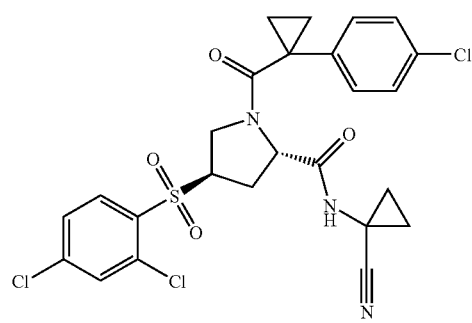

The title compound was prepared in analogy to example 222 using example 15 as a free base (150 mg) as starting material to yield 143 mg (65%) of colorless solid. MS (ESI): m/z=568.2 [M+H]+.

Example 224

(2S,4R)-4-(2,4-Dichloro-benzenesulfonyl)-1-(1-phenyl-cyclopropanecarbonyl)-pyrrolidine-2-carboxylic acid (1-cyano-cyclopropyl)-amide

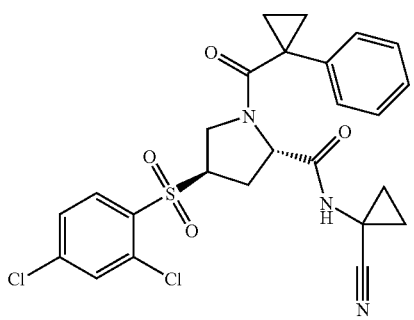

The title compound was prepared in analogy to example 222 using example 15 as a free base (150 mg) as starting material to yield 131 mg (64%) of colorless solid. MS (ESI): m/z=532.1 [M+H]+.

Example 225

(2S,4R)-4-(2,4-Dichloro-benzenesulfonyl)-1-(2,2-dimethyl-propionyl)-pyrrolidine-2-carboxylic Acid (1-cyano-cyclopropyl)-amide

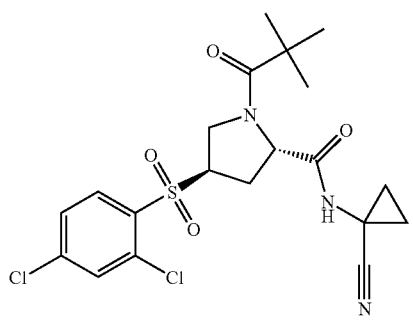

The title compound was prepared in analogy to example 222 using example 15 as a free base (150 mg) as starting material to yield 99 mg (54%) of colorless foam. MS (ESI): m/z=472.1 [M+H]⁺.

Example 226

(2S,4R)-4-(2,4-Dichloro-benzenesulfonyl)-1-isobutyryl-pyrrolidine-2-carboxylic acid (1-cyano-cyclopropyl)-amide

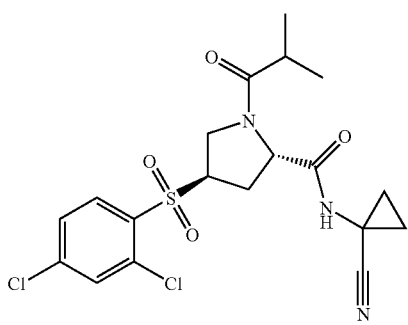

The title compound was prepared in analogy to example 222 using example 15 as a free base (150 mg) as starting material to yield 103 mg (58%) of colorless amorphous solid. MS (ESI): m/z=458.1 [M+H]⁺.

Example 227

(2S,4R)-4-(2,4-Dichloro-benzenesulfonyl)-1-(3,3,3-trifluoro-propionyl)-pyrrolidine-2-carboxylic acid (1-cyano-cyclopropyl)-amide

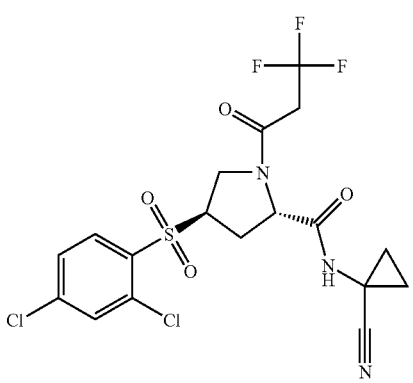

The title compound was prepared in analogy to example 222 using example 15 as a free base (150 mg) as starting material to yield 98 mg (51%) of colorless foam. MS (ESI): m/z=498.0 [M+H]⁺.

Example 228

(2S,4R)-4-(2,4-Dichloro-benzenesulfonyl)-1-(3-methyl-butyryl)-pyrrolidine-2-carboxylic acid (1-cyano-cyclopropyl)-amide

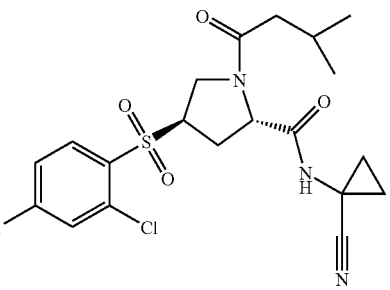

The title compound was prepared in analogy to example 222 using example 15 as a free base (150 mg) as starting material to yield 90 mg (49%) of colorless amorphous material. MS (ESI): m/z=472.1 [M+H]⁺.

Example 229

(2S,4R)-4-[2-Chloro-4-((S)-2,2,2-trifluoro-1-methylethoxy)-benzenesulfonyl]-2-(1-cyano-cyclopropylcarbamoyl)-pyrrolidine-1-carboxylic acid tert-butyl ester

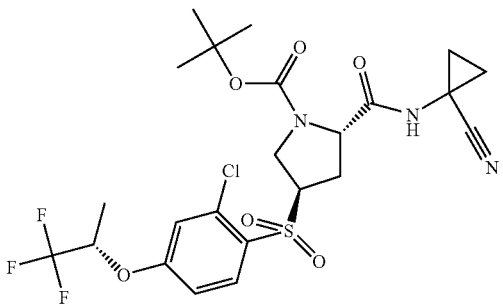

The title compound was prepared in analogy to example 122 using (S)-trifluoroisopropanol as starting material to yield 74% of colorless foam. MS (ESI): m/z=566.1 [M+H]⁺.

Example 230

(2S,4R)-4-[2-Chloro-4-((S)-2,2,2-trifluoro-1-methylethoxy)-benzenesulfonyl]-pyrrolidine-2-carboxylic acid (1-cyano-cyclopropyl)-amide

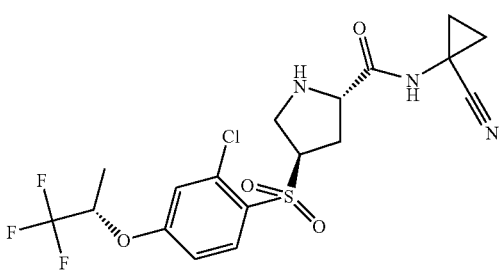

Example 229 (8.1 g) was dissolved in formic acid (40.0 mL) and stirred at ambient temperature for totally 8.0 h. The reaction mixture was treated carefully with cold aq. 10%-Na₂CO₃-solution (400 ml) until pH=8 was reached. The mixture was extracted with CH₂Cl₂ (500 mL). The aqueous phase was washed totally 4 times with CH₂Cl₂, the combined organic layers were washed with brine, dried over Na₂SO₄, filtered and evaporated to dryness to yield 6.43 g (96%) of colorless amorphous material. MS (ESI): m/z=466.1 [M+H]⁺.

Example 231

4-{5-[(2S,4R)-2-(1-Cyano-cyclopropylcarbamoyl)-4-(2-trifluoromethyl-benzenesulfonyl)-pyrrolidin-1-yl]-3-methyl-pyrazol-1-yl}-2-oxo-2H-pyridine-1-carboxylic acid Isobutyl ester

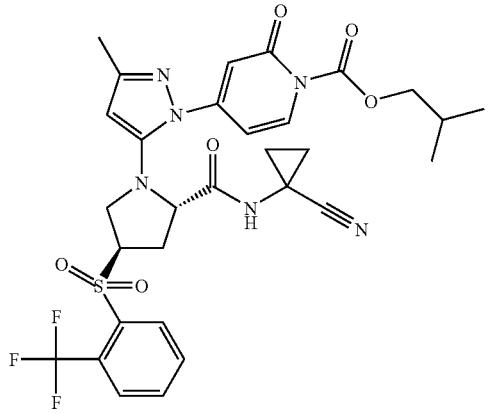

The title compound was prepared in analogy to example 192, by substituting phenyl hydrazine with 4-hydrazino-1H-pyridin-2-one in step h. MS (ESI): m/z=661 [M+H]⁺.

Example 232

(2S,4R)-1-[5-Methyl-2-(4-trifluoromethyl-phenyl)-2H-pyrazol-3-yl]-4-(2-trifluoromethyl-benzenesulfonyl)-pyrrolidine-2-carboxylic acid (1-cyano-cyclopropyl)-amide

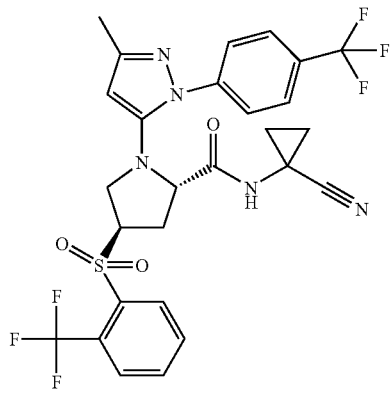

The title compound was prepared in analogy to example 192, by substituting phenyl hydrazine with 4-trifluoromethyl-phenylhydrazine in step h. MS (ESI): m/z=612.2 [M+H]⁺.

Example 233

(2S,4R)-1-[2-(3-Chloro-phenyl)-5-methyl-2H-pyrazol-3-yl]-4-(2-trifluoromethyl-benzenesulfonyl)-pyrrolidine-2-carboxylic acid (1-cyano-cyclopropyl)-amide

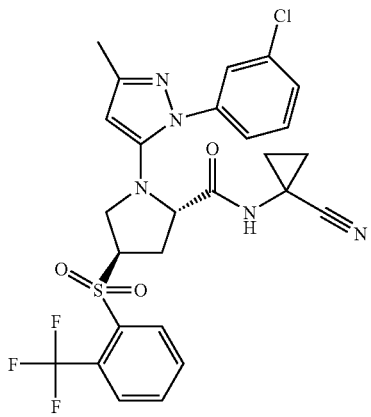

The title compound was prepared in analogy to example 192, by substituting phenyl hydrazine with 3-chloro-phenyl-hydrazine in step h. MS (ESI): m/z=578.1 [M+H]⁺.

Example 234

(2S,4R)-1-(5-Methyl-2-thiazol-2-yl-2H-pyrazol-3-yl)-4-(2-trifluoromethyl-benzenesulfonyl)-pyrrolidine-2-carboxylic acid (1-cyano-cyclopropyl)-amide

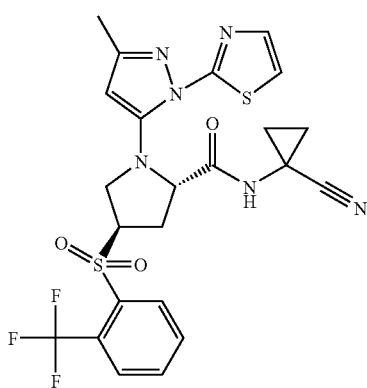

The title compound was prepared in analogy to example 192, by substituting phenyl hydrazine with 2-hydrazino-1,3-thiazole in step h. MS (ESI): m/z=551.1 [M+H]⁺.

Example 235

(2S,4R)-1-[1-(4-Chloro-phenyl)-cyclopropanecarbonyl]-4-(2,4-difluoro-benzenesulfonyl)-pyrrolidine-2-carboxylic acid (1-cyano-cyclopropyl)-amide

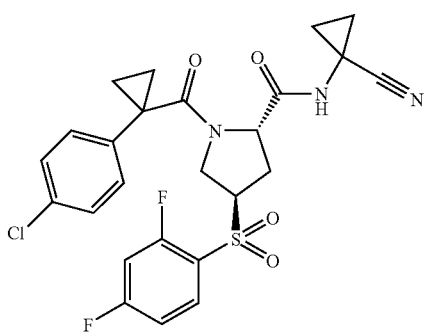

The title compound was prepared in analogy to example 215 using example 17 (44 mg) as starting material to yield 25 mg (42%) of colorless solid. MS (ESI): m/z=534.1 [M+H]⁺.

Example 236

(2S,4R)-1-[1-(4-Chloro-phenyl)-cyclopropanecarbonyl]-4-(2-methyl-propane-1-sulfonyl)-pyrrolidine-2-carboxylic acid (1-cyano-cyclopropyl)-amide

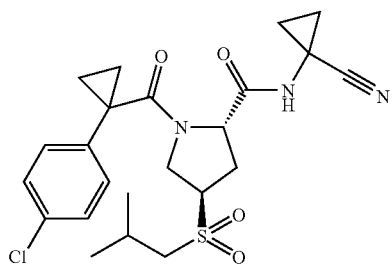

The title compound was prepared in analogy to example 215 using example 114 (28 mg) as starting material to yield 25 mg (63%) of colorless solid. MS (ESI): m/z=472.1 [M+H]⁺.

Example 237

(2S,4R)-4-[4-(2,2,2-Trifluoro-ethoxy)-2-trifluoromethyl-benzenesulfonyl]-1-(1-trifluoromethyl-cyclopropanecarbonyl)-pyrrolidine-2-carboxylic acid (1-cyano-cyclopropyl)-amide

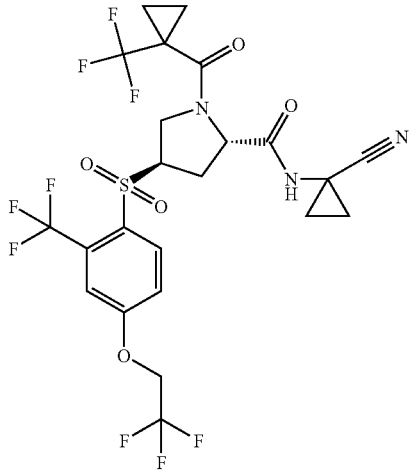

(2S,4R)-4-[4-(2,2,2-Trifluoro-ethoxy)-2-trifluoromethyl-benzenesulfonyl]-pyrrolidine-2-carboxylic acid (1-cyano-cyclopropyl)-amide (20 mg, 41 umol; example 211a) was dissolved in DMF (0.4 ml) under a N₂-atmosphere at ambient temperature. 1-Trifluoromethyl-cyclopropanecarboxylic acid (10 mg, 62 umol; CAS Reg. No. 277756-46-4), HATU (23 mg, 62 umol) and DIEA (10 ul, 62 umol) were added and the reaction mixture was stirred for 48 h at ambient temperature. Ice water/brine 1/1 and iPrOAc were added and the layers were separated. The aqueous layer was extracted one more time with iPrOAc, the combined organic layers were washed with ice water/brine 1/1 and dried over Na₂SO₄. The solvent was removed under reduced pressure to give a yellow oil which was purified by preparative thin layer chromatography (silica gel, iPrOAc/heptane) to obtain the title compound (13 mg, 21 umol; 51%) as colorless solid. MS (ESI): m/z=622.3 [M+H]⁺.

Example 238

(2S,4R)-4-[4-(1-Methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

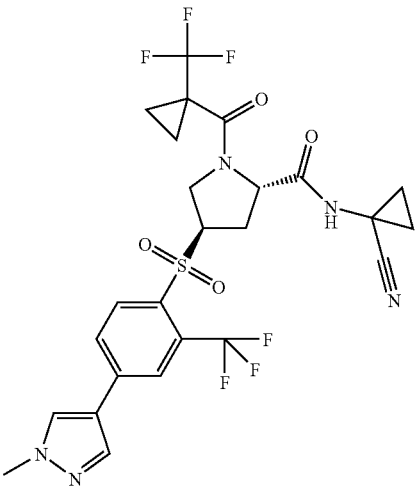

a) Synthesis of (2S,4R)-4-(4-Bromo-2-trifluoromethyl-benzenesulfonyl)-1-(1-trifluoromethyl-cyclopropanecarbonyl)-pyrrolidine-2-carboxylic acid (1-cyano-cyclopropyl)-amide

Example 239

(2S,4R)-4-[2-Chloro-4-(2,2,2-trifluoro-ethoxy)-benzenesulfonyl]-1-[1-(3,4-dichloro-phenyl)-cyclopropanecarbonyl]-pyrrolidine-2-carboxylic acid (1-cyano-cyclopropyl)-amide

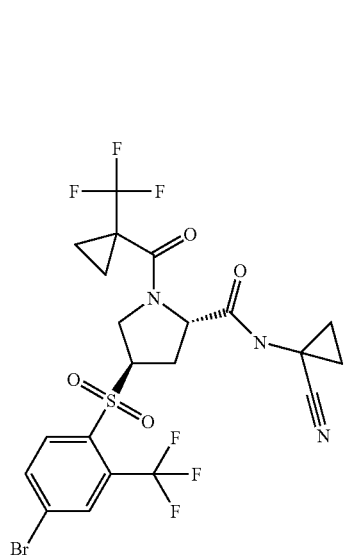

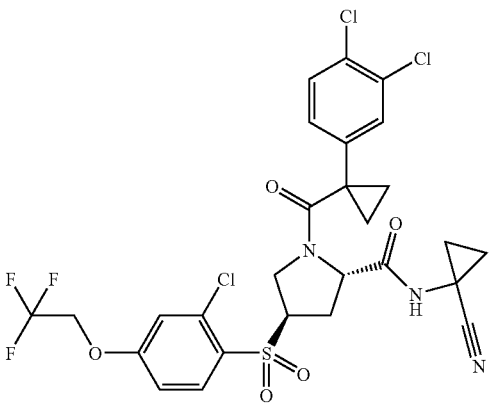

Example 173 (75 mg) was dissolved in acetonitrile (1 ml). To this solution (2-(7-aza-1H-benzotriazole-1-yl)-1,1,3,3-tetramethyluronium hexafluorophosphate) (126 mg), diisopropylethylamine (44 mg) and 1-(3,4-dichlorophenyl)cyclopropane carboxylic acid (46 mg) were added and stirred for 24 h at ambient temperature. The reaction mixture was purified by chromatography on silica gel to yield the title compound as a colorless semisolid (79 mg; 68%). MS (ESI): m/z=664.1 [M−H]⁻.

Example 238a was prepared in analogy to example 145 using example 18 (375 mg) as a starting material to yield 297 mg (61%) of white foam. MS (ESI): m/z=604.0 [M+H]⁺.

b) Synthesis of (2S,4R)-4-[4-(1-Methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

Example 240

(2S,4R)-4-[2-Chloro-4-(2,2,2-trifluoro-ethoxy)-benzenesulfonyl]-1-(1-phenyl-cyclopropanecarbonyl)-pyrrolidine-2-carboxylic acid (1-cyano-cyclopropyl)-amide Argon was bubbled for 15 minutes through a mixture of 238a (0.100 g), 1-methyl-4-(4.4.5.5-tetramethyl-1.3.2-dioxaborolan)-1H-pyrazole (0.048 g, 1.4 eq.) and Na₂CO₃ (0.048 g, 2.7 eq.) in DMF (3.0 mL) and water (226 μL). Then [1,1-bis(diphenyl-phosphino) ferrocene]palladium (II) chloride 1:1 complex with CH₂Cl₂ (0.014 g, 0.1 eq.) was added and the orange mixture was heated at 80° C. for 3 hours (TLC-check revealed complete reaction). The mixture was cooled to 25° C., then poured into a mixture of aqueous 5% NaHCO₃-solution/ice and extracted with EtOAc (3×50 mL). The organic layers were washed with water and brine, dried over Na₂SO₄, filtered and evaporated. The crude material was absorbed on Si-amine silica gel and purified once by flash chromatography (20 g Si-amine CH₂Cl₂/EtOAc). After that the obtained mixture was purified with chiral preparative HPLC to yield 17 mg (17%) of an amorphous colorless material. MS (ESI): m/z=604.2 [M+H]⁺.

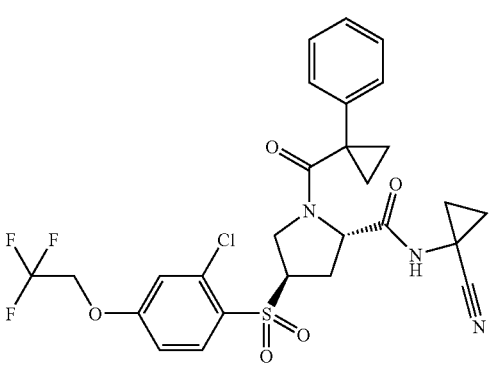

The title compound was prepared in analogy to example 239 using example 173 (75 mg) and 1-phenyl-1-cyclopropanecarboxylic acid to yield 53 mg (53%) of colorless semisolid. MS (ESI): m/z=696.12 [M+H]⁺.

Example 241

(2S,4R)-4-[2-Chloro-4-(2,2,2-trifluoro-ethoxy)-benzenesulfonyl]-1-(2,2-difluoro-cyclopropanecarbonyl)-pyrrolidine-2-carboxylic acid (1-cyano-cyclopropyl)-amide

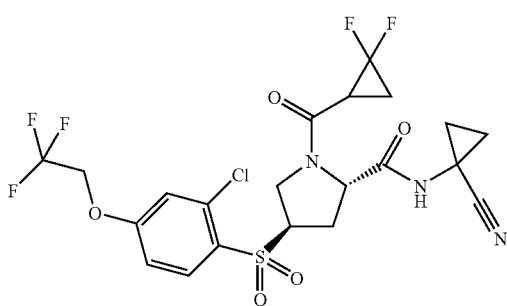

The title compound was prepared in analogy to example 239 using example 173 (75 mg) and 2,2-difluorocyclopropane carboxylic acid to yield 59 mg (59%) of colorless semi-solid. MS (ESI): m/z=554.0 [M–H]⁻.

Example 242

{1-[(2S,4R)-4-[2-Chloro-4-(2,2,2-trifluoro-ethoxy)-benzenesulfonyl]-2-(1-cyano-cyclopropylcarbamoyl)-pyrrolidine-1-carbonyl]-cyclopropyl}-carbamic Acid Tert-butyl ester

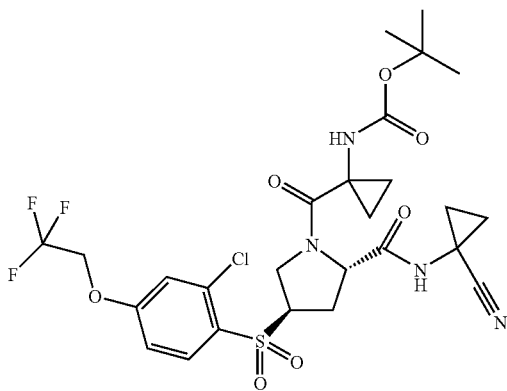

The title compound was prepared in analogy to example 239 using example 173 (75 mg) and 1 [(tert-butoxycarbonyl)amino]cyclopropanecarboxylic acid to yield 30 mg (27%) of white solid. MS (ESI): m/z=657.1 [M-FNa]⁺.

Example 243

(2S,4R)-4-[2-Chloro-4-(2,2,2-trifluoro-ethoxy)-benzenesulfonyl]-1-(1-cyano-cyclopropanecarbonyl)-pyrrolidine-2-carboxylic acid (1-cyano-cyclopropyl)-amide

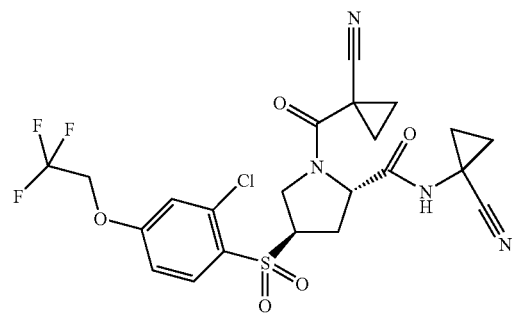

The title compound was prepared in analogy to example 239 using example 173 (75 mg) and 1-cyanocyclopropanecarboxylic acid to yield 55 mg (58%) of a colorless semi-solid. MS (ESI): m/z=662.1 [M+Na]⁺.

Example 244

(2S,4R)-1-[2-(4-Chloro-phenyl)-acetyl]-4-[2-chloro-4-(2,2,2-trifluoro-ethoxy)-benzenesulfonyl]-pyrrolidine-2-carboxylic acid (1-cyano-cyclopropyl)-amide

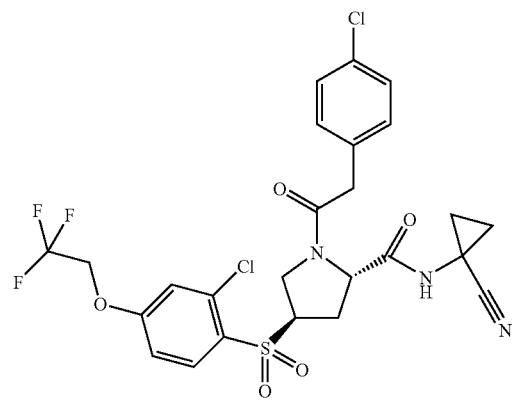

The title compound was prepared in analogy to example 239 using example 173 (75 mg) and 4-chlorophenylacetic acid to yield 100 mg (quant.) of a colorless liquid. MS (ESI): m/z=604.1 [M+H]⁺.

Example 245

(2S,4R)-4-[4-(2-Chloro-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

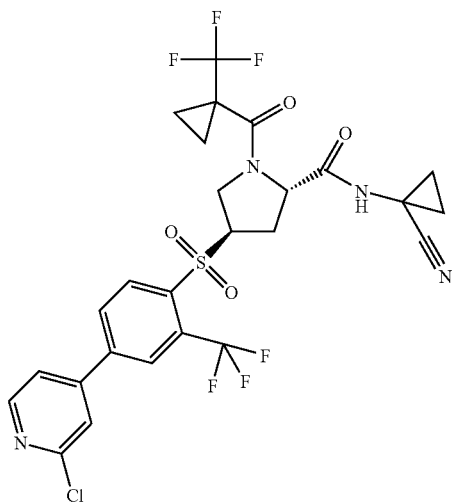

The title compound was prepared in analogy to example 238 using example 238a) (100 mg) as starting material to yield 53 mg (50%) of colorless amorphous material. MS (ESI): m/z=634.1 [M+H]$^+$.

Example 246

2S,4R)-4-[2-Chloro-4-(2,2,2-trifluoro-ethoxy)-benzenesulfonyl]-1-(2-phenyl-cyclopropanecarbonyl)-pyrrolidine-2-carboxylic acid (1-cyano-cyclopropyl)-amide

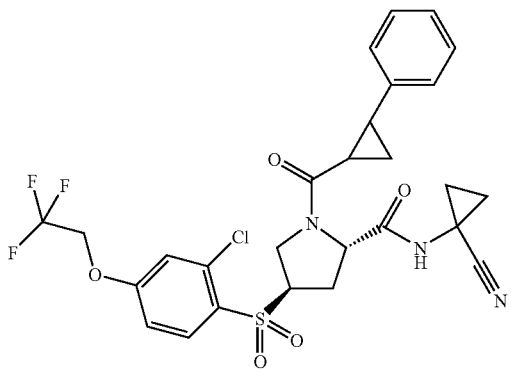

Example 173 (75 mg) was dissolved in acetonitrile (1 mL). To this solution (2-(7-aza-1H-benzotriazole-1-yl)-1,1,3,3-tetramethyluronium hexafluorophosphate) (126 mg), diisopropylethylamine (44 mg) and trans-2-phenyl-1-cyclopropanecarboxylic acid (32 mg) were added and stirred for 24 h at ambient temperature. The reaction mixture was purified by chromatography on silica gel to afford a mixture of diastereoisomer. This mixture was further purified using preparative chiral HPLC (reprosil chiral NR stationary phase; solvent: ethanol/heptane 3:7) to yield the title compound as the first to be eluted; white solid (21 mg; 28%). MS (ESI): m/z=596.1 [M+H]$^+$.

Example 247

(2S,4R)-4-[2-Chloro-4-(2,2,2-trifluoro-ethoxy)-benzenesulfonyl]-1-(1-pyridin-4-yl-cyclopropanecarbonyl)-pyrrolidine-2-carboxylic acid (1-cyano-cyclopropyl)-amide

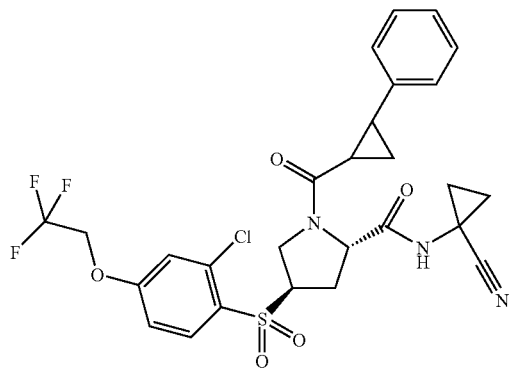

The title compound was prepared in analogy to example 246 to yield the title compound as the second to be eluted; white solid (24 mg; 32%). MS (ESI): m/z=596.1 [M−H]+.

Example 248

(2S,4R)-4-[4-(2-Methyl-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

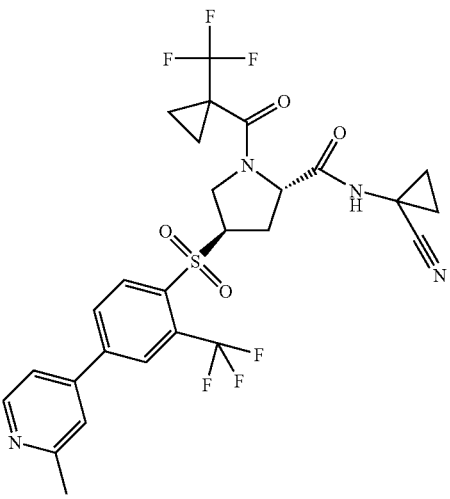

The title compound was prepared in analogy to example 238 using example 238a) (100 mg) as starting material to yield 46 mg (45%) of colorless amorphous material. MS (ESI): m/z=615.1 [M+H]+.

Example 249

(2S,4R)-1-(1-Methyl-cyclopropanecarbonyl)-4-[4-(1-methyl-1H-pyrazol-4-yl)-2-trifluoromethyl-benzenesulfonyl]-pyrrolidine-2-carboxylic acid (1-cyano-cyclopropyl)-amide

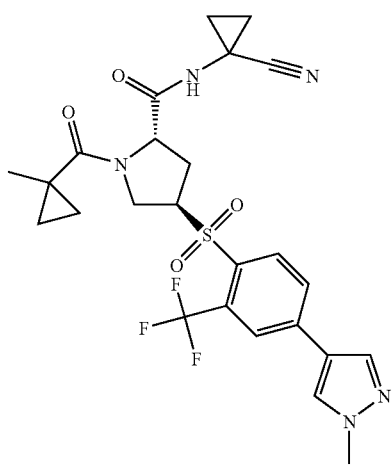

The title compound was prepared in analogy to example 238 using (2S,4R)-4-(4-Bromo-2-trifluoromethyl-benzenesulfonyl)-1-(1-methyl-cyclopropanecarbonyl)-pyrrolidine-2-carboxylic acid (1-cyano-cyclopropyl)-amide (example 270, 120 mg) as starting material to yield 111 mg (92%) of light brown solid. MS (ESI): m/z=550.2 [M+H]+.

Example 250

(2S,4R)-4-[4-(2-Methyl-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

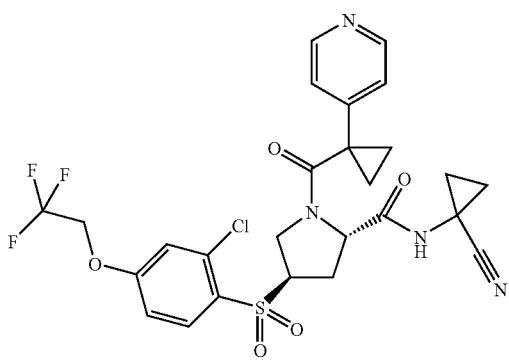

The title compound was prepared in analogy to example 239 using example 173 (75 mg) and 1-(pyridine-4-yl)cyclopropane carboxylic acid to yield 114 mg (99%) of an orange foam. MS (ESI): m/z=597.1.1 [M+H]+.

Example 251

(2S,4R)-4-[2-Chloro-4-(2,2,2-trifluoro-ethoxy)-benzenesulfonyl]-1-(2,2-difluoro-2-phenyl-acetyl)-pyrrolidine-2-carboxylic acid (1-cyano-cyclopropyl)-amide

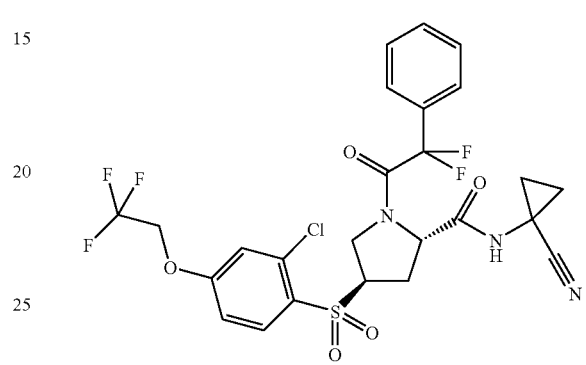

The title compound was prepared in analogy to example 239 using example 173 (75 mg) and 2,2-difluoro-2-phenylacetic acid to yield 86 mg (86%) of white foam. MS (ESI): m/z=623.1 [M+Na]+.

Example 252

(2S,4R)-4-[2-Chloro-4-(2,2,2-trifluoro-ethoxy)-benzenesulfonyl]-2-(1-cyano-cyclopropylcarbamoyl)-pyrrolidine-1-carboxylic acid 4-chloro-phenyl ester

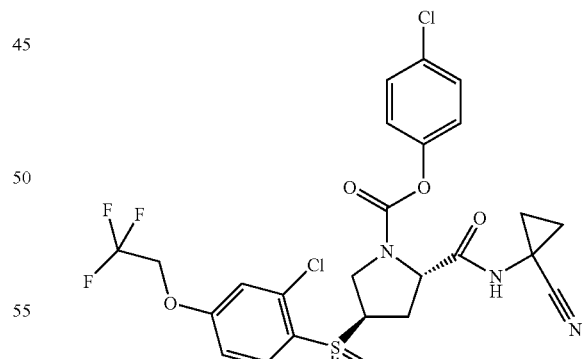

Example 173 (75 mg) was dissolved in acetonitrile (1 mL). To this solution, 4-chlorophenyl chlorocarbonate (39 mg) and diisopropylethylamine (44 mg) were added and stirred for 6 h at ambient temperature. The reaction mixture was purified by chromatography on silica gel to yield the title compound as a colorless gum (86 mg; 84%). MS (ESI): m/z=623.1 [M+NH4]+.

Example 253

(2S,4R)-4-(2-Chloro-benzenesulfonyl)-1-[5-methyl-2-(4-trifluoromethyl-phenyl)-2H-pyrazol-3-yl]-pyrrolidine-2-carboxylic acid (1-cyano-cyclopropyl)-amide

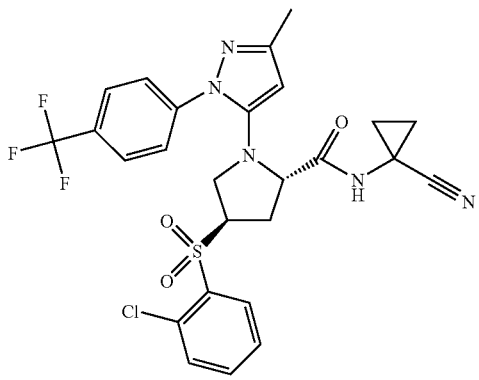

a) (2S,4R)-4-(2-Chloro-benzenesulfonyl)-pyrrolidine-2-carboxylic acid methyl ester To an ice cold solution of (2S,4R)-4-(2-chloro-benzenesulfonyl)-pyrrolidine-1,2-dicarboxylic acid 1-tert-butyl ester 2-methyl ester (2.97 g, 7 mmol; example 14) in dichloromethane (25 ml) was added trifluoroacetic acid (2.82 ml, 37 mmol) under an argon atmosphere. The reaction mixture was stirred for 14 h at ambient temperature. The solvent was removed under reduced pressure. The residue was dissolved in iPrOAc (200 ml) and cooled to 0° C. Saturated aqueous sodium carbonate solution (100 ml) was carefully added and the layers were separated. The aqueous layer was extracted two more times with iPrOAc, the combined organic layers were washed with ice water and brine and dried over sodium sulfate. The solvent was removed under reduced pressure to give the title compound (1.8 g, 7 mmol; 81%) as red oil which was sufficiently pure to be used in the next step. MS (ESI): m/z=304.1 [M+H]$^+$.

b) (2S,4R)-4-(2-chloro-benzenesulfonyl)-1-(3-oxobutyryl)-pyrrolidine-2-carboxylic acid Methyl Ester In analogy to the procedure described in example 192f, (2S,4R)-4-(2-chloro-benzenesulfonyl)-pyrrolidine-2-carboxylic acid methyl ester was reacted with tert-butyl acetoacetate to give the title compound as yellow solid.

c) (2S,4R)-4-(2-Chloro-benzenesulfonyl)-1-(3-oxo-thiobutyryl)-pyrrolidine-2-carboxylic acid methyl ester In analogy to the procedure described in example 192 g, (2S,4R)-4-(2-chloro-benzenesulfonyl)-1-(3-oxo-butyryl)-pyrrolidine-2-carboxylic acid methyl ester was reacted with Lawesson's reagent to give the title compound as red solid. MS (ESI): m/z=404.1 [M+H]$^+$.

d) (2S,4R)-4-(2-Chloro-benzenesulfonyl)-1-[5-methyl-2-(4-trifluoromethyl-phenyl)-2H-pyrazol-3-yl]-pyrrolidine-2-carboxylic acid methyl ester In analogy to the procedure described in example 192 h, (2S,4R)-4-(2-chloro-benzenesulfonyl)-1-(3-oxo-thiobutyryl)-pyrrolidine-2-carboxylic acid methyl ester was reacted with 4-(trifluoromethyl)phenylhydrazine (CAS Reg. No. 368-90-1) to give the title compound as colorless solid. MS (ESI): m/z=528.2 [M+H]$^+$.

e) (2S,4R)-4-(2-Chloro-benzenesulfonyl)-1-[5-methyl-2-(4-trifluoromethyl-phenyl)-2H-pyrazol-3-yl]-pyrrolidine-2-carboxylic acid (2S,4R)-4-(2-Chloro-benzenesulfonyl)-1-[5-methyl-2-(4-trifluoromethyl-phenyl)-2H-pyrazol-3-yl]-pyrrolidine-2-carboxylic acid methyl ester (27 mg, 51 umol) was dissolved in THF (0.2 ml). A solution of lithium hydroxide monohydrate (3 mg, 72 umol) in water (0.2 ml) was added and the mixture was stirred at ambient temperature for 14 h. Ice water/0.1 N aqueous HCl solution 1/1 and iPrOAc were added and the layers were separated. The aqueous layer was extracted one more time with iPrOAc, the combined organic layers were washed with ice water/brine 1/1 and dried over Na$_2$SO$_4$. The solvent was removed under reduced pressure to give the title compound compound (26 mg, 51 umol; quant.) as a yellow oil which was used in the next step without further purification. MS (ESI): m/z=514.3 [M+H]$^+$.

f) (2S,4R)-4-(2-Chloro-benzenesulfonyl)-1-[5-methyl-2-(4-trifluoromethyl-phenyl)-2H-pyrazol-3-yl]-pyrrolidine-2-carboxylic acid (1-cyano-cyclopropyl)-amide In analogy to the procedure described in example 237, (2S,4R)-4-(2-chloro-benzenesulfonyl)-1-[5-methyl-2-(4-trifluoromethyl-phenyl)-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as colorless solid. MS (ESI): m/z=578.1 [M+H]$^+$.

Example 254

(2S,4R)-4-(2-Chloro-benzenesulfonyl)-1-[2-(2-chloro-pyridin-4-yl)-5-methyl-2H-pyrazol-3-yl]-pyrrolidine-2-carboxylic acid (1-cyano-cyclopropyl)-amide

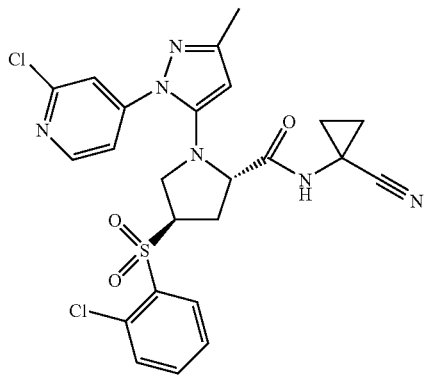

a) (2S,4R)-4-(2-Chloro-benzenesulfonyl)-1-[2-(2-chloro-pyridin-4-yl)-5-methyl-2H-pyrazol-3-yl]-pyrrolidine-2-carboxylic acid methyl ester In analogy to the procedure described in example 192 h, (2S,4R)-4-(2-chloro-benzenesulfonyl)-1-(3-oxo-thiobutyryl)-pyrrolidine-2-carboxylic acid methyl ester (example 253c) was reacted with (2-chloro-pyridin-4-yl)-hydrazine (CAS Reg. No. 700811-29-6) to give the title compound as colorless solid. MS (ESI): m/z=495.1 [M+H]$^+$.

b) (2S,4R)-4-(2-Chloro-benzenesulfonyl)-1-[2-(2-chloro-pyridin-4-yl)-5-methyl-2H-pyrazol-3-yl]-pyrrolidine-2-carboxylic acid In analogy to the procedure described in example 253e, (2S,4R)-4-(2-chloro-benzenesulfonyl)-1-[2-(2-chloro-pyridin-4-yl)-5-methyl-2H-pyrazol-3-yl]-pyrrolidine-2-carboxylic acid methyl ester was saponified in the presence of lithium hydroxide to give the title compound as yellow oil. MS (ESI): m/z=481.0 [M+H]$^+$.

c) (2S,4R)-4-(2-Chloro-benzenesulfonyl)-1-[2-(2-chloro-pyridin-4-yl)-5-methyl-2H-pyrazol-3-yl]-pyrrolidine-2-carboxylic acid (1-cyano-cyclopropyl)-amide In analogy to the procedure described in example 237, (2S,4R)-4-(2-chloro-benzenesulfonyl)-1-[2-(2-chloro-pyridin-4-yl)-5-methyl-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as colorless solid. MS (ESI): m/z=545.2 [M+H]$^+$.

Example 255

(2S,4R)-1-(1,5-Dimethyl-1H-pyrazol-3-yl)-4-(2-trifluoromethyl-benzenesulfonyl)-pyrrolidine-2-carboxylic acid (1-cyano-cyclopropyl)-amide

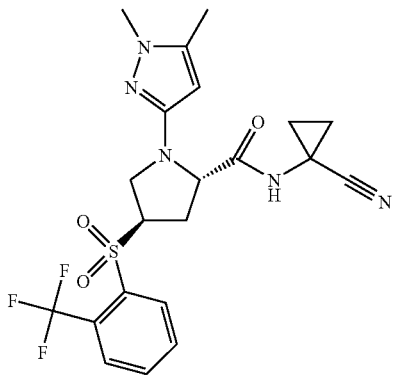

a) (2S,4R)-1-(1,5-Dimethyl-1H-pyrazol-3-yl)-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with methyl-hydrazine (CAS Reg. No. 60-34-4) to give the title compound as yellow solid. MS (ESI): m/z=432.1 [M+H]$^+$.

b) (2S,4R)-1-(1,5-Dimethyl-1H-pyrazol-3-yl)-4-(2-trifluoromethyl-benzenesulfonyl)-pyrrolidine-2-carboxylic acid In analogy to the procedure described in example 253e, (2S,4R)-1-(1,5-dimethyl-1H-pyrazol-3-yl)-4-(2-trifluoromethyl-benzenesulfonyl)-pyrrolidine-2-carboxylic acid methyl ester was saponified in the presence of lithium hydroxide to give the title compound as off-white solid. MS (ESI): m/z=418.2 [M+H]$^+$.

c) (2S,4R)-1-(1,5-Dimethyl-1H-pyrazol-3-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(1,5-dimethyl-1H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=482.2 [M+H]$^+$.

Example 256

(2S,4R)-4-(4-Cyclopropyl-2-trifluoromethyl-benzenesulfonyl)-1-(1-trifluoromethyl-cyclopropanecarbonyl)-pyrrolidine-2-carboxylic acid (1-cyano-cyclopropyl)-amide

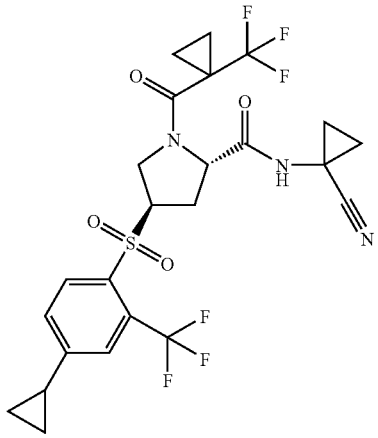

Example 238a) (50 mg) was dissolved in toluene (2.0 mL) and water (0.1 mL) in a sealed tube. Argon was introduced for 15 minutes. Tricyclohexylphosphine (0.15 eq.), potassium phosphate tribasic (3.5 eq.) and palladium(II)acetate (0.1 eq.) were added to the solution under an argon stream. The mixture was stirred at 100° C. for 4 h, then at 25° C. over night. LC-MS-analysis revealed complete turnover of the starting material. The reaction mixture was dissolved with AcOEt (10 mL) and extracted with H$_2$O (2×5 mL), the water layers were washed with AcOEt, the combined organic layers were washed with brine, dried over Na$_2$SO$_4$, filtered off and evaporated to dryness. The reaction mixture was purified with flash chromatography (4 g SiO$_2$, gradient n-heptan 15%->n-heptan/EtOAc 1:4 within 45 min) to yield 32 mg (68%) of an amorphous colorless material. MS (ESI): m/z=564.2 [M+H]$^+$.

Example 257

(2S,4R)-1-(1-Methyl-cyclopropanecarbonyl)-4-[4-(2-methyl-pyridin-4-yl)-2-trifluoromethyl-benzenesulfonyl]-pyrrolidine-2-carboxylic acid (1-cyano-cyclopropyl)-amide

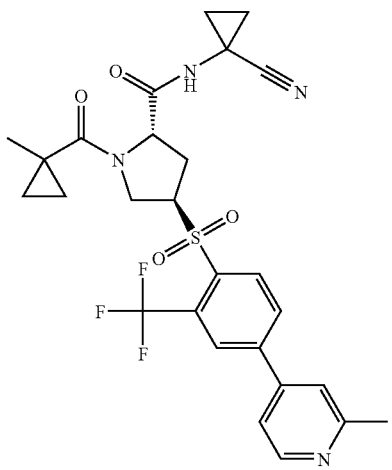

The title compound was prepared in analogy to example 249 using (2S,4R)-4-(4-Bromo-2-trifluoromethyl-benzenesulfonyl)-1-(1-methyl-cyclopropanecarbonyl)-pyrrolidine-2-carboxylic acid (1-cyano-cyclopropyl)-amide (example 270, 100 mg) as starting material to yield 84 mg (82%) of light brown foam. MS (ESI): m/z=561.2 [M+H]$^+$.

Example 258

(2S,4R)-4-[4-(2-Chloro-pyridin-4-yl)-2-trifluoromethyl-benzenesulfonyl]-1-(1-methyl-cyclopropanecarbonyl)-pyrrolidine-2-carboxylic acid (1-cyano-cyclopropyl)-amide

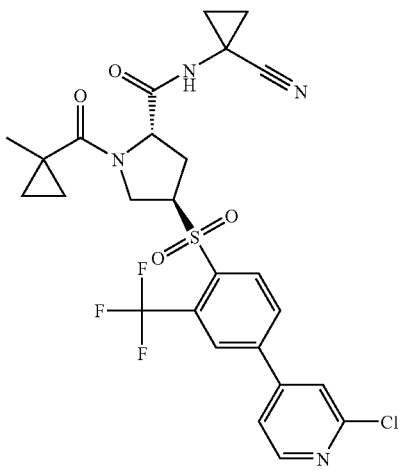

The title compound was prepared in analogy to example 249 using (2S,4R)-4-(4-Bromo-2-trifluoromethyl-benzenesulfonyl)-1-(1-methyl-cyclopropanecarbonyl)-pyrrolidine-2-carboxylic acid (1-cyano-cyclopropyl)-amide (example 270, 100 mg) as starting material to yield 64 mg (60%) of an off-white solid. MS (ESI): m/z=581.2 [M+H]$^+$.

Example 259

(2S,4R)-4-(2',4'-Difluoro-3-trifluoromethyl-biphenyl-4-sulfonyl)-1-(1-methyl-cyclopropanecarbonyl)-pyrrolidine-2-carboxylic acid (1-cyano-cyclopropyl)-amide

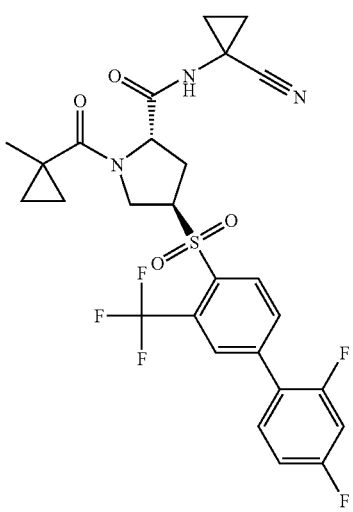

The title compound was prepared in analogy to example 249 using (2S,4R)-4-(4-Bromo-2-trifluoromethyl-benzenesulfonyl)-1-(1-methyl-cyclopropanecarbonyl)-pyrrolidine-2-carboxylic acid (1-cyano-cyclopropyl)-amide (example 270, 100 mg) as starting material to yield 90 mg (85%) of a light brown foam. MS (ESI): m/z=582.2 [M+H]$^+$.

Example 260

(2S,4R)-4-[4-(4-Methyl-piperazin-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide

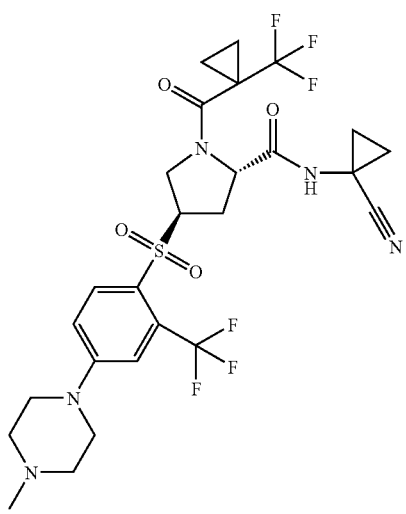

Example 238a) (70 mg) was dissolved in ACN (2 ml). 1-Methyl-piperazine (0.02 mL, 1.4 eq.) and Hünig's base (0.05 mL, 2 eq.) were added to the solution at 25° C. The mixture was stirred over night. LC/MS-analysis revealed no reaction. Therefore additional 1-methyl-piperazine (0.5 eq.) was added to the reaction mixture and the mixture was stirred at 55° C. for 24 h. Since the reaction was still not complete additional 1-methyl-piperazine (0.2 eq.) was added to the solution and stirred at 80° C. for 24 h. The reaction mixture was cooled to 25° C. and purified with preparative HPLC to yield 17 mg (20%) of an amorphous colorless material. MS (ESI): m/z=622.4 [M+H]+.

Example 261

(2S,4R)-4-Benzenesulfonyl-1-[5-methyl-2-(4-trifluoromethyl-phenyl)-2H-pyrazol-3-yl]-pyrrolidine-2-carboxylic acid (1-cyano-cyclopropyl)-amide

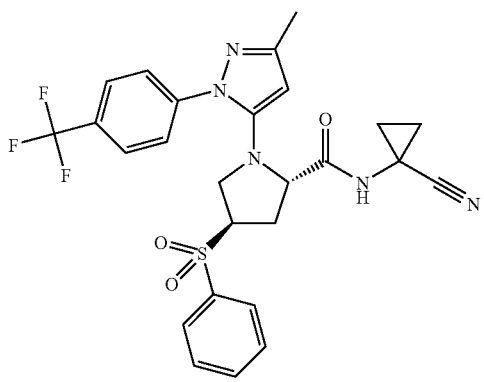

a) (2S,4R)-4-Benzenesulfonyl-pyrrolidine-1,2-dicarboxylic acid 1-tert-butyl ester 2-methyl ester According to general procedure C, (2S,4R)-4-phenylsulfanyl-pyrrolidine-1,2-dicarboxylic acid 1-tert-butyl ester 2-methyl ester (Kyle, Donald James; Hiner, Roger Neal PCT Int. Appl. (1992), WO 9218155 A1) was oxidized with m-chloroperbenzoic acid to give the title compound as yellow oil. MS (ESI): m/z=370.1 [M+H]+.

b) (2S,4R)-4-(2-Chloro-benzenesulfonyl)-pyrrolidine-2-carboxylic acid methyl ester In analogy to the procedure described in example 253a, (2S,4R)-4-benzenesulfonyl-pyrrolidine-1,2-dicarboxylic acid 1-tert-butyl ester 2-methyl ester was treated with trifluoroacetic acid in dichloromethane to give the title compound as yellow oil. MS (ESI): m/z=270.2 [M+H]+.

c) (2S,4R)-4-Benzenesulfonyl-1-(3-oxo-butyryl)-pyrrolidine-2-carboxylic acid Methyl Ester In analogy to the procedure described in example 192f, (2S,4R)-4-benzenesulfonyl-pyrrolidine-2-carboxylic acid methyl ester was reacted with tert-butyl acetoacetate to give the title compound as yellow solid.

d) (2S,4R)-4-Benzenesulfonyl-1-(3-oxo-thiobutyryl)-pyrrolidine-2-carboxylic acid Methyl Ester In analogy to the procedure described in example 192 g, (2S,4R)-4-benzenesulfonyl-1-(3-oxo-butyryl)-pyrrolidine-2-carboxylic acid methyl ester was reacted with Lawesson's reagent to give the title compound as red oil.

e) (2S,4R)-4-Benzenesulfonyl-1-[5-methyl-2-(4-trifluoromethyl-phenyl)-2H-pyrazol-3-yl]-pyrrolidine-2-carboxylic acid methyl ester In analogy to the procedure described in example 192 h, (2S,4R)-4-benzenesulfonyl-1-(3-oxo-thiobutyryl)-pyrrolidine-2-carboxylic acid methyl ester was reacted with 4-(trifluoromethyl)phenylhydrazine (CAS Reg. No. 368-90-1) to give the title compound as yellow solid. MS (ESI): m/z=394.1 [M+H]+.

f) (2S,4R)-4-Benzenesulfonyl-1-[5-methyl-2-(4-trifluoromethyl-phenyl)-2H-pyrazol-3-yl]-pyrrolidine-2-carboxylic acid In analogy to the procedure described in example 253e, (2S,4R)-4-benzenesulfonyl-1-[5-methyl-2-(4-trifluoromethyl-phenyl)-2H-pyrazol-3-yl]-pyrrolidine-2-carboxylic acid methyl ester was saponified in the presence of lithium hydroxide to give the title compound as yellow solid. MS (ESI): m/z=480.1 [M+H]+.

g) (2S,4R)-4-Benzenesulfonyl-1-[5-methyl-2-(4-trifluoromethyl-phenyl)-2H-pyrazol-3-yl]-pyrrolidine-2-carboxylic acid (1-cyano-cyclopropyl)-amide In analogy to the procedure described in example 237, (2S,4R)-4-benzenesulfonyl-1-[5-methyl-2-(4-trifluoromethyl-phenyl)-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as yellow solid. MS (ESI): m/z=544.2 [M+H]+.

Example 262

(2S,4R)-4-Benzenesulfonyl-1-[2-(2-chloro-pyridin-4-yl)-5-methyl-2H-pyrazol-3-yl]-pyrrolidine-2-carboxylic acid (1-cyano-cyclopropyl)-amide

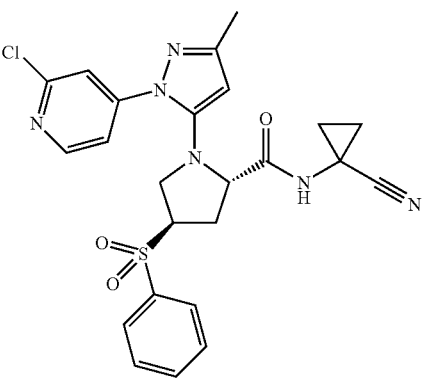

a) (2S,4R)-4-Benzenesulfonyl-1-[2-(2-chloro-pyridin-4-yl)-5-methyl-2H-pyrazol-3-yl]-pyrrolidine-2-carboxylic acid methyl ester In analogy to the procedure described in example 192 h, (2S,4R)-4-benzenesulfonyl-1-(3-oxo-thiobutyryl)-pyrrolidine-2-carboxylic acid methyl ester (example 261d) was reacted with (2-chloro-pyridin-4-yl)-hydrazine (CAS Reg. No. 700811-29-6) to give the title compound as yellow solid. MS (ESI): m/z=461.3 [M+H]$^+$.

b) (2S,4R)-4-Benzenesulfonyl-1-[2-(2-chloro-pyridin-4-yl)-5-methyl-2H-pyrazol-3-yl]-pyrrolidine-2-carboxylic acid In analogy to the procedure described in example 253e, (2S,4R)-4-benzenesulfonyl-1-[2-(2-chloro-pyridin-4-yl)-5-methyl-2H-pyrazol-3-yl]-pyrrolidine-2-carboxylic acid methyl ester was saponified in the presence of lithium hydroxide to give the title compound as yellow solid. MS (ESI): m/z=447.2 [M+H]$^+$.

c) (2S,4R)-4-Benzenesulfonyl-1-[2-(2-chloro-pyridin-4-yl)-5-methyl-2H-pyrazol-3-yl]-pyrrolidine-2-carboxylic acid (1-cyano-cyclopropyl)-amide In analogy to the procedure described in example 237, (2S,4R)-4-benzenesulfonyl-1-[2-(2-chloro-pyridin-4-yl)-5-methyl-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as yellow oil. MS (ESI): m/z=511.2 [M+H]$^+$.

Example 263

(2S,4R)-4-(2',4'-Difluoro-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide

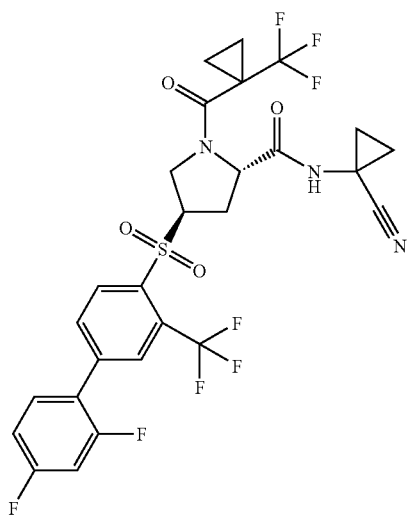

The title compound was prepared in analogy to example 238 using example 238a) (100 mg) as starting material to yield 92 mg (87%) of colorless foam. MS (ESI): m/z=636.2 [M+H]$^+$.

Example 264

(4-{2-[(2S,4R)-4-[2-Chloro-4-(2,2,2-trifluoro-ethoxy)-benzenesulfonyl]-2-(1-cyano-cyclopropyl-carbamoyl)-pyrrolidin-1-yl]-2-oxo-ethyl}-cyclohexyl)-carbamic Acid Tert-butyl ester

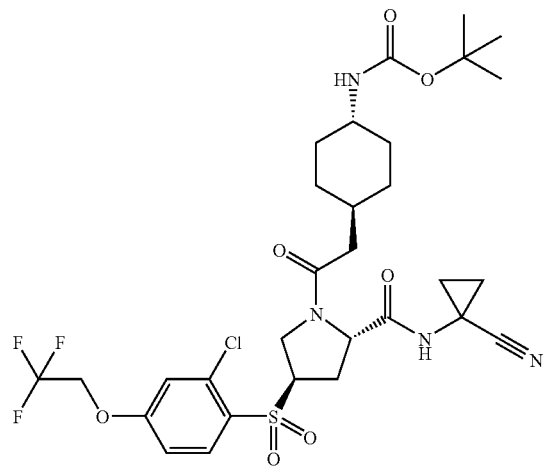

The title compound was prepared in analogy to example 239 using example 173 (75 mg) and trans-4-tert-butoxycarbonylaminocyclohexylacetic acid to yield 107 mg (33%) of white foam. MS (ESI): m/z=691.1 [M+H]$^+$.

Example 265

(2S,4R)-1-[2-(4-Amino-cyclohexyl)-acetyl]-4-[2-chloro-4-(2,2,2-trifluoro-ethoxy)-benzenesulfonyl]-pyrrolidine-2-carboxylic acid (1-cyano-cyclopropyl)-amide

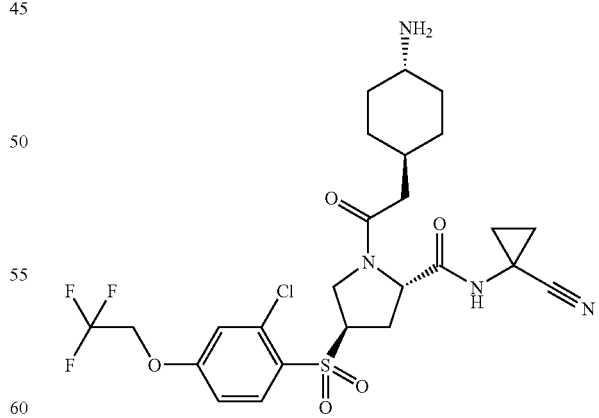

Example 264 (87 mg) was dissolved in formic acid (0.4 mL) and stirred for overnight at ambient temperature. The reaction mixture partitioned between ice water and dichloromethane. pH was adjusted to 10 by addition of solid sodium carbonate. The aqueous layer was extracted with dichloromethane and the combined organic layers were washed with brine, concentrated to dryness and purified by chromatography on silica gel to yield the title compound as a colorless gum (74 mg; 96%). MS (ESI): m/z=591.3 [M+H]+.

Example 266

(2S,4R)-1-[2-(2-Chloro-pyridin-4-yl)-5-methyl-2H-pyrazol-3-yl]-4-(4-fluoro-2-trifluoromethyl-benzenesulfonyl)-pyrrolidine-2-carboxylic acid (1-cyano-cyclopropyl)-amide

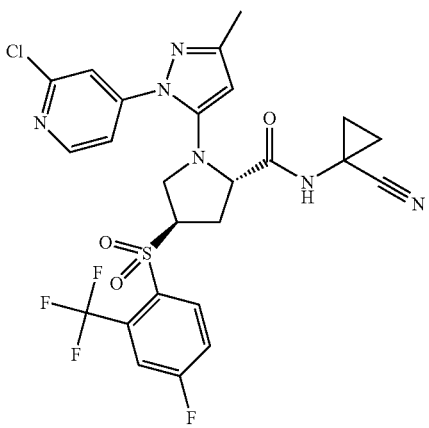

a) (2S,4R)-4-(4-Fluoro-2-trifluoromethyl-benzenesulfonyl)-pyrrolidine-2-carboxylic acid methyl ester In analogy to the procedure described in example 253a, (2S,4R)-4-(4-fluoro-2-trifluoromethyl-benzenesulfonyl)-pyrrolidine-1,2-dicarboxylic acid 1-tert-butyl ester 2-methyl ester (example 208 c) was treated with trifluoroacetic acid in dichloromethane to give the title compound as yellow oil. MS (ESI): m/z=356.1 [M+H]+.

b) (2S,4R)-4-(4-Fluoro-2-trifluoromethyl-benzenesulfonyl)-1-(3-oxo-butyryl)-pyrrolidine-2-carboxylic acid methyl ester In analogy to the procedure described in example 192f, (2S,4R)-4-(4-fluoro-2-trifluoromethyl-benzenesulfonyl)-pyrrolidine-2-carboxylic acid methyl ester was reacted with tert-butyl acetoacetate to give the title compound as yellow oil. MS (ESI): m/z=440.2 [M+H]+.

c) (2S,4R)-4-(4-Fluoro-2-trifluoromethyl-benzenesulfonyl)-1-(3-oxo-thiobutyryl)-pyrrolidine-2-carboxylic acid methyl ester In analogy to the procedure described in example 192 g, (2S,4R)-4-(4-fluoro-2-trifluoromethyl-benzenesulfonyl)-1-(3-oxo-butyryl)-pyrrolidine-2-carboxylic acid methyl ester was reacted with Lawesson's reagent to give the title compound as brown solid.

d) (2S,4R)-1-[2-(2-Chloro-pyridin-4-yl)-5-methyl-2H-pyrazol-3-yl]-4-(4-fluoro-2-trifluoromethyl-benzenesulfonyl)-pyrrolidine-2-carboxylic acid methyl ester In analogy to the procedure described in example 192 h, (2S,4R)-4-(4-fluoro-2-trifluoromethyl-benzenesulfonyl)-1-(3-oxo-thiobutyryl)-pyrrolidine-2-carboxylic acid methyl ester was reacted with (2-chloro-pyridin-4-yl)-hydrazine (CAS Reg. No. 700811-29-6) to give the title compound as colorless solid. MS (ESI): m/z=547.2 [M+H]+.

e) (2S,4R)-1-[2-(2-Chloro-pyridin-4-yl)-5-methyl-2H-pyrazol-3-yl]-4-(4-fluoro-2-trifluoromethyl-benzenesulfonyl)-pyrrolidine-2-carboxylic acid In analogy to the procedure described in example 253e, (2S,4R)-1-[2-(2-chloro-pyridin-4-yl)-5-methyl-2H-pyrazol-3-yl]-4-(4-fluoro-2-trifluoromethyl-benzenesulfonyl)-pyrrolidine-2-carboxylic acid methyl ester was saponified in the presence of lithium hydroxide to give the title compound as yellow solid. MS (ESI): m/z=533.1 [M+H]+.

f) (2S,4R)-1-[2-(2-Chloro-pyridin-4-yl)-5-methyl-2H-pyrazol-3-yl]-4-(4-fluoro-2-trifluoromethyl-benzenesulfonyl)-pyrrolidine-2-carboxylic acid (1-cyano-cyclopropyl)-amide In analogy to the procedure described in example 237, (2S,4R)-1-[2-(2-chloro-pyridin-4-yl)-5-methyl-2H-pyrazol-3-yl]-4-(4-fluoro-2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless solid. MS (ESI): m/z=597.2 [M+H]+.

Example 267

(2S,4R)-4-(4-Fluoro-2-trifluoromethyl-benzenesulfonyl)-1-[5-methyl-2-(4-trifluoromethyl-phenyl)-2H-pyrazol-3-yl]-pyrrolidine-2-carboxylic acid (1-cyano-cyclopropyl)-amide

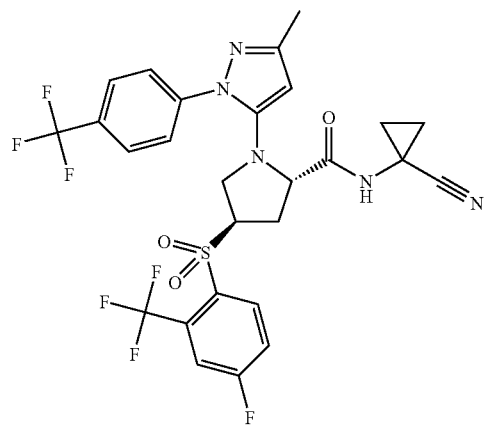

a) (2S,4R)-4-(4-Fluoro-2-trifluoromethyl-benzenesulfonyl)-1-[5-methyl-2-(4-trifluoromethyl-phenyl)-2H-pyrazol-3-yl]-pyrrolidine-2-carboxylic acid methyl ester In analogy to the procedure described in example 192 h, (2S,4R)-4-(4-fluoro-2-trifluoromethyl-benzenesulfonyl)-1-(3-oxo-thiobutyryl)-pyrrolidine-2-carboxylic acid methyl ester (example 266 c) was reacted with 4-(trifluoromethyl)phenylhydrazine (CAS Reg. No. 368-90-1) to give the title compound as yellow solid. MS (ESI): m/z=580.3 [M+H]+.

b) (2S,4R)-4-(4-Fluoro-2-trifluoromethyl-benzene-sulfonyl)-1-[5-methyl-2-(4-trifluoromethyl-phenyl)-2H-pyrazol-3-yl]-pyrrolidine-2-carboxylic acid In analogy to the procedure described in example 253e, (2S,4R)-4-(4-fluoro-2-trifluoromethyl-benzenesulfonyl)-1-[5-methyl-2-(4-trifluoromethyl-phenyl)-2H-pyrazol-3-yl]-pyrrolidine-2-carboxylic acid methyl ester was saponified in the presence of lithium hydroxide to give the title compound as yellow oil. MS (ESI): m/z=566.1 [M+H]$^+$.

c) (2S,4R)-4-(4-Fluoro-2-trifluoromethyl-benzene-sulfonyl)-1-[5-methyl-2-(4-trifluoromethyl-phenyl)-2H-pyrazol-3-yl]-pyrrolidine-2-carboxylic acid (1-cyano-cyclopropyl)-amide In analogy to the procedure described in example 237, (2S,4R)-4-(4-fluoro-2-trifluoromethyl-benzenesulfonyl)-1-[5-methyl-2-(4-trifluoromethyl-phenyl)-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as yellow solid. MS (ESI): m/z=630.2 [M+H]$^+$.

Example 268

(2S,4R)-1-(2-Isopropyl-5-methyl-2H-pyrazol-3-yl)-4-(2-trifluoromethyl-benzenesulfonyl)-pyrrolidine-2-carboxylic acid (1-cyano-cyclopropyl)-amide

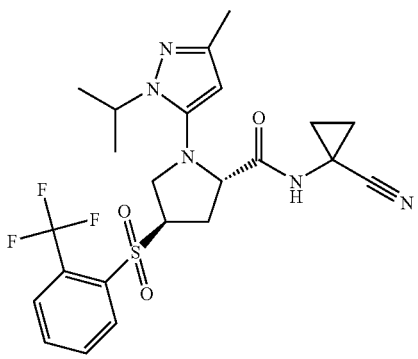

a) (2S,4R)-1-(2-isopropyl-5-methyl-2H-pyrazol-3-yl)-4-(2-trifluoromethyl-benzenesulfonyl)-pyrroli-dine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with isopropylhydrazine hydrochloride (CAS Reg. No. 16726-41-3) to give the title compound as yellow solid. MS (ESI): m/z=460.3 [M+H]$^+$.

b) (2S,4R)-1-(2-Isopropyl-5-methyl-2H-pyrazol-3-yl)-4-(2-trifluoromethyl-benzenesulfonyl)-pyrroli-dine-2-carboxylic acid In analogy to the procedure described in example 253e, (2S,4R)-1-(2-isopropyl-5-methyl-2H-pyrazol-3-yl)-4-(2-trifluoromethyl-benzenesulfonyl)-pyrrolidine-2-carboxylic acid methyl ester was saponified in the presence of lithium hydroxide to give the title compound as yellow solid. MS (ESI): m/z=446.3 [M+H]$^+$.

c) (2S,4R)-1-(2-Isopropyl-5-methyl-2H-pyrazol-3-yl)-4-(2-trifluoromethyl-benzenesulfonyl)-pyrroli-dine-2-carboxylic acid (1-cyano-cyclopropyl)-amide In analogy to the procedure described in example 237, (2S,4R)-1-(2-isopropyl-5-methyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless solid. MS (ESI): m/z=510.2 [M+H]$^+$.

Example 269

(2S,4R)-1-[5-Methyl-2-(2,2,2-trifluoro-ethyl)-2H-pyrazol-3-yl]-4-(2-trifluoromethyl-benzenesulfonyl)-pyrrolidine-2-carboxylic acid (1-cyano-cyclopropyl)-amide

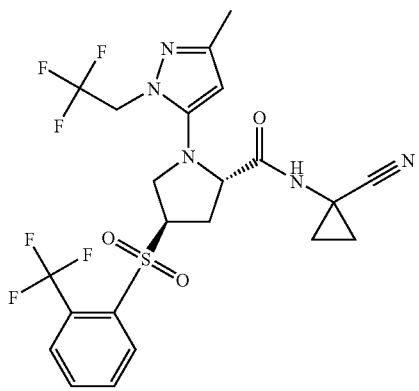

a) (2S,4R)-1-[5-Methyl-2-(2,2,2-trifluoro-ethyl)-2H-pyrazol-3-yl]-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with 2,2,2-trifluoroethylhydrazine (CAS Reg. No. 5042-30-8) to give the title compound as yellow solid. MS (ESI): m/z=500.2 [M+H]$^+$.

b) (2S,4R)-1-[5-Methyl-2-(2,2,2-trifluoro-ethyl)-2H-pyrazol-3-yl]-4-(2-trifluoromethyl-benzenesulfonyl)-pyrrolidine-2-carboxylic acid In analogy to the procedure described in example 253e, (2S,4R)-1-[5-methyl-2-(2,2,2-trifluoro-ethyl)-2H-pyrazol-3-yl]-4-(2-trifluoromethyl-benzenesulfonyl)-pyrrolidine-2-carboxylic acid methyl ester was saponified in the presence of lithium hydroxide to give the title compound as yellow solid. MS (ESI): m/z=486.2 [M+H]$^+$.

c) (2S,4R)-1-[5-Methyl-2-(2,2,2-trifluoro-ethyl)-2H-pyrazol-3-yl]-4-(2-trifluoromethyl-benzenesulfonyl)-pyrrolidine-2-carboxylic acid (1-cyano-cyclopropyl)-amide In analogy to the procedure described in example 237, (2S,4R)-1-[5-methyl-2-(2,2,2-trifluoro-ethyl)-2H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=550.1 [M+H]⁺.

Example 270

(2S,4R)-4-(4-Bromo-2-trifluoromethyl-benzene-sulfonyl)-1-(1-methyl-cyclopropanecarbonyl)-pyrrolidine-2-carboxylic acid (1-cyano-cyclopropyl)-amide

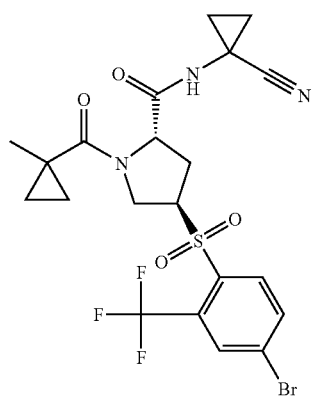

The title compound was prepared in analogy to example 238a) to yield 1230 mg (76%) of a white foam. MS (ESI): m/z=548.0 [M+H]⁺.

Example 271

(2S,4R)-4-(4-Cyclopropyl-2-trifluoromethyl-benzenesulfonyl)-1-(1-methyl-cyclopropanecarbonyl)-pyrrolidine-2-carboxylic acid (1-cyano-cyclopropyl)-amide

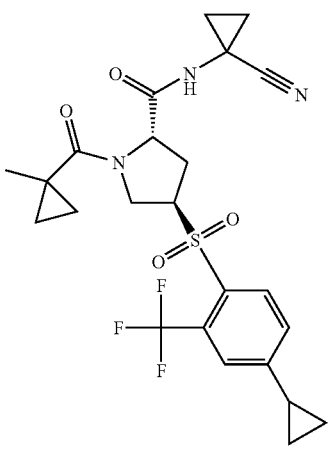

The title compound was prepared in analogy to example 256 to yield 13 mg (23%) of an off-white wax. MS (ESI): m/z=510.2 [M+H]⁺.

Example 272

(2S,4R)-1-(1-Methyl-cyclopropanecarbonyl)-4-[4-(4-methyl-piperazin-1-yl)-2-trifluoromethyl-benzenesulfonyl]-pyrrolidine-2-carboxylic acid (1-cyano-cyclopropyl)-amide

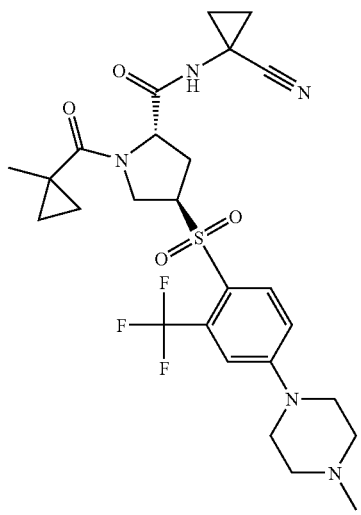

The title compound was prepared in analogy to example 260 to yield 32 mg (31%) of light red solid. MS (ESI): m/z=568.4 [M+H]⁺.

Example 273

(2S,4R)-1-[1-(4-Bromo-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide

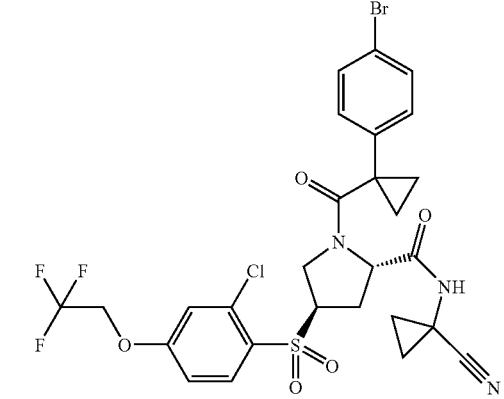

The title compound was prepared in analogy to example 239 using example 173 (1.0 g) and 1-(4-bromophenyl)cyclopropanecarboxylic acid to yield 1.24 g (83%) of white foam. MS (ESI): m/z=676.0 [M+H]$^+$.

Example 274

(2S,4R)-1-[2-(4-Acetylamino-cyclohexyl)-acetyl]-4-[2-chloro-4-(2,2,2-trifluoro-ethoxy)-benzenesulfonyl]-pyrrolidine-2-carboxylic acid (1-cyano-cyclopropyl)-amide

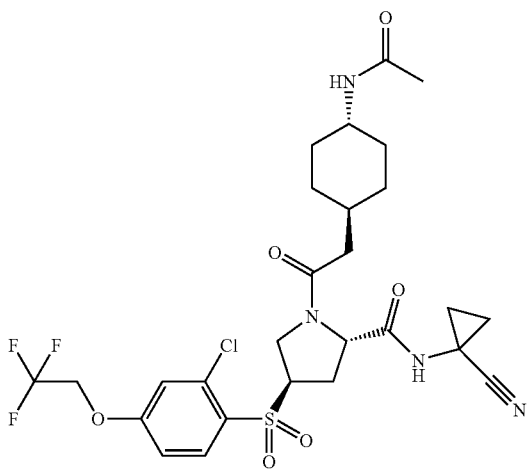

The title compound was prepared in analogy to example 252 using example 265 (41 mg) and acetyl chloride to yield 34 mg (77%) of white solid. MS (ESI): m/z=633.0 [M+H]$^+$.

Example 275

(2S,4R)-1-[2,2-Bis-(4-chloro-phenyl)-acetyl]-4-[2-chloro-4-(2,2,2-trifluoro-ethoxy)-benzenesulfonyl]-pyrrolidine-2-carboxylic acid (1-cyano-cyclopropyl)-amide

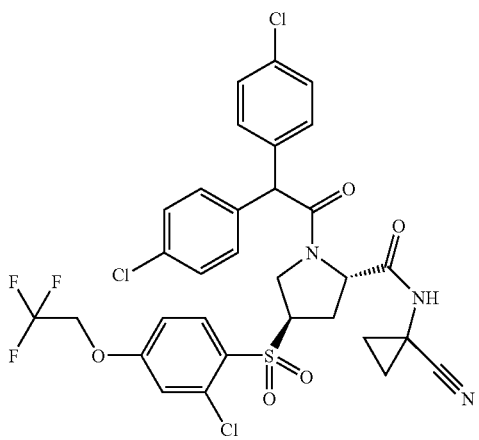

The title compound was prepared in analogy to example 239 using example 173 (200 mg) and bis-(4-chloro-phenyl)-acetic acid to yield 264 mg (84%) of white foam. MS (ESI): m/z=716.10 [M+H]$^+$.

Example 276

(2S,4R)-1-(5-Methyl-2-m-tolyl-2H-pyrazol-3-yl)-4-(2-trifluoromethyl-benzenesulfonyl)-pyrrolidine-2-carboxylic acid (1-cyano-cyclopropyl)-amide

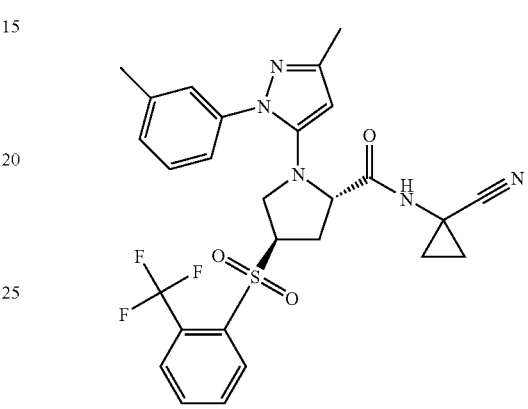

a) (2S,4R)-1-(5-Methyl-2-m-tolyl-2H-pyrazol-3-yl)-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with 3-methylphenylhydrazine hydrochloride (CAS Reg. No. 637-04-7) to give the title compound as yellow solid. MS (ESI): m/z=508.1 [M+H]$^+$.

b) (2S,4R)-1-(5-Methyl-2-m-tolyl-2H-pyrazol-3-yl)-4-(2-trifluoromethyl-benzenesulfonyl)-pyrrolidine-2-carboxylic acid In analogy to the procedure described in example 253e, (2S,4R)-1-(5-methyl-2-m-tolyl-2H-pyrazol-3-yl)-4-(2-trifluoromethyl-benzenesulfonyl)-pyrrolidine-2-carboxylic acid methyl ester was saponified in the presence of lithium hydroxide to give the title compound as yellow solid. MS (ESI): m/z=494.1 [M+H]$^+$.

c) (2S,4R)-1-(5-Methyl-2-m-tolyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(5-methyl-2-m-tolyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as yellow solid. MS (ESI): m/z=558.2 [M+H]$^+$.

Example 277

(2S,4R)-1-[1-(4-Carbamoyl-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide

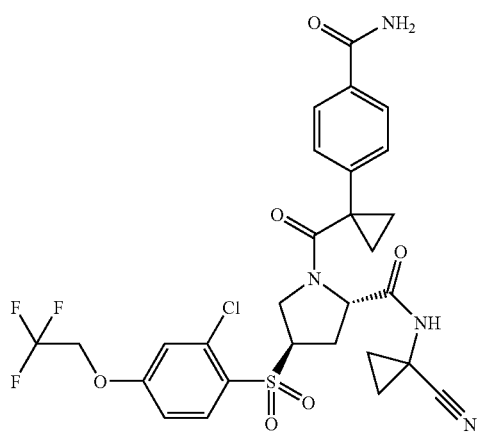

Example 273 (200 mg), molybdenum hexacarbonyl (209 mg), Hermann's catalyst (36 mg), tri-ter-butylphosphonium tetrafluoroborate (23 mg), hydroxylamine hydrochloride (220 mg), 1,8-diazabicyclo[5.4.0]undec-7-ene (0.235 mL) and diisopropylethylamine (365 mg) were suspended in dioxane (4 mL). The reaction mixture was irradiated in microwave reactor at 120° C. for 20 min. The reaction mixture was then filtered over dicalite pad. The pad washed with dichloromethane, ethyl acetate. The crude mixture was concentrated to dryness and purified by chromatography on silica gel to yield the title compound as a colorless gum (42 mg; 21%). MS (ESI): m/z=638.1 [M+H]$^+$.

Example 278

(2S,4R)-1-[1-(4-Chloro-phenyl)-cyclobutanecarbonyl]-4-[2-chloro-4-(2,2,2-trifluoro-ethoxy)-benzenesulfonyl]-pyrrolidine-2-carboxylic acid (1-cyano-cyclopropyl)-amide

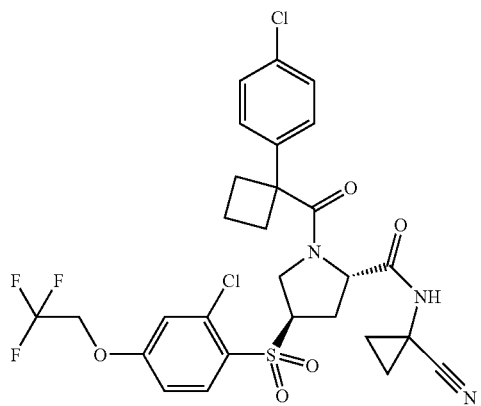

The title compound was prepared in analogy to example 239 using example 173 (75 mg) and 1-(4-chlorophenyl)-1-cyclobutanecarboxylic acid to yield 78 mg (73%) of white wax. MS (ESI): m/z=644.10 [M+H]$^+$.

Example 279

(2S,4R)-1-[2-(4-Chloro-phenyl)-2-methyl-propionyl]-4-[2-chloro-4-(2,2,2-trifluoro-ethoxy)-benzenesulfonyl]-pyrrolidine-2-carboxylic acid (1-cyano-cyclopropyl)-amide

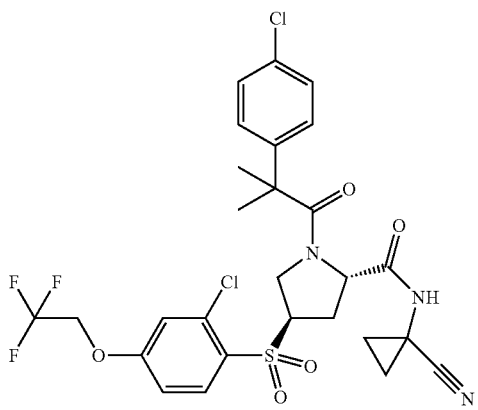

The title compound was prepared in analogy to example 239 using example 173 (75 mg) and 4-chloro-dimethylphenyl acetic acid to yield 51 mg (49%) of a white foam. MS (ESI): m/z=632.10 [M+H]$^+$.

Example 280

(2R,4S)-4-[2-Chloro-4-(2,2,2-trifluoro-ethoxy)-benzenesulfonyl]-1-(1-trifluoromethyl-cyclopropanecarbonyl)-pyrrolidine-2-carboxylic acid (1-cyano-cyclopropyl)-amide

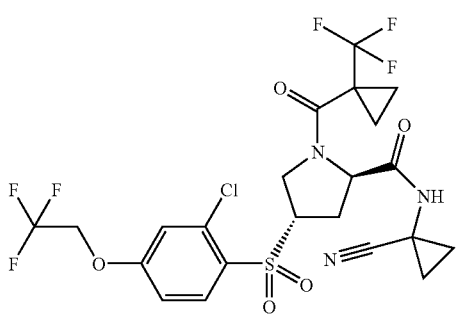

The title compound was prepared in analogy to example 239 using example 173 (75 mg) and 1-trifluoromethyl-cyclopropanecarboxylic acid to yield 50 mg (50%) of a pink oil. MS (ESI): m/z=605.1 [M+NH$_4$]$^+$.

Example 281

(2S,4R)-4-(2-Chloro-benzenesulfonyl)-1-[1-(4-trifluoromethoxy-phenyl)-cyclopropanecarbonyl]-pyrrolidine-2-carboxylic acid (1-cyano-cyclopropyl)-amide

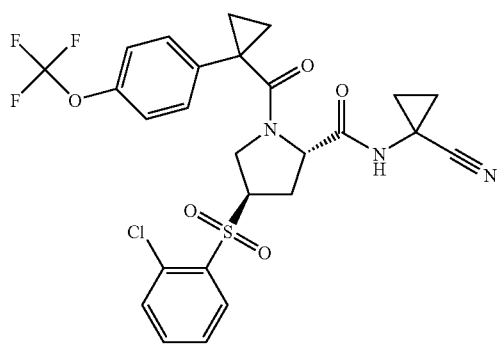

The title compound was prepared in analogy to example 215 using example 42 as a free base (100 mg) as starting material to yield 78 mg (47%) of colorless amorphous material. MS (ESI): m/z=582.2 [M+H]$^+$.

Example 282

(2S,4R)-4-(2-Chloro-benzenesulfonyl)-1-[2-(4-chloro-phenyl)-2-methyl-propionyl]pyrrolidine-2-carboxylic acid (1-cyano-cyclopropyl)-amide

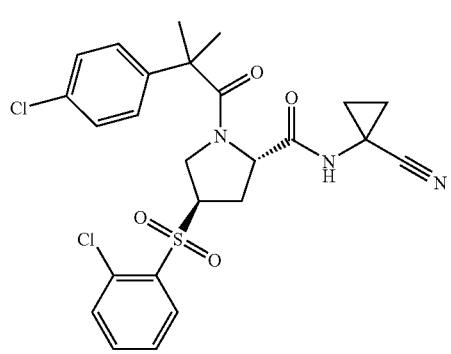

The title compound was prepared in analogy to example 215 using example 42 as a free base (100 mg) as starting material to yield 24 mg (16%) of colorless amorphous material. MS (ESI): m/z=534.1 [M+H]$^+$.

Example 283

(2S,4R)-4-(2-Chloro-benzenesulfonyl)-1-[1-(4-chloro-phenyl)-cyclobutanecarbonyl]-pyrrolidine-2-carboxylic acid (1-cyano-cyclopropyl)-amide

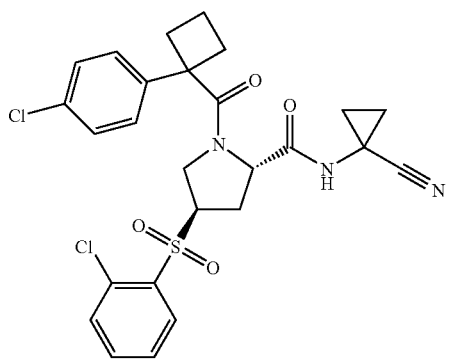

The title compound was prepared in analogy to example 215 using example 42 as a free base (100 mg) as starting material to yield 92 mg (60%) of a colorless amorphous material. MS (ESI): m/z=546.2 [M+H]$^+$.

Example 284

(2S,4R)-4-(2-Chloro-benzenesulfonyl)-1-[1-(3,4-dichloro-phenyl)-cyclopropanecarbonyl]-pyrrolidine-2-carboxylic acid (1-cyano-cyclopropyl)-amide

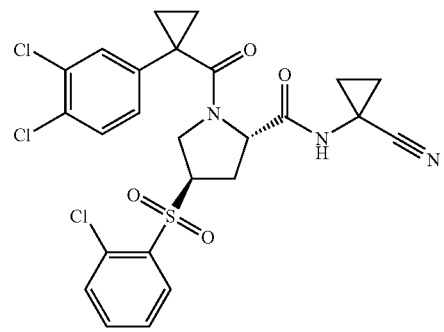

The title compound was prepared in analogy to example 215 using example 42 as a free base (100 mg) as starting material to yield 57 mg (36%) of a colorless amorphous material. MS (ESI): m/z=568.2 [M+H]$^+$.

Example 285

(2S,4R)-4-(2-Chloro-benzenesulfonyl)-1-(1-pyridin-4-yl-cyclopropanecarbonyl)-pyrrolidine-2-carboxylic acid (1-cyano-cyclopropyl)-amide

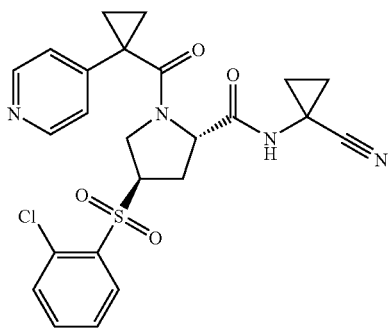

The title compound was prepared in analogy to example 215 using example 42 as a free base (100 mg) as starting material to yield 33 mg (23%) of a colorless foam. MS (ESI): m/z=499.2 [M+H]$^+$.

Example 286

(2S,4R)-1-(5-Methyl-1H-pyrazol-3-yl)-4-(2-trifluoromethyl-benzenesulfonyl)-pyrrolidine-2-carboxylic acid (1-cyano-cyclopropyl)-amide

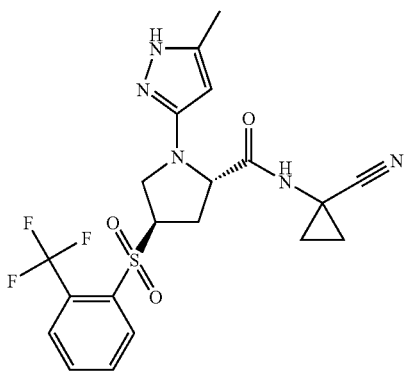

a) (2S,4R)-1-(5-Methyl-1H-pyrazol-3-yl)-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with hydrazine monohydrate (CAS Reg. No. 7803-57-8) to give the title compound as yellow solid.

b) (2S,4R)-1-(5-Methyl-1H-pyrazol-3-yl)-4-(2-trifluoromethyl-benzenesulfonyl)-pyrrolidine-2-carboxylic acid In analogy to the procedure described in example 253e, (2S,4R)-1-(5-methyl-1H-pyrazol-3-yl)-4-(2-trifluoromethyl-benzenesulfonyl)-pyrrolidine-2-carboxylic acid methyl ester was saponified in the presence of lithium hydroxide to give the title compound as yellow solid. MS (ESI): m/z=404.4 [M+H]$^+$.

c) (2S,4R)-1-(5-Methyl-1H-pyrazol-3-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(5-methyl-1H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as brown solid. MS (ESI): m/z=468.2 [M+H]$^+$.

Example 287

(2S,4R)-4-[2-Chloro-4-(2,2,2-trifluoro-ethoxy)-benzenesulfonyl]-1-(4-phenyl-tetrahydro-pyran-4-carbonyl)-pyrrolidine-2-carboxylic acid (1-cyano-cyclopropyl)-amide

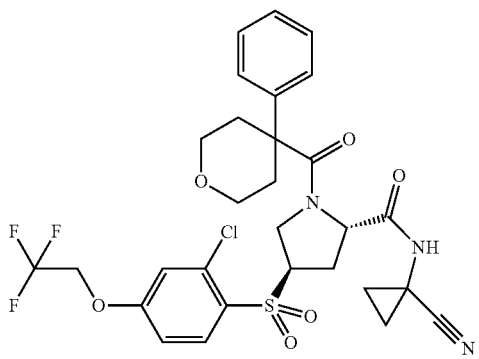

The title compound was prepared in analogy to example 239 using example 173 (90 mg) and 1-phenylcyclohexanecarboxylic acid [CAS #1135-67-7] to yield 28 mg (22%) of a yellow solid. MS (ESI): m/z=640.1 [M+H]$^+$.

Example 288

(2S,4R)-4-[2-Chloro-4-(2,2,2-trifluoro-ethoxy)-benzenesulfonyl]-1-{1-[4-(1-methyl-1H-pyrazol-4-yl)-phenyl]-cyclopropanecarbonyl}-pyrrolidine-2-carboxylic acid (1-cyano-cyclopropyl)-amide

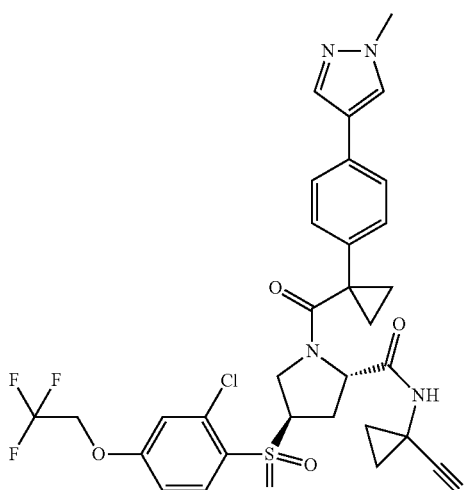

Example 273

Example 273 (200 mg), 1-methyl-4-(4,4,5,5-tetramethyl-1,3,2-dioxaborolan-2-yl)1H-pyrazole, (89 mg), sodium carbonate (85 mg), [1,1'-bis(diphenylphosphino)ferrocene] palladium(II) chloride 1:1 complex with dichloromethane (24 mg) were suspended in dimethylformamide (4 mL) and water (0.4 mL) then degazed with nitrogen. The reaction mixture was stirred at 75° C. over 2 days. The reaction mixture was partitioned between ethyl acetate and a saturated aqueous solution of sodium hydrogenocarbonate. The aqueous layer was extracted with ethyl acetate and the combined organic layers were washed with water and brine. The crude mixture was concentrated to dryness and purified by HPLC to yield the title compound as a light yellow solid (10 mg; 5%). MS (ESI): m/z=674.3 [M–H]⁻.

Example 289

(2S,4R)-1-[5-Methyl-2-(2-methyl-pyridin-4-yl)-2H-pyrazol-3-yl]-4-(2-trifluoromethyl-benzenesulfonyl)-pyrrolidine-2-carboxylic acid (1-cyano-cyclopropyl)-amide

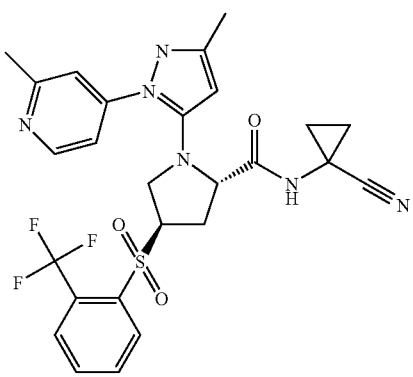

a) (2S,4R)-1-[5-Methyl-2-(2-methyl-pyridin-4-yl)-2H-pyrazol-3-yl]-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with 2-hydrazino-2-methylpyridine (CAS Reg. No. 100518-39-6) to give the title compound as brown solid. MS (ESI): m/z=509.3 [M+H]⁺.

b) (2S,4R)-1-[5-Methyl-2-(2-methyl-pyridin-4-yl)-2H-pyrazol-3-yl]-4-(2-trifluoromethyl-benzenesulfonyl)-pyrrolidine-2-carboxylic acid In analogy to the procedure described in example 253e, (2S,4R)-1-[5-methyl-2-(2-methyl-pyridin-4-yl)-2H-pyrazol-3-yl]-4-(2-trifluoromethyl-benzenesulfonyl)-pyrrolidine-2-carboxylic acid methyl ester was saponified in the presence of lithium hydroxide to give the title compound as yellow solid. MS (ESI): m/z=495.2 [M+H]⁺.

c) (2S,4R)-1-[5-Methyl-2-(2-methyl-pyridin-4-yl)-2H-pyrazol-3-yl]-4-(2-trifluoromethyl-benzenesulfonyl)-pyrrolidine-2-carboxylic acid (1-cyano-cyclopropyl)-amide In analogy to the procedure described in example 237, (2S,4R)-1-[5-methyl-2-(2-methyl-pyridin-4-yl)-2H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as brown solid. MS (ESI): m/z=559.2 [M+H]⁺.

Example 290

(2S,4R)-4-[2-Chloro-4-(4-methyl-piperazin-1-yl)-benzenesulfonyl]-1-(1-trifluoromethyl-cyclopropanecarbonyl)-pyrrolidine-2-carboxylic acid (1-cyano-cyclopropyl)-amide

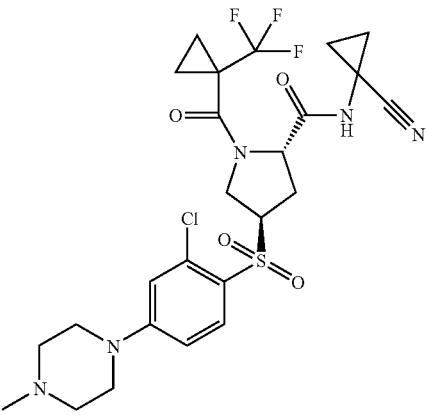

Example 145 (40 mg) was dissolved in acetonitrile (2 mL), Hünig's base (30 µL) and 1-methylpiperazine (16 mg) were added. The reaction mixture was stirred for 24 h at 25° C. LC/MS revealed that still starting material was present. Additional 1-methylpiperazine (16 mg, 2.0 eq.) was added and stirred for 24 h at 25° C. LC/MS revealed that still starting material was present. Additional 1-methylpiperazine (16 mg, 2.0 eq.) was added and stirred for 48 h at 25° C. LC/MS revealed complete conversion. The reaction mixture was purified with prep. HPLC to yield 38 mg (82%) of an off-white solid. MS (ESI): m/z=588.2 [M+H]⁺.

Example 291

(2S,4R)-4-{2-Chloro-4-[4-(2,2,2-trifluoro-ethyl)-piperazin-1-yl]-benzenesulfonyl}-1-(1-trifluoromethyl-cyclopropanecarbonyl)-pyrrolidine-2-carboxylic acid (1-cyano-cyclopropyl)-amide

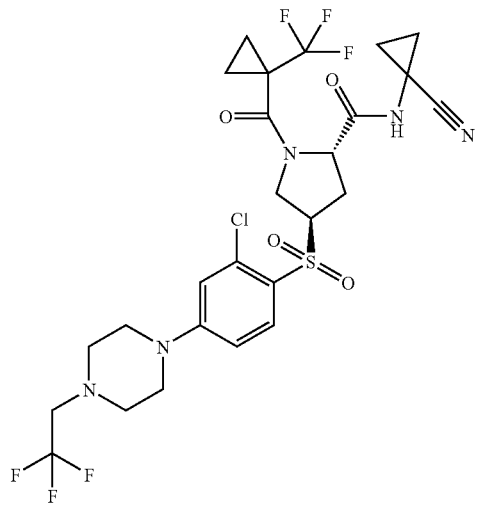

The title compound was prepared in analogy to example 290 using example 145 (80 mg) as starting material to yield 7 mg (7%) of light brown solid. MS (ESI): m/z=656.3 [M+H]⁺.

Example 292

(2S,4R)-4-(2-Chloro-4-dimethylamino-benzene-sulfonyl)-1-(1-trifluoromethyl-cyclopropanecarbonyl)-pyrrolidine-2-carboxylic acid (1-cyano-cyclopropyl)-amide

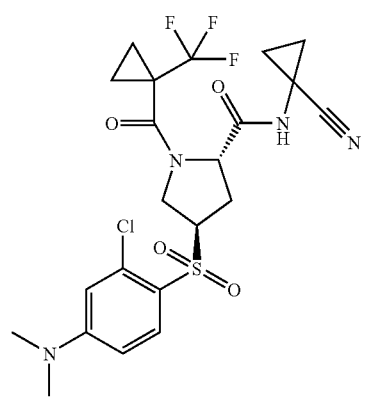

The title compound was obtained as a by-product of example 301 to yield 27 mg (32%) of a white foam. MS (ESI): m/z=533.1 [M+H]⁺.

Example 293

(2S,4R)-4-[2-Chloro-4-(4-isopropyl-piperazin-1-yl)-benzenesulfonyl]-1-(1-trifluoromethyl-cyclopropanecarbonyl)-pyrrolidine-2-carboxylic acid (1-cyano-cyclopropyl)-amide

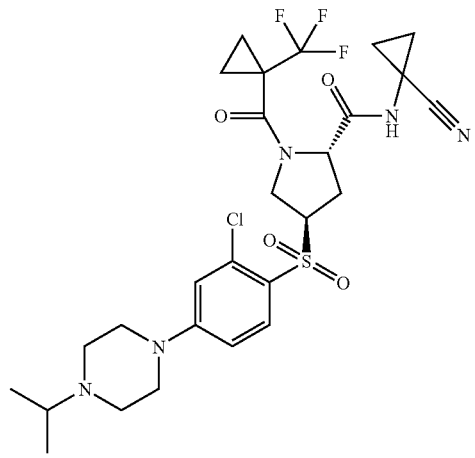

The title compound was prepared in analogy to example 290 using example 145 (20 mg) as starting material to yield 16 mg (66%) of a white solid. MS (ESI): m/z=616.3 [M+H]⁺.

Example 294

(2S,4R)-4-[2-Chloro-4-(2,2,2-trifluoro-ethoxy)-benzenesulfonyl]-1-(3-methyl-oxetane-3-carbonyl)-pyrrolidine-2-carboxylic acid (1-cyano-cyclopropyl)-amide

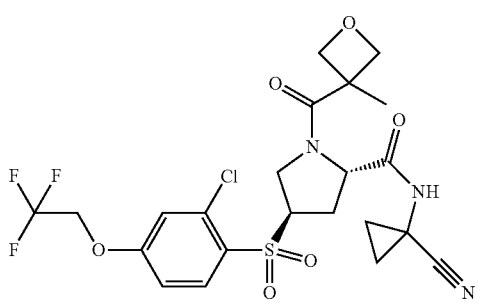

The title compound was prepared in analogy to example 239 using example 173 (75 mg) and 3-oxetanecarboxylic acid (23 mg) to yield 90 mg (99%) of a yellow oil. MS (ESI): m/z=567.1 [M+NH₄]⁺.

Example 295

(2S,4R)-4-[2-Chloro-4-(2,2,2-trifluoro-ethoxy)-benzenesulfonyl]-1-[1-(4-fluoro-phenyl)-cyclopropanecarbonyl]-pyrrolidine-2-carboxylic acid (1-cyano-cyclopropyl)-amide

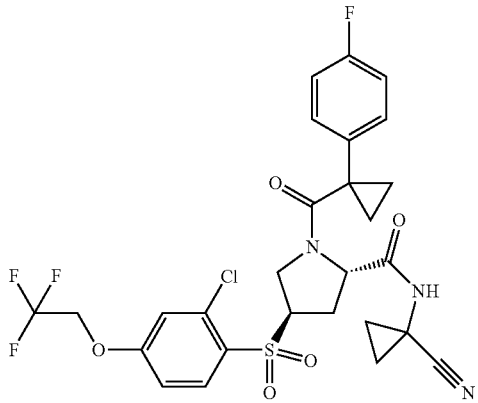

The title compound was prepared in analogy to example 239 using example 173 (75 mg) and 1-(4-fluoro-phenyl)-cyclopropane carboxylic acid (36 mg) to yield 81 mg (76%) of a light yellow foam. MS (ESI): m/z=612.2 [M−H]⁻.

Example 296

(2S,4R)-4-[4-(4-tert-Butyl-piperazin-1-yl)-2-chloro-benzenesulfonyl]-1-(1-trifluoromethyl-cyclopropanecarbonyl)-pyrrolidine-2-carboxylic acid (1-cyano-cyclopropyl)-amide

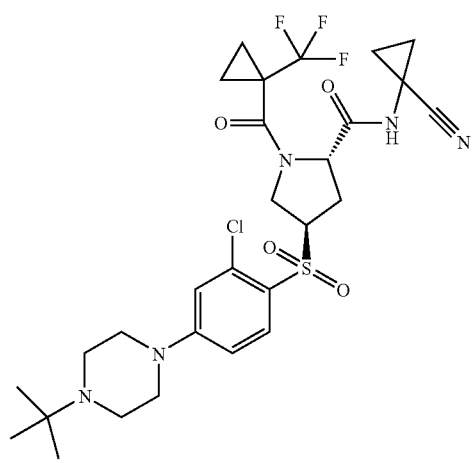

The title compound was prepared in analogy to example 290 using example 145 (60 mg) as starting material to yield 74 mg (99%) of an off-white solid. MS (ESI): m/z=630.5 [M+H]+.

Example 297

(2S,4R)-4-{2-Chloro-4-[4-(2-methoxy-ethyl)-piperazin-1-yl]-benzenesulfonyl}-1-(1-trifluoromethyl-cyclopropanecarbonyl)-pyrrolidine-2-carboxylic acid (1-cyano-cyclopropyl)-amide

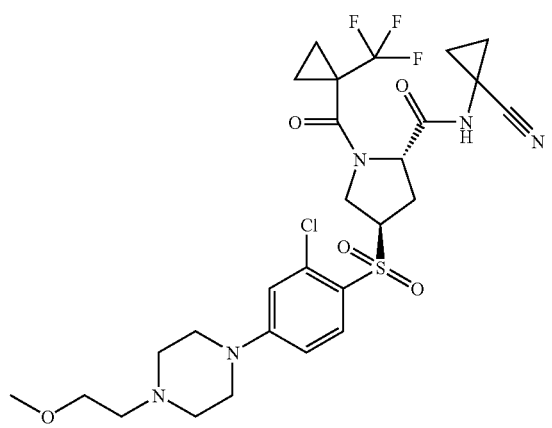

The title compound was prepared in analogy to example 290 using example 145 (60 mg) as starting material to yield 57 mg (76%) of an off-white solid. MS (ESI): m/z=632.4 [M+H]+.

Example 298

(2S,4R)-4-[2-Chloro-4-(4-cyclopropyl-piperazin-1-yl)-benzenesulfonyl]-1-(1-trifluoromethyl-cyclopropanecarbonyl)-pyrrolidine-2-carboxylic acid (1-cyano-cyclopropyl)-amide

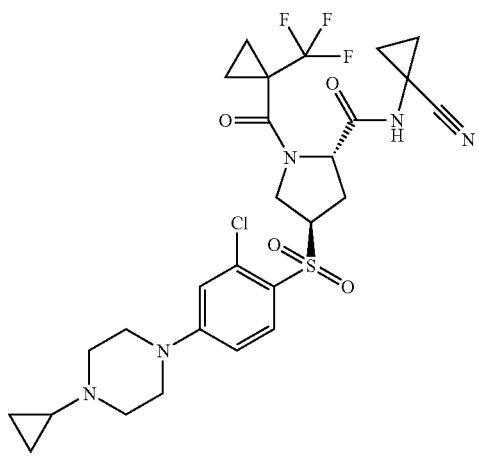

The title compound was prepared in analogy to example 290 using example 145 (60 mg) as starting material to yield 51 mg (70%) of an off-white solid. MS (ESI): m/z=614.2 [M+H]+.

Example 299

(2S,4R)-4-((S)-2-Chloro-4-hexahydro-pyrrolo[1,2-a]pyrazin-2-yl-benzenesulfonyl)-1-(1-trifluoromethyl-cyclopropanecarbonyl)-pyrrolidine-2-carboxylic acid (1-cyano-cyclopropyl)-amide

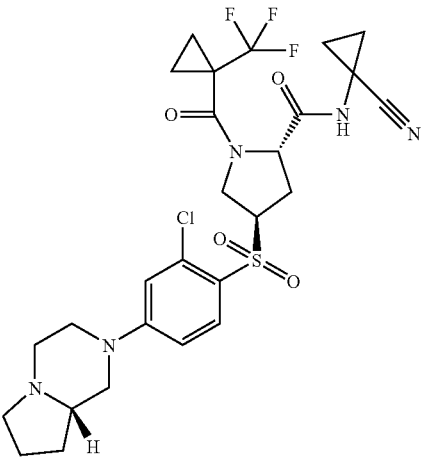

The title compound was prepared in analogy to example 290 using example 145 (60 mg) as starting material to yield 59 mg (81%) of an off-white solid. MS (ESI): m/z=614.2 [M+H]+.

Example 300

(2S,4R)-1-(2,5-Dimethyl-2H-pyrazol-3-yl)-4-(2-trifluoromethyl-benzenesulfonyl)-pyrrolidine-2-carboxylic acid (1-cyano-cyclopropyl)-amide

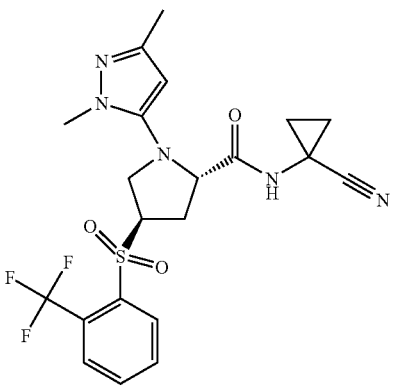

a) (2S,4R)-1-[3-(tert-Butoxycarbonyl-methyl-hydrazono)-thiobutyryl]-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with N-methyl-hydrazinecarboxylic acid tert-butyl ester (CAS Reg. No. 21075-83-2) to give the title compound as off-white solid. MS (ESI): m/z=566.2 [M+H]+.

b) (2S,4R)-1-(2,5-Dimethyl-2H-pyrazol-3-yl)-4-(2-trifluoromethyl-benzenesulfonyl)-pyrrolidine-2-carboxylic acid methyl ester Trifluoroacetic acid (61 ul, 0.8 mmol) was added to a solution of (2S,4R)-1-[3-(tert-butoxycarbonyl-methyl-hydrazono)-thiobutyryl]-4-(2-trifluoromethyl-benzenesulfonyl)-pyrrolidine-2-carboxylic acid methyl ester (90 mg, 160 umol) in dichloromethane (0.3 ml) under an argon atmosphere. The mixture was stirred at ambient temperature for 72 h. Ice water/10% aqueous sodium carbonate solution 1/1 and iPrOAc were added and the layers were separated. The aqueous layer was extracted four more times with iPrOAc, the combined organic layers were washed with ice water/brine 1/1 and dried over Na2SO4. The solvent was removed under reduced pressure to give a brown oil which was purified by preparative thin layer chromatography (silica gel, iPrOAc) to obtain the title compound (20 mg, 46 umol; 29%) as yellow solid. MS (ESI): m/z=432.1 [M+H]+.

c) (2S,4R)-1-(2,5-Dimethyl-2H-pyrazol-3-yl)-4-(2-trifluoromethyl-benzenesulfonyl)-pyrrolidine-2-carboxylic acid In analogy to the procedure described in example 253e, (2S,4R)-1-(2,5-dimethyl-2H-pyrazol-3-yl)-4-(2-trifluoromethyl-benzenesulfonyl)-pyrrolidine-2-carboxylic acid methyl ester was saponified in the presence of lithium hydroxide to give the title compound as off-white solid. MS (ESI): m/z=418.2 [M+H]+.

d) (2S,4R)-1-(2,5-Dimethyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(2,5-dimethyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as brown solid. MS (ESI): m/z=482.1 [M+H]+.

Example 301

(2S,4R)-4-[2-Chloro-4-(5,6-dihydro-8H-[1,2,4]triazolo[4,3-a]pyrazin-7-yl)-benzenesulfonyl]-1-(1-trifluoromethyl-cyclopropanecarbonyl)-pyrrolidine-2-carboxylic acid (1-cyano-cyclopropyl)-amide

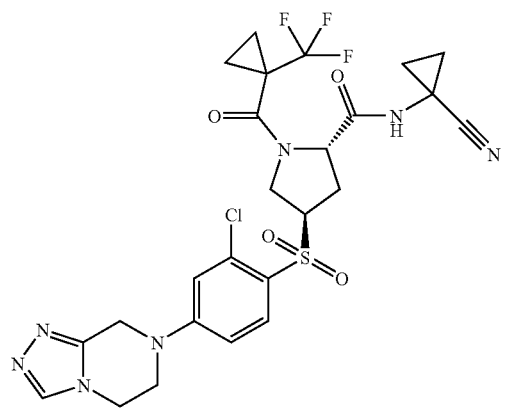

The title compound was prepared in analogy to example 290 using example 145 (20 mg) as starting material and stirring for 48 h at 70° C. to yield 6 mg (25%) of an off-white solid. MS (ESI): m/z=612.2 [M+H]+.

Example 302

(2S,4R)-1-[1-(4-Chloro-phenyl)-cyclopentanecarbonyl]-4-[2-chloro-4-(2,2,2-trifluoro-ethoxy)-benzenesulfonyl]-pyrrolidine-2-carboxylic acid (1-cyano-cyclopropyl)-amide

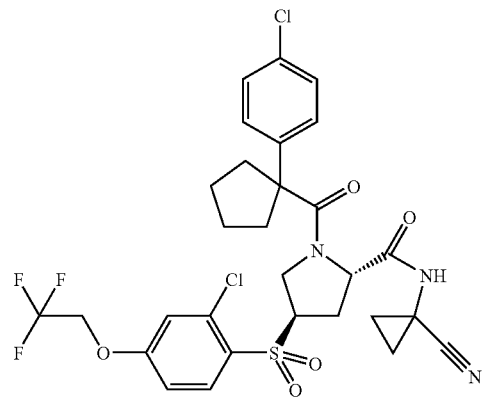

The title compound was prepared in analogy to example 239 using example 173 (75 mg) and 1-(4-chlorophenyl)-1cyclopentane carboxylic acid (46 mg) to yield 47 mg (43%) of a white foam. MS (ESI): m/z=658.2 [M+H]+.

Example 303

(2S,4R)-4-[2-Chloro-4-(2,2,2-trifluoro-ethoxy)-benzenesulfonyl]-1-(1-phenyl-cyclohexanecarbonyl)-pyrrolidine-2-carboxylic acid (1-cyano-cyclopropyl)-amide

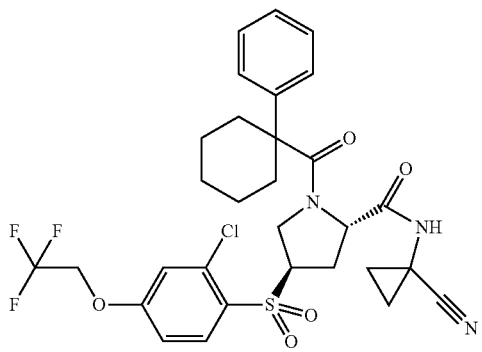

The title compound was prepared in analogy to example 239 using example 173 (75 mg) and 1-phenyl-1-cyclohexanecarboxylic acid (43 mg) to yield 15 mg (14%) of a white foam. MS (ESI): m/z=638.2 [M+H]+.

Example 304

(2S,4R)-4-[2-Chloro-4-(2,2,2-trifluoro-ethoxy)-benzenesulfonyl]-1-(1-p-tolyl-cyclopropanecarbonyl)-pyrrolidine-2-carboxylic acid (1-cyano-cyclopropyl)-amide

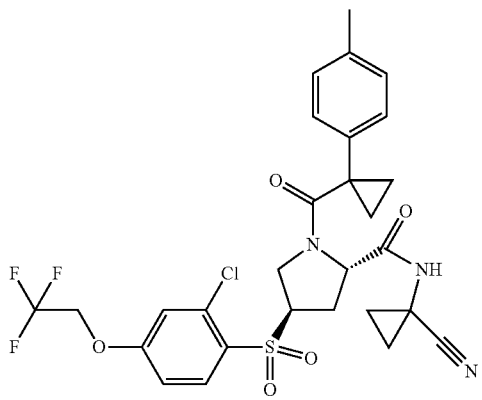

The title compound was prepared in analogy to example 288 using example 273 (200 mg) and trimethylboroxine in tetrahydrofuran (50% w/w, 104 mg) to yield 12 mg (7%) of a colorless oil. MS (ESI): m/z=608.1 [M−H]−.

Example 305

(R)-4-[2-Chloro-4-(4-methyl-piperazin-1-yl)-benzenesulfonyl]-1-(1-trifluoromethyl-cyclopropanecarbonyl)-pyrrolidine-2-carboxylic acid (1-cyano-cyclopropyl)-amide

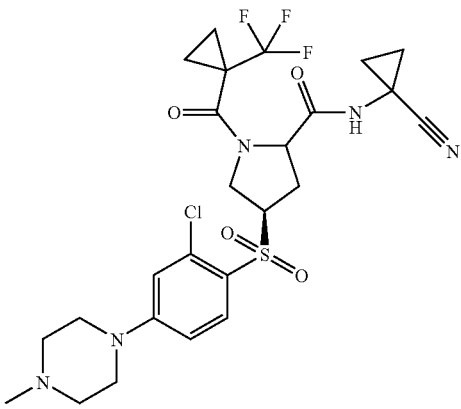

The title compound was obtained as a by-product during the synthesis of example 290 using example 145 (60 mg) as starting material to yield 9 mg (10%) of a light brown solid. MS (ESI): m/z=588.1 [M+H]+.

Example 306

(2S,4R)-1-[5-Methyl-2-(4-trifluoromethyl-phenyl)-2H-pyrazol-3-yl]-4-[4-(2,2,2-trifluoro-ethoxy)-2-trifluoromethyl-benzenesulfonyl]-pyrrolidine-2-carboxylic acid (1-cyano-cyclopropyl)-amide

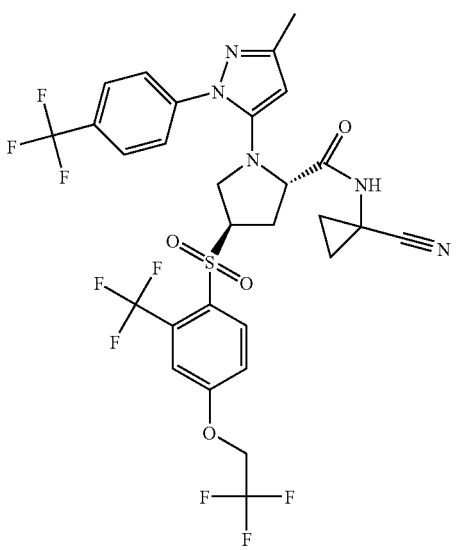

2,2,2-Trifluoroethanol (2.2 ul, 29 umol) and cesium carbonate (9 mg, 29 umol) were added to a solution of (2S,4R)-

4-(4-fluoro-2-trifluoromethyl-benzenesulfonyl)-1-[5-methyl-2-(4-trifluoromethyl-phenyl)-2H-pyrazol-3-yl]-pyrrolidine-2-carboxylic acid (1-cyano-cyclopropyl)-amide (15 mg, 24 umol; example 267c) in N,N-dimethylacetamide (0.2 ml) under an argon atmosphere. The mixture was stirred for 12 h at ambient temperature and for 5 h at 40° C. Ice water/0.1 N aqueous HCl solution 1/1 and iPrOAc were added and the layers were separated. The aqueous layer was extracted one more time with iPrOAc, the combined organic layers were washed with ice water/brine 1/1 and dried over Na$_2$SO$_4$. The solvent was removed under reduced pressure to give a yellow oil which was purified by preparative thin layer chromatography (silica gel, iPrOAc/heptane) to obtain the title compound (7 mg, 9.9 umol; 44%) as colorless oil. MS (ESI): m/z=710.1 [M+H]$^+$.

Example 307

(2S,4R)-1-[5-Methyl-2-(tetrahydro-pyran-4-yl)-2H-pyrazol-3-yl]-4-(2-trifluoromethyl-benzenesulfonyl)-pyrrolidine-2-carboxylic acid (1-cyano-cyclopropyl)-amide

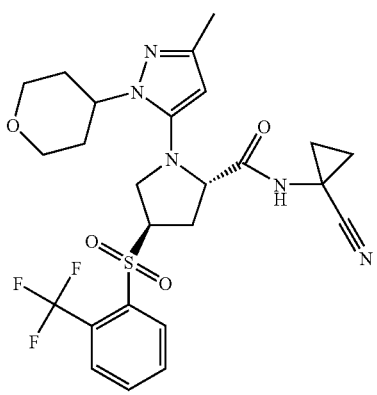

a) (2S,4R)-1-[5-Methyl-2-(tetrahydro-pyran-4-yl)-2H-pyrazol-3-yl]-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with (tetrahydropyran-4-yl)hydrazine hydrochloride (CAS Reg. No. 194543-22-1) to give the title compound as orange oil. MS (ESI): m/z=502.1 [M+H]$^+$.

b) (2S,4R)-1-[5-Methyl-2-(tetrahydro-pyran-4-yl)-2H-pyrazol-3-yl]-4-(2-trifluoromethyl-benzenesulfonyl)-pyrrolidine-2-carboxylic acid In analogy to the procedure described in example 253e, (2S,4R)-1-[5-methyl-2-(tetrahydro-pyran-4-yl)-2H-pyrazol-3-yl]-4-(2-trifluoromethyl-benzenesulfonyl)-pyrrolidine-2-carboxylic acid methyl ester was saponified in the presence of lithium hydroxide to give the title compound as orange oil.

c) (2S,4R)-1-[5-Methyl-2-(tetrahydro-pyran-4-yl)-2H-pyrazol-3-yl]-4-(2-trifluoromethyl-benzenesulfonyl)-pyrrolidine-2-carboxylic acid (1-cyano-cyclopropyl)-amide In analogy to the procedure described in example 237, (2S,4R)-1-[5-methyl-2-(tetrahydro-pyran-4-yl)-2H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless oil. MS (ESI): m/z=552.3 [M+H]$^+$.

Example 308

(2S,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide

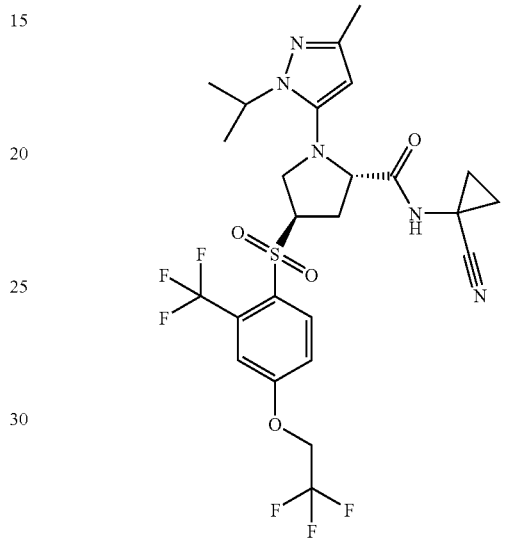

a) (2S,4R)-4-[4-(2,2,2-Trifluoro-ethoxy)-2-trifluoromethyl-benzenesulfonyl]-pyrrolidine-1,2-dicarboxylic acid 1-tert-butyl ester 2-methyl ester In analogy to the procedure described in example 306, (2S,4R)-4-(4-fluoro-2-trifluoromethyl-benzenesulfonyl)-pyrrolidine-1,2-dicarboxylic acid 1-tert-butyl ester 2-methyl ester (example 208 c) was treated with 2,2,2-trifluoroethanol and cesium carbonate to give a mixture of the title compound and starting material as yellow oil. MS (ESI): m/z=436.1 [M+H]$^+$.

b) (2S,4R)-4-[4-(2,2,2-Trifluoro-ethoxy)-2-trifluoromethyl-benzenesulfonyl]-pyrrolidine-2-carboxylic acid methyl ester In analogy to the procedure described in example 253a, (2S,4R)-4-[4-(2,2,2-trifluoro-ethoxy)-2-trifluoromethyl-benzenesulfonyl]-pyrrolidine-1,2-dicarboxylic acid 1-tert-butyl ester 2-methyl ester containing (2S,4R)-4-(4-fluoro-2-trifluoromethyl-benzenesulfonyl)-pyrrolidine-1,2-dicarboxylic acid 1-tert-butyl ester 2-methyl ester was treated with trifluoroacetic acid in dichloromethane to give a mixture of the title compound and (2S,4R)-4-(4-fluoro-2-trifluoromethyl-benzenesulfonyl)-pyrrolidine-2-carboxylic acid methyl ester as yellow oil. MS (ESI): m/z=436.2 [M+H]$^+$.

c) (2S,4R)-1-(3-Oxo-butyryl)-4-[4-(2,2,2-trifluoro-ethoxy)-2-trifluoromethyl-benzenesulfonyl]-pyrrolidine-2-carboxylic acid methyl ester In analogy to the procedure described in example 192f, (2S,4R)-4-[4-(2,2,2-trifluoro-ethoxy)-2-trifluoromethyl-benzenesulfonyl]-pyrrolidine-2-carboxylic acid methyl ester containing (2S,4R)-4-(4-fluoro-2-trifluoromethyl-benzenesulfonyl)-pyrrolidine-2-carboxylic acid methyl ester was reacted with tert-butyl acetoacetate to give a mixture of the title compound and (2S,4R)-4-(4-fluoro-2-trifluoromethyl-benzenesulfonyl)-1-(3-oxo-butyryl)-pyrrolidine-2-carboxylic acid methyl ester as colorless oil. MS (ESI): m/z=520.2 [M+H]+.

d) (2S,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid methyl ester Lawesson's reagent (39 mg, 106 umol; CAS Reg. No. 19172-47-5) and isopropylhydrazine hydrochloride (12 mg, 106 umol; CAS Reg. No. 16726-41-3) were added to a solution of (2S,4R)-1-(3-oxo-butyryl)-4-[4-(2,2,2-trifluoro-ethoxy)-2-trifluoromethyl-benzenesulfonyl]-pyrrolidine-2-carboxylic acid methyl ester and (2S,4R)-4-(4-fluoro-2-trifluoromethyl-benzenesulfonyl)-1-(3-oxo-butyryl)-pyrrolidine-2-carboxylic acid methyl ester (50 mg, 96 umol) in tetrahydrofuran (2.9 ml) and pyridine (0.1 ml) under an argon atmosphere. The mixture was stirred for 16 h at 55° C. and for additional 48 h at ambient temperature. Ice water/0.1 N aqueous HCl solution 1/1 and iPrOAc were added and the layers were separated. The aqueous layer was extracted one more time with iPrOAc, the combined organic layers were washed with ice water/10% aqueous sodium carbonate solution, ice water/brine 1/1 and dried over Na$_2$SO$_4$. The solvent was removed under reduced pressure to give a yellow oil which was purified by preparative thin layer chromatography (silica gel, iPrOAc/heptane) to obtain a mixture of the title compound and (2S,4R)-4-(4-fluoro-2-trifluoromethyl-benzenesulfonyl)-1-(2-isopropyl-5-methyl-2H-pyrazol-3-yl)-pyrrolidine-2-carboxylic acid methyl ester (39 mg, 70 umol; 73%) as colorless oil. MS (ESI): m/z=558.2 [M+H]+.

e) (2S,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid methyl ester In analogy to the procedure described in example 306, a mixture of (2S,4R)-4-(4-fluoro-2-trifluoromethyl-benzenesulfonyl)-1-(2-isopropyl-5-methyl-2H-pyrazol-3-yl)-pyrrolidine-2-carboxylic acid methyl ester and (2S,4R)-1-(2-isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid methyl ester was treated with 2,2,2-trifluoroethanol and cesium carbonate to give a mixture of the title compound and (2R,4R)-1-(2-isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid methyl ester as colorless oil. MS (ESI): m/z=558.2 [M+H]+.

f) (2S,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid In analogy to the procedure described in example 253e, a mixture of (2S,4R)-1-(2-isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid methyl ester and (2R,4R)-1-(2-isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid methyl ester was saponified in the presence of lithium hydroxide to give the title compound as colorless solid. MS (ESI): m/z=544.2 [M+H]+.

g) (2S,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide In analogy to the procedure described in example 237, a mixture of (2S,4R)-1-(2-isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid and (2R,4R)-1-(2-isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid was reacted with 1-amino-cyclopropanecarbonitrile hydrochloride (CAS Reg. No. 127946-77-4) in the presence of HATU and DIEA to give the title compound after purification by preparative thin layer chromatography (silica gel, iPrOAc) as colorless oil. MS (ESI): m/z=608.2 [M+H]+.

Example 309

(2R,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide

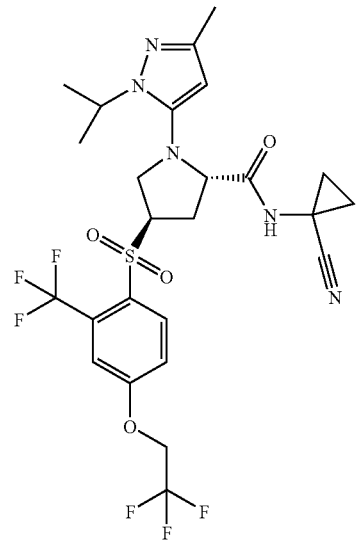

In analogy to the procedure described in example 237, a mixture of (2S,4R)-1-(2-isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid and (2R,4R)-1-(2-isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid (example 308f) was reacted with 1-amino-cyclopropanecarbonitrile hydrochloride (CAS Reg. No. 127946-77-4) in the presence of HATU and DIEA to give the

Example 310

(2S,4R)-4-[2-Chloro-4-(2,2,2-trifluoro-ethoxy)-benzenesulfonyl]-1-[1-(4-trifluoromethyl-phenyl)-cyclopropanecarbonyl]-pyrrolidine-2-carboxylic acid (1-cyano-cyclopropyl)-amide

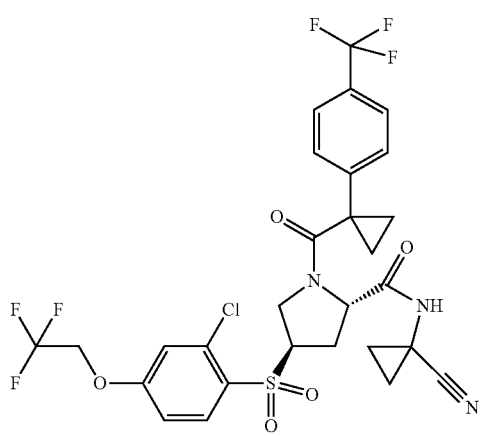

The title compound was prepared in analogy to example 239 using example 173 (75 mg) and 1-(4-trifluoromethyl) phenylcyclopropane carboxylic acid (48 mg) to yield 119 mg (98%) of a white foam. MS (ESI): m/z=664.1 [M+H]⁺.

Example 311

(2S,4R)-4-[2-Chloro-4-(2,2,2-trifluoro-ethoxy)-benzenesulfonyl]-1-[1-(3-trifluoromethyl-phenyl)-cyclopropanecarbonyl]-pyrrolidine-2-carboxylic acid (1-cyano-cyclopropyl)-amide

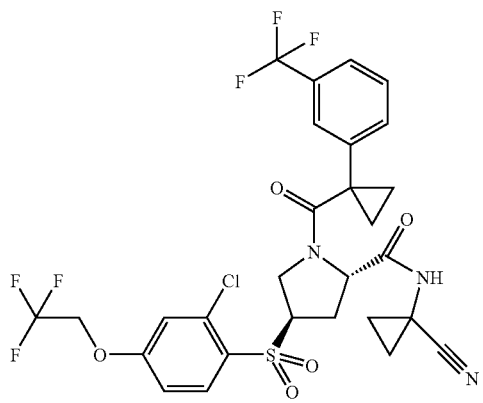

The title compound was prepared in analogy to example 239 using example 173 (75 mg) and 1-(3-trifluoromethyl) phenylcyclopropane carboxylic acid (48 mg) to yield 112 mg (93%) of a white foam. MS (ESI): m/z=664.1 [M+H]⁺.

Example 312

(2S,4R)-4-(2-Chloro-4-fluoro-benzenesulfonyl)-1-[1-(4-chloro-phenyl)-cyclopropanecarbonyl]-pyrrolidine-2-carboxylic acid (1-cyano-cyclopropyl)-amide

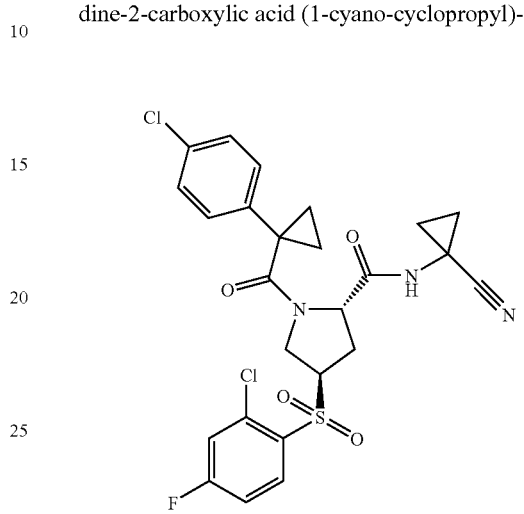

The title compound was prepared in analogy to example 215 using example 144 (1.8 g) as starting material to yield 1.8 g (68%) of a white foam. MS (ESI): m/z=550.2 [M+H]⁺.

Example 313

(2S,4R)-4-(2-Chloro-benzenesulfonyl)-1-(naphthalene-2-sulfonyl)-pyrrolidine-2-carboxylic Acid (1-cyano-cyclopropyl)-amide

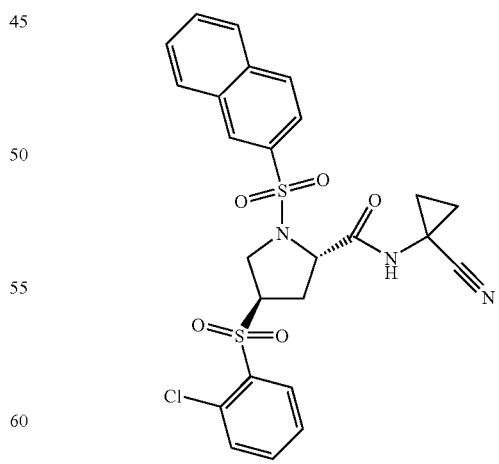

Example 42 as a free base (70 mg) was dissolved in THF (4 mL). 2-Naphthalensulfonyl chloride (54 mg) and Hünig's base (70 µL) were added. The mixture was stirred for 18 h at room temperature. The reaction mixture was evaporated to

Example 314

(2S,4R)-1-[1-(4-Chloro-phenyl)-cyclohexanecarbonyl]-4-[2-chloro-4-(2,2,2-trifluoro-ethoxy)-benzenesulfonyl]-pyrrolidine-2-carboxylic acid (1-cyano-cyclopropyl)-amide

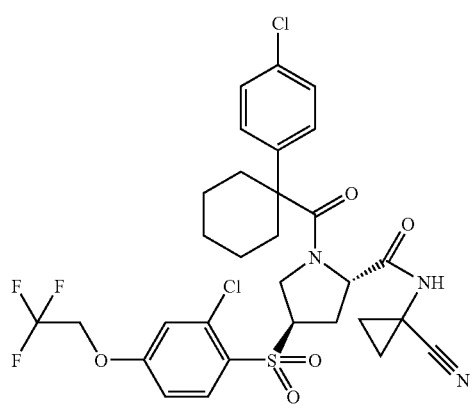

The title compound was prepared in analogy to example 239 using example 173 (75 mg) and 1-(4-chlorophenyl)-1-cyclohexane carboxylic acid (50 mg) to yield 17 mg (15%) of a colorless gum. MS (ESI): m/z=670.3 [M−H]⁻.

Example 315

(2S,4R)-4-(2-Chloro-benzenesulfonyl)-1-(4-chloro-benzenesulfonyl)-pyrrolidine-2-carboxylic Acid (1-cyano-cyclopropyl)-amide

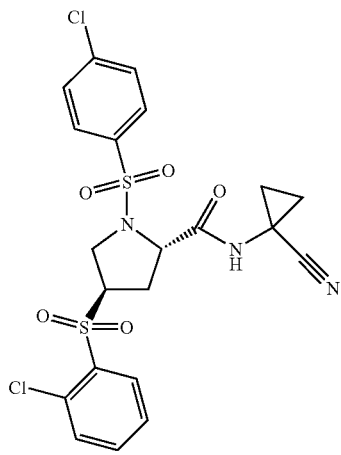

The title compound was prepared in analogy to example 313 using CH₂Cl₂ (2 mL) instead of THF as a solvent to yield 91 mg (87%) of a white foam. MS (ESI): m/z=528.1 [M+H]⁺.

Example 316

(2S,4R)-1-(Biphenyl-4-sulfonyl)-4-(2-chloro-benzenesulfonyl)-pyrrolidine-2-carboxylic acid (1-cyano-cyclopropyl)-amide

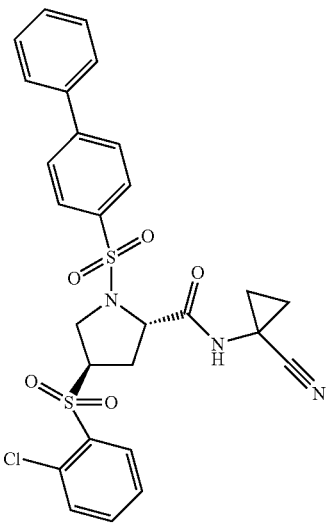

The title compound was prepared in analogy to example 315 to yield 54 mg (48%) of a white foam. MS (ESI): m/z=570.2 [M+H]⁺.

Example 317

(2S,4R)-1-(5-Methyl-2-pyridazin-3-yl-2H-pyrazol-3-yl)-4-(2-trifluoromethyl-benzenesulfonyl)-pyrrolidine-2-carboxylic acid (1-cyano-cyclopropyl)-amide

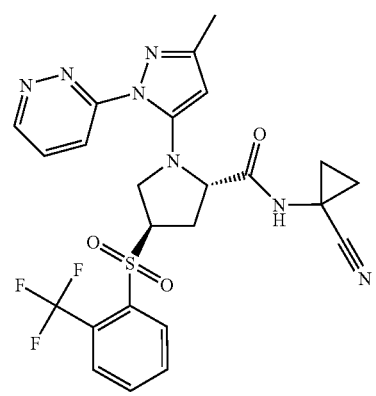

a) (2S,4R)-1-(5-Methyl-2-pyridazin-3-yl-2H-pyrazol-3-yl)-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with pyridazin-3-yl-hydrazine (CAS Reg. No. 40972-16-5) to give the title compound as colorless oil. MS (ESI): m/z=496.3 [M+H]⁺.

231 b) (2S,4R)-1-(5-Methyl-2-pyridazin-3-yl-2H-pyrazol-3-yl)-4-(2-trifluoromethyl-benzenesulfonyl)-pyrrolidine-2-carboxylic acid In analogy to the procedure described in example 253e, (2S,4R)-1-(5-methyl-2-pyridazin-3-yl-2H-pyrazol-3-yl)-4-(2-trifluoromethyl-benzenesulfonyl)-pyrrolidine-2-carboxylic acid methyl ester was saponified in the presence of lithium hydroxide. The reaction mixture was brought to dryness to give the title compound in the form of its lithium salt as yellow solid. MS (ESI): m/z=482.2 [M+H]$^+$.

c) (2S,4R)-1-(5-Methyl-2-pyridazin-3-yl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(5-methyl-2-pyridazin-3-yl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless oil. MS (ESI): m/z=546.3 [M+H]$^+$.

Example 318

(2S,4R)-1-(2-Cyclohexyl-5-methyl-2H-pyrazol-3-yl)-4-(2-trifluoromethyl-benzenesulfonyl)-pyrrolidine-2-carboxylic acid (1-cyano-cyclopropyl)-amide

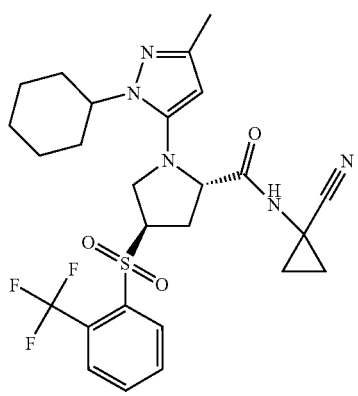

a) (2S,4R)-1-(2-Cyclohexyl-5-methyl-2H-pyrazol-3-yl)-4-(2-trifluoromethyl-benzenesulfonyl)-pyrrolidine-2-carboxylic acid methyl ester In analogy to the procedure described in example 308d, a mixture of (2S,4R)-1-(3-oxo-butyryl)-4-(2-trifluoromethyl-benzenesulfonyl)-pyrrolidine-2-carboxylic acid methyl ester (example 192 f) and of (2R,4R)-1-(3-oxo-butyryl)-4-(2-trifluoromethyl-benzenesulfonyl)-pyrrolidine-2-carboxylic acid methyl ester was reacted with Lawesson's reagent (CAS Reg. No. 19172-47-5) and cyclohexylhydrazine hydrochloride (CAS Reg. No. 24214-73-1) to give a mixture of the title compound and (2R,4R)-1-(2-cyclohexyl-5-methyl-2H-pyrazol-3-yl)-4-(2-trifluoromethyl-benzenesulfonyl)-pyrrolidine-2-carboxylic acid methyl ester as brown oil. MS (ESI): m/z=500.3 [M+H]$^+$.

232 b) (2S,4R)-1-(2-Cyclohexyl-5-methyl-2H-pyrazol-3-yl)-4-(2-trifluoromethyl-benzenesulfonyl)-pyrrolidine-2-carboxylic acid In analogy to the procedure described in example 253e, a mixture of (2S,4R)-1-(2-cyclohexyl-5-methyl-2H-pyrazol-3-yl)-4-(2-trifluoromethyl-benzenesulfonyl)-pyrrolidine-2-carboxylic acid methyl ester and (2R,4R)-1-(2-cyclohexyl-5-methyl-2H-pyrazol-3-yl)-4-(2-trifluoromethyl-benzenesulfonyl)-pyrrolidine-2-carboxylic acid methyl ester was saponified in the presence of lithium hydroxide to give a mixture of the title compound and (2R,4R)-1-(2-cyclohexyl-5-methyl-2H-pyrazol-3-yl)-4-(2-trifluoromethyl-benzenesulfonyl)-pyrrolidine-2-carboxylic acid as colorless solid which was used in the next step without further purification.

c) (2S,4R)-1-(2-Cyclohexyl-5-methyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, a mixture of (2S,4R)-1-(2-cyclohexyl-5-methyl-2H-pyrazol-3-yl)-4-(2-trifluoromethyl-benzenesulfonyl)-pyrrolidine-2-carboxylic acid and (2R,4R)-1-(2-cyclohexyl-5-methyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as colorless oil. MS (ESI): m/z=550.2 [M+H]$^+$.

Example 319

(2S,4R)-1-(2-Benzyl-5-methyl-2H-pyrazol-3-yl)-4-(2-trifluoromethyl-benzenesulfonyl)-pyrrolidine-2-carboxylic acid (1-cyano-cyclopropyl)-amide

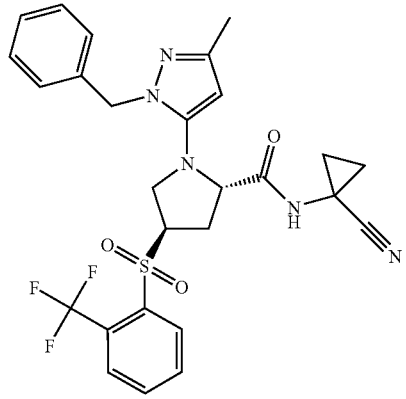

a) (2S,4R)-1-(2-Benzyl-5-methyl-2H-pyrazol-3-yl)-4-(2-trifluoromethyl-benzenesulfonyl)-pyrrolidine-2-carboxylic acid methyl ester In analogy to the procedure described in example 192 h, a mixture of (2S,4R)-1-(3-oxo-thiobutyryl)-4-(2-trifluoromethyl-benzenesulfonyl)-pyrrolidine-2-carboxylic acid methyl ester (example 192 g) and of (2R,4R)-1-(3-oxo-thiobutyryl)-4-(2-trifluoromethyl-benzenesulfonyl)-pyrrolidine-2-carboxylic acid methyl ester was reacted with benzyl-hydrazine dihydrochloride (CAS Reg. No. 20570-96-1) to give a mixture of the title compound and (2R,4R)-1-(2-benzyl-5-methyl-2H-pyrazol-3-yl)-4-(2-trifluoromethyl-benzenesulfonyl)-pyrrolidine-2-carboxylic acid methyl ester as orange oil. MS (ESI): m/z=508.2 [M+H]⁺.

b) (2S,4R)-1-(2-Benzyl-5-methyl-2H-pyrazol-3-yl)-4-(2-trifluoromethyl-benzenesulfonyl)-pyrrolidine-2-carboxylic acid In analogy to the procedure described in example 253e, a mixture of (2S,4R)-1-(2-benzyl-5-methyl-2H-pyrazol-3-yl)-4-(2-trifluoromethyl-benzenesulfonyl)-pyrrolidine-2-carboxylic acid methyl ester and (2R,4R)-1-(2-benzyl-5-methyl-2H-pyrazol-3-yl)-4-(2-trifluoromethyl-benzenesulfonyl)-pyrrolidine-2-carboxylic acid methyl ester was saponified in the presence of lithium hydroxide to give a mixture of the title compound and (2R,4R)-1-(2-benzyl-5-methyl-2H-pyrazol-3-yl)-4-(2-trifluoromethyl-benzenesulfonyl)-pyrrolidine-2-carboxylic acid as orange oil which was used in the next step without further purification. MS (ESI): m/z=492.3 [M–H]⁻.

c) (2S,4R)-1-(2-Benzyl-5-methyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, a mixture of (2S,4R)-1-(2-benzyl-5-methyl-2H-pyrazol-3-yl)-4-(2-trifluoromethyl-benzenesulfonyl)-pyrrolidine-2-carboxylic acid and (2R,4R)-1-(2-benzyl-5-methyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as colorless oil. MS (ESI): m/z=558.2 [M+H]⁺.

Example 320

(2R,4R)-1-(2-Cyclohexyl-5-methyl-2H-pyrazol-3-yl)-4-(2-trifluoromethyl-benzenesulfonyl)-pyrrolidine-2-carboxylic acid (1-cyano-cyclopropyl)-amide

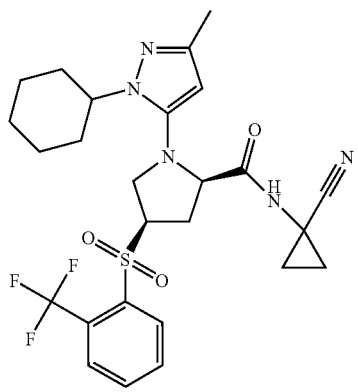

In analogy to the procedure described in example 237, a mixture of (2S,4R)-1-(2-cyclohexyl-5-methyl-2H-pyrazol-3-yl)-4-(2-trifluoromethyl-benzenesulfonyl)-pyrrolidine-2-carboxylic acid and (2R,4R)-1-(2-cyclohexyl-5-methyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as colorless oil. MS (ESI): m/z=550.2 [M+H]⁺.

Example 321

(2R,4R)-1-(2-Benzyl-5-methyl-2H-pyrazol-3-yl)-4-(2-trifluoromethyl-benzenesulfonyl)-pyrrolidine-2-carboxylic acid (1-cyano-cyclopropyl)-amide

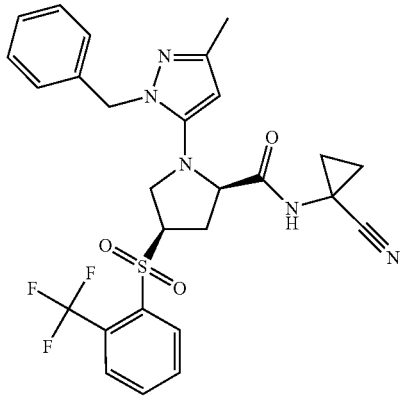

In analogy to the procedure described in example 237, a mixture of (2S,4R)-1-(2-benzyl-5-methyl-2H-pyrazol-3-yl)-4-(2-trifluoromethyl-benzenesulfonyl)-pyrrolidine-2-carboxylic acid and (2R,4R)-1-(2-benzyl-5-methyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as colorless oil. MS (ESI): m/z=558.2 [M+H]⁺.

Example 322

(2S,4R)-1-(2-Cyclobutyl-5-methyl-2H-pyrazol-3-yl)-4-(2-trifluoromethyl-benzenesulfonyl)-pyrrolidine-2-carboxylic acid (1-cyano-cyclopropyl)-amide

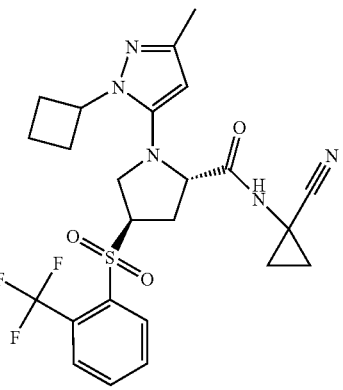

a) (2S,4R)-1-(2-Cyclobutyl-5-methyl-2H-pyrazol-3-yl)-4-(2-trifluoromethyl-benzenesulfonyl)-pyrrolidine-2-carboxylic acid methyl ester In analogy to the procedure described in example 308d, a mixture of (2S,4R)-1-(3-oxo-butyryl)-4-(2-trifluoromethyl-benzenesulfonyl)-pyrrolidine-2-carboxylic acid methyl ester (example 192 f) and of (2R,4R)-1-(3-oxo-butyryl)-4-(2-trifluoromethyl-benzenesulfonyl)-pyrrolidine-2-carboxylic acid methyl ester was reacted with Lawesson's reagent (CAS Reg. No. 19172-47-5) and cyclobutylhydrazine hydrochloride (CAS Reg. No. 158001-21-9) to give a mixture of the title compound and (2R,4R)-1-(2-cyclobutyl-5-methyl-2H-pyrazol-3-yl)-4-(2-trifluoromethyl-benzenesulfonyl)-pyrrolidine-2-carboxylic acid methyl ester as white solid. MS (ESI): m/z=472.3 [M+H]⁺.

b) (2S,4R)-1-(2-Cyclobutyl-5-methyl-2H-pyrazol-3-yl)-4-(2-trifluoromethyl-benzenesulfonyl)-pyrrolidine-2-carboxylic acid In analogy to the procedure described in example 253e, a mixture of (2S,4R)-1-(2-cyclobutyl-5-methyl-2H-pyrazol-3-yl)-4-(2-trifluoromethyl-benzenesulfonyl)-pyrrolidine-2-carboxylic acid methyl ester and (2R,4R)-1-(2-cyclobutyl-5-methyl-2H-pyrazol-3-yl)-4-(2-trifluoromethyl-benzenesulfonyl)-pyrrolidine-2-carboxylic acid methyl ester was saponified in the presence of lithium hydroxide to give a mixture of the title compound and (2R,4R)-1-(2-cyclobutyl-5-methyl-2H-pyrazol-3-yl)-4-(2-trifluoromethyl-benzenesulfonyl)-pyrrolidine-2-carboxylic acid as white solid which was used in the next step without further purification. MS (ESI): m/z=456.1 [M−H]⁻.

c) (2S,4R)-1-(2-Cyclobutyl-5-methyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, a mixture of (2S,4R)-1-(2-cyclobutyl-5-methyl-2H-pyrazol-3-yl)-4-(2-trifluoromethyl-benzenesulfonyl)-pyrrolidine-2-carboxylic acid and (2R,4R)-1-(2-cyclobutyl-5-methyl-2H-pyrazol-3-yl)-4-(2-trifluoromethyl-benzenesulfonyl)-pyrrolidine-2-carboxylic acid was reacted with 1-aminocyclopropanecarbonitrile hydrochloride (CAS Reg. No. 127946-77-4) in the presence of HATU and DIEA to give the title compound after purification by chiral preparative HPLC as yellow solid. MS (ESI): m/z=522.3 [M+H]⁺.

Example 323

(2S,4R)-4-(2-Chloro-benzenesulfonyl)-1-(4-oxazol-5-yl-benzenesulfonyl)-pyrrolidine-2-carboxylic acid (1-cyano-cyclopropyl)-amide

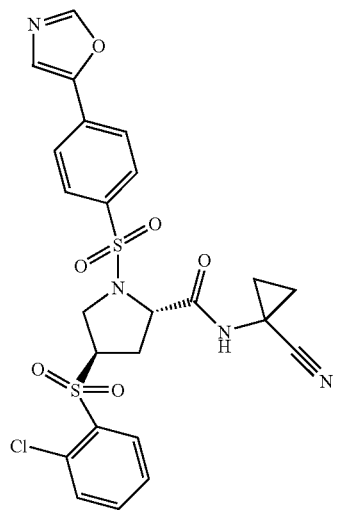

The title compound was prepared in analogy to example 315 to yield 60 mg (54%) of a white foam. MS (ESI): m/z=570.2 [M+H]⁺.

Example 324

(2S,4R)-4-[2-Chloro-4-(4-methyl-piperazin-1-yl)-benzenesulfonyl]-1-[1-(4-chloro-phenyl)-cyclopropanecarbonyl]-pyrrolidine-2-carboxylic acid (1-cyano-cyclopropyl)-amide

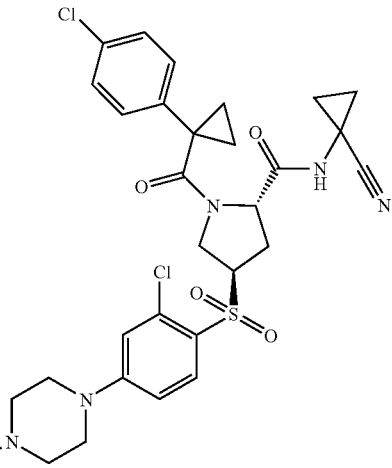

Example 312 (100 mg) was dissolved in acetonitrile (4 mL). Hilnig's base (60 µL) and 1-methylpiperazine (40 µL) were added. The reaction mixture was stirred for 24 h at 25° C. The reaction was not complete. Therefore, additional 1-methylpiperazine (40 µL, 2.0 eq.) was added and the mixture was stirred for 24 h at 25° C. Still the reaction was not complete. Additional 1-methylpiperazine (40 µL, 2.0 eq.) was added and the mixture was stirred for 24 h at 25° C. The reaction was complete as revealed with LC-MS analysis. The reaction mixture was purified with preparative HPLC to yield the title compound (104 mg, 91%) as a white solid. MS (ESI): m/z=630.1 [M+H]⁺.

Example 325

(2S,4R)-4-(2-Chloro-4-imidazol-1-yl-benzenesulfonyl)-1-[1-(4-chloro-phenyl)-cyclopropanecarbonyl]-pyrrolidine-2-carboxylic acid (1-cyano-cyclopropyl)-amide

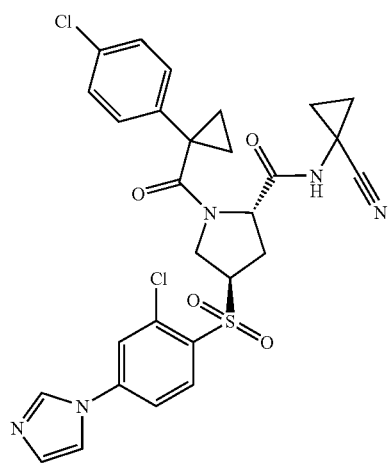

Example 312 (100 mg) was dissolved in acetonitrile (4 mL). Hünig's base (60 μL) and imidazole (25 mg) were added. The reaction mixture was stirred for 24 h at 25° C. The reaction mixture contained only starting materials. Therefore, additional imidazole (25 mg, 2.0 eq.) was added and the mixture was stirred for 24 h at 80° C. Still the reaction was not complete. Additional imidazole (50 mg, 4.0 eq.) was added and the mixture was stirred for 3 d at 80° C. The reaction was complete as revealed with LC-MS analysis. The reaction mixture was purified with preparative HPLC to yield the title compound (51 mg, 47%) as a white foam. MS (ESI): m/z=598.2 [M+H]+.

Example 326

(2S,4R)-4-[2-Chloro-4-(2-methyl-imidazol-1-yl)-benzenesulfonyl]-1-[1-(4-chloro-phenyl)-cyclopropanecarbonyl]-pyrrolidine-2-carboxylic acid (1-cyano-cyclopropyl)-amide

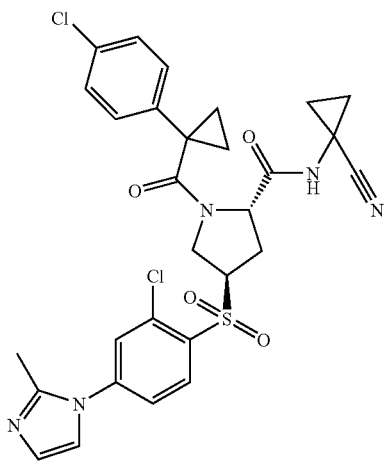

The title compound was prepared in analogy to example 325 to yield 67 mg (60%) of a white foam. MS (ESI): m/z=612.2 [M+H]+.

Example 327

(2S,4R)-1-[1-(4-Chloro-phenyl)-cyclopropanecarbonyl]-4-(2-chloro-4-pyrazol-1-yl-benzenesulfonyl)-pyrrolidine-2-carboxylic acid (1-cyano-cyclopropyl)-amide

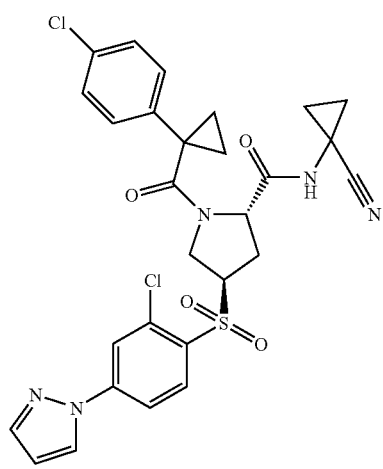

Example 312 (50 mg) was dissolved in DMA (2 mL). Cesium carbonate (59 mg) and pyrazole (12 mg) were added. The reaction mixture was stirred in the microwave oven at 80° C. for 30 min at 80° C. The reaction mixture was purified with preparative HPLC to yield the title compound (32 mg, 59%) as a white foam. MS (ESI): m/z=598.2 [M+H]+.

Example 328

(2S,4R)-4-(4-Azetidin-1-yl-2-chloro-benzenesulfonyl)-1-[1-(4-chloro-phenyl)-cyclopropanecarbonyl]-pyrrolidine-2-carboxylic acid (1-cyano-cyclopropyl)-amide

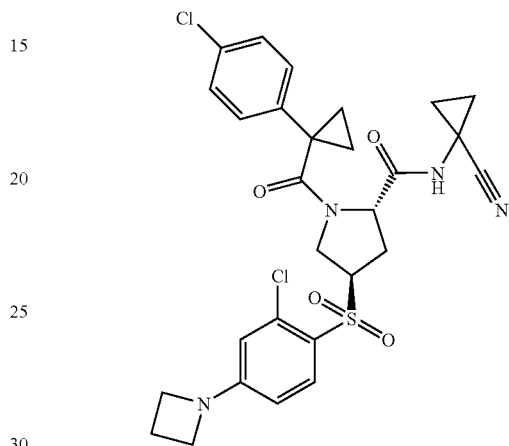

Example 312 (100 mg) was dissolved in acetonitrile (4 mL). Hünig's base (60 μL) and azetidine (20 μL) were added. The reaction mixture was stirred for 2 h at 25° C. After that additional azetidine (20 μL, 2.0 eq.) was added and the mixture was stirred for 24 h at 40° C. The reaction mixture was purified with preparative HPLC to yield the title compound (90 mg, 84%) as a white foam. MS (ESI): m/z=587.1 [M+H]+.

Example 329

(2S,4R)-4-[4-(4-tert-Butyl-piperazin-1-yl)-2-chloro-benzenesulfonyl]-1-[1-(4-chloro-phenyl)-cyclopropanecarbonyl]-pyrrolidine-2-carboxylic acid (1-cyano-cyclopropyl)-amide

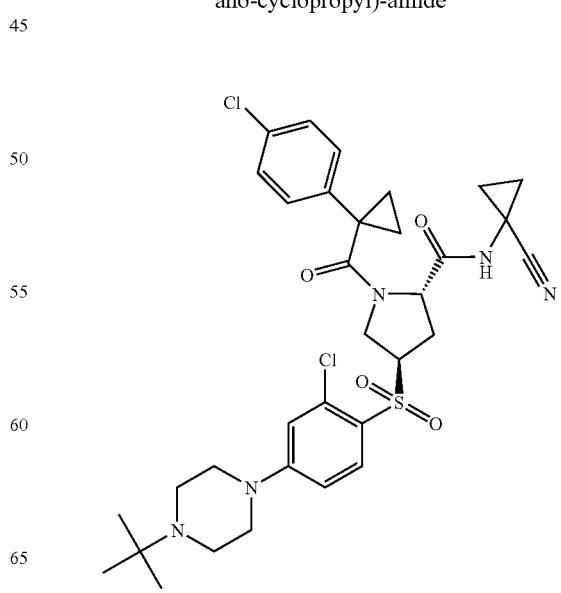

The title compound was prepared in analogy to example 328 to yield 80 mg (65%) of a white foam. MS (ESI): m/z=672.2 [M+H]⁺.

Example 330

(2S,4R)-4-[2-Chloro-4-(4-cyclopropyl-piperazin-1-yl)-benzenesulfonyl]-1-[1-(4-chloro-phenyl)-cyclopropanecarbonyl]-pyrrolidine-2-carboxylic acid (1-cyano-cyclopropyl)-amide

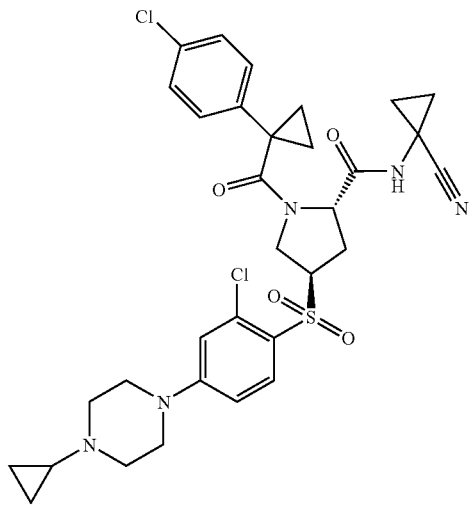

Example 312 (100 mg) was dissolved in acetonitrile (4 mL). Hilnig's base (604) and 1-cyclopropylpiperazine dihydrochloride were added (72 mg) were added. The reaction mixture was stirred for 2 h at 25° C. After that additional 1-cyclopropylpiperazine dihydrochloride (72 mg, 2.0 eq.) and Hilnig's base (604) were added and the mixture was stirred for 24 h at 80° C. After that again additional 1-cyclopropylpiperazine dihydrochloride (72 mg, 2.0 eq.) and Hilnig's base (604) were added and the mixture was stirred for 24 h at 80° C. The reaction mixture was purified with preparative HPLC to yield the title compound (68 mg, 57%) as a light brown foam. MS (ESI): m/z=656.2 [M+H]⁺.

Example 331

(2S,4R)-1-[1-(3-Chloro-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide

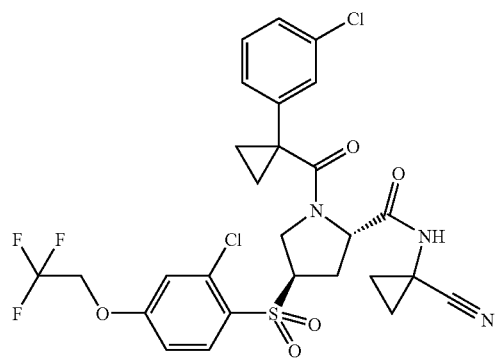

The title compound was prepared in analogy to example 239 using example 173 (75 mg) and 1-(3-chlorophenyl)-1-cyclopropane carboxylic acid (39 mg) to yield 94 mg (90%) of a white foam. MS (ESI): m/z=630.0 [M+H]⁺.

Example 332

(2S,4R)-1-[1-(3-Bromo-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide

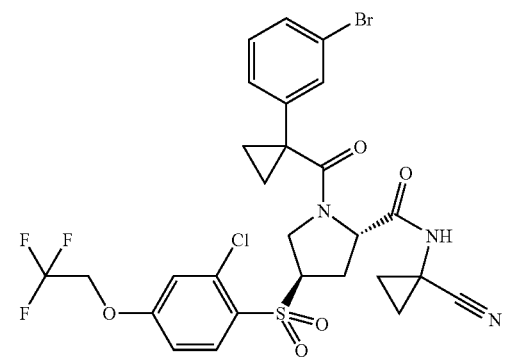

The title compound was prepared in analogy to example 239 using example 173 (200 mg) and 1-(3-bromophenyl)-cyclopropane carboxylic acid (128 mg) to yield 238 mg (80%) of a white solid. MS (ESI): m/z=698.0 [M+Na]⁺.

Example 333

(2S,4R)-1-[2-(3-Methoxy-phenyl)-5-methyl-2H-pyrazol-3-yl]-4-(2-trifluoromethyl-benzenesulfonyl)-pyrrolidine-2-carboxylic acid (1-cyano-cyclopropyl)-amide

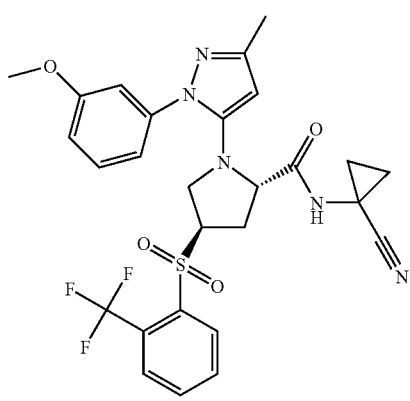

a) (2S,4R)-1-[2-(3-Methoxy-phenyl)-5-methyl-2H-pyrazol-3-yl]-4-(2-trifluoromethyl-benzenesulfonyl)-pyrrolidine-2-carboxylic acid methyl ester In analogy to the procedure described in example 192 h, a mixture of (2S,4R)-1-(3-oxo-thiobutyryl)-4-(2-trifluoromethyl-benzenesulfonyl)-pyrrolidine-2-carboxylic acid methyl ester (example 192 g) and of (2R,4R)-1-(3-oxo-thiobutyryl)-4-(2-trifluoromethyl-benzenesulfonyl)-pyrrolidine-2-carboxylic acid methyl ester was reacted with 3-methoxyphenylhydrazin hydrochloride (CAS Reg. No. 39232-91-

2) to give a mixture of the title compound and (2R,4R)-1-[2-(3-methoxy-phenyl)-5-methyl-2H-pyrazol-3-yl]-4-(2-trifluoromethyl-benzenesulfonyl)-pyrrolidine-2-carboxylic acid methyl ester as orange oil. MS (ESI): m/z=524.3 [M+H]⁺.

b) (2S,4R)-1-[2-(3-Methoxy-phenyl)-5-methyl-2H-pyrazol-3-yl]-4-(2-trifluoromethyl-benzenesulfonyl)-pyrrolidine-2-carboxylic acid In analogy to the procedure described in example 253e, a mixture of (2S,4R)-1-[2-(3-methoxy-phenyl)-5-methyl-2H-pyrazol-3-yl]-4-(2-trifluoromethyl-benzenesulfonyl)-pyrrolidine-2-carboxylic acid methyl ester and (2R,4R)-1-[2-(3-methoxy-phenyl)-5-methyl-2H-pyrazol-3-yl]-4-(2-trifluoromethyl-benzenesulfonyl)-pyrrolidine-2-carboxylic acid methyl ester was saponified in the presence of lithium hydroxide to give a mixture of the title compound and (2R,4R)-1-[2-(3-methoxy-phenyl)-5-methyl-2H-pyrazol-3-yl]-4-(2-trifluoromethyl-benzenesulfonyl)-pyrrolidine-2-carboxylic acid as orange solid which was used in the next step without further purification. MS (ESI): m/z=510.2 [M+H]⁺.

c) (2S,4R)-1-[2-(3-Methoxy-phenyl)-5-methyl-2H-pyrazol-3-yl]-4-(2-trifluoromethyl-benzenesulfonyl)-pyrrolidine-2-carboxylic acid (1-cyano-cyclopropyl)-amide In analogy to the procedure described in example 237, a mixture of (2S,4R)-1-[2-(3-methoxy-phenyl)-5-methyl-2H-pyrazol-3-yl]-4-(2-trifluoromethyl-benzenesulfonyl)-pyrrolidine-2-carboxylic acid and (2R,4R)-1-[2-(3-methoxy-phenyl)-5-methyl-2H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as colorless oil. MS (ESI): m/z=574.2 [M+H]⁺.

Example 334

(2R,4R)-1-[2-(3-Methoxy-phenyl)-5-methyl-2H-pyrazol-3-yl]-4-(2-trifluoromethyl-benzenesulfonyl)-pyrrolidine-2-carboxylic acid (1-cyano-cyclopropyl)-amide

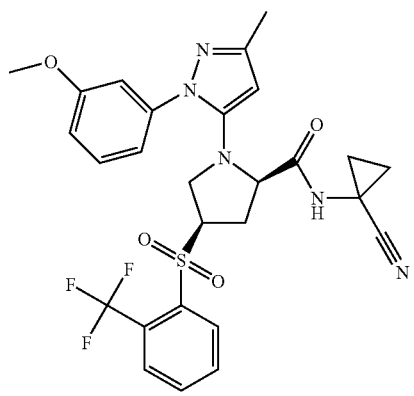

In analogy to the procedure described in example 237, a mixture of (2S,4R)-1-[2-(3-methoxy-phenyl)-5-methyl-2H-pyrazol-3-yl]-4-(2-trifluoromethyl-benzenesulfonyl)-pyrrolidine-2-carboxylic acid and (2R,4R)-1-[2-(3-methoxy-phenyl)-5-methyl-2H-pyrazol-3-yl]-4-(2-trifluoromethyl-benzenesulfonyl)-pyrrolidine-2-carboxylic acid (example 333b) was reacted with 1-amino-cyclopropanecarbonitrile hydrochloride (CAS Reg. No. 127946-77-4) in the presence of HATU and DIEA to give the title compound after purification by chiral preparative HPLC as colorless oil. MS (ESI): m/z=574.3 [M+H]⁺.

Example 335

(2S,4R)-4-(2-Trifluoromethyl-benzenesulfonyl)-1-(5-trifluoromethyl-[1,3,4]thiadiazol-2-yl)-pyrrolidine-2-carboxylic acid (1-cyano-cyclopropyl)-amide

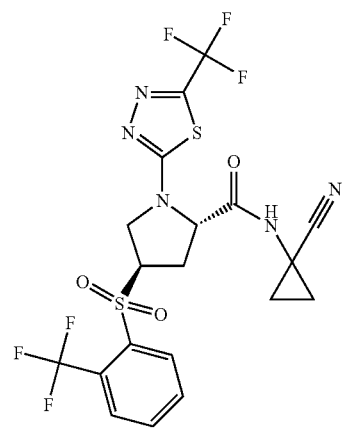

a) (2S,4R)-4-(2-Trifluoromethyl-benzenesulfonyl)-1-(5-trifluoromethyl-[1,3,4]thiadiazol-2-yl)-pyrrolidine-2-carboxylic acid methyl ester Potassium fluoride (26 mg, 445 umol) and triethylamine (62 ul, 445 umol) were added to a solution of (2S,4R)-4-(2-trifluoromethyl-benzenesulfonyl)-pyrrolidine-2-carboxylic acid methyl ester (50 mg, 148 umol; prepared as described for the corresponding (2S,4S)-4-(2-trifluoromethyl-benzenesulfonyl)-pyrrolidine-2-carboxylic acid ethyl ester in example 192e) and 2-chloro-5-trifluoromethyl-[1,3,4]thiadiazole (31 mg, 163 umol; CAS Reg. No. 53645-98-0) in N,N-dimethylacetamide (1 ml). The reaction mixture was heated in a microwave oven to 120° C. for 90 min. Ice water/0.1 N aqueous HCl solution 1/1 and iPrOAc were added and the layers were separated. The aqueous layer was extracted one more time with iPrOAc, the combined organic layers were washed with ice water/brine 1/1 and dried over Na₂SO₄. The solvent was removed under reduced pressure to give the title compound as yellow solid (50 mg, 102 umol; 69%) which was sufficiently pure to be used in the next reaction step. MS (ESI): m/z=558.2 [M+H]⁺.

b) (2S,4R)-4-(2-Trifluoromethyl-benzenesulfonyl)-1-(5-trifluoromethyl-[1,3,4]thiadiazol-2-yl)-pyrrolidine-2-carboxylic acid In analogy to the procedure described in example 253e, (2S,4R)-4-(2-trifluoromethyl-benzenesulfonyl)-1-(5-trifluoromethyl-[1,3,4]thiadiazol-2-yl)-pyrrolidine-2-carboxylic acid methyl ester was saponified in the presence of lithium hydroxide to give the title compound as yellow solid. MS (ESI): m/z=476.0 [M+H]⁺.

c) (2S,4R)-4-(2-Trifluoromethyl-benzenesulfonyl)-1-(5-trifluoromethyl-[1,3,4]thiadiazol-2-yl)-pyrrolidine-2-carboxylic acid (1-cyano-cyclopropyl)-amide In analogy to the procedure described in example 237, (2S,4R)-4-(2-trifluoromethyl-benzenesulfonyl)-1-(5-trifluoromethyl-[1,3,4]thiadiazol-2-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as red solid. MS (ESI): m/z=540.2 [M+H]⁺.

Example 336

(2S,4R)-4-[2-Chloro-4-(2-isopropyl-imidazol-1-yl)-benzenesulfonyl]-1-[1-(4-chloro-phenyl)-cyclopropanecarbonyl]-pyrrolidine-2-carboxylic acid (1-cyano-cyclopropyl)-amide

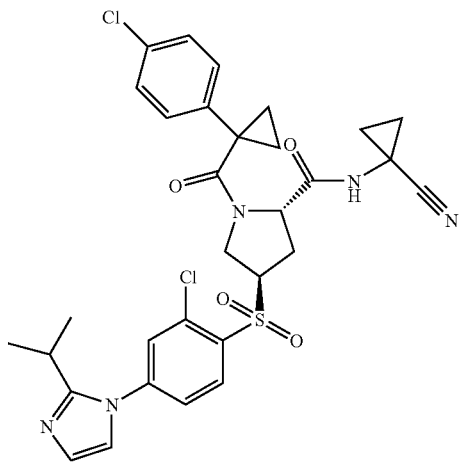

Example 312 (50 mg) was dissolved in DMA (2 mL). Cesium carbonate (59 mg) and 2-isopropyl-imidazole (20 mg) were added. The reaction mixture was stirred in the microwave oven at 80° C. for 30 min at 80° C. The reaction mixture was purified with preparative HPLC to yield the title compound (32 mg, 59%) as a light brown solid. MS (ESI): m/z=642.2 [M+H]$^+$.

Example 337

(2S,4R)-1-(5-Methyl-2-phenethyl-2H-pyrazol-3-yl)-4-(2-trifluoromethyl-benzenesulfonyl)-pyrrolidine-2-carboxylic acid (1-cyano-cyclopropyl)-amide

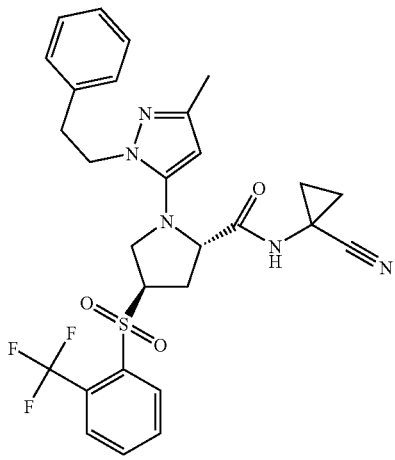

a) (2S,4R)-1-(5-Methyl-2-phenethyl-2H-pyrazol-3-yl)-4-(2-trifluoromethyl-benzenesulfonyl)-pyrrolidine-2-carboxylic acid methyl ester In analogy to the procedure described in example 192 h, a mixture of (2S,4R)-1-(3-oxo-thiobutyryl)-4-(2-trifluoromethyl-benzenesulfonyl)-pyrrolidine-2-carboxylic acid methyl ester (example 192 g) and of (2R,4R)-1-(3-oxo-thiobutyryl)-4-(2-trifluoromethyl-benzenesulfonyl)-pyrrolidine-2-carboxylic acid methyl ester was reacted with 2-phenethyl-hydrazine sulfate (CAS Reg. No. 56-51-4) to give a mixture of the title compound and (2R,4R)-1-(5-methyl-2-phenethyl-2H-pyrazol-3-yl)-4-(2-trifluoromethyl-benzenesulfonyl)-pyrrolidine-2-carboxylic acid methyl ester as orange oil. MS (ESI): m/z=522.3 [M+H]$^+$.

b) (2S,4R)-1-(5-Methyl-2-phenethyl-2H-pyrazol-3-yl)-4-(2-trifluoromethyl-benzenesulfonyl)-pyrrolidine-2-carboxylic acid In analogy to the procedure described in example 253e, a mixture of (2S,4R)-1-(5-methyl-2-phenethyl-2H-pyrazol-3-yl)-4-(2-trifluoromethyl-benzenesulfonyl)-pyrrolidine-2-carboxylic acid methyl ester and (2R,4R)-1-(5-methyl-2-phenethyl-2H-pyrazol-3-yl)-4-(2-trifluoromethyl-benzenesulfonyl)-pyrrolidine-2-carboxylic acid methyl ester was saponified in the presence of lithium hydroxide to give a mixture of the title compound and (2R,4R)-1-(5-methyl-2-phenethyl-2H-pyrazol-3-yl)-4-(2-trifluoromethyl-benzenesulfonyl)-pyrrolidine-2-carboxylic acid as yellow oil which was used in the next step without further purification.

c) (2S,4R)-1-(5-Methyl-2-phenethyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, a mixture of (2S,4R)-1-(5-methyl-2-phenethyl-2H-pyrazol-3-yl)-4-(2-trifluoromethyl-benzenesulfonyl)-pyrrolidine-2-carboxylic acid and (2R,4R)-1-(5-methyl-2-phenethyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as colorless oil. MS (ESI): m/z=572.3 [M+H]$^+$.

Example 338

(2R,4R)-1-(5-Methyl-2-phenethyl-2H-pyrazol-3-yl)-4-(2-trifluoromethyl-benzenesulfonyl)-pyrrolidine-2-carboxylic acid (1-cyano-cyclopropyl)-amide

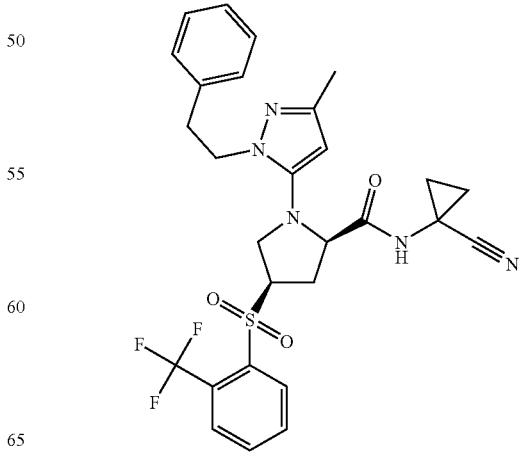

In analogy to the procedure described in example 237, a mixture of (2S,4R)-1-(5-methyl-2-phenethyl-2H-pyrazol-3-yl)-4-(2-trifluoromethyl-benzenesulfonyl)-pyrrolidine-2-carboxylic acid and (2R,4R)-1-(5-methyl-2-phenethyl-2H-pyrazol-3-yl)-4-(2-trifluoromethyl-benzenesulfonyl)-pyrrolidine-2-carboxylic acid (example 337b) was reacted with 1-amino-cyclopropanecarbonitrile hydrochloride (CAS Reg. No. 127946-77-4) in the presence of HATU and DIEA to give the title compound after purification by chiral preparative HPLC as colorless solid. MS (ESI): m/z=572.3 [M+H]$^+$.

Example 339

(2S,4R)-1-(2-tert-Butyl-5-methyl-2H-pyrazol-3-yl)-4-(2-trifluoromethyl-benzenesulfonyl)-pyrrolidine-2-carboxylic acid (1-cyano-cyclopropyl)-amide

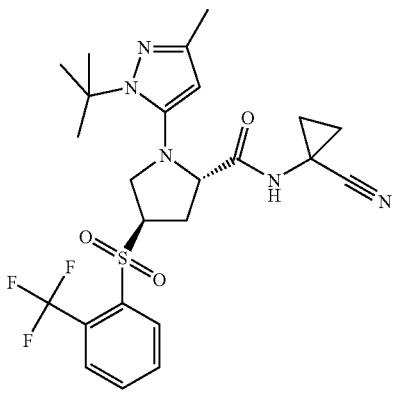

a) (2S,4R)-1-(2-tert-Butyl-5-methyl-2H-pyrazol-3-yl)-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with tert-butylhydrazine hydrochloride (CAS Reg. No. 7400-27-3) to give the title compound as brown solid. MS (ESI): m/z=474.2 [M+H]$^+$.

b) (2S,4R)-1-(2-tert-Butyl-5-methyl-2H-pyrazol-3-yl)-4-(2-trifluoromethyl-benzenesulfonyl)-pyrrolidine-2-carboxylic acid In analogy to the procedure described in example 253e, (2S,4R)-1-(2-tert-butyl-5-methyl-2H-pyrazol-3-yl)-4-(2-trifluoromethyl-benzenesulfonyl)-pyrrolidine-2-carboxylic acid methyl ester was saponified in the presence of lithium hydroxide to give the title compound as yellow solid which was used in the next step without further purification. MS (ESI): m/z=458.1 [M−H]$^-$.

c) (2S,4R)-1-(2-tert-Butyl-5-methyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(2-tert-butyl-5-methyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as yellow solid. MS (ESI): m/z=524.3 [M+H]$^+$.

Example 340

(2S,4R)-1-(2-Isobutyl-5-methyl-2H-pyrazol-3-yl)-4-(2-trifluoromethyl-benzenesulfonyl)-pyrrolidine-2-carboxylic acid (1-cyano-cyclopropyl)-amide

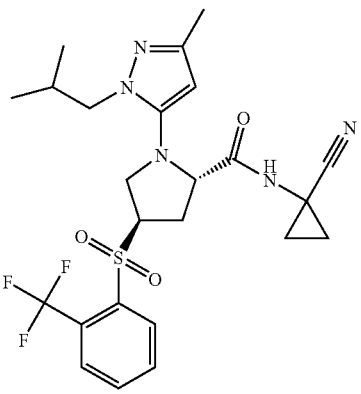

a) (2S,4R)-1-(2-Isobutyl-5-methyl-2H-pyrazol-3-yl)-4-(2-trifluoromethyl-benzenesulfonyl)-pyrrolidine-2-carboxylic acid methyl ester In analogy to the procedure described in example 308d, a mixture of (2S,4R)-1-(3-oxo-butyryl)-4-(2-trifluoromethyl-benzenesulfonyl)-pyrrolidine-2-carboxylic acid methyl ester (example 192 f) and of (2R,4R)-1-(3-oxo-butyryl)-4-(2-trifluoromethyl-benzenesulfonyl)-pyrrolidine-2-carboxylic acid methyl ester was reacted with Lawesson's reagent (CAS Reg. No. 19172-47-5) and (2-methylpropyl)-hydrazine 4-methylbenzenesulfonate (CAS Reg. No. 112306-59-9) to give a mixture of the title compound and (2R,4R)-1-(2-isobutyl-5-methyl-2H-pyrazol-3-yl)-4-(2-trifluoromethyl-benzenesulfonyl)-pyrrolidine-2-carboxylic acid methyl ester as yellow solid. MS (ESI): m/z=474.2 [M+H]$^+$.

b) (2S,4R)-1-(2-Isobutyl-5-methyl-2H-pyrazol-3-yl)-4-(2-trifluoromethyl-benzenesulfonyl)-pyrrolidine-2-carboxylic acid In analogy to the procedure described in example 253e, a mixture of (2S,4R)-1-(2-isobutyl-5-methyl-2H-pyrazol-3-yl)-4-(2-trifluoromethyl-benzenesulfonyl)-pyrrolidine-2-carboxylic acid methyl ester and (2R,4R)-1-(2-isobutyl-5-methyl-2H-pyrazol-3-yl)-4-(2-trifluoromethyl-benzenesulfonyl)-pyrrolidine-2-carboxylic acid methyl ester was saponified in the presence of lithium hydroxide to give a mixture of the title compound and (2R,4R)-1-(2-isobutyl-5-methyl-2H-pyrazol-3-yl)-4-(2-trifluoromethyl-benzenesulfonyl)-pyrrolidine-2-carboxylic acid as colorless oil which was used in the next step without further purification. MS (ESI): m/z=460.4 [M+H]$^+$.

c) (2S,4R)-1-(2-Isobutyl-5-methyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, a mixture of (2S,4R)-1-(2-isobutyl-5-methyl-2H-pyrazol-3-yl)-4-(2-trifluoromethyl-benzenesulfonyl)-pyrrolidine-2-carboxylic acid and (2R,4R)-1-(2-isobutyl-5-methyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as yellow oil. MS (ESI): m/z=524.2 [M+H]$^+$.

Example 341

(2R,4R)-1-(2-Isobutyl-5-methyl-2H-pyrazol-3-yl)-4-(2-trifluoromethyl-benzenesulfonyl)-pyrrolidine-2-carboxylic acid (1-cyano-cyclopropyl)-amide

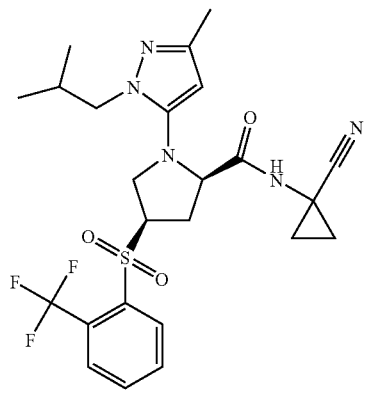

In analogy to the procedure described in example 237, a mixture of (2S,4R)-1-(2-isobutyl-5-methyl-2H-pyrazol-3-yl)-4-(2-trifluoromethyl-benzenesulfonyl)-pyrrolidine-2-carboxylic acid and (2R,4R)-1-(2-isobutyl-5-methyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as yellow solid. MS (ESI): m/z=524.2 [M+H]$^+$.

Example 342

(2S,4R)-4-[2-Chloro-4-(2-methoxy-ethoxy)-benzenesulfonyl]-1-[1-(4-chloro-phenyl)-cyclopropanecarbonyl]-pyrrolidine-2-carboxylic acid (1-cyano-cyclopropyl)-amide

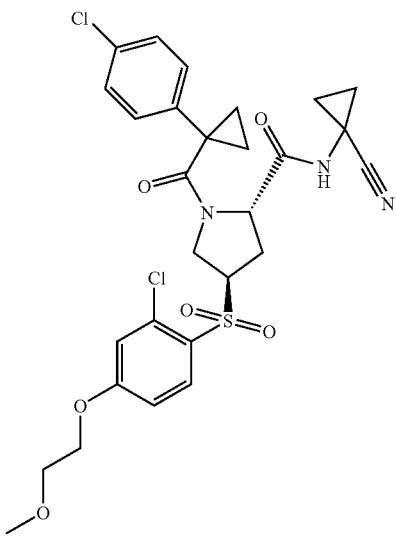

Example 312 (50 mg) was dissolved in DMA (2 mL). Cesium carbonate (59 mg) and 2-methoxyethanol (14 μL) were added. The reaction mixture was stirred at 25° C. for 96 h. The reaction mixture was purified with preparative HPLC to yield the title compound (22 mg, 40%) as a white solid. MS (ESI): m/z=606.2 [M+H]$^+$.

Example 343

1-Biphenyl-2-yl-4-(2-trifluoromethyl-benzenesulfonyl)-pyrrolidine-2-carboxylic acid (1-cyano-cyclopropyl)-amide

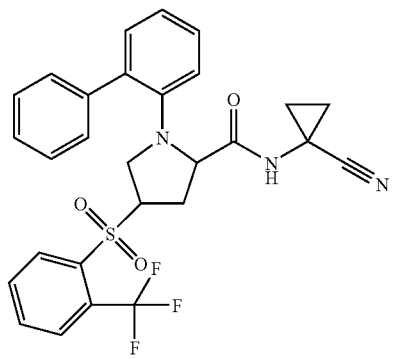

a) 1-(2-Bromo-ethylsulfanyl)-2-trifluoromethyl-benzene

To a stirred solution of 2-(trifluoromethyl)thiophenol (2.96 ml, 22 mmol; CAS Reg. No. 13333-97-6) in DMF (65 ml) were added 1,2-dibromoethane (9.67 ml, 112 mmol) and potassium carbonate (3.41 g, 25 mmol). The reaction mixture was stirred for 2 h 30 min at ambient temperature. AcOEt (30 ml) and water (30 ml) were added and the layers were separated. The aqueous layer was extracted three times with AcOEt (3×20 ml). The combined organic layers were washed with brine, dried over sodium sulfate and filtered. The solvent was removed under reduced pressure to give the title compound as yellow oil (6.0 g, 22 mmol; quant.) which was sufficiently pure to be used in the next step.

b) 1-(2-Bromo-ethylsulfonyl)-2-trifluoromethyl-benzene

To a stirred solution of 1-(2-bromo-ethylsulfanyl)-2-trifluoromethyl-benzene (6.0 g, 22 mmol) in dichloromethane (50 ml) was added MCPBA (9.68 g, 56 mmol) in four portions over 8 min. The reaction mixture was stirred at ambient temperature for 12 h and filtered to remove the solids. The filtrate was diluted with dichloromethane (50 ml), 1 M aqueous sodium carbonate solution (30 ml) was added and the layers were separated. The aqueous layer was extracted two more times with dichloromethane (70 ml). The combined extracts were washed with water (50 ml), dried over sodium sulfate and filtered. The solvent was removed under reduced pressure to give the title compound as off-white solid (5.4 g, 19 mmol; 84%) which was used in the next step without further purification.

c) 1-Ethenesulfonyl-2-trifluoromethyl-benzene

To a stirred solution of 1-(2-bromo-ethylsulfonyl)-2-trifluoromethyl-benzene (5.4 g, 19 mmol) in dichloromethane (50 ml) was added triethylamine (4.66 ml, 34 mmol). The reaction mixture was heated under reflux conditions to 50° C. for 12 h. The solvent was removed under reduced pressure and the residue was purified by column chromatography (silica gel, EtOAc/heptane) to yield the title compound (3.68 g, 16 mmol; 69%) as off-white semi-solid. MS (ESI): m/z=254.1 [M+NH$_4$]$^+$.

d) 1-Biphenyl-2-yl-4-(2-trifluoromethyl-benzene-sulfonyl)-pyrrolidine-2-carboxylic acid Ethyl Ester Paraformaldehyde (74 mg, 2.4 mmol) was added to a solution of (biphenyl-2-ylamino)-acetic acid ethyl ester (125 mg, 490 umol; CAS Reg. No. 39950-19-1) in toluene (9 ml) under an argon atmosphere. The mixture was stirred for 1 h at ambient temperature. A solution of 1-ethenesulfonyl-2-trifluoromethyl-benzene (231 mg, 979 umol) in toluene (1 ml) and acetic acid (10 ul, 98 umol) were added and the reaction mixture was heated under reflux conditions to 120° C. for 12 h. The solvent was removed under reduced pressure and purified by column chromatography (silica gel, EtOAc/heptane) to obtain the title compound (47 mg, 93 umol; 19%) as colorless oil. MS (ESI): m/z=504.1 [M+H]$^+$.

e) 1-Biphenyl-2-yl-4-(2-trifluoromethyl-benzene-sulfonyl)-pyrrolidine-2-carboxylic acid In analogy to the procedure described in example 253e, 1-biphenyl-2-yl-4-(2-trifluoromethyl-benzenesulfonyl)-pyrrolidine-2-carboxylic acid ethyl ester was saponified in the presence of lithium hydroxide to give the title compound as white solid which was used in the next step without further purification. MS (ESI): m/z=476.1 [M+H]$^+$.

f) 1-Biphenyl-2-yl-4-(2-trifluoromethyl-benzene-sulfonyl)-pyrrolidine-2-carboxylic acid (1-cyano-cyclopropyl)-amide In analogy to the procedure described in example 237, 1-biphenyl-2-yl-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=540.4 [M+H]$^+$.

Example 344

(2S,4R)-4-(4-Fluoro-2-trifluoromethyl-benzenesulfonyl)-1-(1-methyl-cyclopropanecarbonyl)-pyrrolidine-2-carboxylic acid (1-cyano-cyclopropyl)-amide

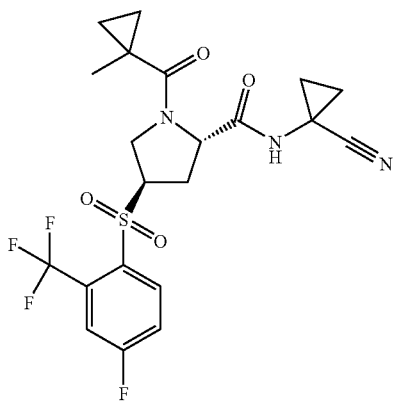

a) Synthesis of 4-fluoro-2-trifluoromethyl-benzenethiol

4-Fluoro-2-(trifluoromethyl)benzenesulphonyl chloride (2 g) was dissolved in 1,4-dioxane (12 mL) and water (3 mL) under a nitrogen atmosphere. Tris-(2-carboxylethyl)phosphine hydrochloride (8.73 g) was added and the mixture was stirred under reflux for 6 h. The reaction mixture was cooled to 25° C. and water (20 mL) was added. The product was extracted 3 times with CH$_2$Cl$_2$ (20 mL). The combined organic layers were dried over Na$_2$SO$_4$ filtrated and evaporated to dryness to yield the title compound (1.27 g, 85%) as a colorless liquid. MS (ESI): m/z=194.9 [M−H]$^-$.

b) Synthesis of (2S,4R)-4-(4-Fluoro-2-trifluoromethyl-benzenesulfonyl)-1-(1-methyl-cyclopropanecarbonyl)-pyrrolidine-2-carboxylic acid (1-cyano-cyclopropyl)-amide The title compound was prepared in analogy to example 207 using example 344a) as starting material to yield 16 mg (13%) of a white solid. MS (ESI): m/z=488.3 [M+H]$^+$.

Example 345

1-Naphthalen-1-yl-4-(2-trifluoromethyl-benzene-sulfonyl)-pyrrolidine-2-carboxylic acid (1-cyano-cyclopropyl)-amide

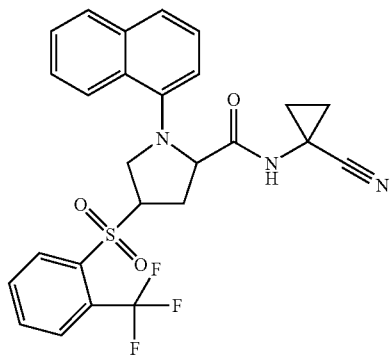

a) 1-Naphthalen-1-yl-4-(2-trifluoromethyl-benzene-sulfonyl)-pyrrolidine-2-carboxylic Acid Ethyl Ester In analogy to the procedure described in example 343d, (naphthalen-1-ylamino)-acetic acid ethyl ester (CAS Reg. No. 107456-67-7) was reacted with paraformaldehyde and 1-ethenesulfonyl-2-trifluoromethyl-benzene (example 243c) to give the title compound as brown oil. MS (ESI): m/z=478.2 [M+H]$^+$.

b) 1-Naphthalen-1-yl-4-(2-trifluoromethyl-benzene-sulfonyl)-pyrrolidine-2-carboxylic Acid In analogy to the procedure described in example 253e, 1-naphthalen-1-yl-4-(2-trifluoromethyl-benzenesulfonyl)-pyrrolidine-2-carboxylic acid ethyl ester was saponified in the presence of lithium hydroxide to give the title compound as off-white solid which was used in the next step without further purification. MS (ESI): m/z=450.1 [M+H]$^+$.

c) 1-Naphthalen-1-yl-4-(2-trifluoromethyl-benzene-sulfonyl)-pyrrolidine-2-carboxylic Acid (1-cyano-cyclopropyl)-amide In analogy to the procedure described in example 237, 1-naphthalen-1-yl-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=514.5 [M+H]⁺.

Example 346

(2S,4R)-1-[2-(4-Bromo-phenyl)-[1,3]dioxolane-2-carbonyl]-4-[2-chloro-4-(2,2,2-trifluoro-ethoxy)-benzenesulfonyl]-pyrrolidine-2-carboxylic acid (1-cyano-cyclopropyl)-amide

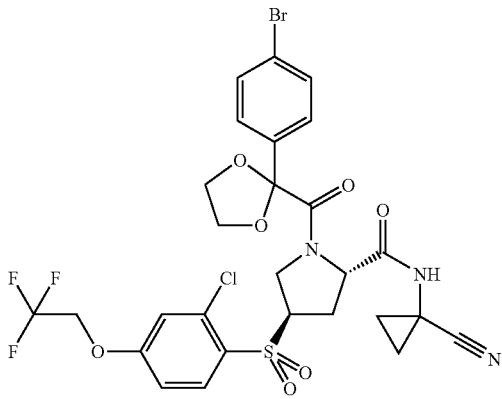

a) 2-(4-Bromo-phenyl)-[1,3]dioxolane-2-carboxylic acid ethyl ester

To a solution of ethyl-4-bromobenzoylformate (940 mg) and 2-chloroethanol (0.360 mL) in a 2:1 mixture of dimethylformamide:tetrahydrofuran (2.1 mL) was added dropwise at −60° C. a solution of potassium tert-butanol (0.597 mg) in dimethylformamide (2 mL). The reaction mixture was stirred at −60° C. for 4 h then allowed to warm up to room temperature and stirred at room temperature overnight. The reaction mixture was partitioned between an aqueous solution of ammonium chloride and ethyl acetate. The aqueous layer was extracted with ethyl acetate and the combined organic layer were washed with brine. The crude mixture was concentrated to dryness and purified by chromatography on silica gel to yield the title compound as a colorless liquid (616 mg; 58%). MS (ESI): m/z=300.8 [M+H]⁺.

b) 2-(4-Bromo-phenyl)-[1,3]dioxolane-2-carboxylic acid

To a solution of 2-(4-Bromo-phenyl)-[1,3]dioxolane-2-carboxylic acid ethyl ester (example 346a), 300 mg) in tetrahydrofuran (2 mL) and water (2 mL) was added lithium hydroxide (41 mg) in two portions. The reaction mixture was stirred at room temperature over 2 days then concentrated in vacuo. The residue was acidified to pH=1 with aqueous hydrochloric acid solution (0.1N) extracted with ethyl acetate. The combined organic layer were washed with brine, dried over sodium sulfate, filtered and evaporated in vacuo to yield the title compound as a colorless oil (225 mg; 66%). MS (ESI): m/z=271.1 [M−H]⁻.

c) (2S,4R)-1-[2-(4-Bromo-phenyl)-[1,3]dioxolane-2-carbonyl]-4-[2-chloro-4-(2,2,2-trifluoro-ethoxy)-benzenesulfonyl]-pyrrolidine-2-carboxylic acid (1-cyano-cyclopropyl)-amide The title compound was prepared in analogy to example 239 using example 173 (75 mg) and 2-(4-Bromo-phenyl)-[1,3]dioxolane-2-carboxylic acid (Example 346b); 68 mg) to yield 39 mg (30%) of a white solid. MS (ESI): m/z=708.0 [M+H]⁺.

Example 347

(2S,4R)-4-[2-Chloro-4-(2,2,2-trifluoro-ethoxy)-benzenesulfonyl]-1-(1-naphthalen-1-yl-cyclopropanecarbonyl)-pyrrolidine-2-carboxylic acid (1-cyano-cyclopropyl)-amide

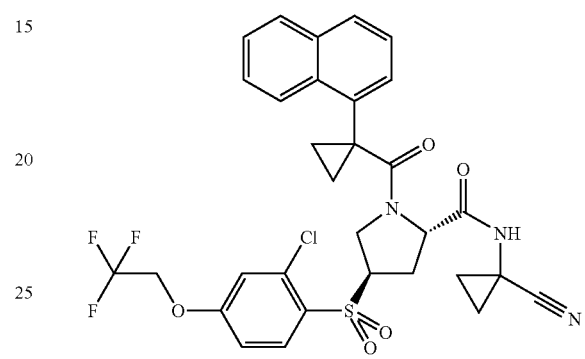

The title compound was prepared in analogy to example 239 using example 173 (75 mg) and 1-naphthalen-1-yl-cyclopropanecarboxylic acid (CAS #[124276-38-6]; 42 mg) to yield 53 mg (49%) of a yellow oil. MS (ESI): m/z=646.14 [M+H]⁺.

Example 348

(2S,4R)-4-[2-Chloro-4-(2,2,2-trifluoro-ethoxy)-benzenesulfonyl]-1-(1-naphthalen-2-yl-cyclopropanecarbonyl)-pyrrolidine-2-carboxylic acid (1-cyano-cyclopropyl)-amide

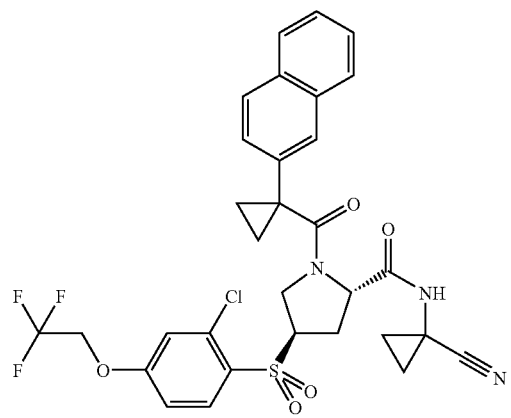

The title compound was prepared in analogy to example 239 using example 173 (75 mg) and 1-naphthalen-2-yl-cyclopropanecarboxylic acid (CAS #[623583-91-5]; 42 mg) to yield 70 mg (65%) of a yellow oil. MS (ESI): m/z=646.14 [M+H]⁺.

Example 349

(2S,4R)-4-(2-Chloro-4-imidazo[4,5-c]pyridin-1-yl-benzenesulfonyl)-1-[1-(4-chloro-phenyl)-cyclopropanecarbonyl]-pyrrolidine-2-carboxylic acid (1-cyano-cyclopropyl)-amide

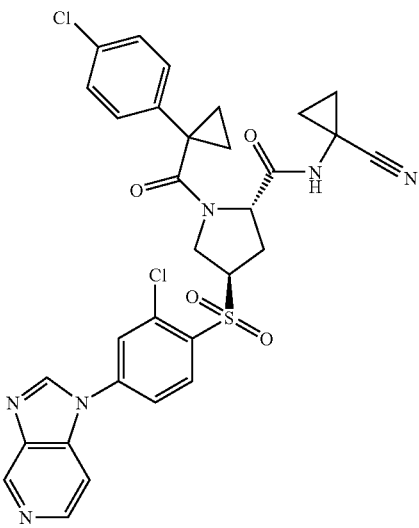

Example 312 (100 mg) was dissolved in acetonitrile (4 mL). Hünig's base (60 µL) and 5-azabenzimidazole were added (43 mg) were added. The reaction mixture was stirred for 2 h at 25° C. After that additional 5-azabenzimidazole (43 mg, 2.0 eq.) was added and the mixture was stirred for 24 h at 25° C. After that again additional 5-azabenzimidazole (43 mg, 2.0 eq.) was added and the mixture was stirred for 24 h at 25° C. The reaction mixture was purified with preparative HPLC to yield the title compound (7 mg, 6%) as a white solid. MS (ESI): m/z=649.3 [M+H]$^+$.

Example 350

(2S,4R)-4-(2-Chloro-4-imidazo[4,5-c]pyridin-5-yl-benzenesulfonyl)-1-[1-(4-chloro-phenyl)-cyclopropanecarbonyl]-pyrrolidine-2-carboxylic acid (1-cyano-cyclopropyl)-amide

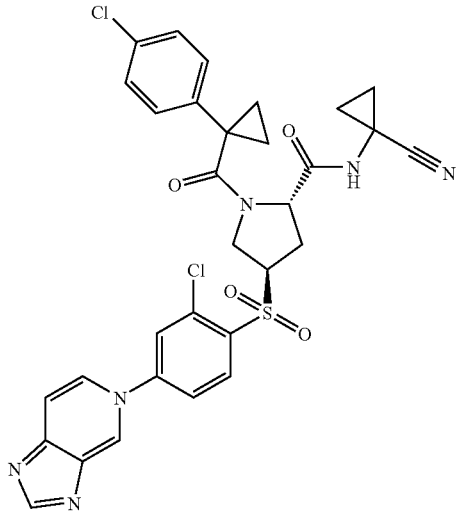

The title compound was obtained as a by-product during the synthesis of example 349 to yield 16 mg (14%) of a white solid. MS (ESI): m/z=649.3 [M+H]$^+$.

Example 351

(2S,4R)-1-[2-(2,6-Dimethyl-pyridin-4-yl)-5-methyl-2H-pyrazol-3-yl]-4-(2-trifluoromethyl-benzenesulfonyl)-pyrrolidine-2-carboxylic acid (1-cyano-cyclopropyl)-amide)

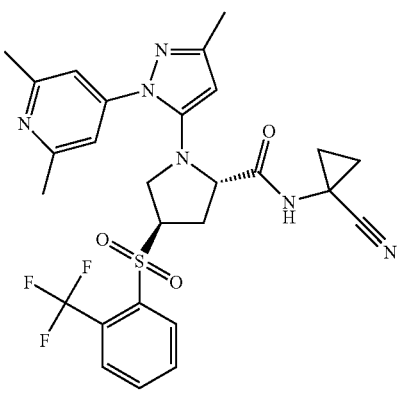

a) (2S,4R)-1-[2-(2,6-Dimethyl-pyridin-4-yl)-5-methyl-2H-pyrazol-3-yl]-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with (2,6-dimethyl-pyridin-4-yl)-hydrazine hydrochloride (CAS Reg. No. 1187853-32-2) to give the title compound as brown oil. MS (ESI): m/z=523.2 [M+H]

b) (2S,4R)-1-[2-(2,6-Dimethyl-pyridin-4-yl)-5-methyl-2H-pyrazol-3-yl]-4-(2-trifluoromethyl-benzenesulfonyl)-pyrrolidine-2-carboxylic acid In analogy to the procedure described in example 253e, (2S,4R)-1-[2-(2,6-dimethyl-pyridin-4-yl)-5-methyl-2H-pyrazol-3-yl]-4-(2-trifluoromethyl-benzenesulfonyl)-pyrrolidine-2-carboxylic acid methyl ester was saponified in the presence of lithium hydroxide. The reaction mixture was brought to dryness to give the title compound in the form of its lithium salt as red solid which was used in the next step without further purification. MS (ESI): m/z=509.3 [M+H]$^+$.

c) (2S,4R)-1-[2-(2,6-Dimethyl-pyridin-4-yl)-5-methyl-2H-pyrazol-3-yl]-4-(2-trifluoromethyl-benzenesulfonyl)-pyrrolidine-2-carboxylic acid (1-cyano-cyclopropyl)-amide In analogy to the procedure described in example 237, (2S,4R)-1-[2-(2,6-dimethyl-pyridin-4-yl)-5-methyl-2H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4)

Example 352

(2S,4R)-1-(5-Methyl-2-quinolin-4-yl-2H-pyrazol-3-yl)-4-(2-trifluoromethyl-benzenesulfonyl)-pyrrolidine-2-carboxylic acid (1-cyano-cyclopropyl)-amide

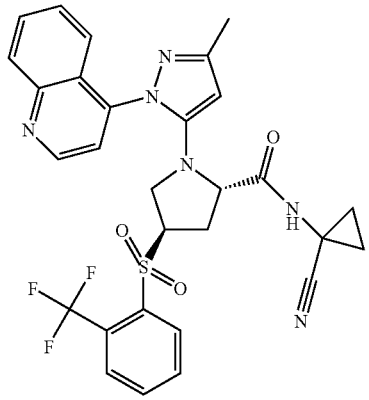

a) (2S,4R)-1-(5-Methyl-2-quinolin-4-yl-2H-pyrazol-3-yl)-4-(2-trifluoromethyl-benzenesulfonyl)-pyrrolidine-2-carboxylic acid methyl ester In analogy to the procedure described in example 192 h, (2S,4R)-1-(3-oxo-thiobutyryl)-4-(2-trifluoromethyl-benzenesulfonyl)-pyrrolidine-2-carboxylic acid methyl ester (example 192 g) was reacted with quinolin-4-yl-hydrazine hydrochloride (CAS Reg. No. 68500-41-4) to give the title compound as orange oil. MS (ESI): m/z=545.2 [M+H]$^+$.

b) (2S,4R)-1-(5-Methyl-2-quinolin-4-yl-2H-pyrazol-3-yl)-4-(2-trifluoromethyl-benzenesulfonyl)-pyrrolidine-2-carboxylic acid In analogy to the procedure described in example 253e, (2S,4R)-1-(5-methyl-2-quinolin-4-yl-2H-pyrazol-3-yl)-4-(2-trifluoromethyl-benzenesulfonyl)-pyrrolidine-2-carboxylic acid methyl ester was saponified in the presence of lithium hydroxide to give the title compound as red solid which was used in the next step without further purification.

c) (2S,4R)-1-(5-Methyl-2-quinolin-4-yl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(5-methyl-2-quinolin-4-yl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as orange oil. MS (ESI): m/z=573.2 [M+H]$^+$.

Example 353

(2S,4R)-4-(2-Chloro-benzenesulfonyl)-1-(2-cyclobutyl-5-methyl-2H-pyrazol-3-yl)-pyrrolidine-2-carboxylic acid (1-cyano-cyclopropyl)-amide

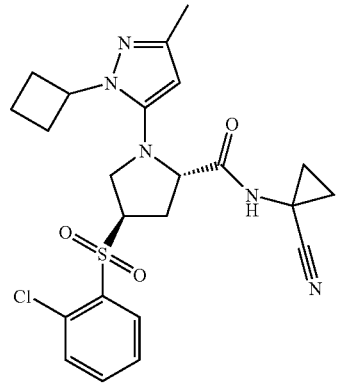

a) (2S,4R)-4-(2-Chloro-benzenesulfonyl)-1-(2-cyclobutyl-5-methyl-2H-pyrazol-3-yl)-pyrrolidine-2-carboxylic acid methyl ester In analogy to the procedure described in example 192 h, (2S,4R)-4-(2-chloro-benzenesulfonyl)-1-(3-oxo-thiobutyryl)-pyrrolidine-2-carboxylic acid methyl ester (example 253c) was reacted with cyclobutylhydrazine hydrochloride (CAS Reg. No. 158001-21-9) to give the title compound as orange oil. MS (ESI): m/z=438.3 [M+H]$^+$.

b) (2S,4R)-4-(2-Chloro-benzenesulfonyl)-1-(2-cyclobutyl-5-methyl-2H-pyrazol-3-yl)-pyrrolidine-2-carboxylic acid In analogy to the procedure described in example 253e, (2S,4R)-4-(2-chloro-benzenesulfonyl)-1-(2-cyclobutyl-5-methyl-2H-pyrazol-3-yl)-pyrrolidine-2-carboxylic acid methyl ester was saponified in the presence of lithium hydroxide to give the title compound as yellow oil which was used in the next step without further purification. MS (ESI): m/z=424.2 [M+H]$^+$.

c) (2S,4R)-4-(2-Chloro-benzenesulfonyl)-1-(2-cyclobutyl-5-methyl-2H-pyrazol-3-yl)-pyrrolidine-2-carboxylic acid (1-cyano-cyclopropyl)-amide In analogy to the procedure described in example 237, (2S,4R)-4-(2-chloro-benzenesulfonyl)-1-(2-cyclobutyl-5-methyl-2H-pyrazol-3-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as yellow oil. MS (ESI): m/z=488.4 [M+H]$^+$.

Example 354

4-(2-Trifluoromethyl-benzenesulfonyl)-1-(3-trifluoromethyl-phenyl)-pyrrolidine-2-carboxylic Acid (1-cyano-cyclopropyl)-amide

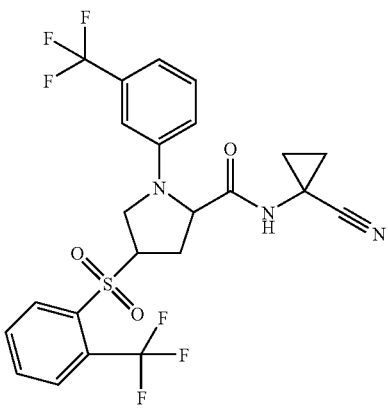

a) 4-(2-Trifluoromethyl-benzenesulfonyl)-1-(3-trifluoromethyl-phenyl)-pyrrolidine-2-carboxylic acid ethyl ester In analogy to the procedure described in example 343d, (3-trifluoromethyl-phenylamino)-acetic acid ethyl ester (CAS Reg. No. 2445-84-3) was reacted with paraformaldehyde and 1-ethenesulfonyl-2-trifluoromethyl-benzene (example 243c) to give the title compound as off-white solid. MS (ESI): m/z=496.3 [M+H]$^+$.

b) 4-(2-Trifluoromethyl-benzenesulfonyl)-1-(3-trifluoromethyl-phenyl)-pyrrolidine-2-carboxylic acid In analogy to the procedure described in example 253e, 4-(2-trifluoromethyl-benzenesulfonyl)-1-(3-trifluoromethyl-phenyl)-pyrrolidine-2-carboxylic acid ethyl ester was saponified in the presence of lithium hydroxide to give the title compound as white solid which was used in the next step without further purification. MS (ESI): m/z=468.1 [M+H]$^+$.

c) 4-(2-Trifluoromethyl-benzenesulfonyl)-1-(3-trifluoromethyl-phenyl)-pyrrolidine-2-carboxylic acid (1-cyano-cyclopropyl)-amide In analogy to the procedure described in example 237, 4-(2-trifluoromethyl-benzenesulfonyl)-1-(3-trifluoromethyl-phenyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=532.0 [M+H]$^+$.

Example 355

1-(2-tert-Butyl-phenyl)-4-(2-trifluoromethyl-benzenesulfonyl)-pyrrolidine-2-carboxylic acid (1-cyano-cyclopropyl)-amide

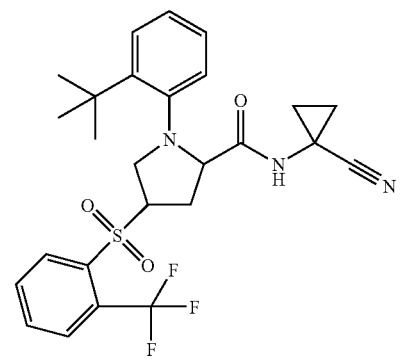

a) 1-(2-tert-Butyl-phenyl)-4-(2-trifluoromethyl-benzenesulfonyl)-pyrrolidine-2-carboxylic Acid Ethyl Ester In analogy to the procedure described in example 343d, (2-tert-butyl-phenylamino)-acetic acid ethyl ester (CAS Reg. No. 959563-17-8) was reacted with paraformaldehyde and 1-ethenesulfonyl-2-trifluoromethyl-benzene (example 243c) to give the title compound as colorless oil. MS (ESI): m/z=484.4 [M+H]$^+$.

b) 1-(2-tert-Butyl-phenyl)-4-(2-trifluoromethyl-benzenesulfonyl)-pyrrolidine-2-carboxylic acid In analogy to the procedure described in example 253e, 1-(2-tert-butyl-phenyl)-4-(2-trifluoromethyl-benzenesulfonyl)-pyrrolidine-2-carboxylic acid ethyl ester was saponified in the presence of lithium hydroxide to give the title compound as off-white solid which was used in the next step without further purification. MS (ESI): m/z=456.2 [M+H]$^+$.

c) 1-(2-tert-Butyl-phenyl)-4-(2-trifluoromethyl-benzenesulfonyl)-pyrrolidine-2-carboxylic acid (1-cyano-cyclopropyl)-amide In analogy to the procedure described in example 237, 1-(2-tert-butyl-phenyl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=520.2 [M+H]$^+$.

Example 356

(2S,4R)-1-[2-(3-Acetylamino-phenyl)-5-methyl-2H-pyrazol-3-yl]-4-(2-trifluoromethyl-benzenesulfonyl)-pyrrolidine-2-carboxylic acid (1-cyano-cyclopropyl)-amide

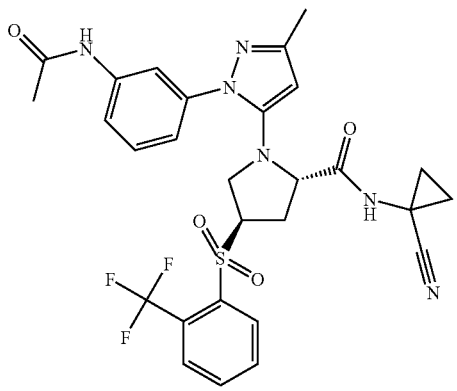

a) (2S,4R)-1-[2-(3-Acetylamino-phenyl)-5-methyl-2H-pyrazol-3-yl]-4-(2-trifluoromethyl-benzenesulfonyl)-pyrrolidine-2-carboxylic acid methyl ester In analogy to the procedure described in example 308d, a mixture of (2S,4R)-1-(3-oxo-thiobutyryl)-4-(2-trifluoromethyl-benzenesulfonyl)-pyrrolidine-2-carboxylic acid methyl ester (example 192 g) and of (2R,4R)-1-(3-oxo-thiobutyryl)-4-(2-trifluoromethyl-benzenesulfonyl)-pyrrolidine-2-carboxylic acid methyl ester was reacted with N-(3-hydrazino-phenyl)-acetamide hydrochloride (CAS Reg. No. 1187369-44-3) to give a mixture of the title compound and (2R,4R)-1-[2-(3-acetylamino-phenyl)-5-methyl-2H-pyrazol-3-yl]-4-(2-trifluoromethyl-benzenesulfonyl)-pyrrolidine-2-carboxylic acid methyl ester as yellow solid. MS (ESI): m/z=551.2 [M+H]$^+$.

b) (2S,4R)-1-[2-(3-Acetylamino-phenyl)-5-methyl-2H-pyrazol-3-yl]-4-(2-trifluoromethyl-benzenesulfonyl)-pyrrolidine-2-carboxylic acid In analogy to the procedure described in example 253e, a mixture of (2S,4R)-1-[2-(3-acetylamino-phenyl)-5-methyl-2H-pyrazol-3-yl]-4-(2-trifluoromethyl-benzenesulfonyl)-pyrrolidine-2-carboxylic acid methyl ester and (2R,4R)-1-[2-(3-acetylamino-phenyl)-5-methyl-2H-pyrazol-3-yl]-4-(2-trifluoromethyl-benzenesulfonyl)-pyrrolidine-2-carboxylic acid methyl ester was saponified in the presence of lithium hydroxide to give a mixture of the title compound and (2R,4R)-1-[2-(3-acetylamino-phenyl)-5-methyl-2H-pyrazol-3-yl]-4-(2-trifluoromethyl-benzenesulfonyl)-pyrrolidine-2-carboxylic acid as orange solid which was used in the next step without further purification. MS (ESI): m/z=537.2 [M+H]$^+$.

c) (2S,4R)-1-[2-(3-Acetylamino-phenyl)-5-methyl-2H-pyrazol-3-yl]-4-(2-trifluoromethyl-benzenesulfonyl)-pyrrolidine-2-carboxylic acid (1-cyano-cyclopropyl)-amide In analogy to the procedure described in example 237, a mixture of (2S,4R)-1-[2-(3-acetylamino-phenyl)-5-methyl-2H-pyrazol-3-yl]-4-(2-trifluoromethyl-benzenesulfonyl)-pyrrolidine-2-carboxylic acid and (2R,4R)-1-[2-(3-acetylamino-phenyl)-5-methyl-2H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as orange oil. MS (ESI): m/z=601.4 [M+H]$^+$.

Example 357

(2R,4R)-1-[2-(3-Acetylamino-phenyl)-5-methyl-2H-pyrazol-3-yl]-4-(2-trifluoromethyl-benzenesulfonyl)-pyrrolidine-2-carboxylic acid (1-cyano-cyclopropyl)-amide

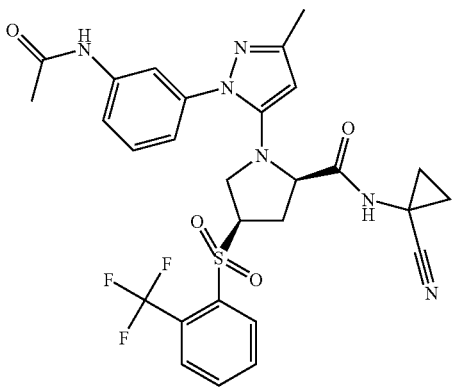

In analogy to the procedure described in example 237, a mixture of (2S,4R)-1-[2-(3-acetylamino-phenyl)-5-methyl-2H-pyrazol-3-yl]-4-(2-trifluoromethyl-benzenesulfonyl)-pyrrolidine-2-carboxylic acid and (2R,4R)-1-[2-(3-acetylamino-phenyl)-5-methyl-2H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound after purification by chiral preparative HPLC as yellow oil. MS (ESI): m/z=601.3 [M+H]$^+$.

Example 358

1-(3-Cyano-phenyl)-4-(2-trifluoromethyl-benzenesulfonyl)-pyrrolidine-2-carboxylic acid (1-cyano-cyclopropyl)-amide

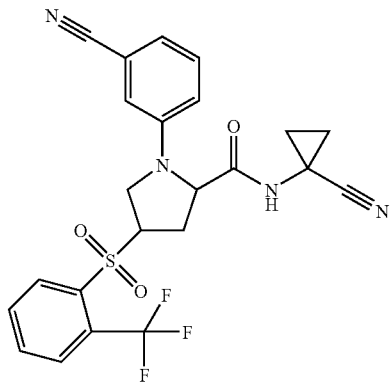

a) 1-(3-Cyano-phenyl)-4-(2-trifluoromethyl-benzenesulfonyl)-pyrrolidine-2-carboxylic Acid Ethyl Ester In analogy to the procedure described in example 343d, (3-cyano-phenylamino)-acetic acid ethyl ester (CAS Reg. No. 92316-76-2) was reacted with paraformaldehyde and 1-ethenesulfonyl-2-trifluoromethyl-benzene (example 243c) to give the title compound as brown oil. MS (ESI): m/z=453.1 [M+H]+.

b) 1-(3-Cyano-phenyl)-4-(2-trifluoromethyl-benzenesulfonyl)-pyrrolidine-2-carboxylic Acid In analogy to the procedure described in example 253e, 1-(3-cyano-phenyl)-4-(2-trifluoromethyl-benzenesulfonyl)-pyrrolidine-2-carboxylic acid ethyl ester was saponified in the presence of lithium hydroxide to give the title compound as off-white solid which was used in the next step without further purification. MS (ESI): m/z=425.1 [M+H]+.

c) 1-(3-Cyano-phenyl)-4-(2-trifluoromethyl-benzenesulfonyl)-pyrrolidine-2-carboxylic Acid (1-cyano-cyclopropyl)-amide In analogy to the procedure described in example 237, 1-(3-cyano-phenyl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=489.3 [M+H]+.

Example 359

(2S,4R)-4-(2-Chloro-benzenesulfonyl)-1-(5-methyl-2-phenethyl-2H-pyrazol-3-yl)-pyrrolidine-2-carboxylic acid (1-cyano-cyclopropyl)-amide

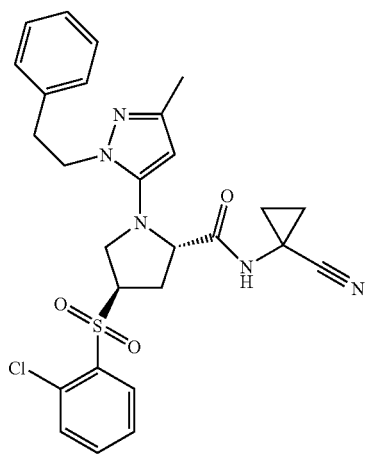

a) (2S,4R)-4-(2-Chloro-benzenesulfonyl)-1-(5-methyl-2-phenethyl-2H-pyrazol-3-yl)-pyrrolidine-2-carboxylic acid methyl ester In analogy to the procedure described in example 192 h, (2S,4R)-4-(2-chloro-benzenesulfonyl)-1-(3-oxo-thiobutyryl)-pyrrolidine-2-carboxylic acid methyl ester (example 253c) was reacted with 2-phenethyl-hydrazine sulfate (CAS Reg. No. 56-51-4) to give the title compound as orange oil. MS (ESI): m/z=488.3 [M+H]+.

b) (2S,4R)-4-(2-Chloro-benzenesulfonyl)-1-(5-methyl-2-phenethyl-2H-pyrazol-3-yl)-pyrrolidine-2-carboxylic acid In analogy to the procedure described in example 253e, (2S,4R)-4-(2-chloro-benzenesulfonyl)-1-(5-methyl-2-phenethyl-2H-pyrazol-3-yl)-pyrrolidine-2-carboxylic acid methyl ester was saponified in the presence of lithium hydroxide to give the title compound as brown oil which was used in the next step without further purification. MS (ESI): m/z=472.2 [M−H]−.

c) (2S,4R)-4-(2-Chloro-benzenesulfonyl)-1-(5-methyl-2-phenethyl-2H-pyrazol-3-yl)-pyrrolidine-2-carboxylic acid (1-cyano-cyclopropyl)-amide In analogy to the procedure described in example 237, (2S,4R)-4-(2-chloro-benzenesulfonyl)-1-(5-methyl-2-phenethyl-2H-pyrazol-3-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as orange oil. MS (ESI): m/z=538.4 [M+H]+.

Example 360

(2S,4R)-1-[1-(4-Chloro-phenyl)-cyclobutanecarbonyl]-4-(2-trifluoromethyl-benzenesulfonyl)-pyrrolidine-2-carboxylic acid (1-cyano-cyclopropyl)-amide

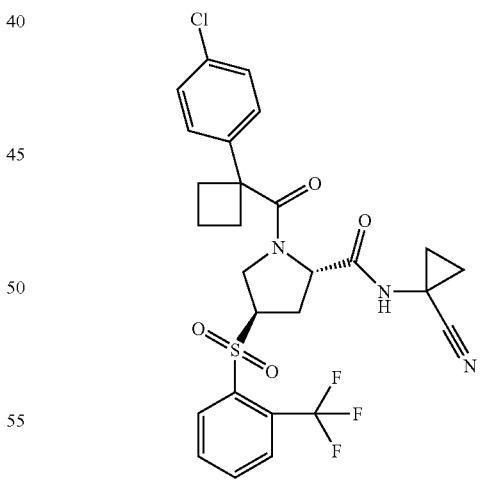

Example 43 (100 mg) was suspended in DMF (1.5 mL). HATU (196 mg), Hünig's base (90 μL) and 1-(4-chlorophenyl)-1-cyclobutanecarboxylic acid (71 mg) were added to the suspension. The reaction mixture was stirred for 18 h at 25° C. The reaction mixture was purified with preparative HPLC to yield the title compound (85 mg; 57%) as an amorphous colorless solid. MS (ESI): m/z=580.3 [M+H]+.

Example 361

(2S,4R)-1-[1-(6-Chloro-pyridin-3-yl)-cyclopropanecarbonyl]-4-(2-trifluoromethyl-benzenesulfonyl)-pyrrolidine-2-carboxylic acid (1-cyano-cyclopropyl)-amide

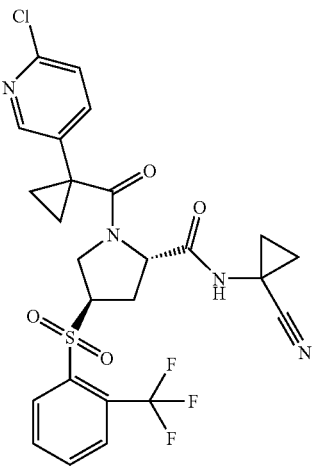

The title compound was prepared in analogy to example 360 using 1-(6-chloro-pyridin-3-yl)-cyclopropanecarboxylic acid (CAS 854267-90-6) as starting material to yield 75 mg (51%) of a colorless amorphous material. MS (ESI): m/z=567.3 [M+H]$^+$.

Example 362

1-(Tetrahydro-pyran-4-yl)-4-(2-trifluoromethyl-benzenesulfonyl)-pyrrolidine-2-carboxylic acid (1-cyano-cyclopropyl)-amide

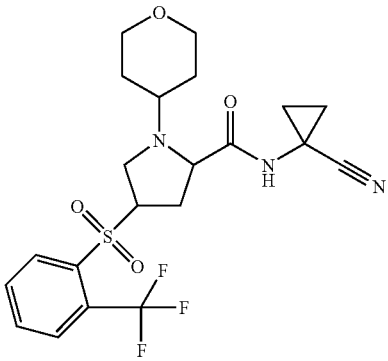

a) 1-(Tetrahydro-pyran-4-yl)-4-(2-trifluoromethyl-benzenesulfonyl)-pyrrolidine-2-carboxylic acid ethyl ester In analogy to the procedure described in example 343d, (tetrahydro-pyran-4-ylamino)-acetic acid ethyl ester (CAS Reg. No. 1153226-50-6) was reacted with paraformaldehyde and 1-ethenesulfonyl-2-trifluoromethyl-benzene (example 243c) to give the title compound.

b) 1-(Tetrahydro-pyran-4-yl)-4-(2-trifluoromethyl-benzenesulfonyl)-pyrrolidine-2-carboxylic acid In analogy to the procedure described in example 253e, 1-(tetrahydro-pyran-4-yl)-4-(2-trifluoromethyl-benzenesulfonyl)-pyrrolidine-2-carboxylic acid ethyl ester was saponified in the presence of lithium hydroxide to give the title compound as white solid which was used in the next step without further purification. MS (ESI): m/z=408.4 [M+H]$^+$.

c) 1-(Tetrahydro-pyran-4-yl)-4-(2-trifluoromethyl-benzenesulfonyl)-pyrrolidine-2-carboxylic acid (1-cyano-cyclopropyl)-amide In analogy to the procedure described in example 237, 1-(tetrahydro-pyran-4-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white foam. MS (ESI): m/z=472.3 [M+H]$^+$.

Example 363

(2S,4R)-1-[5-Cyclopropyl-2-(4-trifluoromethyl-phenyl)-2H-pyrazol-3-yl]-4-(2-trifluoromethyl-benzenesulfonyl)-pyrrolidine-2-carboxylic acid (1-cyano-cyclopropyl)-amide

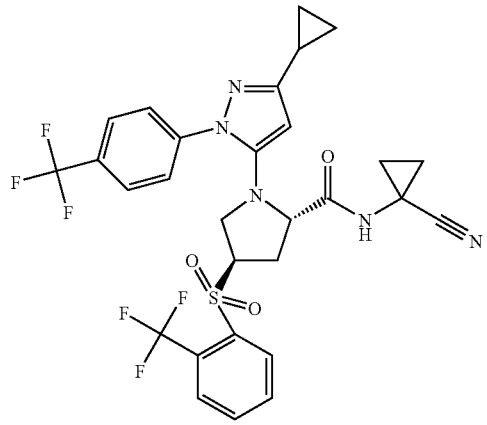

a) (2S,4R)-1-(3-Cyclopropyl-3-oxo-propionyl)-4-(2-trifluoromethyl-benzenesulfonyl)-pyrrolidine-2-carboxylic acid methyl ester In analogy to the procedure described in example 192f, (2S,4R)-4-(2-trifluoromethyl-benzenesulfonyl)-pyrrolidine-2-carboxylic acid methyl ester (example 192e) was reacted with 3-cyclopropyl-3-oxo-propionic acid tert-butyl ester (CAS Reg. No. 134302-07-1) to give the title compound as brown oil. MS (ESI): m/z=448.1 [M+H]$^+$.

b) (2S,4R)-1-[5-Cyclopropyl-2-(4-trifluoromethyl-phenyl)-2H-pyrazol-3-yl]-4-(2-trifluoromethyl-benzenesulfonyl)-pyrrolidine-2-carboxylic acid methyl ester In analogy to the procedure described in example 192 h, (2S,4R)-1-(3-cyclopropyl-3-oxo-propionyl)-4-(2-trifluoromethyl-benzenesulfonyl)-pyrrolidine-2-carboxylic acid methyl ester was reacted with was reacted with Lawesson's reagent (CAS Reg. No. 19172-47-5) and 4-(trifluoromethyl) phenylhydrazine (CAS Reg. No. 368-90-1) to give the title compound as yellow oil.

c) (2S,4R)-1-[5-Cyclopropyl-2-(4-trifluoromethyl-phenyl)-2H-pyrazol-3-yl]-4-(2-trifluoromethyl-benzenesulfonyl)-pyrrolidine-2-carboxylic acid In analogy to the procedure described in example 253e, (2S,4R)-1-[5-cyclopropyl-2-(4-trifluoromethyl-phenyl)-2H-pyrazol-3-yl]-4-(2-trifluoromethyl-benzenesulfonyl)-pyrrolidine-2-carboxylic acid methyl ester was saponified in the presence of lithium hydroxide to give the title compound as white solid which was used in the next step without further purification. MS (ESI): m/z=574.3 [M+H]$^+$.

d) (2S,4R)-1-[5-Cyclopropyl-2-(4-trifluoromethyl-phenyl)-2H-pyrazol-3-yl]-4-(2-trifluoromethyl-benzenesulfonyl)-pyrrolidine-2-carboxylic acid (1-cyano-cyclopropyl)-amide In analogy to the procedure described in example 237, (2S,4R)-1-[5-cyclopropyl-2-(4-trifluoromethyl-phenyl)-2H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=638.2 [M+H]$^+$.

Example 364

4-[2-(1-Cyano-cyclopropylcarbamoyl)-4-(2-trifluoromethyl-benzenesulfonyl)-pyrrolidin-1-yl]-piperidine-1-carboxylic acid tert-butyl ester

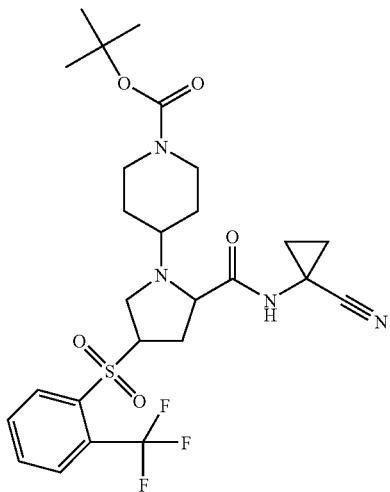

a) 4-[2-Ethoxycarbonyl-4-(2-trifluoromethyl-benzenesulfonyl)-pyrrolidin-1-yl]-piperidine-1-carboxylic acid tert-butyl ester In analogy to the procedure described in example 343d, 4-(ethoxycarbonylmethyl-amino)-piperidine-1-carboxylic acid tert-butyl ester (CAS Reg. No. 177276-49-2) was reacted with paraformaldehyde and 1-ethenesulfonyl-2-trifluoromethyl-benzene (example 243c) to give the title compound.

b) 4-[2-Carboxy-4-(2-trifluoromethyl-benzenesulfonyl)-pyrrolidin-1-yl]-piperidine-1-carboxylic acid tert-butyl ester In analogy to the procedure described in example 253e, 4-[2-ethoxycarbonyl-4-(2-trifluoromethyl-benzenesulfonyl)-pyrrolidin-1-yl]-piperidine-1-carboxylic acid tert-butyl ester was saponified in the presence of lithium hydroxide to give the title compound as off-white solid which was used in the next step without further purification. MS (ESI): m/z=507.3 [M+H]$^+$.

c) 4-[2-(1-Cyano-cyclopropylcarbamoyl)-4-(2-trifluoromethyl-benzenesulfonyl)-pyrrolidin-1-yl]-piperidine-1-carboxylic acid tert-butyl ester In analogy to the procedure described in example 237, 4-[2-carboxy-4-(2-trifluoromethyl-benzenesulfonyl)-pyrrolidin-1-yl]-piperidine-1-carboxylic acid tert-butyl ester was reacted with 1-amino-cyclopropanecarbonitrile hydrochloride (CAS Reg. No. 127946-77-4) in the presence of HATU and DIEA to give the title compound as white solid. MS (ESI): m/z=571.3 [M+H]$^+$.

Example 365

(2S,4R)-1-[1-(4-Chloro-phenyl)-cyclopropylmethyl]-4-[2-chloro-4-(2,2,2-trifluoro-ethoxy)-benzenesulfonyl]-pyrrolidine-2-carboxylic acid (1-cyano-cyclopropyl)-amide

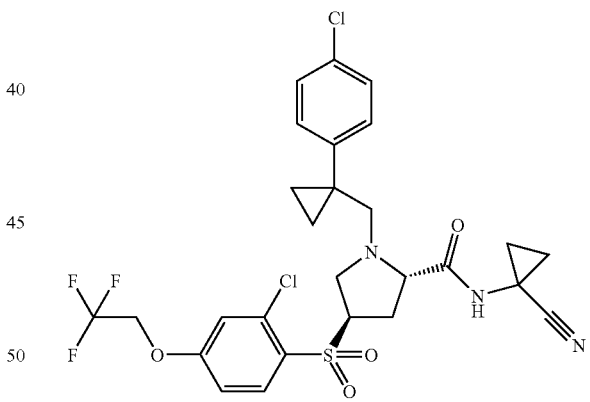

Example 173 (50 mg) and 1-(4-Chloro-phenyl)-cyclopropanecarbaldehyde (CAS #100845-90-7; 22 mg) were suspended in tetrahydrofuran (1.2 mL) and stirred at 80° C. for 1 h. The reaction mixture was cooled down to room temperature then sodium acetoxyborohydride (52 mg) was added and the reaction mixture was stirred at 80° C. for 20 h. The reaction mixture was partitioned between ethyl acetate and a saturated aqueous solution of sodium hydrogenocarbonate. The aqueous layer was extracted with ethyl acetate and the combined organic layers were washed with a saturated aqueous solution of sodium hydrogenocarbonate. The crude mixture was concentrated to dryness and purified by chromatography on silica gel to yield the title compound as a colorless oil (40 mg; 59%). MS (ESI): m/z=616.1 [M+H]$^+$.

Example 366

(2S,4R)-4-[4-(2,2,2-Trifluoro-ethoxy)-2-trifluoromethyl-benzenesulfonyl]-1-(5-trifluoromethyl-[1,3,4]thiadiazol-2-yl)-pyrrolidine-2-carboxylic acid (1-cyano-cyclopropyl)-amide

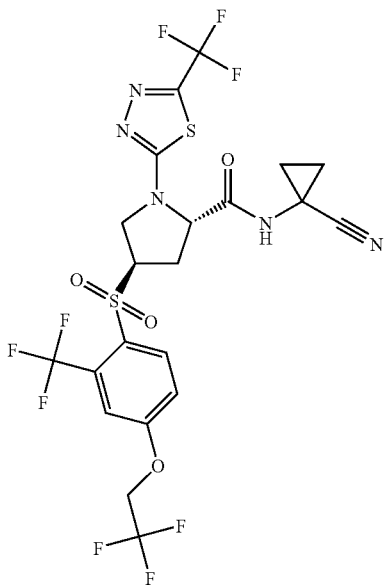

In analogy to the procedure described in example 335a, (2S,4R)-4-[4-(2,2,2-trifluoro-ethoxy)-2-trifluoromethyl-benzenesulfonyl]-pyrrolidine-2-carboxylic acid (1-cyano-cyclopropyl)-amide (example 211a) was reacted with 2-chloro-5-trifluoromethyl-[1,3,4]thiadiazole (CAS Reg. No. 53645-98-0) in a shaking reactor at 55° C. for 12 h to give the title compound as yellow solid. MS (ESI): m/z=638.1 [M+H]$^+$.

Example 367

1-(3-Trifluoromethoxy-phenyl)-4-(2-trifluoromethyl-benzenesulfonyl)-pyrrolidine-2-carboxylic acid (1-cyano-cyclopropyl)-amide

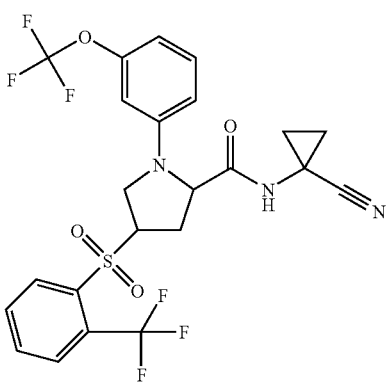

a) 1-(3-Trifluoromethoxy-phenyl)-4-(2-trifluoromethyl-benzenesulfonyl)-pyrrolidine-2-carboxylic acid ethyl ester In analogy to the procedure described in example 343d, (3-trifluoromethoxy-phenylamino)-acetic acid ethyl ester (CAS Reg. No. 1021237-80-8) was reacted with paraformaldehyde and 1-ethenesulfonyl-2-trifluoromethyl-benzene (example 243c) to give the title compound as off-white solid. MS (ESI): m/z=512.3 [M+H]$^+$.

b) 1-(3-Trifluoromethoxy-phenyl)-4-(2-trifluoromethyl-benzenesulfonyl)-pyrrolidine-2-carboxylic acid In analogy to the procedure described in example 253e, 1-(3-trifluoromethoxy-phenyl)-4-(2-trifluoromethyl-benzenesulfonyl)-pyrrolidine-2-carboxylic acid ethyl ester was saponified in the presence of lithium hydroxide to give the title compound as yellow oil which was used in the next step without further purification. MS (ESI): m/z=484.2 [M+H]$^+$.

c) 1-(3-Trifluoromethoxy-phenyl)-4-(2-trifluoromethyl-benzenesulfonyl)-pyrrolidine-2-carboxylic acid (1-cyano-cyclopropyl)-amide In analogy to the procedure described in example 237, 1-(3-trifluoromethoxy-phenyl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=548.2 [M+H]$^+$.

Example 368

(2S,4R)-4-(2-Chloro-4-fluoro-benzenesulfonyl)-1-[1-(6-chloro-pyridin-3-yl)-cyclopropanecarbonyl]-pyrrolidine-2-carboxylic acid (1-cyano-cyclopropyl)-amide

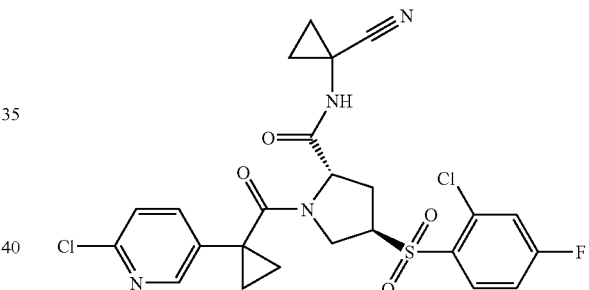

The title compound was prepared in analogy to example 312 to yield 2.1 g (52%) of a white solid. MS (ESI): m/z=551.2 [M+H]$^+$.

Example 369

(2S,4R)-4-[2-Chloro-4-(4-methyl-piperazin-1-yl)-benzenesulfonyl]-1-[1-(6-chloro-pyridin-3-yl)-cyclopropanecarbonyl]-pyrrolidine-2-carboxylic acid (1-cyano-cyclopropyl)-amide; Compound with Formic Acid

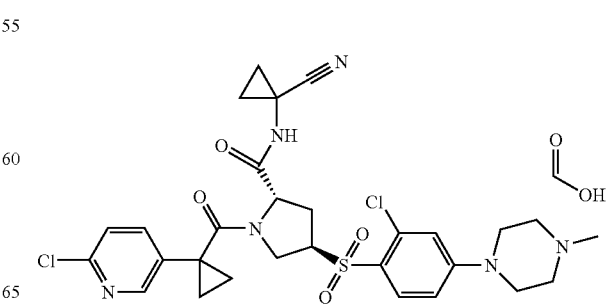

Example 368 (100 mg) was dissolved in ACN (1.5 mL) at 25° C. 1-Methylpiperazine (0.04 mL) and Hilnig's base (0.06 mL) were added to the obtained solution. The reaction mixture was stirred at 25° C. for 96 h. After that, additional 1-methyl-piperazine (0.01 mL) was given to the reaction mixture and stirred for 18 h at 25° C. The mixture was then purified with preparative HPLC to yield the title compound (101 mg; 84%) as an amorphous colorless solid. MS (ESI): m/z=631.3 [M+H]$^+$.

Example 370

(2S,4R)-4-[2-Chloro-4-(4-isopropyl-piperazin-1-yl)-benzenesulfonyl]-1-[1-(6-chloro-pyridin-3-yl)-cyclopropanecarbonyl]-pyrrolidine-2-carboxylic acid (1-cyano-cyclopropyl)-amide; Compound with Formic Acid

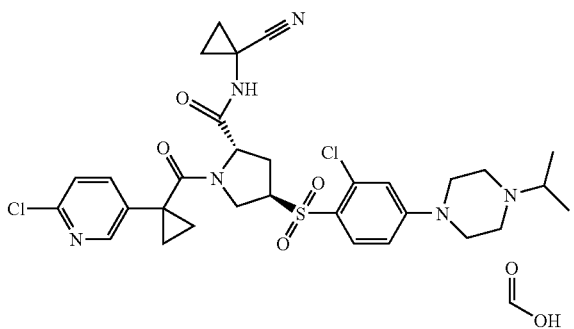

The title compound was prepared in analogy to example 369 to yield 76 mg (63%) of a colorless amorphous material. MS (ESI): m/z=659.3 [M+H]$^+$.

Example 371

(2S,4R)-4-[4-(4-tert-Butyl-piperazin-1-yl)-2-chloro-benzenesulfonyl]-1-[1-(6-chloro-pyridin-3-yl)-cyclopropanecarbonyl]-pyrrolidine-2-carboxylic acid (1-cyano-cyclopropyl)-amide; Compound with Formic Acid

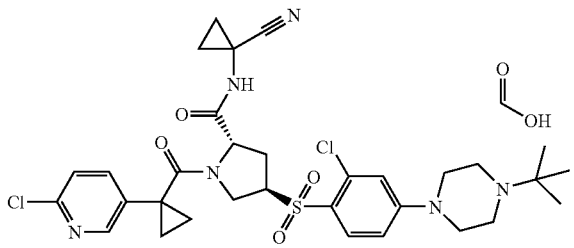

The title compound was prepared in analogy to example 369 to yield 117 mg (96%) of a colorless amorphous material. MS (ESI): m/z=673.4 [M+H]$^+$.

Example 372

(2S,4R)-4-{2-Chloro-4-[4-(2-methoxy-ethyl)-piperazin-1-yl]-benzenesulfonyl}-1-[1-(6-chloro-pyridin-3-yl)-cyclopropanecarbonyl]-pyrrolidine-2-carboxylic acid (1-cyano-cyclopropyl)-amide; Compound with Formic Acid

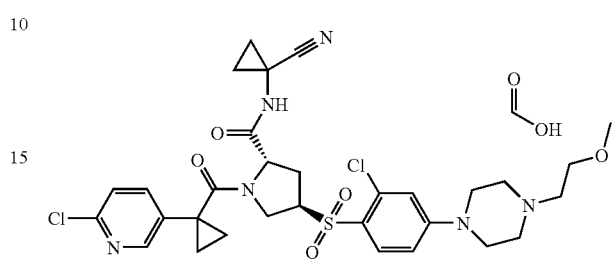

The title compound was prepared in analogy to example 369 to yield 86 mg (66%) of a colorless amorphous material. MS (ESI): m/z=675.3 [M+H]$^+$.

Example 373

(2S,4R)-4-((S)-2-Chloro-4-hexahydro-pyrrolo[1,2-a]pyrazin-2-yl-benzenesulfonyl)-1-[1-(6-chloro-pyridin-3-yl)-cyclopropanecarbonyl]-pyrrolidine-2-carboxylic acid (1-cyano-cyclopropyl)-amide; Compound with Formic Acid

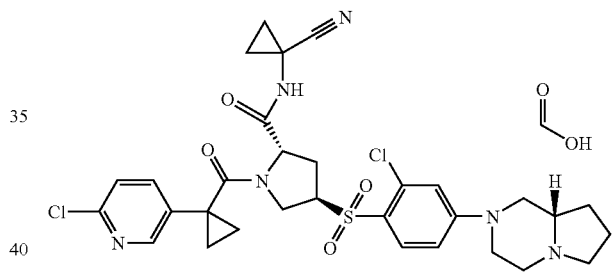

The title compound was prepared in analogy to example 369 to yield 108 mg (91%) of a colorless amorphous material. MS (ESI): m/z=657.3 [M+H]$^+$.

Example 374

(2S,4R)-4-[2-Chloro-4-(4-cyclopropyl-piperazin-1-yl)-benzenesulfonyl]-1-[1-(6-chloro-pyridin-3-yl)-cyclopropanecarbonyl]-pyrrolidine-2-carboxylic acid (1-cyano-cyclopropyl)-amide; Compound with Formic Acid

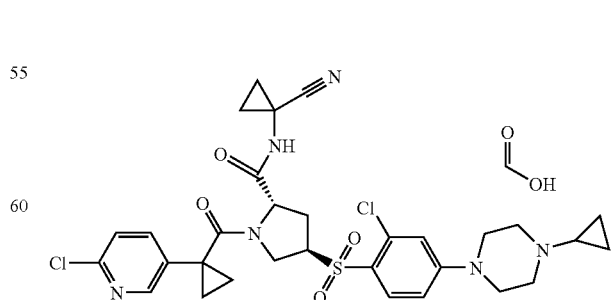

The title compound was prepared in analogy to example 369 to yield 78 mg (65%) of a colorless amorphous material. MS (ESI): m/z=657.3 [M+H]$^+$.

Example 375

(2S,4R)-4-(2-Chloro-4-methoxy-benzenesulfonyl)-1-(2-cyclobutyl-5-methyl-2H-pyrazol-3-yl)-pyrrolidine-2-carboxylic acid (1-cyano-cyclopropyl)-amide

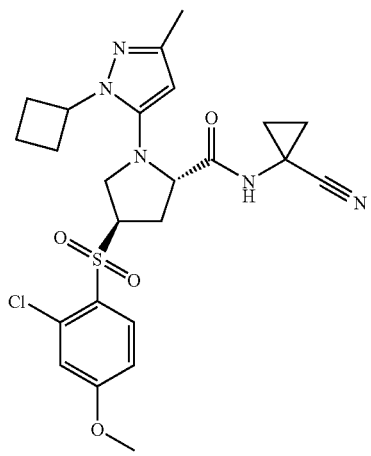

a) (2S,4R)-4-(2-Chloro-4-fluoro-benzenesulfonyl)-pyrrolidine-2-carboxylic acid Methyl Ester In analogy to the procedure described in example 253a, (2S,4R)-4-(2-chloro-4-fluoro-benzenesulfonyl)-pyrrolidine-1,2-dicarboxylic acid 1-tert-butyl ester 2-methyl ester (example 171) was treated with trifluoroacetic acid in dichloromethane to give the title compound as colorless oil. MS (ESI): m/z=322.2 [M+H]$^+$.

b) (2S,4R)-4-(2-Chloro-4-fluoro-benzenesulfonyl)-1-(3-oxo-butyryl)-pyrrolidine-2-carboxylic acid methyl ester In analogy to the procedure described in example 192f, (2S,4R)-4-(2-chloro-4-fluoro-benzenesulfonyl)-pyrrolidine-2-carboxylic acid methyl ester was reacted with tert-butyl acetoacetate to give the title compound as yellow foam. MS (ESI): m/z=406.3 [M+H]$^+$.

c) (2S,4R)-4-(2-Chloro-4-fluoro-benzenesulfonyl)-1-(2-cyclobutyl-5-methyl-2H-pyrazol-3-yl)-pyrrolidine-2-carboxylic acid methyl ester In analogy to the procedure described in example 192 h, (2S,4R)-4-(2-chloro-4-fluoro-benzenesulfonyl)-1-(3-oxo-butyryl)-pyrrolidine-2-carboxylic acid methyl ester was reacted with Lawesson's reagent (CAS Reg. No. 19172-47-5) and cyclobutylhydrazine hydrochloride (CAS Reg. No. 158001-21-9) to give the title compound as colorless oil. MS (ESI): m/z=456.2 [M+H]$^+$.

d) (2S,4R)-4-(2-Chloro-4-methoxy-benzenesulfonyl)-1-(2-cyclobutyl-5-methyl-2H-pyrazol-3-yl)-pyrrolidine-2-carboxylic acid In analogy to the procedure described in example 253e, (2S,4R)-4-(2-chloro-4-fluoro-benzenesulfonyl)-1-(2-cyclobutyl-5-methyl-2H-pyrazol-3-yl)-pyrrolidine-2-carboxylic acid methyl ester was saponified in the presence of lithium hydroxide to give the title compound as brown oil which was used in the next step without further purification.

e) (2S,4R)-4-(2-Chloro-4-methoxy-benzenesulfonyl)-1-(2-cyclobutyl-5-methyl-2H-pyrazol-3-yl)-pyrrolidine-2-carboxylic acid (1-cyano-cyclopropyl)-amide In analogy to the procedure described in example 237, (2S,4R)-4-(2-chloro-4-methoxy-benzenesulfonyl)-1-(2-cyclobutyl-5-methyl-2H-pyrazol-3-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=518.2 [M+H]$^+$.

Example 376

(2S,4R)-1-(2-Benzyl-5-methyl-2H-pyrazol-3-yl)-4-(2-chloro-4-methoxy-benzenesulfonyl)-pyrrolidine-2-carboxylic acid (1-cyano-cyclopropyl)-amide

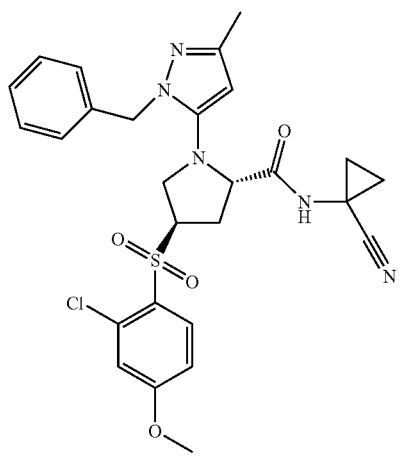

a) (2S,4R)-1-(2-Benzyl-5-methyl-2H-pyrazol-3-yl)-4-(2-chloro-4-fluoro-benzenesulfonyl)-pyrrolidine-2-carboxylic acid methyl ester In analogy to the procedure described in example 192 h, (2S,4R)-4-(2-chloro-4-fluoro-benzenesulfonyl)-1-(3-oxo-butyryl)-pyrrolidine-2-carboxylic acid methyl ester (example 375b) was reacted with Lawesson's reagent (CAS Reg. No. 19172-47-5) and benzylhydrazine dihydrochloride (CAS Reg. No. 20570-96-1) to give the title compound as yellow oil. MS (ESI): m/z=492.3 [M+H]$^+$.

b) (2S,4R)-1-(2-Benzyl-5-methyl-2H-pyrazol-3-yl)-4-(2-chloro-4-methoxy-benzenesulfonyl)-pyrrolidine-2-carboxylic acid In analogy to the procedure described in example 253e, (2S,4R)-1-(2-benzyl-5-methyl-2H-pyrazol-3-yl)-4-(2-chloro-4-fluoro-benzenesulfonyl)-pyrrolidine-2-carboxylic acid methyl ester was saponified in the presence of lithium hydroxide to give the title compound as white solid which was used in the next step without further purification. MS (ESI): m/z=490.3 [M+H]$^+$.

c) (2S,4R)-1-(2-Benzyl-5-methyl-2H-pyrazol-3-yl)-4-(2-chloro-4-methoxy-benzenesulfonyl)-pyrrolidine-2-carboxylic acid (1-cyano-cyclopropyl)-amide In analogy to the procedure described in example 237, (2S,4R)-1-(2-benzyl-5-methyl-2H-pyrazol-3-yl)-4-(2-chloro-4-methoxy-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless foam. MS (ESI): m/z=554.4 [M+H]⁺.

Example 377

(R)-1-[1-(6-Chloro-pyridin-3-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide

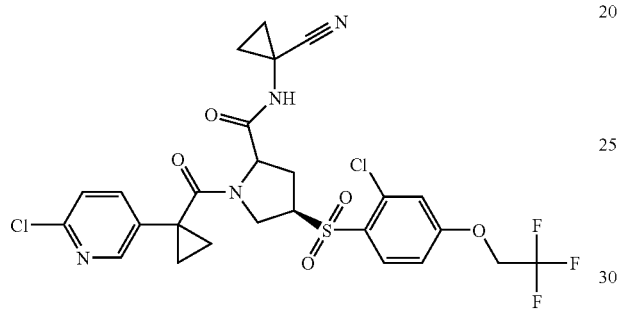

Example 368 (80 mg) was dissolved in DMF (1.0 mL) at 25° C. 2,2,2-Trifluoroethanole (0.020 mL) and cesium carbonate (95 mg) were added to the solution. The reaction mixture was stirred at 25° C. for 96 h. The mixture was then purified with preparative HPLC to yield the title compound (59 mg; 64%) as an amorphous colorless solid. MS (ESI): m/z=631.2 [M+H]⁺.

Example 378

(R)-4-[2-Chloro-4-(2-methoxy-ethoxy)-benzenesulfonyl]-1-[1-(6-chloro-pyridin-3-yl)-cyclopropanecarbonyl]-pyrrolidine-2-carboxylic acid (1-cyano-cyclopropyl)-amide

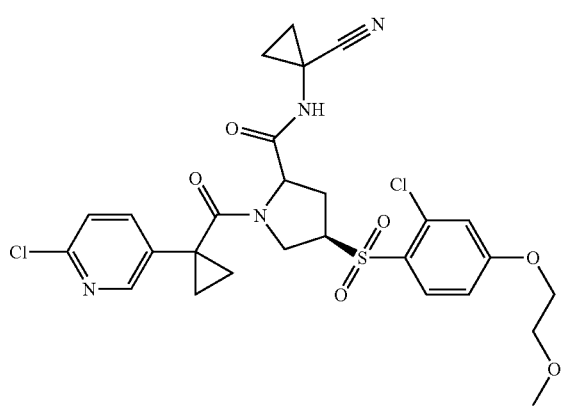

The title compound was prepared in analogy to example 377 to yield 62 mg (70%) of a colorless amorphous material. MS (ESI): m/z=607.3 [M+H]⁺.

Example 379

(2S,4R)-1-(2-Benzyl-5-methyl-2H-pyrazol-3-yl)-4-(2-chloro-benzenesulfonyl)-pyrrolidine-2-carboxylic acid (1-cyano-cyclopropyl)-amide

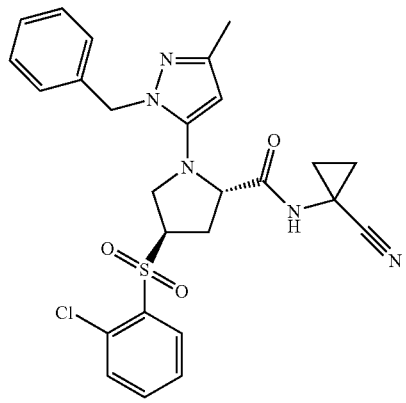

a) (2S,4R)-1-(2-Benzyl-5-methyl-2H-pyrazol-3-yl)-4-(2-chloro-benzenesulfonyl)-pyrrolidine-2-carboxylic acid methyl ester In analogy to the procedure described in example 192 h, (2S,4R)-4-(2-chloro-benzenesulfonyl)-1-(3-oxo-thiobutyryl)-pyrrolidine-2-carboxylic acid methyl ester (example 253c) was reacted with benzylhydrazine dihydrochloride (CAS Reg. No. 20570-96-1) to give the title compound as orange oil. MS (ESI): m/z=474.2 [M+H]⁺.

b) (2S,4R)-1-(2-Benzyl-5-methyl-2H-pyrazol-3-yl)-4-(2-chloro-benzenesulfonyl)-pyrrolidine-2-carboxylic acid In analogy to the procedure described in example 253e, (2S,4R)-1-(2-benzyl-5-methyl-2H-pyrazol-3-yl)-4-(2-chloro-benzenesulfonyl)-pyrrolidine-2-carboxylic acid methyl ester was saponified in the presence of lithium hydroxide to give the title compound as yellow oil which was used in the next step without further purification. MS (ESI): m/z=460.3 [M+H]⁺.

c) (2S,4R)-1-(2-Benzyl-5-methyl-2H-pyrazol-3-yl)-4-(2-chloro-benzenesulfonyl)-pyrrolidine-2-carboxylic acid (1-cyano-cyclopropyl)-amide In analogy to the procedure described in example 237, (2S,4R)-1-(2-benzyl-5-methyl-2H-pyrazol-3-yl)-4-(2-chloro-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless oil. MS (ESI): m/z=524.3 [M+H]⁺.

Example 380

(2S,4R)-4-(2-Chloro-4-pyrazol-1-yl-benzenesulfonyl)-1-[1-(6-chloro-pyridin-3-yl)-cyclopropanecarbonyl]-pyrrolidine-2-carboxylic acid (1-cyano-cyclopropyl)-amide

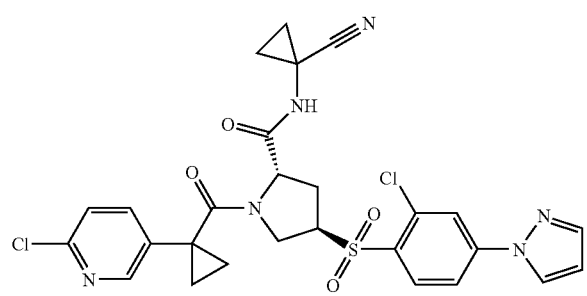

Example 368 (80 mg) was dissolved in DMA (2.0 mL) at 25° C. Pyrazole (18 mg) and cesium carbonate (95 mg) were added to the solution. The reaction mixture was stirred at 100° C. for 30 min in the microwave oven. Additional pyrazole (0.2 eq.) was given to the suspension and the mixture was heated twice at 100° C. for 30 min in the microwave oven. The mixture was then purified with preparative HPLC to yield the title compound (31 mg; 36%) as an amorphous colorless solid. MS (ESI): m/z=599.2 [M+H]$^+$.

Example 381

(2S,4R)-1-[1-(6-Chloro-pyridin-3-yl)-cyclopropanecarbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide

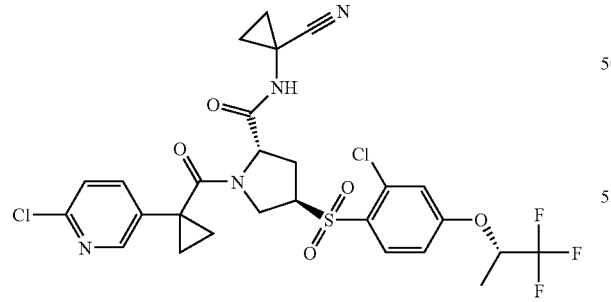

The title compound was prepared in analogy to example 380 to yield 42 mg (45%) of a colorless amorphous material. MS (ESI): m/z=645.1 [M+H]$^+$.

Example 382

(2S,4R)-4-(2-Chloro-4-imidazol-1-yl-benzenesulfonyl)-1-[1-(6-chloro-pyridin-3-yl)-cyclopropanecarbonyl]-pyrrolidine-2-carboxylic acid (1-cyano-cyclopropyl)-amide

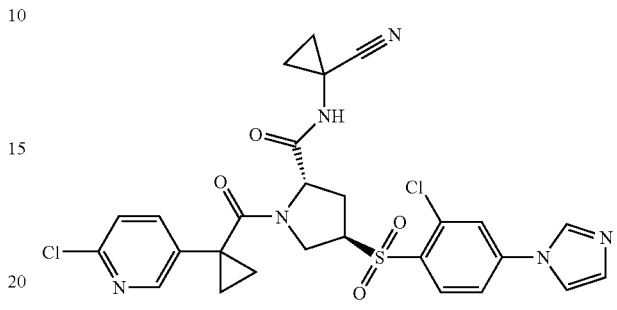

Example 368 (80 mg) was dissolved in acetonitrile (1.0 mL) at 25° C. Imidazole (20 mg) and Hünig's base (0.05 mL) were added to the obtained solution. The reaction mixture was stirred at 25° C. for 96 h. The mixture was then stirred at 90° C. for further 72 h. The mixture was then purified with preparative HPLC to yield the title compound (31 mg; 36%) as an amorphous colorless solid. MS (ESI): m/z=599.2 [M+H]$^+$.

Example 383

(6R,7aS)-6-(2-Chloro-4-fluoro-benzenesulfonyl)-1-cyano-tetrahydro-pyrrolizine-7a-carboxylic Acid (1-cyano-cyclopropyl)-amide

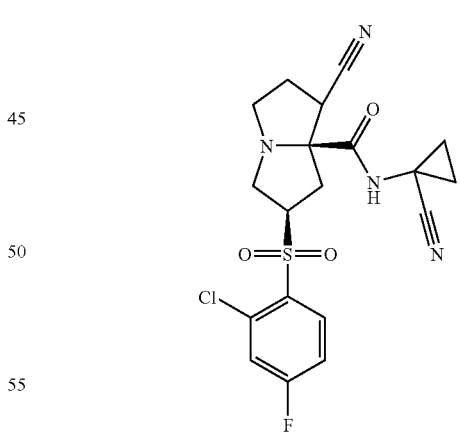

a) (6R,7aR)-6-(2-Chloro-4-fluoro-benzenesulfonyl)-1-cyano-tetrahydro-pyrrolizine-7a-carboxylic acid methyl ester (2S,4R)-4-(2-Chloro-4-fluoro-benzenesulfonyl)-pyrrolidine-2-carboxylic acid methyl ester (380 mg) was dissolved in THF (10 mL). Formaldehyde (120 µL; 36.5% aqueous solution), acrylnitrile (80 μL) and TFA (10 μL) were added. The reaction mixture was stirred for 12 h at 65° C. The reaction mixture was purified with preparative HPLC to yield the title compound (mixture of epimers; 130 mg; 28%) as a light brown viscous oil. MS (ESI): m/z=387.1 [M+H]⁺.

b) (6R,7aR)-6-(2-Chloro-4-fluoro-benzenesulfonyl)-1-cyano-tetrahydro-pyrrolizine-7a-carboxylic Acid Example 383a) (125 mg) and lithium hydroxide (13 mg) were dissolved in THF/water (7 mL; 4:1). The reaction mixture was stirred for 18 h at 25° C. The reaction mixture was then adjusted to pH 3 with 0.5 N aqueous HCl-solution and extracted with CH₂Cl₂. The combined organic layers were washed with brine. The combined organic layers were dried over Na₂SO₄, filtered off and evaporated to dryness to yield example 383b) (101 mg, 84%) as a colorless solid. MS (ESI): m/z=371.0 [M−H]⁻.

c) (6R,7aS)-6-(2-Chloro-4-fluoro-benzenesulfonyl)-1-cyano-tetrahydro-pyrrolizine-7a-carboxylic Acid (1-cyano-cyclopropyl)-amide Example 383b) (101 mg), HATU (206 mg) and 1-amino-1-cyclopropane carbonitrile hydrochloride (39 mg) were dissolved in acetonitrile (7 mL). 0. Hünig's base (60 μL) was added and the reaction mixture was stirred for 20 h at 25° C. The solvent was evaporated, the residue was dissolved in AcOEt (15 mL) and extracted with 10% aqueous Na₂CO₃ solution, aqueous 0.5 N—HCl-solution and brine. The organic layers were dried over Na₂SO₄, filtered off and evaporated to dryness. The title compound was purified with preparative HPLC to yield 38 mg (32%) of a colorless solid. MS (ESI): m/z=437.1 [M+H]⁺.

Example 384

(2S,4R)-1-(1-Benzo[1,3]dioxol-5-yl-cyclopropan-ecarbonyl)-4-[2-chloro-4-(2,2,2-trifluoro-ethoxy)-benzenesulfonyl]-pyrrolidine-2-carboxylic acid (1-cyano-cyclopropyl)-amide

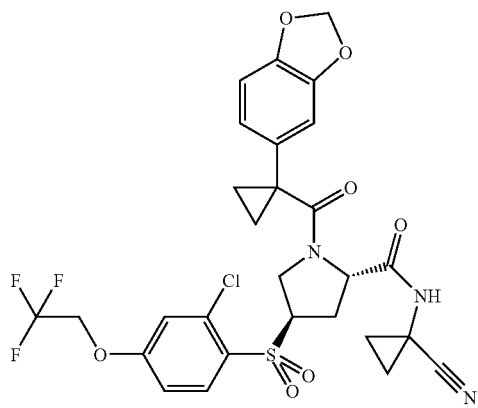

The title compound was prepared in analogy to example 239 using example 173 (75 mg) and 1-benzo[1,3]dioxol-5-yl-cyclopropanecarboxylic acid (CAS #[862574-89-8]; 41 mg) to yield 105 mg (99%) of a white foam. MS (ESI): m/z=640.11 [M+H]⁺.

Example 385

(2S,4R)-4-(2-Chloro-4-fluoro-benzenesulfonyl)-1-(2-cyclobutyl-5-methyl-2H-pyrazol-3-yl)-pyrrolidine-2-carboxylic acid (1-cyano-cyclopropyl)-amide

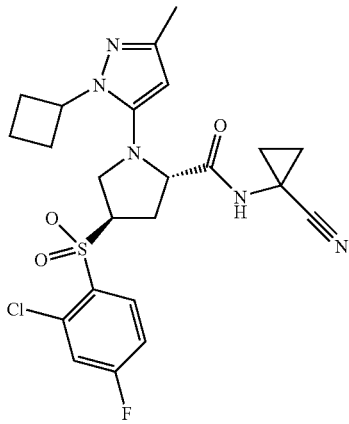

a) (2S,4R)-4-(2-Chloro-4-fluoro-benzenesulfonyl)-1-(2-cyclobutyl-5-methyl-2H-pyrazol-3-yl)-pyrrolidine-2-carboxylic acid In analogy to the procedure described in example 253e, (2S,4R)-4-(2-chloro-4-fluoro-benzenesulfonyl)-1-(2-cyclobutyl-5-methyl-2H-pyrazol-3-yl)-pyrrolidine-2-carboxylic acid methyl ester (example 375c) was saponified in the presence of lithium hydroxide avoiding methanol as a cosolvent to give the title compound as yellow oil which was used in the next step without further purification. MS (ESI): m/z=442.2 [M+H]⁺.

b) (2S,4R)-4-(2-Chloro-4-fluoro-benzenesulfonyl)-1-(2-cyclobutyl-5-methyl-2H-pyrazol-3-yl)-pyrrolidine-2-carboxylic acid (1-cyano-cyclopropyl)-amide In analogy to the procedure described in example 237, (2S,4R)-4-(2-chloro-4-fluoro-benzenesulfonyl)-1-(2-cyclobutyl-5-methyl-2H-pyrazol-3-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless foam. MS (ESI): m/z=506.2 [M+H]⁺.

Example 386

(2S,4R)-1-(5-tert-Butyl-2-methyl-2H-pyrazole-3-carbonyl)-4-[2-chloro-4-(2,2,2-trifluoro-ethoxy)-benzenesulfonyl]-pyrrolidine-2-carboxylic acid (1-cyano-cyclopropyl)-amide

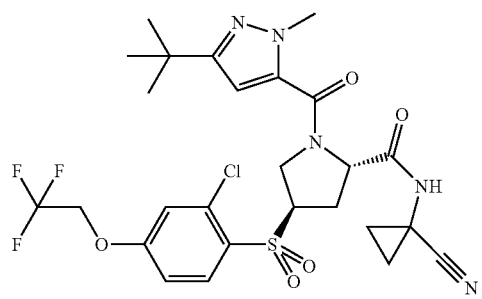

The title compound was prepared in analogy to example 239 using example 173 (37 mg) and 3-(tert-butyl)-1H-pyrazole-5-carboxylic acid (19 mg) to yield 47 mg (93%) of a white foam. MS (ESI): m/z=616.16 [M+H]⁺.

Example 387

(2S,4R)-4-(2-Chloro-4-methoxy-benzenesulfonyl)-2-(1-cyano-cyclopropylcarbamoyl)-pyrrolidine-1-carboxylic acid tert-butyl ester

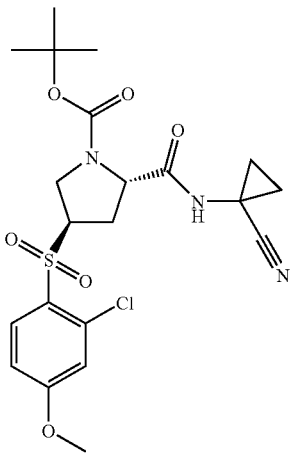

The title compound was obtained as a by-product during the synthesis of example 124 to yield 18% of an off-white foam. MS (ESI): m/z=484.1 [M+H]⁺.

Example 388

(2S,4R)-1-(2-Cyclobutyl-5-methyl-2H-pyrazol-3-yl)-4-(4-fluoro-2-trifluoromethyl-benzenesulfonyl)-pyrrolidine-2-carboxylic acid (1-cyano-cyclopropyl)-amide

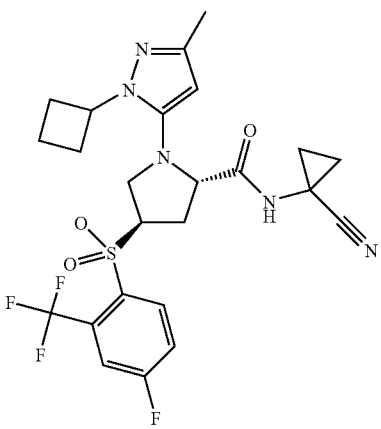

a) (2S,4R)-4-(4-Fluoro-2-trifluoromethyl-benzenesulfonyl)-pyrrolidine-2-carboxylic acid methyl ester In analogy to the procedure described in example 253a, (2S,4R)-4-(4-fluoro-2-trifluoromethyl-benzenesulfonyl)-pyrrolidine-1,2-dicarboxylic acid 1-tert-butyl ester 2-methyl ester (example 208 c) was treated with trifluoroacetic acid in dichloromethane to give the title compound as yellow oil. MS (ESI): m/z=356.1 [M+H]⁺.

b) (2S,4R)-4-(4-Fluoro-2-trifluoromethyl-benzenesulfonyl)-pyrrolidine-2-carboxylic acid Methyl Ester In analogy to the procedure described in example 253a, (2S,4R)-4-(4-fluoro-2-trifluoromethyl-benzenesulfonyl)-pyrrolidine-1,2-dicarboxylic acid 1-tert-butyl ester 2-methyl ester was treated with trifluoroacetic acid in dichloromethane to give the title compound as yellow oil. MS (ESI): m/z=356.1 [M+H]⁺.

c) (2S,4R)-4-(4-Fluoro-2-trifluoromethyl-benzenesulfonyl)-1-(3-oxo-butyryl)-pyrrolidine-2-carboxylic acid methyl ester In analogy to the procedure described in example 192f, (2S,4R)-4-(4-fluoro-2-trifluoromethyl-benzenesulfonyl)-pyrrolidine-2-carboxylic acid methyl ester was reacted with tert-butyl acetoacetate to give the title compound as yellow oil. MS (ESI): m/z=440.2 [M+H]⁺.

d) (2S,4R)-4-(4-Fluoro-2-trifluoromethyl-benzenesulfonyl)-1-(3-oxo-thiobutyryl)-pyrrolidine-2-carboxylic acid methyl ester In analogy to the procedure described in example 192f, (2S,4R)-4-(4-fluoro-2-trifluoromethyl-benzenesulfonyl)-1-(3-oxo-butyryl)-pyrrolidine-2-carboxylic acid methyl ester was reacted with Lawesson's reagent to give the title compound as brown solid.

e) (2S,4R)-1-(2-Cyclobutyl-5-methyl-2H-pyrazol-3-yl)-4-(4-fluoro-2-trifluoromethyl-benzenesulfonyl)-pyrrolidine-2-carboxylic acid methyl ester In analogy to the procedure described in example 192 h, (2S,4R)-4-(4-fluoro-2-trifluoromethyl-benzenesulfonyl)-1-(3-oxo-thiobutyryl)-pyrrolidine-2-carboxylic acid methyl ester was reacted with cyclobutylhydrazine hydrochloride (CAS Reg. No. 158001-21-9) to give the title compound as yellow oil. MS (ESI): m/z=490.1 [M+H]⁺.

f) (2S,4R)-1-(2-Cyclobutyl-5-methyl-2H-pyrazol-3-yl)-4-(4-fluoro-2-trifluoromethyl-benzenesulfonyl)-pyrrolidine-2-carboxylic acid In analogy to the procedure described in example 253e, (2S,4R)-1-(2-cyclobutyl-5-methyl-2H-pyrazol-3-yl)-4-(4-fluoro-2-trifluoromethyl-benzenesulfonyl)-pyrrolidine-2-carboxylic acid methyl ester was saponified in the presence of lithium hydroxide avoiding methanol as a cosolvent to give the title compound as yellow foam which was used in the next step without further purification. MS (ESI): m/z=476.2 [M+H]⁺.

g) (2S,4R)-1-(2-Cyclobutyl-5-methyl-2H-pyrazol-3-yl)-4-(4-fluoro-2-trifluoromethyl-benzenesulfonyl)-pyrrolidine-2-carboxylic acid (1-cyano-cyclopropyl)-amide In analogy to the procedure described in example 237, (2S,4R)-1-(2-cyclobutyl-5-methyl-2H-pyrazol-3-yl)-4-(4-fluoro-2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as brown oil. MS (ESI): m/z=540.2 [M+H]⁺.

Example 389

(2S,4R)-1-(2-Cyclobutyl-5-methyl-2H-pyrazol-3-yl)-4-[4-(4-methyl-piperazin-1-yl)-2-trifluoromethyl-benzenesulfonyl]-pyrrolidine-2-carboxylic acid (1-cyano-cyclopropyl)-amide

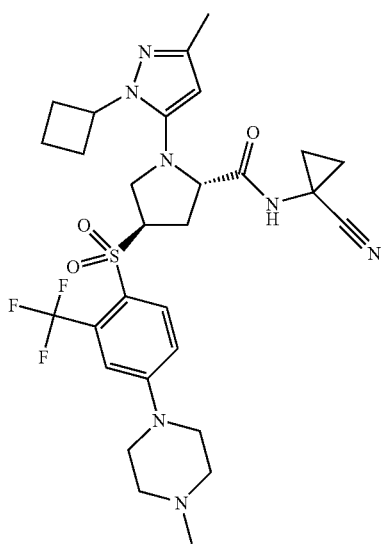

Methylpiperazine (10 ul, 116 umol; CAS Reg. No. 109-01-3) and DIEA (20 ul, 93 umol) were added to a solution of (2S,4R)-1-(2-cyclobutyl-5-methyl-2H-pyrazol-3-yl)-4-(4-fluoro-2-trifluoromethyl-benzenesulfonyl)-pyrrolidine-2-carboxylic acid (1-cyano-cyclopropyl)-amide (25 mg, 46 umol; example 388 g) in acetonitrile (400 ul) under an argon atmosphere. The reaction mixture was stirred at ambient temperature for 72 h, the solvent was removed under reduced pressure and the residue was purified by preparative HPLC to give the title compound (14 mg, 23 umol; 49%) as colorless oil. MS (ESI): m/z=618.2 [M−H]⁻.

Example 390

(2S,4R)-4-[2-Chloro-4-(2,2,2-trifluoro-ethoxy)-benzenesulfonyl]-1-(2-naphthalen-1-yl-[1,3]dioxolane-2-carbonyl)-pyrrolidine-2-carboxylic acid (1-cyano-cyclopropyl)-amide

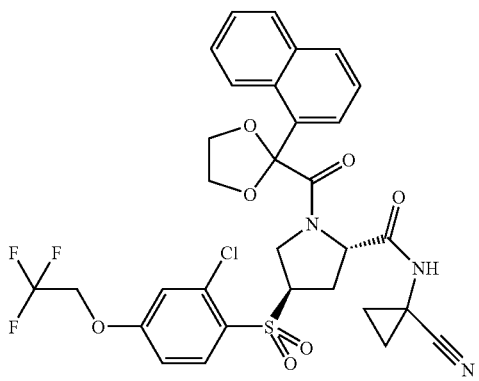

a) 2-Naphthalen-1-yl-[1,3]dioxolane-2-carboxylic acid ethyl ester

The title compound was prepared in analogy to example 346a) using ethyl-2-(1-naphtyl)glyoxylate (500 mg) to yield 439 mg (77%) of a colorless liquid. MS (ESI): m/z=199 [M−CO₂Et]⁺.

b) 2-Naphthalen-1-yl-[1,3]dioxolane-2-carboxylic acid

The title compound was prepared in analogy to example 346b) using 2-Naphthalen-1-yl-[1,3]dioxolane-2-carboxylic acid ethyl ester (400 mg) to yield 331 mg (92%) of a white solid. MS (ESI): m/z=243.07 [M−H]⁻.

c) (2S,4R)-4-[2-Chloro-4-(2,2,2-trifluoro-ethoxy)-benzenesulfonyl]-1-(2-naphthalen-1-yl-[1,3]dioxolane-2-carbonyl)-pyrrolidine-2-carboxylic acid (1-cyano-cyclopropyl)-amide The title compound was prepared in analogy to example 239 using example 173 (50 mg) and 2-Naphthalen-1-yl-[1,3]dioxolane-2-carboxylic acid (Example 390b), 32 mg) to yield 55 mg (73%) of a white solid. MS (ESI): m/z=678.13 [M+H]⁺.

Example 391

(2S,4R)-1-(2-Cyclobutyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide

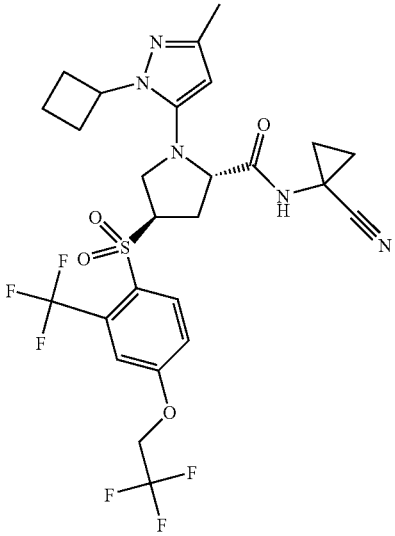

2,2,2,-Trifluoroethanol (10 ul, 137 umol; CAS Reg. No. 75-89-8 99) and cesium carbonate (45 mg, 137 umol) were added to a solution of (2S,4R)-1-(2-cyclobutyl-5-methyl-2H-pyrazol-3-yl)-4-(4-fluoro-2-trifluoromethyl-benzenesulfonyl)-pyrrolidine-2-carboxylic acid (1-cyano-cyclopropyl)-amide (37 mg, 69 umol; example 388 g) in DMF (500 ul) under an argon atmosphere. The reaction mixture was stirred for 72 h at ambient temperature and partitioned between ice water/brine 1/1 and iPrOAc. The layers were separated and the aqueous layer was extracted one more time with iPrOAc. The combined extracts were washed with ice water/brine 1/1, dried over sodium sulfate and filtered. The solvent was removed under reduced pressure to give a yellow foam which was purified by preparative chiral HPLC to give the title compound (13 mg, 21 umol; 31%) as colorless foam. MS (ESI): m/z=620.2 [M+H]⁺.

Example 392

(2R,4R)-1-(2-Cyclobutyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide

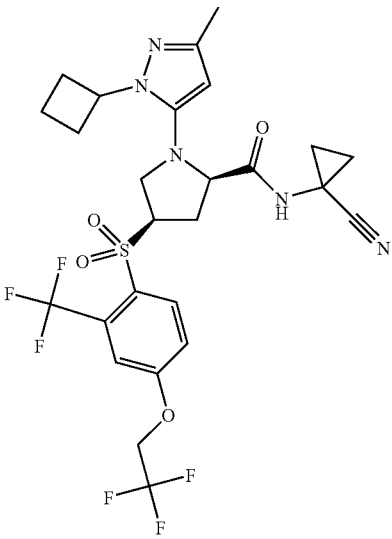

2,2,2,-Trifluoroethanol (10 ul, 137 umol; CAS Reg. No. 75-89-8 99) and cesium carbonate (45 mg, 137 umol) were added to a solution of (2S,4R)-1-(2-cyclobutyl-5-methyl-2H-pyrazol-3-yl)-4-(4-fluoro-2-trifluoromethyl-benzenesulfonyl)-pyrrolidine-2-carboxylic acid (1-cyano-cyclopropyl)-amide (37 mg, 69 umol; example 388 g) in DMF (500 ul) under an argon atmosphere. The reaction mixture was stirred for 72 h at ambient temperature and partitioned between ice water/brine 1/1 and iPrOAc. The layers were separated and the aqueous layer was extracted one more time with iPrOAc. The combined extracts were washed with ice water/brine 1/1, dried over sodium sulfate and filtered. The solvent was removed under reduced pressure to give a yellow foam which was purified by preparative chiral HPLC to give the title compound (6 mg, 10 umol; 14%) as colorless oil. MS (ESI): m/z=620.2 [M+H]$^+$.

Example 393

(2S,4R)-1-[1-Methyl-5-(tetrahydro-pyran-4-yl)-1H-pyrazol-3-yl]-4-(2-trifluoromethyl-benzenesulfonyl)-pyrrolidine-2-carboxylic acid (1-cyano-cyclopropyl)-amide

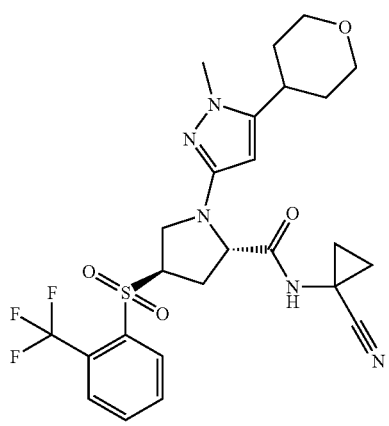

2,2-Dimethyl-5-(tetrahydro-pyran-4-carbonyl)-[1,3]dioxane-4,6-dione Pyridine (1.26 ml, 16 mmol) was added to an ice cold solution of 2,2-dimethyl-[1,3]dioxane-4,6-dione (750 mg, 5 mmol; CAS Reg. No. 2033-24-1) in dichloromethane (5.3 ml) under an argon atmosphere. Tetrahydro-pyran-4-carbonyl chloride (1 g, 7 mmol; CAS Reg. No. 40191-32-0) was added dropwise within 30 min keeping the temperature at 0° C. The mixture was stirred for 2 h at 0° C., 1 N aqueous HCl solution was carefully added until a pH of 1 was adjusted. Dichloromethane (25 ml) was added and the layers were separated. The aqueous layer was extracted two more times with dichlormethane (2×25 ml). The combined extracts were washed with brine, dried over sodium sulfate and filtered. The solvent was removed under reduced pressure to give the title compound (1.24 g, 5 mmol; 93%) as yellow oil which was sufficiently pure to be used in the next reaction step. MS (ESI): m/z=255.1 [M–H]$^-$.

b) 3-Oxo-3-(tetrahydro-pyran-4-yl)-propionic Acid Tert-butyl ester tert-Butanol (600 ul, 6 mmol) was added to a solution of 2,2-dimethyl-5-(tetrahydro-pyran-4-carbonyl)-[1,3]dioxane-4,6-dione (1.1 g, 4 mmol) in toluene (9.6 ml). The reaction mixture was heated under reflux conditions for 6 h and partitioned between ice water/brine 1/1 and iPrOAc. The layers were separated and the aqueous layer was extracted one more time with iPrOAc. The combined extracts were washed with ice water/brine 1/1, dried over sodium sulfate and filtered. The solvent was removed under reduced pressure to give the title compound (891 mg, 3.9 mmol; 91%) as brown oil which was sufficiently pure to be used in the next reaction step. MS (EI): m/z=228 [M]$^+$.

c) (2S,4R)-1-[3-oxo-3-(tetrahydro-pyran-4-yl)-propionyl]-4-(2-trifluoromethyl-benzenesulfonyl)-pyrrolidine-2-carboxylic acid methyl ester In analogy to the procedure described in example 192f, (2S,4R)-4-(2-trifluoromethyl-benzenesulfonyl)-pyrrolidine-2-carboxylic acid methyl ester (example 192e) was reacted with 3-oxo-3-(tetrahydro-pyran-4-yl)-propionic acid tert-butyl ester to give the title compound as yellow foam. MS (ESI): m/z=492.2 [M+H]$^+$.

d) (2S,4R)-1-[3-oxo-3-(tetrahydro-pyran-4-yl)-thio-propionyl]-4-(2-trifluoromethyl-benzenesulfonyl)-pyrrolidine-2-carboxylic acid methyl ester In analogy to the procedure described in example 192f, (2S,4R)-1-[3-oxo-3-(tetrahydro-pyran-4-yl)-propionyl]-4-(2-trifluoromethyl-benzenesulfonyl)-pyrrolidine-2-carboxylic acid methyl ester was reacted with Lawesson's reagent to give the title compound as yellow oil. MS (ESI): m/z=508.1 [M+H]$^+$.

e) (2S,4R)-1-[1-Methyl-5-(tetrahydro-pyran-4-yl)-1H-pyrazol-3-yl]-4-(2-trifluoromethyl-benzenesulfonyl)-pyrrolidine-2-carboxylic acid methyl ester In analogy to the procedure described in example 192 h, (2S,4R)-1-[3-oxo-3-(tetrahydro-pyran-4-yl)-thiopropionyl]-4-(2-trifluoromethyl-benzenesulfonyl)-pyrrolidine-2-carboxylic acid methyl ester was reacted with methylhydrazine (CAS Reg. No. 60-34-4) to give the title compound as colorless foam. MS (ESI): m/z=502.2 [M+H]$^+$.

f) (2S,4R)-1-[1-Methyl-5-(tetrahydro-pyran-4-yl)-1H-pyrazol-3-yl]-4-(2-trifluoromethyl-benzenesulfonyl)-pyrrolidine-2-carboxylic acid In analogy to the procedure described in example 253e, (2S,4R)-1-[1-methyl-5-(tetrahydro-pyran-4-yl)-1H-pyrazol-3-yl]-4-(2-trifluoromethyl-benzenesulfonyl)-pyrrolidine-2-carboxylic acid methyl ester was saponified in the presence of lithium hydroxide to give the title compound as yellow oil which was used in the next step without further purification. MS (ESI): m/z=488.3 [M+H]$^+$.

g) (2S,4R)-1-[1-Methyl-5-(tetrahydro-pyran-4-yl)-1H-pyrazol-3-yl]-4-(2-trifluoromethyl-benzenesulfonyl)-pyrrolidine-2-carboxylic acid (1-cyano-cyclopropyl)-amide In analogy to the procedure described in example 237, (2S,4R)-1-[1-methyl-5-(tetrahydro-pyran-4-yl)-1H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless foam. MS (ESI): m/z=552.2 [M+H]$^+$.

Example 394

(2S,4R)-1-(3-Chloro-4-fluoro-phenyl)-4-(2-trifluoromethyl-benzenesulfonyl)-pyrrolidine-2-carboxylic acid (1-cyano-cyclopropyl)-amide

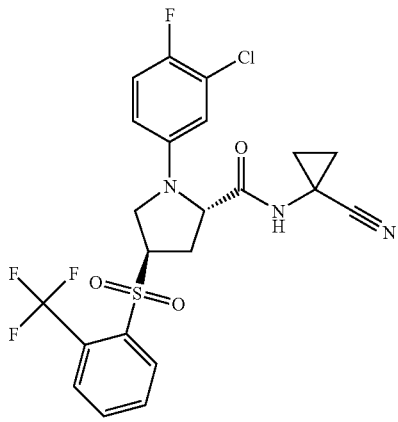

a) 1-(3-Chloro-4-fluoro-phenyl)-4-(2-trifluoromethyl-benzenesulfonyl)-pyrrolidine-2-carboxylic acid ethyl ester In analogy to the procedure described in example 343d, (3-chloro-4-fluoro-phenylamino)-acetic acid ethyl ester (CAS Reg. No. 2344-98-1) was reacted with paraformaldehyde and 1-ethenesulfonyl-2-trifluoromethyl-benzene (example 243c) to give the title compound as off-white solid.

b) 1-(3-Chloro-4-fluoro-phenyl)-4-(2-trifluoromethyl-benzenesulfonyl)-pyrrolidine-2-carboxylic acid In analogy to the procedure described in example 253e, 1-(3-chloro-4-fluoro-phenyl)-4-(2-trifluoromethyl-benzenesulfonyl)-pyrrolidine-2-carboxylic acid ethyl ester was saponified in the presence of lithium hydroxide to give the title compound as yellow solid which was used in the next step without further purification.

c) (2S,4R)-1-(3-Chloro-4-fluoro-phenyl)-4-(2-trifluoromethyl-benzenesulfonyl)-pyrrolidine-2-carboxylic acid (1-cyano-cyclopropyl)-amide In analogy to the procedure described in example 237, 1-(3-chloro-4-fluoro-phenyl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give 1-(3-chloro-4-fluoro-phenyl)-4-(2-trifluoromethyl-benzenesulfonyl)-pyrrolidine-2-carboxylic acid (1-cyano-cyclopropyl)-amide as mixture of stereoisomers which was purified by preparative chiral HPLC to obtain the title compound as white solid. MS (EI): m/z=515 [M]$^+$.

Example 395

(2R,4S)-1-(3-Chloro-4-fluoro-phenyl)-4-(2-trifluoromethyl-benzenesulfonyl)-pyrrolidine-2-carboxylic acid (1-cyano-cyclopropyl)-amide

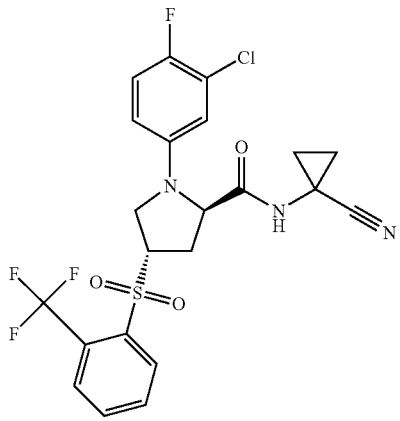

In analogy to the procedure described in example 237, 1-(3-chloro-4-fluoro-phenyl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give 1-(3-chloro-4-fluoro-phenyl)-4-(2-trifluoromethyl-benzenesulfonyl)-pyrrolidine-2-carboxylic acid (1-cyano-cyclopropyl)-amide as mixture of stereoisomers which was purified by preparative chiral HPLC to obtain the title compound as white solid. MS (ESI): m/z=516.1 [M+H]$^+$.

Example 396

(2S,4R)-4-(4-Fluoro-2-trifluoromethyl-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide

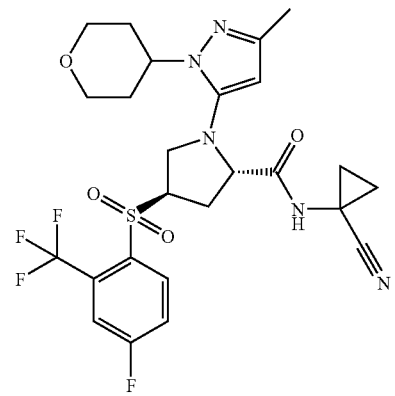

287 a) (2S,4R)-4-(4-fluoro-2-trifluoromethyl-benzene-sulfonyl)-1-[5-methyl-2-(tetrahydro-pyran-4-yl)-2H-pyrazol-3-yl]-pyrrolidine-2-carboxylic acid methyl ester In analogy to the procedure described in example 192 h, (2S,4R)-4-(4-fluoro-2-trifluoromethyl-benzenesulfonyl)-1-(3-oxo-thiobutyryl)-pyrrolidine-2-carboxylic acid methyl ester (example 388 d) was reacted with (tetrahydro-pyran-4-yl)-hydrazine hydrochloride (CAS Reg. No. 116312-69-7) to give the title compound as brown solid. MS (ESI): m/z=520.3 [M+H]$^+$.

b) (2S,4R)-4-(4-Fluoro-2-trifluoromethyl-benzene-sulfonyl)-1-[5-methyl-2-(tetrahydro-pyran-4-yl)-2H-pyrazol-3-yl]-pyrrolidine-2-carboxylic acid In analogy to the procedure described in example 253e, (2S,4R)-4-(4-fluoro-2-trifluoromethyl-benzenesulfonyl)-1-[5-methyl-2-(tetrahydro-pyran-4-yl)-2H-pyrazol-3-yl]-pyrrolidine-2-carboxylic acid methyl ester was saponified in the presence of lithium hydroxide avoiding methanol as a cosolvent to give the title compound as yellow foam which was used in the next step without further purification. MS (ESI): m/z=506.1 [M+H]$^+$.

c) (2S,4R)-4-(4-Fluoro-2-trifluoromethyl-benzene-sulfonyl)-1-[5-methyl-2-(tetrahydro-pyran-4-yl)-2H-pyrazol-3-yl]-pyrrolidine-2-carboxylic acid (1-cyano-cyclopropyl)-amide In analogy to the procedure described in example 237, (2S,4R)-4-(4-fluoro-2-trifluoromethyl-benzenesulfonyl)-1-[5-methyl-2-(tetrahydro-pyran-4-yl)-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as colorless foam. MS (ESI): m/z=570.3 [M+H]$^+$.

Example 397

(2S,4R)-1-[2-Cyclobutyl-5-(tetrahydro-pyran-4-yl)-2H-pyrazol-3-yl]-4-(2-trifluoromethyl-benzenesulfonyl)-pyrrolidine-2-carboxylic acid (1-cyano-cyclopropyl)-amide

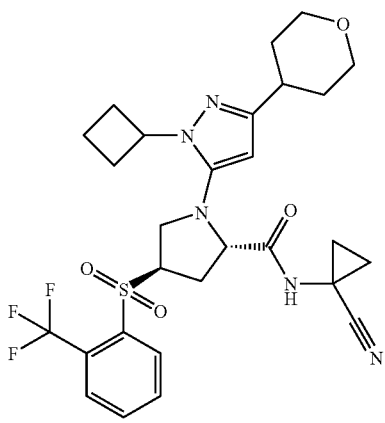

288 a) (2S,4R)-1-[2-Cyclobutyl-5-(tetrahydro-pyran-4-yl)-2H-pyrazol-3-yl]-4-(2-trifluoromethyl-benzene-sulfonyl)-pyrrolidine-2-carboxylic acid methyl ester In analogy to the procedure described in example 192 h, (2S,4R)-1-[3-oxo-3-(tetrahydro-pyran-4-yl)-thiopropionyl]-4-(2-trifluoromethyl-benzenesulfonyl)-pyrrolidine-2-carboxylic acid methyl ester (example 393d) was reacted with cyclobutylhydrazine hydrochloride (CAS Reg. No. 158001-21-9) to give the title compound as yellow oil. MS (ESI): m/z=542.4 [M+H]$^+$.

b) (2S,4R)-1-[2-Cyclobutyl-5-(tetrahydro-pyran-4-yl)-2H-pyrazol-3-yl]-4-(2-trifluoromethyl-benzene-sulfonyl)-pyrrolidine-2-carboxylic acid In analogy to the procedure described in example 253e, (2S,4R)-1-[2-cyclobutyl-5-(tetrahydro-pyran-4-yl)-2H-pyrazol-3-yl]-4-(2-trifluorom ethyl-benzenesulfonyl)-pyrrolidine-2-carboxylic acid methyl ester was saponified in the presence of lithium hydroxide to give the title compound as yellow oil which was used in the next step without further purification. MS (ESI): m/z=528.3 [M+H]$^+$.

c) (2S,4R)-1-[2-Cyclobutyl-5-(tetrahydro-pyran-4-yl)-2H-pyrazol-3-yl]-4-(2-trifluoromethyl-benzene-sulfonyl)-pyrrolidine-2-carboxylic acid (1-cyano-cyclopropyl)-amide In analogy to the procedure described in example 237, (2S,4R)-1-[2-cyclobutyl-5-(tetrahydro-pyran-4-yl)-2H-pyrazol-3-yl]-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless foam. MS (ESI): m/z=592.3 [M+H]$^+$.

Example 398

(2S,4R)-1-(2-Cyclobutyl-5-cyclopropyl-2H-pyrazol-3-yl)-4-(2-trifluoromethyl-benzenesulfonyl)-pyrrolidine-2-carboxylic acid (1-cyano-cyclopropyl)-amide

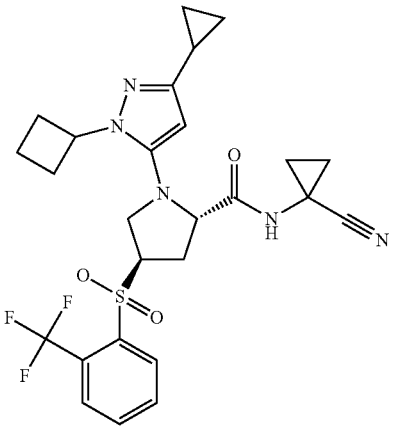

a) (2S,4R)-1-(3-Cyclopropyl-3-oxo-thiopropionyl)-4-(2-trifluoromethyl-benzenesulfonyl)-pyrrolidine-2-carboxylic acid methyl ester In analogy to the procedure described in example 192f, (2S,4R)-1-(3-cyclopropyl-3-oxo-propionyl)-4-(2-trifluoromethyl-benzenesulfonyl)-pyrrolidine-2-carboxylic acid methyl ester (example 363a) was reacted with Lawesson's reagent to give the title compound as brown oil. MS (ESI): m/z=364.1 [M+H]

b) (2S,4R)-1-(2-Cyclobutyl-5-cyclopropyl-2H-pyrazol-3-yl)-4-(2-trifluoromethyl-benzenesulfonyl)-pyrrolidine-2-carboxylic acid methyl ester In analogy to the procedure described in example 192 h, (2S,4R)-1-(3-cyclopropyl-3-oxo-thiopropionyl)-4-(2-trifluoromethyl-benzenesulfonyl)-pyrrolidine-2-carboxylic acid methyl ester was reacted with cyclobutylhydrazine hydrochloride (CAS Reg. No. 158001-21-9) to give the title compound as yellow foam.

c) (2S,4R)-1-(2-Cyclobutyl-5-cyclopropyl-2H-pyrazol-3-yl)-4-(2-trifluoromethyl-benzenesulfonyl)-pyrrolidine-2-carboxylic acid In analogy to the procedure described in example 253e, (2S,4R)-1-(2-cyclobutyl-5-cyclopropyl-2H-pyrazol-3-yl)-4-(2-trifluoromethyl-benzenesulfonyl)-pyrrolidine-2-carboxylic acid methyl ester was saponified in the presence of lithium hydroxide to give the title compound as yellow solid which was used in the next step without further purification.

d) (2S,4R)-1-(2-Cyclobutyl-5-cyclopropyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(2-cyclobutyl-5-cyclopropyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as yellow oil. MS (ESI): m/z=548.2 [M+H]⁺.

Example 399

(2S,4R)-4-(2-Chloro-benzenesulfonyl)-1-(5-trifluoromethyl-[1,3,4]thiadiazol-2-yl)-pyrrolidine-2-carboxylic acid (1-cyano-cyclopropyl)-amide)

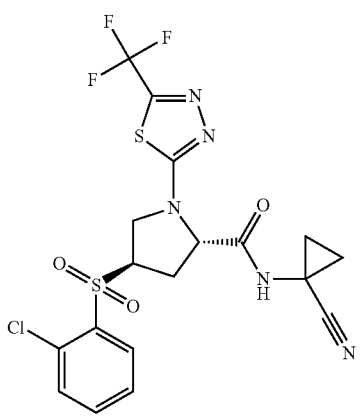

a) (2S,4R)-4-(2-Chloro-benzenesulfonyl)-1-(5-trifluoromethyl-[1,3,4]thiadiazol-2-yl)-pyrrolidine-2-carboxylic acid methyl ester In analogy to the procedure described in example 335a, (2S,4R)-4-(2-chloro-benzenesulfonyl)-pyrrolidine-2-carboxylic acid methyl ester (example 253a) was reacted with 2-chloro-5-trifluoromethyl-[1,3,4]thiadiazole (CAS Reg. No. 53645-98-0) in a shaking reactor at 55° C. for 12 h to give the title compound as orange oil. MS (ESI): m/z=456.0 [M+H]

b) (2S,4R)-4-(2-Chloro-benzenesulfonyl)-1-(5-trifluoromethyl-[1,3,4]thiadiazol-2-yl)-pyrrolidine-2-carboxylic acid In analogy to the procedure described in example 253e, (2S,4R)-4-(2-chloro-benzenesulfonyl)-1-(5-trifluoromethyl-[1,3,4]thiadiazol-2-yl)-pyrrolidine-2-carboxylic acid methyl ester was saponified in the presence of lithium hydroxide to give the title compound as yellow oil. MS (ESI): m/z=442.0 [M+H]⁺.

c) (2S,4R)-4-(2-Chloro-benzenesulfonyl)-1-(5-trifluoromethyl-[1,3,4]thiadiazol-2-yl)-pyrrolidine-2-carboxylic acid (1-cyano-cyclopropyl)-amide In analogy to the procedure described in example 237, (2S,4R)-4-(2-chloro-benzenesulfonyl)-1-(5-trifluoromethyl-[1,3,4]thiadiazol-2-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as colorless oil. MS (ESI): m/z=506.0 [M+H]⁺.

Example 400

(2S,4R)-1-(5-Cyclopropyl-2H-pyrazol-3-yl)-4-(2-trifluoromethyl-benzenesulfonyl)-pyrrolidine-2-carboxylic acid (1-cyano-cyclopropyl)-amide

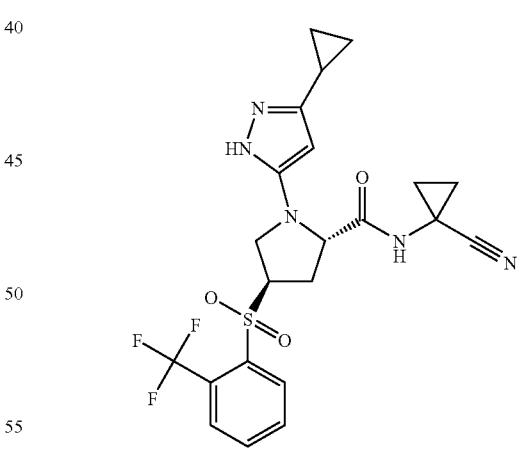

a) (2S,4R)-1-(5-Cyclopropyl-2H-pyrazol-3-yl)-4-(2-trifluoromethyl-benzenesulfonyl)-pyrrolidine-2-carboxylic acid methyl ester In analogy to the procedure described in example 192 h, (2S,4R)-1-(3-cyclopropyl-3-oxo-thiopropionyl)-4-(2-trifluoromethyl-benzenesulfonyl)-pyrrolidine-2-carboxylic acid methyl ester (example 398a) was reacted with hydrazine hydrochloride (CAS Reg. No. 2644-70-4) to give the title compound as brown oil.

b) (2S,4R)-1-(5-Cyclopropyl-2H-pyrazol-3-yl)-4-(2-trifluoromethyl-benzenesulfonyl)-pyrrolidine-2-carboxylic acid In analogy to the procedure described in example 253e, (2S,4R)-1-(5-cyclopropyl-2H-pyrazol-3-yl)-4-(2-trifluoromethyl-benzenesulfonyl)-pyrrolidine-2-carboxylic acid methyl ester was saponified in the presence of lithium hydroxide to give the title compound as brown solid which was used in the next step without further purification.

c) (2S,4R)-1-(5-Cyclopropyl-2H-pyrazol-3-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(5-cyclopropyl-2H-pyrazol-3-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as yellow solid. MS (ESI): m/z=494.2 [M+H]$^+$.

Example 401

(2S,4R)-4-[2-Chloro-4-(4-methyl-piperazin-1-yl)-benzenesulfonyl]-1-(2-cyclobutyl-5-methyl-2H-pyrazol-3-yl)-pyrrolidine-2-carboxylic acid (1-cyano-cyclopropyl)-amide

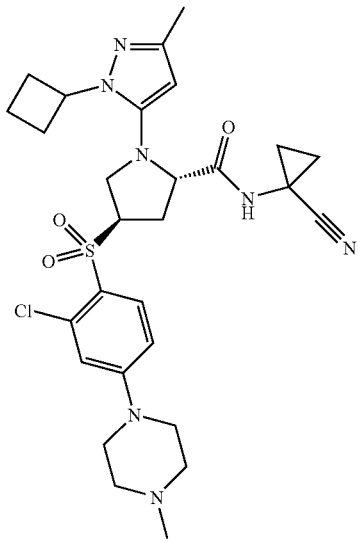

In analogy to the procedure described in example 389, (2S,4R)-4-(2-chloro-4-fluoro-benzenesulfonyl)-1-(2-cyclobutyl-5-methyl-2H-pyrazol-3-yl)-pyrrolidine-2-carboxylic acid (1-cyano-cyclopropyl)-amide (example 385b) was reacted with 1-methylpiperazine (CAS Reg. No. 109-01-3) to give the title compound as colorless foam. MS (ESI): m/z=586.1 [M+H]$^+$.

Example 402

(2S,4R)-1-(3-Methanesulfonyl-phenyl)-4-(2-trifluoromethyl-benzenesulfonyl)-pyrrolidine-2-carboxylic acid (1-cyano-cyclopropyl)-amide

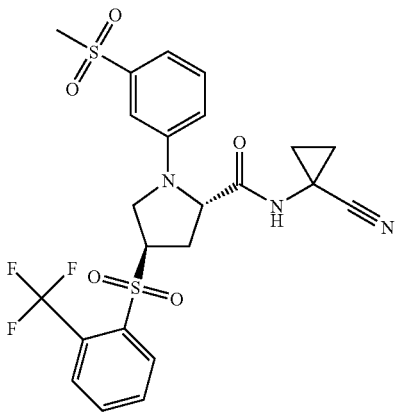

a) (3-Methanesulfonyl-phenylamino)-acetic Acid Ethyl Ester

A 0.5 M solution of ethyl glyoxalate in toluene (0.95 ml, 5 mmol; CAS Reg. No. 924-44-7) and acetic acid (0.4 ml) were added to an ice cold solution of 3-(methylsulfonyl)aniline (500 mg, 2 mmol; CAS Reg. No. 5470-49-5) in methanol (6.3 ml) under an argon atmosphere. Sodium cyanoborohydride (356 mg, 5 mmol) was added in 3 portions within 10 min. The reaction mixture was stirred for 45 min at 0° C. and then at ambient temperature over night. The reaction mixture was poured onto ice water (100 ml). iPrOAc (100 ml) was added and the layers were separated. The aqueous layer was extracted one more time with iPrOAc (100 ml). The combined extracts were washed two times with ice water/brine 1/1 and dried over sodium sulfate. After filtering the solvent was removed under reduced pressure to give the crude product as yellow foam which was purified by column chromatography (silica gel, iPrOAc/n-heptane) to obtain the title compound (350 mg, 1 mmol; 56%) as white solid. MS (ESI): m/z=258.2 [M+H]$^+$.

b) 1-(3-Methanesulfonyl-phenyl)-4-(2-trifluoromethyl-benzenesulfonyl)-pyrrolidine-2-carboxylic acid ethyl ester In analogy to the procedure described in example 343d, (3-methanesulfonyl-phenylamino)-acetic acid ethyl ester was reacted with paraformaldehyde and 1-ethenesulfonyl-2-trifluoromethyl-benzene (example 243c) to give the title compound as yellow oil. MS (ESI): m/z=506.1 [M+H]$^+$.

c) 1-(3-Methanesulfonyl-phenyl)-4-(2-trifluoromethyl-benzenesulfonyl)-pyrrolidine-2-carboxylic acid In analogy to the procedure described in example 253e, 1-(3-methanesulfonyl-phenyl)-4-(2-trifluoromethyl-benzenesulfonyl)-pyrrolidine-2-carboxylic acid ethyl ester was saponified in the presence of lithium hydroxide to give the title compound as white solid which was used in the next step without further purification. MS (ESI): m/z=476.1 [M–H]⁻.

d) (2S,4R)-1-(3-Methanesulfonyl-phenyl)-4-(2-trifluoromethyl-benzenesulfonyl)-pyrrolidine-2-carboxylic acid (1-cyano-cyclopropyl)-amide In analogy to the procedure described in example 237, 1-(3-methanesulfonyl-phenyl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give 1-(3-methanesulfonyl-phenyl)-4-(2-trifluoromethyl-benzenesulfonyl)-pyrrolidine-2-carboxylic acid (1-cyano-cyclopropyl)-amide as mixture of stereoisomers which was purified by preparative chiral HPLC to obtain the title compound as white solid. MS (ESI): m/z=542 [M+H]⁺.

Example 403

(2S,4R)-4-[4-(3,3-Difluoro-azetidin-1-yl)-2-trifluoromethyl-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide

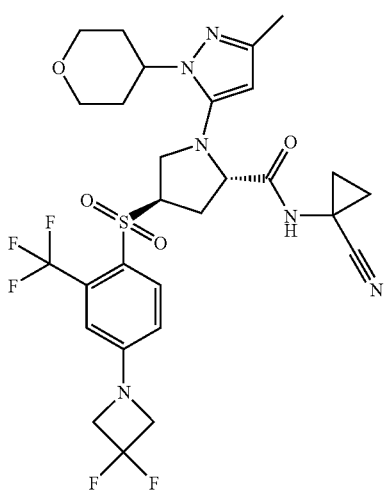

In analogy to the procedure described in example 389, (2S,4R)-4-(4-fluoro-2-trifluoromethyl-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide (example 396c) was reacted with 3,3-difluoroazetidine hydrochloride (CAS Reg. No. 288315-03-7) in acetonitrile at 55° C. for 48 h to give the title compound as colorless foam. MS (ESI): m/z=643.3 [M+H]⁺.

Example 404

(2S,4R)-4-[4-(4-Methyl-piperazin-1-yl)-2-trifluoromethyl-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide

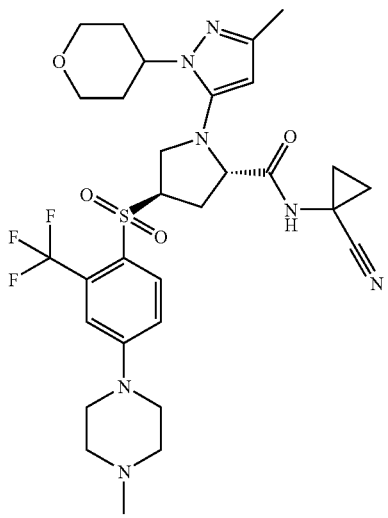

In analogy to the procedure described in example 389, (2S,4R)-4-(4-fluoro-2-trifluoromethyl-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide (example 396c) was reacted with 1-methylpiperazine (CAS Reg. No. 109-01-3) to give the title compound as colorless foam. MS (ESI): m/z=650.4 [M+H]⁺.

Example 405

(2S,4R)-1-(3-Chloro-[1,2,4]thiadiazol-5-yl)-4-(2-trifluoromethyl-benzenesulfonyl)-pyrrolidine-2-carboxylic acid (1-cyano-cyclopropyl)-amide

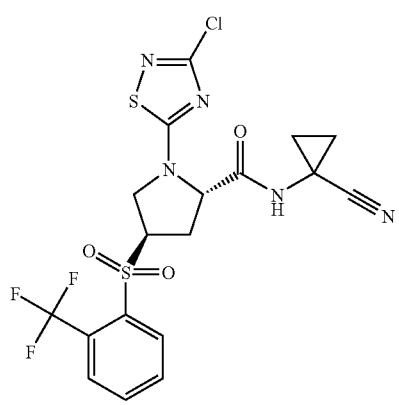

a) (2S,4R)-1-(3-Chloro-[1,2,4]thiadiazol-5-yl)-4-(2-trifluoromethyl-benzenesulfonyl)-pyrrolidine-2-carboxylic acid methyl ester In analogy to the procedure described in example 335a, (2S,4R)-4-(2-trifluoromethyl-benzenesulfonyl)-pyrrolidine-2-carboxylic acid methyl ester (prepared as described for the corresponding (2S,4S)-4-(2-trifluoromethyl-benzenesulfonyl)-pyrrolidine-2-carboxylic acid ethyl ester in example 192e) was reacted with 3,5-dichloro-[1,2,4]thiadiazole (CAS Reg. No. 2254-88-8) in a shaking reactor at 55° C. for 12 h to give the title compound as orange solid. MS (ESI): m/z=456.2 [M+H]$^+$.

b) (2S,4R)-1-(3-Chloro-[1,2,4]thiadiazol-5-yl)-4-(2-trifluoromethyl-benzenesulfonyl)-pyrrolidine-2-carboxylic acid In analogy to the procedure described in example 253e, (2S,4R)-1-(3-chloro-[1,2,4]thiadiazol-5-yl)-4-(2-trifluoromethyl-benzenesulfonyl)-pyrrolidine-2-carboxylic acid methyl ester was saponified in the presence of lithium hydroxide to give the title compound as brown solid. MS (ESI): m/z=442.1 [M+H]$^+$.

c) (2S,4R)-1-(3-Chloro-[1,2,4]thiadiazol-5-yl)-4-(2-trifluoromethyl-benzenesulfonyl)-pyrrolidine-2-carboxylic acid (1-cyano-cyclopropyl)-amide In analogy to the procedure described in example 237, (2S,4R)-1-(3-chloro-[1,2,4]thiadiazol-5-yl)-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as yellow foam. MS (ESI): m/z=506.0 [M+H]$^+$.

Example 406

4-{5-[(2S,4R)-2-(1-Cyano-cyclopropylcarbamoyl)-4-(2-trifluoromethyl-benzenesulfonyl)-pyrrolidin-1-yl]-3-methyl-pyrazol-1-yl}-piperidine-1-carboxylic acid Benzyl Ester

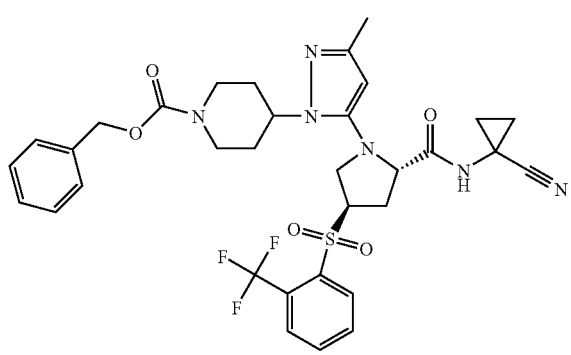

a) 4-{5-[(2S,4R)-2-Methoxycarbonyl-4-(2-trifluoromethyl-benzenesulfonyl)-pyrrolidin-1-yl]-3-methyl-pyrazol-1-yl}-piperidine-1-carboxylic acid Benzyl Ester In analogy to the procedure described in example 308d, (2S,4R)-1-(3-oxo-butyryl)-4-(2-trifluoromethyl-benzenesulfonyl)-pyrrolidine-2-carboxylic acid methyl ester (example 192f) was reacted with Lawesson's reagent (CAS Reg. No. 19172-47-5) and 4-hydrazino-piperidine-1-carboxylic acid benzyl ester (CAS Reg. No. 280111-51-5) to give the title compound as yellow oil.

b) 4-{5-[(2S,4R)-2-Carboxy-4-(2-trifluoromethyl-benzenesulfonyl)-pyrrolidin-1-yl]-3-methyl-pyrazol-1-yl}-piperidine-1-carboxylic acid Benzyl Ester In analogy to the procedure described in example 253e, 4-{5-[(2S,4R)-2-methoxycarbonyl-4-(2-trifluoromethyl-benzenesulfonyl)-pyrrolidin-1-yl]-3-methyl-pyrazol-1-yl}-piperidine-1-carboxylic acid benzyl ester was saponified in the presence of lithium hydroxide to give the title compound as yellow solid. MS (ESI): m/z=619.4 [M–H]$^-$.

c) 4-{5-[(2S,4R)-2-(1-Cyano-cyclopropylcarbamoyl)-4-(2-trifluoromethyl-benzenesulfonyl)-pyrrolidin-1-yl]-3-methyl-pyrazol-1-yl}-piperidine-1-carboxylic acid benzyl ester In analogy to the procedure described in example 237, 4-{5-[(2S,4R)-2-carboxy-4-(2-trifluoromethyl-benzenesulfonyl)-pyrrolidin-1-yl]-3-methyl-pyrazol-1-yl}-piperidine-1-carboxylic acid benzyl ester was reacted with 1-amino-cyclopropanecarbonitrile hydrochloride (CAS Reg. No. 127946-77-4) in the presence of HATU and DIEA to give the title compound as yellow gum. MS (ESI): m/z=685.2 [M+H]$^+$.

Example 407

(2S,4R)-1-(5-Methyl-2-piperidin-4-yl-2H-pyrazol-3-yl)-4-(2-trifluoromethyl-benzenesulfonyl)-pyrrolidine-2-carboxylic acid (1-cyano-cyclopropyl)-amide

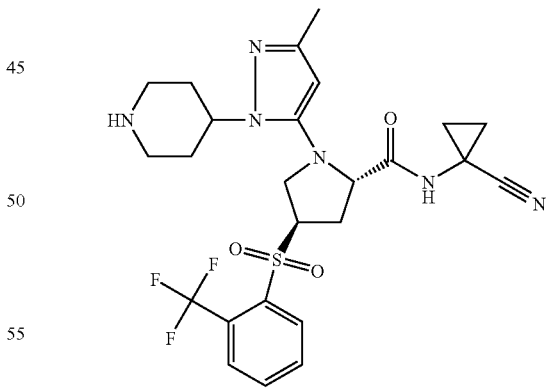

Palladium on charcoal 10% (5 mg) was added to a solution of 4-{5-[(2S,4R)-2-(1-cyano-cyclopropylcarbamoyl)-4-(2-trifluoromethyl-benzenesulfonyl)-pyrrolidin-1-yl]-3-methyl-pyrazol-1-yl}-piperidine-1-carboxylic acid benzyl ester (12 mg, 18 umol; example 406c) in ethanol (1 ml). The reaction mixture was put under an hydrogen atmosphere and stirred at ambient temperature for 12 h. After filtration over dicalite the filtrate was brought to dryness to give the title compound (4.4 mg, 8 umol; 46%) as white solid. MS (ESI): m/z=551 [M+H]⁺.

Example 408

(2S,4R)-1-Pyrimidin-2-yl-4-(2-trifluoromethyl-benzenesulfonyl)-pyrrolidine-2-carboxylic acid (1-cyano-cyclopropyl)-amide

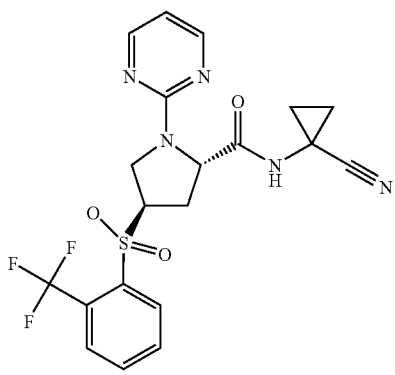

(2S,4R)-1-Pyrimidin-2-yl-4-(2-trifluoromethyl-benzenesulfonyl)-pyrrolidine-2-carboxylic acid methyl ester In analogy to the procedure described in example 335a, (2S,4R)-4-(2-trifluoromethyl-benzenesulfonyl)-pyrrolidine-2-carboxylic acid methyl ester (prepared as described for the corresponding (2S,4S)-4-(2-trifluoromethyl-benzenesulfonyl)-pyrrolidine-2-carboxylic acid ethyl ester in example 192e) was reacted with 2-chloro-pyrimidine (CAS Reg. No. 1722-12-9) in a shaking reactor at 150° C. for 48 h to give the title compound as yellow oil. MS (ESI): m/z=416.1 [M+H]⁺.

(2S,4R)-1-Pyrimidin-2-yl-4-(2-trifluoromethyl-benzenesulfonyl)-pyrrolidine-2-carboxylic acid In analogy to the procedure described in example 253e, (2S,4R)-1-pyrimidin-2-yl-4-(2-trifluoromethyl-benzenesulfonyl)-pyrrolidine-2-carboxylic acid methyl ester was saponified in the presence of lithium hydroxide to give the title compound as white solid. MS (ESI): m/z=402.1 [M+H]⁺.

c) (2S,4R)-1-Pyrimidin-2-yl-4-(2-trifluoromethyl-benzenesulfonyl)-pyrrolidine-2-carboxylic acid (1-cyano-cyclopropyl)-amide In analogy to the procedure described in example 237, (2S,4R)-1-pyrimidin-2-yl-4-(2-trifluoromethyl-benzenesulfonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as yellow oil. MS (ESI): m/z=466.2 [M+H]⁺.

Example 409

(2S,4R)-1-[1-(4-Chloro-phenyl)-cyclopropanecarbonyl]-4-methanesulfonyl-pyrrolidine-2-carboxylic acid (1-cyano-cyclopropyl)-amide

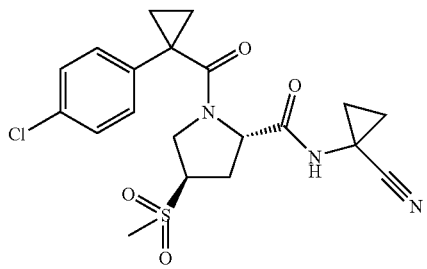

a) (2S,4R)-4-Mercapto-pyrrolidine-1,2-dicarboxylic acid 1-tert-butyl ester 2-methyl ester To a solution of (2S,4R)-4-acetylsulfanyl-pyrrolidine-1,2-dicarboxylic acid 1-tert-butyl ester 2-methyl ester (12.5 g, 41 mmol; CAS Reg. No. 188111-18-4) in MeOH (200 ml) and dichloromethane (20 ml) was added potassium carbonate (5.7 g, 41.2 mmol) at 0° C. The resulting mixture was stirred at 0° C. for 1 h. After the starting material was consumed the solvent was evaporated. The residue was dissolved in water and extracted with EtOAc (2×200 ml). The combined organic layers were washed with brine, dried over anhydrous sodium sulfate and evaporated to get the crude title compound (9.5 g, 36.1 mmol; 88%) which was used in next step without further purification. MS (ESI): m/z=262.0 [M+H]⁺.

b) (2S,4R)-4-Methylsulfanyl-pyrrolidine-1,2-dicarboxylic acid 1-tert-butyl ester 2-methyl Ester To a solution of (2S,4R)-4-mercapto-pyrrolidine-1,2-dicarboxylic acid 1-tert-butyl ester 2-methyl ester (9.5 g, 35.4 mmol) in MeOH (300 ml) were added methyl iodide (24 ml, 363.5 mmol) and NaHCO₃ (3.4 g, 39.98 mmol). The reaction mixture was stirred for 12 h at 25° C. After complete consumption of the starting material, the solvent was removed under reduced pressure to get the crude material that was purified by column chromatography over silica gel (25-40% EtOAc/hexane) to obtain the title compound as white solid (6.9 g, 24.4 mmol; 69%). MS (ESI): m/z=276.4 [M+H]⁺.

c) (2S,4R)-4-Methanesulfonyl-pyrrolidine-1,2-dicarboxylic acid 1-tert-butyl ester 2-methyl ester To a solution of (2S,4R)-4-methylsulfanyl-pyrrolidine-1,2-dicarboxylic acid 1-tert-butyl ester 2-methyl ester (6.6 g, 23.96 mmol) in dichloromethane at 0° C. was added MCPBA (20.7 g, 119.8 mmol) and the mixture was stirred for 16 h at 25° C. The suspension was filtered; the filtrate was poured onto ice/aqueous Na₂CO₃ solution. The organic layer was separated, and the aqueous layer was extracted with dichloromethane (2×150 ml). The combined organic layers were washed with aqueous Na₂CO₃ solution and brine, dried over anhydrous sodium sulfate and evaporated to get the crude material (9.7 g) that was purified by column chromatography over silica gel (25-50% EtOAc/hexane) to obtain the title compound as white solid (6.9 g, 22.4 mmol; 94%). MS (ESI): m/z=308.2 [M+H]⁺.

d) (2S,4R)-4-Methanesulfonyl-pyrrolidine-1,2-dicarboxylic acid 1-Tert-butyl ester In analogy to the procedure described in example 253e, (2S,4R)-4-methanesulfonyl-pyrrolidine-1,2-dicarboxylic acid 1-tert-butyl ester 2-methyl ester was saponified in the presence of lithium hydroxide to give the title compound as yellow solid. MS (ESI): m/z=294.2 [M+H]$^+$.

e) (2S,4R)-2-(1-Cyano-cyclopropylcarbamoyl)-4-methanesulfonyl-pyrrolidine-1-carboxylic acid tert-butyl ester In analogy to the procedure described in example 237, (2S,4R)-4-methanesulfonyl-pyrrolidine-1,2-dicarboxylic acid 1-tert-butyl ester was reacted with 1-amino-cyclopropanecarbonitrile hydrochloride (CAS Reg. No. 127946-77-4) in the presence of HATU and DIEA to give the title compound as white solid. MS (ESI): m/z=358.4 [M+H]$^+$.

f) (2S,4R)-4-Methanesulfonyl-pyrrolidine-2-carboxylic acid (1-cyano-cyclopropyl)-amide Trifluoroacetate To a solution of (2S,4R)-2-(1-cyano-cyclopropylcarbamoyl)-4-methanesulfonyl-pyrrolidine-1-carboxylic acid tert-butyl ester (500 mg, 1.39 mmol) in dichloromethane was added trifluoroacetic acid (0.5 ml, 6.99 mmol) at 0° C. The resulting mixture was stirred at 25° C. for 16 h. After complete consumption of starting material, the reaction mixture was evaporated in vacuo to get the crude title compound (500 mg, 1.39 mmol; quant.) which was used in next step without further purification. MS: m/z=258.0 [M+H]$^+$.

g) (2S,4R)-1-[1-(4-Chloro-phenyl)-cyclopropanecarbonyl]-4-methanesulfonyl-pyrrolidine-2-carboxylic acid (1-cyano-cyclopropyl)-amide In analogy to the procedure described in example 237, (2S,4R)-4-methanesulfonyl-pyrrolidine-2-carboxylic acid (1-cyano-cyclopropyl)-amide trifluoroacetate was reacted with 1-(4-chloro-phenyl)-cyclopropanecarboxylic acid (CAS Reg. No. 72934-37-3) in the presence of HATU and DIEA to give the title compound as white solid. MS (ESI): m/z=436.2 [M+H]$^+$.

Example 410

(2S,4R)-4-(2-Chloro-benzenesulfonyl)-1-(6-chloro-1H-indazole-3-carbonyl)-pyrrolidine-2-carboxylic acid (1-cyano-cyclopropyl)-amide

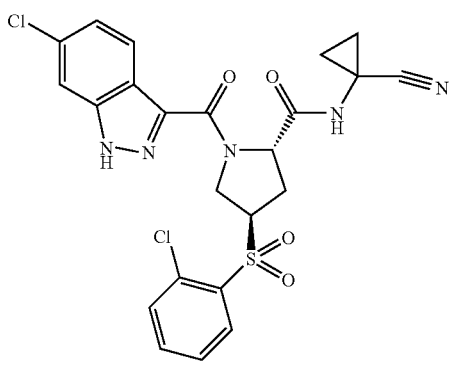

The title compound was prepared in analogy to example 215 to yield 26 mg (17%) of colorless amorphous material. MS (ESI): m/z=M+H 532.1 [M+H]$^+$.

Example 411

(2S,4R)-4-(2-Chloro-benzenesulfonyl)-1-[(R)-2-(4-chloro-phenyl)-2-hydroxy-acetyl]-pyrrolidine-2-carboxylic acid (1-cyano-cyclopropyl)-amide

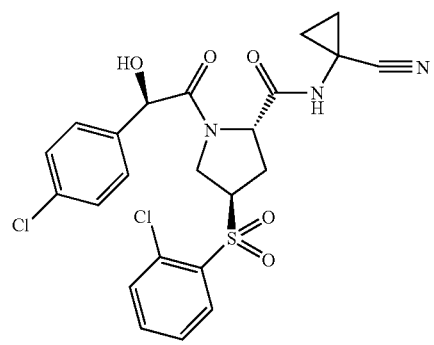

The title compound was prepared in analogy to example 215 using example 42 as a free base (100 mg) as starting material to yield 85 mg (57.6%) of colorless amorphous material. MS (ESI): m/z=M+H 522.1 [M+H]$^+$.

Example 412

[(R)-2-[(2S,4R)-4-(2-Chloro-benzenesulfonyl)-2-(1-cyano-cyclopropylcarbamoyl)-pyrrolidin-1-yl]-1-(4-chloro-phenyl)-2-oxo-ethyl]-carbamic Acid Tert-butyl ester

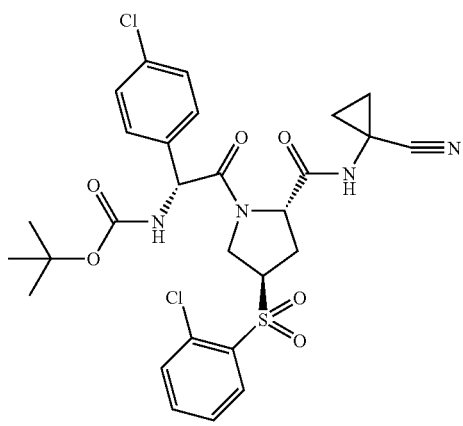

The title compound was prepared in analogy to example 215 using example 42 as a free base (150 mg) as starting material to yield 91 mg (52%) of colorless amorphous material. MS (ESI): m/z=M+H 521.1 (M-Boc), M+H 621.3472.1 [M+H]$^+$.

Example 413

(2S,4R)-4-(2-Chloro-benzenesulfonyl)-1-[1-(4-methyl-thiazol-2-yl)-cyclopropanecarbonyl]-pyrrolidine-2-carboxylic acid (1-cyano-cyclopropyl)-amide

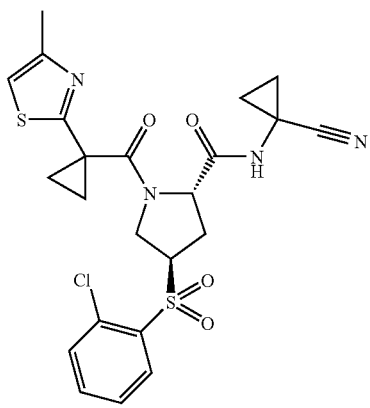

s) Synthesis of 1-(4-methyl-thiazol-2-yl)-cyclopropanecarboxylic acid ethyl ester Ethyl 2-(4-methylthiazol-2-yl)acetate (1 g, 5.4 mmol, Eq: 1.00) was dissolved in DMF (5 mL). 1,2-dibromoethane (1.62 g, 744 μL, 8.64 mmol, Eq: 1.60) and $Cs_2CO_3$ (4.4 g, 13.5 mmol, Eq: 2.50) were added. The reaction mixture was stirred 48 h at RT. The reaction mixture was poured into 0.5 M aqueous HCl (100 mL) and extracted with EtOAc (3×50 mL). The combined organic layers were dried over $Na_2SO_4$, filtered and evaporated. The crude material was purified by flash chromatography (silica gel, 50 g, 0% to 50% EtOAc in heptane) to yield 1.14 g (73.6%) of a light yellow liquid. MS (ESI): m/z=212.0 $[M+H]^+$.

b) Synthesis of 1-(4-methyl-thiazol-2-yl)-cyclopropanecarboxylic acid

Example 413a) (840 mg, 3.98 mmol, Eq: 1.00) was dissolved in THF (5 mL) and Water (7.5 mL). Now LiOH (162 mg, 6.76 mmol, Eq: 1.7) was added and the reaction mixture was stirred 3 h at RT. The reaction mixture was extracted with 10% aqueous $Na_2CO_3$— solution/$CH_2Cl_2$, 0.5N HCl-solution aq./$CH_2Cl_2$. The organic layers were dried over $Na_2SO_4$, filtered and concentrated in vacuo to yield 650 mg (89%) of a white solid. MS (ESI): m/z=181.8 $[M-H]^-$.

c) Synthesis of the Title Compound (2S,4R)-4-(2-Chloro-benzenesulfonyl)-1-[1-(4-methyl-thiazol-2-yl)-cyclopropanecarbonyl]-pyrrolidine-2-carboxylic acid (1-cyano-cyclopropyl)-amide The title compound was prepared in analogy to example 215 using example 42 as a free base (100 mg) as starting material to yield 69 mg (47%) of an oil. MS (ESI): m/z=519.1 $[M+H]^+$.

Example 414

(2S,4R)-4-(2-Chloro-benzenesulfonyl)-1-[2-(5-chloro-pyrimidin-2-yl)-acetyl]-pyrrolidine-2-carboxylic acid (1-cyano-cyclopropyl)-amide

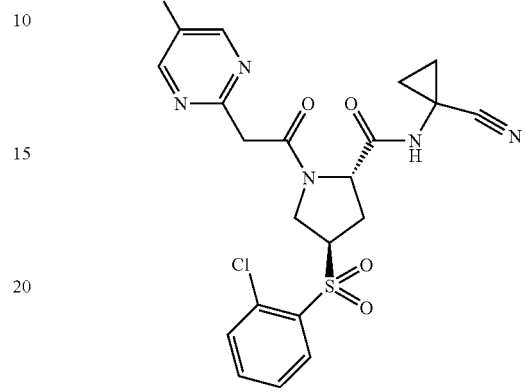

The title compound was prepared in analogy to example 215 using example 42 as a free base (100 mg) as starting material to yield 89 mg (62%) of off-white foam. MS (ESI): m/z=508.0 $[M+H]^+$.

Example 415

(2S,4R)-1-(2-Cyclobutyl-5-methyl-2H-pyrazol-3-yl)-4-[4-(3,3-difluoro-azetidin-1-yl)-2-trifluoromethyl-benzenesulfonyl]-pyrrolidine-2-carboxylic acid (1-cyano-cyclopropyl)-amide

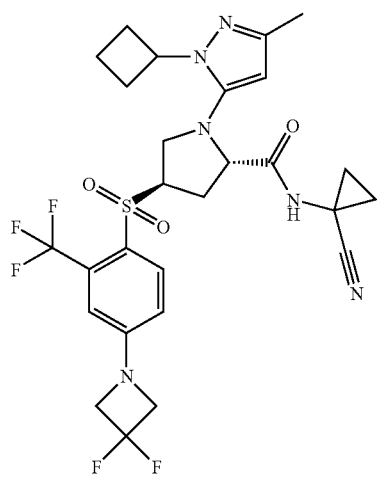

In analogy to the procedure described in example 389, (2S,4R)-1-(2-cyclobutyl-5-methyl-2H-pyrazol-3-yl)-4-(4-fluoro-2-trifluoromethyl-benzenesulfonyl)-pyrrolidine-2-carboxylic acid (1-cyano-cyclopropyl)-amide (example 388 g) was reacted with 3,3-difluoroazetidine hydrochloride (CAS Reg. No. 288315-03-7) in acetonitrile at 90° C. for 48 h to give the title compound as colorless oil. MS (ESI): m/z=613.1 $[M+H]^+$.

Example 416

(2S,4R)-1-(2-Cyclobutyl-5-methyl-2H-pyrazol-3-yl)-4-(4-pyrazol-1-yl-2-trifluoromethyl-benzenesulfonyl)-pyrrolidine-2-carboxylic acid (1-cyano-cyclopropyl)-amide

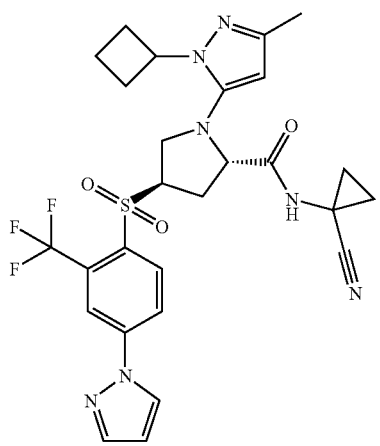

Pyrazole (5 mg, 67 umol; CAS Reg. No. 288-11-9) and cesium carbonate (18 mg, 56 umol) were added to a solution of (2S,4R)-1-(2-cyclobutyl-5-methyl-2H-pyrazol-3-yl)-4-(4-fluoro-2-trifluoromethyl-benzenesulfonyl)-pyrrolidine-2-carboxylic acid (1-cyano-cyclopropyl)-amide (30 mg, 56 umol; example 388 g) in DMA (0.9 ml) under an argon atmosphere. The mixture was heated for 48 h to 90° C. and for additional 4 h to 120° C. in a shaking reactor. Ice water/brine 1/1 and iPrOAc were added and the layers were separated. The aqueous layer was extracted one more time with iPrOAc. The combined extracts were washed with ice water/brine 1/1, dried over sodium sulfate and filtered. The solvent was removed under reduced pressure to give a brown oil which was purified by preparative HPLC to give the title compound (6.5 mg, 11 umol; 20%) as colorless oil. MS (ESI): m/z=588.4 [M+H]$^+$.

Example 417

(2S,4R)-1-[(R)-2-Amino-2-(4-chloro-phenyl)-acetyl]-4-(2-chloro-benzenesulfonyl)-pyrrolidine-2-carboxylic acid (1-cyano-cyclopropyl)-amide

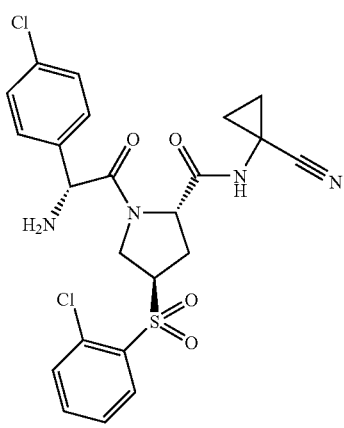

Example 412 (80 mg, 129 μmol, Eq: 1.00) was dissolved in formic acid (1.8 g, 1.5 mL, 39.1 mmol, Eq: 304) and stirred at 25° C. for 4 h. The reaction mixture was adjusted carefully with ice-cold aqueous 10% Na$_2$CO$_3$-solution to pH=8 and extracted with CH$_2$Cl$_2$. The water layer was washed totally 3 times with CH$_2$Cl$_2$, the combined organic layers were dried over Na$_2$SO$_4$, filtered and evaporated to yield the title compound (53 mg; 79%) as a light yellow foam. MS (ESI): m/z=521.1 [M+H]$^+$.

Example 418

(2S,4R)-4-(2-Chloro-benzenesulfonyl)-1-[2-(4-chloro-benzyl)-5-methyl-2H-pyrazol-3-yl]-pyrrolidine-2-carboxylic acid (1-cyano-cyclopropyl)-amide

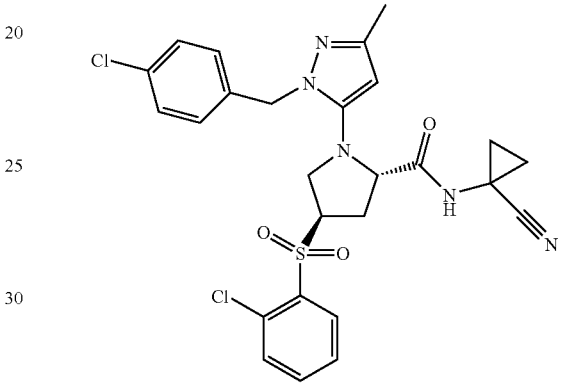

(2S,4R)-4-(2-Chloro-benzenesulfonyl)-1-[2-(4-chloro-benzyl)-5-methyl-2H-pyrazol-3-yl]-pyrrolidine-2-carboxylic acid methyl ester In analogy to the procedure described in example 192 h, (2S,4R)-4-(2-chloro-benzenesulfonyl)-1-(3-oxo-thiobutyryl)-pyrrolidine-2-carboxylic acid methyl ester (example 253c) was reacted with (4-chloro-benzyl)-hydrazine (CAS Reg. No. 25198-45-2) to give the title compound as orange oil. MS (ESI): m/z=508.0 [M+H]$^+$.

(2S,4R)-4-(2-Chloro-benzenesulfonyl)-1-[2-(4-chloro-benzyl)-5-methyl-2H-pyrazol-3-yl]-pyrrolidine-2-carboxylic acid In analogy to the procedure described in example 253e, (2S,4R)-4-(2-chloro-benzenesulfonyl)-1-[2-(4-chloro-benzyl)-5-methyl-2H-pyrazol-3-yl]-pyrrolidine-2-carboxylic acid methyl ester was saponified in the presence of lithium hydroxide to give the title compound as off-white solid which was used in the next step without further purification. MS (ESI): m/z=494.1 [M+H]$^+$.

(2S,4R)-4-(2-Chloro-benzenesulfonyl)-1-[2-(4-chloro-benzyl)-5-methyl-2H-pyrazol-3-yl]-pyrrolidine-2-carboxylic acid (1-cyano-cyclopropyl)-amide In analogy to the procedure described in example 237, (2S,4R)-4-(2-chloro-benzenesulfonyl)-1-[2-(4-chloro-benzyl)-5-methyl-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound after purification by preparative HPLC as yellow oil. MS (ESI): m/z=558.1 [M+H]⁺.

Example 419

(2S,4R)-1-(2-Cyclobutyl-5-methyl-2H-pyrazol-3-yl)-4-(4-pyrimidin-4-yl-2-trifluoromethyl-benzenesulfonyl)-pyrrolidine-2-carboxylic acid (1-cyano-cyclopropyl)-amide

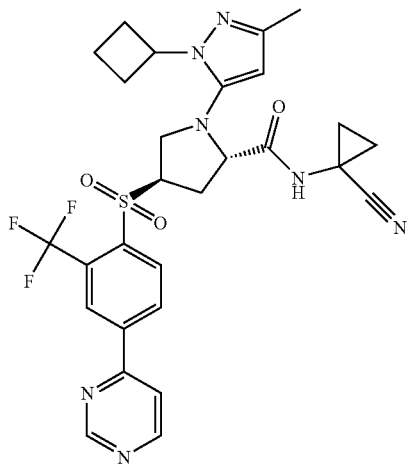

(2S,4R)-4-(4-Bromo-2-trifluoromethyl-benzenesulfonyl)-1-(3-oxo-butyryl)-pyrrolidine-2-carboxylic acid methyl ester In analogy to the procedure described in example 192f, (2S,4R)-4-(4-bromo-2-trifluoromethyl-benzenesulfonyl)-pyrrolidine-2-carboxylic acid methyl ester (example 18) was reacted with tert-butyl acetoacetate to give the title compound as brown oil.

(2S,4R)-4-(4-Bromo-2-trifluoromethyl-benzenesulfonyl)-1-(2-cyclobutyl-5-methyl-2H-pyrazol-3-yl)-pyrrolidine-2-carboxylic acid methyl ester In analogy to the procedure described in example 308d, (2S,4R)-4-(4-bromo-2-trifluoromethyl-benzenesulfonyl)-1-(3-oxo-butyryl)-pyrrolidine-2-carboxylic acid methyl ester was reacted with Lawesson's reagent (CAS Reg. No. 19172-47-5) and cyclobutylhydrazine hydrochloride (CAS Reg. No. 158001-21-9) to give the title compound as brown oil. MS (ESI): m/z=549.8 [M+H]⁺.

(2S,4R)-4-(4-Bromo-2-trifluoromethyl-benzenesulfonyl)-1-(2-cyclobutyl-5-methyl-2H-pyrazol-3-yl)-pyrrolidine-2-carboxylic acid In analogy to the procedure described in example 253e, (2S,4R)-4-(4-bromo-2-trifluoromethyl-benzenesulfonyl)-1-(2-cyclobutyl-5-methyl-2H-pyrazol-3-yl)-pyrrolidine-2-carboxylic acid methyl ester was saponified in the presence of lithium hydroxide to give the title compound brown solid which was used in the next step without further purification. MS (ESI): m/z=538.1 [M+H]⁺.

d) (2S,4R)-4-(4-Bromo-2-(trifluoromethyl)phenylsulfonyl)-N-(1-cyanocyclopropyl)-1-(1-cyclobutyl-3-methyl-1H-pyrazol-5-yl)pyrrolidine-2-carboxamide In analogy to the procedure described in example 237, (2S,4R)-4-(4-bromo-2-trifluoromethyl-benzenesulfonyl)-1-(2-cyclobutyl-5-methyl-2H-pyrazol-3-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as brown foam. MS (ESI): m/z=602.1 [M+H]⁺.

e) 4-((3R,5S)-5-(1-Cyanocyclopropylcarbamoyl)-1-(1-cyclobutyl-3-methyl-1H-pyrazol-5-yl)pyrrolidin-3-ylsulfonyl)-3-(trifluoromethyl)phenylboronic Acid A solution of (2S,4R)-4-(4-bromo-2-(trifluoromethyl)phenylsulfonyl)-N-(1-cyanocyclopropyl)-1-(1-cyclobutyl-3-methyl-1H-pyrazol-5-yl)pyrrolidine-2-carboxamide (40 mg, 66.6 umol), 4,4,4',4',5,5,5',5'-octamethyl-2,2'-bi(1,3,2-dioxaborolane) (33.8 mg, 133 umol; CAS Reg. No. 73183-34-3), [1,1'-bis(diphenylphosphino)ferrocene]palladium(II) chloride 1:1 complex with dichloromethane (10.9 mg, 13.3 umol) and potassium acetate (32.7 mg, 333 umol) in DMSO (0.8 ml) was heated to 80° C. for 20 h. The reaction mixture was cooled to ambient temperature and poured onto 20 ml 0.1 N HCl/ice/brine and extracted with iPrOAc (2×25 ml). The combined organic layers were washed with 0.1 N HCl/ice/brine (3×), icewater/brine (3×), dried over sodium sulfate and filtered. The solvent was evaporated under reduced pressure to give the crude title compound (66 mg; quant.) which was used in the next reaction step without further purification. MS (ESI): m/z=566.2 [M+H]⁺.

f) (2S,4R)-1-(2-Cyclobutyl-5-methyl-2H-pyrazol-3-yl)-4-(4-pyrimidin-4-yl-2-trifluoromethyl-benzenesulfonyl)-pyrrolidine-2-carboxylic acid (1-cyano-cyclopropyl)-amide

[1,1'-bis(Diphenylphosphino)ferrocene]palladium(II) chloride 1:1 complex with dichloromethan (6.23 mg, 7.62 umol) was added to a solution of 4-((3R,5S)-5-(1-cyanocyclopropylcarbamoyl)-1-(1-cyclobutyl-3-methyl-1H-pyrazol-5-yl)pyrrolidin-3-ylsulfonyl)-3-(trifluoromethyl)phenylboronic acid (43.1 mg, 76.2 umol), 4-bromopyrimidine (15.3 mg, 91.5 umol; CAS Reg. No. 31462-56-3) and sodium carbonate (21.8 mg, 206 umol) in DMF (1.5 ml) and water (125 ul) under an argon atmosphere. The reaction mixture was stirred at 80° C. for 1.75 hours, cooled to ambient temperature, poured onto 100 ml saturated sodium hydrogen carbonate solution/ice and extracted with iPrOAc (2×25 ml). The combined organic layers were washed with icewater/brine 1/1 (2×), dried over sodium sulfate and filtered. The solvent was removed under reduced pressure to give a dark oil (50 mg) which was purified by preparative HPLC (MeCN/water) to give the title compound (16 mg, 27 umol; 35%) as yellow foam. MS (ESI): m/z=600.3 [M+H]⁺.

Example 420

(2S,4R)—N-(1-cyanocyclopropyl)-1-(1-cyclobutyl-3-methyl-1H-pyrazol-5-yl)-4-(4-(1-methyl-1H-pyrazol-5-yl)-2-(trifluoromethyl)phenylsulfonyl)pyrrolidine-2-carboxamide

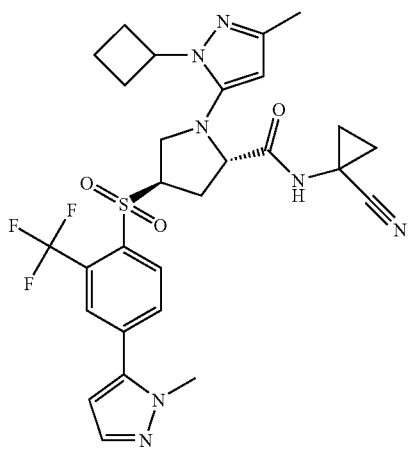

[1,1'-bis(Diphenylphosphino)ferrocene]palladium(II) chloride 1:1 complex with dichloromethan (5.44 mg, 6.66 umol) was added to a solution of (2S,4R)-4-(4-bromo-2-(trifluoromethyl)phenylsulfonyl)-N-(1-cyanocyclopropyl)-1-(1-cyclobutyl-3-methyl-1H-pyrazol-5-yl)pyrrolidine-2-carboxamide (40 mg, 66.6 umol; example 419d), 1-methyl-5-(4,4,5,5-tetramethyl-1,3,2-dioxaborolan-2-yl)-1H-pyrazole (16.6 mg, 79.9 umol, CAS Reg. No. 847818-74-0) and sodium carbonate (19.1 mg, 180 umol) in DMF (2 ml) and water (109 ul) under an argon atmosphere. The mixture was stirred at 80° C. for 3.5 hours, cooled to ambient temperature, poured onto saturated sodium hydrogen carbonate solution (20 ml)/ice (20 ml) and extracted with iPrOAc (2×25 ml). The combined organic layers were washed with ice water/brine (2×), dried over sodium sulfate and filtered. The solvent was removed in vacuo to give a dark oil (48 mg) which was purified by preparative HPLC (MeCN/water) to give the title compound (24 mg, 30 umol; 45%) as light brown oil. MS (ESI): m/z=602.2 [M+H]$^+$.

Example 421

(R)-4-(2-Chloro-benzenesulfonyl)-1-[2-(4-chloro-phenyl)-2-(2,2,2-trifluoro-ethylamino)-acetyl]-pyrrolidine-2-carboxylic acid (1-cyano-cyclopropyl)-amide

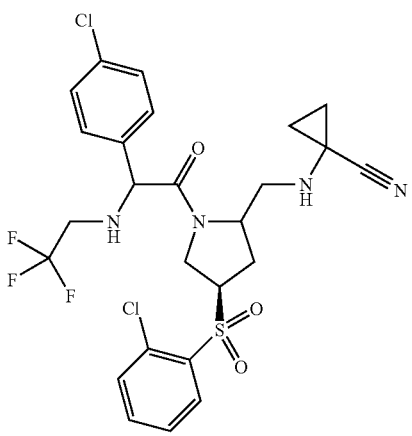

Example 417 (44 mg, 84.4 µmol, Eq: 1.00) was dissolved in THF (1 mL). Diisopropyl amine (9.39 mg, 13.2 µl, 92.8 µmol, Eq: 1.1) and 2,2,2-trifluoroethyl trifluoromethansulfonate (21.5 mg, 13.4 µL, 92.8 µmol, Eq: 1.1) were added. The reaction mixture was stirred at 25° C. for 48 h. The crude material was purified by preparative HPLC, to yield 8 mg (16%) of a white foam. MS (ESI): m/z=603.1 [M+H]$^+$.

Example 422

(2S,4R)-4-(2-Chloro-benzenesulfonyl)-1-[2-(3-trifluoromethyl-pyrazol-1-yl)-acetyl]-pyrrolidine-2-carboxylic acid (1-cyano-cyclopropyl)-amide

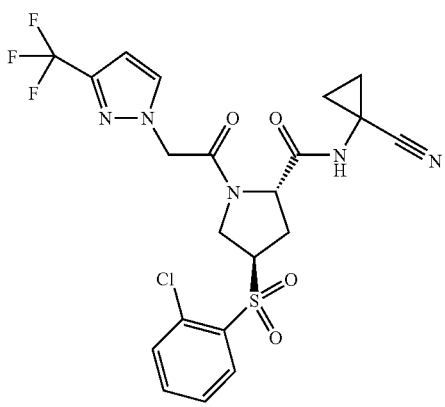

The title compound was prepared in analogy to example 215 using example 42 as a free base (100 mg) as starting material to yield 111 mg (74%) of a light brown foam. MS (ESI): m/z=530.1 [M+H]$^+$.

Example 423

(2S,4R)-4-Cyclopropylmethanesulfonyl-1-(1-trifluoromethyl-cyclopropanecarbonyl)-pyrrolidine-2-carboxylic acid (1-cyano-cyclopropyl)-amide

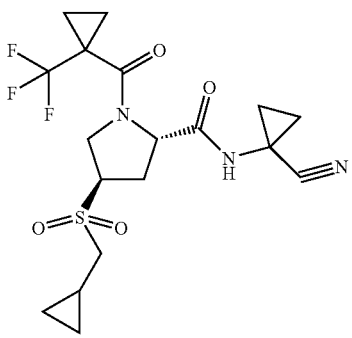

(2S,4R)-4-Cyclopropylmethylsulfanyl-pyrrolidine-1,2-dicarboxylic acid 1-tert-butyl ester 2-methyl ester In analogy to the procedure described in example 409b, (2S,4R)-4-mercapto-pyrrolidine-1,2-dicarboxylic acid 1-tert-butyl ester 2-methyl ester (example 409a) was reacted with cyclopropylmethyl bromide (CAS Reg. No. 7051-34-5) to give the title compound as colorless liquid. MS (ESI): m/z=316.2 [M+H]$^+$.

(2S,4R)-4-Cyclopropylmethanesulfonyl-pyrrolidine-1,2-dicarboxylic acid 1-tert-butyl Ester 2-methyl ester In analogy to the procedure described in example 409c, (2S,4R)-4-cyclopropylmethylsulfanyl-pyrrolidine-1,2-dicarboxylic acid 1-tert-butyl ester 2-methyl ester was oxidized with MCPBA to give the title compound as white solid.

(2S,4R)-4-Cyclopropylmethanesulfonyl-pyrrolidine-1,2-dicarboxylic acid 1-tert-butyl Ester In analogy to the procedure described in example 253e, (2S,4R)-4-cyclopropylmethanesulfonyl-pyrrolidine-1,2-dicarboxylic acid 1-tert-butyl ester 2-methyl ester was saponified in the presence of lithium hydroxide to give the title compound as white solid. MS (ESI): m/z=333.6 [M+H]+.

d) (2S,4R)-2-(1-cyano-cyclopropylcarbamoyl)-4-cyclopropylmethanesulfonyl-pyrrolidine-1-carboxylic acid tert-butyl ester In analogy to the procedure described in example 237, (2S,4R)-4-cyclopropylmethanesulfonyl-pyrrolidine-1,2-dicarboxylic acid 1-tert-butyl ester was reacted with 1-aminocyclopropanecarbonitrile hydrochloride (CAS Reg. No. 127946-77-4) in the presence of HATU and DIEA to give the title compound. MS (ESI): m/z=399.6 [M+H]+.

e) (2S,4R)-4-Cyclopropylmethanesulfonyl-pyrrolidine-2-carboxylic acid (1-cyano-cyclopropyl)-amide Trifluoroacetate In analogy to the procedure described in example 409f, (2S,4R)-2-(1-cyano-cyclopropylcarbamoyl)-4-cyclopropylmethanesulfonyl-pyrrolidine-1-carboxylic acid tert-butyl ester was treated with trifluoroacetic acid in dichloromethane to give the title compound which was used in next step without further purification. MS: m/z=299.2 [M+H]+.

f) (2S,4R)-4-Cyclopropylmethanesulfonyl-1-(1-trifluoromethyl-cyclopropanecarbonyl)-pyrrolidine-2-carboxylic acid (1-cyano-cyclopropyl)-amide In analogy to the procedure described in example 237, (2S,4R)-4-cyclopropylmethanesulfonyl-pyrrolidine-2-carboxylic acid (1-cyano-cyclopropyl)-amide trifluoroacetate was reacted with 1-trifluoromethyl-cyclopropanecarboxylic acid (CAS Reg. No. 277756-46-4) in the presence of HATU and DIEA to give the title compound as yellow solid. MS (ESI): m/z=434.6 [M+H]+.

Example 424

(2S,4R)-1-[1-(4-Chloro-phenyl)-cyclopropanecarbonyl]-4-cyclopropylmethanesulfonyl-pyrrolidine-2-carboxylic acid (1-cyano-cyclopropyl)-amide

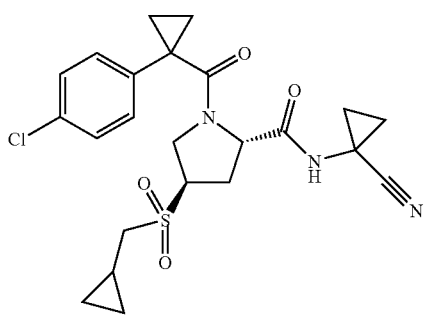

In analogy to the procedure described in example 237, (2S,4R)-4-cyclopropylmethanesulfonyl-pyrrolidine-2-carboxylic acid (1-cyano-cyclopropyl)-amide trifluoroacetate (example 423e) was reacted with 1-(4-chloro-phenyl)-cyclopropanecarboxylic acid (CAS Reg. No. 72934-37-3) in the presence of HATU and DIEA to give the title compound as white solid. MS (ESI): m/z=476.0 [M+H]+.

Example 425

(2S,4R)-4-(2-chlorophenylsulfonyl)-N-(1-cyanocyclopropyl)-1-(1-(4-fluorophenyl)-cyclopropanecarbonyl)pyrrolidine-2-carboxamide

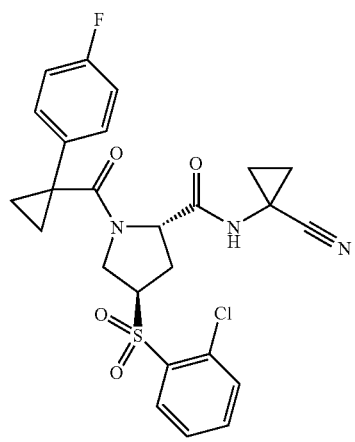

The title compound was prepared in analogy to example 215 using example 42 as a free base (100 mg) as starting material to yield 141 mg (97%) of a white solid. MS (ESI): m/z=512.3 [M+H]+.

Example 426

(2S,4R)-1-(1-(4-bromophenyl)cyclopropanecarbonyl)-4-(2-chlorophenylsulfonyl)-N-(1-cyanocyclopropyl)pyrrolidine-2-carboxamide

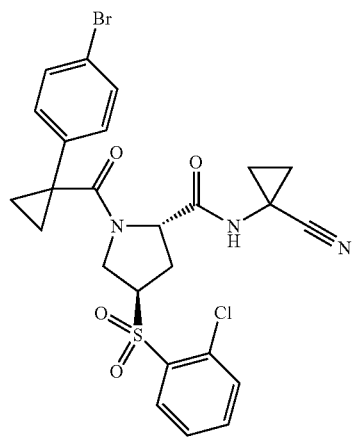

The title compound was prepared in analogy to example 425 to yield 91 mg (56%) of a white foam. MS (ESI): m/z=578.0 [M+H]+.

Example 427

(2S,4R)-4-(2-chlorophenylsulfonyl)-N-(1-cyanocyclopropyl)-1-(1-(4-(trifluoromethyl)phenyl)cyclopropanecarbonyl)pyrrolidine-2-carboxamide

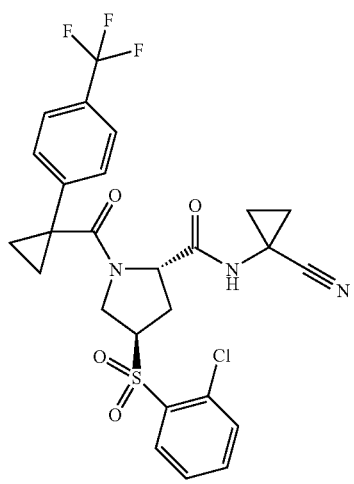

The title compound was prepared in analogy to example 425 to yield 127 mg (79%) of a light yellow solid. MS (ESI): m/z=566.2 [M+H]+.

Example 428

(2S,4R)-1-(1-(3-chlorophenyl)cyclopropanecarbonyl)-4-(2-chlorophenylsulfonyl)-N-(1-cyanocyclopropyl)pyrrolidine-2-carboxamide

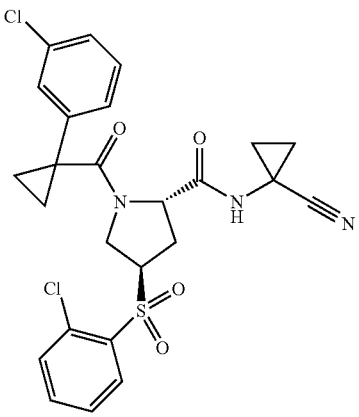

The title compound was prepared in analogy to example 425 to yield 113 mg (75%) of a light yellow solid. MS (ESI): m/z=532.1 [M+H]+.

Example 429

(2S,4R)-4-(2-chlorophenylsulfonyl)-N-(1-cyanocyclopropyl)-1-(1-(3-(trifluoromethyl)phenyl)cyclopropanecarbonyl)pyrrolidine-2-carboxamide

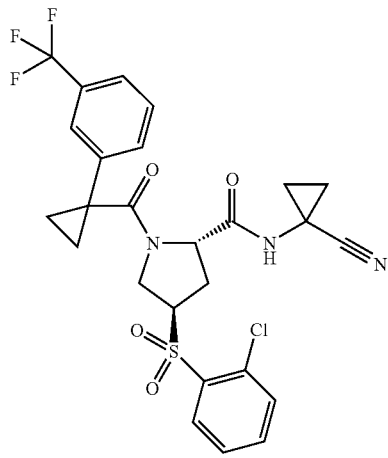

The title compound was prepared in analogy to example 425 to yield 148 mg (92%) of a light yellow solid. MS (ESI): m/z=566.2 [M+H]+.

Example 430

(2S,4R)-1-(2-(4-chlorophenyl)propanoyl)-4-(2-chlorophenylsulfonyl)-N-(1-cyanocyclopropyl)pyrrolidine-2-carboxamide [EPIMERS 1:12]

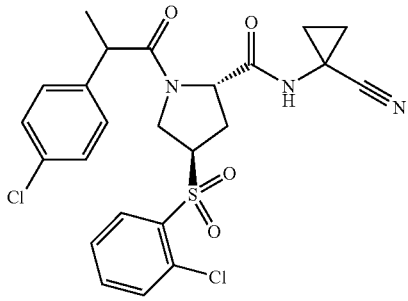

The title compound was prepared in analogy to example 425 to yield 15 mg (10.2%) of a white solid. MS (ESI): m/z=522.2 [M+H]+.

Example 431

(2S,4R)-1-(2-(4-chlorophenyl)propanoyl)-4-(2-chlorophenylsulfonyl)-N-(1-cyanocyclopropynnyrrolidine-2-carboxamide [EPIMERS 4:1]

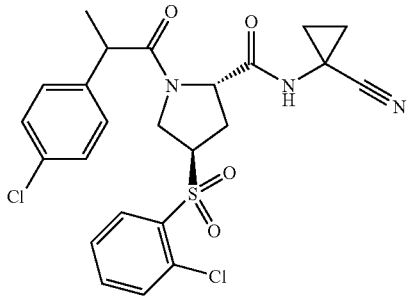

The title compound was prepared in analogy to example 425 to yield 72 mg (49%) of a white solid. MS (ESI): m/z=522.2 [M+H]+.

Example 432

(2S,4R)-1-(2-(4-chlorophenyl)-3-methylbutanoyl)-4-(2-chlorophenylsulfonyl)-N-(1-cyanocyclopropyl)pyrrolidine-2-carboxamide [EPIMERS 1:1]

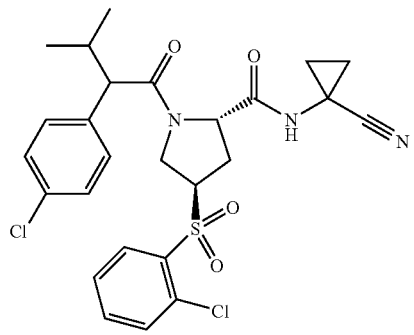

The title compound was prepared in analogy to example 425 to yield 100 mg (64.4%) of a light yellow solid. MS (ESI): m/z=548.2 [M+H]+.

Example 433 tert-butyl 4-(4-chlorophenyl)-4-((2S,4R)-4-(2-chlorophenylsulfonyl)-2-(1-cyanocyclopropylcarbamoyl)pyrrolidine-1-carbonyl)piperidine-1-carboxylate

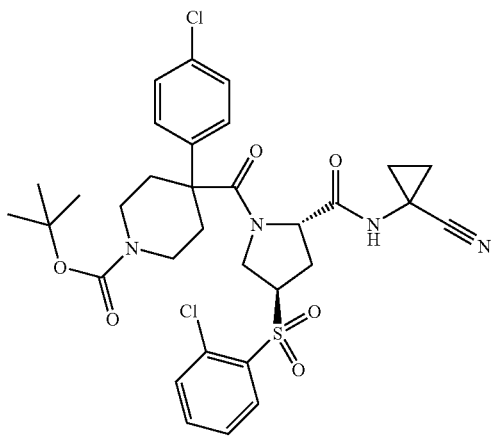

The title compound was prepared in analogy to example 425 to yield 21 mg (11%) of an off-white solid. MS (ESI): m/z=619.2 [M+H]+.

Example 434

(2S,4R)-4-(2-Chloro-benzenesulfonyl)-1-[2-(4-chloro-phenyl)-2-morpholin-4-yl-acetyl]-pyrrolidine-2-carboxylic acid (1-cyano-cyclopropyl)-amide [EPIMERS 4:3]

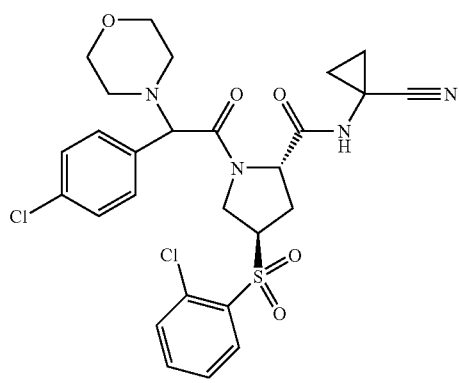

The title compound was prepared in analogy to example 425 to yield 16 mg (10%) of an off-white solid. MS (ESI): m/z=591.1 [M+H]+.

Example 435

(2S,4R)-4-(2-Chloro-benzenesulfonyl)-1-[2-(4-chloro-phenyl)-2-morpholin-4-yl-acetyl]-pyrrolidine-2-carboxylic acid (1-cyano-cyclopropyl)-amide [EPIMERS 1:2]

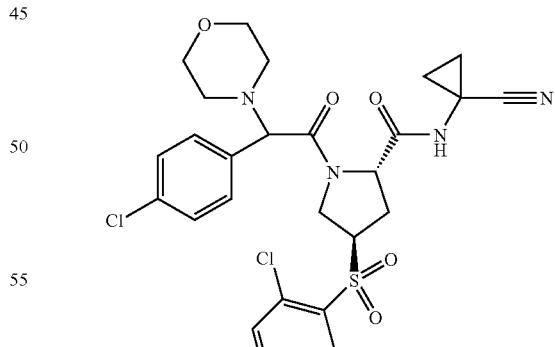

The title compound was prepared in analogy to example 425 to yield 75 mg (45%) of an off-white solid. MS (ESI): m/z=591.1 [M+H]+.

Example 436

(2S,4R)-4-(2-Chloro-benzenesulfonyl)-1-[2-(4-chloro-phenyl)-2-morpholin-4-yl-acetyl]-pyrrolidine-2-carboxylic acid (1-cyano-cyclopropyl)-amide [1 EPIMER]

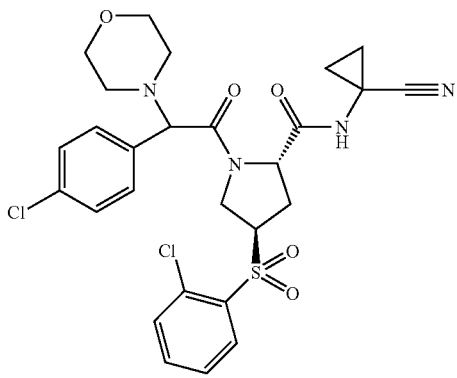

The title compound was prepared in analogy to example 425 to yield 41 mg (25%) of an off-white solid. MS (ESI): m/z=591.1 [M+H]$^+$.

Example 437

(2S,4R)-4-(2-Chloro-benzenesulfonyl)-1-[2-(3,4-dichloro-phenyl)-2,2-difluoro-acetyl]-pyrrolidine-2-carboxylic acid (1-cyano-cyclopropyl)-amide

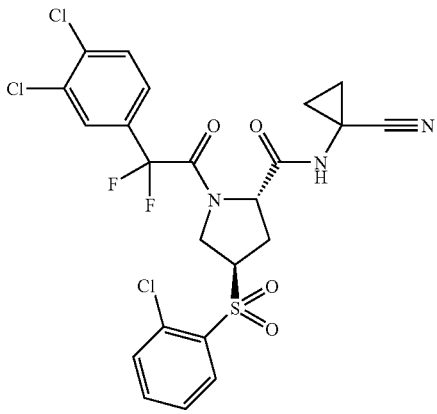

The title compound was prepared in analogy to example 425 to yield 98 mg (60%) of an off-white solid. MS (ESI): m/z=576.0 [M+H]$^+$.

Example 438

(2S,4R)-4-(2-chlorophenylsulfonyl)-N-(1-cyanocyclopropyl)-1-(1-p-tolylcyclopropane-carbonyl)pyrrolidine-2-carboxamide

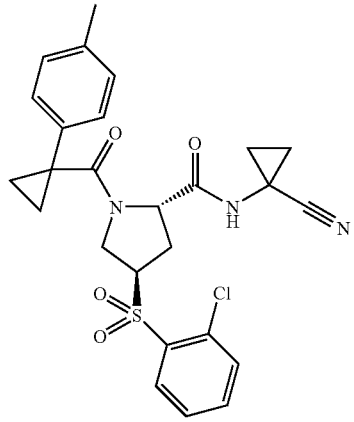

The title compound was prepared in analogy to example 425 to yield 141 mg (97%) of a white solid. MS (ESI): m/z=512.3 [M+H]$^+$.

Example 439

(2S,4R)-1-(1-(4-chloro-2-fluorophenyl)cyclopropanecarbonyl)-4-(2-chlorophenylsulfonyl)-N-(1-cyanocyclopropyl)pyrrolidine-2-carboxamide

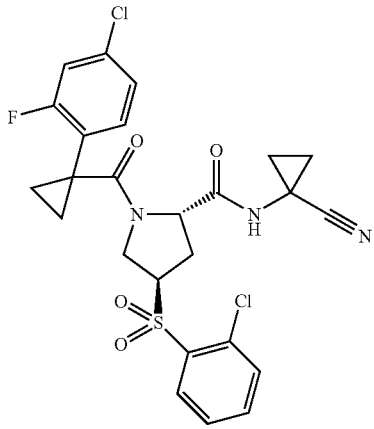

The title compound was prepared in analogy to example 425 to yield 92 mg (59%) of an off-white solid. MS (ESI): m/z=550.2 [M+H]$^+$.

Example 440

(2S,4R)-4-Methanesulfonyl-1-(1-trifluoromethyl-cyclopropanecarbonyl)-pyrrolidine-2-carboxylic acid (1-cyano-cyclopropyl)-amide

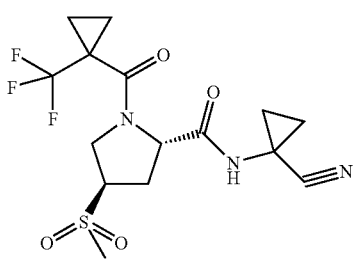

In analogy to the procedure described in example 237, (2S,4R)-4-methanesulfonyl-pyrrolidine-2-carboxylic acid (1-cyano-cyclopropyl)-amide trifluoroacetate (example 409f) was reacted with 1-trifluoromethyl-cyclopropanecarboxylic acid (CAS Reg. No. 277756-46-4) in the presence of HATU and DIEA to give the title compound as off-white solid. MS (ESI): m/z=394.2 [M+H]+.

Example 441

(2S,4R,5S)-5-(4-tert-butylphenyl)-N-(1-cyanocyclopropyl)-4-(phenylsulfonyl)-2-(2-(phenylsulfonyl)ethyl)pyrrolidine-2-carboxamide

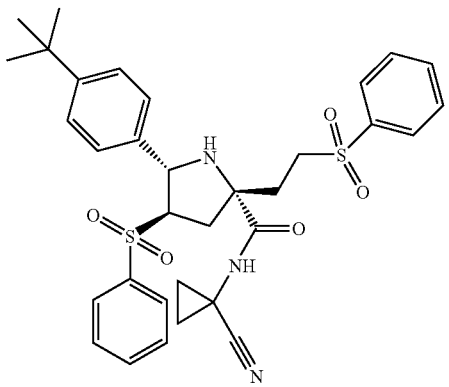

a) (E)-Ethyl 2-(4-tert-butylbenzylideneamino)acetate

To a suspension of gylcine ethylester hydrochloride (2.4 g, 17 mmol; CAS Reg. No. 623-33-6) and magnesium sulfate dihydrate (4.8 g) in dichloromethane (25 ml) was added triethylamine (2.4 ml). The mixture was stirred at ambient temperature for 1 h, then tert-butylbenzaldehyde (2.5 g, 15.4 mmol; CAS Reg. No. 939-97-9) was added and the reaction mixture was stirred at ambient temperature for 18 h. The mixture was washed with water (2×100 ml) and brine (100 ml). The aqueous layer was extracted with dichloromethane (200 ml). The combined extracts were dried over magnesium sulfate and filtered. The solvent was removed under reduced pressure to give the title compound (3.41 g, 15.3 mmol; 90%) as yellow liquid which was sufficiently pure to be used in the next reaction step. MS (ESI): m/z=248.3 [M+H]

b) 4-Benzenesulfonyl-2-(2-benzenesulfonyl-ethyl)-5-(4-tert-butyl-phenyl)-pyrrolidine-2-carboxylic acid ethyl ester To a stirred solution of (E)-ethyl 2-(4-tert-butylbenzylideneamino)acetate (226 mg, 914 umol) in THF (5 ml) under an argon atmosphere were added lithium bromide (119 mg, 1.37 mmol), triethylamine (191 ul, 1.37 mmol) and phenyl vinyl sulfone (154 mg, 914 umol; CAS Reg. No. 5535-48-8). The mixture was stirred at ambient temperature for 20 h. iPrOAc (50 ml) and ice water (40 ml) were added and the layers were separated. The organic layer was washed with brine (40 ml), dried over sodium sulfate and filtered. The solvent was removed under reduced pressure to give a yellow oil which was purified by column chromatography (silica gel, iPrOAc/n-heptane) to obtain the title compound (37 mg, 64 umol; 7%) as colorless oil. MS (ESI): m/z=584.2 [M+H]+.

c) 4-Benzenesulfonyl-2-(2-benzenesulfonyl-ethyl)-5-(4-tert-butyl-phenyl)-pyrrolidine-2-carboxylic acid In analogy to the procedure described in example 253e, 4-benzenesulfonyl-2-(2-benzenesulfonyl-ethyl)-5-(4-tert-butyl-phenyl)-pyrrolidine-2-carboxylic acid ethyl ester was saponified in the presence of lithium hydroxide to give the title compound as yellow solid which was used in the next step without further purification. MS (ESI): m/z=556.2 [M+H]+.

d) (2S,4R,5S)-5-(4-tert-butylphenyl)-N-(1-cyanocyclopropyl)-4-(phenylsulfonyl)-2-(2-(phenylsulfonyl)ethyl)pyrrolidine-2-carboxamide In analogy to the procedure described in example 237, 4-benzenesulfonyl-2-(2-benzenesulfonyl-ethyl)-5-(4-tert-butyl-phenyl)-pyrrolidine-2-carboxylic acid was reacted with 1-amino-cyclopropanecarbonitrile hydrochloride (CAS Reg. No. 127946-77-4) in the presence of HATU and DIEA to give a mixture of the title compound and its enantiomer after purification by preparative HPLC as yellow oil. MS (ESI): m/z=620.2 [M+H]+.

Example 442

(2S,4R)-4-(2-Chloro-benzenesulfonyl)-1-[2-(4-chloro-phenyl)-2,2-difluoro-acetyl]-pyrrolidine-2-carboxylic acid (1-cyano-cyclopropyl)-amide

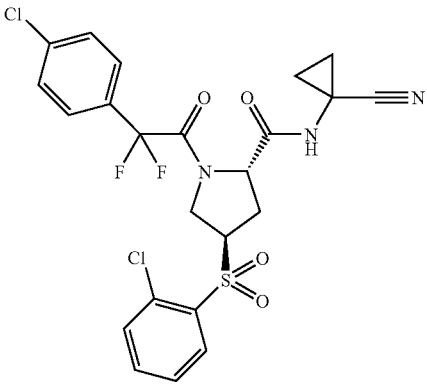

The title compound was prepared in analogy to example 425 to yield 84 mg (55%) of white foam. MS (ESI): m/z=540.2 [M−H]−.

Example 443

(2S,4R)-4-(2-Chloro-benzenesulfonyl)-1-[1-(2,4-dichloro-phenyl)-cyclopropanecarbonyl]-pyrrolidine-2-carboxylic acid (1-cyano-cyclopropyl)-amide

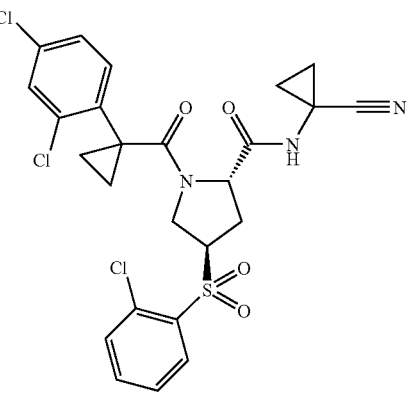

The title compound was prepared in analogy to example 425 to yield 36 mg (23%) of an off-white solid. MS (ESI): m/z=566.0 [M−H]⁻.

Example 444

(2S,4R)-4-(2-Chloro-benzenesulfonyl)-1-[2-(4-chloro-3-fluoro-phenyl)-acetyl]-pyrrolidine-2-carboxylic acid (1-cyano-cyclopropyl)-amide

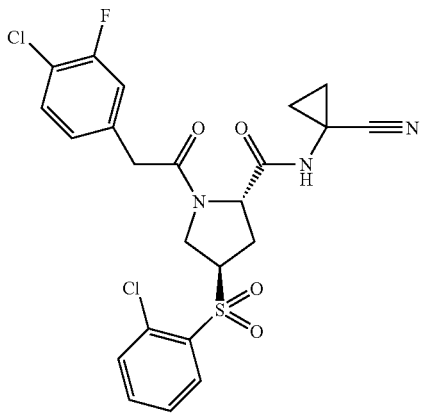

The title compound was prepared in analogy to example 425 to yield 96 mg (65%) of an off-white solid. MS (ESI): m/z=522.1 [M−H]⁻.

Example 445

(2S,4R)-1-(2-Benzyl-5-methyl-2H-pyrazol-3-yl)-4-cyclopropylmethanesulfonyl-pyrrolidine-2-carboxylic acid (1-cyano-cyclopropyl)-amide

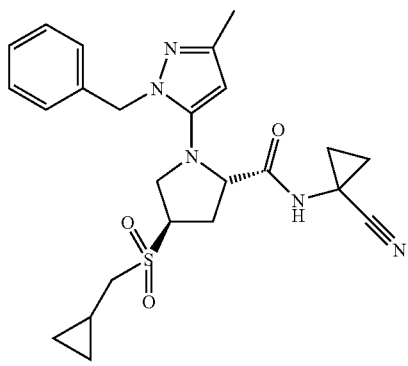

a) (2S,4R)-4-Cyclopropylmethanesulfonyl-pyrrolidine-2-carboxylic acid methyl ester Trifluoroacetate In analogy to the procedure described in example 409f, (2S,4R)-4-cyclopropylmethanesulfonyl-pyrrolidine-1,2-dicarboxylic acid 1-tert-butyl ester 2-methyl ester (example 423c) was reacted with trifluoroacetic acid to give the title compound as yellow liquid.

b) (2S,4R)-4-cyclopropylmethanesulfonyl-1-(3-oxo-butyryl)-pyrrolidine-2-carboxylic acid methyl ester In analogy to the procedure described in example 192f, (2S,4R)-4-cyclopropylmethanesulfonyl-pyrrolidine-2-carboxylic acid methyl ester trifluoroacetate was reacted with tert-butyl acetoacetate in the presence of triethylamine to give the title compound as brown solid. MS (ESI): m/z=332.2 [M+H]⁺.

c) (2S,4R)-4-Cyclopropylmethanesulfonyl-1-(3-oxo-thiobutyryl)-pyrrolidine-2-carboxylic acid methyl ester In analogy to the procedure described in example 192 g, (2S,4R)-4-cyclopropylmethanesulfonyl-1-(3-oxo-butyryl)-pyrrolidine-2-carboxylic acid methyl ester was reacted with Lawesson's reagent to give the title compound as brown solid. MS (ESI): m/z=348.4 [M+H]⁺.

d) (2S,4R)-1-(2-benzyl-5-methyl-2H-pyrazol-3-yl)-4-cyclopropylmethanesulfonyl-pyrrolidine-2-carboxylic acid methyl ester In analogy to the procedure described in example 192 h, (2S,4R)-4-cyclopropylmethanesulfonyl-1-(3-oxo-thiobutyryl)-pyrrolidine-2-carboxylic acid methyl ester was reacted with benzylhydrazine (CAS Reg. No. 555-96-4) to give the title compound as brown solid. MS (ESI): m/z=418.2 [M+H]⁺.

e) (2S,4R)-1-(2-Benzyl-5-methyl-2H-pyrazol-3-yl)-4-cyclopropylmethanesulfonyl-pyrrolidine-2-carboxylic acid In analogy to the procedure described in example 253e, (2S,4R)-1-(2-benzyl-5-methyl-2H-pyrazol-3-yl)-4-cyclopropylmethanesulfonyl-pyrrolidine-2-carboxylic acid methyl ester was saponified in the presence of lithium hydroxide to give the title compound as off-white solid which was used in the next step without further purification. MS (ESI): m/z=404.2 [M+H]⁺.

f) (2S,4R)-1-(2-Benzyl-5-methyl-2H-pyrazol-3-yl)-4-cyclopropylmethanesulfonyl-pyrrolidine-2-carboxylic acid (1-cyano-cyclopropyl)-amide In analogy to the procedure described in example 237, (2S,4R)-1-(2-benzyl-5-methyl-2H-pyrazol-3-yl)-4-cyclopropylmethanesulfonyl-pyrrolidine-2-carboxylic acid was reacted with 1-amino-cyclopropanecarbonitrile hydrochloride (CAS Reg. No. 127946-77-4) in the presence of HATU and DIEA to give the title compound as brown solid. MS (ESI): m/z=468.0 [M+H]⁺.

Example 446

(2S,4R)-4-(2-Chloro-benzenesulfonyl)-1-[1-(4-chloro-3-fluoro-phenyl)-cyclopropanecarbonyl]-pyrrolidine-2-carboxylic acid (1-cyano-cyclopropyl)-amide

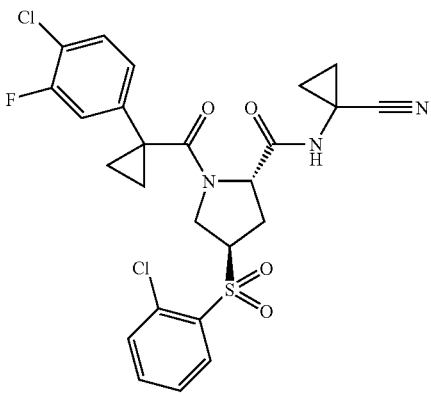

The title compound was prepared in analogy to example 425 to yield 92 mg (59%) of light yellow solid. MS (ESI): m/z=548.1 [M−H]⁻.

Example 447

4-Benzenesulfonyl-5-(4-tert-butyl-phenyl)-pyrrolidine-2-carboxylic acid (1-cyano-cyclopropyl)-amide

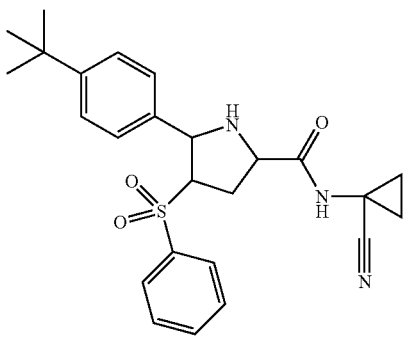

a) 5-(4-tert-Butylphenyl)-4-(phenylsulfonyl)pyrrolidine-2-carboxylic acid ethyl ester To a stirred solution of (E)-ethyl 2-(4-tert-butylbenzylideneamino)acetate (226 mg, 914 umol; example 441a) in THF (5 ml) under an argon atmosphere were added lithium bromide (119 mg, 1.37 mmol), triethylamine (191 ul, 1.37 mmol) and phenyl vinyl sulfone (154 mg, 914 umol; CAS Reg. No. 5535-48-8). The mixture was stirred at ambient temperature for 20 h. iPrOAc (50 ml) and ice water (40 ml) were added and the layers were separated. The organic layer was washed with brine (40 ml), dried over sodium sulfate and filtered. The solvent was removed under reduced pressure to give a yellow oil which was purified by column chromatography (silica gel, iPrOAc/n-heptane) to obtain the title compound (56 mg, 73 umol; 8%) as colorless solid. MS (ESI): m/z=416.2 [M+H]

b) 5-(4-tert-Butylphenyl)-4-(phenylsulfonyl)pyrrolidine-2-carboxylic acid

In analogy to the procedure described in example 253e, 5-(4-tert-butylphenyl)-4-(phenylsulfonyl)pyrrolidine-2-carboxylic acid ethyl ester was saponified in the presence of lithium hydroxide to give the title compound as colorless solid which was used in the next step without further purification. MS (ESI): m/z=388.2 [M+H]

c) 4-Benzenesulfonyl-5-(4-tert-butyl-phenyl)-pyrrolidine-2-carboxylic acid (1-cyano-cyclopropyl)-amide In analogy to the procedure described in example 237, 5-(4-tert-butylphenyl)-4-(phenylsulfonyl)pyrrolidine-2-carboxylic acid was reacted with 1-amino-cyclopropanecarbonitrile hydrochloride (CAS Reg. No. 127946-77-4) in the presence of HATU and DIEA to give the title compound as yellow foam. MS (ESI): m/z=452.2 [M+H]⁺.

Example 448

(2S,4R)-4-Methanesulfonyl-1-(5-methyl-2-phenethyl-2H-pyrazol-3-yl)-pyrrolidine-2-carboxylic acid (1-cyano-cyclopropyl)-amide

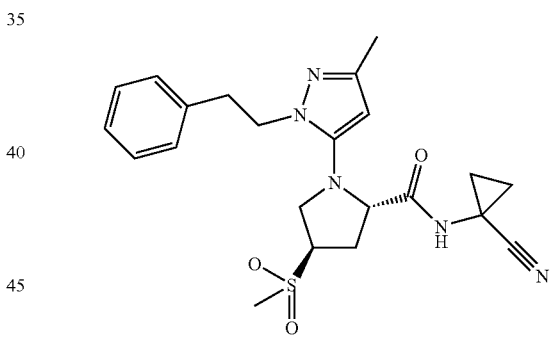

a) (2S,4R)-4-Methanesulfonyl-pyrrolidine-2-carboxylic acid methyl ester Trifluoroacetate In analogy to the procedure described in example 409f, (2S,4R)-4-methanesulfonyl-pyrrolidine-1,2-dicarboxylic acid 1-tert-butyl ester 2-methyl ester (example 409c) was reacted with trifluoroacetic acid to give the title compound as brown solid.

b) (2S,4R)-4-Methanesulfonyl-1-(3-oxo-butyryl)-pyrrolidine-2-carboxylic acid Methyl Ester In analogy to the procedure described in example 192f, (2S,4R)-4-methanesulfonyl-pyrrolidine-2-carboxylic acid methyl ester trifluoroacetate was reacted with tert-butyl acetoacetate in the presence of triethylamine to give the title compound. MS (ESI): m/z=292.2 [M+H]⁺.

c) (2S,4R)-4-M ethanesulfonyl-1-(3-oxo-thiobutyryl)-pyrrolidine-2-carboxylic acid Methyl Ester In analogy to the procedure described in example 192 g, (2S,4R)-4-methanesulfonyl-1-(3-oxo-butyryl)-pyrrolidine-2-carboxylic acid methyl ester was reacted with Lawesson's reagent to give the title compound as brown solid. MS (ESI): m/z=308.4 [M+H]+.

d) (2S,4R)-4-Methanesulfonyl-1-(5-methyl-2-phenethyl-2H-pyrazol-3-yl)-pyrrolidine-2-carboxylic acid methyl ester In analogy to the procedure described in example 192 h, (2S,4R)-4-methanesulfonyl-1-(3-oxo-thiobutyryl)-pyrrolidine-2-carboxylic acid methyl ester was reacted with 1-(2-phenylethyl)hydrazine (CAS Reg. No. 51-71-8) to give the title compound as brown solid. MS (ESI): m/z=392.6 [M+H]+.

e) (2S,4R)-4-Methanesulfonyl-1-(5-methyl-2-phenethyl-2H-pyrazol-3-yl)-pyrrolidine-2-carboxylic acid In analogy to the procedure described in example 253e, (2S,4R)-4-methanesulfonyl-1-(5-methyl-2-phenethyl-2H-pyrazol-3-yl)-pyrrolidine-2-carboxylic acid methyl ester was saponified in the presence of lithium hydroxide to give the title compound as off-white solid which was used in the next step without further purification. MS (ESI): m/z=378.0 [M+H]+.

f) (2S,4R)-4-Methanesulfonyl-1-(5-methyl-2-phenethyl-2H-pyrazol-3-yl)-pyrrolidine-2-carboxylic acid (1-cyano-cyclopropyl)-amide In analogy to the procedure described in example 237, (2S,4R)-4-methanesulfonyl-1-(5-methyl-2-phenethyl-2H-pyrazol-3-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=442.6 [M+H]+.

Example 449

(2S,4R)-1-(2-Benzyl-5-methyl-2H-pyrazol-3-yl)-4-methanesulfonyl-pyrrolidine-2-carboxylic Acid (1-cyano-cyclopropyl)-amide

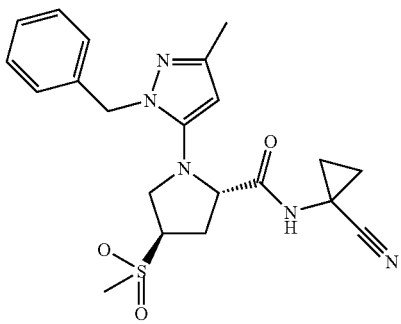

a) (2S,4R)-1-(2-Benzyl-5-methyl-2H-pyrazol-3-yl)-4-methanesulfonyl-pyrrolidine-2-carboxylic acid methyl ester In analogy to the procedure described in example 192 h, (2S,4R)-4-methanesulfonyl-1-(3-oxo-thiobutyryl)-pyrrolidine-2-carboxylic acid methyl ester (example 448c) was reacted with benzylhydrazine (CAS Reg. No. 555-96-4) to give the title compound. MS (ESI): m/z=378.5 [M+H]+.

b) (2S,4R)-1-(2-Benzyl-5-methyl-2H-pyrazol-3-yl)-4-methanesulfonyl-pyrrolidine-2-carboxylic acid In analogy to the procedure described in example 253e, (2S,4R)-1-(2-benzyl-5-methyl-2H-pyrazol-3-yl)-4-methanesulfonyl-pyrrolidine-2-carboxylic acid methyl ester was saponified in the presence of lithium hydroxide to give the title compound which was used in the next step without further purification. MS (ESI): m/z=364.3 [M+H]+.

c) (2S,4R)-1-(2-Benzyl-5-methyl-2H-pyrazol-3-yl)-4-methanesulfonyl-pyrrolidine-2-carboxylic acid (1-cyano-cyclopropyl)-amide In analogy to the procedure described in example 237, (2S,4R)-1-(2-benzyl-5-methyl-2H-pyrazol-3-yl)-4-methanesulfonyl-pyrrolidine-2-carboxylic acid was reacted with 1-amino-cyclopropanecarbonitrile hydrochloride (CAS Reg. No. 127946-77-4) in the presence of HATU and DIEA to give the title compound as brown solid. MS (ESI): m/z=428.2 [M+H]+.

Example 450

(2S,4R)-4-(2-Allyloxy-benzenesulfonyl)-2-(1-cyano-cyclopropylcarbamoyl)-pyrrolidine-1-carboxylic acid tert-butyl ester

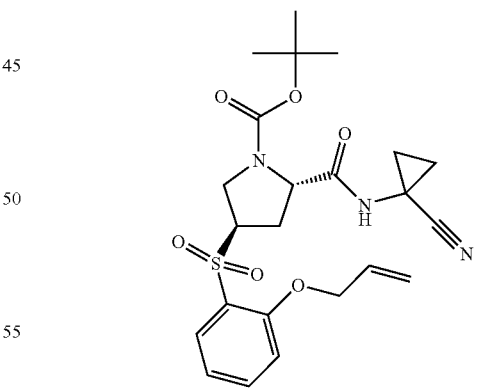

a) Synthesis of (2S,4R)-4-(2-fluoro-benzenesulfonyl)-pyrrolidine-1,2-dicarboxylic acid 1-tert-butyl ester 2-methyl ester The title compound was prepared according to the methods described for example 120a-c) to yield 8.1 g (92%) of colorless gum. MS (ESI): m/z=388.1 [M+H]+.

b) Synthesis of (2S,4R)-4-(2-Allyloxy-benzenesulfonyl)-pyrrolidine-1,2-dicarboxylic acid 1-tert-butyl ester 2-ethyl Ester In a 50 mL round-bottomed flask, sodium hydride, 60% dispersion in mineral oil (434 mg, 10.8 mmol, Eq: 1.4) was combined with DMF (20.00 mL) to give a white suspension. Prop-2-en-1-ol (630 mg, 739 µL, 10.8 mmol, Eq: 1.4) was slowly added (caution: formation of gas and heat!). The light yellow thin suspension was added to a solution of example 450a) (3 g, 7.74 mmol, Eq: 1.00) in DMF (10 mL). The reaction mixture was heated to 50° C. and stirred for 1.5 h. The crude reaction mixture was evaporated, then 150 ml AcOEt (150 ml) and water (40 mL), were added to the remainder. Transesterefication to the ethyl ester was observed. (LC/MS-check). The aqueous layer was extracted with EtOAc (3×150 mL). The organic layers were combined and washed with brine. The organic layers were dried over Na$_2$SO$_4$ and concentrated in vacuo. The crude material was purified by flash chromatography (silica gel, 25% to 60% EtOAc in hexanes) to yield the title compound (1.3 g; 38%) as a colorless gum. MS (ESI): m/z=440.2 [M+H]$^+$, 340.1 [M+H-Boc]$^+$.

c) Synthesis of (2S,4R)-4-(2-Allyloxy-benzenesulfonyl)-pyrrolidine-1,2-dicarboxylic acid 1-tert-butyl ester In a 25 mL round-bottomed flask, example 450b) (1.48 g, 3.37 mmol, Eq: 1.00) was combined with tetrahydrofuran (8 mL) to give a colorless solution. Lithium hydroxide (129 mg, 5.39 mmol, Eq: 1.6) in Water (4.00 mL) was added. The reaction mixture was stirred for 5 h. The reaction mixture was adjusted to pH=2-3 with 0.5 N aqueous HCl and extracted with EtOAc (2×25 mL). The aqueous layer was extracted with EtOAc (3×25 mL). The organic layers were combined and washed with brine. The organic layers were dried over Na$_2$SO$_4$ and concentrated in vacuo to yield the title compound (1.36 g; 98%) as a colorless foam. MS (ESI): m/z=410.1 [M–H]$^-$.

d) Synthesis of (2S,4R)-4-(2-Allyloxy-benzenesulfonyl)-2-(1-cyano-cyclopropylcarbamoyl)-pyrrolidine-1-carboxylic acid tert-butyl ester In a 25 mL round-bottomed flask, example 450c) (1.363 g, 3.31 mmol, Eq: 1.00) was combined with acetonitrile (15 mL) to give a colorless solution. HATU (2.52 g, 6.63 mmol, Eq: 2.0) and DIPEA (856 mg, 1.16 mL, 6.63 mmol, Eq: 2.0) were added. The color of the solution was changed to yellow. 1-Aminocyclopropanecarbonitrile hydrochloride (471 mg, 3.98 mmol, Eq: 1.2) was added and stirred at ambient temperature for 6 h. The reaction mixture was evaporated to dryness and purified with flash chromatography to yield the title compound (1.26 g; 80%) as a colorless foam. MS (ESI): m/z=476.1 [M+H]$^+$.

Example 451

(2S,4R)-1-(1-Hydroxymethyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide

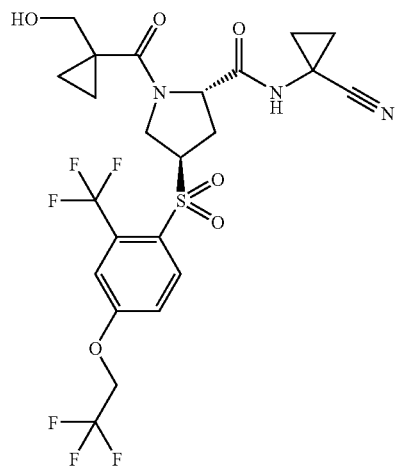

The title compound was prepared in analogy to example 211 using CAS 49640-66-6 as a starting material to yield 25 mg (19%) of a light yellow solid. MS (ESI): m/z=584.1 [M+H]$^+$.

Example 452

(2S,4R)-4-(2-Chloro-benzenesulfonyl)-1-(1-hydroxymethyl-cyclopropanecarbonyl)-pyrrolidine-2-carboxylic acid (1-cyano-cyclopropyl)-amide

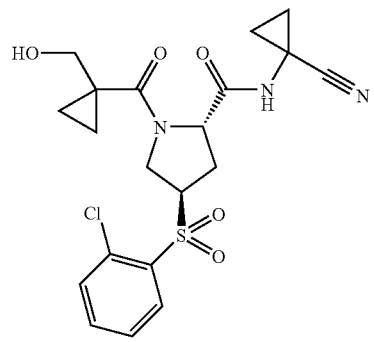

The title compound was prepared in analogy to example 425 using CAS 49640-66-6 as a starting material to yield 59 mg (51%) of an off-white foam. MS (ESI): m/z=452.1 [M+H]$^+$.

Example 453

(2S,4R)-4-(2-Allyloxy-benzenesulfonyl)-pyrrolidine-2-carboxylic acid (1-cyano-cyclopropyl)-amide

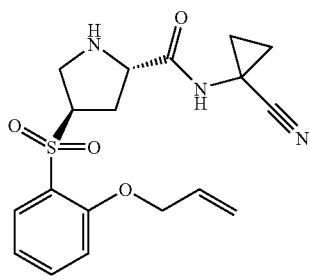

In a 10 mL round-bottomed flask, example 450 (0.6 g, 1.26 mmol, Eq: 1.00) and formic acid (1.74 g, 1.45 mL, 37.9 mmol, Eq: 30) were combined to give a light yellow solution. The reaction mixture was heated to 22° C. and stirred for 18 h. The reaction mixture was adjusted carefully with ice-cold aqueous 10%-$Na_2CO_3$-solution (2 mL) to pH=8 and extracted with EtOAc (1×35 mL). The aqueous layer was extracted with EtOAc (2×30 mL). The combined organic layers were washed with brine, dried over $Na_2SO_4$, filtered and evaporated to yield the title compound (460 mg; 97%) as a colorless foam. MS (ESI): m/z=376.1 [M+H]$^+$.

Example 454

(2S,4R)-4-Cyclopropylmethanesulfonyl-1-(1-methyl-cyclopropanecarbonyl)-pyrrolidine-2-carboxylic acid (1-cyano-cyclopropyl)-amide

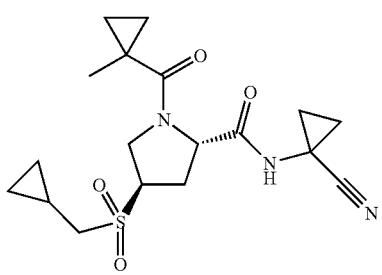

a) (2S,4R)-4-Cyclopropylmethanesulfonyl-1-(1-methyl-cyclopropanecarbonyl)-pyrrolidine-2-carboxylic acid methyl ester In analogy to the procedure described in example 237, (2S,4R)-4-cyclopropylmethanesulfonyl-pyrrolidine-2-carboxylic acid methyl ester trifluoroacetate (example 445a) was reacted with 1-methyl-cyclopropanecarboxylic acid (CAS Reg. No. 6914-76-7) in the presence of HATU and DIEA to give the title compound. MS (ESI): m/z=330.0 [M+H]$^+$.

b) (2S,4R)-4-Cyclopropylmethanesulfonyl-1-(1-methyl-cyclopropanecarbonyl)-pyrrolidine-2-carboxylic acid In analogy to the procedure described in example 253e, (2S,4R)-4-cyclopropylmethanesulfonyl-1-(1-methyl-cyclopropanecarbonyl)-pyrrolidine-2-carboxylic acid methyl ester was saponified in the presence of lithium hydroxide to give the title compound which was used in the next step without further purification.

c) (2S,4R)-4-Cyclopropylmethanesulfonyl-1-(1-methyl-cyclopropanecarbonyl)-pyrrolidine-2-carboxylic acid (1-cyano-cyclopropyl)-amide In analogy to the procedure described in example 237, (2S,4R)-4-cyclopropylmethanesulfonyl-1-(1-methyl-cyclopropanecarbonyl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=380.0 [M+H]$^+$.

Example 455

(2S,4R)-1-[(R)-2-Allylamino-2-(4-chloro-phenyl)-acetyl]-4-(2-allyloxy-benzenesulfonyl)-pyrrolidine-2-carboxylic acid (1-cyano-cyclopropyl)-amide

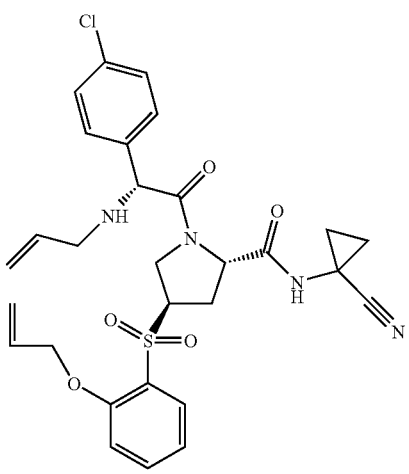

Synthesis of (R)-allylamino-(4-chloro-phenyl)-acetic acid methyl ester

In a 25 mL round-bottomed flask, (R)-methyl 2-amino-2-(4-chlorophenyl)acetate hydrochloride (1.000 g, 4.24 mmol, Eq: 1.00) and 3-bromoprop-1-ene (564 mg, 394 µL, 4.66 mmol, Eq: 1.1) were combined with dichloromethane (10.0 mL) to give a light yellow solution. The reaction mixture was heated to 22° C. and stirred for 1 h. The reaction mixture was stirred at 25° C. for 18 h. The crude reaction mixture was concentrated in vacuo. The crude material was purified by flash chromatography (silica gel, 40 g, 25% to 60% EtOAc in hexanes) to yield the title compound (331 mg; 33%) as a yellow oil. MS (ESI): m/z=376.1 [M+H]$^+$.

Synthesis of (R)-allylamino-(4-chloro-phenyl)-acetic Acid

In a 25 mL round-bottomed flask, example 455a) (0.33 g, 1.38 mmol, Eq: 1.00) was combined with tetrahydrofuran (1.6 mL) to give a yellow solution. Lithium hydroxide (52.8 mg, 2.2 mmol, Eq: 1.6) in water (0.8 ml) was added. The reaction mixture was stirred for 2 h. The reaction mixture was adjusted to pH=2-3 with 0.5 N aqueous HCl solution and extracted with EtOAc (2×25 mL). The aqueous layer was extracted with EtOAc (3×25 mL). The organic layers were combined and washed with brine. The organic layers were dried over $Na_2SO_4$ and concentrated in vacuo. The aqueous layer was concentrated in vacuo to yield the title compound (300 mg; 97%) as a white solid. MS (ESI): m/z=226.2 $[M+H]^+$.

c) Synthesis of (2S,4R)-1-[(R)-2-Allylamino-2-(4-chloro-phenyl)-acetyl]-4-(2-allyloxy-benzenesulfonyl)-pyrrolidine-2-carboxylic acid (1-cyano-cyclopropyl)-amide In a 10 mL round-bottomed flask, example 453 (83.2 mg, 222 umol, Eq: 1.00) was combined with DMF (1.00 mL) to give a light yellow solution. HATU (169 mg, 443 umol, Eq: 2.0) and DIPEA (57.3 mg, 77.4 μL, 443 umol, Eq: 2.0) were added. The color of solution was changed to yellow. Example 455b) (65.0 mg, 288 umol, Eq: 1.3) and 2.0 eq. of DIPEA (77.4 μL, 443 μmol) was added and stirred at 25° C. for 0.5 h. The crude material was purified by preparative HPLC to yield the title compound (60 mg; 46%) as a light yellow foam. MS (ESI): m/z=583.2 $[M+H]^+$.

Example 456

(2S,4R)-4-(2-chloro-4-(3,3-difluoroazetidin-1-yl)phenylsulfonyl)-N-(1-cyanocyclopropyl)-1-(1-cyclobutyl-3-methyl-1H-pyrazol-5-yl)pyrrolidine-2-carboxamide

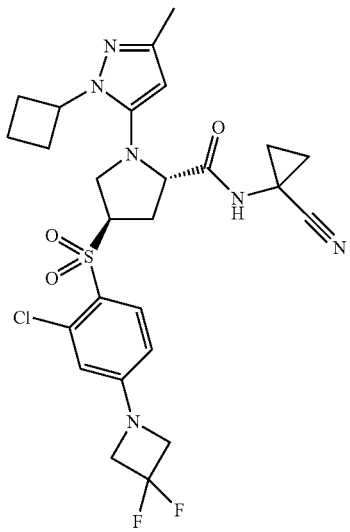

In analogy to the procedure described in example 389, (2S,4R)-4-(2-chloro-4-fluoro-benzenesulfonyl)-1-(2-cyclobutyl-5-methyl-2H-pyrazol-3-yl)-pyrrolidine-2-carboxylic acid (1-cyano-cyclopropyl)-amide (example 385b) was reacted with 3,3-difluoroazetidine hydrochloride (CAS Reg. No. 288315-03-7) in acetonitrile at 90° C. for 48 h to give the title compound as off-white foam. MS (ESI): m/z=579.3 $[M+H]^+$.

Example 457

(2S,4R)-1-(1-(4-chlorophenyl)cyclopropanecarbonyl)-N-(1-cyanocyclopropyl)-4-(phenylsulfonyl)pyrrolidine-2-carboxamide

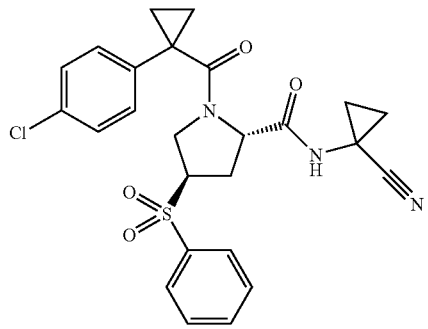

a) (1S,4S)-5-(1-(4-chlorophenyl)cyclopropanecarbonyl)-2-oxa-5-azabicyclo[2.2.1]heptan-3-one 1-(4-chlorophenyl)cyclopropanecarboxylic acid (8.58 g) and dimethylformamide (136 mg) were suspended in toluene (20 mL). The mixture was cooled down to room temperature then a solution of oxalyl chloride (5.25 g) in toluene (6.7 mL) was dropped within 10 min. The reaction mixture was stirred at 0° C. for 30 min and at room temperature for 3 h. At 0-5° C., (1S,4S)-2-oxa-5-azabicyclo[2.2.1]heptan-3-one methanesulfonate (CAS #: 769167-53-5; 8 g) and tetrahydrofuran (13.2 mL) were added to the reaction mixture, followed by a dropwise addition of triethylamine (14.5 g). The mixture was stirred at 22° C. for 16 hr. An aqueous solution of citric acid (10%, 30 mL) was added and the phases were separated. The aqueous layer was extracted with ethyl acetate. The combined organic layers were washed with brine (20 mL), dried over sodium sulfate, filtered and concentrated in vacuo. The crude mixture was crystallized in a mixture of dichloromethane, ethyl acetate and heptane to yield 10.6 g (95%) of the title compound as a white solid. MS (ESI): m/z=292.07 $[M+H]^+$.

b) (2S,4S)-1-(1-(4-chlorophenyl)cyclopropanecarbonyl)-N-(1-cyanocyclopropyl)-4-hydroxypyrrolidine-2-carboxamide A mixture of (1S,4S)-5-(1-(4-chlorophenyl)cyclopropanecarbonyl)-2-oxa-5-azabicyclo[2.2.1]heptan-3-one (Example 457a; 10.578 g), 1-aminocyclopropanecarbonitrile hydrochloride (5.94 g), sodium 2-ethylhexanoate (9.44 g) in water (54 mL) was stirred at 52-54° C. for 20 hr. The reaction mixture was diluted with 36 mL tetrahydrofuran. Concentrated hydrochloric acid (1.9 mL) and sodium chloride (18.09 g) were added. The reaction mixture was stirred for 15 min, then extracted with ethyl acetate. The combined organic lay ers were dried over sodium sulfate, filtered and concentrated in vacuo. The crude mixture was crystallized in a mixture of ethyl acetate and heptane to yield 11.94 g (88%) of the title compound as a white solid. MS (ESI): m/z=374.12 [M+H]$^+$.

c) (3S,5S)-1-(1-(4-chlorophenyl)cyclopropanecarbonyl)-5-(1-cyanocyclopropylcarbamoyl)pyrrolidin-3-yl Benzenesulfonate To a solution of (2S,4S)-1-(1-(4-chlorophenyl)cyclopropanecarbonyl)-N-(1-cyanocyclopropyl)-4-hydroxypyrrolidine-2-carboxamide (Example 457b; 5 g) in tetrahydrofuran (22 mL) at 0-5° C., was added benzenesulfonyl chloride (2.89 g, 2.1 ml, 16.2 mmol, Eq: 1.21), dimethylaminopyridine (88.7 mg) and triethylamine (2.41 g) within 5 minutes. The mixture was stirred at 0-5° C. for 15 min, then at 22° C. for 22 hr. Water (6.7 mL) and methanol (15.6 mL) were added at 0-5° C. and the mixture was concentrated in vacuo to afford a gum. This gum was washed with methanol and dried in vacuo to yield 6.82 g (99%) of the title compound as a light brown foam. MS (ESI): m/z=531.15 [M+NH$_4$]$^+$.

d) (2S,4R)-1-(1-(4-chlorophenyl)cyclopropanecarbonyl)-N-(1-cyanocyclopropyl)-4-(phenylthio)pyrrolidine-2-carboxamide To a suspension of (3S,5S)-1-(1-(4-chlorophenyl)cyclopropanecarbonyl)-5-(1-cyanocyclopropylcarbamoyl)pyrrolidin-3-yl benzenesulfonate (example 457c; 200 mg) and potassium carbonate (134 mg) in dimethylacetamide (1 mL) was added at tetrahydrofuran (1.2 mL) at room temperature THF and benzenethiol (50.7 mg). The reaction mixture was stirred at 22° C. for 20 hr then poured into water and extracted with ethyl acetate. The combined organic layers were washed with brine, dried over sodium sulfate and filtered. The crude mixture was concentrated to dryness and purified by chromatography on silica gel to yield the title compound as a colorless oil (184 mg; 89%). MS (ESI): m/z=466.13 [M+H]$^+$.

e) (2S,4R)-1-(1-(4-chlorophenyl)cyclopropanecarbonyl)-N-(1-cyanocyclopropyl)-4-(phenylsulfonyl)pyrrolidine-2-carboxamide To a suspension of oxone (873 mg) in methanol (0.7 mL) and water (0.2 mL) was added at 10-15° C. over 45 min a solution of (2S,4R)-1-(1-(4-chlorophenyl)cyclopropanecarbonyl)-N-(1-cyanocyclopropyl)-4-(phenylthio)pyrrolidine-2-carboxamide (Example 457d, 147 mg) in methanol (0.5 mL). The mixture was stirred at 22° C. for 20 hr. The reaction mixture was filtered and the residue washed with methanol. Water (2 mL) was added and the filtrate was concentrated in vacuo (50° C., 150-80 mbar). The aqueous layer was extracted with methyltertiobutylether and the combined organic layers were washed with and aqueous solution of sodium metabisulfite (10% w/w), an aqueous solution of potassium hydrogenocarbonate (1M), and brine then dried over sodium sulfate and filtered over a pad of silica gel. The pad was washed with methyltertiobutylether the filtrate was concentrated in vacuo to yield 42 mg (30%) of the desired compound as a white solid. MS (ESI): m/z=498.12 [M+H]$^+$.

Example 458

(2S,4R)-4-(benzylsulfonyl)-1-(1-(4-chlorophenyl)cyclopropanecarbonyl)-N-(1-cyanocyclopropyl)pyrrolidine-2-carboxamide

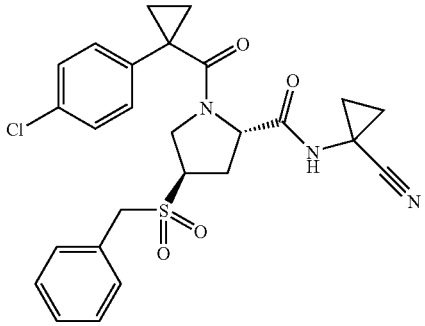

a) (2S,4R)-4-(benzylthio)-1-(1-(4-chlorophenyl)cyclopropanecarbonyl)-N-(1-cyanocyclopropyl)pyrrolidine-2-carboxamide The title compound was prepared in analogy to example 457d) using (3S,5S)-1-(1-(4-chlorophenyl)cyclopropanecarbonyl)-5-(1-cyanocyclopropylcarbamoyl)pyrrolidin-3-yl benzenesulfonate (example 457, step 3; 200 mg) and phenylmethanethiol (57 mg) to yield 109 mg (53%) of a white solid. MS (ESI): m/z=480.15 [M−H]$^+$.

b) (2S,4R)-4-(benzylsulfonyl)-1-(1-(4-chlorophenyl)cyclopropanecarbonyl)-N-(1-cyanocyclopropyl)pyrrolidine-2-carboxamide

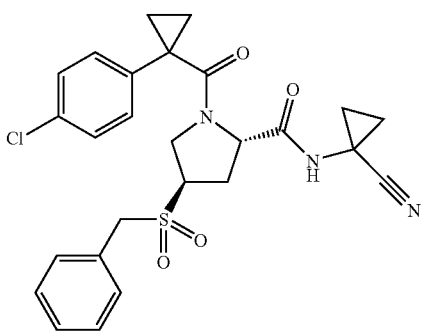

The title compound was prepared in analogy to example 457e) using (2S,4R)-4-(benzylthio)-1-(1-(4-chlorophenyl)cyclopropanecarbonyl)-N-(1-cyanocyclopropyl)pyrrolidine-2-carboxamide (example 458, step 1; 96 mg) to yield 50 mg (55%) of a white gum. MS (ESI): m/z=512.14 [M+H]$^+$.

Example 459

(2S,4R)-4-(2-Chloro-benzenesulfonyl)-1-[1-(4-iodo-phenyl)-cyclopropanecarbonyl]-pyrrolidine-2-carboxylic acid (1-cyano-cyclopropyl)-amide

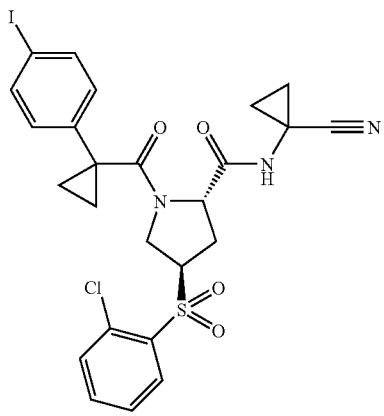

The title compound was prepared in analogy to example 425 to yield 112 mg (64%) of white solid. MS (ESI): m/z=624.1 [M+H]$^+$.

Example 460

(2S,4R)-4-(2-Chloro-benzenesulfonyl)-1-[1-(2,4-dichloro-5-methoxy-phenyl)-cyclopropanecarbonyl]-pyrrolidine-2-carboxylic acid (1-cyano-cyclopropyl)-amide

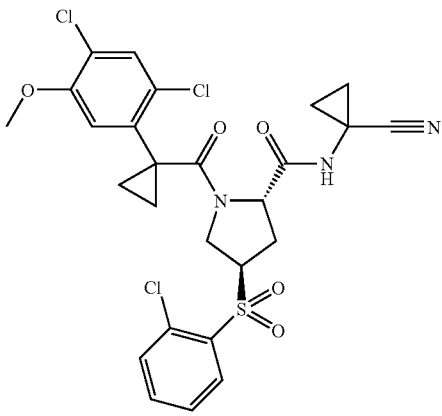

The title compound was obtained as a by-product during the synthesis of example 461 to yield 22 mg (11%) of a white solid. MS (ESI): m/z=596.2 [M+H]$^+$.

Example 461

(2S,4R)-4-(2-Chloro-benzenesulfonyl)-1-[1-(2,4-dichloro-5-fluoro-phenyl)-cyclopropanecarbonyl]-pyrrolidine-2-carboxylic acid (1-cyano-cyclopropyl)-amide

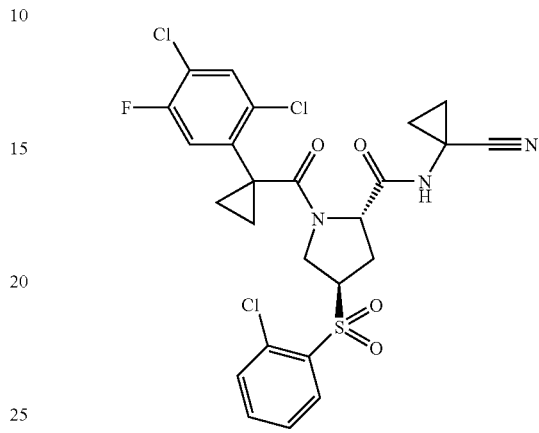

a) Synthesis of 1-(2,4-dichloro-5-fluoro-phenyl)-cyclopropanecarbonitrile 2-(2,4-dichloro-5-fluorophenyl)acetonitrile (1 g, 4.9 mmol, Eq: 1.00) was dissolved in toluene (4 mL). 1,2-Dibromoethane (1.38 g, 634 µL, 7.35 mmol, Eq: 1.50), aqueous NaOH-solution (4.31 mL, 12.5 M; 53.9 mmol, Eq: 11.0) and tertrabutylammonium bromide (348 mg, 1.08 mmol, Eq: 0.22) were added to the above suspension and vigorously stirred at RT for 4 h. The reaction mixture was diluted with water and extracted with AcOEt. The organic solution was washed with 1 N aqueous HCl, then with brine, dried over Na$_2$SO$_4$, filtered and evaporated to dryness. The crude material was purified by flash chromatography (silica gel, 50 g, 0% to 50% EtOAc in heptane) to yield example 461a) (1.13 g; 100%) as an off-white solid. $^1$H-NMR (CDCl$_3$, 250 MHz) δ [ppm]: 7.51 (1 proton, d, 6.7 Hz); 7.16 (1, proton, d; 8.9 Hz); 1.76-1.80 (2 protons, m); 1.31-1.36 (2 protons, m)

b) Synthesis of 1-(2,4-Dichloro-5-fluoro-phenyl)-cyclopropanecarboxylic acid and 1-(2,4-dichloro-5-methoxy-phenyl)-cyclopropanecarboxylic acid (1:1 Mixture)

1-(2,4-dichloro-5-fluorophenyl)cyclopropanecarbonitrile (1.13 g, 4.91 mmol, Eq: 1.00) was dissolved in methanol (2.5 mL). 9 N aqueous NaOH (10 ml, 90.0 mmol, Eq: 18.3) was added and the reaction mixture was stirred 3 h at 25° C. The reaction mixture was acidified with 2 N aqueous HCl-solution and extracted with CH$_2$Cl$_2$. The organic layers were dried over Na$_2$SO$_4$, filtered and concentrated in vacuo to yield a 1:1 mixture of the title compounds. F-derivative: $^1$H-NMR (CDCl$_3$, 250 MHz) δ [ppm]: 11.15 (broad, 1 proton); 7.43 (1 proton, d, 6.86 Hz); 7.10 (d; 1 proton, 9.29 Hz); 1.78-1.82 (2 protons, m); 1.23-1.29 (2 protons, m) Methoxy-derivative: $^1$H-NMR (CDCl$_3$, 250 MHz) δ [ppm]: 11.15 (broad, 1 proton); 7.38 (1 proton, s); 6.85 (s; 1 proton); 3.88 (s, 3 protons); 1.78-1.82 (2 protons, m); 1.23-1.29 (2 protons, m)

c) 2S,4R)-4-(2-Chloro-benzenesulfonyl)-1-[1-(2,4-dichloro-5-fluoro-phenyl)-cyclopropanecarbonyl]-pyrrolidine-2-carboxylic acid (1-cyano-cyclopropyl)-amide The title compound was prepared in analogy to example 425 using the mixture of example 461b) as starting material to yield 42 mg (21%) of white solid. MS (ESI): m/z=586.0 [M+H]⁺.

Example 462

(2S,4R)-4-Methanesulfonyl-1-[5-methyl-2-(4-trifluoromethyl-phenyl)-2H-pyrazol-3-yl]-pyrrolidine-2-carboxylic acid (1-cyano-cyclopropyl)-amide

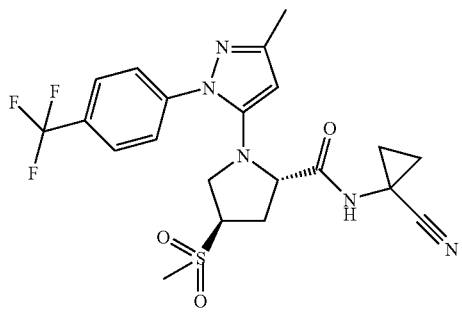

a) (2S,4R)-4-Methanesulfonyl-1-[5-methyl-2-(4-trifluoromethyl-phenyl)-2H-pyrazol-3-yl]-pyrrolidine-2-carboxylic acid methyl ester In analogy to the procedure described in example 192 h, (2S,4R)-4-methanesulfonyl-1-(3-oxo-thiobutyryl)-pyrrolidine-2-carboxylic acid methyl ester (example 448c) was reacted with 4-(trifluoromethyl)phenylhydrazine (CAS Reg. No. 368-90-1) to give the title compound. MS (ESI): m/z=432.0 [M+H]⁺.

b) (2S,4R)-4-Methanesulfonyl-1-[5-methyl-2-(4-trifluoromethyl-phenyl)-2H-pyrazol-3-yl]-pyrrolidine-2-carboxylic acid In analogy to the procedure described in example 253e, (2S,4R)-4-methanesulfonyl-1-[5-methyl-2-(4-trifluoromethyl-phenyl)-2H-pyrazol-3-yl]-pyrrolidine-2-carboxylic acid methyl ester was saponified in the presence of lithium hydroxide to give the title compound which was used in the next step without further purification. MS (ESI): m/z=418.4 [M+H]⁺.

c) (2S,4R)-4-Methanesulfonyl-1-[5-methyl-2-(4-trifluoromethyl-phenyl)-2H-pyrazol-3-yl]-pyrrolidine-2-carboxylic acid (1-cyano-cyclopropyl)-amide In analogy to the procedure described in example 237, (2S,4R)-4-methanesulfonyl-1-[5-methyl-2-(4-trifluoromethyl-phenyl)-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=482.4 [M+H]⁺.

Example 463

(2S,4R)-1-[2-(2-Chloro-pyridin-4-yl)-5-methyl-2H-pyrazol-3-yl]-4-methanesulfonyl-pyrrolidine-2-carboxylic acid (1-cyano-cyclopropyl)-amide

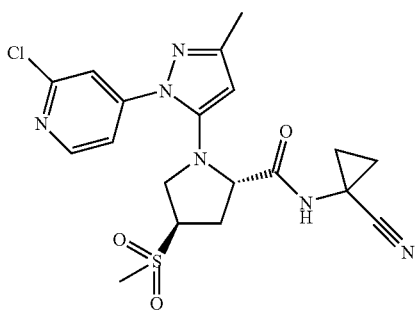

a) (2S,4R)-1-[2-(2-Chloro-pyridin-4-yl)-5-methyl-2H-pyrazol-3-yl]-4-methanesulfonyl-pyrrolidine-2-carboxylic acid methyl ester In analogy to the procedure described in example 192 h, (2S,4R)-4-methanesulfonyl-1-(3-oxo-thiobutyryl)-pyrrolidine-2-carboxylic acid methyl ester (example 448c) was reacted with (2-chloro-pyridin-4-yl)-hydrazine (CAS Reg. No. 700811-29-6) to give the title compound.

b) (2S,4R)-1-[2-(2-Chloro-pyridin-4-yl)-5-methyl-2H-pyrazol-3-yl]-4-methanesulfonyl-pyrrolidine-2-carboxylic acid In analogy to the procedure described in example 253e, (2S,4R)-1-[2-(2-chloro-pyridin-4-yl)-5-methyl-2H-pyrazol-3-yl]-4-methanesulfonyl-pyrrolidine-2-carboxylic acid methyl ester was saponified in the presence of lithium hydroxide to give the title compound which was used in the next step without further purification.

c) (2S,4R)-1-[2-(2-Chloro-pyridin-4-yl)-5-methyl-2H-pyrazol-3-yl]-4-methanesulfonyl-pyrrolidine-2-carboxylic acid (1-cyano-cyclopropyl)-amide In analogy to the procedure described in example 237, (2S,4R)-1-[2-(2-chloro-pyridin-4-yl)-5-methyl-2H-pyrazol-3-yl]-4-methanesulfonyl-pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=449.6 [M+H]⁺.

Example 464

(2S,4R)-4-(2-chloro-4-(3,3-difluoroazetidin-1-yl)
phenylsulfonyl)-N-(1-cyanocyclopropyl)-1-(3-methyl-1-(tetrahydro-2H-pyran-4-yl)-1H-pyrazol-5-yl)
pyrrolidine-2-carboxamide

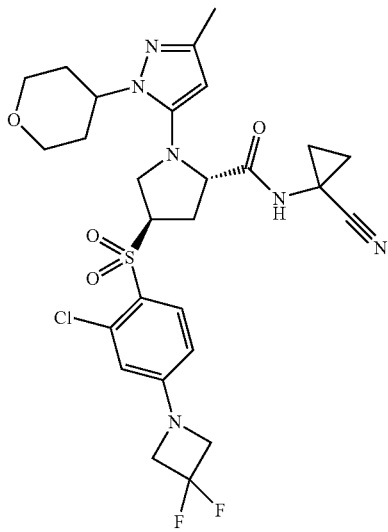

a) (2S,4R)-Methyl 4-(2-chloro-4-fluorophenylsulfonyl)-1-(3-oxobutanethioyl)pyrrolidine-2-carboxylate In analogy to the procedure described in example 192 g, (2S,4R)-methyl 4-(2-chloro-4-fluorophenylsulfonyl)-1-(3-oxobutanoyl)pyrrolidine-2-carboxylate (example 375b) was reacted with Lawesson's reagent (CAS Reg. No. 19172-47-5) to give the title compound as orange foam. MS (ESI): m/z=421.9 [M+H]$^+$.

b) (2S,4R)-4-(2-Chloro-4-fluorophenylsulfonyl)-1-(3-methyl-1-(tetrahydro-2H-pyran-4-yl)-1H-pyrazol-5-yl)pyrrolidine-2-carboxylic acid methyl ester In analogy to the procedure described in example 192 h, (2S,4R)-methyl 4-(2-chloro-4-fluorophenylsulfonyl)-1-(3-oxobutanethioyl)pyrrolidine-2-carboxylate was reacted with (tetrahydro-pyran-4-yl)-hydrazine hydrochloride (CAS Reg. No. 116312-69-7) to give the title compound as yellow solid. MS (ESI): m/z=486.2 [M+H]$^+$.

c) (2S,4R)-4-(2-Chloro-4-fluorophenylsulfonyl)-1-(3-methyl-1-(tetrahydro-2H-pyran-4-yl)-1H-pyrazol-5-yl)pyrrolidine-2-carboxylic acid In analogy to the procedure described in example 253e, (2S,4R)-4-(2-chloro-4-fluorophenylsulfonyl)-1-(3-methyl-1-(tetrahydro-2H-pyran-4-yl)-1H-pyrazol-5-yl)pyrrolidine-2-carboxylic acid methyl ester was saponified in the presence of lithium hydroxide to give the title compound as yellow foam which was used in the next step without further purification. MS (ESI): m/z=472.1 [M+H]$^+$.

d) (2S,4R)-4-(2-chloro-4-fluorophenylsulfonyl)-N-(1-cyanocyclopropyl)-1-(3-methyl-1-(tetrahydro-2H-pyran-4-yl)-1H-pyrazol-5-yl)pyrrolidine-2-carboxamide In analogy to the procedure described in example 237, (2S,4R)-4-(2-chloro-4-fluorophenylsulfonyl)-1-(3-methyl-1-(tetrahydro-2H-pyran-4-yl)-1H-pyrazol-5-yl)pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=536.1 [M+H]$^+$.

e) (2S,4R)-4-(2-chloro-4-(3,3-difluoroazetidin-1-yl)
phenylsulfonyl)-N-(1-cyanocyclopropyl)-1-(3-methyl-1-(tetrahydro-2H-pyran-4-yl)-1H-pyrazol-5-yl)
pyrrolidine-2-carboxamide In analogy to the procedure described in example 389, (2S,4R)-4-(2-chloro-4-fluorophenylsulfonyl)-N-(1-cyanocyclopropyl)-1-(3-methyl-1-(tetrahydro-2H-pyran-4-yl)-1H-pyrazol-5-yl)pyrrolidine-2-carboxamide was reacted with 3,3-difluoroazetidine hydrochloride (CAS Reg. No. 288315-03-7) in acetonitrile at 90° C. for 48 h to give the title compound as off-white foam. MS (ESI): m/z=609.2 [M+H]$^+$.

Example 465

(2S,4R)-4-(2-chlorophenylsulfonyl)-N-(1-cyanocyclopropyl)-1-(3-methyl-1-(tetrahydro-2H-thiopyran-4-yl)-1H-pyrazol-5-yl)pyrrolidine-2-carboxamide

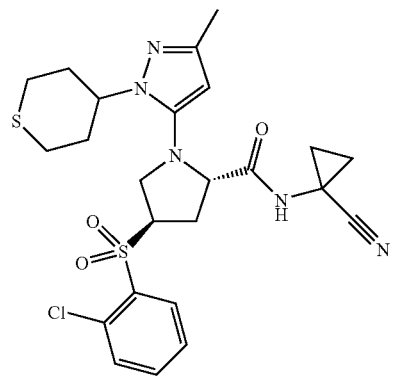

(2S,4R)-4-(2-Chlorophenylsulfonyl)-1-(3-methyl-1-(tetrahydro-2H-thiopyran-4-yl)-1H-pyrazol-5-yl)
pyrrolidine-2-carboxylic acid methyl ester In analogy to the procedure described in example 192 h, (2S,4R)-methyl 4-(2-chlorophenylsulfonyl)-1-(3-oxobutanethioyl)pyrrolidine-2-carboxylate (example 253c) was reacted with (tetrahydro-2H-thiopyran-4-yl)hydrazine 2,2,2-trifluoroacetate (CAS Reg. No. 693287-87-5) to give the title compound as yellow foam. MS (ESI): m/z=484.1 [M+H]$^+$.

(2S,4R)-4-(2-Chlorophenylsulfonyl)-1-(3-methyl-1-(tetrahydro-2H-thiopyran-4-yl)-1H-pyrazol-5-yl)
pyrrolidine-2-carboxylic acid In analogy to the procedure described in example 253e, (2S,4R)-4-(2-chlorophenylsulfonyl)-1-(3-methyl-1-(tetrahydro-2H-thiopyran-4-yl)-1H-pyrazol-5-yl)pyrrolidine-2-carboxylic acid methyl ester was saponified in the presence of lithium hydroxide to give the title compound as brown liquid which was used in the next step without further purification. MS (ESI): m/z=470.0 [M+H]$^+$.

(2S,4R)-4-(2-chlorophenylsulfonyl)-N-(1-cyanocyclopropyl)-1-(3-methyl-1-(tetrahydro-2H-thiopyran-4-yl)-1H-pyrazol-5-yl)pyrrolidine-2-carboxamide In analogy to the procedure described in example 237, (2S,4R)-4-(2-chlorophenylsulfonyl)-1-(3-methyl-1-(tetrahydro-2H-thiopyran-4-yl)-1H-pyrazol-5-yl)pyrrolidine-2-carboxylic acid was reacted with 1-amino-cyclopropanecarbonitrile hydrochloride (CAS Reg. No. 127946-77-4) in the presence of HATU and DIEA to give the title compound as off-white foam. MS (ESI): m/z=534.1 [M+H]⁺.

Example 466

(2S,4R)-4-Methanesulfonyl-1-[5-methyl-2-(2,2,2-trifluoro-ethyl)-2H-pyrazol-3-yl]-pyrrolidine-2-carboxylic acid (1-cyano-cyclopropyl)-amide

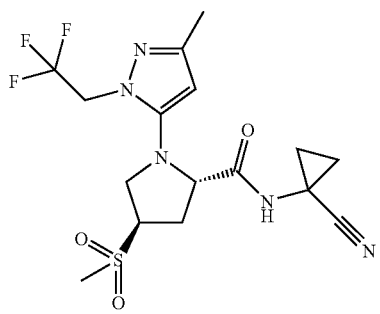

a) (2S,4R)-4-Methanesulfonyl-1-[5-methyl-2-(2,2,2-trifluoro-ethyl)-2H-pyrazol-3-yl]-pyrrolidine-2-carboxylic acid methyl ester In analogy to the procedure described in example 192 h, (2S,4R)-4-methanesulfonyl-1-(3-oxo-thiobutyryl)-pyrrolidine-2-carboxylic acid methyl ester (example 448c) was reacted with 2,2,2-trifluoroethylhydrazine (CAS Reg. No. 5042-30-8) to give the title compound. MS (ESI): m/z=370.4 [M+H]⁺.

b) (2S,4R)-4-Methanesulfonyl-1-[5-methyl-2-(2,2,2-trifluoro-ethyl)-2H-pyrazol-3-yl]-pyrrolidine-2-carboxylic acid In analogy to the procedure described in example 253e, (2S,4R)-4-methanesulfonyl-1-[5-methyl-2-(2,2,2-trifluoro-ethyl)-2H-pyrazol-3-yl]-pyrrolidine-2-carboxylic acid methyl ester was saponified in the presence of lithium hydroxide to give the title compound which was used in the next step without further purification. MS (ESI): m/z=356.3 [M+H]⁺.

c) (2S,4R)-4-Methanesulfonyl-1-[5-methyl-2-(2,2,2-trifluoro-ethyl)-2H-pyrazol-3-yl]-pyrrolidine-2-carboxylic acid (1-cyano-cyclopropyl)-amide In analogy to the procedure described in example 237, (2S,4R)-4-methanesulfonyl-1-[5-methyl-2-(2,2,2-trifluoro-ethyl)-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=420.0 [M+H]⁺.

Example 467

(2S,4R)-4-Cyclopropylmethanesulfonyl-1-[5-methyl-2-(2,2,2-trifluoro-ethyl)-2H-pyrazol-3-yl]-pyrrolidine-2-carboxylic acid (1-cyano-cyclopropyl)-amide

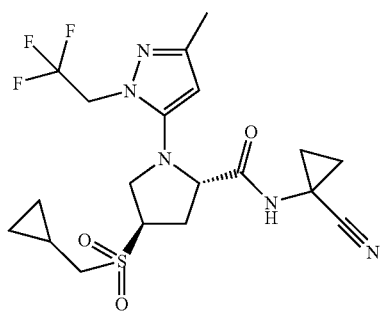

a) (2S,4R)-4-Cyclopropylmethanesulfonyl-1-[5-methyl-2-(2,2,2-trifluoro-ethyl)-2H-pyrazol-3-yl]-pyrrolidine-2-carboxylic acid methyl ester In analogy to the procedure described in example 192 h, (2S,4R)-4-cyclopropylmethanesulfonyl-1-(3-oxo-thiobutyryl)-pyrrolidine-2-carboxylic acid methyl ester (example 445c) was reacted with 2,2,2-trifluoroethylhydrazine (CAS Reg. No. 5042-30-8) to give the title compound as brown solid. MS (ESI): m/z=409.9 [M+H]⁺.

b) (2S,4R)-4-Cyclopropylmethanesulfonyl-1-[5-methyl-2-(2,2,2-trifluoro-ethyl)-2H-pyrazol-3-yl]-pyrrolidine-2-carboxylic acid In analogy to the procedure described in example 253e, (2S,4R)-4-cyclopropylmethanesulfonyl-1-[5-methyl-2-(2,2,2-trifluoro-ethyl)-2H-pyrazol-3-yl]-pyrrolidine-2-carboxylic acid methyl ester was saponified in the presence of lithium hydroxide to give the title compound as off-white solid which was used in the next step without further purification. MS (ESI): m/z=396.2 [M+H]⁺.

c) (2S,4R)-4-Cyclopropylmethanesulfonyl-1-[5-methyl-2-(2,2,2-trifluoro-ethyl)-2H-pyrazol-3-yl]-pyrrolidine-2-carboxylic acid (1-cyano-cyclopropyl)-amide In analogy to the procedure described in example 237, (2S,4R)-4-cyclopropylmethanesulfonyl-1-[5-methyl-2-(2,2,2-trifluoro-ethyl)-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as yellow solid. MS (ESI): m/z=460.0 [M+H]$^+$.

Example 468

(2S,4R)-4-Methanesulfonyl-1-[5-methyl-2-(2,2,2-trifluoro-ethyl)-2H-pyrazol-3-yl]-pyrrolidine-2-carboxylic acid (1-cyano-cyclopropyl)-amide

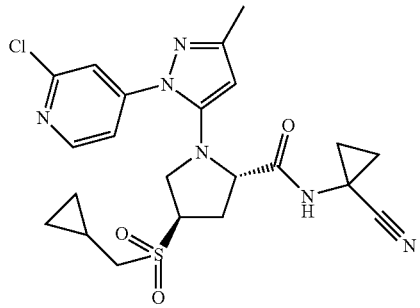

a) (2S,4R)-1-[2-(2-Chloro-pyridin-4-yl)-5-methyl-2H-pyrazol-3-yl]-4-cyclopropylmethanesulfonyl-pyrrolidine-2-carboxylic acid methyl ester In analogy to the procedure described in example 192 h, (2S,4R)-4-cyclopropylmethanesulfonyl-1-(3-oxo-thiobutyryl)-pyrrolidine-2-carboxylic acid methyl ester (example 445c) was reacted with (2-chloro-pyridin-4-yl)-hydrazine (CAS Reg. No. 700811-29-6) to give the title compound as brown solid. MS (ESI): m/z=439.4 [M+H]$^+$.

b) (2S,4R)-1-[2-(2-Chloro-pyridin-4-yl)-5-methyl-2H-pyrazol-3-yl]-4-cyclopropylmethanesulfonyl-pyrrolidine-2-carboxylic acid In analogy to the procedure described in example 253e, (2S,4R)-1-[2-(2-chloro-pyridin-4-yl)-5-methyl-2H-pyrazol-3-yl]-4-cyclopropylmethanesulfonyl-pyrrolidine-2-carboxylic acid methyl ester was saponified in the presence of lithium hydroxide to give the title compound as off-white solid which was used in the next step without further purification. MS (ESI): m/z=425.0 [M+H]$^+$.

c) (2S,4R)-4-Methanesulfonyl-1-[5-methyl-2-(2,2,2-trifluoro-ethyl)-2H-pyrazol-3-yl]-pyrrolidine-2-carboxylic acid (1-cyano-cyclopropyl)-amide In analogy to the procedure described in example 237, (2S,4R)-1-[2-(2-chloro-pyridin-4-yl)-5-methyl-2H-pyrazol-3-yl]-4-cyclopropylmethanesulfonyl-pyrrolidine-2-carboxylic acid was reacted with 1-amino-cyclopropanecarbonitrile hydrochloride (CAS Reg. No. 127946-77-4) in the presence of HATU and DIEA to give the title compound as yellow solid. MS (ESI): m/z=489.0 [M+H]$^+$.

Example 469

(2S,4R)-4-Cyclopropylmethanesulfonyl-1-[5-methyl-2-(4-trifluoromethyl-phenyl)-2H-pyrazol-3-yl]-pyrrolidine-2-carboxylic acid (1-cyano-cyclopropyl)-amide

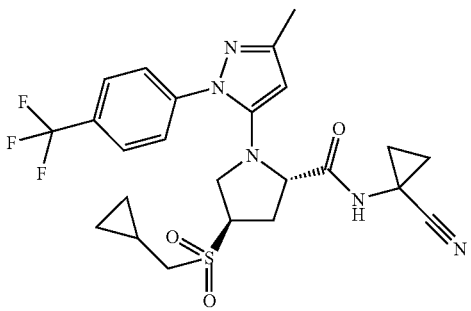

a) (2S,4R)-4-Cyclopropylmethanesulfonyl-1-[5-methyl-2-(4-trifluoromethyl-phenyl)-2H-pyrazol-3-yl]-pyrrolidine-2-carboxylic acid methyl ester In analogy to the procedure described in example 192 h, (2S,4R)-4-cyclopropylmethanesulfonyl-1-(3-oxo-thiobutyryl)-pyrrolidine-2-carboxylic acid methyl ester (example 445c) was reacted with 4-(trifluoromethyl)phenylhydrazine (CAS Reg. No. 368-90-1) to give the title compound as brown solid. MS (ESI): m/z=472.6 [M+H]$^+$.

b) (2S,4R)-4-Cyclopropylmethanesulfonyl-1-[5-methyl-2-(4-trifluoromethyl-phenyl)-2H-pyrazol-3-yl]-pyrrolidine-2-carboxylic acid In analogy to the procedure described in example 253e, (2S,4R)-4-cyclopropylmethanesulfonyl-1-[5-methyl-2-(4-trifluoromethyl-phenyl)-2H-pyrazol-3-yl]-pyrrolidine-2-carboxylic acid methyl ester was saponified in the presence of lithium hydroxide to give the title compound as off-white solid which was used in the next step without further purification. MS (ESI): m/z=458.0 [M+H]$^+$.

c) (2S,4R)-4-Cyclopropylmethanesulfonyl-1-[5-methyl-2-(4-trifluoromethyl-phenyl)-2H-pyrazol-3-yl]-pyrrolidine-2-carboxylic acid (1-cyano-cyclopropyl)-amide In analogy to the procedure described in example 237, (2S,4R)-4-cyclopropylmethanesulfonyl-1-[5-methyl-2-(4-trifluoromethyl-phenyl)-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=522.0 [M+H]$^+$.

Example 470

(2S,4R)-4-Cyclopropylmethanesulfonyl-1-(5-methyl-2-phenethyl-2H-pyrazol-3-yl)-pyrrolidine-2-carboxylic acid (1-cyano-cyclopropyl)-amide

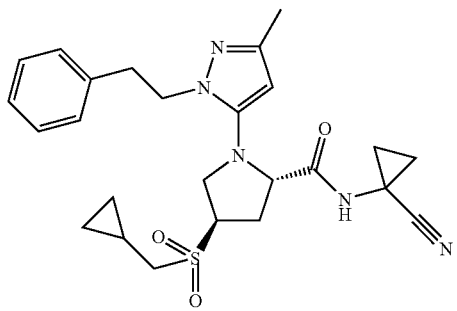

a) (2S,4R)-4-Cyclopropylmethanesulfonyl-1-(5-methyl-2-phenethyl-2H-pyrazol-3-yl)-pyrrolidine-2-carboxylic acid methyl ester In analogy to the procedure described in example 192 h, (2S,4R)-4-cyclopropylmethanesulfonyl-1-(3-oxo-thiobutyryl)-pyrrolidine-2-carboxylic acid methyl ester (example 445c) was reacted with 1-(2-phenylethyl)hydrazine (CAS Reg. No. 51-71-8) to give the title compound as brown solid. MS (ESI): m/z=432.6 [M+H]$^+$.

b) (2S,4R)-4-Cyclopropylmethanesulfonyl-1-(5-methyl-2-phenethyl-2H-pyrazol-3-yl)-pyrrolidine-2-carboxylic acid In analogy to the procedure described in example 253e, (2S,4R)-4-cyclopropylmethanesulfonyl-1-(5-methyl-2-phenethyl-2H-pyrazol-3-yl)-pyrrolidine-2-carboxylic acid methyl ester was saponified in the presence of lithium hydroxide to give the title compound as off-white solid which was used in the next step without further purification. MS (ESI): m/z=417.6 [M+H]$^+$.

c) (2S,4R)-4-Cyclopropylmethanesulfonyl-1-(5-methyl-2-phenethyl-2H-pyrazol-3-yl)-pyrrolidine-2-carboxylic acid (1-cyano-cyclopropyl)-amide In analogy to the procedure described in example 237, (2S,4R)-4-cyclopropylmethanesulfonyl-1-(5-methyl-2-phenethyl-2H-pyrazol-3-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=482.7 [M+H]$^+$.

Example 471

(2S,4R)-1-(2-Cyclobutyl-5-methyl-2H-pyrazol-3-yl)-4-methanesulfonyl-pyrrolidine-2-carboxylic acid (1-cyano-cyclopropyl)-amide

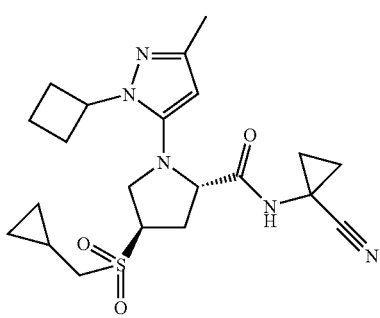

a) (2S,4R)-1-(2-Cyclobutyl-5-methyl-2H-pyrazol-3-yl)-4-cyclopropylmethanesulfonyl-pyrrolidine-2-carboxylic acid methyl ester In analogy to the procedure described in example 192 h, (2S,4R)-4-cyclopropylmethanesulfonyl-1-(3-oxo-thiobutyryl)-pyrrolidine-2-carboxylic acid methyl ester (example 445c) was reacted with cyclobutylhydrazine (CAS Reg. No. 742673-64-9) to give the title compound as brown solid. MS (ESI): m/z=382.2 [M+H]$^+$.

b) (2S,4R)-1-(2-Cyclobutyl-5-methyl-2H-pyrazol-3-yl)-4-cyclopropylmethanesulfonyl-pyrrolidine-2-carboxylic acid In analogy to the procedure described in example 253e, (2S,4R)-1-(2-cyclobutyl-5-methyl-2H-pyrazol-3-yl)-4-cyclopropylmethanesulfonyl-pyrrolidine-2-carboxylic acid methyl ester was saponified in the presence of lithium hydroxide to give the title compound as off-white solid which was used in the next step without further purification. MS (ESI): m/z=367.2 [M+H]$^+$.

c) (2S,4R)-1-(2-Cyclobutyl-5-methyl-2H-pyrazol-3-yl)-4-methanesulfonyl-pyrrolidine-2-carboxylic acid (1-cyano-cyclopropyl)-amide In analogy to the procedure described in example 237, (2S,4R)-1-(2-cyclobutyl-5-methyl-2H-pyrazol-3-yl)-4-cyclopropylmethanesulfonyl-pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=381.8 [M+H]$^+$.

Example 472

(2S,4R)-1-[1-(4-Bromo-naphthalen-1-yl)-cyclopropanecarbonyl]-4-(2-chloro-benzenesulfonyl)-pyrrolidine-2-carboxylic acid (1-cyano-cyclopropyl)-amide

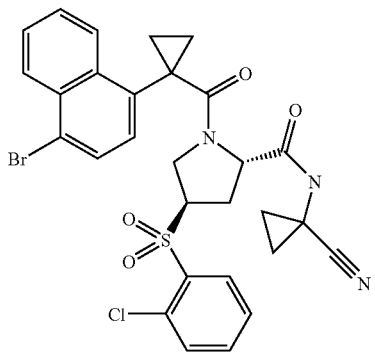

a) (4-Bromo-naphthalen-1-yl)-acetic acid methyl ester

To a solution of 2-(naphthalen-1-yl)acetic acid (2 g) in acetic acid (10 mL) at room temperature, was added bromine (1.7 g). The mixture was stirred at 80° C. for 2 hr, then allowed to cool down to room temperature over the week-end (formation of crystals by stirring). The reaction mixture was diluted with water and the crystals were filtered off, washed with water and dried to afford 2.5 g of a crude mixture containing (4-Bromo-naphthalen-1-yl)-acetic acid as light brown solid.

To a solution of this solid (2.5 g), dimethylaminopyridine (86.4 mg) and triethylamine (787 mg) in dichloromethane (20 mL) was added methyl chloroformate (668 mg) at 0° C. the reaction mixture was stirred for 6 h at room temperature. The reaction mixture was diluted with dichloromethane and washed with a saturated aqueous solution of sodium hydrogenocarbonate, the hydrochloric acid (0.1 N) and brine, then dried over sodium sulfate and filtered. The crude mixture was concentrated to dryness and purified by chromatography on silica gel than further purified on Preparative Chiral HPLC over Reprosil Chiral-NR to yield the title compound as a white solid (669 mg; 23%). MS (ESI): m/z=278 [M+H]+.

b) 1-(4-Bromo-naphthalen-1-yl)-cyclopropanecarboxylic acid

To a solution of (4-Bromo-naphthalen-1-yl)-acetic acid methyl ester (Example 472a), 687 mg) in tetrahydrofuran (13 mL) and Hexamethylphosphoramide (1.3 mL) was added at −78° C. a solution of lithiumdiisopropylamide (2M, 2.71 mL) in tetrahydrofuran/heptane/ethylbenzene within 5 min. 1,2-dibromoethane (695 mg) was added rapidly and the reaction mixture was stirred at room temperature for 3 hr. The reaction mixture was concentrated under vacuo and the residue partitioned between ethylacetate and a saturated aqueous solution of ammonium chloride. The aqueous layer was extracted with ethyl acetate and the combined organic layers were washed with water and brine, dried over sodium sulfate, filtered and concentrated in vacuo to afford a crude mixture containing 4-Bromo-2-(4-bromo-naphthalen-1-yl)-butyric acid methyl ester. This crude material was dissolved in tetrahydrofuran (13 mL) at room temperature and potassium carbonate (692 mg) was added. The mixture was stirred at room temperature for 36 hr, concentrated under vacuo, partitioned between ethyl acetate and a hydrochloric acid (0.1N). The aqueous layer was extracted with ethyl acetate and the combined organic layers were concentrated in vacuo. The crude mixture was concentrated to dryness and purified by chromatography on silica gel to yield the title compound as a colorless oil (215 mg; 30%). MS (ESI): m/z=290 [M−H]−.

c) (2S,4R)-1-[1-(4-Bromo-naphthalen-1-yl)-cyclopropanecarbonyl]-4-(2-chloro-benzenesulfonyl)-pyrrolidine-2-carboxylic acid (1-cyano-cyclopropyl)-amide The title compound was prepared in analogy to example 239 using example 15 (112 mg) and 1-(4-Bromo-naphthalen-1-yl)-cyclopropanecarboxylic acid (Example 472b) to yield 95 mg (53%) of colorless semisolid. MS (ESI): m/z=627.1 [M+H]+.

Example 473

(2S,4R)-4-(2-Chloro-benzenesulfonyl)-1-[1-(4-chloro-phenoxy)-cyclopropanecarbonyl]-pyrrolidine-2-carboxylic acid (1-cyano-cyclopropyl)-amide

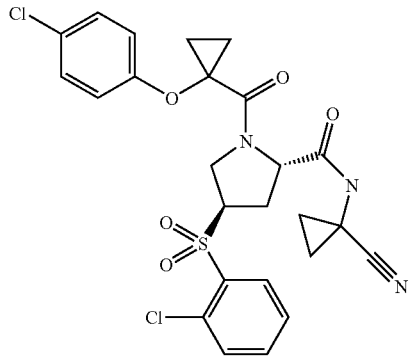

a) 3-(4-Chloro-phenoxy)-dihydro-furan-2-one

Cesium fluoride (7.6 g) was added to a solution of 4-chlorophenol (1.29 g) in dimethylformamide (35 mL) and the mixture was stirred at 100° C. for 5 min. 3-bromodihydrofuran-2(3H)-one (3.3 g) was added and the reaction mixture was heated to 120° C. for 1.5 h. The reaction mixture was poured into water and extracted with EtOAc. The aqueous layer was extracted with ethylacetate. The organic layers were washed with water, dried over sodium sulfate and filtered. The crude mixture was concentrated to dryness and purified by chromatography on silica gel to yield the title compound as a colorless oil (1.17 g; 55%). MS (ESI): m/z=212 [M]+.

b) 2-(4-Chloro-phenoxy)-4-hydroxy-butyric acid methyl ester 3-(4-chlorophenoxy)dihydro-furan-2(3H)-one, (Example 473a), 1.136 g), iodine (30.0 mg) and methanol (28.9 mL) were stirred at 65° C. for 24 hr. The reaction mixture was concentrated in vacuo. Exces of iodine was eliminante by adding an aqueous solution of sodium sulfite (10% w/w, 15 mL). The mixture was extracted with ethyl acetate. The organic layers were washed with brine (10 mL), dried over sodium sulfate and filtered. The crude mixture was concentrated to dryness and purified by chromatography on silica gel to yield the title compound as a colorless oil (433 mg; 33%). MS (ESI): m/z=244 [M]+.

c) 2-(4-Chloro-phenoxy)-4-(toluene-4-sulfonyloxy)-butyric acid methyl ester

To a solution of 2-(4-Chloro-phenoxy)-4-hydroxy-butyric acid methyl ester (Example 473b), 0.225 g) in dichloromethane (1.88 mL) at room temperature, was added triethylamine (116 mg) and 4-methylbenzene-1-sulfonyl chloride (177 mg). The mixture was stirred at 22° C. for 48 hr. The reaction mixture was partitioned between water and ethyl acetate. The phases were separated. The aqueous layer was extracted with ethyl acetate. The organic layers were washed with brine, dried over $Na_2SO_4$ and filtered. The crude mixture was concentrated to dryness and purified by chromatography on silica gel to yield the title compound as a colorless oil (169 mg; 46%). MS (ESI): m/z=419 [M+$NH_4$]+.

d) 1-(4-Chloro-phenoxy)-cyclopropanecarboxylic acid methyl ester

A suspension of sodium hydride in oil (55% w/w, 36.4 mg) was added to a solution of 2-(4-Chloro-phenoxy)-4-(toluene-4-sulfonyloxy)-butyric acid methyl ester (Example 473c), 145 mg) in 1,2-dimethoxyethane (2.27 mL) at room temperature. The mixture was stirred at 22° C. for 48 hr. The reaction mixture was filtered and the solid was washed with ethyl acetate. Water was added to the filtrate. The phases were separated and the aqueous layer was extracted with ethylacetate. The organic layers were washed with brine, dried over sodium sulfate and filtered. The crude mixture was concentrated to dryness and purified by chromatography on silica gel to yield the title compound as a colorless oil (56 mg; 68%). MS (ESI): m/z=226 [M]+.

e) 1-(4-Chloro-phenoxy)-cyclopropanecarboxylic acid as lithium salt

A mixture of 1-(4-Chloro-phenoxy)-cyclopropanecarboxylic acid methyl ester (Example 473d), 51 mg) and lithium hydroxide monohydrate (15.1 mg) in tetrahydrofuran (0.6 mL), water (0.3 mL) and MeOH (0.2 mL) was stirred at 22° C. for 2 hr. The reaction mixture was concentrated under vacuo to yield the title compound as a colorless oil (49 mg; 99%). MS (ESI): m/z=211.6 [M−H]−.

f) (2S,4R)-4-(2-Chloro-benzenesulfonyl)-1-[1-(4-chloro-phenoxy)-cyclopropanecarbonyl]-pyrrolidine-2-carboxylic acid (1-cyano-cyclopropyl)-amide The title compound was prepared in analogy to example 239 using example 42 (75 mg) and 1-(4-Chloro-phenoxy)-cyclopropanecarboxylic acid as lithium salt (Example 473 step 5) to yield 31 mg (30%) of white solid. MS (ESI): m/z=549.5 [M+H]+.

Example 474

(2S,4R)-4-(2-Chloro-benzenesulfonyl)-1-[5-methyl-2-(3-phenyl-propyl)-2H-pyrazol-3-yl]-pyrrolidine-2-carboxylic acid (1-cyano-cyclopropyl)-amide

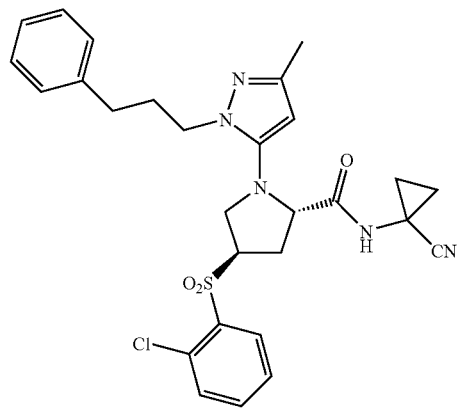

a) (2S,4R)-4-(2-Chlorophenylsulfonyl)-1-(3-methyl-1-(3-phenylpropyl)-1H-pyrazol-5-yl)pyrrolidine-2-carboxylic acid methyl ester In analogy to the procedure described in example 192 h, (2S,4R)-methyl 4-(2-chlorophenylsulfonyl)-1-(3-oxobutanethioyl)pyrrolidine-2-carboxylate (example 253c) was reacted with 1-(3-phenylpropyl)hydrazine (CAS Reg. No. 3381-02-0) to give the title compound as yellow oil. MS (ESI): m/z=502.1 [M+H]+.

b) (2S,4R)-4-(2-Chlorophenylsulfonyl)-1-(3-methyl-1-(3-phenylpropyl)-1H-pyrazol-5-yl)pyrrolidine-2-carboxylic acid In analogy to the procedure described in example 253e, (2S,4R)-4-(2-chlorophenylsulfonyl)-1-(3-methyl-1-(3-phenylpropyl)-1H-pyrazol-5-yl)pyrrolidine-2-carboxylic acid methyl ester was saponified in the presence of lithium hydroxide to give the title compound as colorless oil which was used in the next step without further purification. MS (ESI): m/z=486.2 [M−H]−.

c) (2S,4R)-4-(2-Chloro-benzenesulfonyl)-1-[5-methyl-2-(3-phenyl-propyl)-2H-pyrazol-3-yl]-pyrrolidine-2-carboxylic acid (1-cyano-cyclopropyl)-amide In analogy to the procedure described in example 237, (2S,4R)-4-(2-chlorophenylsulfonyl)-1-(3-methyl-1-(3-phenylpropyl)-1H-pyrazol-5-yl)pyrrolidine-2-carboxylic acid was reacted with 1-amino-cyclopropanecarbonitrile hydrochloride (CAS Reg. No. 127946-77-4) in the presence of

Example 475

Formate 4-(2-{5-[(2S,4R)-4-(2-chloro-benzenesulfonyl)-2-(1-cyano-cyclopropylcarbamoyl)-pyrrolidin-1-yl]-3-methyl-pyrazol-1-yl}-ethyl)-morpholin-4-ium

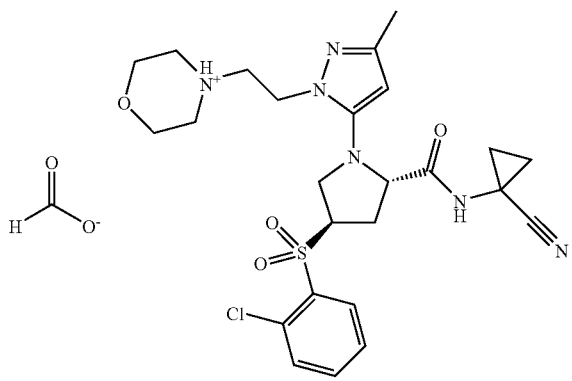

a) (2S,4R)-4-(2-Chlorophenylsulfonyl)-1-(3-methyl-1-(2-morpholinoethyl)-1H-pyrazol-5-yl)pyrrolidine-2-carboxylic acid methyl ester. In analogy to the procedure described in example 192 h, (2S,4R)-methyl 4-(2-chlorophenylsulfonyl)-1-(3-oxobutanethioyl)pyrrolidine-2-carboxylate (example 253c) was reacted with 4-(2-hydrazinoethyl)morpholine (CAS Reg. No. 2154-24-7) to give the title compound as yellow oil. MS (ESI): m/z=497.3 [M+H]+.

b) (2S,4R)-4-(2-Chlorophenylsulfonyl)-1-(3-methyl-1-(2-morpholinoethyl)-1H-pyrazol-5-yl)pyrrolidine-2-carboxylic acid In analogy to the procedure described in example 253e, (2S,4R)-4-(2-chlorophenylsulfonyl)-1-(3-methyl-1-(2-morpholinoethyl)-1H-pyrazol-5-yl)pyrrolidine-2-carboxylic acid methyl ester was saponified in the presence of lithium hydroxide to give the title compound as brown oil which was used in the next step without further purification. MS (ESI): m/z=483.4 [M+H]+.

c) Formate 4-(2-{5-[(2S,4R)-4-(2-chloro-benzenesulfonyl)-2-(1-cyano-cyclopropylcarbamoyl)-pyrrolidin-1-yl]-3-methyl-pyrazol-1-yl}-ethyl)-morpholin-4-ium In analogy to the procedure described in example 237, (2S,4R)-4-(2-chlorophenylsulfonyl)-1-(3-methyl-1-(2-morpholinoethyl)-1H-pyrazol-5-yl)pyrrolidine-2-carboxylic acid was reacted with 1-amino-cyclopropanecarbonitrile hydrochloride (CAS Reg. No. 127946-77-4) in the presence of HATU and DIEA to give the title compound as colorless oil HATU and DIEA to give the title compound as off-white semi-solid. MS (ESI): m/z=552.2 [M+H]+.

Example 476

(2S,4R)-4-(2-Chloro-benzenesulfonyl)-1-[5-methyl-2-(3-methyl-3H-imidazol-4-ylmethyl)-2H-pyrazol-3-yl]-pyrrolidine-2-carboxylic acid (1-cyano-cyclopropyl)-amide

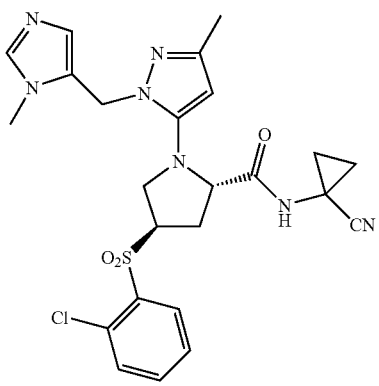

a) (2S,4R)-Methyl 4-(2-chlorophenylsulfonyl)-1-(3-methyl-1-((1-methyl-1H-imidazol-5-yl)methyl)-1H-pyrazol-5-yl)pyrrolidine-2-carboxylate In analogy to the procedure described in example 192 h, (2S,4R)-methyl 4-(2-chlorophenylsulfonyl)-1-(3-oxobutanethioyl)pyrrolidine-2-carboxylate (example 253c) was reacted with 5-(hydrazinylmethyl)-1-methyl-1H-imidazole (CAS Reg. No. 887592-51-0) to give the title compound as yellow oil. MS (ESI): m/z=478.1 [M+H]

b) Lithium (2S,4R)-4-(2-chlorophenylsulfonyl)-1-(3-methyl-1-((1-methyl-1H-imidazol-5-yl)methyl)-1H-pyrazol-5-yl)pyrrolidine-2-carboxylate In analogy to the procedure described in example 253e, (2S,4R)-methyl 4-(2-chlorophenylsulfonyl)-1-(3-methyl-1-((1-methyl-1H-imidazol-5-yl)methyl)-1H-pyrazol-5-yl)pyrrolidine-2-carboxylate was saponified in the presence of lithium hydroxide to give the title compound as brown solid which was used in the next step without further purification. MS (ESI): m/z=462.1 [M−H]−.

c) (2S,4R)-4-(2-Chloro-benzenesulfonyl)-1-[5-methyl-2-(3-methyl-3H-imidazol-4-ylmethyl)-2H-pyrazol-3-yl]-pyrrolidine-2-carboxylic acid (1-cyano-cyclopropyl)-amide In analogy to the procedure described in example 237, lithium (2S,4R)-4-(2-chlorophenylsulfonyl)-1-(3-methyl-1-((1-methyl-1H-imidazol-5-yl)methyl)-1H-pyrazol-5-yl)pyrrolidine-2-carboxylate was reacted with 1-amino-cyclopropanecarbonitrile hydrochloride (CAS Reg. No. 127946-77-4) after purification by preparative HPLC using formic acid as coeluent. MS (ESI): m/z=545.2 [M−H]−.

in the presence of HATU and DIEA to give the title compound as orange solid. MS (ESI): m/z=528.2 [M+H]+.

Example 477

(2S,4R)-4-(2-Chloro-benzenesulfonyl)-1-(2-cyclohexyl-5-methyl-2H-pyrazol-3-yl)-pyrrolidine-2-carboxylic acid (1-cyano-cyclopropyl)-amide

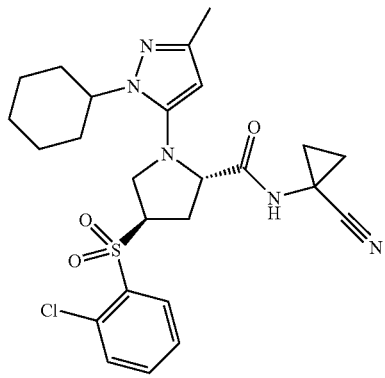

a) (2S,4R)-4-(2-Chloro-benzenesulfonyl)-1-(2-cyclohexyl-5-methyl-2H-pyrazol-3-yl)-pyrrolidine-2-carboxylic acid methyl ester In analogy to the procedure described in example 192 h, (2S,4R)-methyl 4-(2-chlorophenylsulfonyl)-1-(3-oxobutanethioyl)pyrrolidine-2-carboxylate (example 253c) was reacted with cyclohexylhydrazine hydrochloride (CAS Reg. No. 24214-73-1) to give the title compound as orange oil. MS (ESI): m/z=466.2 [M+H]+.

b) (2S,4R)-4-(2-Chloro-benzenesulfonyl)-1-(2-cyclohexyl-5-methyl-2H-pyrazol-3-yl)-pyrrolidine-2-carboxylic acid In analogy to the procedure described in example 253e, (2S,4R)-4-(2-chloro-benzenesulfonyl)-1-(2-cyclohexyl-5-methyl-2H-pyrazol-3-yl)-pyrrolidine-2-carboxylic acid methyl ester was saponified in the presence of lithium hydroxide to give the title compound as yellow oil which was used in the next step without further purification. MS (ESI): m/z=450.0 [M−H]−.

c) (2S,4R)-4-(2-Chloro-benzenesulfonyl)-1-(2-cyclohexyl-5-methyl-2H-pyrazol-3-yl)-pyrrolidine-2-carboxylic acid (1-cyano-cyclopropyl)-amide In analogy to the procedure described in example 237, (2S,4R)-4-(2-chloro-benzenesulfonyl)-1-(2-cyclohexyl-5-methyl-2H-pyrazol-3-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as off-white solid. MS (ESI): m/z=516.3 [M+H]+.

Example 478

(2S,4R)-4-(2-Chloro-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide

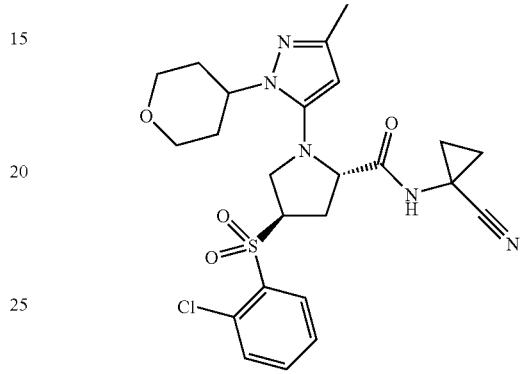

a) (2S,4R)-4-(2-Chloro-benzenesulfonyl)-1-[5-methyl-2-(tetrahydro-pyran-4-yl)-2H-pyrazol-3-yl]-pyrrolidine-2-carboxylic acid methyl ester In analogy to the procedure described in example 192 h, (2S,4R)-methyl 4-(2-chlorophenylsulfonyl)-1-(3-oxobutanethioyl)pyrrolidine-2-carboxylate (example 253c) was reacted with (tetrahydropyran-4-yl)hydrazine hydrochloride (CAS Reg. No. 194543-22-1) to give the title compound as orange oil. MS (ESI): m/z=468.1 [M+H]+.

b) (2S,4R)-4-(2-Chloro-benzenesulfonyl)-1-[5-methyl-2-(tetrahydro-pyran-4-yl)-2H-pyrazol-3-yl]-pyrrolidine-2-carboxylic acid In analogy to the procedure described in example 253e, (2S,4R)-4-(2-chloro-benzenesulfonyl)-1-[5-methyl-2-(tetrahydro-pyran-4-yl)-2H-pyrazol-3-yl]-pyrrolidine-2-carboxylic acid methyl ester was saponified in the presence of lithium hydroxide to give the title compound as yellow oil which was used in the next step without further purification. MS (ESI): m/z=453.8 [M+H]+.

c) (2S,4R)-4-(2-Chloro-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide In analogy to the procedure described in example 237, (2S,4R)-4-(2-chloro-benzenesulfonyl)-1-[5-methyl-2-(tetrahydro-pyran-4-yl)-2H-pyrazol-3-yl]-pyrrolidine-2-carboxylic acid was reacted with 1-amino-cyclopropanecarbonitrile hydrochloride (CAS Reg. No. 127946-77-4) in the presence of HATU and DIEA to give the title compound as yellow oil. MS (ESI): m/z=518.2 [M+H]+.

Example 479

(2S,4R)-4-[(2-Chlorophenyl)sulfonyl]-N-(1-cyano-cyclopropyl)-1-[1-(1,1-dioxidotetrahydro-2H-thiopyran-4-yl)-3-methyl-1H-pyrazol-5-yl]-L-prolinamide

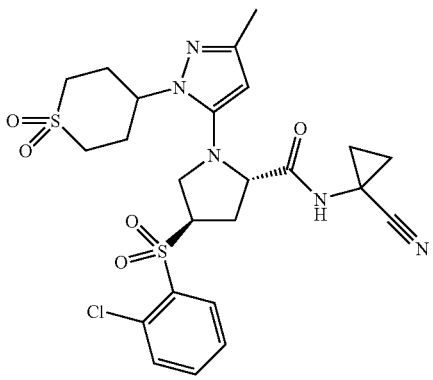

To an ice cold solution of (2S,4R)-4-(2-chlorophenylsulfonyl)-N-(1-cyanocyclopropyl)-1-(3-methyl-1-(tetrahydro-2H-thiopyran-4-yl)-1H-pyrazol-5-yl)pyrrolidine-2-carboxamide (20 mg, 37.4 umol; example 465c) in dichloromethane (0.4 ml) was added MCPBA (5.45 mg, 77.9 umol). The mixture was stirred at ambient temperature for 20 hours. Additional MCPBA (5.45 mg, 77.9 umol) was added. The reaction mixture was stirred for 48 h at ambient temperature. MCPBA (5.45 mg, 77.9 umol) was added and the reaction mixture was stirred for 3 d at ambient temperature, poured into 25 ml aqueous sodium sulfite solution and extracted with dichloromethane (2×50 ml). The organic layers were washed with saturated aqueous sodium hydrogen carbonate solution (3×15 ml). The combined organic layers were washed with brine (2×25 ml), dried over sodium sulfate and filtered. The solvent was removed in vacuo to give 15 mg of a colorless oil. The crude material was purified by preparative thin layer chromatography (silica gel, dichloromethane/MeOH) to give the title compound (2 mg, 3.4 umol; 9%) as colorless oil. MS (ESI): m/z=518.2 [M+H]$^+$.

Example 480

(2S,4R)-4-[2-Chloro-4-(2,2,2-trifluoro-ethoxy)-benzenesulfonyl]-1-(2-cyclobutyl-5-methyl-2H-pyrazol-3-yl)-pyrrolidine-2-carboxylic acid (1-cyano-cyclopropyl)-amide

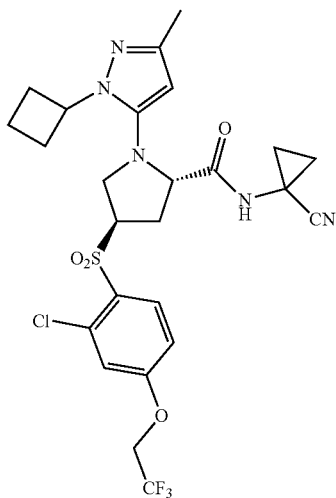

In analogy to the procedure described in example 392, (2S,4R)-4-(2-chloro-4-fluoro-benzenesulfonyl)-1-(2-cyclobutyl-5-methyl-2H-pyrazol-3-yl)-pyrrolidine-2-carboxylic acid (1-cyano-cyclopropyl)-amide (example 385b) was reacted with 2,2,2,-trifluoroethanol (CAS Reg. No. 75-89-8 99) to give the title compound as colorless solid. MS (ESI): m/z=586.0 [M+H]$^+$.

Example 481

(2S,4R)-4-[4-(4-tert-Butyl-piperazin-1-yl)-2-chloro-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide

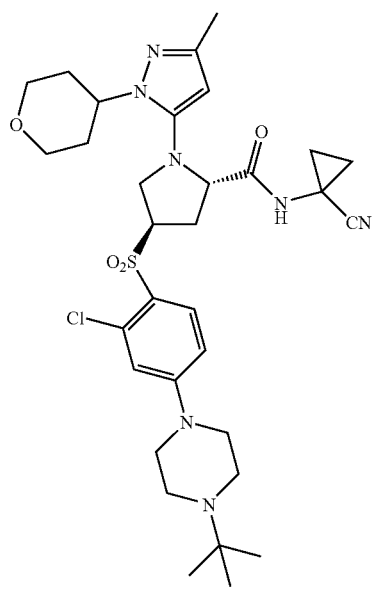

In analogy to the procedure described in example 389, (2S,4R)-4-(2-chloro-4-fluorophenylsulfonyl)-N-(1-cyano-cyclopropyl)-1-(3-methyl-1-(tetrahydro-2H-pyran-4-yl)-1H-pyrazol-5-yl)pyrrolidine-2-carboxamide (example 464d) was reacted with 1-tert-butylpiperazine (CAS Reg. No. 38216-72-7) to give the title compound as colorless oil. MS (ESI): m/z=658.4 [M+H]$^+$.

Example 482

(2S,4R)-4-[2-Chloro-4-(2,2,2-trifluoro-ethoxy)-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide

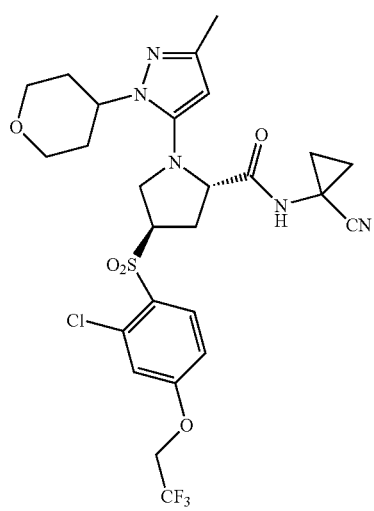

In analogy to the procedure described in example 392, (2S,4R)-4-(2-chloro-4-fluorophenylsulfonyl)-N-(1-cyano-cyclopropyl)-1-(3-methyl-1-(tetrahydro-2H-pyran-4-yl)-1H-pyrazol-5-yl)pyrrolidine-2-carboxamide (example 464d) was reacted with 2,2,2,-trifluoroethanol (CAS Reg. No. 75-89-8 99) to give the title compound after purification by preparative chiral HPLC as colorless oil. MS (ESI): m/z=616.1 [M+H]$^+$.

Example 483

(2S,4R)-4-[2-Chloro-4-(3,3-difluoro-azetidin-1-yl)-benzenesulfonyl]-1-(5-methyl-2-phenethyl-2H-pyrazol-3-yl)-pyrrolidine-2-carboxylic acid (1-cyano-cyclopropyl)-amide

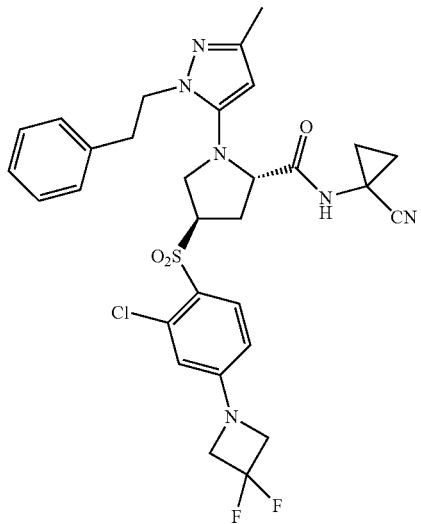

a) (2S,4R)-4-(2-Chloro-4-fluorophenylsulfonyl)-1-(3-methyl-1-phenethyl-1H-pyrazol-5-yl)pyrrolidine-2-carboxylic acid methyl ester In analogy to the procedure described in example 192 h, (2S,4R)-methyl 4-(2-chloro-4-fluorophenylsulfonyl)-1-(3-oxobutanethioyl)pyrrolidine-2-carboxylate (example 464 a) was reacted with 2-phenethyl-hydrazine sulfate (CAS Reg. No. 56-51-4) to give the title compound as yellow oil. MS (ESI): m/z=506.1 [M+H]$^+$.

b) (2S,4R)-4-(2-Chloro-4-fluorophenylsulfonyl)-1-(3-methyl-1-phenethyl-1H-pyrazol-5-yl)pyrrolidine-2-carboxylic acid In analogy to the procedure described in example 253e, (2S,4R)-4-(2-chloro-4-fluorophenylsulfonyl)-1-(3-methyl-1-phenethyl-1H-pyrazol-5-yl)pyrrolidine-2-carboxylic acid methyl ester was saponified in the presence of lithium hydroxide to give the title compound as yellow foam which was used in the next step without further purification. MS (ESI): m/z=492.1 [M+H]$^+$.

c) (2S,4R)-4-(2-Chloro-4-fluorophenylsulfonyl)-N-(1-cyanocyclopropyl)-1-(3-methyl-1-phenethyl-1H-pyrazol-5-yl)pyrrolidine-2-carboxamide In analogy to the procedure described in example 237, (2S,4R)-4-(2-chloro-4-fluorophenylsulfonyl)-1-(3-methyl-1-phenethyl-1H-pyrazol-5-yl)pyrrolidine-2-carboxylic acid was reacted with 1-amino-cyclopropanecarbonitrile hydrochloride (CAS Reg. No. 127946-77-4) in the presence of HATU and DIEA to give the title compound as off-white foam. MS (ESI): m/z=556.2 [M+H]$^+$.

d) (2S,4R)-4-[2-Chloro-4-(3,3-difluoro-azetidin-1-yl)-benzenesulfonyl]-1-(5-methyl-2-phenethyl-2H-pyrazol-3-yl)-pyrrolidine-2-carboxylic acid (1-cyano-cyclopropyl)-amide In analogy to the procedure described in example 389, (2S,4R)-4-(2-chloro-4-fluorophenylsulfonyl)-N-(1-cyanocyclopropyl)-1-(3-methyl-1-phenethyl-1H-pyrazol-5-yl)pyrrolidine-2-carboxamide was reacted with 3,3-difluoro-azetidine hydrochloride (CAS Reg. No. 288315-03-7) in acetonitrile at 90° C. for 48 h to give the title compound as off-white foam. MS (ESI): m/z=629.2 [M+H]$^+$.

Example 484

(2S,4R)-4-[2-Chloro-4-(2,2,2-trifluoro-ethoxy)-benzenesulfonyl]-1-(5-methyl-2-phenethyl-2H-pyrazol-3-yl)-pyrrolidine-2-carboxylic acid (1-cyano-cyclopropyl)-amide

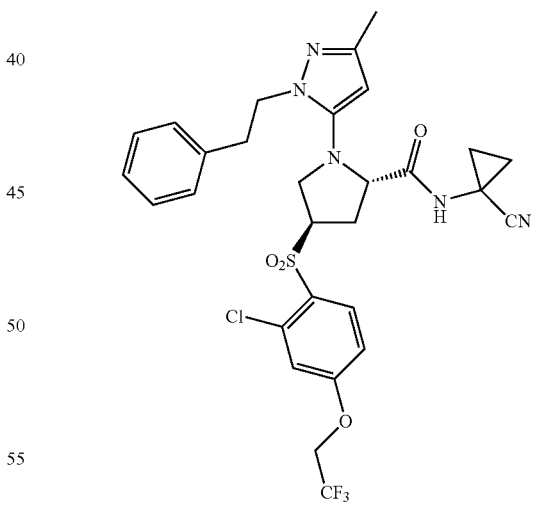

In analogy to the procedure described in example 392, (2S,4R)-4-(2-chloro-4-fluorophenylsulfonyl)-N-(1-cyanocyclopropyl)-1-(3-methyl-1-phenethyl-1H-pyrazol-5-yl)pyrrolidine-2-carboxamide (example 484c) was reacted with 2,2,2,-trifluoroethanol (CAS Reg. No. 75-89-8 99) to give the title compound as colorless oil. MS (ESI): m/z=636.2 [M+H]$^+$.

Example 485

(2S,4R)-4-[4-(4-tert-Butyl-piperazin-1-yl)-2-chloro-benzenesulfonyl]-1-(5-methyl-2-phenethyl-2H-pyrazol-3-yl)-pyrrolidine-2-carboxylic acid (1-cyano-cyclopropyl)-amide

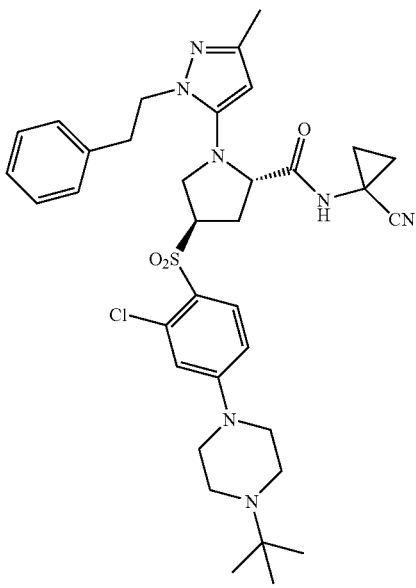

In analogy to the procedure described in example 392, (2S,4R)-4-(2-chloro-4-fluorophenylsulfonyl)-N-(1-cyano-cyclopropyl)-1-(3-methyl-1-phenethyl-1H-pyrazol-5-yl)pyrrolidine-2-carboxamide (example 484c) was reacted with 1-tert-butylpiperazine (CAS Reg. No. 38216-72-7) to give the title compound as colorless oil. MS (ESI): m/z=678.3 $[M+H]^+$.

Example 486

(2S,4R)-4-(2-Chloro-benzenesulfonyl)-1-(3-chloro-[1,2,4]thiadiazol-5-yl)-pyrrolidine-2-carboxylic acid (1-cyano-cyclopropyl)-amide

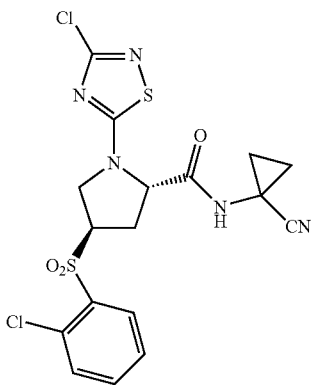

a) (2S,4R)-4-(2-Chloro-benzenesulfonyl)-1-(3-chloro-[1,2,4]thiadiazol-5-yl)-pyrrolidine-2-carboxylic acid methyl ester In analogy to the procedure described in example 335a, (2S,4R)-4-(2-chloro-benzenesulfonyl)-pyrrolidine-2-carboxylic acid methyl ester (example 253a) was reacted with 3,5-dichloro-[1,2,4]thiadiazole (CAS Reg. No. 2254-88-8) in a shaking reactor at 55° C. for 48 h to give the title compound as red oil. MS (ESI): m/z=422.0 $[M+H]^+$.

b) (2S,4R)-4-(2-Chloro-benzenesulfonyl)-1-(3-chloro-[1,2,4]thiadiazol-5-yl)-pyrrolidine-2-carboxylic acid In analogy to the procedure described in example 253e, (2S,4R)-4-(2-chloro-benzenesulfonyl)-1-(3-chloro-[1,2,4]thiadiazol-5-yl)-pyrrolidine-2-carboxylic acid methyl ester was saponified in the presence of lithium hydroxide to give the title compound as yellow oil which was used in the next step without further purification. MS (ESI): m/z=406.0 $[M-H]^-$.

c) (2S,4R)-4-(2-Chloro-benzenesulfonyl)-1-(3-chloro-[1,2,4]thiadiazol-5-yl)-pyrrolidine-2-carboxylic acid (1-cyano-cyclopropyl)-amide In analogy to the procedure described in example 237, (2S,4R)-4-(2-chloro-benzenesulfonyl)-1-(3-chloro-[1,2,4]thiadiazol-5-yl)-pyrrolidine-2-carboxylic acid was reacted with 1-amino-cyclopropanecarbonitrile hydrochloride (CAS Reg. No. 127946-77-4) in the presence of HATU and DIEA to give the title compound as white solid. MS (ESI): m/z=472.0 $[M+H]^+$.

Example 487

(2R,4R)-4-[2-Chloro-4-(2,2,2-trifluoro-ethoxy)-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide

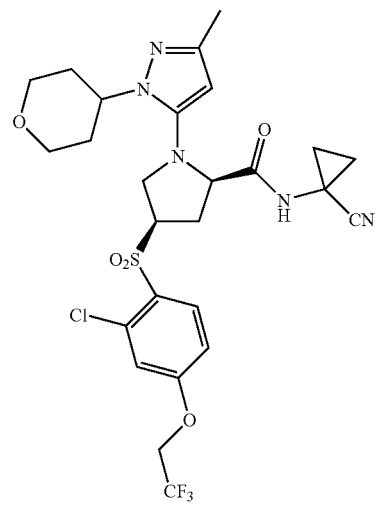

In analogy to the procedure described in example 392, (2S,4R)-4-(2-chloro-4-fluorophenylsulfonyl)-N-(1-cyano-cyclopropyl)-1-(3-methyl-1-(tetrahydro-2H-pyran-4-yl)-1H-pyrazol-5-yl)pyrrolidine-2-carboxamide (example 464d) was reacted with 2,2,2-trifluoroethanol (CAS Reg. No. 75-89-8 99) to give the title compound after purification by preparative chiral HPLC as colorless oil. MS (ESI): m/z=616.1 $[M+H]^+$.

Example 488

(2S,4R)-4-[2-Chloro-4-(2-methoxy-ethoxy)-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide

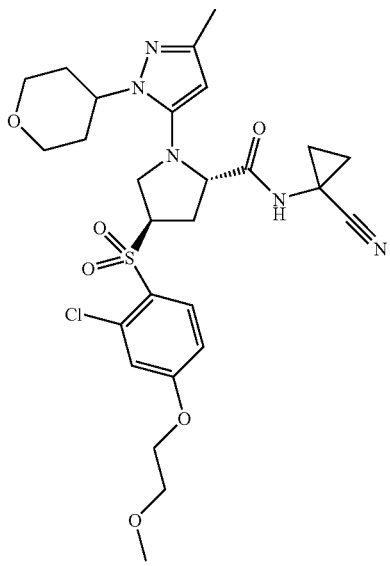

In analogy to the procedure described in example 392, (2S,4R)-4-(2-chloro-4-fluorophenylsulfonyl)-N-(1-cyano-cyclopropyl)-1-(3-methyl-1-(tetrahydro-2H-pyran-4-yl)-1H-pyrazol-5-yl)pyrrolidine-2-carboxamide (example 464d) was reacted with 2-methoxyethanol (CAS Reg. No. 109-86-4) to give the title compound as colorless oil. MS (ESI): m/z=592.2 [M+H]$^+$.

Example 489

(2S,4R)-4-[2-Chloro-4-(2-methoxy-ethoxy)-benzenesulfonyl]-1-(2-cyclobutyl-5-methyl-2H-pyrazol-3-yl)-pyrrolidine-2-carboxylic acid (1-cyano-cyclopropyl)-amide

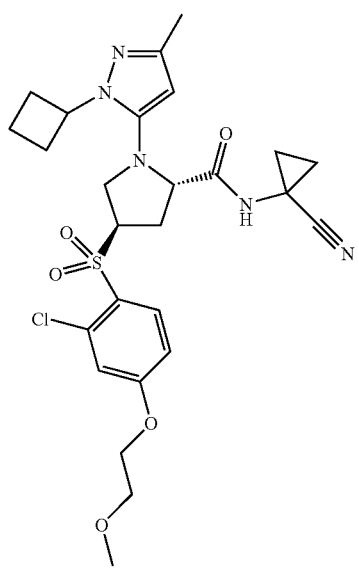

In analogy to the procedure described in example 392, (2S,4R)-4-(2-chloro-4-fluoro-benzenesulfonyl)-1-(2-cyclobutyl-5-methyl-2H-pyrazol-3-yl)-pyrrolidine-2-carboxylic acid (1-cyano-cyclopropyl)-amide (example 385b) was reacted with 2-methoxyethanol (CAS Reg. No. 109-86-4) to give the title compound as colorless oil. MS (ESI): m/z=562.2 [M+H]$^+$.

Example 490

2S,4R)-4-(2-Chloro-4-pyrazol-1-yl-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide

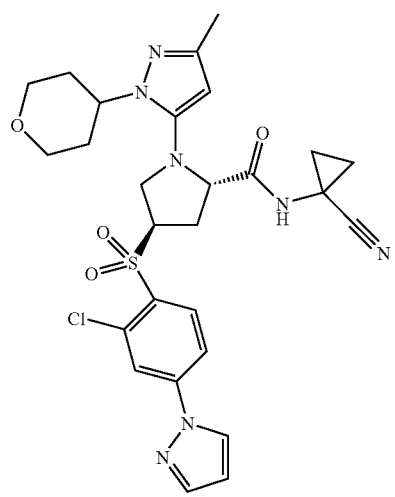

In analogy to the procedure described in example 416, (2S,4R)-4-(2-chloro-4-fluorophenylsulfonyl)-N-(1-cyano-cyclopropyl)-1-(3-methyl-1-(tetrahydro-2H-pyran-4-yl)-1H-pyrazol-5-yl)pyrrolidine-2-carboxamide (example 464d) was reacted with pyrazole (CAS Reg. No. 288-11-9) to give the title compound as colorless oil. MS (ESI): m/z=584.2 [M+H]$^+$.

Example 491

(2S,4R)-4-(2-Chloro-4-pyrazol-1-yl-benzenesulfonyl)-1-(2-cyclobutyl-5-methyl-2H-pyrazol-3-yl)-pyrrolidine-2-carboxylic acid (1-cyano-cyclopropyl)-amide

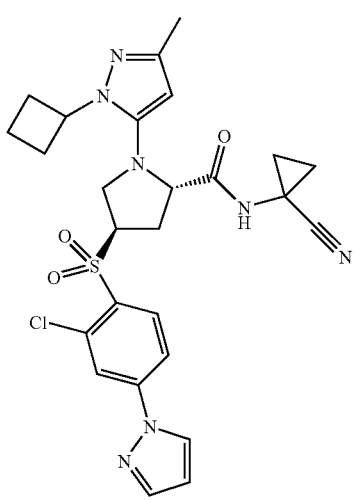

In analogy to the procedure described in example 392, (2S,4R)-4-(2-chloro-4-fluoro-benzenesulfonyl)-1-(2-cyclobutyl-5-methyl-2H-pyrazol-3-yl)-pyrrolidine-2-carboxylic acid (1-cyano-cyclopropyl)-amide (example 385b) was reacted with pyrazole (CAS Reg. No. 288-11-9) to give the title compound as colorless oil. MS (ESI): m/z=554.3 [M+H]$^+$.

Example 492

(2S,4R)-4-(2-Chloro-4-fluoro-benzenesulfonyl)-1-(5-methyl-2-phenethyl-2H-pyrazol-3-yl)-pyrrolidine-2-carboxylic acid (1-cyano-cyclopropyl)-amide

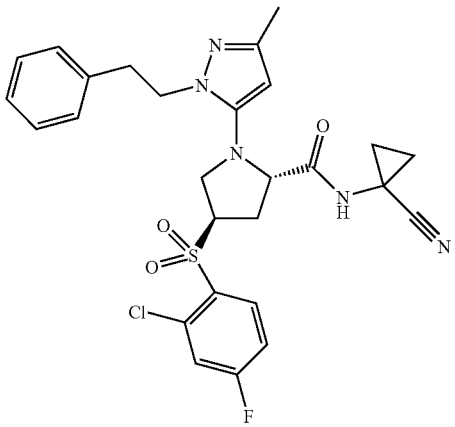

In analogy to the procedure described in example 237, (2S,4R)-4-(2-chloro-4-fluorophenylsulfonyl)-1-(3-methyl-1-phenethyl-1H-pyrazol-5-yl)pyrrolidine-2-carboxylic acid (example 484b) was reacted with 1-amino-cyclopropanecarbonitrile hydrochloride (CAS Reg. No. 127946-77-4) in the presence of HATU and DIEA to give the title compound as off-white foam. MS (ESI): m/z=556.2 [M+H]$^+$.

Example 493

(2S,4R)-4-(2-Chloro-4-fluoro-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide

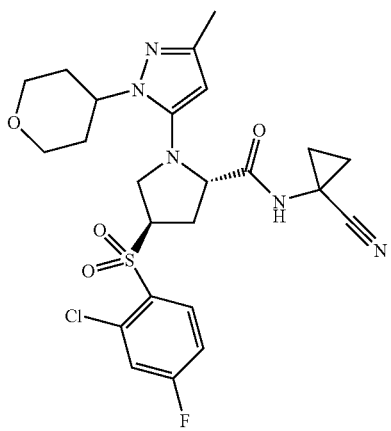

In analogy to the procedure described in example 237, (2S,4R)-4-(2-chloro-4-fluorophenylsulfonyl)-1-(3-methyl-1-(tetrahydro-2H-pyran-4-yl)-1H-pyrazol-5-yl)pyrrolidine-2-carboxylic acid (example 464c) was reacted with 1-amino-cyclopropanecarbonitrile hydrochloride (CAS Reg. No. 127946-77-4) in the presence of HATU and DIEA to give the title compound as off-white solid. MS (ESI): m/z=536.1 [M+H]$^+$.

Example 494

Cathepsin Enzyme Inhibition Assay

Enzyme activity is measured by observing the increase in fluorescence intensity caused by cleavage of a peptide substrate containing a fluorophore whose emission is quenched in the intact peptide.

Assay buffer: 100 mM potassium phosphate pH 6.5, EDTA-Na 5 mM, Triton X-100 0.001%, DDT 5 mM.

Enzymes (all at 1 nM): human and mouse Cathepsin S, Cat K, Cat B, Cat L Substrate (20 µM): Z-Val-Val-Arg-AMC, except for Cat K which uses Z-Leu-Arg-AMC (both from Bachem).

Z=Benzyloxycarbonyl.

AMC=7-Amino-4-Methyl-Coumarin.

Final volume: 100 µL.

Excitation 360 nm, Emission 465 nm.

Enzyme is added to the substance dilutions in 96-well microtitre plates and the reaction is started with substrate. Fluorescence emission is measured over 20 minutes, during which time a linear increase is observed in the absence of inhibitor. $IC_{50}$ are calculated by standard methods. The results are expressed in µM in the following table.

In the foregoing assay, the compounds according to the invention have an $IC_{50}$ for Cathepsin S which is between 0.00001 and 100 µM, preferably between 0.00001 and 50 µM, more preferably between 0.00001 and 20 µM.

In the foregoing assay, the compounds according to the invention have an $IC_{50}$ for Cathepsin L which is between 0.00001 and 200 µM, preferably between 0.00001 and 100 µM, more preferably between 0.00001 and 80 µM.

| Example | CatS $IC_{50}$ | CatL $IC_{50}$ |
|---|---|---|
| 1 | 0.015 | 25 |
| 2 | 0.0435 | 25 |
| 3 | 0.011 | 25 |
| 4 | 0.0052 | 16.5 |
| 5 | 0.0008 | 9.7733 |
| 6 | 0.0385 | 25 |
| 7 | 0.0027 | 25 |
| 8 | 0.0007 | 25 |
| 9 | 0.0006 | 25 |
| 10 | 0.0007 | 25 |
| 11 | 0.03 | 25 |
| 12 | 0.018 | 42.23 |
| 13 | 0.0465 | 25 |
| 14 | 0.0032 | 25 |
| 15 | 0.0045 | 4.925 |
| 16 | 0.0132 | 25 |
| 17 | 0.032 | 25 |
| 18 | 0.0033 | 30.29 |
| 19 | 0.0013 | 25 |
| 20 | 0.001 | 25 |
| 21 | 0.0008 | 40.79 |
| 22 | 0.0005 | 25 |
| 23 | 0.0009 | 25 |
| 24 | 0.0026 | 25 |
| 25 | 0.0023 | 25 |
| 26 | 0.0028 | 25 |
| 27 | 0.0022 | 25 |
| 28 | 0.0015 | 25 |

| Example | CatS IC$_{50}$ | CatL IC$_{50}$ |
|---|---|---|
| 29 | 0.0008 | 39.86 |
| 30 | 0.003 | 25 |
| 31 | 0.002 | 25 |
| 32 | 0.005 | 25 |
| 33 | 0.6752 | 25 |
| 34 | 0.7656 | 25 |
| 35 | 4.0976 | 25 |
| 36 | 0.0005 | 1.275 |
| 37 | 1.03 | 25 |
| 38 | 0.005 | 25 |
| 39 | 0.0022 | 50.21 |
| 40 | 0.0052 | 41.41 |
| 41 | 0.0312 | 25 |
| 42 | 0.005 | 9.43 |
| 43 | 0.0022 | 25 |
| 44 | 0.1515 | 25 |
| 45 | 0.3783 | 25 |
| 46 | 0.2078 | 25 |
| 47 | 0.0014 | |
| 48 | 0.235 | 25 |
| 49 | 0.0018 | 6.92 |
| 50 | 0.0044 | 8.77 |
| 51 | 0.026 | 25 |
| 52 | 0.014 | 25 |
| 53 | 0.0052 | 25 |
| 54 | 0.21 | 5.34 |
| 55 | 0.0148 | 25 |
| 56 | 0.0427 | 25 |
| 57 | 0.0143 | 16.9767 |
| 58 | 0.0016 | 27.36 |
| 59 | 0.0018 | 12.155 |
| 60 | 0.0005 | 12.79 |
| 61 | 0.0012 | 22.465 |
| 62 | 0.0012 | 21.025 |
| 63 | 0.1 | 25 |
| 64 | 0.109 | 25 |
| 65 | 0.0006 | 25 |
| 66 | 0.0006 | 25 |
| 67 | 0.0002 | 25 |
| 68 | 0.0003 | 25 |
| 69 | 0.0004 | 25 |
| 70 | 0.0016 | 25.175 |
| 71 | 0.0005 | 25 |
| 72 | 0.0008 | 25 |
| 73 | 0.0127 | 25 |
| 74 | 0.0066 | 25 |
| 75 | 0.0008 | 6.7867 |
| 76 | 0.0014 | 8.8 |
| 77 | 0.0002 | 8.2533 |
| 78 | 0.0185 | 25 |
| 79 | 0.0014 | 29.715 |
| 80 | 0.0008 | 9.7733 |
| 81 | 0.0032 | 6.035 |
| 82 | 0.0087 | 6.8 |
| 83 | 0.0305 | 62.15 |
| 84 | 0.055 | 25 |
| 85 | 0.0094 | 25 |
| 86 | 0.023 | 14.57 |
| 87 | 0.0375 | 4.7167 |
| 88 | 0.275 | 25 |
| 89 | 0.11 | 25 |
| 90 | 0.0845 | 25 |
| 91 | 0.12 | 25 |
| 92 | 0.041 | 61.72 |
| 93 | 0.9655 | 25 |
| 94 | 0.945 | 39.985 |
| 95 | 0.0076 | 25 |
| 96 | 0.0026 | 31.5433 |
| 97 | 0.0024 | 22.79 |
| 98 | 0.0011 | 15.6767 |
| 99 | 0.0026 | 25 |
| 100 | 0.0077 | 25 |
| 101 | 0.0067 | 25 |
| 102 | 0.0036 | 25 |
| 103 | 0.0016 | 25 |
| 104 | 0.0002 | 25 |
| 105 | 0.0003 | 25 |
| 106 | 0.0004 | 25 |
| 107 | 0.025 | 16.64 |
| 108 | 0.0058 | 47.705 |
| 109 | 0.0127 | 25 |
| 110 | 0.0605 | 25 |
| 111 | 0.0007 | 25 |
| 112 | 0.0008 | 25 |
| 113 | 3.135 | 25 |
| 114 | 3.505 | 25 |
| 115 | 0.048 | 3.47 |
| 116 | 0.0355 | 25 |
| 117 | 0.0865 | 25 |
| 118 | 0.0009 | 25 |
| 119 | 0.0071 | 25 |
| 120 | 0.0028 | 25 |
| 121 | 0.0041 | 23.695 |
| 122 | 0.0094 | 23.815 |
| 123 | 2.61 | 25 |
| 124 | 0.0125 | 25 |
| 125 | 0.195 | 25 |
| 126 | 1.25 | 25 |
| 127 | 0.002 | 5.995 |
| 128 | 0.0014 | 17.3 |
| 129 | 0.008 | 20.42 |
| 130 | 0.0024 | 25 |
| 131 | 0.0009 | 33.93 |
| 132 | 0.0038 | 34.955 |
| 133 | 0.0009 | 23.36 |
| 134 | 0.0062 | 25 |
| 135 | 0.0003 | 3.15 |
| 136 | 0.0022 | 12.565 |
| 137 | 0.001 | 25 |
| 138 | 0.0034 | 28.6 |
| 139 | 0.0078 | 25 |
| 140 | 0.0059 | 24.53 |
| 141 | 0.0006 | 3.46 |
| 142 | 0.0003 | 2.48 |
| 143 | 0.0043 | 28.075 |
| 144 | 0.0097 | 28.2033 |
| 145 | 0.0006 | 11.755 |
| 146 | 0.0064 | 25.5367 |
| 147 | 0.0004 | 13.644 |
| 148 | 0.016 | 25 |
| 149 | 0.0007 | 8.1033 |
| 150 | 0.0017 | 27.9367 |
| 151 | 0.0058 | 25 |
| 152 | 0.0022 | 30.83 |
| 153 | 0.0025 | 43.98 |
| 154 | 0.0018 | 6.63 |
| 155 | 0.0025 | 8.32 |
| 156 | 0.0004 | 4.395 |
| 157 | 0.0004 | 4.405 |
| 158 | 0.12 | 25 |
| 159 | 2.605 | 25 |
| 160 | 0.006 | 25 |
| 161 | 0.0004 | 6.065 |
| 162 | 0.0235 | 25 |
| 163 | 0.0003 | 2.62 |
| 164 | 0.0008 | 25 |
| 165 | 0.1097 | 25 |
| 166 | 0.0006 | 25 |
| 167 | 0.0014 | 17.445 |
| 168 | 0.0006 | 8.7975 |
| 169 | 0.0004 | 7.585 |
| 170 | 0.001 | 18.38 |
| 171 | 0.007 | 25 |
| 172 | 0.0004 | 8.93 |
| 173 | 0.0059 | 27.33 |
| 174 | 0.0033 | 41.5133 |
| 175 | 0.00049 | 15.8733 |
| 176 | 0.00098 | 35.825 |
| 177 | 0.00029 | 5.8333 |
| 178 | 0.00016 | 0.036 |
| 179 | 0.00042 | 17.6333 |
| 180 | 0.00047 | 21.37 |
| 181 | 0.0037 | 16.4733 |
| 182 | 0.0097 | 25 |

| Example | CatS IC$_{50}$ | CatL IC$_{50}$ |
|---|---|---|
| 183 | 0.00044 | 9.6682 |
| 184 | 0.032 | 25 |
| 185 | 0.0032 | 25 |
| 186 | 0.0034 | 25 |
| 187 | 0.0463 | 25 |
| 188 | 0.0064 | 16.72 |
| 189 | 0.665 | 25 |
| 190 | 0.0015 | 5.1567 |
| 191 | 0.107 | 25 |
| 192 | 0.0005 | 43.74 |
| 193 | 0.0002 | 28.54 |
| 194 | 0.0004 | 16.585 |
| 195 | 0.0036 | 25 |
| 196 | 0.0003 | 41.39 |
| 197 | 0.0009 | 19.0233 |
| 198 | 0.027 | 25 |
| 199 | 0.0005 | 7.74 |
| 200 | 0.0467 | 25 |
| 201 | 0.0034 | 25 |
| 202 | 0.0001 | 0.606 |
| 203 | 0.0008 | 9.33 |
| 204 | 0.205 | 25 |
| 205 | 0.0002 | 71.99 |
| 206 | 0.0002 | 25 |
| 207 | 0.0003 | 25 |
| 208 | 0.0008 | 25 |
| 209 | 0.0002 | 25 |
| 210 | 0.0004 | 25 |
| 211 | 0.0003 | 63.862 |
| 212 | 0.0003 | 25 |
| 213 | 0.0004 | 7.9667 |
| 214 | 0.0005 | 11.26 |
| 215 | 0.0002 | 0.022 |
| 216 | 0.0002 | 0.285 |
| 217 | 0.0007 | 13.9567 |
| 218 | 0.0004 | 14.5533 |
| 219 | 0.0003 | 12.64 |
| 220 | 0.0004 | 17.8 |
| 221 | 0.13 | 25 |
| 222 | 0.0012 | 18.5967 |
| 223 | 0.0001 | 0.045 |
| 224 | 0.0002 | 1 |
| 225 | 0.0012 | 18.28 |
| 226 | 0.0006 | 13.55 |
| 227 | 0.0006 | 15.5733 |
| 228 | 0.0009 | 15.3767 |
| 229 | 0.014667 | 23.88333 |
| 230 | 0.015333 | 14.83 |
| 231 | 0.0005 | >25 |
| 232 | 0.00021 | 12.76 |
| 233 | 0.000465 | 21.095 |
| 234 | 0.001567 | 25 |
| 235 | 0.00095 | 0.55 |
| 236 | 0.24 | 25 |
| 237 | 0.000168 | 25 |
| 238 | 0.00005 | 20.82 |
| 239 | 0.00008 | 0.084 |
| 240 | 0.00009 | 0.59 |
| 241 | 0.00033 | 31.82 |
| 242 | 0.00475 | 1.43 |
| 243 | 0.000455 | 12.275 |
| 244 | 0.00315 | 5.9 |
| 245 | 0.000168 | 39.165 |
| 246 | 0.000245 | 0.185 |
| 247 | 0.000385 | 3.44 |
| 248 | 0.00055 | 54.675 |
| 249 | 0.000255 | 25.81 |
| 250 | 0.000347 | 1.55 |
| 251 | 0.00029 | 1.25 |
| 252 | 0.00175 | 25 |
| 253 | 0.0011 | 1.3825 |
| 254 | 0.00083 | 2.265 |
| 255 | 0.00565 | 50 |
| 256 | 0.00026 | 45.725 |
| 257 | 0.000195 | 48.21 |
| 258 | 0.00019 | 58.04 |
| 259 | 0.00019 | 79.525 |
| 260 | 0.000245 | 16.545 |
| 261 | 0.012 | 27.04 |
| 262 | 0.0044 | 28.72 |
| 263 | 0.00033 | 50 |
| 264 | 0.000495 | 8.38 |
| 265 | 0.00135 | 2.05 |
| 266 | 0.0013 | 22.14 |
| 267 | 0.0023 | 7.81 |
| 268 | 0.00235 | 47.32 |
| 269 | 0.0016 | 75.07 |
| 270 | 0.000395 | 25 |
| 271 | 0.00175 | 85.59 |
| 272 | 0.0006 | 17.1 |
| 273 | 0.00029 | 0.00806 |
| 274 | 0.000935 | 9.135 |
| 275 | 0.00038 | 2.685 |
| 276 | 0.000392 | 9.4325 |
| 277 | 0.00014 | 0.445 |
| 278 | 0.000003 | 2.75 |
| 279 | 0.00002 | 1.31 |
| 280 | 0.0245 | 46.54 |
| 281 | 0.00028 | 0.145 |
| 282 | 0.00024 | 0.27 |
| 283 | 0.00012 | 0.024 |
| 284 | 0.00007 | 0.463333 |
| 285 | 0.000227 | 2.6 |
| 286 | 0.015 | 50 |
| 287 | 0.000175 | 3.165 |
| 288 | 0.00008 | 3.48 |
| 289 | 0.000385 | 35.095 |
| 290 | 0.00013 | 1.6 |
| 291 | 0.014667 | 50 |
| 292 | 0.000157 | 4.13 |
| 293 | 0.00018 | 1.4 |
| 294 | 0.000353 | 7.835 |
| 295 | 0.00003 | 0.925 |
| 296 | 0.000123 | 1.183333 |
| 297 | 0.00008 | 1.336667 |
| 298 | 0.00022 | 1.58 |
| 299 | 0.00017 | 1.176667 |
| 300 | 0.000885 | 50.74 |
| 301 | 0.00012 | 1.535 |
| 302 | 0.00003 | 0.575 |
| 303 | 0.00003 | 1.485 |
| 304 | 0.000445 | 0.805 |
| 305 | 0.019667 | 50 |
| 306 | 0.000555 | 64.47 |
| 307 | 0.000205 | 52.125 |
| 308 | 0.000745 | 25 |
| 309 | 0.0365 | 25 |
| 310 | 0.00026 | 0.22 |
| 311 | 0.000155 | 0.745 |
| 312 | 0.000195 | |
| 313 | 0.00046 | 1.39 |
| 314 | 0.00037 | 1.68 |
| 315 | 0.00039 | 2.5 |
| 316 | 0.0003 | 5.236667 |
| 317 | 0.02282 | 25 |
| 318 | 0.000437 | 11.32333 |
| 319 | 0.001433 | 40.82333 |
| 320 | 0.0805 | 25 |
| 321 | 0.068333 | 25 |
| 322 | 0.0003 | 28.48333 |
| 323 | 0.00044 | 4.816667 |
| 324 | 0.00009 | |
| 325 | 0.00008 | |
| 326 | 0.00018 | |
| 327 | 0.000175 | |
| 328 | 0.00016 | 0.13 |
| 329 | 0.000115 | |
| 330 | 0.00008 | |
| 331 | 0.00018 | 1.055 |
| 332 | 0.000195 | 0.58 |
| 333 | 0.0019 | 7.985 |
| 334 | 0.78 | 25 |
| 335 | 0.000484 | 25 |
| 336 | 0.00033 | |

| Example | CatS IC$_{50}$ | CatL IC$_{50}$ |
|---|---|---|
| 337 | 0.00165 | 13.04 |
| 338 | 0.375 | 25 |
| 339 | 0.0625 | 25 |
| 340 | 0.000975 | 26.405 |
| 341 | 0.15 | 25 |
| 342 | 0.00008 | 0.0495 |
| 343 | 0.099333 | 25 |
| 344 | 0.00054 | 25 |
| 345 | 0.000915 | 70.28 |
| 346 | 0.000101 | 0.0285 |
| 347 | 0.000855 | 0.06 |
| 348 | 0.00017 | 0.051 |
| 349 | 0.00003 | 0.22 |
| 350 | 0.00006 | 0.26 |
| 351 | 0.0195 | 25 |
| 352 | 0.00025 | 7.225 |
| 353 | 0.00099 | 13.475 |
| 354 | 0.000175 | 25 |
| 355 | 2.45 | 25 |
| 356 | 0.00006 | 31.77 |
| 357 | 0.0175 | 25 |
| 358 | 0.0005 | 25 |
| 359 | 0.00067 | 1.05 |
| 360 | 0.000185 | 1.1825 |
| 361 | 0.00002 | 0.995 |
| 362 | 0.38 | 25 |
| 363 | 0.0015 | 10.775 |
| 364 | 0.295 | 25 |
| 365 | 0.24 | 25 |
| 366 | 0.000327 | 25 |
| 367 | 0.001567 | 25 |
| 368 | 0.00021 | 0.266667 |
| 369 | 0.00007 | 0.026333 |
| 370 | 0.00007 | 0.021667 |
| 371 | 0.00008 | 0.026333 |
| 372 | 0.00008 | 0.044333 |
| 373 | 0.00008 | 0.042667 |
| 374 | 0.00007 | 0.050333 |
| 375 | 0.00029 | 5.37 |
| 376 | 0.000657 | 1.756667 |
| 377 | 0.00024 | 0.293333 |
| 378 | 0.0001 | 0.2 |
| 379 | 0.00175 | 2.71 |
| 380 | 0.00005 | 0.13 |
| 381 | 0.000295 | 0.1015 |
| 382 | 0.00004 | 0.068 |
| 383 | 0.014 | 19.995 |
| 384 | 0.00005 | 0.1 |
| 385 | 0.00054 | 6.46 |
| 386 | 0.00175 | 4.025 |
| 387 | 0.0067 | 52.455 |
| 388 | 0.00048 | 35.61 |
| 389 | 0.0002 | 8.06 |
| 390 | 0.00083 | 0.12 |
| 391 | 0.00022 | 16.74 |
| 392 | 0.00091 | 25 |
| 393 | 0.00375 | 25 |
| 394 | 0.00295 | 25 |
| 395 | 0.155 | 25 |
| 396 | 0.00165 | 57.46 |
| 397 | 0.000435 | 7.2 |
| 398 | 0.000555 | 18.805 |
| 399 | 0.00098 | >25 |
| 400 | 0.0033 | 25 |
| 401 | 0.00046 | 1.076667 |
| 402 | 0.0014 | 25 |
| 403 | 0.00049 | |
| 404 | 0.000405 | |
| 405 | 0.000935 | 25 |
| 406 | 0.004 | 25 |
| 407 | 0.0385 | 25 |
| 408 | 0.042 | 25 |
| 409 | 2.53 | 25 |
| 410 | 0.0048 | 29.71 |
| 411 | 0.000525 | 0.55 |
| 412 | 0.00275 | 0.785 |
| 413 | 0.00031 | 1.095 |
| 414 | 0.000295 | 5.45 |
| 415 | 0.000215 | 11.67 |
| 416 | 0.000338 | 21.415 |
| 417 | 0.00245 | 0.0555 |
| 418 | 0.004 | 1.62 |
| 419 | 0.000415 | 16.885 |
| 420 | 0.000395 | 14.05 |
| 421 | 0.0115 | 4.955 |
| 422 | 0.00185 | 4.36 |
| 423 | 1.47 | 25 |
| 424 | 0.41 | 25 |
| 425 | 0.00026 | 0.335 |
| 426 | 0.00047 | 0.045 |
| 427 | 0.00051 | 0.095 |
| 428 | 0.000415 | 0.335 |
| 429 | 0.000365 | 0.46 |
| 430 | 0.00082 | 2.59 |
| 431 | 0.000875 | 0.13 |
| 432 | 0.000595 | 0.115 |
| 433 | 0.00195 | 0.945 |
| 434 | 0.0012 | 3.44 |
| 435 | 0.000535 | 0.525 |
| 436 | 0.00048 | 0.109 |
| 437 | 0.00145 | 0.335 |
| 438 | 0.00052 | 0.13 |
| 439 | 0.000895 | 0.0295 |
| 440 | 7.475 | 25 |
| 441 | 0.0855 | 25 |
| 442 | 0.000615 | 0.24 |
| 443 | 0.000605 | 0.022 |
| 444 | 0.000895 | 0.26 |
| 445 | 0.725 | 25 |
| 446 | 0.000275 | 0.0215 |
| 447 | 6.13 | 25 |
| 448 | 8.37 | 25 |
| 449 | 10.47 | 25 |
| 450 | 0.675 | 25 |
| 451 | 0.000758 | 6.375 |
| 452 | 0.001168 | 7.925 |
| 453 | 0.845 | 25 |
| 454 | 1.665 | 25 |
| 455 | 0.077 | 25 |
| 456 | 0.000725 | 3.995 |
| 457 | 34.01546 | 0.53 |
| 458 | 61.855 | |
| 459 | 0.000505 | 0.0065 |
| 460 | 0.00585 | 0.0525 |
| 461 | 0.000985 | 0.0225 |
| 462 | 9.495 | >25 |
| 463 | 5.13 | >25 |
| 464 | 0.00115 | 3.02 |
| 465 | 0.00305 | 2.74 |
| 466 | 8.6 | 95% @25 uM |
| 467 | 2.08 | 95% @25 uM |
| 468 | 0.5065 | 96% @25 uM |
| 469 | 0.84 | 97% @25 uM |
| 470 | 2.795 | 94% @25 uM |
| 471 | 3.69 | 96% @25 uM |
| 472 | | |
| 473 | 0.07 | 4.41 |
| 474 | 0.0024 | 1.54 |
| 475 | | |
| 476 | 0.0066 | 4.76 |
| 477 | 0.0006 | 0.3185 |
| 478 | 0.0031 | 3.67 |
| 479 | 0.00324 | 3.07 |
| 480 | 0.00105 | 5.365 |
| 481 | 0.0006 | 1.275 |
| 482 | 0.000765 | 2.71 |
| 483 | 0.00134 | 0.521 |
| 484 | 0.00331 | 1.547 |
| 485 | 0.0009 | 0.275 |
| 486 | 0.00085 | 21.95 |
| 487 | | |
| 488 | 0.0025 | 3.88 |
| 489 | 0.00051 | 3.538 |
| 490 | 0.00094 | 4.33 |

-continued

| Example | CatS IC$_{50}$ | CatL IC$_{50}$ |
|---|---|---|
| 491 | 0.000655 | 5.285 |
| 492 | | |
| 493 | | |

Example A

A compound of formula (I) can be used in a manner known per se as the active ingredient for the production of tablets of the following composition:

| | Per tablet |
|---|---|
| Active ingredient | 200 mg |
| Macrocrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:
1. A compound of formula (I)

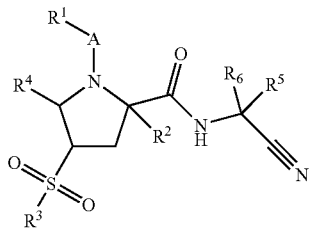

(I)

wherein
$R^1$ is selected from the group consisting of: hydrogen, alkyl, haloalkyl, alkoxy, alkoxyalkyl, cycloalkyl, cycloalkylalkyl, alkylcycloalkyl, haloalkylcycloalkyl, phenylcycloalkyl, halocycloalkyl, phenylhaloalkyl, haloalkoxycycloalkyl, alkoxycarbonylaminocycloalkyl, cyanoalkylcycloalkyl, halophenylalkyl, pyridinylcycloalkyl, aminocycloalkylalkyl, aminocarbonylphenylcycloalkyl, haloalkyloxyphenylcycloalkyl, alkylpyrazolylphenylcycloalkyl, bis(halophenyl)alkyl, phenylcycloalkyl, alkylphenylcycloalkyl, haloalkylphenylcycloalkyl, halophenyldioxolane, naphthylcycloalkyl, halopyridinylcycloalkyl, benzo[1,3]dioxolyl, naphthyldioxolane, halo-1H-indazolyl, halophenylhydroxyalkyl, (halophenyl)(alkoxycarbonylamino)alkyl, alkylthiazolylcycloalkyl, halopyrimidinylalkyl, (halophenyl)(amino)alkyl, (halophenyl)(haloalkylamino)alkyl, haloalkylpyrazolylalkyl, (halophenyl)(alkoxycarbonylpiperidinyl), (halophenyl)(morpholinyl)alkyl, halophenylhaloalkyl, alkylphenylcycloalkyl, hydroxyalkylcycloalkyl, (halophenyl)(alkenylamino)alkyl, alkoxyhalophenylcycloalkyl, halonaphthylcycloalkyl, halophenyloxycycloalkyl, phenyltetrahydropyranyl and $R^{11}$;

A is absent or selected from the group consisting of: —CH$_2$—, —CH$_2$CH$_2$—, carbonyl, —C(O)O—, and —SO$_2$—;

$R^2$ is selected from the group consisting of: hydrogen, alkyl, haloalkyl, cycloalkyl, phenyl, phenylalkyl and phenylsulfonylalkyl;

or A, $R^1$ and $R^2$ together form —CH$_2$CH$_2$—, —CH$_2$CF$_2$CH$_2$—, —CH$_2$CH$_2$CH$_2$—, —CH$_2$CH$_2$CH$_2$CH$_2$—; —CH$_2$CH$_2$OCH$_2$— or —CH$_2$CH$_2$CH(CN)—;

$R^3$ is selected from the group consisting of: alkyl, hydroxyalkyl, cycloalkyl, phenyl, phenylalkyl and substituted phenyl, wherein said substituted phenyl is phenyl substituted with one to three substituents independently selected from the group consisting of: alkyl, haloalkyl, hydroxyalkyl, alkoxy, haloalkyloxy, halogen, pyrazolyl, alkylopyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, haloalkylpiperidinyl, piperidinylalkoxy, oxetanyloxy, alkylpyrazolyl, halopyridinyl, alkylpyridinyl, cycloalkyl, cycloalkylalkyl, halophenyl, alkylcarbonylaminocycloalkylalkyl, haloalkylpiperazinyl, alkylamino, alkoxyalkylpiperazinyl, cycloalkylpiperazinyl, hexahydropyrrolo[1,2-a]pyrazinyl, 5,6-dihydro-8H-[1,2,4]triazolo[4,3-a]pyrazin-7-yl, alkylimidazolyl, azetidinyl, cycloalkylpiperazinyl, alkylimidazolyl, alkoxyalkoxy, imidazo[4,5-c]pyridinyl, alkylpiperazinyl, hexahydro-pyrrolo[1,2-a]pyrazinyl, haloazetidinyl, pyrimindinyl and alkenyloxy;

$R^4$ is selected from the group consisting of: hydrogen, alkyl, haloalkyl, alkoxy, alkoxyalkyl, cycloalkyl, cycloalkyloxy, phenyl, alkylphenyl, halophenyl, phenyloxy and halophenyloxy;

$R^5$ and $R^6$ are each independently selected from the group consisting of: hydrogen, alkyl, cycloalkyl, alkyloxy, hydroxyalkyl, haloalkyl, haloalkyloxy, phenyl and phenylalkyloxy;

or $R^5$ and $R^6$, together with the carbon atom to which they are attached, form cycloalkyl, pyrrolidinyl or piperidinyl; and $R^{11}$ is selected from the group consisting of: phenyl, substituted phenyl, tetrahydropyranyl, pyridinyl, alkylpyridinyl, haloalkylpyridinyl, oxetanyl, alkyloxetanyl, pyrrolidinyl, alkylpyrrolidinyl, pyrimidinyl, haloalkylpyrimidinyl, alkylpiperidinyl, naphthyl, biphenyl, haloalkyl-[1,3,4]thiadiazolyl, alkoxycarbonylpiperidinyl, halo-[1,2,4]thiadiazolyl, pyrazolyl and substituted pyrazolyl, wherein substituted phenyl and substituted pyrazolyl are phenyl and pyrazolyl each substituted with one to three substituents independently selected from the group consisting of: alkyl, halogen, haloalkyl, alkoxy, alkoxycarbonyl, halophenyl, halopyridinyl, oxodihydropyridinyl, nitro, thiazolyl, haloalkylphenyl, alkylphenyl, phenyl, alkylpyridinyl, tetrahydropyranyl, pyridazinyl, cycloalkyl, phenylalkyl, oxazolyl, alkoxyphenyl, quinolinyl, alkylcarbonylaminophenyl, haloalkoxy, alkylsulfonyl, phenylalkoxycarbonylpiperidinyl, piperidinyl, thiopyranyl, dioxothiopyranyl, morpholinylalkyl and alkylimidazolyl;

or a pharmaceutically acceptable salt thereof.

2. A compound according to claim 1, wherein
$R^1$ is selected from the group consisting of: hydrogen, alkyl, haloalkyl, alkoxy, alkoxyalkyl, cycloalkyl, cycloalkylalkyl, alkylcycloalkyl, haloalkylcycloalkyl, phenylcycloalkyl, halocycloalkyl, phenylhaloalkyl and $R^{11}$;

A is absent or selected from the group consisting of: —CH$_2$—, —CH$_2$CH$_2$—, carbonyl, —C(O)O—, and —SO$_2$—;

$R^2$ is selected from the group consisting of: hydrogen, alkyl, haloalkyl, cycloalkyl, phenyl and phenylalkyl;

or A, $R^1$ and $R^2$ together form —CH$_2$CH$_2$—, —CH$_2$CF$_2$CH$_2$—, —CH$_2$CH$_2$CH$_2$—, —CH$_2$CH$_2$CH$_2$CH$_2$— or —CH$_2$CH$_2$OCH$_2$—;

$R^3$ is selected from the group consisting of: alkyl, hydroxyalkyl, cycloalkyl, phenyl and substituted phenyl, wherein said substituted phenyl is phenyl substituted with one to three substituents independently selected from the group consisting of: alkyl, haloalkyl, hydroxyalkyl, haloalkyloxy, halogen, pyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxopyrrolidinyl, oxo-oxazolidinyl, morpholinyl, oxomorpholinyl, oxo-pyridinyl, 2-oxo-2H-pyrazinyl, difluoropiperidinyl, haloalkylpiperidinyl, piperidinylalkoxy and oxetanyloxy;

$R^4$ is selected from the group consisting of: hydrogen, alkyl, haloalkyl, alkoxy, alkoxyalkyl, cycloalkyl, cycloalkyloxy, phenyl, halophenyl, phenyloxy and halophenyloxy;

$R^5$ and $R^6$ are each independently selected from the group consisting of: hydrogen, alkyl, cycloalkyl, alkyloxy, hydroxyalkyl, haloalkyl, haloalkyloxy, phenyl and phenylalkyloxy;

or $R^5$ and $R^6$, together with the carbon atom to which they are attached, form cycloalkyl, pyrrolidinyl or piperidinyl; and $R^{11}$ is selected from the group consisting of: phenyl, substituted phenyl, tetrahydropyranyl, pyridinyl, alkylpyridinyl, haloalkylpyridinyl, oxetanyl, pyrrolidinyl, alkylpyrrolidinyl, pyrimidinyl, haloalkylpyrimidinyl, alkylpiperidinyl, pyrazolyl and substituted pyrazolyl, wherein said substituted phenyl and substituted pyrazolyl are respectively phenyl and pyrazolyl each substituted with one to three substituents independently selected from the group consisting of alkyl, halogen, haloalkyl, alkoxy, alkoxycarbonyl, halophenyl, halopyridinyl, oxodihydropyridinyl and nitro;

or a pharmaceutically acceptable salt thereof.

3. A compound according to claim 1, wherein $R^1$ is selected from the group consisting of: hydrogen, alkyl, haloalkyl, alkoxy, alkoxyalkyl, cycloalkyl, cycloalkylalkyl, alkylcycloalkyl, haloalkylcycloalkyl, phenylcycloalkyl, halocycloalkyl, phenylhaloalkyl and $R^{11}$.

4. A compound according to claim 1, wherein $R^1$ is selected from the group consisting of: hydrogen, alkyl, fluoroalkyl, phenylfluoroalkyl, alkoxy, alkoxymethyl, alkylcyclopropyl, difluorocyclopropyl, trifluoromethylcyclopropyl, phenylcyclopropyl, chlorophenylcyclopropyl, cyclobutyl, cyclohexyl, trifluoromethylcyclohexyl, trifluoromethylcyclobutyl and cyclopentyloxy.

5. A compound according to claim 1, wherein $R^1$ is selected from the group consisting of: hydrogen, methyl, ethyl, propyl, butyl, difluoromethyl, trifluoromethyl, trifluoroethyl, pentafluoroethyl, trifluoropropyl, phenyltrifluoroethyl, methoxy, propyloxy, butyloxy, methoxymethyl, methylcyclopropyl, difluorocyclopropyl, trifluoromethylcyclopropyl, phenylcyclopropyl, chlorophenylcyclopropyl, cyclobutyl, cyclohexyl, trifluoromethylcyclohexyl, trifluoromethylcyclobutyl and cyclopentyloxy.

6. A compound according to claim 1, wherein $R^1$ is selected from the group consisting of: tert-butyl, trifluoromethylcyclopropyl, methylcyclopropyl and chlorophenylcyclopropyl.

7. A compound according to claim 1, wherein A is absent or selected from the group consisting of: —CH$_2$—, —CH$_2$CH$_2$—, and carbonyl.

8. A compound according to claim 1, wherein A is carbonyl.

9. A compound according to claim 1, wherein $R^2$ is hydrogen or alkyl.

10. A compound according to claim 1, wherein $R^2$ is hydrogen.

11. A compound according to claim 1, wherein $R^3$ is selected from the group consisting of: alkyl, hydroxyalkyl, cycloalkyl, phenyl and substituted phenyl, wherein said substituted phenyl is phenyl substituted with one to three substituents independently selected from the group consisting of: alkyl, haloalkyl, haloalkoxy, hydroxyalkyl, halogen, pyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxopyrrolidinyl, oxo-oxazolidinyl, morpholinyl, oxo-morpholinyl, oxo-pyridinyl, 2-oxo-2H-pyrazinyl, difluoropiperidinyl, trifluoromethylpiperidinyl, piperidinylmethoxy and oxetanyloxy.

12. A compound according to claim 1, wherein $R^3$ is selected from the group consisting of: alkyl, hydroxyalkyl, cycloalkyl, phenyl and substituted phenyl, wherein said substituted phenyl is phenyl substituted with one to three substituents independently selected from the group consisting of: methyl, trifluoromethyl, trifluoroethyloxy, trifluoromethoxy, hydroxymethyl, fluoro, bromo, chloro, pyrazolyl, imidazolyl, benzoimidazolyl, 6-oxo-6H-pyridazinyl, alkyl-6-oxo-6H-pyridazinyl, piperazinyl, N-alkylpiperazinyl, piperidinyl, difluoropyrrolidinyl, phenylimidazolyl, oxo-pyrrolidinyl, oxo-oxazolidinyl, morpholinyl, oxo-morpholinyl, oxo-pyridinyl, 2-oxo-2H-pyrazinyl, difluoropiperidinyl, trifluoromethylpiperidinyl, piperidinylmethoxy and oxetanyloxy.

13. A compound according to claim 1, wherein $R^3$ is phenyl substituted with one or two substituents independently selected from the group consisting of: chloro, trifluoromethyl, trifluoromethoxy, trifluoroethyloxy and pyrazolyl.

14. A compound according to claim 1, wherein $R^3$ is selected from the group consisting of: dichlorophenyl, (chloro)(pyrazolyl)phenyl, (chloro)(trifluoroethoxy)phenyl, (chloro)(trifluoropropoxy)phenyl, trifluoromethylphenyl, (trifluoroethoxy)(trifluoromethyl)phenyl and chlorophenyl.

15. A compound according to claim 1, wherein $R^4$ is hydrogen.

16. A compound according to claim 1, wherein $R^5$ is selected from the group consisting of: hydrogen, alkyl, cycloalkyl and phenyl.

17. A compound according to claim 1, wherein $R^5$ is selected from the group consisting of: hydrogen, methyl, cyclopropyl and phenyl.

18. A compound according to claim 1, wherein $R^6$ is hydrogen.

19. A compound according to claim 1, wherein $R^5$ and $R^6$, together with the carbon atom to which they are attached, form cyclopropyl, cyclobutyl, or cyclohexyl.

20. A compound according to claim 1, wherein $R^5$ and $R^6$, together with the carbon atom to which they are attached, form cyclopropyl.

21. A compound according to claim 1, wherein $R^{11}$ is selected from the group consisting of: phenyl, substituted phenyl, tetrahydropyranyl, pyridinyl, alkylpyridinyl, alkylpyridinyl, oxetanyl, pyrrolidinyl, alkylpyrrolidinyl, pyrimidinyl, haloalkylpyrimidinyl, alkylpiperidinyl, pyrazolyl and substituted pyrazolyl, wherein said substituted phenyl and substituted pyrazolyl are respectively phenyl and pyrazolyl each substituted with one to three substituents independently selected from the group consisting of: alkyl, halogen, alkoxy, alkoxycarbonyl, haloalkoxy, haloalkyl, halophenyl, halopyridinyl, oxodihydropyridinyl and nitro.

22. A compound according to claim 1, wherein $R^{11}$ is selected from the group consisting of: phenyl, substituted phenyl, tetrahydropyranyl, pyridinyl, methylpyridinyl, trifluoromethylpyridinyl, oxetanyl, pyrrolidinyl, methylpyrrolidinyl, pyrimidinyl, trifluoromethylpyrimidinyl, methylpiperidinyl, pyrazolyl and substituted pyrazolyl, wherein said substituted phenyl and substituted pyrazolyl are respectively phenyl and pyrazolyl each substituted with one to three substituents independently selected from the group consisting of: methyl, fluoro, methoxy, methoxycarbonyl, trifluoromethoxy, trifluoromethyl, chlorophenyl, fluorophenyl, chloropyridinyl, oxodihydropyridinyl and nitro.

23. A compound according to claim 1, wherein $R^{11}$ is selected from the group consisting of: phenyl, fluorophenyl, chlorophenyl, methoxyphenyl, methoxycarbonylphenyl, trifluoromethylphenyl, nitrophenyl, tetrahydropyranyl, pyridinyl, methylpyridinyl, trifluoromethylpyridinyl, oxetanyl, pyrrolidinyl, methylpyrrolidinyl, pyrimidinyl, trifluoromethylpyrimidinyl, methylpiperidinyl, pyrazolyl, methyl-phenyl-pyrazolyl, chloropyridinyl-methyl-pyrazolyl, chlorophenyl-methyl-pyrazolyl, fluorophenyl-methyl-pyrazolyl and oxodihydropyridinyl-methyl-pyrazolyl.

24. A compound according to any one of claim 1 selected from the group consisting of:

(2S,4R)-4-Benzenesulfonyl-1-benzoyl-pyrrolidine-2-carboxylic acid cyanomethyl-amide;

(2S,4R)-4-Benzenesulfonyl-1-benzyl-pyrrolidine-2-carboxylic acid cyanomethyl-amide;

(2S,4R)-4-Benzenesulfonyl-1-cyclohexylmethyl-pyrrolidine-2-carboxylic acid cyanomethyl-amide;

(2S,4R)-4-Benzenesulfonyl-1-(2,2,2-trifluoro-1-phenyl-ethyl)-pyrrolidine-2-carboxylic acid cyanomethyl-amide;

(2S,4R)-4-Benzenesulfonyl-1-cyclohexanecarbonyl-pyrrolidine-2-carboxylic acid cyanomethyl-amide;

(2S,4R)-1-Benzoyl-4-(2-chloro-benzenesulfonyl)-pyrrolidine-2-carboxylic acid cyanomethyl-amide;

(2S,4R)-4-Benzenesulfonyl-1-benzoyl-pyrrolidine-2-carboxylic acid (1-cyano-cyclopropyl)-amide;

(2S,4R)-4-Benzenesulfonyl-1-(tetrahydro-pyran-4-carbonyl)-pyrrolidine-2-carboxylic acid (1-cyano-cyclopropyl)-amide;

(2S,4R)-4-(2-Chloro-benzenesulfonyl)-1-(2,2,2-trifluoro-1-phenyl-ethyl)-pyrrolidine-2-carboxylic acid cyanomethyl-amide;

(2S,4R)-4-(2-Chloro-benzenesulfonyl)-1-(4-fluoro-benzoyl)-pyrrolidine-2-carboxylic acid (1-cyano-cyclopropyl)-amide;

(2S,4R)-4-(2-Trifluoromethyl-benzenesulfonyl)-pyrrolidine-2-carboxylic acid (1-cyano-cyclopropyl)-amide;

(2S,4R)-1-Cyclohexanecarbonyl-4-(2-trifluoromethyl-benzenesulfonyl)-pyrrolidine-2-carboxylic acid (1-cyano-cyclopropyl)-amide;

(2S,4R)-1-(4-Fluoro-benzoyl)-4-(2-trifluoromethyl-benzenesulfonyl)-pyrrolidine-2-carboxylic acid (1-cyano-cyclopropyl)-amide;

(2S,4R)-4-(2-Trifluoromethyl-benzenesulfonyl)-1-(4-trifluoromethyl-cyclohexanecarbonyl)-pyrrolidine-2-carboxylic acid (1-cyano-cyclopropyl)-amide;

(2S,4R)-4-(2-Chloro-benzenesulfonyl)-pyrrolidine-2-carboxylic acid (1-cyano-cyclopropyl)-amide;

(2S,4R)-1-(2,2,3,3,3-Pentafluoro-propyl)-4-(2-trifluoromethyl-benzenesulfonyl)-pyrrolidine-2-carboxylic acid (1-cyano-cyclopropyl)-amide;

(2S,4R)-1-Benzoyl-4-(2-chloro-benzenesulfonyl)-pyrrolidine-2-carboxylic acid (1-cyano-cyclopropyl)-amide;

(2S,4R)-4-(2-Chloro-benzenesulfonyl)-1-cyclohexanecarbonyl-pyrrolidine-2-carboxylic acid (1-cyano-cyclopropyl)-amide;

(2S,4R)-4-(2-Chloro-benzenesulfonyl)-2-(1-cyano-cyclopropylcarbamoyl)-pyrrolidine-1-carboxylic acid ethyl ester;

(2S,4R)-4-(2-Chloro-benzenesulfonyl)-2-(1-cyano-cyclopropylcarbamoyl)-pyrrolidine-1-carboxylic acid cyclopentyl ester;

(2S,4R)-4-(2-Chloro-benzenesulfonyl)-2-(1-cyano-cyclopropylcarbamoyl)-pyrrolidine-1-carboxylic acid 4-fluoro-phenyl ester;

(2S,4R)-4-(2-Chloro-benzenesulfonyl)-1-pyridin-4-ylmethyl-pyrrolidine-2-carboxylic acid (1-cyano-cyclopropyl)-amide;

(2S,4R)-4-(2-Chloro-benzenesulfonyl)-1-ethyl-pyrrolidine-2-carboxylic acid (1-cyano-cyclopropyl)-amide;

(2S,4R)-4-(2-Chloro-benzenesulfonyl)-1-phenethyl-pyrrolidine-2-carboxylic acid (1-cyano-cyclopropyl)-amide;

(2S,4R)-4-(2-Chloro-benzenesulfonyl)-1-cyclobutyl-pyrrolidine-2-carboxylic acid (1-cyano-cyclopropyl)-amide;

(2S,4R)-4-(2-Chloro-benzenesulfonyl)-1-cyclohexyl-pyrrolidine-2-carboxylic acid (1-cyano-cyclopropyl)-amide;

(2S,4R)-4-(2-Chloro-benzenesulfonyl)-1-methyl-pyrrolidine-2-carboxylic acid (1-cyano-cyclopropyl)-methyl-amide; salt with formic acid;

(2S,4R)-4-(2-Chloro-benzenesulfonyl)-1-(2,2,2-trifluoro-ethyl)-pyrrolidine-2-carboxylic acid (1-cyano-cyclopropyl)-amide;

(2S,4R)-4-(2-Chloro-benzenesulfonyl)-1-(2,2-difluoro-ethyl)-pyrrolidine-2-carboxylic acid (1-cyano-cyclopropyl)-amide;

(2S,4R)-4-(2-Chloro-benzenesulfonyl)-1-(4-fluoro-benzoyl)-pyrrolidine-2-carboxylic acid cyanomethyl-amide;

(2S,4R)-4-(2-Chloro-benzenesulfonyl)-1-cyclohexanecarbonyl-pyrrolidine-2-carboxylic acid cyanomethyl-amide;

(2S,4R)-4-(2-Chloro-benzenesulfonyl)-1-propionyl-pyrrolidine-2-carboxylic acid cyanomethyl-amide;

(2S,4R)-4-(2-Chloro-benzenesulfonyl)-1-(2-methoxy-acetyl)-pyrrolidine-2-carboxylic acid cyanomethyl-amide;
(2S,4R)-4-(2-Chloro-benzenesulfonyl)-1-oxetan-3-yl-pyrrolidine-2-carboxylic acid cyanomethyl-amide;
(2S,4R)-4-(2-Chloro-benzenesulfonyl)-1-(tetrahydro-pyran-4-yl)-pyrrolidine-2-carboxylic acid cyanomethyl-amide;
(2S,4R)-1-Benzoyl-4-(2-trifluoromethyl-benzenesulfonyl)-pyrrolidine-2-carboxylic acid cyanomethyl-amide;
(2S,4R)-1-(4-Fluoro-benzoyl)-4-(2-trifluoromethyl-benzenesulfonyl)-pyrrolidine-2-carboxylic acid cyanomethyl-amide;
(2S,4R)-1-(4-Methyl-benzoyl)-4-(2-trifluoromethyl-benzenesulfonyl)-pyrrolidine-2-carboxylic acid cyanomethyl-amide;
(2S,4R)-1-Cyclohexanecarbonyl-4-(2-trifluoromethyl-benzenesulfonyl)-pyrrolidine-2-carboxylic acid cyanomethyl-amide;
(2S,4R)-1-(Tetrahydro-pyran-4-carbonyl)-4-(2-trifluoromethyl-benzenesulfonyl)-pyrrolidine-2-carboxylic acid cyanomethyl-amide;
(2S,4R)-1-(Pyridine-4-carbonyl)-4-(2-trifluoromethyl-benzenesulfonyl)-pyrrolidine-2-carboxylic acid cyanomethyl-amide;
(2S,4R)-1-(1-Methyl-piperidine-4-carbonyl)-4-(2-trifluoromethyl-benzenesulfonyl)-pyrrolidine-2-carboxylic acid cyanomethyl-amide;
(2S,4R)-2-(Cyanomethyl-carbamoyl)-4-(2-trifluoromethyl-benzenesulfonyl)-pyrrolidine-1-carboxylic acid cyclopentyl ester;
(2S,4R)-4-(2-Chloro-benzenesulfonyl)-1-(2,2,3,3,3-pentafluoro-propyl)-pyrrolidine-2-carboxylic acid (1-cyano-cyclopropyl)-amide;
(2S,4R)-4-(2-Chloro-benzenesulfonyl)-1-(3,3,3-trifluoro-2-methyl-propyl)-pyrrolidine-2-carboxylic acid (1-cyano-cyclopropyl)-amide;
(2S,4R)-4-(2-Chloro-benzenesulfonyl)-1-(3,3,3-trifluoro-propyl)-pyrrolidine-2-carboxylic acid (1-cyano-cyclopropyl)-amide;
6-Benzenesulfonyl-2,2-difluoro-tetrahydro-pyrrolizine-7a-carboxylic acid cyanomethyl-amide;
1-Benzenesulfonyl-6,6-difluoro-tetrahydro-pyrrolizine-7a-carboxylic acid cyanomethyl-amide;
1-Benzenesulfonyl-6,6-difluoro-tetrahydro-pyrrolizine-7a-carboxylic acid cyanomethyl-amide;
(2S,4R)-1-Acetyl-4-(2-chloro-benzenesulfonyl)-pyrrolidine-2-carboxylic acid (1-cyano-cyclopropyl)-amide;
(2S,4R)-4-(2-Chloro-benzenesulfonyl)-2-(1-cyano-cyclopropylcarbamoyl)-pyrrolidine-1-carboxylic acid methyl ester;
(2S,4R)-4-(2-Chloro-benzenesulfonyl)-2-(1-cyano-cyclopropylcarbamoyl)-pyrrolidine-1-carboxylic acid isopropyl ester;
(2S,4R)-4-(2-Chloro-benzenesulfonyl)-1-(2,2,2-trifluoro-acetyl)-pyrrolidine-2-carboxylic acid (1-cyano-cyclopropyl)-amide;
(2S,4R)-2-(1-Cyano-cyclopropylcarbamoyl)-4-(2,4-dimethyl-benzenesulfonyl)-pyrrolidine-1-carboxylic acid tert-butyl ester;
(2S,4R)-4-(2,4-Dimethyl-benzenesulfonyl)-pyrrolidine-2-carboxylic acid (1-cyano-cyclopropyl)-amide;
(2S,4R)-4-(2-Chloro-benzenesulfonyl)-2-[(cyano-phenyl-methyl)-carbamoyl]-pyrrolidine-1-carboxylic acid tert-butyl ester;
(2S,4R)-4-(2-Chloro-benzenesulfonyl)-2-[(cyano-methyl-phenyl-methyl)-carbamoyl]-pyrrolidine-1-carboxylic acid tert-butyl ester;
(2S,4R)-1-Benzyl-4-(2-trifluoromethyl-benzenesulfonyl)-pyrrolidine-2-carboxylic acid (1-cyano-cyclopropyl)-amide;
(2S,4R)-1-Pyridin-4-ylmethyl-4-(2-trifluoromethyl-benzenesulfonyl)-pyrrolidine-2-carboxylic acid (1-cyano-cyclopropyl)-amide;
(2S,4R)-4-(4-Chloro-2-methyl-benzenesulfonyl)-2-(1-cyano-cyclopropylcarbamoyl)-pyrrolidine-1-carboxylic acid tert-butyl ester;
(2S,4R)-4-(4-Chloro-2-methyl-benzenesulfonyl)-pyrrolidine-2-carboxylic acid (1-cyano-cyclopropyl)-amide;
(2S,4R)-4-(2-Chloro-benzenesulfonyl)-pyrrolidine-2-carboxylic acid (cyano-phenyl-methyl)-amide;
(2S,4R)-4-(2-Chloro-benzenesulfonyl)-pyrrolidine-2-carboxylic acid (cyano-methyl-phenyl-methyl)-amide;
(2S,4R)-1-Acetyl-4-(2-trifluoromethyl-benzenesulfonyl)-pyrrolidine-2-carboxylic acid (1-cyano-cyclopropyl)-amide;
(2S,4R)-1-(2,2,2-Trifluoro-acetyl)-4-(2-trifluoromethyl-benzenesulfonyl)-pyrrolidine-2-carboxylic acid (1-cyano-cyclopropyl)-amide;
(2S,4R)-4-(2-Chloro-benzenesulfonyl)-1-methyl-pyrrolidine-2-carboxylic acid (1-cyano-cyclopropyl)-amide;
(2S,4R)-4-(2-Chloro-benzenesulfonyl)-2-[(cyano-dimethyl-methyl)-carbamoyl]-pyrrolidine-1-carboxylic acid tert-butyl ester;
(2S,4R)-4-(2-Chloro-benzenesulfonyl)-2-(1-cyano-cyclobutylcarbamoyl)-pyrrolidine-1-carboxylic acid tert-butyl ester;
(2S,4R)-4-(2-Chloro-benzenesulfonyl)-2-(1-cyano-cyclohexylcarbamoyl)-pyrrolidine-1-carboxylic acid tert-butyl ester;
(2S,4R)-4-(2-Chloro-benzenesulfonyl)-pyrrolidine-2-carboxylic acid (1-cyano-cyclohexyl)-amide;
(2S,4R)-4-(2-Chloro-benzenesulfonyl)-pyrrolidine-2-carboxylic acid (cyano-dimethyl-methyl)-amide;
(2S,4R)-4-(2-Chloro-benzenesulfonyl)-pyrrolidine-2-carboxylic acid (1-cyano-cyclobutyl)-amide;
(2S,4R)-2-(1-Cyano-cyclopropylcarbamoyl)-4-(2,3-dichloro-benzenesulfonyl)-pyrrolidine-1-carboxylic acid tert-butyl ester;
(2S,4R)-4-(2,3-Dichloro-benzenesulfonyl)-pyrrolidine-2-carboxylic acid (1-cyano-cyclopropyl)-amide;
(R)-4-(2-Chloro-benzenesulfonyl)-1-((S)-1-methyl-pyrrolidine-2-carbonyl)-pyrrolidine-2-carboxylic acid (1-cyano-cyclopropyl)-amide;
(2S,4R)-1-Propionyl-4-(2-trifluoromethyl-benzenesulfonyl)-pyrrolidine-2-carboxylic acid (1-cyano-cyclopropyl)-amide;
(2S,4R)-4-(2-Chloro-benzenesulfonyl)-1-(1-methyl-piperidine-4-carbonyl)-pyrrolidine-2-carboxylic acid (1-cyano-cyclopropyl)-amide;
(2S,4R)-1-(2-Methoxy-ethyl)-4-(2-trifluoromethyl-benzenesulfonyl)-pyrrolidine-2-carboxylic acid (1-cyano-cyclopropyl)-amide;
(2S,4R)-4-(2-Ethyl-benzenesulfonyl)-pyrrolidine-2-carboxylic acid (1-cyano-cyclopropyl)-amide;
(2S,4R)-2-(1-Cyano-cyclopropylcarbamoyl)-4-(2,4-dichloro-benzenesulfonyl)-pyrrolidine-1-carboxylic acid tert-butyl ester;
(2S,4R)-4-(2,4-Dichloro-benzenesulfonyl)-pyrrolidine-2-carboxylic acid (1-cyano-cyclopropyl)-amide;

(2S,4R)-2-(1-Cyano-cyclopropylcarbamoyl)-4-(2,6-dichloro-benzenesulfonyl)-pyrrolidine-1-carboxylic acid tert-butyl ester;
(2S,4R)-4-(2,6-Dichloro-benzenesulfonyl)-pyrrolidine-2-carboxylic acid (1-cyano-cyclopropyl)-amide;
(2S,4R)-2-(1-Cyano-cyclopropylcarbamoyl)-4-(2-hydroxymethyl-benzenesulfonyl)-pyrrolidine-1-carboxylic acid tert-butyl ester;
(2S,4R)-4-(2-Hydroxymethyl-benzenesulfonyl)-pyrrolidine-2-carboxylic acid (1-cyano-cyclopropyl)-amide;
4-[(2S,4R)-2-(1-Cyano-cyclopropylcarbamoyl)-4-(2-trifluoromethyl-benzenesulfonyl)-pyrrolidine-1-carbonyl]-benzoic acid methyl ester;
(2S,4R)-1-Phenyl-4-(2-trifluoromethyl-benzenesulfonyl)-pyrrolidine-2-carboxylic acid (1-cyano-cyclopropyl)-amide;
(2S,4R)-2-(1-Cyano-cyclopropylcarbamoyl)-4-(2-trifluoromethoxy-benzenesulfonyl)-pyrrolidine-1-carboxylic acid tert-butyl ester;
(2S,4R)-2-(1-Cyano-cyclopropylcarbamoyl)-4-(2,4-difluoro-benzenesulfonyl)-pyrrolidine-1-carboxylic acid tert-butyl ester;
(2S,4R)-2-(1-Cyano-cyclopropylcarbamoyl)-4-(4-imidazol-1-yl-benzenesulfonyl)-pyrrolidine-1-carboxylic acid tert-butyl ester;
(2S,4R)-4-(2-Trifluoromethoxy-benzenesulfonyl)-pyrrolidine-2-carboxylic acid (1-cyano-cyclopropyl)-amide;
(2S,4R)-4-(2,4-Difluoro-benzenesulfonyl)-pyrrolidine-2-carboxylic acid (1-cyano-cyclopropyl)-amide;
(2S,4R)-2-[(Cyano-cyclopropyl-methyl)-carbamoyl]-4-(2-trifluoromethyl-benzenesulfonyl)-pyrrolidine-1-carboxylic acid tert-butyl ester;
(2S,4R)-4-(4-Imidazol-1-yl-benzenesulfonyl)-pyrrolidine-2-carboxylic acid (1-cyano-cyclopropyl)-amide;
(2S,4R)-4-(4-Bromo-2-trifluoromethyl-benzenesulfonyl)-2-(1-cyano-cyclopropylcarbamoyl)-pyrrolidine-1-carboxylic acid tert-butyl ester;
(2S,4R)-4-(4-Bromo-2-trifluoromethyl-benzenesulfonyl)-pyrrolidine-2-carboxylic acid (1-cyano-cyclopropyl)-amide;
(2S,4R)-4-(2-Chloro-benzenesulfonyl)-1-formyl-pyrrolidine-2-carboxylic acid (1-cyano-cyclopropyl)-amide;
(2S,4R)-4-(2-Chloro-4-pyrazol-1-yl-benzenesulfonyl)-2-(1-cyano-cyclopropylcarbamoyl)-pyrrolidine-1-carboxylic acid tert-butyl ester;
(2S,4R)-4-(2-Chloro-4-piperidin-1-yl-benzenesulfonyl)-2-(1-cyano-cyclopropylcarbamoyl)-pyrrolidine-1-carboxylic acid tert-butyl ester;
(2S,4R)-4-[2-Chloro-4-(2,2,2-trifluoro-1-methyl-ethoxy)-benzenesulfonyl]-2-(1-cyano-cyclopropylcarbamoyl)-pyrrolidine-1-carboxylic acid tert-butyl ester;
(2R,4S,5R)-5-(4-Fluoro-phenyl)-2-isobutyl-4-methanesulfonyl-pyrrolidine-2-carboxylic acid (1-cyano-cyclopropyl)-amide;
(2S,4R)-4-(2-Chloro-4-fluoro-benzenesulfonyl)-2-(1-cyano-cyclopropylcarbamoyl)-pyrrolidine-1-carboxylic acid tert-butyl ester;
(2R,4S,5R)-2-(1-Cyano-cyclopropylcarbamoyl)-5-(4-fluoro-phenyl)-2-isobutyl-4-methanesulfonyl-pyrrolidine-1-carboxylic acid tert-butyl ester;
(2R,4S,5R)-4-Benzenesulfonyl-5-(4-fluoro-phenyl)-2-isobutyl-pyrrolidine-2-carboxylic acid (1-cyano-cyclopropyl)-amide;
(2S,4R)-1-Formyl-4-(2-trifluoromethyl-benzenesulfonyl)-pyrrolidine-2-carboxylic acid (1-cyano-cyclopropyl)-amide;
(2S,4R)-4-(4-Pyrazol-1-yl-2-trifluoromethyl-benzenesulfonyl)-pyrrolidine-2-carboxylic acid (1-cyano-cyclopropyl)-amide;
(2S,4R)-4-(4-Imidazol-1-yl-2-trifluoromethyl-benzenesulfonyl)-pyrrolidine-2-carboxylic acid (1-cyano-cyclopropyl)-amide;
(2S,4R)-2-(1-Cyano-cyclopropylcarbamoyl)-4-(2-methyl-propane-1-sulfonyl)-pyrrolidine-1-carboxylic acid tert-butyl ester;
(2S,4R)-4-(2-Methyl-propane-1-sulfonyl)-pyrrolidine-2-carboxylic acid (1-cyano-cyclopropyl)-amide;
(2S,4R)-4-(4-Benzoimidazol-1-yl-2-trifluoromethyl-benzenesulfonyl)-2-(1-cyano-cyclopropylcarbamoyl)-pyrrolidine-1-carboxylic acid tert-butyl ester;
(2S,4R)-2-(1-Cyano-cyclopropylcarbamoyl)-4-[4-(3-methyl-6-oxo-6H-pyridazin-1-yl)-2-trifluoromethyl-benzenesulfonyl]-pyrrolidine-1-carboxylic acid tert-butyl ester;
(2S,4R)-2-(1-Cyano-cyclopropylcarbamoyl)-4-[4-(4-methyl-piperazin-1-yl)-2-trifluoromethyl-benzenesulfonyl]-pyrrolidine-1-carboxylic acid tert-butyl ester;
(2S,4R)-4-(2-Chloro-4-piperidin-1-yl-benzenesulfonyl)-pyrrolidine-2-carboxylic acid (1-cyano-cyclopropyl)-amide;
(2S,4R)-4-(2-Chloro-4-pyrazol-1-yl-benzenesulfonyl)-pyrrolidine-2-carboxylic acid (1-cyano-cyclopropyl)-amide;
(2S,4R)-4-[2-Chloro-4-(2,2,2-trifluoro-1-methyl-ethoxy)-benzenesulfonyl]-pyrrolidine-2-carboxylic acid (1-cyano-cyclopropyl)-amide;
(2S,4R)-4-[2-Chloro-4-(3,3-difluoro-pyrrolidin-1-yl)-benzenesulfonyl]-2-(1-cyano-cyclopropylcarbamoyl)-pyrrolidine-1-carboxylic acid tert-butyl ester;
(2S,4R)-1-Acetyl-4-(2-chloro-4-pyrazol-1-yl-benzenesulfonyl)-pyrrolidine-2-carboxylic acid (1-cyano-cyclopropyl)-amide;
(2S,4R)-1-Acetyl-4-[2-chloro-4-(2,2,2-trifluoro-1-methyl-ethoxy)-benzenesulfonyl]-pyrrolidine-2-carboxylic acid (1-cyano-cyclopropyl)-amide;
(2S,4R)-1-Acetyl-4-(2-chloro-4-piperidin-1-yl-benzenesulfonyl)-pyrrolidine-2-carboxylic acid (1-cyano-cyclopropyl)-amide;
(2S,4R)-1-Acetyl-4-(2-chloro-4-fluoro-benzenesulfonyl)-pyrrolidine-2-carboxylic acid (1-cyano-cyclopropyl)-amide;
(2S,4R)-4-(2-Chloro-4-piperidin-1-yl-benzenesulfonyl)-1-(1-trifluoromethyl-cyclopropanecarbonyl)-pyrrolidine-2-carboxylic acid (1-cyano-cyclopropyl)-amide;
(2S,4R)-4-[4-(4-Methyl-piperazin-1-yl)-2-trifluoromethyl-benzenesulfonyl]-pyrrolidine-2-carboxylic acid (1-cyano-cyclopropyl)-amide;
(2S,4R)-4-(4-Benzoimidazol-1-yl-2-trifluoromethyl-benzenesulfonyl)-pyrrolidine-2-carboxylic acid (1-cyano-cyclopropyl)-amide;
(2S,4R)-4-[2-Chloro-4-(3,3-difluoro-pyrrolidin-1-yl)-benzenesulfonyl]-pyrrolidine-2-carboxylic acid (1-cyano-cyclopropyl)-amide;
4-[(2S,4R)-2-(Cyanomethyl-carbamoyl)-4-(2-trifluoromethyl-benzenesulfonyl)-pyrrolidine-1-carbonyl]-benzoic acid methyl ester;
(2S,4R)-4-[4-(3-Methyl-6-oxo-6H-pyridazin-1-yl)-2-trifluoromethyl-benzenesulfonyl]-pyrrolidine-2-carboxylic acid (1-cyano-cyclopropyl)-amide;
(2S,4R)-4-[2-Chloro-4-(4-ethyl-piperazin-1-yl)-benzenesulfonyl]-2-(1-cyano-cyclopropylcarbamoyl)-pyrrolidine-1-carboxylic acid tert-butyl ester;

(2S,4R)-4-[2-Chloro-4-(2-piperidin-1-yl-ethoxy)-benzenesulfonyl]-2-(1-cyano-cyclopropylcarbamoyl)-pyrrolidine-1-carboxylic acid tert-butyl ester;
(2S,4R)-4-[2-Chloro-4-(4-ethyl-piperazin-1-yl)-benzenesulfonyl]-pyrrolidine-2-carboxylic acid (1-cyano-cyclopropyl)-amide;
(2S,4R)-4-[4-(2-Methyl-imidazol-1-yl)-2-trifluoromethyl-benzenesulfonyl]-pyrrolidine-2-carboxylic acid (1-cyano-cyclopropyl)-amide;
(2S,4R)-4-[4-(2-Phenyl-imidazol-1-yl)-2-trifluoromethyl-benzenesulfonyl]-pyrrolidine-2-carboxylic acid (1-cyano-cyclopropyl)-amide;
(2S,4R)-4-[4-(2-oxo-pyrrolidin-1-yl)-2-trifluoromethyl-benzenesulfonyl]-pyrrolidine-2-carboxylic acid (1-cyano-cyclopropyl)-amide;
(2S,4R)-4-[4-(2-Oxo-oxazolidin-3-yl)-2-trifluoromethyl-benzenesulfonyl]-pyrrolidine-2-carboxylic acid (1-cyano-cyclopropyl)-amide;
(2S,4R)-4-[4-(3,3-Difluoro-pyrrolidin-1-yl)-2-trifluoromethyl-benzenesulfonyl]-pyrrolidine-2-carboxylic acid (1-cyano-cyclopropyl)-amide;
(2S,4R)-4-(4-Morpholin-4-yl-2-trifluoromethyl-benzenesulfonyl)-pyrrolidine-2-carboxylic acid (1-cyano-cyclopropyl)-amide;
(2S,4R)-4-[4-(3-oxo-morpholin-4-yl)-2-trifluoromethyl-benzenesulfonyl]-pyrrolidine-2-carboxylic acid (1-cyano-cyclopropyl)-amide;
(2S,4R)-4-[4-(2-oxo-2H-pyridin-1-yl)-2-trifluoromethyl-benzenesulfonyl]-pyrrolidine-2-carboxylic acid (1-cyano-cyclopropyl)-amide;
(2S,4R)-4-[4-(2-oxo-2H-pyrazin-1-yl)-2-trifluoromethyl-benzenesulfonyl]-pyrrolidine-2-carboxylic acid (1-cyano-cyclopropyl)-amide;
(2S,4R)-4-[2-Chloro-4-(4-ethyl-piperazin-1-yl)-benzenesulfonyl]-1-(1-trifluoromethyl-cyclopropanecarbonyl)-pyrrolidine-2-carboxylic acid (1-cyano-cyclopropyl)-amide;
(2S,4R)-4-[2-Chloro-4-(4-ethyl-piperazin-1-yl)-benzenesulfonyl]-1-(1-trifluoromethyl-cyclopropanecarbonyl)-pyrrolidine-2-carboxylic acid (1-cyano-cyclopropyl)-amide;
(2S,4R)-4-[2-Chloro-4-(4-ethyl-piperazin-1-yl)-benzenesulfonyl]-1-formyl-pyrrolidine-2-carboxylic acid (1-cyano-cyclopropyl)-amide;
(2S,4R)-1-Acetyl-4-(4-imidazol-1-yl-2-trifluoromethyl-benzenesulfonyl)-pyrrolidine-2-carboxylic acid (1-cyano-cyclopropyl)-amide;
(2S,4R)-1-Acetyl-4-(4-pyrazol-1-yl-2-trifluoromethyl-benzenesulfonyl)-pyrrolidine-2-carboxylic acid (1-cyano-cyclopropyl)-amide;
(2S,4R)-4-(2-Chloro-4-fluoro-benzenesulfonyl)-pyrrolidine-2-carboxylic acid (1-cyano-cyclopropyl)-amide;
(2S,4R)-4-(2-Chloro-4-fluoro-benzenesulfonyl)-1-(1-trifluoromethyl-cyclopropanecarbonyl)-pyrrolidine-2-carboxylic acid (1-cyano-cyclopropyl)-amide;
(2S,4R)-4-(2-Chloro-4-piperidin-1-yl-benzenesulfonyl)-1-formyl-pyrrolidine-2-carboxylic acid (1-cyano-cyclopropyl)-amide;
(2S,4R)-4-(2-Chloro-4-pyrazol-1-yl-benzenesulfonyl)-1-(1-trifluoromethyl-cyclopropanecarbonyl)-pyrrolidine-2-carboxylic acid (1-cyano-cyclopropyl)-amide;
(2S,4R)-4-(2-Chloro-4-pyrazol-1-yl-benzenesulfonyl)-1-formyl-pyrrolidine-2-carboxylic acid (1-cyano-cyclopropyl)-amide;
(2S,4R)-4-[2-Chloro-4-(2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide;
(2S,4R)-4-[2-Chloro-4-(2,2,2-trifluoro-1-methyl-ethoxy)-benzenesulfonyl]-1-formyl-pyrrolidine-2-carboxylic acid (1-cyano-cyclopropyl)-amide
(2S,4R)-1-Phenyl-4-(2-trifluoromethyl-benzenesulfonyl)-pyrrolidine-2-carboxylic acid cyanomethyl-amide;
(2S,4R)-4-[2-Chloro-4-(4,4-difluoro-piperidin-1-yl)-benzenesulfonyl]-2-(1-cyano-cyclopropylcarbamoyl)-pyrrolidine-1-carboxylic acid tert-butyl ester;
(2S,4R)-4-[2-Chloro-4-(4-trifluoromethyl-piperidin-1-yl)-benzenesulfonyl]-2-(1-cyano-cyclopropylcarbamoyl)-pyrrolidine-1-carboxylic acid tert-butyl ester;
(2S,4R)-4-[2-Chloro-4-(4-trifluoromethyl-piperidin-1-yl)-benzenesulfonyl]-pyrrolidine-2-carboxylic acid (1-cyano-cyclopropyl)-amide;
(2S,4R)-4-[2-Chloro-4-(4,4-difluoro-piperidin-1-yl)-benzenesulfonyl]-pyrrolidine-2-carboxylic acid (1-cyano-cyclopropyl)-amide;
(2S,4R)-4-[2-Chloro-4-(4-trifluoromethyl-piperidin-1-yl)-benzenesulfonyl]-1-(1-trifluoromethyl-cyclopropanecarbonyl)-pyrrolidine-2-carboxylic acid (1-cyano-cyclopropyl)-amide;
(2S,4R)-4-[2-Chloro-4-(4,4-difluoro-piperidin-1-yl)-benzenesulfonyl]-1-(1-trifluoromethyl-cyclopropanecarbonyl)-pyrrolidine-2-carboxylic acid (1-cyano-cyclopropyl)-amide;
(2S,4S)-2-(1-Cyano-cyclopropylcarbamoyl)-4-(2-trifluoromethyl-benzenesulfonyl)-pyrrolidine-1-carboxylic acid tert-butyl ester;
(2S,4S)-4-(2-Trifluoromethyl-benzenesulfonyl)-pyrrolidine-2-carboxylic acid (1-cyano-cyclopropyl)-amide;
(2S,4R)-1-(4-Methoxy-phenyl)-4-(2-trifluoromethyl-benzenesulfonyl)-pyrrolidine-2-carboxylic acid (1-cyano-cyclopropyl)-amide;
(2S,4R)-4-(2-Chloro-4-morpholin-4-yl-benzenesulfonyl)-1-(1-trifluoromethyl-cyclopropanecarbonyl)-pyrrolidine-2-carboxylic acid (1-cyano-cyclopropyl)-amide;
(2S,4R)-4-(2-Chloro-4-morpholin-4-yl-benzenesulfonyl)-1-(1-trifluoromethyl-cyclopropanecarbonyl)-pyrrolidine-2-carboxylic acid (1-cyano-cyclopropyl)-amide;
(2S,4R)-4-(2-Chloro-4-piperazin-1-yl-benzenesulfonyl)-1-(1-trifluoromethyl-cyclopropanecarbonyl)-pyrrolidine-2-carboxylic acid (1-cyano-cyclopropyl)-amide;
(2S,4R)-1-(2-Nitro-phenyl)-4-(2-trifluoromethyl-benzenesulfonyl)-pyrrolidine-2-carboxylic acid cyanomethyl-amide;
(2S,4R)-4-(2-Chloro-4-pyrazol-1-yl-benzenesulfonyl)-1-(1-trifluoromethyl-cyclopropanecarbonyl)-pyrrolidine-2-carboxylic acid (1-cyano-cyclopropyl)-amide;
(2S,4R)-1-(2-Nitro-phenyl)-4-(2-trifluoromethyl-benzenesulfonyl)-pyrrolidine-2-carboxylic acid (1-cyano-cyclopropyl)-amide;
(2S,4R)-4-(2,4-Dichloro-benzenesulfonyl)-1-(2-nitro-phenyl)-pyrrolidine-2-carboxylic acid (1-cyano-cyclopropyl)-amide;
(2S,4R)-4-(2,4-Dichloro-benzenesulfonyl)-1-(1-trifluoromethyl-cyclopropanecarbonyl)-pyrrolidine-2-carboxylic acid (1-cyano-cyclopropyl)-amide;
(2S,4R)-4-(2,4-Dichloro-benzenesulfonyl)-1-(1-trifluoromethyl-cyclobutanecarbonyl)-pyrrolidine-2-carboxylic acid (1-cyano-cyclopropyl)-amide;

(2S,4R)-4-(2,4-Dichloro-benzenesulfonyl)-1-(2,2-difluoro-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-2-(1-cyano-cyclopropylcarbamoyl)-pyrrolidine-1-carboxylic acid tert-butyl ester;

(2S,4R)-4-[2-Chloro-4-(2,2,2-trifluoro-ethoxy)-benzenesulfonyl]-1-(1-trifluoromethyl-cyclopropanecarbonyl)-pyrrolidine-2-carboxylic acid (1-cyano-cyclopropyl)-amide;

(R)-4-[2-Chloro-4-(2,2,2-trifluoro-ethoxy)-benzenesulfonyl]-pyrrolidine-2-carboxylic acid (1-cyano-cyclopropyl)-amide;

(2S,4R)-4-[2-Chloro-4-(oxetan-3-yloxy)-benzenesulfonyl]-2-(1-cyano-cyclopropylcarbamoyl)-pyrrolidine-1-carboxylic acid tert-butyl ester;

(2S,4R)-4-[2-Chloro-4-(2,2,2-trifluoro-ethoxy)-benzenesulfonyl]-1-(1-methyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2,2-dimethyl-propionyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2-trifluoromethyl-benzoyl)-pyrrolidine-2-carboxylic acid (1-cyano-cyclopropyl)-amide;

(2S,4R)-1-[1-(4-Chloro-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-isobutyryl-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(3-methyl-butyryl)-pyrrolidine-2-carboxylic acid (1-cyano-cyclopropyl)-amide;

(2S,4R)-4-[2-Chloro-4-(oxetan-3-yloxy)-benzenesulfonyl]-pyrrolidine-2-carboxylic acid (1-cyano-cyclopropyl)-amide;

(R)-4-[2-Chloro-4-(2,2,2-trifluoro-ethoxy)-benzenesulfonyl]-1-formyl-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide;

(2S,4R)-4-(2-Trifluoromethyl-benzenesulfonyl)-1-(2-trifluoromethyl-pyrimidin-4-yl)-pyrrolidine-2-carboxylic acid (1-cyano-cyclopropyl)-amide;

(2S,4R)-4-(2-Trifluoromethyl-benzenesulfonyl)-1-(3-trifluoromethyl-pyridin-2-yl)-pyrrolidine-2-carboxylic acid (1-cyano-cyclopropyl)-amide;

(2S,4R)-4-(2-Trifluoromethyl-benzenesulfonyl)-1-(3-trifluoromethyl-pyridin-2-yl)-pyrrolidine-2-carboxylic acid (1-cyano-cyclopropyl)-amide;

(2S,4R)-4-(2,4-Dichloro-benzenesulfonyl)-1-(3-trifluoromethyl-pyridin-2-yl)-pyrrolidine-2-carboxylic acid (1-cyano-cyclopropyl)-amide;

(2S,4R)-4-(2,4-Dichloro-benzenesulfonyl)-1-(3-trifluoromethyl-pyridin-2-yl)-pyrrolidine-2-carboxylic acid (1-cyano-cyclopropyl)-amide;

(2S,4R)-4-[2-Chloro-4-(4-ethyl-piperazin-1-yl)-benzenesulfonyl]-1-(3-trifluoromethyl-pyridin-2-yl)-pyrrolidine-2-carboxylic acid (1-cyano-cyclopropyl)-amide;

(2S,4R)-4-[2-Chloro-4-(4-ethyl-piperazin-1-yl)-benzenesulfonyl]-1-(3-trifluoromethyl-pyridin-2-yl)-pyrrolidine-2-carboxylic acid (1-cyano-cyclopropyl)-amide;

(2S,4R)-1-(5-Methyl-2-phenyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-[2-(2-Chloro-pyridin-4-yl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-1-[2-(4-Chloro-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-1-[2-(4-Fluoro-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-1-[5-Methyl-2-(2-oxo-1,2-dihydro-pyridin-4-yl)-2H-pyrazol-3-yl]-4-(2-trifluoromethyl-benzenesulfonyl)-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-cyclopropanecarbonyl-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-cyclopropanecarbonyl-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(1-methyl-cyclopropanecarbonyl)-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(1-methyl-cyclopropanecarbonyl)-pyrrolidine-2-carboxylic acid (1-cyano-cyclopropyl)-amide;

(2S,4R)-4-[2-Chloro-4-(oxetan-3-yloxy)-benzenesulfonyl]-1-(1-trifluoromethyl-cyclopropanecarbonyl)-pyrrolidine-2-carboxylic acid (1-cyano-cyclopropyl)-amide;

(2S,4R)-1-[1-(4-Chloro-phenyl)-cyclopropanecarbonyl]-4-(2-trifluoromethyl-benzenesulfonyl)-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(2,2-dimethyl-propionyl)-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(2,2-dimethyl-propionyl)-pyrrolidine-2-carboxylic acid (1-cyano-cyclopropyl)-amide;

(2S,4R)-4-(2-Trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-4-(2-Trifluoromethyl-benzenesulfonyl)-1-(3,3,3-trifluoro-propionyl)-pyrrolidine-2-carboxylic acid (1-cyano-cyclopropyl)-amide;

(2S,4R)-1-(1-Methyl-cyclopropanecarbonyl)-4-(2-trifluoromethyl-benzenesulfonyl)-pyrrolidine-2-carboxylic acid (1-cyano-cyclopropyl)-amide;

(2S,4R)-2-(1-Cyano-cyclopropylcarbamoyl)-4-[4-(2,2,2-trifluoro-ethoxy)-2-trifluoromethyl-benzenesulfonyl]-pyrrolidine-1-carboxylic acid tert-butyl ester;

(2S,4R)-4-(4-Fluoro-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-1-(2,2-Dimethyl-propionyl)-4-(4-fluoro-2-trifluoromethyl-benzenesulfonyl)-pyrrolidine-2-carboxylic acid (1-cyano-cyclopropyl)-amide;

(2S,4R)-1-(1-Methyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-1-(2,2-Dimethyl-propionyl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-4-(2-Chloro-benzenesulfonyl)-1-(1-trifluoromethyl-cyclopropanecarbonyl)-pyrrolidine-2-carboxylic acid (1-cyano-cyclopropyl)-amide;

(2S,4R)-4-(2-Chloro-benzenesulfonyl)-1-(1-methyl-cyclopropanecarbonyl)-pyrrolidine-2-carboxylic acid (1-cyano-cyclopropyl)-amide;

(2S,4R)-4-(2-Chloro-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-(1-phenyl-cyclopropanecarbonyl)-pyrrolidine-2-carboxylic acid (1-cyano-cyclopropyl)-amide;

(2S,4R)-4-(2-Chloro-benzenesulfonyl)-1-(2,2-dimethyl-propionyl)-pyrrolidine-2-carboxylic acid (1-cyano-cyclopropyl)-amide;

(2S,4R)-4-(2-Chloro-benzenesulfonyl)-1-isobutyryl-pyrrolidine-2-carboxylic acid (1-cyano-cyclopropyl)-amide;

(2S,4R)-4-(2-Chloro-benzenesulfonyl)-1-(3,3,3-trifluoro-propionyl)-pyrrolidine-2-carboxylic acid (1-cyano-cyclopropyl)-amide;

(2S,4R)-4-(2-Chloro-benzenesulfonyl)-1-(3-methyl-butyryl)-pyrrolidine-2-carboxylic acid (1-cyano-cyclopropyl)-amide;

(2S,4R)-4-[4-Chloro-2-(2,2,2-trifluoro-ethoxy)-benzenesulfonyl]-2-(1-cyano-cyclopropylcarbamoyl)-pyrrolidine-1-carboxylic acid tert-butyl ester;

(2S,4R)-4-(2,4-Dichloro-benzenesulfonyl)-1-(1-methyl-cyclopropanecarbonyl)-pyrrolidine-2-carboxylic acid (1-cyano-cyclopropyl)-amide;

(2S,4R)-1-[1-(4-Chloro-phenyl)-cyclopropanecarbonyl]-4-(2,4-dichloro-benzenesulfonyl)-pyrrolidine-2-carboxylic acid (1-cyano-cyclopropyl)-amide;

(2S,4R)-4-(2,4-Dichloro-benzenesulfonyl)-1-(1-phenyl-cyclopropanecarbonyl)-pyrrolidine-2-carboxylic acid (1-cyano-cyclopropyl)-amide;

(2S,4R)-4-(2,4-Dichloro-benzenesulfonyl)-1-(2,2-dimethyl-propionyl)-pyrrolidine-2-carboxylic acid (1-cyano-cyclopropyl)-amide;

(2S,4R)-4-(2,4-Dichloro-benzenesulfonyl)-1-isobutyryl-pyrrolidine-2-carboxylic acid (1-cyano-cyclopropyl)-amide;

(2S,4R)-4-(2,4-Dichloro-benzenesulfonyl)-1-(3,3,3-trifluoro-propionyl)-pyrrolidine-2-carboxylic acid (1-cyano-cyclopropyl)-amide; and (2S,4R)-4-(2,4-Dichloro-benzenesulfonyl)-1-(3-methyl-butyryl)-pyrrolidine-2-carboxylic acid (1-cyano-cyclopropyl)-amide.

25. A compound according to claim 1 selected from the group consisting of:

(2S,4R)-4-(2-Chloro-4-pyrazol-1-yl-benzenesulfonyl)-1-(1-trifluoromethyl-cyclopropanecarbonyl)-pyrrolidine-2-carboxylic acid (1-cyano-cyclopropyl)-amide;

(2S,4R)-4-(2,4-Dichloro-benzenesulfonyl)-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-methyl-cyclopropanecarbonyl)-pyrrolidine-2-carboxylic acid (1-cyano-cyclopropyl)-amide;

(2S,4R)-1-[1-(4-Chloro-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(1-methyl-cyclopropanecarbonyl)-pyrrolidine-2-carboxylic acid (1-cyano-cyclopropyl)-amide;

(2S,4R)-4-[2-Chloro-4-((S)-2,2,2-trifluoro-1-methyl-ethoxy)-benzenesulfonyl]-1-(2,2-dimethyl-propionyl)-pyrrolidine-2-carboxylic acid (1-cyano-cyclopropyl)-amide;

(2S,4R)-4-(2-Trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-1-(1-Methyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-1-(2,2-Dimethyl-propionyl)-4-[4-(2,2,2-trifluoro-ethoxy)-2-trifluoromethyl-benzenesulfonyl]-pyrrolidine-2-carboxylic acid (1-cyano-cyclopropyl)-amide; and (2S,4R)-4-(2-Chloro-benzenesulfonyl)-1-[1-(4-chloro-phenyl)-cyclopropanecarbonyl]-pyrrolidine-2-carboxylic acid (1-cyano-cyclopropyl)-amide.

26. A compound according to claim 1 selected from the group consisting of:

(2S,4R)-4-[2-Chloro-4-((S)-2,2,2-trifluoro-1-methyl-ethoxy)-benzenesulfonyl]-2-(1-cyano-cyclopropylcarbamoyl)-pyrrolidine-1-carboxylic acid tert-butyl ester;

(2S,4R)-4-[2-Chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-1-[5-Methyl-2-(2-oxo-1,2-dihydro-pyridin-4-yl)-2H-pyrazol-3-yl]-4-(2-trifluoromethyl-benzenesulfonyl)-pyrrolidine-2-carboxylic acid (1-cyano-cyclopropyl)-amide;

(2S,4R)-1-[5-Methyl-2-(4-trifluoromethyl-phenyl)-2H-pyrazol-3-yl]-4-(2-trifluoromethyl-benzenesulfonyl)-pyrrolidine-2-carboxylic acid (1-cyano-cyclopropyl)-amide;

(2S,4R)-1-[2-(3-Chloro-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-1-(5-Methyl-2-thiazol-2-yl-2H-pyrazol-3-yl)-4-(2-trifluoromethyl-benzenesulfonyl)-pyrrolidine-2-carboxylic acid (1-cyano-cyclopropyl)-amide;

(2S,4R)-1-[1-(4-Chloro-phenyl)-cyclopropanecarbonyl]-4-(2,4-difluoro-b enzenesulfonyl)-pyrrolidine-2-carboxylic acid (1-cyano-cyclopropyl)-amide;

(2S,4R)-1-[1-(4-Chloro-phenyl)-cyclopropanecarbonyl]-4-(2-methyl-propane-1-sulfonyl)-pyrrolidine-2-carboxylic acid (1-cyano-cyclopropyl)-amide;

(2S,4R)-4-[4-(2,2,2-Trifluoro-ethoxy)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[4-(1-Methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[1-(3,4-dichloro-phenyl)-cyclopropanecarbonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-phenyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2,2-difluoro-cyclopropanecarbonyl)-pyrrolidine-2-carboxylic acid (1-cyano-cyclopropyl)-amide;

{1-[(2S,4R)-4-[2-Chloro-4-(2,2,2-trifluoro-ethoxy)-benzenesulfonyl]-2-(1-cyano-cyclopropylcarbamoyl)-pyrrolidine-1-carbonyl]-cyclopropyl}-carbamic acid tert-butyl ester;

(2S,4R)-4-[2-Chloro-4-(2,2,2-trifluoro-ethoxy)-benzenesulfonyl]-1-(1-cyano-cyclopropanecarbonyl)-pyrrolidine-2-carboxylic acid (1-cyano-cyclopropyl)-amide;

(2S,4R)-1-[2-(4-Chloro-phenyl)-acetyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[4-(2-Chloro-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2-phenyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2-phenyl-cyclopropanecarbonyl)-pyrrolidine-2-carboxylic acid (1-cyano-cyclopropyl)-amide;

(2S,4R)-4-[4-(2-Methyl-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-1-(1-Methyl-cyclopropanecarbonyl)-4-[4-(1-methyl-1H-pyrazol-4-yl)-2-trifluoromethyl-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-pyridin-4-yl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2,2-difluoro-2-phenyl-acetyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-2-(1-cyano-cyclopropylcarbamoyl)-pyrrolidine-1-carboxylic acid 4-chloro-phenyl ester;

(2S,4R)-4-(2-Chloro-benzenesulfonyl)-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-4-(2-Chloro-benzenesulfonyl)-1-[2-(2-chloro-pyridin-4-yl)-5-methyl-2H-pyrazol-3-yl]-pyrrolidine-2-carboxylic acid (1-cyano-cyclopropyl)-amide;

(2S,4R)-1-(1,5-Dimethyl-1H-pyrazol-3-yl)-4-(2-trifluoromethyl-benzenesulfonyl)-pyrrolidine-2-carboxylic acid (1-cyano-cyclopropyl)-amide;

(2S,4R)-4-(4-Cyclopropyl-2-trifluoromethyl-benzenesulfonyl)-1-(1-trifluoromethyl-cyclopropanecarbonyl)-pyrrolidine-2-carboxylic acid (1-cyano-cyclopropyl)-amide;

(2S,4R)-1-(1-Methyl-cyclopropanecarbonyl)-4-[4-(2-methyl-pyridin-4-yl)-2-trifluoromethyl-benzenesulfonyl]-pyrrolidine-2-carboxylic acid (1-cyano-cyclopropyl)-amide;

(2S,4R)-4-[4-(2-Chloro-pyridin-4-yl)-2-trifluoromethyl-benzenesulfonyl]-1-(1-methyl-cyclopropanecarbonyl)-pyrrolidine-2-carboxylic acid (1-cyano-cyclopropyl)-amide;

(2S,4R)-4-(2',4'-Difluoro-3-trifluoromethyl-biphenyl-4-sulfonyl)-1-(1-methyl-cyclopropanecarbonyl)-pyrrolidine-2-carboxylic acid (1-cyano-cyclopropyl)-amide;

(2S,4R)-4-[4-(4-Methyl-piperazin-1-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide;

(2S,4R)-4-Benzenesulfonyl-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-4-Benzenesulfonyl-1-[2-(2-chloro-pyridin-4-yl)-5-methyl-2H-pyrazol-3-yl]-pyrrolidine-2-carboxylic acid (1-cyano-cyclopropyl)-amide;

(2S,4R)-4-(2',4'-Difluoro-3-trifluoromethyl-biphenyl-4-sulfonyl)-1-(1-trifluoromethyl-cyclopropanecarbonyl)-pyrrolidine-2-carboxylic acid (1-cyano-cyclopropyl)-amide;

(4-{2-[(2S,4R)-4-[2-Chloro-4-(2,2,2-trifluoro-ethoxy)-benzenesulfonyl]-2-(1-cyano-cyclopropylcarbamoyl)-pyrrolidin-1-yl]-2-oxo-ethyl}-cyclohexyl)-carbamic acid tert-butyl ester;

(2S,4R)-1-[2-(4-Amino-cyclohexyl)-acetyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2-(2-Chloro-pyridin-4-yl)-5-methyl-2H-pyrazol-3-yl]-4-(4-fluoro-2-trifluoromethyl-benzenesulfonyl)-pyrrolidine-2-carboxylic acid (1-cyano-cyclopropyl)-amide;

(2S,4R)-4-(4-Fluoro-2-trifluoromethyl-benzenesulfonyl)-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-1-(2-Isopropyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-[5-Methyl-2-(2,2,2-trifluoro-ethyl)-2H-pyrazol-3-yl]-4-(2-trifluoromethyl-benzenesulfonyl)-pyrrolidine-2-carboxylic acid (1-cyano-cyclopropyl)-amide;

(2S,4R)-4-(4-Bromo-2-trifluoromethyl-benzenesulfonyl)-1-(1-methyl-cyclopropanecarbonyl)-pyrrolidine-2-carboxylic acid (1-cyano-cyclopropyl)-amide;

(2S,4R)-4-(4-Cyclopropyl-2-trifluoromethyl-benzenesulfonyl)-1-(1-methyl-cyclopropanecarbonyl)-pyrrolidine-2-carboxylic acid (1-cyano-cyclopropyl)-amide;

(2S,4R)-1-(1-Methyl-cyclopropanecarbonyl)-4-[4-(4-methyl-piperazin-1-yl)-2-trifluoromethyl-benzenesulfonyl]-pyrrolidine-2-carboxylic acid (1-cyano-cyclopropyl)-amide;

(2S,4R)-1-[1-(4-Bromo-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2-(4-Acetylamino-cyclohexyl)-acetyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2,2-Bis-(4-chloro-phenyl)-acetyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-(5-Methyl-2-m-tolyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-[1-(4-Carbamoyl-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[1-(4-Chloro-phenyl)-cyclobutanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2-(4-Chloro-phenyl)-2-methyl-propionyl]-4-[2-chloro-4-(2,2,2-trifluoro-ethoxy)-benzenesulfonyl]-pyrrolidine-2-carboxylic acid (1-cyano-cyclopropyl)-amide;

(2R,4S)-4-[2-Chloro-4-(2,2,2-trifluoro-ethoxy)-benzenesulfonyl]-1-(1-trifluoromethyl-cyclopropanecarbonyl)-pyrrolidine-2-carboxylic acid (1-cyano-cyclopropyl)-amide;

(2S,4R)-4-(2-Chloro-benzenesulfonyl)-1-[1-(4-trifluoromethoxy-phenyl)-cyclopropanecarbonyl]-pyrrolidine-2-carboxylic acid (1-cyano-cyclopropyl)-amide;

(2S,4R)-4-(2-Chloro-benzenesulfonyl)-1-[2-(4-chloro-phenyl)-2-methyl-propionyl]-pyrrolidine-2-carboxylic acid (1-cyano-cyclopropyl)-amide;

(2S,4R)-4-(2-Chloro-benzenesulfonyl)-1-[1-(4-chloro-phenyl)-cyclobutanecarbonyl]-pyrrolidine-2-carboxylic acid (1-cyano-cyclopropyl)-amide;

(2S,4R)-4-(2-Chloro-benzenesulfonyl)-1-[1-(3,4-dichloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-(1-pyridin-4-yl-cyclopropanecarbonyl)-pyrrolidine-2-carboxylic acid (1-cyano-cyclopropyl)-amide;

(2S,4R)-1-(5-Methyl-1H-pyrazol-3-yl)-4-(2-trifluoromethyl-benzenesulfonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(4-phenyl-tetrahydro-pyran-4-carbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-{1-[4-(1-methyl-1H-pyrazol-4-yl)-phenyl]-cyclopropanecarbonyl}-pyrrolidine-2-carboxylic acid (1-cyano-cyclopropyl)-amide;

(2S,4R)-1-[5-Methyl-2-(2-methyl-pyridin-4-yl)-2H-pyrazol-3-yl]-4-(2-trifluoromethyl-benzenesulfonyl)-pyrrolidine-2-carboxylic acid (1-cyano-cyclopropyl)-amide;

(2S,4R)-4-[2-Chloro-4-(4-methyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-[4-(2,2,2-trifluoro-ethyl)-piperazin-1-yl]-benzenesulfonyl]-1-(1-trifluoromethyl-cyclopropanecarbonyl)-pyrrolidine-2-carboxylic acid (1-cyano-cyclopropyl)-amide;

(2S,4R)-4-(2-Chloro-4-dimethylamino-benzenesulfonyl)-1-(1-trifluoromethyl-cyclopropanecarbonyl)-pyrrolidine-2-carboxylic acid (1-cyano-cyclopropyl)-amide;

(2S,4R)-4-[2-Chloro-4-(4-isopropyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(3-methyl-oxetane-3-carbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[1-(4-fluoro-phenyl)-cyclopropanecarbonyl]-pyrrolidine-2-carboxylic acid (1-cyano-cyclopropyl)-amide;

(2S,4R)-4-[4-(4-tert-Butyl-piperazin-1-yl)-2-chloro-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-[4-(2-methoxy-ethyl)-piperazin-1-yl]-benzenesulfonyl]-1-(1-trifluoromethyl-cyclopropanecarbonyl)-pyrrolidine-2-carboxylic acid (1-cyano-cyclopropyl)-amide;

(2S,4R)-4-[2-Chloro-4-(4-cyclopropyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-4-((S)-2-Chloro-4-hexahydro-pyrrolo[1,2-a]pyrazin-2-yl-benzenesulfonyl)-1-(1-trifluoromethyl-cyclopropanecarbonyl)-pyrrolidine-2-carboxylic acid (1-cyano-cyclopropyl)-amide;

(2S,4R)-1-(2,5-Dimethyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-[2-Chloro-4-(5,6-dihydro-8H-[1,2,4]triazolo[4,3-a]pyrazin-7-yl)-benzenesulfonyl]-1-(1-trifluoromethyl-cyclopropanecarbonyl)-pyrrolidine-2-carboxylic acid (1-cyano-cyclopropyl)-amide;

(2S,4R)-1-[1-(4-Chloro-phenyl)-cyclopentanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-phenyl-cyclohexanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-p-tolyl-cyclopropanecarbonyl)-pyrrolidine-2-carboxylic acid (1-cyano-cyclopropyl)-amide (R)-4-[2-Chloro-4-(4-methyl-piperazin-1-yl)-benzenesulfonyl]-1-(1-trifluoromethyl-cyclopropanecarbonyl)-pyrrolidine-2-carboxylic acid (1-cyano-cyclopropyl)-amide;

(2S,4R)-1-[5-Methyl-2-(4-trifluoromethyl-phenyl)-2H-pyrazol-3-yl]-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-1-[5-Methyl-2-(tetrahydro-pyran-4-yl)-2H-pyrazol-3-yl]-4-(2-trifluoromethyl-benzenesulfonyl)-pyrrolidine-2-carboxylic acid (1-cyano-cyclopropyl)-amide;

(2S,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-1-(2-Isopropyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[1-(4-trifluoromethyl-phenyl)-cyclopropanecarbonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[1-(3-trifluoromethyl-phenyl)-cyclopropanecarbonyl]-pyrrolidine-2-carboxylic acid (1-cyano-cyclopropyl)-amide;

(2S,4R)-4-(2-Chloro-4-fluoro-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-(naphthalene-2-sulfonyl)-pyrrolidine-2-carboxylic acid (1-cyano-cyclopropyl)-amide;

(2S,4R)-1-[1-(4-Chloro-phenyl)-cyclohexanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-(2-Chloro-benzenesulfonyl)-1-(4-chloro-benzenesulfonyl)-pyrrolidine-2-carboxylic acid (1-cyano-cyclopropyl)-amide;

(2S,4R)-1-(Biphenyl-4-sulfonyl)-4-(2-chloro-benzenesulfonyl)-pyrrolidine-2-carboxylic acid (1-cyano-cyclopropyl)-amide;

(2S,4R)-1-(5-Methyl-2-pyridazin-3-yl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Cyclohexyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Benzyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Cyclohexyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Benzyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Cyclobutyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-(2-Chloro-benzenesulfonyl)-1-(4-oxazol-5-yl-benzenesulfonyl)-pyrrolidine-2-carboxylic acid (1-cyano-cyclopropyl)-amide;

(2S,4R)-4-[2-Chloro-4-(4-methyl-piperazin-1-yl)-benzenesulfonyl]-1-[1-(4-chloro-phenyl)-cyclopropanecarbonyl]-pyrrolidine-2-carboxylic acid (1-cyano-cyclopropyl)-amide;

(2S,4R)-4-(2-Chloro-4-imidazol-1-yl-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-[2-Chloro-4-(2-methyl-imidazol-1-yl)-benzenesulfonyl]-1-[1-(4-chloro-phenyl)-cyclopropanecarbonyl]-pyrrolidine-2-carboxylic acid (1-cyano-cyclopropyl)-amide;

(2S,4R)-1-[1-(4-Chloro-phenyl)-cyclopropanecarbonyl]-4-(2-chloro-4-pyrazol-1-yl-benzenesulfonyl)-pyrrolidine-2-carboxylic acid (1-cyano-cyclopropyl)-amide;

(2S,4R)-4-(4-Azetidin-1-yl-2-chloro-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-[4-(4-tert-Butyl-piperazin-1-yl)-2-chloro-benzenesulfonyl]-1-[1-(4-chloro-phenyl)-cyclopropanecarbonyl]-pyrrolidine-2-carboxylic acid (1-cyano-cyclopropyl)-amide;

(2S,4R)-4-[2-Chloro-4-(4-cyclopropyl-piperazin-1-yl)-benzenesulfonyl]-1-[1-(4-chloro-phenyl)-cyclopropanecarbonyl]-pyrrolidine-2-carboxylic acid (1-cyano-cyclopropyl)-amide;

(2S,4R)-1-[1-(3-Chloro-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[1-(3-Bromo-phenyl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-1-[2-(3-Methoxy-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-1-[2-(3-Methoxy-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-4-(2-Trifluoromethyl-benzenesulfonyl)-1-(5-trifluoromethyl-[1,3,4]thiadiazol-2-yl)-pyrrolidine-2-carboxylic acid (1-cyano-cyclopropyl)-amide;

(2S,4R)-4-[2-Chloro-4-(2-isopropyl-imidazol-1-yl)-benzenesulfonyl]-1-[1-(4-chloro-phenyl)-cyclopropanecarbonyl]-pyrrolidine-2-carboxylic acid (1-cyano-cyclopropyl)-amide;

(2S,4R)-1-(5-Methyl-2-phenethyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(5-Methyl-2-phenethyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-tert-Butyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Isobutyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-1-(2-Isobutyl-5-methyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-[2-Chloro-4-(2-methoxy-ethoxy)-benzenesulfonyl]-1-[1-(4-chloro-phenyl)-cyclopropanecarbonyl]-pyrrolidine-2-carboxylic acid (1-cyano-cyclopropyl)-amide;

1-Biphenyl-2-yl-4-(2-trifluoromethyl-benzenesulfonyl)-pyrrolidine-2-carboxylic acid (1-cyano-cyclopropyl)-amide;

(2S,4R)-4-(4-Fluoro-2-trifluoromethyl-benzenesulfonyl)-1-(1-methyl-cyclopropanecarbonyl)-pyrrolidine-2-carboxylic acid (1-cyano-cyclopropyl)-amide;

1-Naphthalen-1-yl-4-(2-trifluoromethyl-benzenesulfonyl)-pyrrolidine-2-carboxylic acid (1-cyano-cyclopropyl)-amide;

(2S,4R)-1-[2-(4-Bromo-phenyl)-[1,3]dioxolane-2-carbonyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-naphthalen-1-yl-cyclopropanecarbonyl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(1-naphthalen-2-yl-cyclopropanecarbonyl)-pyrrolidine-2-carboxylic acid (1-cyano-cyclopropyl)-amide;

(2S,4R)-4-(2-Chloro-4-imidazo[4,5-c]pyridin-1-yl-benzenesulfonyl)-1-[1-(4-chloro-phenyl)-cyclopropanecarbonyl]-pyrrolidine-2-carboxylic acid (1-cyano-cyclopropyl)-amide;

(2S,4R)-4-(2-Chloro-4-imidazo[4,5-c]pyridin-5-yl-benzenesulfonyl)-1-[1-(4-chloro-phenyl)-cyclopropanecarbonyl]-pyrrolidine-2-carboxylic acid (1-cyano-cyclopropyl)-amide;

(2S,4R)-1-[2-(2,6-Dimethyl-pyridin-4-yl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-1-(5-Methyl-2-quinolin-4-yl-2H-pyrazol-3-yl)-4-(2-trifluoromethyl-benzenesulfonyl)-pyrrolidine-2-carboxylic acid (1-cyano-cyclopropyl)-amide;

(2S,4R)-4-(2-Chloro-benzenesulfonyl)-1-(2-cyclobutyl-5-methyl-2H-pyrazol-3-yl)-pyrrolidine-2-carboxylic acid (1-cyano-cyclopropyl)-amide;

4-(2-Trifluoromethyl-benzenesulfonyl)-1-(3-trifluoromethyl-phenyl)-pyrrolidine-2-carboxylic acid (1-cyano-cyclopropyl)-amide;

1-(2-tert-Butyl-phenyl)-4-(2-trifluoromethyl-benzenesulfonyl)-pyrrolidine-2-carboxylic acid (1-cyano-cyclopropyl)-amide;

(2S,4R)-1-[2-(3-Acetylamino-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

(2S,4R)-1-[2-(3-Acetylamino-phenyl)-5-methyl-2H-pyrazol-3-yl]-4-(2-trifluoromethyl-benzenesulfonyl)-pyrrolidine-2-carboxylic acid (1-cyano-cyclopropyl)-amide;

1-(3-Cyano-phenyl)-4-(2-trifluoromethyl-benzenesulfonyl)-pyrrolidine-2-carboxylic acid (1-cyano-cyclopropyl)-amide;

(2S,4R)-4-(2-Chloro-benzenesulfonyl)-1-(5-methyl-2-phenethyl-2H-pyrazol-3-yl)-pyrrolidine-2-carboxylic acid (1-cyano-cyclopropyl)-amide;

(2S,4R)-1-[1-(4-Chloro-phenyl)-cyclobutanecarbonyl]-4-(2-trifluoromethyl-benzenesulfonyl)-pyrrolidine-2-carboxylic acid (1-cyano-cyclopropyl)-amide;

(2S,4R)-1-[1-(6-Chloro-pyridin-3-yl)-cyclopropanecarbonyl]-4-(2-trifluoromethyl-benzenesulfonyl)-pyrrolidine-2-carboxylic acid (1-cyano-cyclopropyl)-amide;

1-(Tetrahydro-pyran-4-yl)-4-(2-trifluoromethyl-benzenesulfonyl)-pyrrolidine-2-carboxylic acid (1-cyano-cyclopropyl)-amide;

(2S,4R)-1-[5-Cyclopropyl-2-(4-trifluoromethyl-phenyl)-2H-pyrazol-3-yl]-4-(2-trifluoromethyl-benzenesulfonyl)-pyrrolidine-2-carboxylic acid (1-cyano-cyclopropyl)-amide;

4-[2-(1-Cyano-cyclopropylcarbamoyl)-4-(2-trifluoromethyl-benzenesulfonyl)-pyrrolidin-1-yl]-piperidine-1-carboxylic acid tert-butyl ester;

(2S,4R)-1-[1-(4-Chloro-phenyl)-cyclopropylmethyl]-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-[4-(2,2,2-Trifluoro-ethoxy)-2-trifluoromethyl-benzenesulfonyl]-1-(5-trifluoromethyl-[1,3,4]thiadiazol-2-yl)-pyrrolidine-2-carboxylic acid (1-cyano-cyclopropyl)-amide;

1-(3-Trifluoromethoxy-phenyl)-4-(2-trifluoromethyl-benzenesulfonyl)-pyrrolidine-2-carboxylic acid (1-cyano-cyclopropyl)-amide;

(2S,4R)-4-(2-Chloro-4-fluoro-benzenesulfonyl)-1-[1-(6-chloro-pyridin-3-yl)-cyclopropanecarbonyl]-pyrrolidine-2-carboxylic acid (1-cyano-cyclopropyl)-amide;

(2S,4R)-4-[2-Chloro-4-(4-methyl-piperazin-1-yl)-benzenesulfonyl]-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-[2-Chloro-4-(4-isopropyl-piperazin-1-yl)-benzenesulfonyl]-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-[4-(4-tert-Butyl-piperazin-1-yl)-2-chloro-benzenesulfonyl]-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-{2-Chloro-4-[4-(2-methoxy-ethyl)-piperazin-1-yl]-benzenesulfonyl}-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-((S)-2-Chloro-4-hexahydro-pyrrolo[1,2-a]pyrazin-2-yl-benzenesulfonyl)-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-[2-Chloro-4-(4-cyclopropyl-piperazin-1-yl)-benzenesulfonyl]-1-[1-(6-chloro-pyridin-3-yl)-cyclopropanecarbonyl]-pyrrolidine-2-carboxylic acid (1-cyano-cyclopropyl)-amide; compound with formic acid;

(2S,4R)-4-(2-Chloro-4-methoxy-benzenesulfonyl)-1-(2-cyclobutyl-5-methyl-2H-pyrazol-3-yl)-pyrrolidine-2-carboxylic acid (1-cyano-cyclopropyl)-amide;

(2S,4R)-1-[2-Benzyl-5-methyl-2H-pyrazol-3-yl)-4-(2-chloro-4-methoxy-benzenesulfonyl)-pyrrolidine-2-carboxylic acid (1-cyano-cyclopropyl)-amide;

(R)-1-[1-(6-Chloro-pyridin-3-yl)-cyclopropanecarbonyl]-4-[2-chloro-4-(2,2,2-trifluoro-ethoxy)-benzenesulfonyl]-pyrrolidine-2-carboxylic acid (1-cyano-cyclopropyl)-amide;

(R)-4-[2-Chloro-4-(2-methoxy-ethoxy)-benzenesulfonyl]-1-[1-(6-chloro-pyridin-3-yl)-cyclopropanecarbonyl]-pyrrolidine-2-carboxylic acid (1-cyano-cyclopropyl)-amide;

(2S,4R)-1-(2-Benzyl-5-methyl-2H-pyrazol-3-yl)-4-(2-chloro-benzenesulfonyl)-pyrrolidine-2-carboxylic acid (1-cyano-cyclopropyl)-amide;

(2S,4R)-4-(2-Chloro-4-pyrazol-1-yl-benzenesulfonyl)-1-[1-(6-chloro-pyridin-3-yl)-cyclopropanecarbonyl]-pyrrolidine-2-carboxylic acid (1-cyano-cyclopropyl)-amide;

(2S,4R)-1-[1-(6-Chloro-pyridin-3-yl)-cyclopropanecarbonyl]-4-[2-chloro-4-((S)-2,2,2-trifluoro-1-methyl-ethoxy)-benzenesulfonyl]-pyrrolidine-2-carboxylic acid (1-cyano-cyclopropyl)-amide;

(2S,4R)-4-(2-Chloro-4-imidazol-1-yl-benzenesulfonyl)-1-[1-(6-chloro-pyridin-3-yl)-cyclopropanecarbonyl]-pyrrolidine-2-carboxylic acid (1-cyano-cyclopropyl)-amide;

(6R,7aS)-6-(2-Chloro-4-fluoro-benzenesulfonyl)-1-cyano-tetrahydro-pyrrolizine-7a-carboxylic acid (1-cyano-cyclopropyl)-amide;

(2S,4R)-1-(1-Benzo[1,3]dioxol-5-yl-cyclopropanecarbonyl)-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-(2-Chloro-4-fluoro-benzenesulfonyl)-1-(2-cyclobutyl-5-methyl-2H-pyrazol-3-yl)-pyrrolidine-2-carboxylic acid (1-cyano-cyclopropyl)-amide;

(2S,4R)-1-(5-tert-Butyl-2-methyl-2H-pyrazole-3-carbonyl)-4-[2-chloro-4-(2,2,2-trifluoro-ethoxy)-benzenesulfonyl]-pyrrolidine-2-carboxylic acid (1-cyano-cyclopropyl)-amide;

(2S,4R)-4-(2-Chloro-4-methoxy-benzenesulfonyl)-2-(1-cyano-cyclopropylcarbamoyl)-pyrrolidine-1-carboxylic acid tert-butyl ester;

(2S,4R)-1-(2-Cyclobutyl-5-methyl-2H-pyrazol-3-yl)-4-(4-fluoro-2-trifluoromethyl-benzenesulfonyl)-pyrrolidine-2-carboxylic acid (1-cyano-cyclopropyl)-amide;

(2S,4R)-1-(2-Cyclobutyl-5-methyl-2H-pyrazol-3-yl)-4-[4-(4-methyl-piperazin-1-yl)-2-trifluoromethyl-benzenesulfonyl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2-naphthalen-1-yl-[1,3]dioxolane-2-carbonyl)-pyrrolidine-2-carboxylic acid (1-cyano-cyclopropyl)-amide;

(2S,4R)-1-(2-Cyclobutyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-1-(2-Cyclobutyl-5-methyl-2H-pyrazol-3-yl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-1-[1-Methyl-5-(tetrahydro-pyran-4-yl)-1H-pyrazol-3-yl]-4-(2-trifluoromethyl-benzenesulfonyl)-pyrrolidine-2-carboxylic acid (1-cyano-cyclopropyl)-amide;

(2S,4R)-1-(3-Chloro-4-fluoro-phenyl)-4-(2-trifluoromethyl-benzenesulfonyl)-pyrrolidine-2-carboxylic acid (1-cyano-cyclopropyl)-amide;

(2R,4S)-1-(3-Chloro-4-fluoro-phenyl)-4-(2-trifluoromethyl-benzenesulfonyl)-pyrrolidine-2-carboxylic acid (1-cyano-cyclopropyl)-amide;

(2S,4R)-4-(4-Fluoro-2-trifluoromethyl-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-1-[2-Cyclobutyl-5-(tetrahydro-pyran-4-yl)-2H-pyrazol-3-yl]-4-(2-trifluoromethyl-benzenesulfonyl)-pyrrolidine-2-carboxylic acid (1-cyano-cyclopropyl)-amide;

(2S,4R)-1-(2-Cyclobutyl-5-cyclopropyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-(2-Chloro-benzenesulfonyl)-1-(5-trifluoromethyl-[1,3,4]thiadiazol-2-yl)-pyrrolidine-2-carboxylic acid (1-cyano-cyclopropyl)-amide;

(2S,4R)-1-(5-Cyclopropyl-2H-pyrazol-3-yl)-4-(2-trifluoromethyl-benzenesulfonyl)-pyrrolidine-2-carboxylic acid (1-cyano-cyclopropyl)-amide;

(2S,4R)-4-[2-Chloro-4-(4-methyl-piperazin-1-yl)-benzenesulfonyl]-1-(2-cyclobutyl-5-methyl-2H-pyrazol-3-yl)-pyrrolidine-2-carboxylic acid (1-cyano-cyclopropyl)-amide;

(2S,4R)-1-(3-Methanesulfonyl-phenyl)-4-(2-trifluoromethyl-benzenesulfonyl)-pyrrolidine-2-carboxylic acid (1-cyano-cyclopropyl)-amide;

(2S,4R)-4-[4-(3,3-Difluoro-azetidin-1-yl)-2-trifluoromethyl-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-4-[4-(4-Methyl-piperazin-1-yl)-2-trifluoromethyl-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-1-(3-Chloro-[1,2,4]thiadiazol-5-yl)-4-(2-trifluoromethyl-benzenesulfonyl)-pyrrolidine-2-carboxylic acid (1-cyano-cyclopropyl)-amide;

4-{5-[(2S,4R)-2-(1-Cyano-cyclopropylcarbamoyl)-4-(2-trifluoromethyl-benzenesulfonyl)-pyrrolidin-1-yl]-3-methyl-pyrazol-1-yl}-piperidine-1-carboxylic acid benzyl ester;

(2S,4R)-1-(5-Methyl-2-piperidin-4-yl-2H-pyrazol-3-yl)-4-(2-trifluoromethyl-benzenesulfonyl)-pyrrolidine-2-carboxylic acid (1-cyano-cyclopropyl)-amide;

(2S,4R)-1-Pyrimidin-2-yl-4-(2-trifluoromethyl-benzenesulfonyl)-pyrrolidine-2-carboxylic acid (1-cyano-cyclopropyl)-amide;

(2S,4R)-1-[1-(4-Chloro-phenyl)-cyclopropanecarbonyl]-4-methanesulfonyl-pyrrolidine-2-carboxylic acid (1-cyano-cyclopropyl)-amide;

(2S,4R)-4-(2-Chloro-benzenesulfonyl)-1-(6-chloro-1H-indazole-3-carbonyl)-pyrrolidine-2-carboxylic acid (1-cyano-cyclopropyl)-amide;

(2S,4R)-4-(2-Chloro-benzenesulfonyl)-1-[(R)-2-(4-chloro-phenyl)-2-hydroxy-acetyl]-pyrrolidine-2-carboxylic acid (1-cyano-cyclopropyl)-amide;

[(R)-2-[(2S,4R)-4-(2-Chloro-benzenesulfonyl)-2-(1-cyano-cyclopropylcarbamoyl)-pyrrolidin-1-yl]-1-(4-chloro-phenyl)-2-oxo-ethyl]-carbamic acid tert-butyl ester;

(2S,4R)-4-(2-Chloro-benzenesulfonyl)-1-[1-(4-methyl-thiazol-2-yl)-cyclopropanecarbonyl]-pyrrolidine-2-carboxylic acid (1-cyano-cyclopropyl)-amide;

(2S,4R)-4-(2-Chloro-benzenesulfonyl)-1-[2-(5-chloro-pyrimidin-2-yl)-acetyl]-pyrrolidine-2-carboxylic acid (1-cyano-cyclopropyl)-amide;

(2S,4R)-1-(2-Cyclobutyl-5-methyl-2H-pyrazol-3-yl)-4-[4-(3,3-difluoro-azetidin-1-yl)-2-trifluoromethyl-benzenesulfonyl]-pyrrolidine-2-carboxylic acid (1-cyano-cyclopropyl)-amide;

(2S,4R)-1-(2-Cyclobutyl-5-methyl-2H-pyrazol-3-yl)-4-(4-pyrazol-1-yl-2-trifluoromethyl-benzenesulfonyl)-pyrrolidine-2-carboxylic acid (1-cyano-cyclopropyl)-amide;

(2S,4R)-1-[(R)-2-Amino-2-(4-chloro-phenyl)-acetyl]-4-(2-chloro-benzenesulfonyl)-pyrrolidine-2-carboxylic acid (1-cyano-cyclopropyl)-amide;

(2S,4R)-4-(2-Chloro-benzenesulfonyl)-1-[2-(4-chloro-benzyl)-5-methyl-2H-pyrazol-3-yl]-pyrrolidine-2-carboxylic acid (1-cyano-cyclopropyl)-amide;

(2S,4R)-1-(2-Cyclobutyl-5-methyl-2H-pyrazol-3-yl)-4-(4-pyrimidin-4-yl-2-trifluoromethyl-benzenesulfonyl)-pyrrolidine-2-carboxylic acid (1-cyano-cyclopropyl)-amide;

(2S,4R)-N-(1-cyanocyclopropyl)-1-(1-cyclobutyl-3-methyl-1H-pyrazol-5-yl)-4-(4-(1-methyl-1H-pyrazol-5-yl)-2-(trifluoromethyl)phenylsulfonyl)pyrrolidine-2-carboxamide;

(R)-4-(2-Chloro-benzenesulfonyl)-1-[2-(4-chloro-phenyl)-2-(2,2,2-trifluoro-ethylamino)-acetyl]-pyrrolidine-2-carboxylic acid (1-cyano-cyclopropyl)-amide;

(2S,4R)-4-(2-Chloro-benzenesulfonyl)-1-[2-(3-trifluoromethyl-pyrazol-1-yl)-acetyl]-pyrrolidine-2-carboxylic acid (1-cyano-cyclopropyl)-amide;

(2S,4R)-4-Cyclopropylmethanesulfonyl-1-(1-trifluoromethyl-cyclopropane carbonyl)-pyrrolidine-2-carboxylic acid (1-cyano-cyclopropyl)-amide;

(2S,4R)-1-[1-(4-Chloro-phenyl)-cyclopropanecarbonyl]-4-cyclopropylmeth anesulfonyl-pyrrolidine-2-carboxylic acid (1-cyano-cyclopropyl)-amide;

(2S,4R)-4-(2-chlorophenylsulfonyl)-N-(1-cyanocyclopropyl)-1-(1-(4-fluorophenyl)cyclopropanecarbonyl)pyrrolidine-2-carboxamide;

(2S,4R)-1-(1-(4-bromophenyl)cyclopropanecarbonyl)-4-(2-chlorophenylsulfonyl)-N-(1-cyanocyclopropyl)pyrrolidine-2-carboxamide;

(2S,4R)-4-(2-chlorophenylsulfonyl)-N-(1-cyanocyclopropyl)-1-(1-(4-(trifluoromethyl)phenyl)cyclopropanecarbonyl)pyrrolidine-2-carboxamide;

(2S,4R)-1-(1-(3-chlorophenyl)cyclopropanecarbonyl)-4-(2-chlorophenylsulfonyl)-N-(1-cyanocyclopropyl)pyrrolidine-2-carboxamide;

(2S,4R)-4-(2-chlorophenylsulfonyl)-N-(1-cyanocyclopropyl)-1-(1-(3-(trifluoromethyl)phenyl)cyclopropanecarbonyl)pyrrolidine-2-carboxamide;

(2S,4R)-1-(2-(4-chlorophenyl)propanoyl)-4-(2-chlorophenylsulfonyl)-N-(1-cyanocyclopropyl)pyrrolidine-2-carboxamide;

(2S,4R)-1-(2-(4-chlorophenyl)propanoyl)-4-(2-chlorophenylsulfonyl)-N-(1-cyanocyclopropyl)pyrrolidine-2-carboxamide;

(2S,4R)-1-(2-(4-chlorophenyl)-3-methylbutanoyl)-4-(2-chlorophenylsulfonyl)-N-(1-cyanocyclopropyl)pyrrolidine-2-carboxamide;

tert-butyl 4-(4-chlorophenyl)-4-((2S,4R)-4-(2-chlorophenylsulfonyl)-2-(1-cyanocyclopropylcarbamoyl)pyrrolidine-1-carbonyl)piperidine-1-carboxylate;

(2S,4R)-4-(2-Chloro-benzenesulfonyl)-1-[2-(4-chlorophenyl)-2-morpholin-4-yl-acetyl]-pyrrolidine-2-carboxylic acid (1-cyano-cyclopropyl)-amide;

(2S,4R)-4-(2-Chloro-benzenesulfonyl)-1-[2-(4-chlorophenyl)-2-morpholin-4-yl-acetyl]-pyrrolidine-2-carboxylic acid (1-cyano-cyclopropyl)-amide;

(2S,4R)-4-(2-Chloro-benzenesulfonyl)-1-[2-(4-chlorophenyl)-2-morpholin-4-yl-acetyl]-pyrrolidine-2-carboxylic acid (1-cyano-cyclopropyl)-amide;

(2S,4R)-4-(2-Chloro-benzenesulfonyl)-1-[2-(3,4-dichloro-phenyl)-2,2-difluoro-acetyl]-pyrrolidine-2-carboxylic acid (1-cyano-cyclopropyl)-amide;

(2S,4R)-4-(2-chlorophenylsulfonyl)-N-(1-cyanocyclopropyl)-1-(1-p-tolylcyclopropanecarbonyl)pyrrolidine-2-carboxamide;

(2S,4R)-1-(1-(4-chloro-2-fluorophenyl)cyclopropanecarbonyl)-4-(2-chlorophenylsulfonyl)-N-(1-cyanocyclopropyl)pyrrolidine-2-carboxamide;

(2S,4R)-4-Methanesulfonyl-1-(1-trifluoromethyl-cyclopropanecarbonyl)-pyrrolidine-2-carboxylic acid (1-cyano-cyclopropyl)-amide;

(2S,4R,5S)-5-(4-tert-butylphenyl)-N-(1-cyanocyclopropyl)-4-(phenylsulfonyl)-2-(2-(phenylsulfonyl)ethyl)pyrrolidine-2-carboxamide;

(2S,4R)-4-(2-Chloro-benzenesulfonyl)-1-[2-(4-chlorophenyl)-2,2-difluoro-acetyl]-pyrrolidine-2-carboxylic acid (1-cyano-cyclopropyl)-amide;

(2S,4R)-4-(2-Chloro-benzenesulfonyl)-1-[1-(2,4-dichloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-[2-(4-chloro-3-fluoro-phenyl)-acetyl]-pyrrolidine-2-carboxylic acid (1-cyano-cyclopropyl)-amide;

(2S,4R)-1-(2-Benzyl-5-methyl-2H-pyrazol-3-yl)-4-cyclopropylmethanesulfonyl-pyrrolidine-2-carboxylic acid (1-cyano-cyclopropyl)-amide;

(2S,4R)-4-(2-Chloro-benzenesulfonyl)-1-[1-(4-chloro-3-fluoro-phenyl)-cyclopropanecarbonyl]-pyrrolidine-2-carboxylic acid (1-cyano-cyclopropyl)-amide;

4-Benzenesulfonyl-5-(4-tert-butyl-phenyl)-pyrrolidine-2-carboxylic acid (1-cyano-cyclopropyl)-amide;

(2S,4R)-4-Methanesulfonyl-1-(5-methyl-2-phenethyl-2H-pyrazol-3-yl)-pyrrolidine-2-carboxylic acid (1-cyano-cyclopropyl)-amide;

(2S,4R)-1-(2-Benzyl-5-methyl-2H-pyrazol-3-yl)-4-methanesulfonyl-pyrrolidine-2-carboxylic acid (1-cyano-cyclopropyl)-amide;

(2S,4R)-4-(2-Allyloxy-benzenesulfonyl)-2-(1-cyano-cyclopropylcarbamoyl)-pyrrolidine-1-carboxylic acid tert-butyl ester;

(2S,4R)-1-(1-Hydroxymethyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide;

(2S,4R)-4-(2-Chloro-benzenesulfonyl)-1-(1-hydroxymethyl-cyclopropanecarbonyl)-pyrrolidine-2-carboxylic acid (1-cyano-cyclopropyl)-amide;

(2S,4R)-4-(2-Allyloxy-benzenesulfonyl)-pyrrolidine-2-carboxylic acid (1-cyano-cyclopropyl)-amide;

(2S,4R)-4-Cyclopropylmethanesulfonyl-1-(1-methyl-cyclopropanecarbonyl)-pyrrolidine-2-carboxylic acid (1-cyano-cyclopropyl)-amide;

(2S,4R)-1-[(R)-2-Allylamino-2-(4-chloro-phenyl)-acetyl]-4-(2-allyloxy-benzenesulfonyl)-pyrrolidine-2-carboxylic acid (1-cyano-cyclopropyl)-amide;

(2S,4R)-4-(2-chloro-4-(3,3-difluoroazetidin-1-yl)phenylsulfonyl)-N-(1-cyanocyclopropyl)-1-(1-cyclobutyl-3-methyl-1H-pyrazol-5-yl)pyrrolidine-2-carboxamide;

(2S,4R)-1-(1-(4-chlorophenyl)cyclopropanecarbonyl)-N-(1-cyanocyclopropyl)-4-(phenylsulfonyl)pyrrolidine-2-carboxamide;

(2S,4R)-4-(benzylsulfonyl)-1-(1-(4-chlorophenyl)cyclopropanecarbonyl)-N-(1-cyanocyclopropyl)pyrrolidine-2-carboxamide;

(2S,4R)-4-(2-Chloro-benzenesulfonyl)-1-[1-(4-iodo-phenyl)-cyclopropanecarbonyl]-pyrrolidine-2-carboxylic acid (1-cyano-cyclopropyl)-amide;

(2S,4R)-4-(2-Chloro-benzenesulfonyl)-1-[1-(2,4-dichloro-5-methoxy-phenyl)-cyclopropanecarbonyl]-pyrrolidine-2-carboxylic acid (1-cyano-cyclopropyl)-amide;

(2S,4R)-4-(2-Chloro-benzenesulfonyl)-1-[1-(2,4-dichloro-5-fluoro-phenyl)-cyclopropanecarbonyl]-pyrrolidine-2-carboxylic acid (1-cyano-cyclopropyl)-amide;

(2S,4R)-4-Methanesulfonyl-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-1-[2-(2-Chloro-pyridin-4-yl)-5-methyl-2H-pyrazol-3-yl]-4-methanesulfonyl-pyrrolidine-2-carboxylic acid (1-cyano-cyclopropyl)-amide;

(2S,4R)-4-(2-chloro-4-(3,3-difluoroazetidin-1-yl)phenylsulfonyl)-N-(1-cyanocyclopropyl)-1-(3-methyl-1-(tetrahydro-2H-pyran-4-yl)-1H-pyrazol-5-yl)pyrrolidine-2-carboxamide;

(2S,4R)-4-(2-chlorophenylsulfonyl)-N-(1-cyanocyclopropyl)-1-(3-methyl-1-(tetrahydro-2H-thiopyran-4-yl)-1H-pyrazol-5-yl)pyrrolidine-2-carboxamide;

(2S,4R)-4-Methanesulfonyl-1-[5-methyl-2-(2,2,2-trifluoro-ethyl)-2H-pyrazol-3-yl]-pyrrolidine-2-carboxylic acid (1-cyano-cyclopropyl)-amide;

(2S,4R)-4-Cyclopropylmethanesulfonyl-1-[5-methyl-2-(2,2,2-trifluoro-ethyl)-2H-pyrazol-3-yl]-pyrrolidine-2-carboxylic acid (1-cyano-cyclopropyl)-amide;

(2S,4R)-1-[2-(2-Chloro-pyridin-4-yl)-5-methyl-2H-pyrazol-3-yl]-4-cyclopropylmethanesulfonyl-pyrrolidine-2-carboxylic acid (1-cyano-cyclopropyl)-amide;

(2S,4R)-4-Cyclopropylmethanesulfonyl-1-[5-methyl-2-(4-trifluoromethyl-phenyl)-2H-pyrazol-3-yl]-pyrrolidine-2-carboxylic acid (1-cyano-cyclopropyl)-amide;

(2S,4R)-4-Cyclopropylmethanesulfonyl-1-(5-methyl-2-phenethyl-2H-pyrazol-3-yl)-pyrrolidine-2-carboxylic acid (1-cyano-cyclopropyl)-amide;

(2S,4R)-1-(2-Cyclobutyl-5-methyl-2H-pyrazol-3-yl)-4-methanesulfonyl-pyrrolidine-2-carboxylic acid (1-cyano-cyclopropyl)-amide;

(2S,4R)-1-[1-(4-Bromo-naphthalen-1-yl)-cyclopropanecarbonyl]-4-(2-chloro-benzenesulfonyl)-pyrrolidine-2-carboxylic acid (1-cyano-cyclopropyl)-amide;

(2S,4R)-4-(2-Chloro-benzenesulfonyl)-1-[1-(4-chloro-phenoxy)-cyclopropanecarbonyl]-pyrrolidine-2-carboxylic acid (1-cyano-cyclopropyl)-amide;

(2S,4R)-1-[1-(4-Chloro-phenyl)-cyclopropanecarbonyl]-4-(diphenyl-methanesulfonyl)-pyrrolidine-2-carboxylic acid (1-cyano-cyclopropyl)-amide;

(2S,4R)-4-(4-Bromo-phenylmethanesulfonyl)-1-[1-(4-chloro-phenyl)-cyclopropanecarbonyl]-pyrrolidine-2-carboxylic acid (1-cyano-cyclopropyl)-amide;

(2S,4R)-4-[4-(4-tert-Butyl-piperazin-1-yl)-phenyl-methanesulfonyl]-1-[1-(4-chloro-phenyl)-cyclopropanecarbonyl]-pyrrolidine-2-carboxylic acid (1-cyano-cyclopropyl)-amide;

(2S,4R)-4-(2-Chloro-benzenesulfonyl)-1-(2-cyclohexyl-5-methyl-2H-pyrazol-3-yl)-pyrrolidine-2-carboxylic acid (1-cyano-cyclopropyl)-amide;

(2S,4R)-4-(2-Chloro-benzenesulfonyl)-1-[5-methyl-2-(tetrahydro-pyran-4-yl)-2H-pyrazol-3-yl]-pyrrolidine-2-carboxylic acid (1-cyano-cyclopropyl)-amide;

(4R)-4-[(2-chlorophenyl)sulfonyl]-N-(1-cyanocyclopropyl)-1-[1-(1,1-dioxidotetrahydro-2H-thiopyran-4-yl)-3-methyl-1H-pyrazol-5-yl]-L-prolinamide;

(2S,4R)-4-[2-Chloro-4-(3,3-difluoro-azetidin-1-yl)-benzenesulfonyl]-1-(2-cyclobutyl-5-methyl-2H-pyrazol-3-yl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(2-cyclobutyl-5-methyl-2H-pyrazol-3-yl)-pyrrolidine-2-carboxylic acid (1-cyano-cyclopropyl)-amide;

(2S,4R)-4-[4-(4-tert-Butyl-piperazin-1-yl)-2-chloro-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-[5-methyl-2-(tetrahydro-pyran-4-yl)-2H-pyrazol-3-yl]-pyrrolidine-2-carboxylic acid (1-cyano-cyclopropyl)-amide;

(2S,4R)-4-[2-Chloro-4-(3,3-difluoro-azetidin-1-yl)-benzenesulfonyl]-1-(5-methyl-2-phenethyl-2H-pyrazol-3-yl)-pyrrolidine-2-carboxylic acid (1-cyano-cyclopropyl)-amide;

(2S,4R)-4-[2-Chloro-4-(2,2,2-trifluoro-ethoxy)-benzenesulfonyl]-1-(5-methyl-2-phenethyl-2H-pyrazol-3-yl)-pyrrolidine-2-carboxylic acid (1-cyano-cyclopropyl)-amide;

(2S,4R)-4-[4-(4-tert-Butyl-piperazin-1-yl)-2-chloro-benzenesulfonyl]-1-(5-methyl-2-phenethyl-2H-pyrazol-3-yl)-pyrrolidine-2-carboxylic acid (1-cyano-cyclopropyl)-amide;

(2S,4R)-4-(2-Chloro-benzenesulfonyl)-1-(3-chloro-[1,2,4]thiadiazol-5-yl)-pyrrolidine-2-carboxylic acid (1-cyano-cyclopropyl)-amide;

(2S,4R)-4-(2-Chloro-benzenesulfonyl)-1-[5-methyl-2-(3-phenyl-propyl)-2H-pyrazol-3-yl]-pyrrolidine-2-carboxylic acid (1-cyano-cyclopropyl)-amide; and (2S,4R)-4-(2-Chloro-benzenesulfonyl)-1-[5-methyl-2-(2-morpholin-4-yl-ethyl)-2H-pyrazol-3-yl]-pyrrolidine-2-carboxylic acid (1-cyano-cyclopropyl)-amide.

27. A pharmaceutical composition comprising a compound according to claim 1 and a therapeutically inert carrier.

28. A compound according to claim 1 wherein said compound is (2S,4R)-1-(1-methyl-cyclopropanecarbonyl)-4-[4-(2,2,2-trifluoro-ethoxy)-2-trifluoromethyl-benzenesulfonyl]-pyrrolidine-2-carboxylic acid (1-cyano-cyclopropyl)-amide or a pharmaceutically acceptable salt thereof.

29. A compound according to claim 1 wherein said compound is (2S,4R)-4-[2-chloro-4-((S)-2,2,2-trifluoro-1-methyl-ethoxy)-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof.

30. A compound according to claim 1 wherein said compound is (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof.

31. A compound according to claim 1 wherein said compound is (2S,4R)-4-[4-(2-chloro-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof.

32. A compound according to claim 1 wherein said compound is (2S,4R)-4-[4-(2-Methyl-pyridin-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof.

33. A compound according to claim 1 wherein said compound is (2S,4R)-4-((S)-2-chloro-4-hexahydro-pyrrolo[1,2-a]pyrazin-2-yl-benzenesulfonyl)-1-(1-trifluoromethyl-cyclopropanecarbonyl)-pyrrolidine-2-carboxylic acid (1-cyano-cyclopropyl)-amide or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,163,793 B2 | Page 1 of 1 |
| APPLICATION NO. | : 12/761427 | |
| DATED | : April 24, 2012 | |
| INVENTOR(S) | : Sanchez et al. | |

It is certified that error appears in the above-identified patent and that said Letters Patent is hereby corrected as shown below:

TITLE PAGE:

• Assignee information reads: "(73) Assignee: Hoffman-La Roche Inc., Nutley, NJ (US)". The Assignee information should read -- (73) Assignee Hoffmann-La Roche Inc., Nutley, NJ (US) --.

Signed and Sealed this
Seventeenth Day of July, 2012

David J. Kappos
*Director of the United States Patent and Trademark Office*